US009527882B2

(12) United States Patent
Sit et al.

(10) Patent No.: US 9,527,882 B2
(45) Date of Patent: Dec. 27, 2016

(54) TRITERPENOIDS WITH HIV MATURATION INHIBITORY ACTIVITY

(71) Applicant: ViiV HEALTHCARE UK (NO.4) LIMITED, Brentford, Middlesex (GB)

(72) Inventors: Sing-Yuen Sit, Meriden, CT (US); Yan Chen, Wallingford, CT (US); Jie Chen, Madison, CT (US); Jacob Swidorski, Southington, CT (US); Brian Lee Venables, Durham, CT (US); Ny Sin, East Hampton, CT (US); Nicholas A. Meanwell, East Hampton, CT (US); Alicia Regueiro-Ren, Middletown, CT (US); Richard A. Hartz, Middletown, CT (US); Li Xu, Middletown, CT (US); Zheng Liu, Beacon Falls, CT (US)

(73) Assignee: ViiV Healthcare UK (No.4) Limited, Brentford, Middlesex (GB)

( * ) Notice: Subject to any disclaimer, the term of this patent is extended or adjusted under 35 U.S.C. 154(b) by 0 days.

(21) Appl. No.: 14/682,179

(22) Filed: Apr. 9, 2015

(65) Prior Publication Data
US 2015/0291655 A1 Oct. 15, 2015

Related U.S. Application Data

(60) Provisional application No. 61/978,306, filed on Apr. 11, 2014.

(51) Int. Cl.
C07D 279/12 (2006.01)
C07J 63/00 (2006.01)
C07C 309/65 (2006.01)
C07F 5/04 (2006.01)
C07F 5/02 (2006.01)

(52) U.S. Cl.
CPC ............ C07J 63/008 (2013.01); C07C 309/65 (2013.01); C07F 5/025 (2013.01); C07F 5/04 (2013.01); C07C 2101/16 (2013.01)

(58) Field of Classification Search
CPC .................................................. C07D 279/12
See application file for complete search history.

(56) References Cited

U.S. PATENT DOCUMENTS

| 5,679,828 | A | 10/1997 | Lee et al. |
| 7,354,924 | B2 | 4/2008 | Wang et al. |
| 7,365,221 | B2 | 4/2008 | Allaway et al. |
| 7,745,625 | B2 | 6/2010 | Ueda et al. |
| 8,748,415 | B2 | 6/2014 | Regueiro-Ren et al. |
| 8,754,068 | B2 | 6/2014 | Regueiro-Ren et al. |
| 8,802,661 | B2 | 8/2014 | Regueiro-Ren et al. |
| 8,846,647 | B2 | 9/2014 | Regueiro-Ren et al. |
| 8,906,889 | B2 | 12/2014 | Swidorski et al. |
| 2005/0239748 | A1 | 10/2005 | Power et al. |
| 2008/0207573 | A1 | 8/2008 | Yager et al. |

FOREIGN PATENT DOCUMENTS

| WO | WO 2006/053255 | 5/2006 |
| WO | WO 2009/100532 | 8/2009 |
| WO | WO 2011/007230 | 1/2011 |

OTHER PUBLICATIONS

Blair, W.S. et al., "HIV-1 entry—an expanding portal for drug discovery", Drug Discovery Today, vol. 5, No. 5, pp. 183-194 (2000).
Hotoda, H., "Small-molecule inhibitors of HIV-1 entry via chemokine receptors", Drugs of the Future, vol. 24, No. 12, pp. 1355-1362 (1999).
Kashiwada, Y. et al., "Betulinic Acid and Dihydrobetulinic Acid Derivatives as Potent Anti-HIV Agents", Journal of Medicinal Chemistry, vol. 39, No. 5, pp. 1016-1017 (1996).
Meanwell, N.A. et al., "Inhibitors of the entry of HIV into host cells", Current Opinion in Drug Discovery & Development, vol. 6, No. 4, pp. 451-461 (2003).
Pokrovskii, A.G. et al., "Synthesis of derivatives of plant triterpenes and study of their antiviral and immunostimulating activity", Khimiya y Interesakh Ustoichivogo Razvitiya, vol. 9, No. 3, pp. 485-491 (2001) (English abstract).
Sodroski, J.G., "HIV-1 Entry Inhibitors in the Side Pocket: Minireview", Cell, vol. 99, pp. 243-246 (1999).

Primary Examiner — Brian McDowell
(74) Attorney, Agent, or Firm — Robert H. Brink; R. Steve Thomas; Edward R. Gimmi

(57) ABSTRACT

Compounds having drug and bio-affecting properties, their pharmaceutical compositions and methods of use are set forth. In particular, triterpenoids that possess unique antiviral activity are provided as HIV maturation inhibitors, as represented by compounds of Formula I:

Formula I with X selected from $C_{4-8}$ cycloalkyl, $C_{4-8}$ cycloalkenyl, $C_{4-9}$ spirocycloalkyl, $C_{4-9}$ spirocycloalkenyl, $C_{4-8}$ oxacycloalkyl, $C_{4-8}$ dioxacycloalkyl, $C_{6-8}$ oxacycloalkenyl, $C_{6-8}$ dioxacycloalkenyl, $C_6$ cyclodialkenyl, $C_6$ oxacyclodialkenyl, $C_{6-9}$ oxaspirocycloalkyl and $C_{6-9}$ oxaspirocycloalkenyl ring, such that X is substituted with A, wherein A is —$C_{1-6}$ alkyl-halo. These compounds are useful for the treatment of HIV and AIDS.

18 Claims, No Drawings (Continued)

TRITERPENOIDS WITH HIV MATURATION INHIBITORY ACTIVITY

CROSS REFERENCE TO RELATED APPLICATION

This application claims the benefit of U.S. Provisional Application Ser. No. 61/978,306 filed Apr. 11, 2014, which is hereby incorporated by reference in its entirety.

FIELD OF THE INVENTION

The present invention relates to novel compounds useful against HIV and, more particularly, to compounds derived from betulinic acid and other structurally-related compounds which are useful as HIV maturation inhibitors, and to pharmaceutical compositions containing same, as well as to methods for their preparation.

BACKGROUND OF THE INVENTION

HIV-1 (human immunodeficiency virus-1) infection remains a major medical problem, with an estimated 45-50 million people infected worldwide at the end of 2010. The number of cases of HIV and AIDS (acquired immunodeficiency syndrome) has risen rapidly. In 2005, approximately 5.0 million new infections were reported, and 3.1 million people died from AIDS. Currently available drugs for the treatment of HIV include nucleoside reverse transcriptase (RT) inhibitors or approved single pill combinations: zidovudine (or AZT or RETROVIR®), didanosine (or VIDEX®), stavudine (or ZERIT®), lamivudine (or 3TC or EPIVIR®), zalcitabine (or DDC or HIVID®), abacavir succinate (or ZIAGEN®), Tenofovir disoproxil fumarate salt (or VIREAD®), emtricitabine (or FTC-EMTRIVA®), COMBIVIR® (contains-3TC plus AZT), TRIZIVIR® (contains abacavir, lamivudine, and zidovudine), EPZICOM® (contains abacavir and lamivudine), TRUVADA® (contains VIREAD® and) EMTRIVA®; non-nucleoside reverse transcriptase inhibitors: nevirapine (or VIRAMUNE®), delavirdine (or RESCRIPTOR®) and efavirenz (or SUSTIVA®), ATRIPLA® (TRUVADA®+SUSTIVA®), and etravirine, and peptidomimetic protease inhibitors or approved formulations: saquinavir, indinavir, ritonavir, nelfinavir, amprenavir, lopinavir, KALETRA® (lopinavir and Ritonavir), darunavir, atazanavir)(REYATAZ®) and tipranavir (APTIVUS®) and cobicistat, and integrase inhibitors such as raltegravir (ISENTRESS®), and entry inhibitors such as enfuvirtide (T-20) (FUZEON®) and maraviroc (SELZENTRY®).

Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients may ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present. Therefore, novel anti-HIV agents exhibiting distinct resistance patterns, and favorable pharmacokinetic as well as safety profiles are needed to provide more treatment options. Improved HIV fusion inhibitors and HIV entry coreceptor antagonists are two examples of new classes of anti-HIV agents further being studied by a number of investigators.

HIV attachment inhibitors are a further subclass of antiviral compounds that bind to the HIV surface glycoprotein gp120, and interfere with the interaction between the surface protein gp120 and the host cell receptor CD4. Thus, they prevent HIV from attaching to the human CD4 T-cell, and block HIV replication in the first stage of the HIV life cycle. The properties of HIV attachment inhibitors have been improved in an effort to obtain compounds with maximized utility and efficacy as antiviral agents. In particular, U.S. Pat. Nos. 7,354,924 and 7,745,625 are illustrative of HIV attachment inhibitors.

Another emerging class of compounds for the treatment of HIV are called HIV maturation inhibitors. Maturation is the last of as many as 10 or more steps in HIV replication or the HIV life cycle, in which HIV becomes infectious as a consequence of several HIV protease-mediated cleavage events in the gag protein that ultimately results in release of the capsid (CA) protein. Maturation inhibitors prevent the HIV capsid from properly assembling and maturing, from forming a protective outer coat, or from emerging from human cells. Instead, non-infectious viruses are produced, preventing subsequent cycles of HIV infection.

Certain derivatives of betulinic acid have now been shown to exhibit potent anti-HIV activity as HIV maturation inhibitors. For example, U.S. Pat. No. 7,365,221 discloses monoacylated betulin and dihydrobetuline derivatives, and their use as anti-HIV agents. As discussed in the '221 reference, esterification of betulinic acid (1) with certain substituted acyl groups, such as 3',3'-dimethylglutaryl and 3',3'-dimethylsuccinyl groups produced derivatives having enhanced activity (Kashiwada, Y., et al., J. Med. Chem. 39:1016-1017 (1996)). Acylated betulinic acid and dihydrobetulinic acid derivatives that are potent anti-HIV agents are also described in U.S. Pat. No. 5,679,828. Esterification of the hydroxyl in the 3 carbon of betulin with succinic acid also produced a compound capable of inhibiting HIV-1 activity (Pokrovskii, A. G., et al., "Synthesis of derivatives of plant triterpenes and study of their antiviral and immunostimulating activity," Khimiya y Interesakh Ustoichivogo Razvitiya, Vol. 9, No. 3, pp. 485-491 (2001) (English abstract).

Other references to the use of treating HIV infection with compounds derived from betulinic acid include US 2005/0239748 and US 2008/0207573, as well as WO2006/053255, WO2009/100532 and WO2011/007230.

One HIV maturation compound that has been in development has been identified as Bevirimat or PA-457, with the chemical formula of $C_{36}H_{56}O_6$ and the IUPAC name of 3β-(3-carboxy-3-methyl-butanoyloxy) lup-20 (29)-en-28-oic acid.

Reference is also made herein to the applications by Bristol-Myers Squibb entitled "MODIFIED C-3 BETULINIC ACID DERIVATIVES AS HIV MATURATION INHIBITORS" U.S. Ser. No. 13/151,706 filed on Jun. 2, 2011 (now U.S. Pat. No. 8,754,068) and "C-28 AMIDES OF MODIFIED C-3 BETULINIC ACID DERIVATIVES AS HIV MATURATION INHIBITORS" U.S. Ser. No. 13/151, 722, filed on Jun. 2, 2011 (now U.S. Pat. No. 8,802,661). Reference is also made to the application entitled "C-28 AMINES OF C-3 MODIFIED BETULINIC ACID DERIVATIVES AS HIV MATURATION INHIBITORS" U.S. Ser. No. 13/359,680, filed on Jan. 27, 2012 (now U.S. Pat. No. 8,748,415). In addition, reference is made to the application entitled "C-17 AND C-3 MODIFIED TRITERPENOIDS WITH HIV MATURATION INHIBITORY ACTIVITY" U.S. Ser. No. 13/359,727 filed on Jan. 27, 2012 (now U.S. Pat. No. 8,846,647). Further reference is also made to the application "C-3 CYCLOALKENYL TRITERPENOIDS WITH HIV MATURATION INHIBITORY ACTIVITY" filed U.S. Ser. No. 13/760,726 on Feb. 6, 2013 (now U.S. Pat. No. 8,906,889).

What is now needed in the art are new compounds which are useful as HIV maturation inhibitors, as well as new pharmaceutical compositions containing these compounds.

SUMMARY OF THE INVENTION

The present invention provides compounds of Formula I below, including pharmaceutically acceptable salts thereof, their pharmaceutical formulations, and their use in patients suffering from or susceptible to a virus such as HIV. The compounds of Formula I are effective antiviral agents, particularly as inhibitors of HIV. They are useful for the treatment of HIV and AIDS.

One embodiment of the present invention is directed to a compound of Formula I, including pharmaceutically acceptable salts thereof:

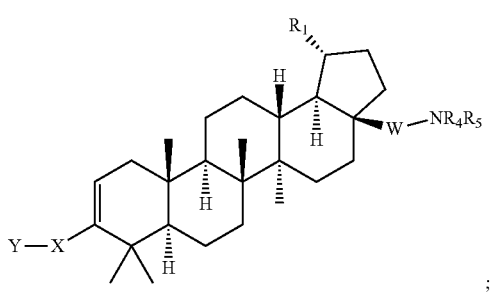

Formula I wherein $R_1$ is isopropenyl or isopropyl;

X is selected from the group of $C_{4-8}$ cycloalkyl, $C_{4-8}$ cycloalkenyl, $C_{4-9}$ spirocycloalkyl, $C_{4-9}$ spirocycloalkenyl, $C_{4-8}$ oxacycloalkyl, $C_{4-8}$ dioxacycloalkyl, $C_{6-8}$ oxacycloalkenyl, $C_{6-8}$ dioxacycloalkenyl, $C_6$ cyclodialkenyl, $C_6$ oxacyclodialkenyl, $C_{6-9}$ oxaspirocycloalkyl and $C_{6-9}$ oxaspirocycloalkenyl ring, wherein X is substituted with A, and wherein A is $-C_{1-6}$ alkyl-halo;

Y is selected from the group of $-COOR_2$, $-C(O)NR_2SO_2R_3$, $-C(O)NHSO_2NR_2R_2$, $-NR_2SO_2R_2$, $-SO_2NR_2R_2$, $-C_{3-6}$ cycloalkyl-$COOR_2$, $-C_{2-6}$ alkenyl-$COOR_2$, $-C_{2-6}$ alkynyl-$COOR_2$, $-C_{1-6}$alkyl-$COOR_2$, -alkylsubstituted $C_{1-6}$ alkyl, $-CF_2-COOR_2$, $-NHC(O)(CH_2)_n-COOR_2$, $-SO_2NR_2C(O)R_2$, -tetrazole, and $-CONHOH$, wherein n=1-6;

$R_2$ is $-H$, $-C_{1-6}$ alkyl, -alkylsubstituted $C_{1-6}$ alkyl or -arylsubstituted $C_{1-6}$ alkyl;

W is absent, or is $-CH_2$ or $-CO$;

$R_3$ is $-H$, $-C_{1-6}$ alkyl or -alkylsubstituted $C_{1-6}$ alkyl;

$R_4$ is selected from the group of $-H$, $-C_{1-6}$ alkyl, $-C_{1-6}$ alkyl-$C_{3-6}$cycloalkyl, $-C_{1-6}$ substituted $-C_{1-6}$ alkyl, $-C_{1-6}$ alkyl-$Q_1$, $-C_{1-6}$ alkyl-$C_{3-6}$ cycloalkyl-$Q_1$, aryl, heteroaryl, substituted heteroaryl, $-COR_6$, $-SO_2R_7$, $-SO_2NR_2R_2$, and

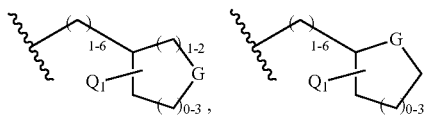

wherein G is selected from the group of $-O-$, $-SO_2-$ and $-NR_{12}$;

wherein $Q_1$ is selected from the group of $-C_{1-6}$ alkyl, $-C_{1-6}$ fluoroalkyl, heteroaryl, substituted heteroaryl, halogen, $-CF_3$, $-OR_2$, $-COOR_2$, $-NR_8R_9$, $-CONR_8R_9$ and $-SO_2R_7$;

$R_5$ is selected from the group of $-H$, $-C_{1-6}$ alkyl, $-C_{3-6}$ cycloalkyl, $-C_{1-6}$ alkylsubstituted alkyl, $-C_{1-6}$alkyl-$NR_8R_9$, $-COR_3$, $-SO_2R_7$ and $-SO_2NR_2R_2$;

with the proviso that $R_4$ or $R_5$ cannot be $-COR_6$ when W is $-CO$;

with the further proviso that only one of $R_4$ or $R_5$ can be selected from the group of $-COR_6$, $-COCOR_6$, $-SO_2R_7$ and $-SO_2NR_2R_2$;

or when W is absent or is $-CH_2$, then $R_4$ and $R_5$ can be taken together with the adjacent N to form

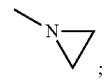

$R_6$ is selected from the group of $-H$, $-C_{1-6}$ alkyl, $-C_{1-6}$ alkyl-substitutedalkyl, $-C_{3-6}$ cycloalkyl, $-C_{3-6}$ substitutedcycloalkyl-$Q_2$, $-C_{1-6}$ alkyl-$Q_2$, $-C_{1-6}$ alkyl-substituted-alkyl-$Q_2$, $-C_{3-6}$ cycloalkyl-$Q_2$, aryl-$Q_2$, $-NR_{13}R_{14}$, and $-OR_{15}$;

wherein $Q_2$ is selected from the group of aryl, heteroaryl, substituted heteroaryl, $-OR_2$, $-COOR_2$, $-NR_8R_9$, $SO_2R_7$, $-CONHSO_2R_3$, and $-CONHSO_2NR_2R_2$;

$R_7$ is selected from the group of $-H$, $-C_{1-6}$ alkyl, $-C_{1-6}$ substituted alkyl, $-C_{3-6}$ cycloalkyl, $-CF_3$, aryl, and heteroaryl;

$R_8$ and $R_9$ are independently selected from the group of $-H$, $-C_{1-6}$ alkyl, $-C_{1-6}$ substituted alkyl, aryl, heteroaryl, substituted aryl, substituted heteroaryl, $-C_{1-6}$ alkyl-$Q_2$, and $-COOR_3$, or $R_8$ and $R_9$ are taken together with the adjacent N to form a cycle selected from the group of:

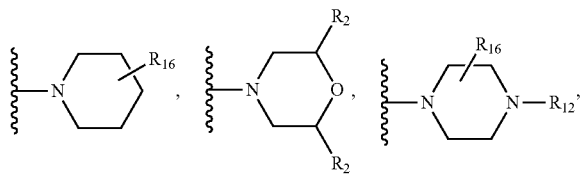

-continued

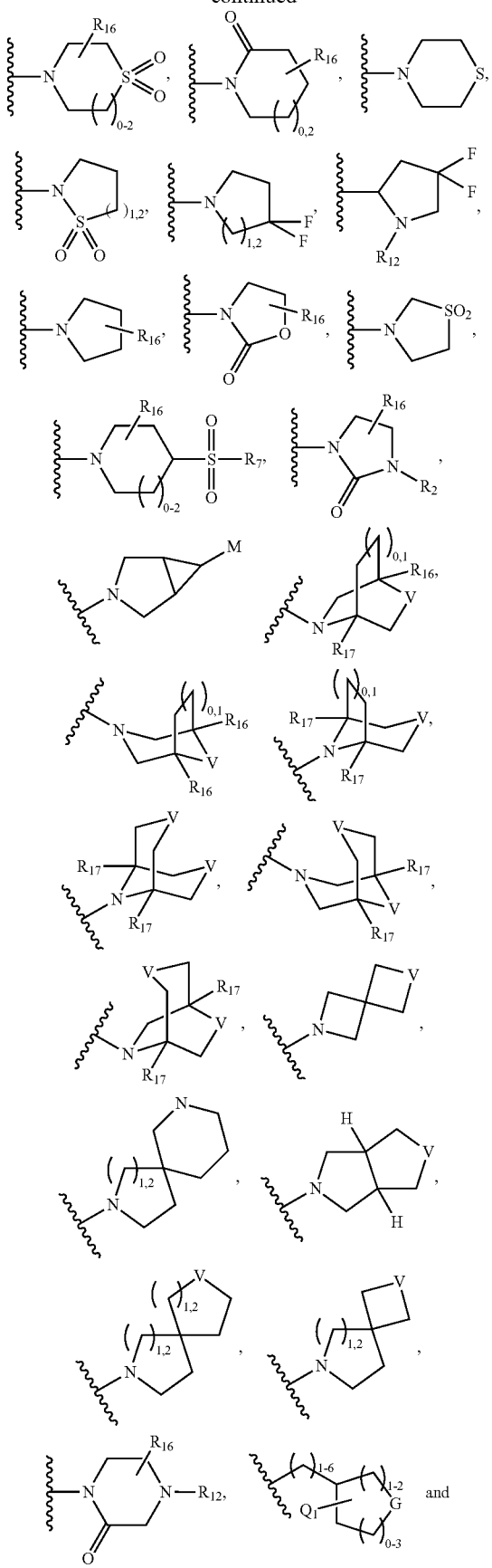

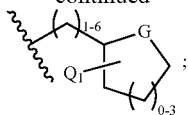

M is selected from the group of —$R_{15}$, —$SO_2R_2$, —$SO_2NR_2R_2$, —OH and —$NR_2R_{12}$;
V is selected from the group of —$CR_{10}R_{11}$—, —$SO_2$—, —O— and —$NR_{12}$—;
with the proviso that only one of $R_8$ or $R_9$ can be —$COOR_3$;
$R_{10}$ and $R_{11}$ are independently selected from the group of —H, —$C_{1-6}$ alkyl, —$C_{1-6}$ substituted alkyl and —$C_{3-6}$ cycloalkyl;
$R_{12}$ is selected from the group of —H, —$C_{1-6}$ alkyl, -alkyl-substituted $C_{1-6}$ alkyl, —$CONR_2R_2$, —$SO_2R_3$, —$SO_2NR_2R_2$;
$R_{13}$ and $R_{14}$ are independently selected from the group of —H, —$C_{1-6}$ alkyl, —$C_{3-6}$ cycloalkyl, —$C_{1-6}$ substituted alkyl, —$C_{1-6}$ alkyl-$Q_3$, —$C_{1-6}$ alkyl-$C_{3-6}$ cycloalkyl-$Q_3$, $C_{1-6}$ substituted alkyl-$Q_3$ and

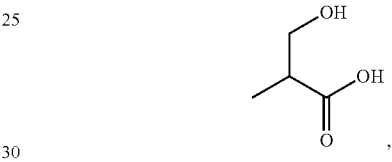

$Q_3$ is selected from the group of heteroaryl, substituted heteroaryl, —$NR_2R_{12}$, —$CONR_2R_2$, —$COOR_2$, —$OR_2$, and —$SO_2R_3$;
$R_{15}$ is selected from the group of —$C_{1-6}$ alkyl, —$C_{3-6}$ cycloalkyl, —$C_{1-6}$ substituted alkyl, —$C_{1-6}$ alkyl-$Q_3$, —$C_{1-6}$ alkyl-$C_{3-6}$ cycloalkyl-$Q_3$ and —$C_{1-6}$ substituted alkyl-$Q_3$,
$R_{16}$ is selected from the group of —H, —$C_{1-6}$ alkyl, —$NR_2R_2$, and —$COOR_2$; with the proviso that when V is —$NR_{12}$—; $R_{16}$ cannot be —$NR_2R_2$; and
$R_{17}$ is selected from the group of —H, —$C_{1-6}$ alkyl, —$COOR_3$, and aryl.

In a further embodiment, there is provided a method for treating mammals infected with a virus, especially wherein said virus is HIV, comprising administering to said mammal an antiviral effective amount of a compound which is selected from the group of compounds of Formula I, and one or more pharmaceutically acceptable carriers, excipients or diluents. Optionally, the compound of Formula I can be administered in combination with an antiviral effective amount of another AIDS treatment agent selected from the group consisting of: (a) an AIDS antiviral agent; (b) an anti-infective agent; (c) an immunomodulator; and (d) other HIV entry inhibitors.

Another embodiment of the present invention is a pharmaceutical composition comprising one or more compounds of Formula I, and one or more pharmaceutically acceptable carriers, excipients, and/or diluents; and optionally in combination with another AIDS treatment agent selected from the group consisting of: (a) an AIDS antiviral agent; (b) an anti-infective agent; (c) an immunomodulator; and (d) other HIV entry inhibitors.

In another embodiment of the invention there is provided one or more methods for making the compounds of Formula I herein.

Also provided herein are intermediate compounds useful in making the compounds of Formula I herein.

The present invention is directed to these, as well as other important ends, hereinafter described.

DETAILED DESCRIPTION OF THE EMBODIMENTS

As used herein, the singular forms "a", "an", and "the" include plural reference unless the context clearly dictates otherwise.

Since the compounds of the present invention may possess asymmetric centers and therefore occur as mixtures of diastereomers, the present disclosure includes the individual diastereoisomeric forms of the compounds of Formula I, in addition to the mixtures thereof Definitions Unless otherwise specifically set forth elsewhere in the application, one or more of the following terms may be used herein, and shall have the following meanings:

"H" refers to hydrogen, including its isotopes, such as deuterium.

The term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"$C_1$-$C_4$ fluoroalkyl" refers to F-substituted $C_1$-$C_4$ alkyl wherein at least one H atom is substituted with F atom, and each H atom can be independently substituted by F atom;

"Halogen" or "halo" refers to chlorine, bromine, iodine or fluorine.

An "aryl" or "Ar" group refers to an all carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group(s) are preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —$NR^xR^y$, wherein $R^x$ and $R^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyl, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —$NR^xR^y$, wherein $R^x$ and $R^y$ are as defined above.

As used herein, a "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encompass systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and its S oxides and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —$NR^xR^y$, wherein $R^x$ and $R^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexene, cycloheptane, cycloheptene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thio-heteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, tri-halo-methanesulfonamido, trihalomethanesulfonyl, silyl, amidino, guanidino, ureido, phosphonyl, amino and —NR$^x$R$^y$ with R$^x$ and R$^y$ as defined above.

An "alkenyl" group refers to an alkyl group, as defined herein, having at least two carbon atoms and at least one carbon-carbon double bond.

An "alkynyl" group refers to an alkyl group, as defined herein, having at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "keto" group refers to a —CC(=O)C— group wherein the carbon on either or both sides of the C=O may be alkyl, cycloalkyl, aryl or a carbon of a heteroaryl or heteroalicyclic group.

A "trihalomethanecarbonyl" group refers to a Z$_3$CC(=O)— group with said Z being a halogen.

A "C-carboxy" group refers to a —C(=O)O—R" groups, with R" as defined herein.

An "O-carboxy" group refers to a R"C(=O)O— group, with R" as defined herein.

A "carboxylic acid" group refers to a C-carboxy group in which R" is hydrogen.

A "trihalomethyl" group refers to a —CZ$_3$, group wherein Z is a halogen group as defined herein.

A "trihalomethanesulfonyl" group refers to an Z$_3$CS(=O)$_2$— groups with Z as defined above.

A "trihalomethanesulfonamido" group refers to a Z$_3$CS(=O)$_2$NR$^x$— group with Z as defined above and R$^x$ being H or (C$_{1-6}$)alkyl.

A "sulfinyl" group refers to a —S(=O)—R" group, with R" being (C$_{1-6}$)alkyl.

A "sulfonyl" group refers to a —S(=O)$_2$R" group with R" being (C$_{1-6}$)alkyl.

A "S-sulfonamido" group refers to a —S(=O)$_2$NR$^X$R$^Y$, with R$^X$ and R$^Y$ independently being H or (C$_{1-6}$)alkyl.

A "N-sulfonamido" group refers to a R"S(=O)$_2$NR$_X$— group, with R$^X$ being H or (C$_{1-6}$)alkyl.

A "O-carbamyl" group refers to a —OC(=O)NR$^x$R$^y$ group, with R$^X$ and R$^Y$ independently being H or (C$_{1-6}$)alkyl.

A "N-carbamyl" group refers to a R$^x$OC(=O)NR$^y$ group, with R$^x$ and R$^y$ independently being H or (C$_{1-6}$)alkyl.

A "O-thiocarbamyl" group refers to a —OC(=S)NR$^x$R$^y$ group, with R$^x$ and R$^y$ independently being H or (C$_{1-6}$)alkyl.

A "N-thiocarbamyl" group refers to a R$^x$OC(=S)NR$^y$— group, with R$^x$ and R$^y$ independently being H or (C$_{1-6}$)alkyl.

An "amino" group refers to an —NH$_2$ group.

A "C-amido" group refers to a —C(=O)NR$^x$R$^y$ group, with R$^x$ and R$^y$ independently being H or (C$_{1-6}$)alkyl.

A "C-thioamido" group refers to a —C(=S)NR$^x$R$^y$ group, with R$^x$ and R$^y$ independently being H or (C$_{1-6}$)alkyl.

A "N-amido" group refers to a R$^x$C(=O)NR$^y$— group, with R$^x$ and R$^y$ independently being H or (C$_{1-6}$)alkyl.

An "ureido" group refers to a —NR$^x$C(=O)NR$^y$R$^{y2}$ group, with R$^x$, R$^y$, and R$^{y2}$ independently being H or (C$_{1-6}$)alkyl.

A "guanidino" group refers to a —R$^x$NC(=N)NR$^y$R$^{y2}$ group, with R$^x$, R$^y$, and R$^{y2}$ independently being H or (C$_{1-6}$)alkyl.

A "amidino" group refers to a R$^x$R$^y$NC(=N)— group, with R$^x$ and R$^y$ independently being H or (C$_{1-6}$)alkyl.

A "cyano" group refers to a —CN group.

A "silyl" group refers to a —Si(R")$_3$, with R" being (C$_{1-6}$)alkyl or phenyl.

A "phosphonyl" group refers to a P(=O)(OR$^x$)$_2$ with R$^x$ being (C$_{1-6}$)alkyl.

A "hydrazino" group refers to a —NR$^x$NR$^y$R$^{y2}$ group, with R$^x$, R$^y$, and R$^{y2}$ independently being H or (C$_{1-6}$)alkyl.

A "4, 5, or 6 membered ring cyclic N-lactam" group refers to

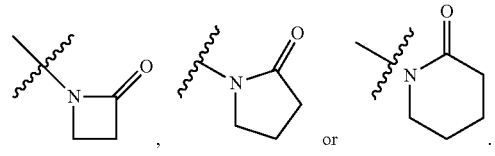

A "spiro" group is a bicyclic organic group with rings connected through just one atom. The rings can be different in nature or identical. The connecting atom is also called the spiroatom, most often a quaternary carbon ("spiro carbon").

An "oxospiro" or "oxaspiro" group is a spiro group having an oxygen contained within the bicyclic ring structure. A "dioxospiro" or "dioxaspiro" group has two oxygens within the bicyclic ring structure.

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present disclosure are based on the known general principles of chemical bonding. It is understood that the claims do not encompass structures known to be unstable or not able to exist based on the literature.

Pharmaceutically acceptable salts and prodrugs of compounds disclosed herein are within the scope of the invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

As stated above, the compounds of the invention also include "prodrugs". The term "prodrug" as used herein encompasses both the term "prodrug esters" and the term "prodrug ethers".

As set forth above, the invention is directed to a compound of Formula I, including pharmaceutically acceptable salts thereof:

Formula I

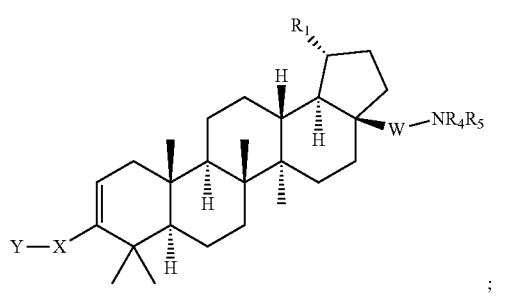

wherein $R_1$ is isopropenyl or isopropyl;
X is selected from the group of $C_{4-8}$ cycloalkyl, $C_{4-8}$ cycloalkenyl, $C_{4-9}$ spirocycloalkyl, $C_{4-9}$ spirocycloalkenyl, $C_{4-8}$ oxacycloalkyl, $C_{4-8}$ dioxacycloalkyl, $C_{6-8}$ oxacycloalkenyl, $C_{6-8}$ dioxacycloalkenyl, $C_6$ cyclodialkenyl, $C_6$ oxacyclodialkenyl, $C_{6-9}$ oxaspirocycloalkyl and $C_{6-9}$ oxaspirocycloalkenyl ring,
wherein X is substituted with A, and wherein A is $-C_{1-6}$ alkyl-halo;
Y is selected from the group of $-COOR_2$, $-C(O)NR_2SO_2R_3$, $-C(O)NHSO_2NR_2R_2$, $-NR_2SO_2R_2$, $-SO_2NR_2R_2$, $-C_{3-6}$ cycloalkyl-$COOR_2$, $-C_{2-6}$ alkenyl-$COOR_2$, $-C_{2-6}$ alkynyl-$COOR_2$, $-C_{1-6}$alkyl-$COOR_2$, -alkylsubstituted $C_{1-6}$ alkyl, $-CF_2-COOR_2$, $-NHC(O)(CH_2)_n-COOR_2$, $-SO_2NR_2C(O)R_2$, -tetrazole, and $-CONHOH$,
wherein n=1-6;
$R_2$ is $-H$, $-C_{1-6}$ alkyl, -alkylsubstituted $C_{1-6}$ alkyl or -arylsubstituted $C_{1-6}$ alkyl;
W is absent, or is $-CH_2$ or $-CO$;
$R_3$ is $-H$, $-C_{1-6}$ alkyl or -alkylsubstituted $C_{1-6}$ alkyl;
$R_4$ is selected from the group of $-H$, $-C_{1-6}$ alkyl, $-C_{1-6}$ alkyl-$C_{3-6}$cycloalkyl, $-C_{1-6}$ substituted $-C_{1-6}$ alkyl, $-C_{1-6}$ alkyl-$Q_1$, $-C_{1-6}$ alkyl-$C_{3-6}$ cycloalkyl-$Q_1$, aryl, heteroaryl, substituted heteroaryl, $-COR_6$, $-SO_2R_7$, $-SO_2NR_2R_2$, and

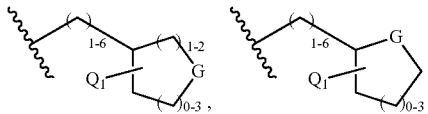

wherein G is selected from the group of $-O-$, $-SO_2-$ and $-NR_{12}$;
wherein $Q_1$ is selected from the group of $-C_{1-6}$ alkyl, $-C_{1-6}$ fluoroalkyl, heteroaryl, substituted heteroaryl, halogen, $-CF_3$, $-OR_2$, $-COOR_2$, $-NR_8R_9$, $-CONR_8R_9$ and $-SO_2R_7$;
$R_5$ is selected from the group of $-H$, $-C_{1-6}$ alkyl, $-C_{3-6}$ cycloalkyl, $-C_{1-6}$ alkylsubstituted alkyl, $-C_{1-6}$alkyl-$NR_8R_9$, $-COR_3$, $-SO_2R_7$ and $-SO_2NR_2R_2$;
with the proviso that $R_4$ or $R_5$ cannot be $-COR_6$ when W is $-CO$;
with the further proviso that only one of $R_4$ or $R_5$ can be selected from the group of $-COR_6$, $-COCOR_6$, $-SO_2R_7$ and $-SO_2NR_2R_2$;
or when W is absent or is $-CH_2$, then $R_4$ and $R_5$ can be taken together with the adjacent N to form

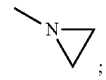

$R_6$ is selected from the group of $-H$, $-C_{1-6}$ alkyl, $-C_{1-6}$ alkyl-substituted alkyl, $-C_{3-6}$ cycloalkyl, $-C_{3-6}$ substituted cycloalkyl-$Q_2$, $-C_{1-6}$ alkyl-$Q_2$, $-C_{1-6}$ alkyl-substituted alkyl-$Q_2$, $-C_{3-6}$ cycloalkyl-$Q_2$, aryl-$Q_2$, $-NR_{13}R_{14}$, and $-OR_{15}$;
wherein $Q_2$ is selected from the group of aryl, heteroaryl, substituted heteroaryl, $-OR_2$, $-COOR_2$, $-NR_8R_9$, $SO_2R_7$, $-CONHSO_2R_3$, and $-CONHSO_2NR_2R_2$;
$R_7$ is selected from the group of $-H$, $-C_{1-6}$ alkyl, $-C_{1-6}$ substituted alkyl, $-C_{3-6}$ cycloalkyl, $-CF_3$, aryl, and heteroaryl;
$R_8$ and $R_9$ are independently selected from the group of $-H$, $-C_{1-6}$ alkyl, $-C_{1-6}$ substituted alkyl, aryl, heteroaryl, substituted aryl, substituted heteroaryl, $-C_{1-6}$ alkyl-$Q_2$, and $-COOR_3$,
or $R_8$ and $R_9$ are taken together with the adjacent N to form a cycle selected from the group of:

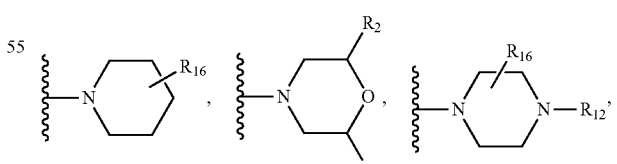

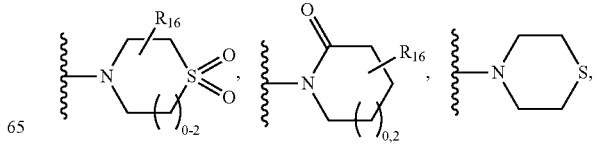

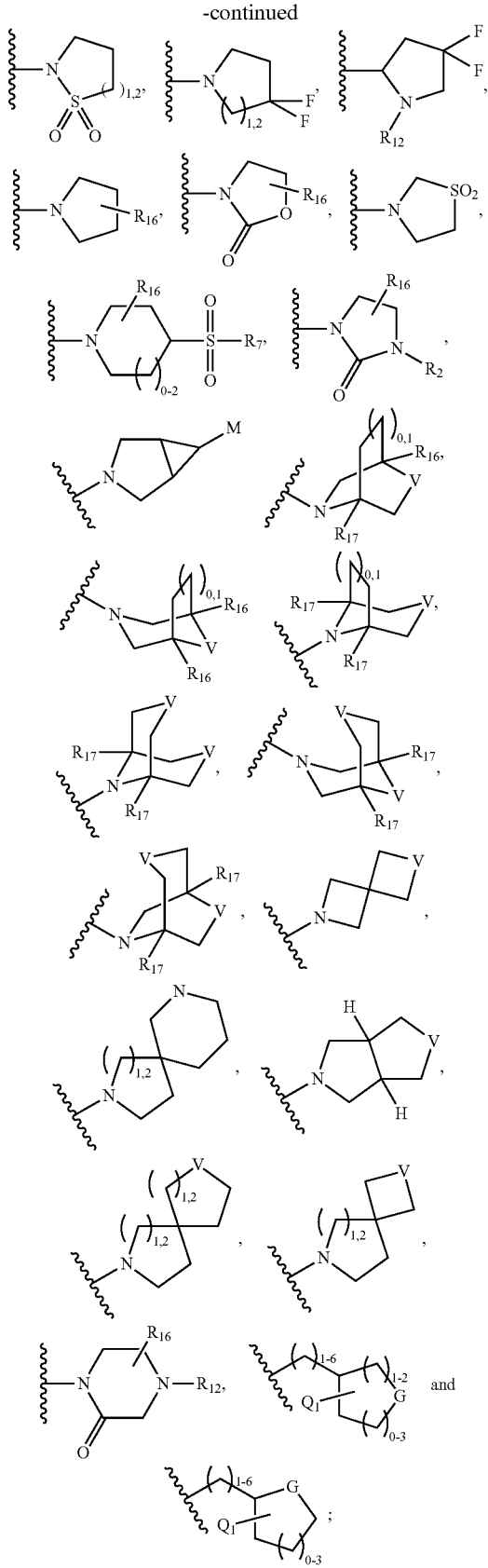

M is selected from the group of —R$_{16}$, —SO$_2$R$_2$, —SO$_2$NR$_2$R$_2$, —OH and —NR$_2$R$_{12}$;

V is selected from the group of —CR$_{10}$R$_{11}$—, —SO$_2$—, —O— and —NR$_{12}$—;

with the proviso that only one of R$_8$ or R$_9$ can be —COOR$_3$;

R$_{10}$ and R$_{11}$ are independently selected from the group of —H, —C$_{1-6}$ alkyl, —C$_{1-6}$ substituted alkyl and —C$_{3-6}$ cycloalkyl;

R$_{12}$ is selected from the group of —H, —C$_{1-6}$ alkyl, -alkyl-substituted C$_{1-6}$ alkyl, —CONR$_2$R$_2$, —SO$_2$R$_3$, —SO$_2$NR$_2$R$_2$;

R$_{13}$ and R$_{14}$ are independently selected from the group of —H, —C$_{1-6}$ alkyl, —C$_{3-6}$cycloalkyl, —C$_{1-6}$ substituted alkyl, —C$_{1-6}$ alkyl-Q$_3$, —C$_{1-6}$ alkyl-C$_{3-6}$cycloalkyl-Q$_3$, C$_{1-6}$ substituted alkyl-Q$_3$ and Q$_3$ is selected from the group of heteroaryl, substituted heteroaryl, —NR$_2$R$_{12}$, —CONR$_2$R$_2$, —COOR$_2$, —OR$_2$, and —SO$_2$R$_3$;

R$_{15}$ is selected from the group of —C$_{1-6}$ alkyl, —C$_{3-6}$ cycloalkyl, —C$_{1-6}$ substituted alkyl, —C$_{1-6}$ alkyl-Q$_3$, —C$_{1-6}$ alkyl-C$_{3-6}$cycloalkyl-Q$_3$ and —C$_{1-6}$ substituted alkyl-Q$_3$, R$_{16}$ is selected from the group of —H, —C$_{1-6}$ alkyl, —NR$_2$R$_2$, and —COOR$_2$;

with the proviso that when V is —NR$_{12}$—; R$_{16}$ cannot be —NR$_2$R$_2$; and R$_{17}$ is selected from the group of —H, —C$_{1-6}$ alkyl, —COOR$_3$, and aryl.

More preferred compounds include those wherein R$_1$ is isopropenyl.

Also preferred are compounds wherein W is absent.

Other preferred compounds include those wherein X is a C$_{4-8}$ cycloalkenyl, and more preferably, C$_6$ cycloalkenyl.

In addition, compounds of Formula I are preferred wherein A is C$_1$-C$_3$ alkyl-halo, and more preferably methyl-halo, and more preferably methyl-fluoro.

Also preferred are compounds wherein A is para-substituted on substituent X.

Also preferred are compounds of Formula I wherein Y is —COOR$_2$, and more preferably —COOH. In certain embodiments, it is also preferred that Y is —COOH and A is methyl-fluoro.

Also preferred are compounds of Formula I wherein Y is in the para position.

Further preferred are compounds of Formula I wherein both substituent A and substituent Y share the same point of attachment on substituent X; more preferably, on the -para position of substituent X.

In many embodiments, it is also preferred that R$_4$ is C$_{1-6}$alkyl-Q$_1$, wherein Q$_1$ is —NR$_8$R$_9$.

In some embodiments, it is preferred that R$_4$ is —C$_{1-6}$ alkyl-C$_{3-6}$cycloalkyl.

In certain embodiments it is also preferred that R$_5$ is C$_{1-6}$alkyl-NR$_8$R$_9$.

Many times it is also preferred that —NR$_8$R$_9$ form the ring structure as set forth above.

Preferred compounds, including pharmaceutically acceptable salts thereof, as part of the invention include the following:

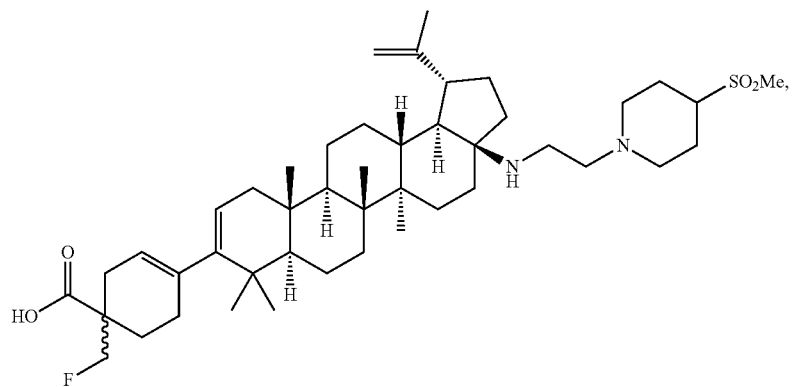
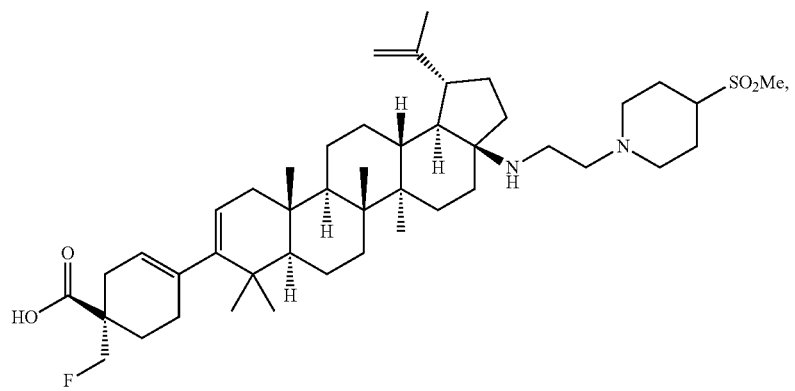
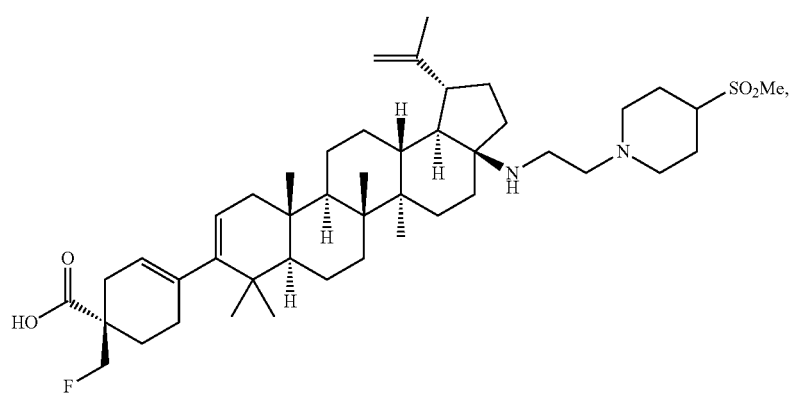
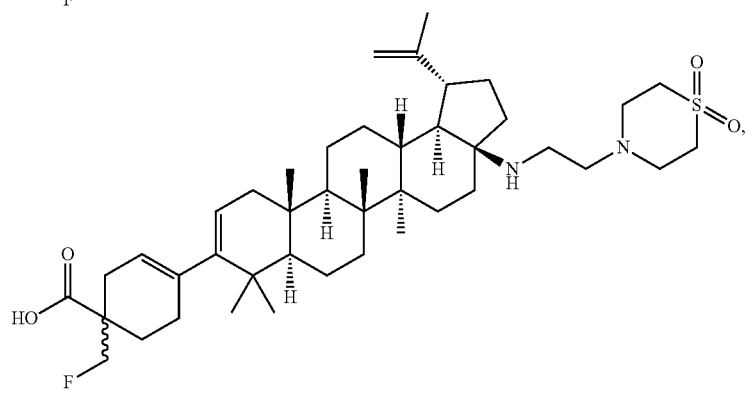

-continued
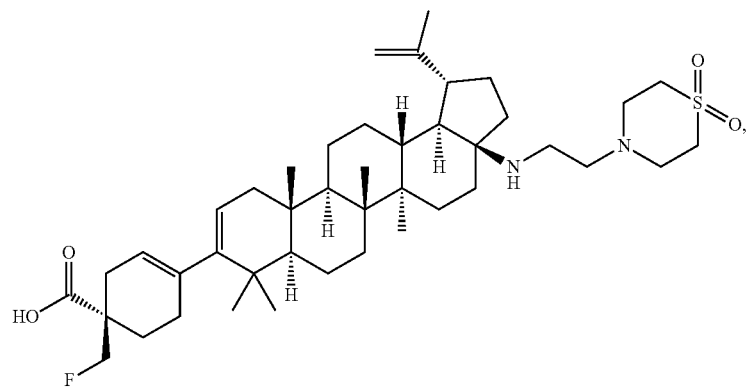
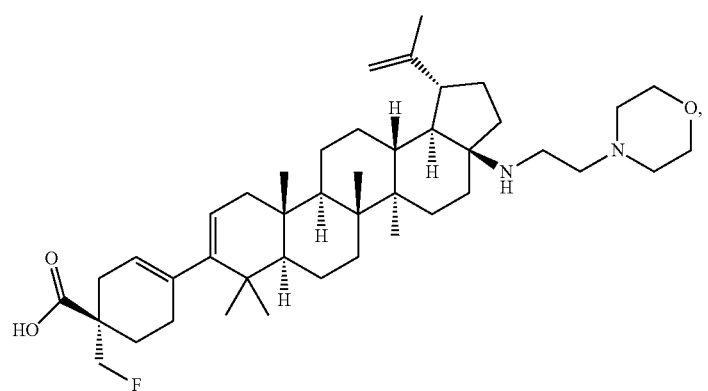
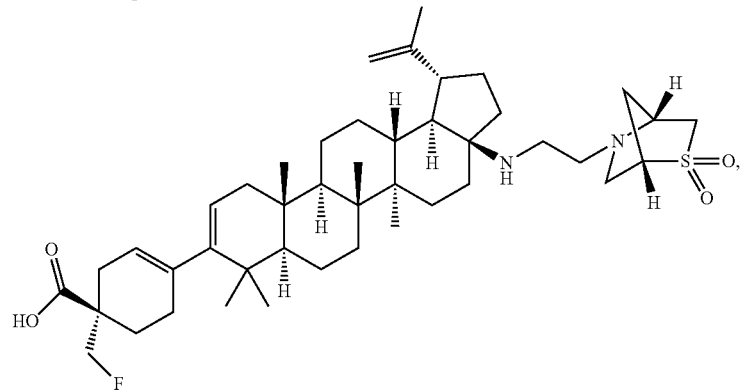

-continued
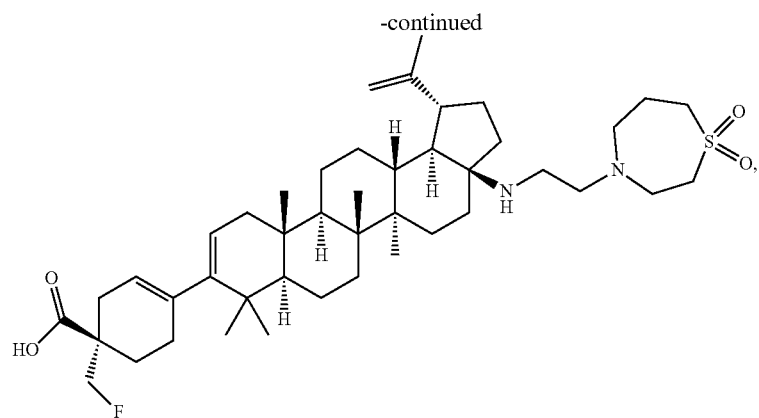
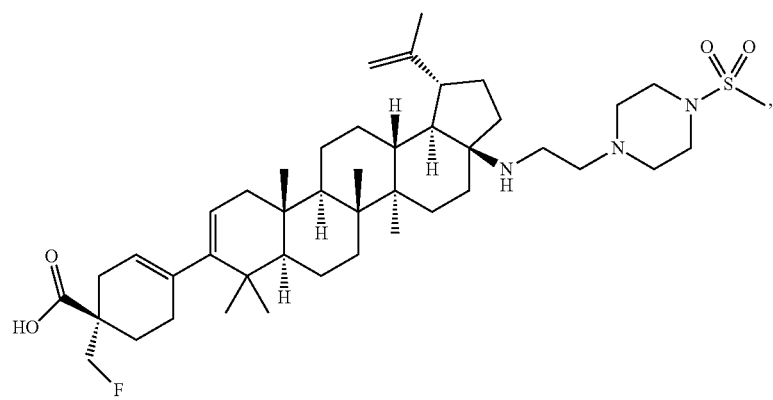
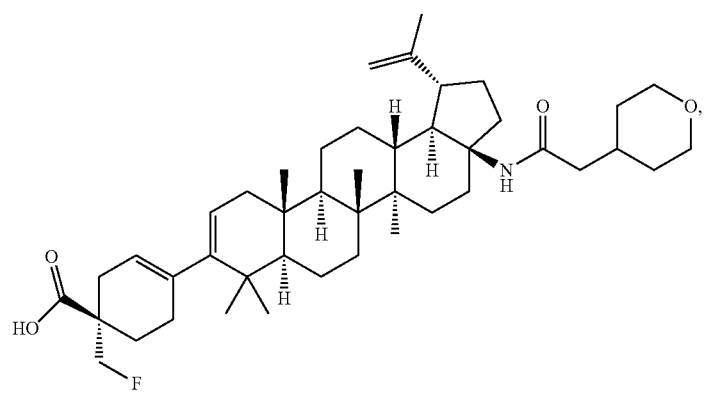
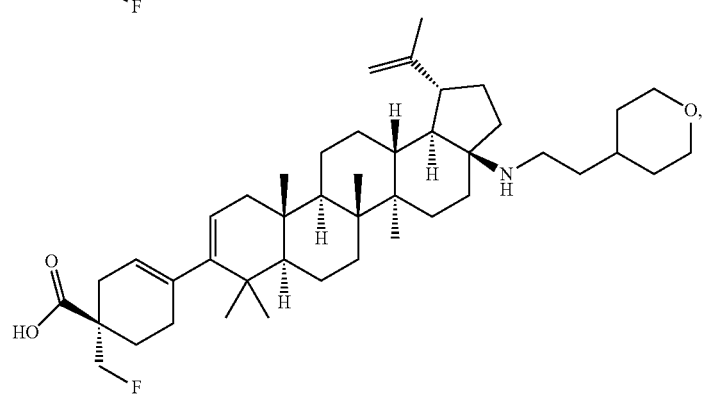

-continued
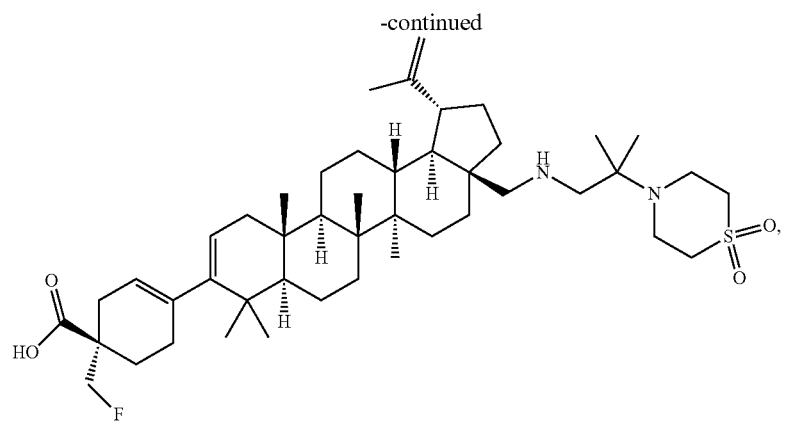
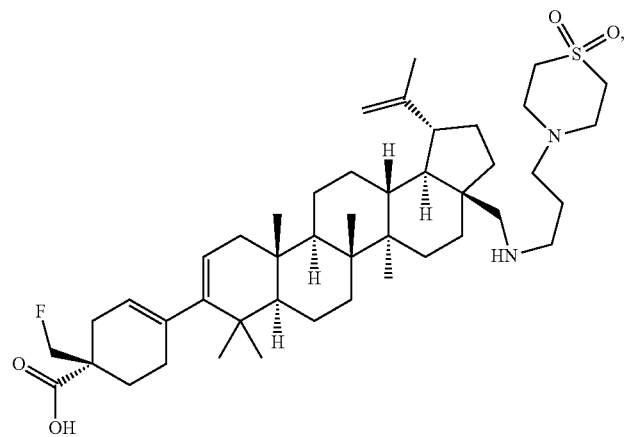
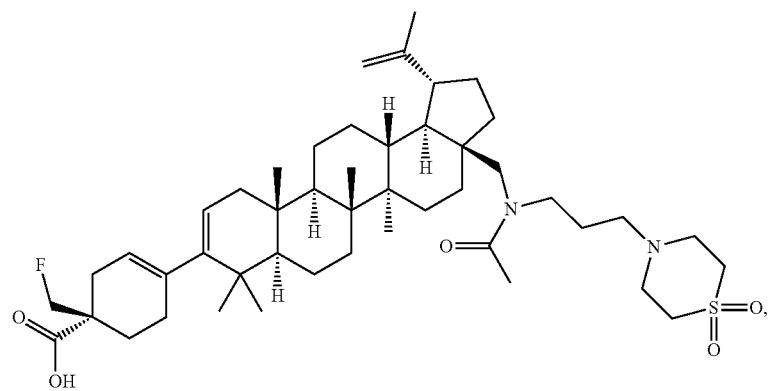
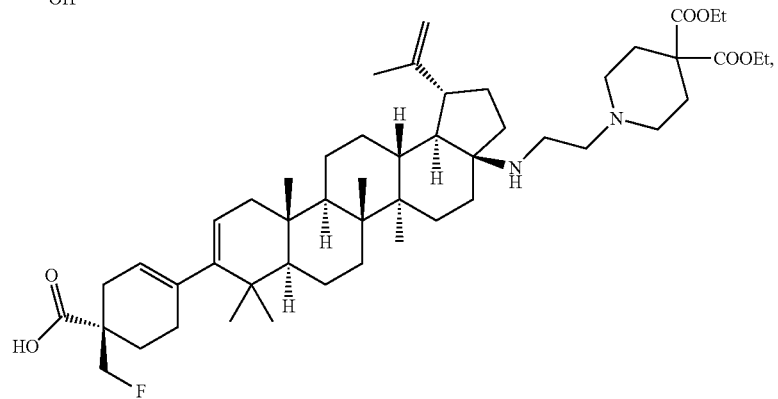

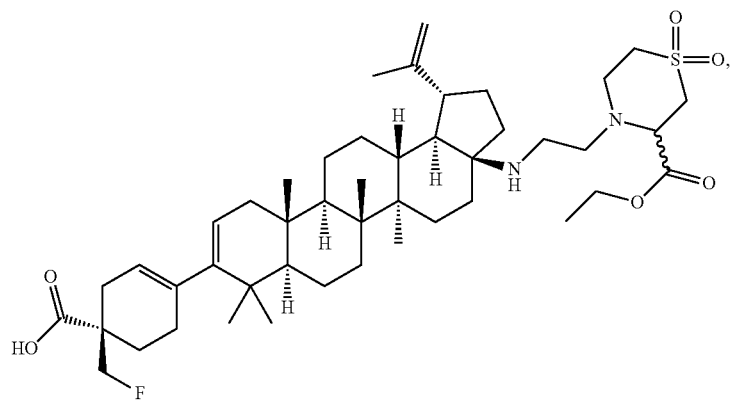
Isomer 1
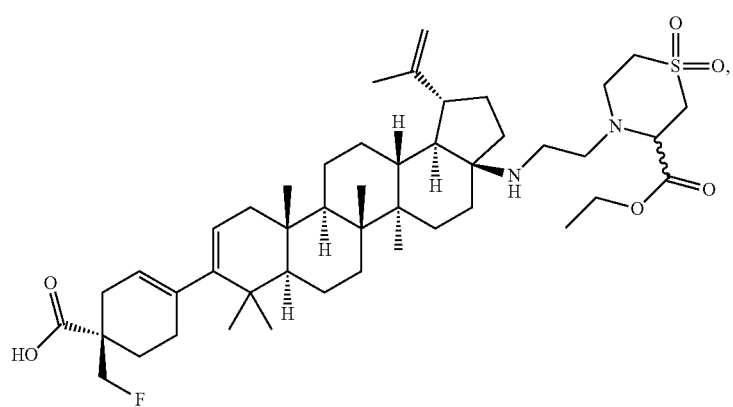
Isomer 2
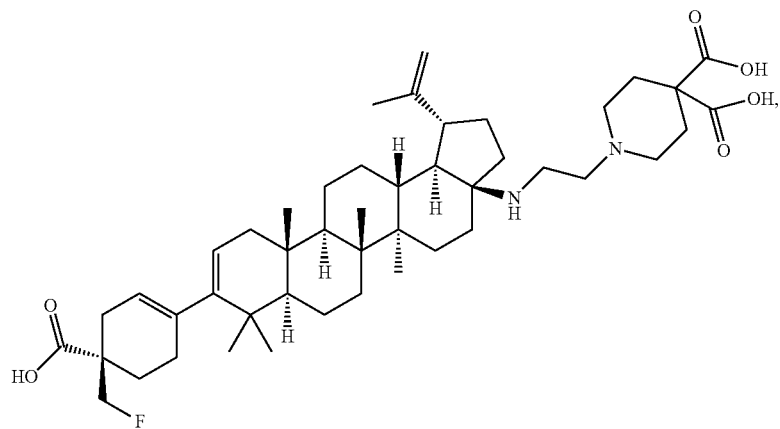

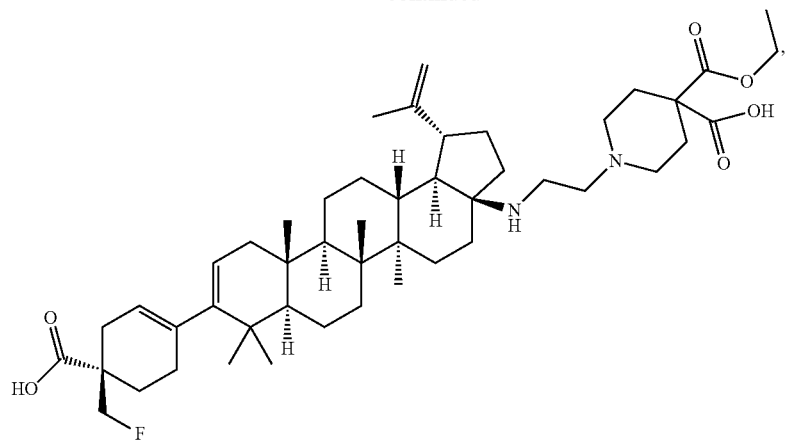
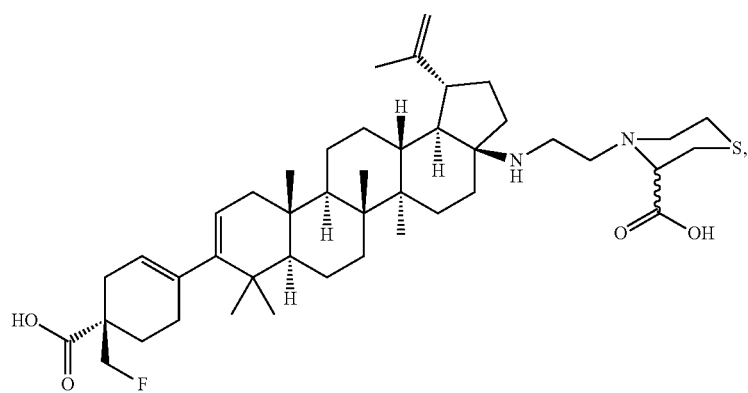
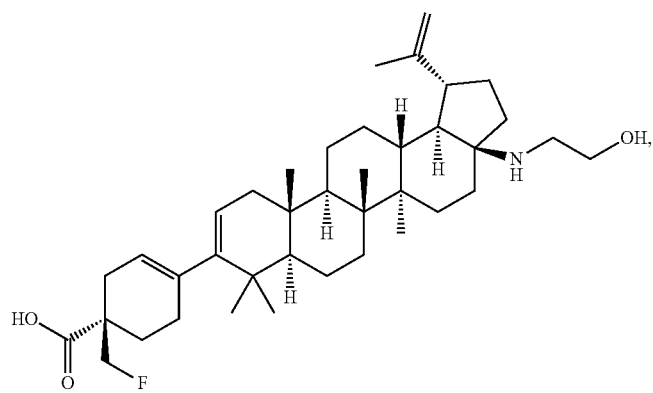
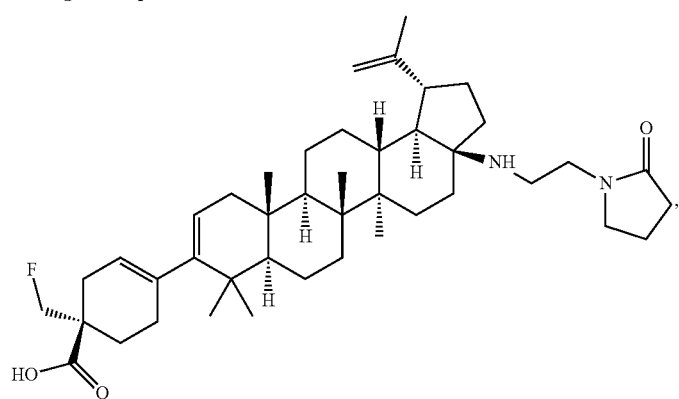

-continued
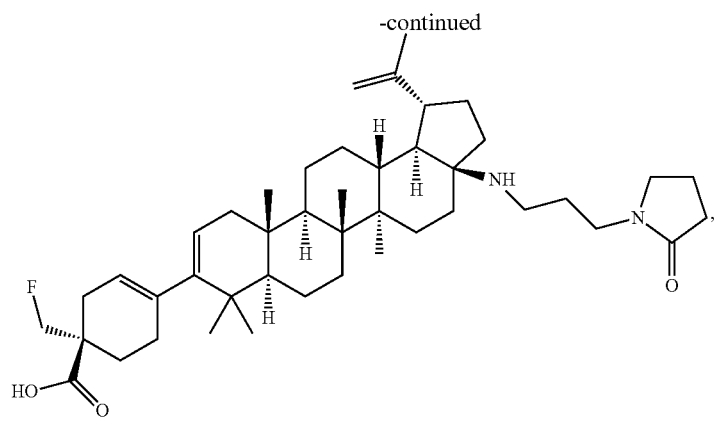
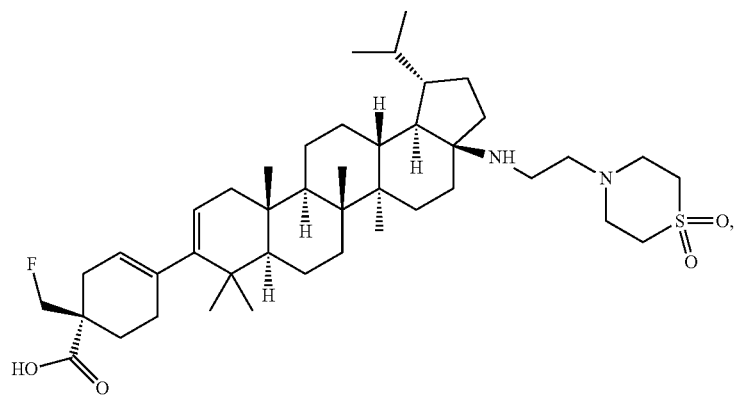
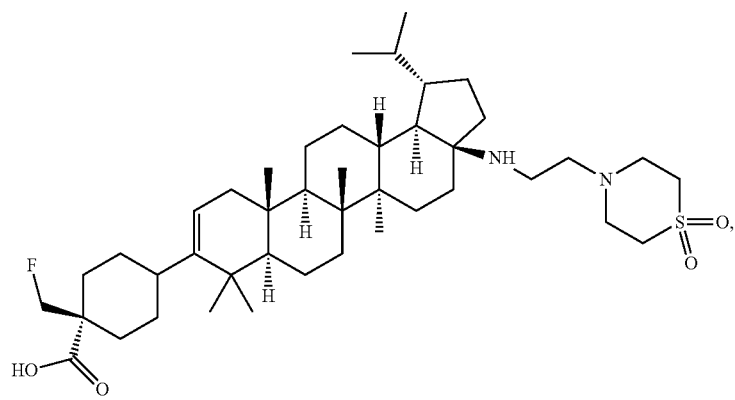
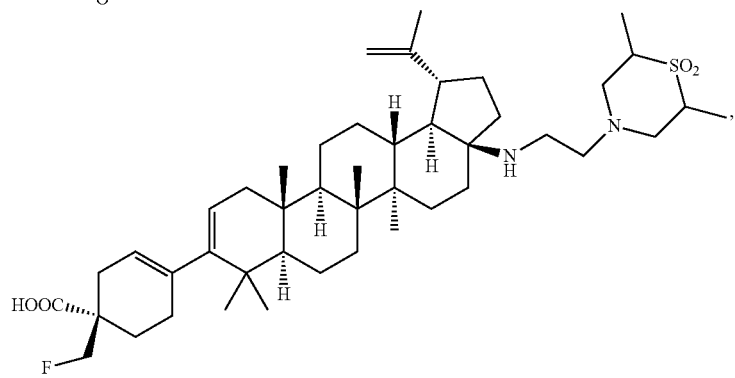

-continued
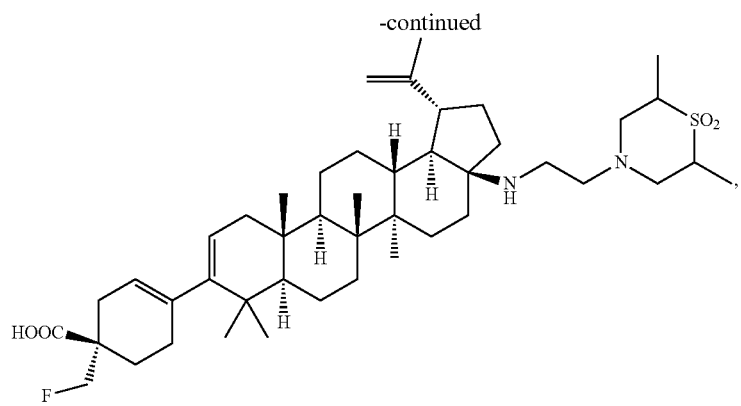
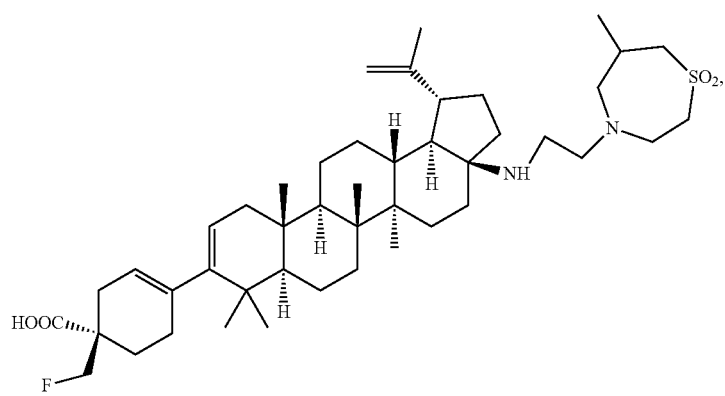
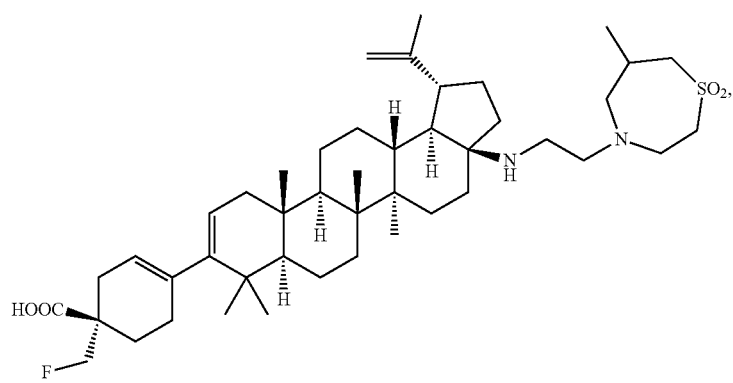
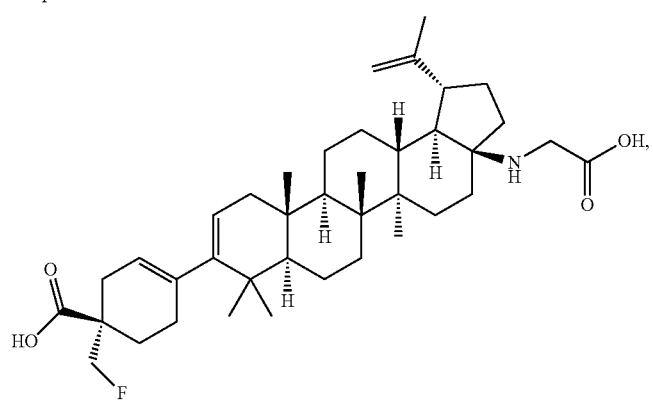

-continued
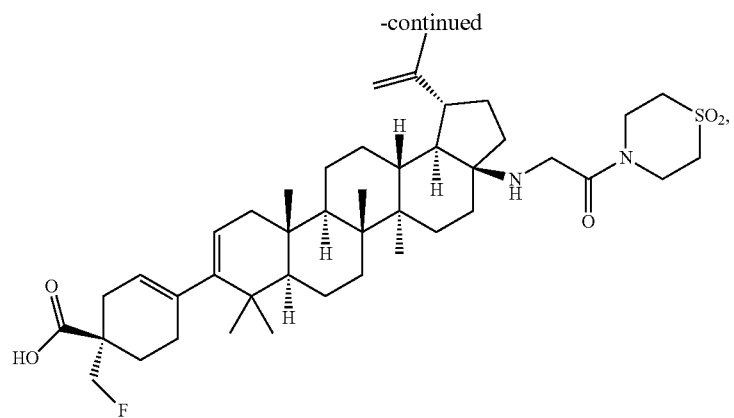
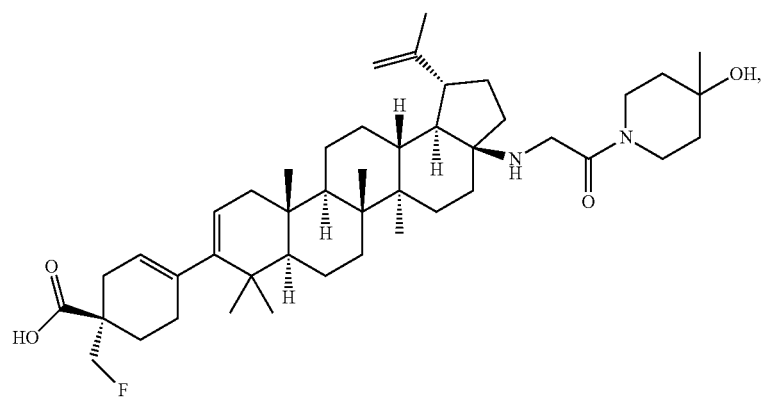
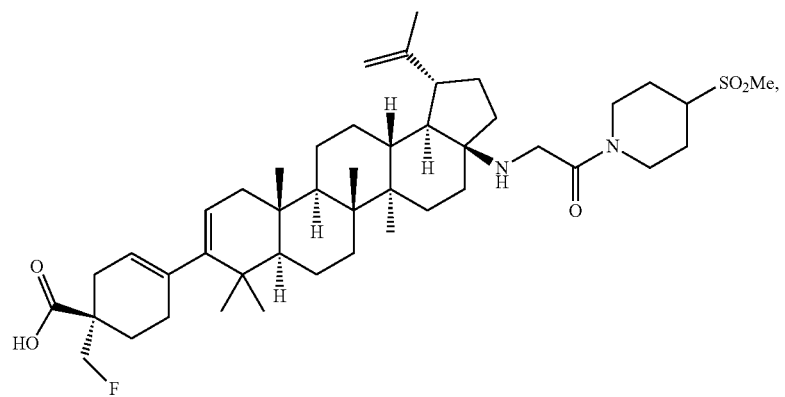
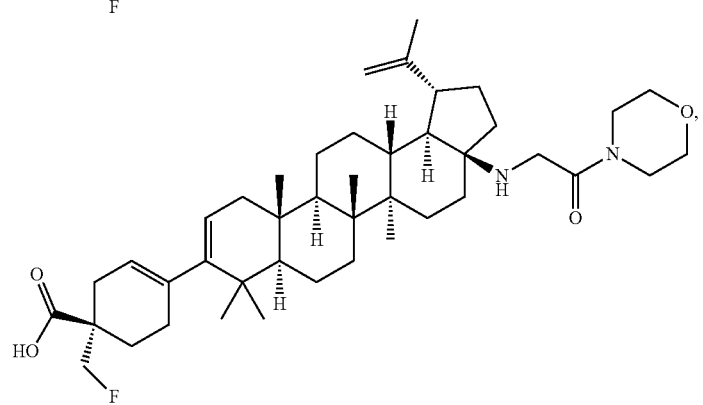

-continued
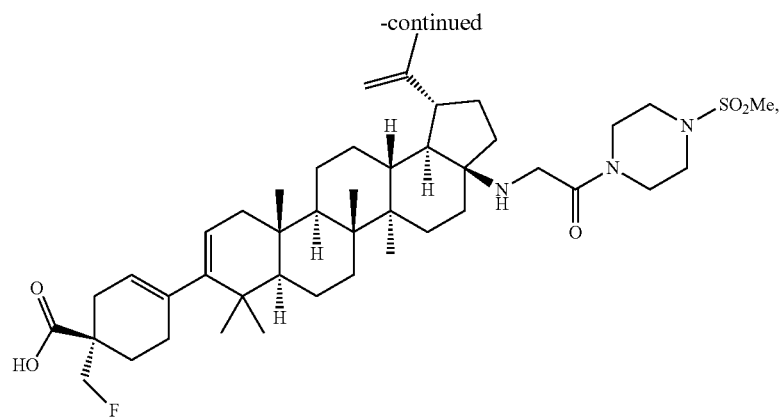
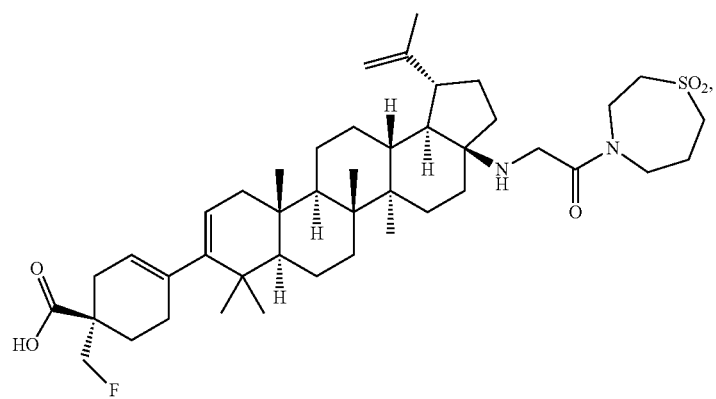
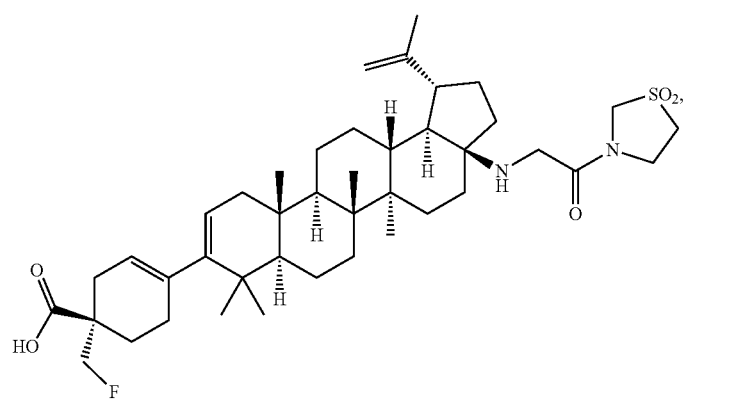
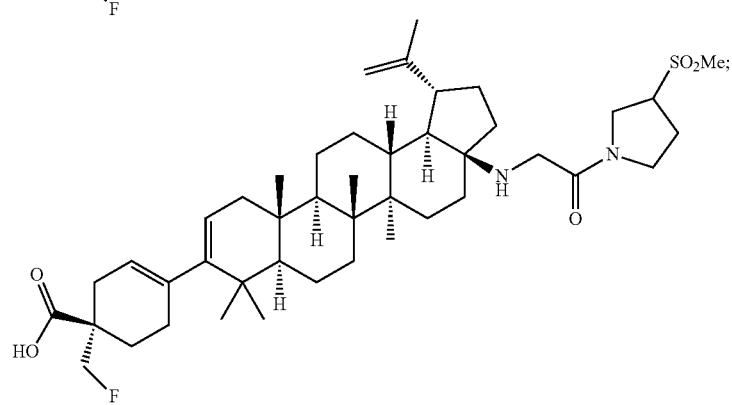

-continued
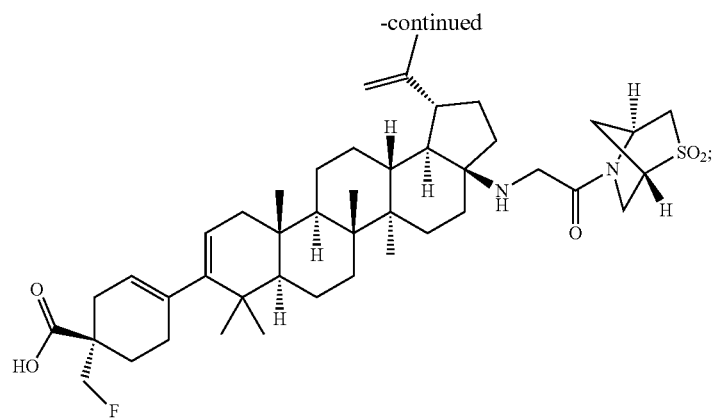
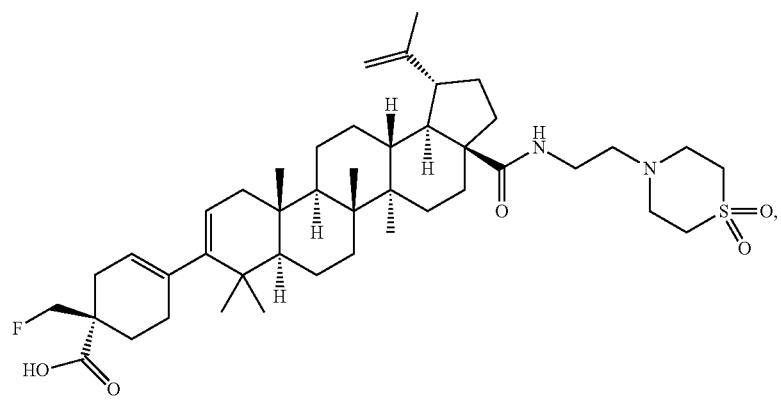
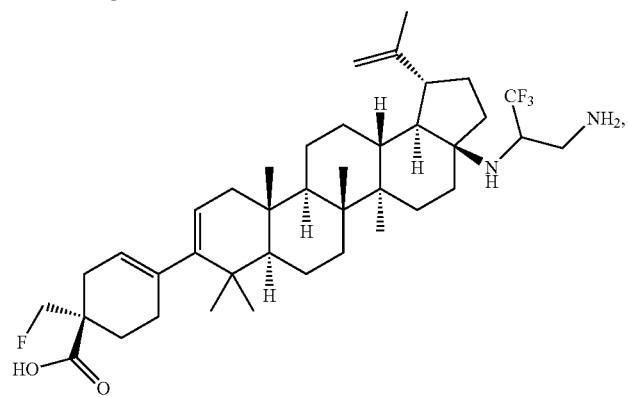
Isomer A
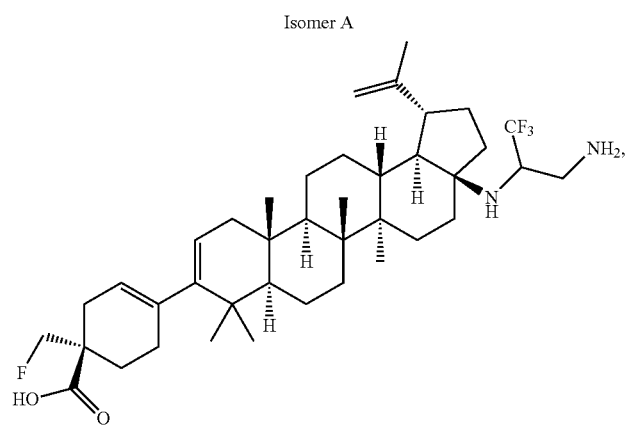
Isomer B

-continued
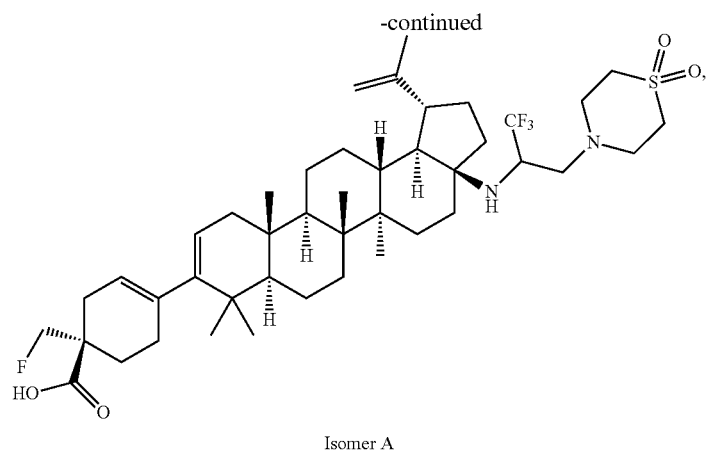
Isomer A
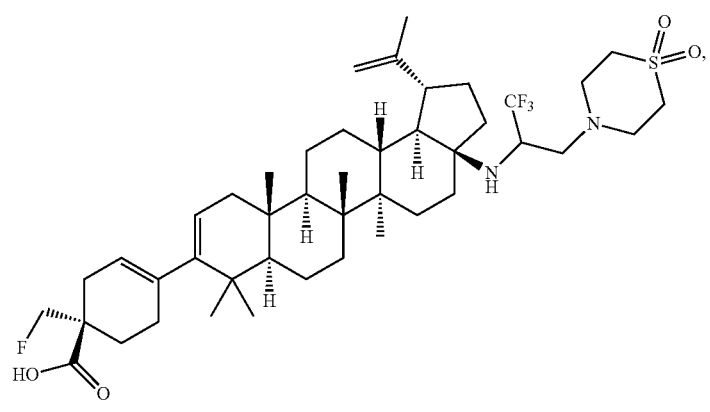
Isomer B
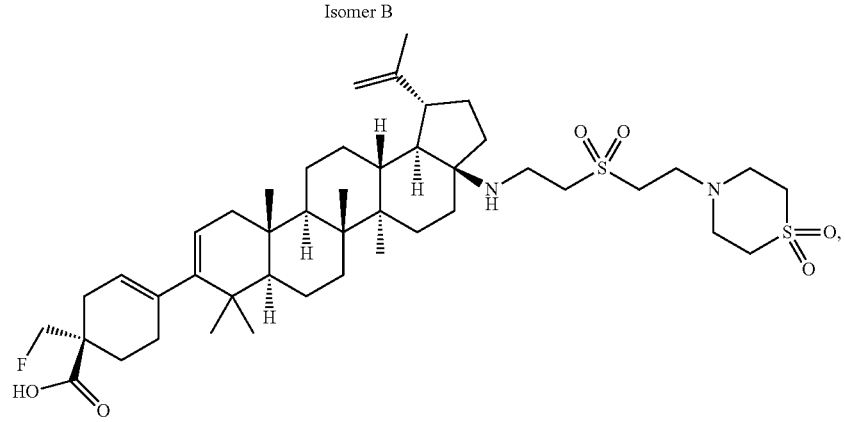
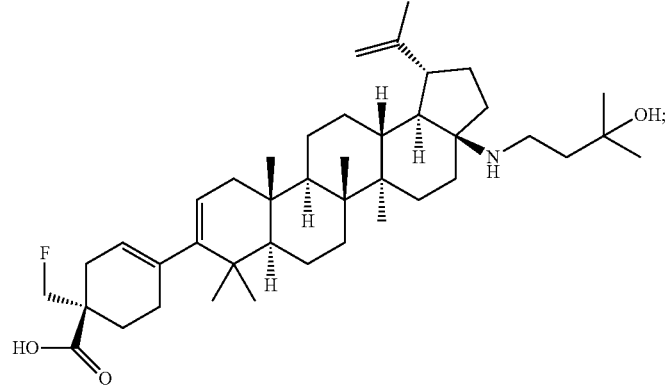

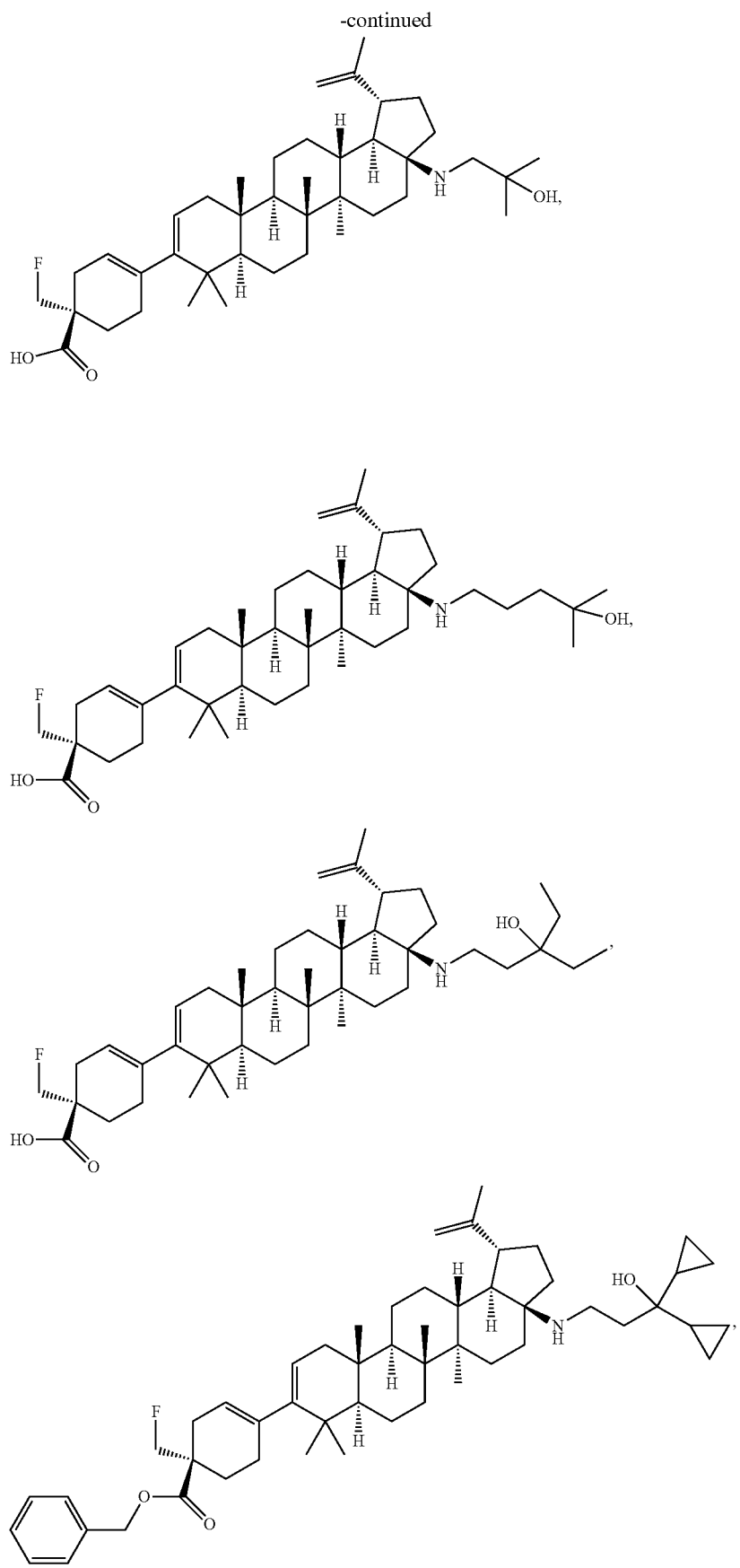

-continued
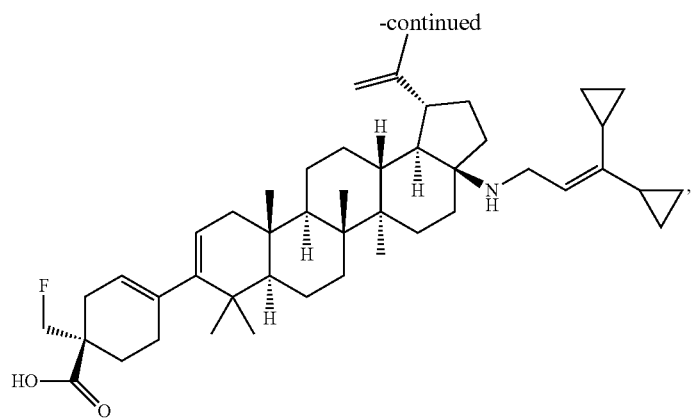
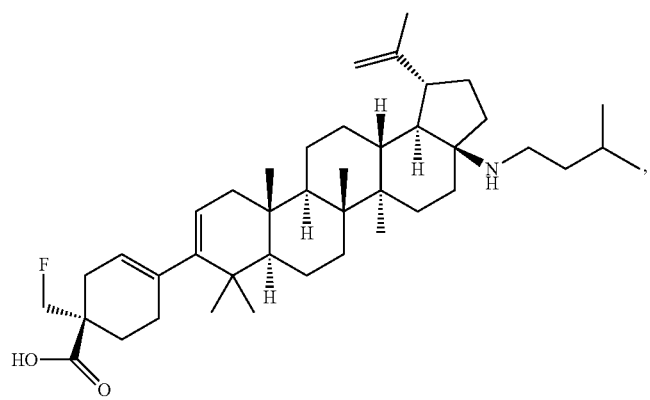
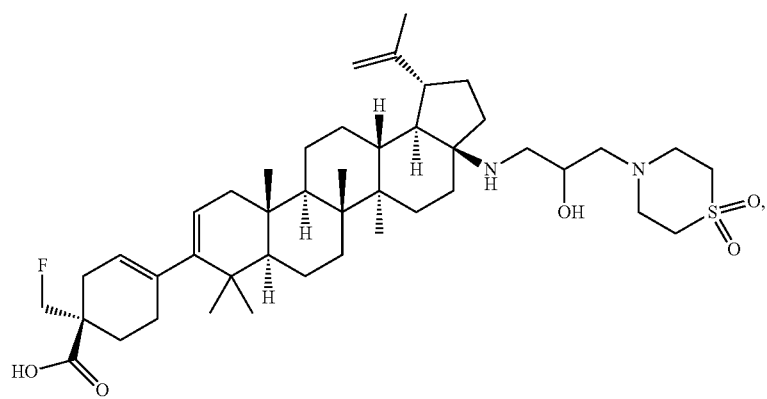
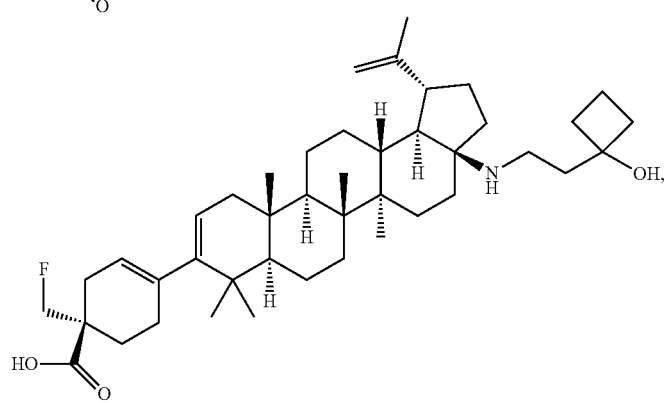

-continued
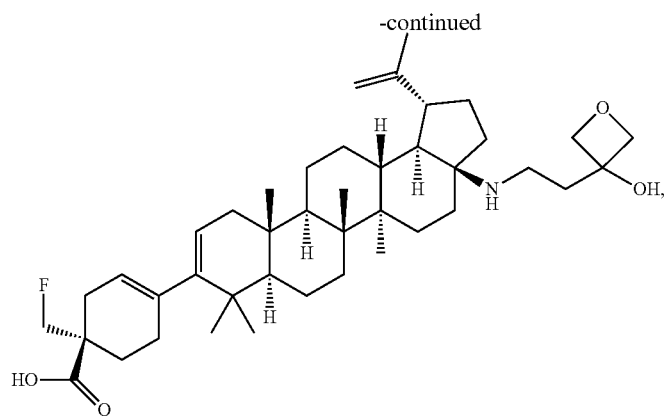
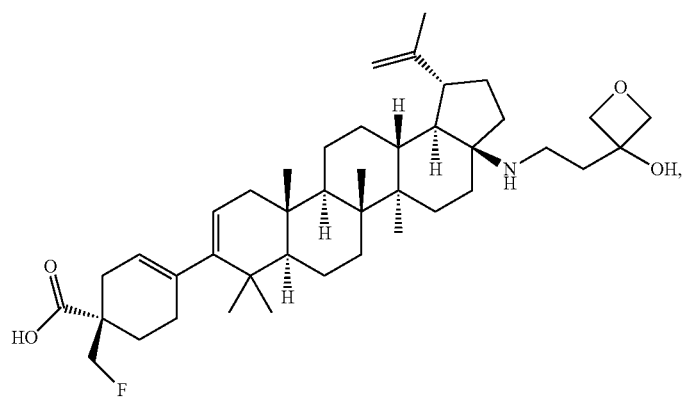
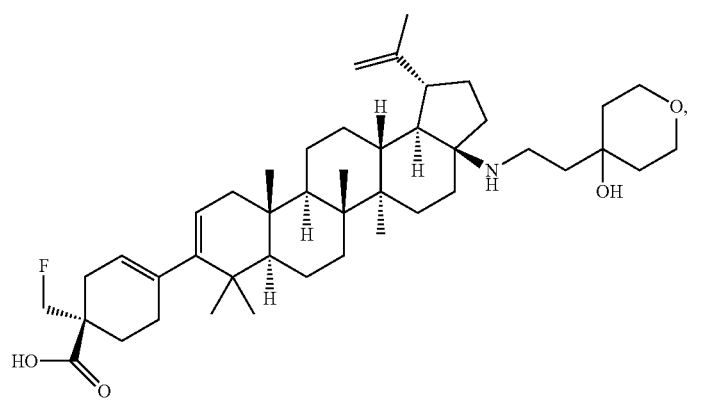
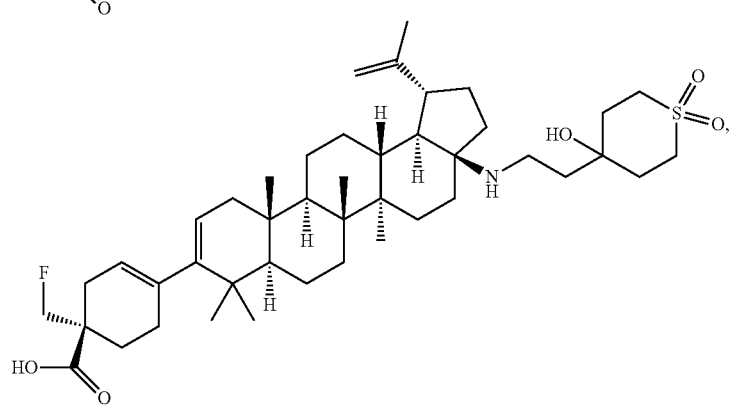

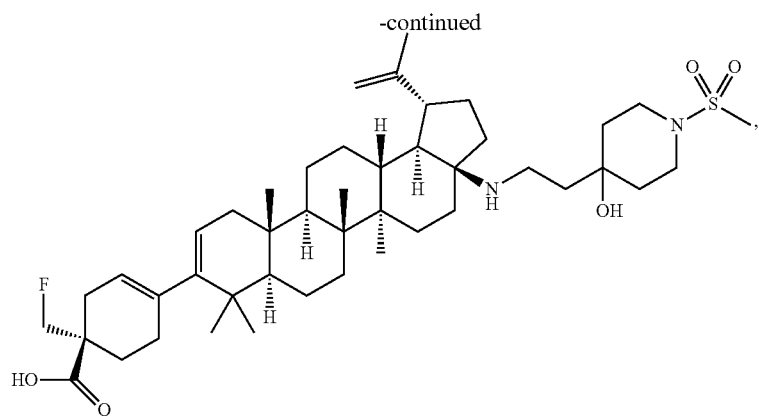
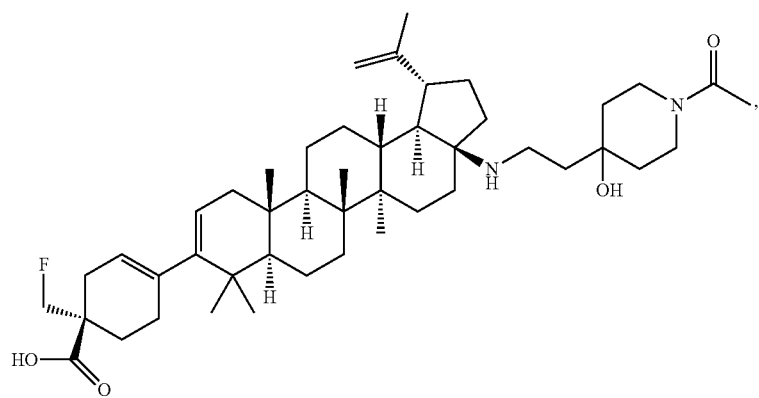
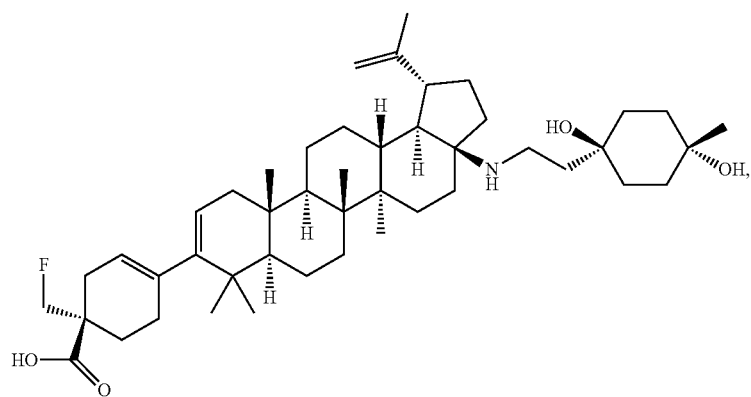
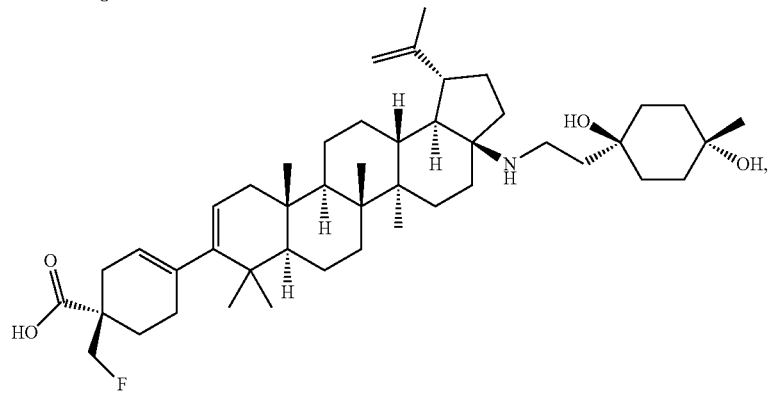

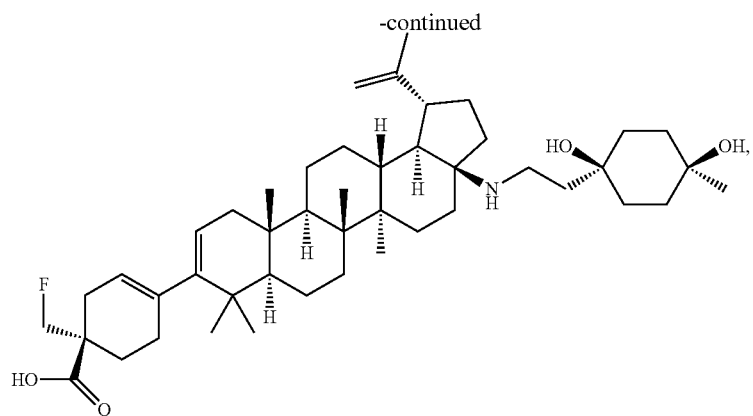
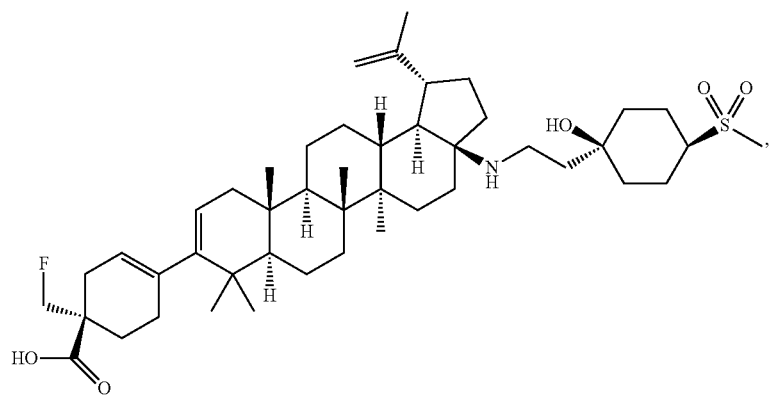
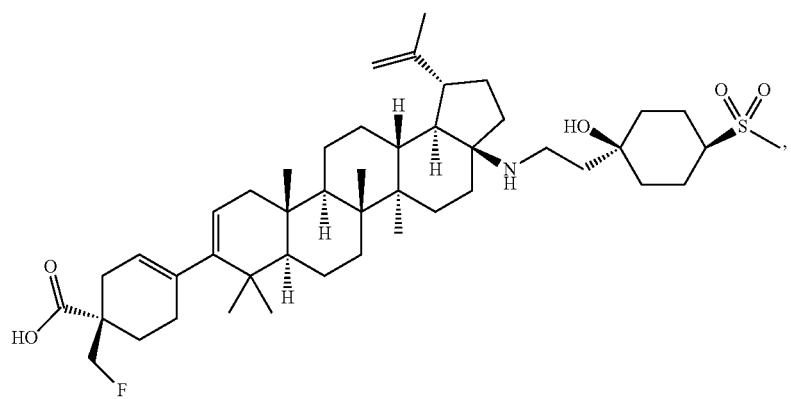
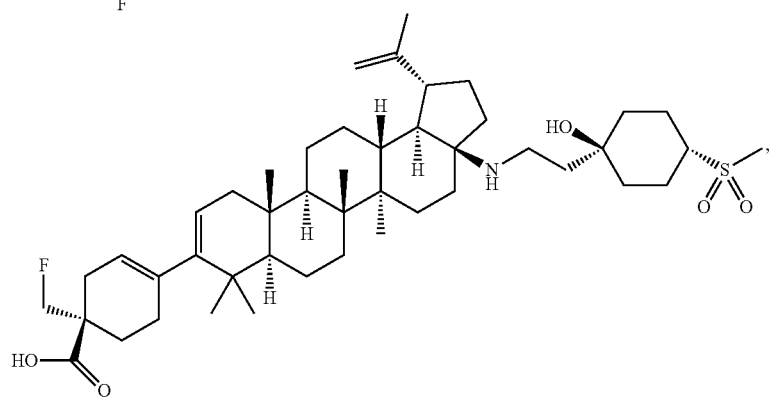

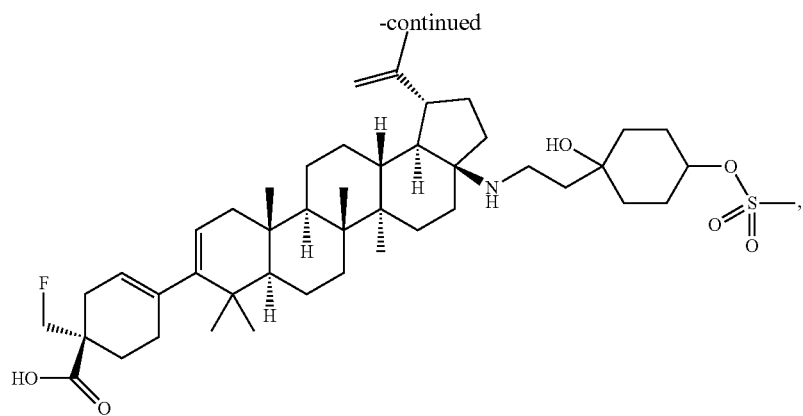
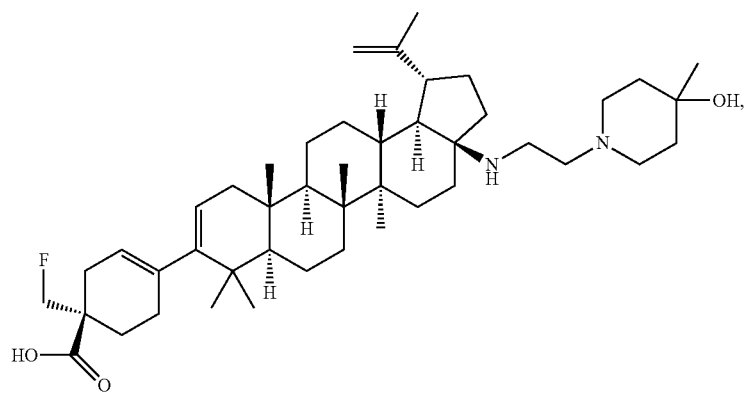
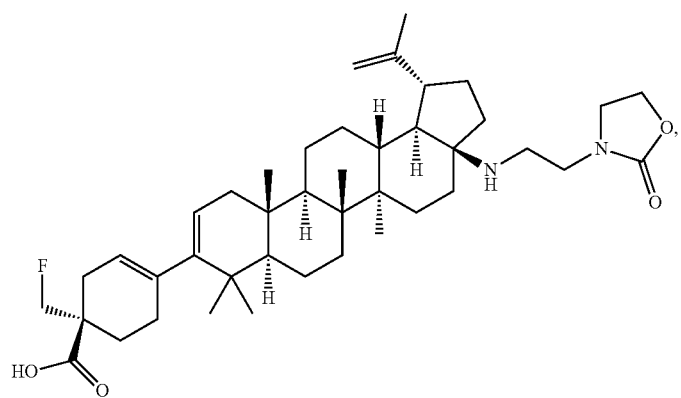
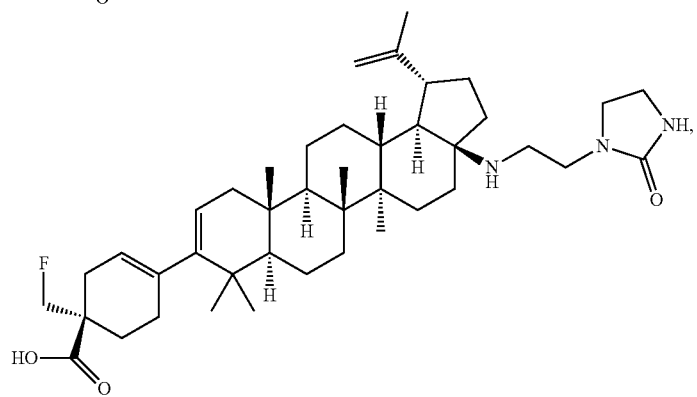

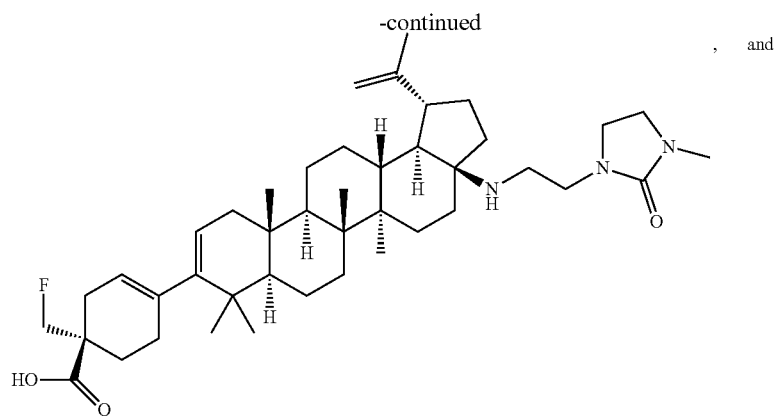

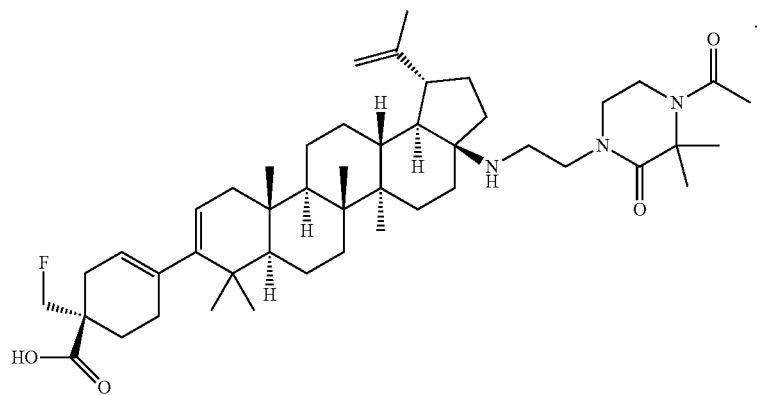

Preferred compounds, including pharmaceutically acceptable salts thereof, as part of the invention also include the following:

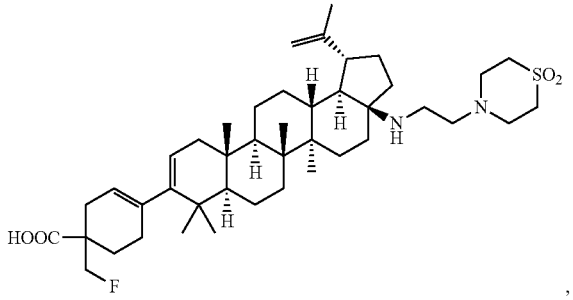

,

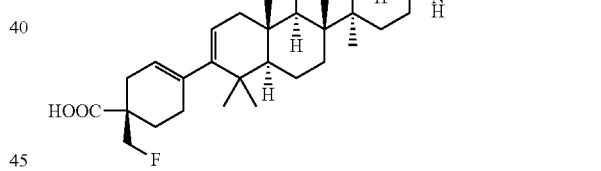

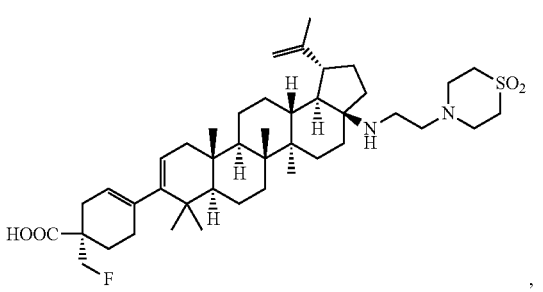

, and

The compounds above represent the mixture of diastereoisomers, and the two individual disastereomers. In certain embodiments, one of the specific diastereomers may be particularly preferred.

The compounds of the present invention, according to all the various embodiments described above, may be administered orally, parenterally (including subcutaneous injections, intravenous, intramuscular, intrasternal injection or infusion techniques), by inhalation spray, or rectally, and by other means, in dosage unit formulations containing non-toxic pharmaceutically acceptable carriers, excipients and diluents available to the skilled artisan. One or more adjuvants may also be included.

Thus, in accordance with the present invention, there is further provided a method of treatment, and a pharmaceutical composition, for treating viral infections such as HIV infection and AIDS. The treatment involves administering to a patient in need of such treatment a pharmaceutical composition which contains an antiviral effective amount of one or more of the compounds of Formula I, together with one or more pharmaceutically acceptable carriers, excipients or diluents. As used herein, the term "antiviral effective amount" means the total amount of each active component of the composition and method that is sufficient to show a meaningful patient benefit, i.e., inhibiting, ameliorating, or healing of acute conditions characterized by inhibition of HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing, inhibiting, ameliorating and/or healing diseases and conditions associated with HIV infection.

The pharmaceutical compositions of the invention may be in the form of orally administrable suspensions or tablets; as well as nasal sprays, sterile injectable preparations, for example, as sterile injectable aqueous or oleaginous suspensions or suppositories. Pharmaceutically acceptable carriers, excipients or diluents may be utilized in the pharmaceutical compositions, and are those utilized in the art of pharmaceutical preparations.

When administered orally as a suspension, these compositions are prepared according to techniques typically known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds herein set forth can be administered orally to humans in a dosage range of about 1 to 100 mg/kg body weight in divided doses, usually over an extended period, such as days, weeks, months, or even years. One preferred dosage range is about 1 to 10 mg/kg body weight orally in divided doses. Another preferred dosage range is about 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also contemplated herein are combinations of the compounds of Formula I herein set forth, together with one or more other agents useful in the treatment of AIDS. For example, the compounds of this disclosure may be effectively administered, whether at periods of pre-exposure and/or post-exposure, in combination with effective amounts of the AIDS antivirals, immunomodulators, antiinfectives, or vaccines, such as those in the following non-limiting table:

| Drug Name | Manufacturer | Indication |
| --- | --- | --- |
| ANTIVIRALS | | |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection ARC, PGL |
| AL-721 | Ethigen (Los Angeles, CA) | HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-234475 (CGP-61755) | Bristol-Myers Squibb/ Novartis | HIV infection, AIDS, ARC (protease inhibitor) |
| CI-1012 | Warner-Lambert | HIV-1 infection |

-continued

| Drug Name | Manufacturer | Indication |
|---|---|---|
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Darunavir | Tibotec- J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, SUSTIVA ®) (−)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomati HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |

-continued

| Drug Name | Manufacturer | Indication |
|---|---|---|
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD ®) | Gilead | HIV infection, AIDS, (reverse transcriptase inhibitor) |
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection AIDs, protease inhibitor |
| FUZEON ® (Enfuvirtide or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| Selzentry Maraviroc; (UK 427857) | Pfizer | HIV infection AIDs, (CCR5 antagonist, in development) |
| Trizivir ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV Infection AIDs in development |
| Triple drug combination ATRIPLA ® | Gilead/Bristol-Myers Squibb | Combination of Tenofovir disoproxil fumarate salt (VIREAD ®), EMTRIVA ® (Emtricitabine), and SUSTIVA ® (Efavirenz) |
| FESTINAVIR ® 4'-ethynyl-d4T | Oncolys BioPharma BMS | HIV infection AIDs in development |
| CMX-157 Lipid conjugate of nucleotide tenofovir | Chimerix | HIV infection AIDs |
| GSK1349572 Integrase inhibitor dolutegravir | GSK | HIV infection AIDs |
| S/GSK1265744 Integrase inhibitor | GSK | HIV infection AIDs |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |

| Drug Name | Manufacturer | Indication |
| --- | --- | --- |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |

| Drug Name | Manufacturer | Indication |
|---|---|---|
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the disclosure herein set forth may be used in combination with HIV entry inhibitors. Examples of such HIV entry inhibitors are discussed in DRUGS OF THE FUTURE 1999, 24 (12), pp. 1355-1362; CELL, Vol. 9, pp. 243-246, Oct. 29, 1999; and DRUG DISCOVERY TODAY, Vol. 5, No. 5, May 2000, pp. 183-194 and *Inhibitors of the entry of HIV into host cells*. Meanwell, Nicholas A.; Kadow, John F., Current Opinion in Drug Discovery & Development (2003), 6 (4), 451-461. Specifically the compounds can be utilized in combination with attachment inhibitors, fusion inhibitors, and chemokine receptor antagonists aimed at either the CCR5 or CXCR4 coreceptor. HIV attachment inhibitors are also set forth in U.S. Pat. Nos. 7,354,924 and 7,745,625.

It will be understood that the scope of combinations of the compounds of this application with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present disclosure and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is REYATAZ® (active ingredient Atazanavir). Typically a dose of 300 to 600 mg is administered once a day. This may be co-administered with a low dose of Ritonavir (50 to 500 mgs). Another preferred inhibitor of HIV protease is KALETRA®. Another useful inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)—N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) tenofovir disoproxil fumarate salt and emtricitabine.

In such combinations the compound of the present invention and other active agents may be administered separately or in conjunction. In addition, the administration of one element may be prior to, concurrent to, or subsequent to the administration of other agent(s).

General Chemistry (Methods of Synthesis)

The present invention comprises compounds of Formula I, their pharmaceutical formulations, and their use in patients suffering from or susceptible to HIV infection. The compounds of Formula I also include pharmaceutically acceptable salts thereof. General procedures to construct compounds of Formula I and intermediates useful for their synthesis are described in the following Schemes (after the Abbreviations).

Abbreviations

One or more of the following abbreviations, most of which are conventional abbreviations well known to those skilled in the art, may be used throughout the description of the disclosure and the examples:

RT=room temperature
BHT=2,6-di-tert-butyl-4-hydroxytoluene
CSA=camphorsulfonic acid
LDA=lithium diisopropylamide
KHMDS=potassium bis(trimethylsilyl)amide
SFC=supercritical fluid chromatography
Quant=quantitative
TBDMS32 tert-butyldimethylsilane
PTFE=polytetrafluoroethylene
NMO=4-methylmorpholine-N-oxide
THF=tetrahydrofuran
TLC=thin layer chromatography
DCM=dichloromethane
DCE=dichloroethane
TFA=trifluoroacetic acid
LCMS=liquid chromatography mass spectroscopy
Prep=preparative
HPLC=high performance liquid chromatography
DAST=(diethylamino)sulfur trifluoride
TEA=triethylamine
DIPEA=N,N-diisopropylethylamine
HATU=[O-(7-azabenzotriazol-1-yl)-1,1,3,3-tetramethyluronium hexafluorophosphate]
DCC=N,N'-dicyclohexylcarbodiimide
DMAP=dimethylaminopyridine
TMS=trimethylsilyl
NMR=nuclear magnetic resonance
DPPA=diphenyl phosphoryl azide
AIBN=azobisisobutyronitrile TBAF=tetrabutylammonium fluoride
DMF=dimethylformamide
TBTU=O-(benzotriazol-1-yl)-N,N,N',N'-tetramethyluronium tetrafluoroborate
Min(s)=minute(s)
h=hour(s)
sat.=saturated
TEA=triethylamine
EtOAc=ethyl acetate
TFA=trifluoroacetic acid
PCC=pyridinium chlorochromate
TLC=thin layer chromatography
Tf$_2$NPh=(trifluoromethylsulfonyl)methanesulfonamide
dioxane=1,4-dioxane
PG=protective group
atm=atmosphere(s)
mol=mole(s)
mmol=milimole(s)
mg=milligram(s)
μg=microgram(s)
μl=microliter(s)
μm=micrometer(s)
mm=millimeter(s)

The terms "C-3" and "C-28" refer to certain positions of a triterpene core as numbered in accordance with IUPAC rules (positions depicted below with respect to an illustrative triterpene: betulin):

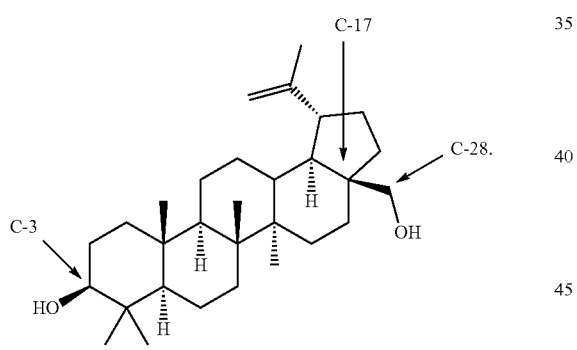

The same numbering is maintained when referring to the compound series in schemes and general descriptions of methods.

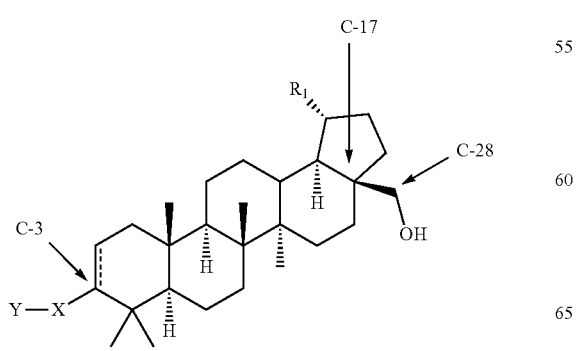

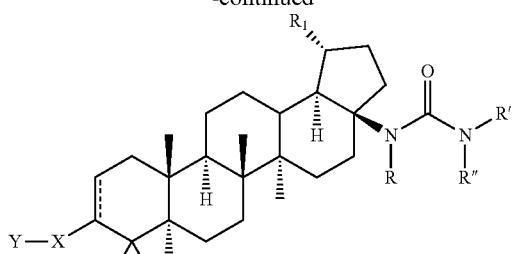

C-17 ureas

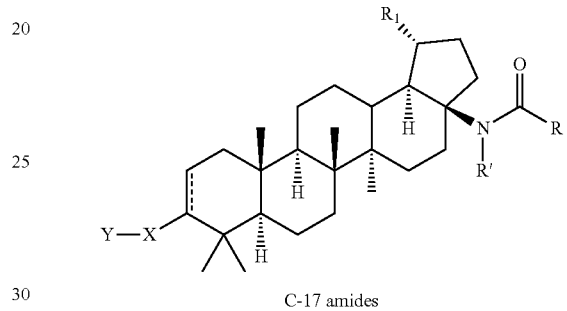

C-17 amides

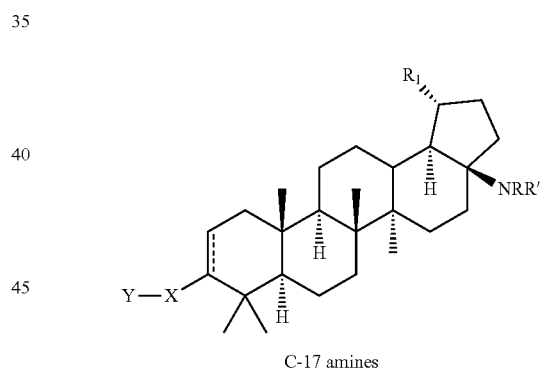

C-17 amines

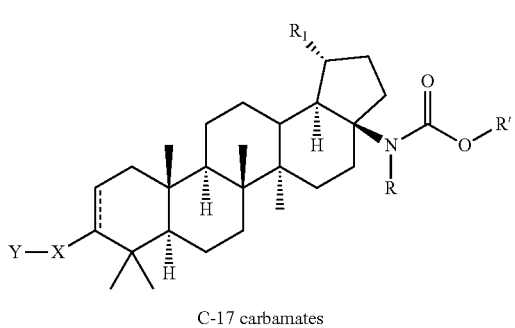

C-17 carbamates

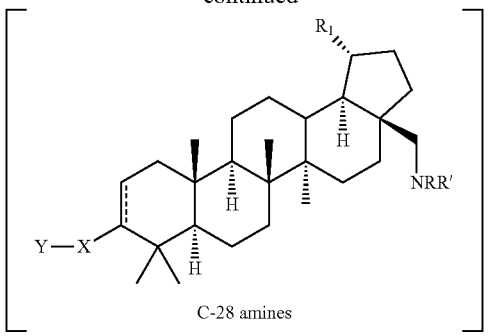
C-28 amines
Preparation of Compounds of Formula I General Chemistry Schemes:
Compounds of Formula I can be prepared from commercially available (Aldrich, others) betulinic acid by chemistry described in the following schemes.
General reaction schemes are set forth as follows:
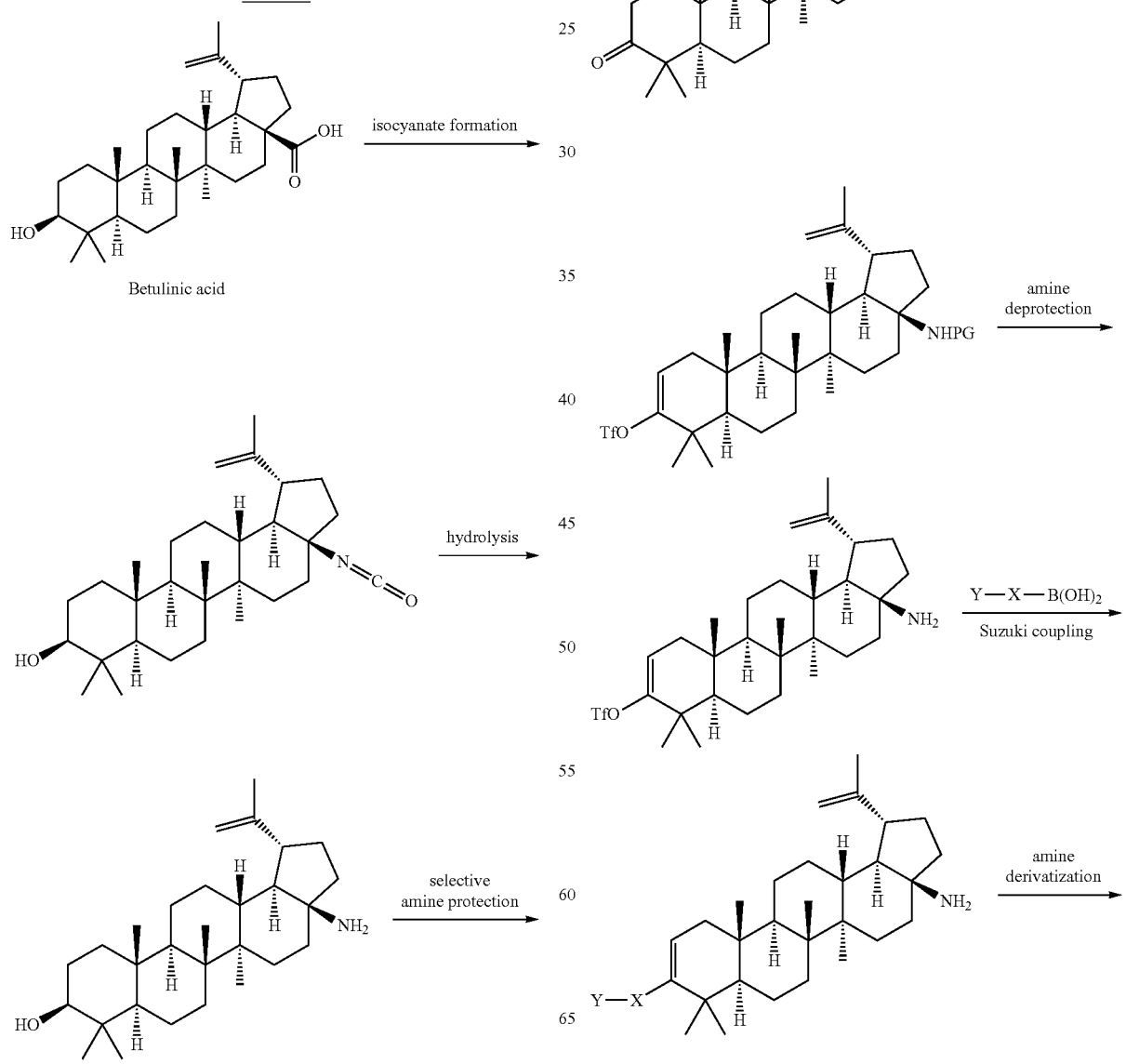
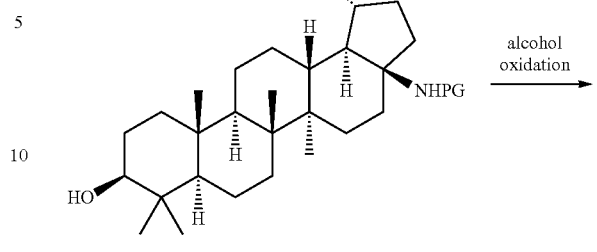

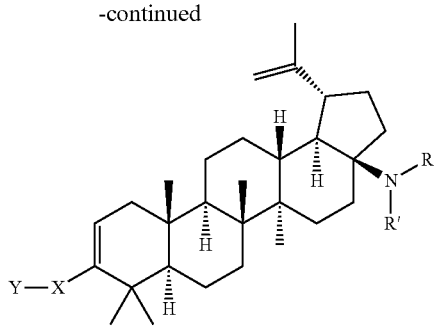

Compounds of Formula I can be prepared from betulinic acid as described in Scheme 1. Curtis rearrangement of betulinic acid can be accomplished without protection of the C-3 hydroxyl group to render the C-17 isocyanate which upon acid hydrolysis affords the C-17 amine. The C-17 amine is then selectively protected with an amine protective group (i.e F-moc, Boc) to then perform the oxidation of the C-3 hydroxy group to a ketone under standard conditions (i.e. PCC, Dess-Martin reagent, etc). Conversion of the ketone into its triflate can be accomplished by methods known to those skilled in the art. The protective group in the amino group is then taken off to produce the C-17 unsubstituted amine Installation of the C-3 moiety is accomplished via Suzuki coupling of the triflate with the corresponding boronic acid as described above. Alternatively, the triflate coupling with the corresponding boronic acid can be performed before the deprotection of the C-17 amine Once deprotected, the C-17 amino group can then be further derivatized by methods know to those skilled in the art such as alkylation, reductive amination, acylation, etc. Several of these methods are described in the Schemes below (Scheme 2-7). In some cases, an additional step is needed to unmask any functional group that may be functionalized with a protective group (i.e. when Y is COOH, is always masked as the corresponding ester COOR until this last step).

The C-17 primary amine can be further modified using standard methods, known to those skill in the art. Some examples are shown in the following schemes.

Scheme 2

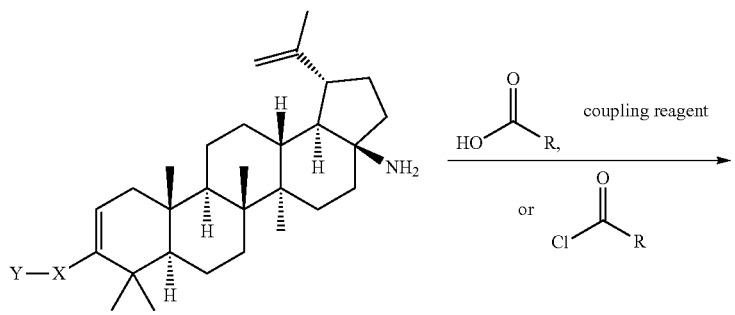

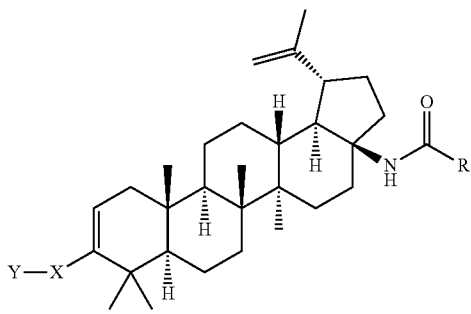

C-17 amides can be prepared by reacting a carboxylic acid with the C-17 primary amine in the presence of an adequate coupling reagent such as HATU, DCC, and others known to those skilled in the art, in the presence of a base such as Hunig's base, TEA, etc., in the appropriate solvent (DCM, THF, DMF, etc.). Hydrolysis of the carboxylic ester affords the benzoic acid. Alternatively, some amides can be prepared by treating the C-17 primary amine with the corresponding carboxylic acid chloride reagent instead of an acid. Similarly, sulfonamines and sulfonamides can be prepared from the C-17 primary amine by using a sulfonyl chloride as the sulfonylating agent.

Scheme 3

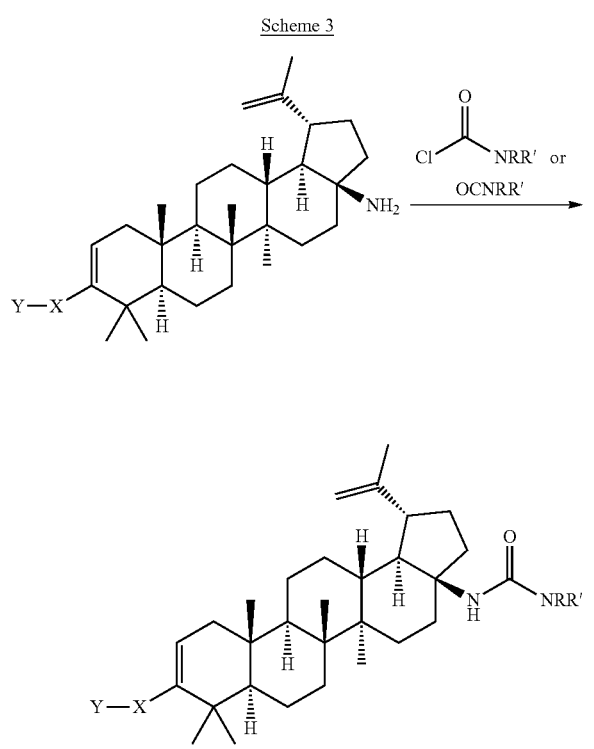

C-17 ureas can be prepared by reacting the corresponding carbamoyl chloride or isocyanate in the presence of a base such as Hunig's base, TEA, etc., in the appropriate solvent (DCM, THF, DMF, etc.). C-17 carbamates can be prepared in a similar manner using a chloroformate instead of the carbamoyl chloride.

Scheme 4

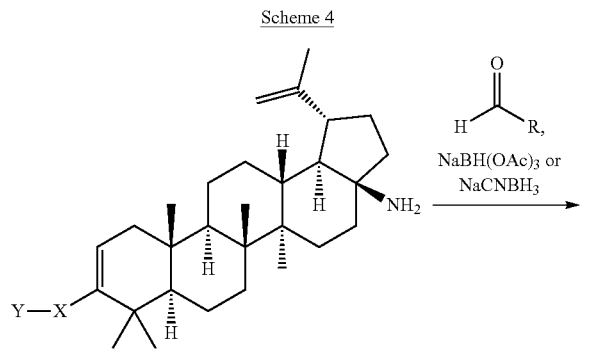

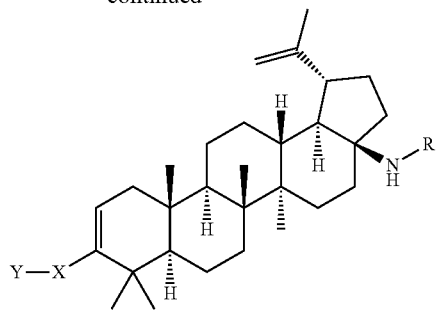

The C-17 primary amine can be treated with an aldehyde under reductive amination conditions (e.g. NaBH(OAc)$_3$ in the presence of AcOH/NaOAc or Ti(OPr)$_4$ in a solvent such as THF, 1,4-dioxane, DCE or DCM) to afford C-17 secondary amines Scheme 5

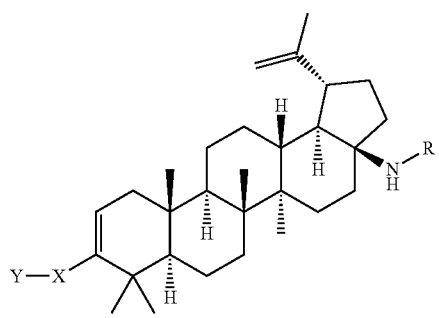

Some C-17 amines can be prepared by alkylation of the C-17 primary amine with an alkylating agent (R-LG), where LG is a leaving group such as, but not limited to Br, Cl, I, mesylate, tosylate or triflate in the presence of a base. Heating may be needed in some cases. Hydrolysis of the carboxylic ester renders the benzoic acid product.

Scheme 6

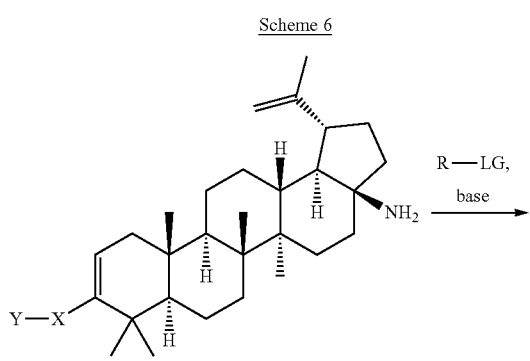

In some cases, by prolonging the reaction times and heating the reaction mixture, the dialkylated product can also be formed.

Scheme 7

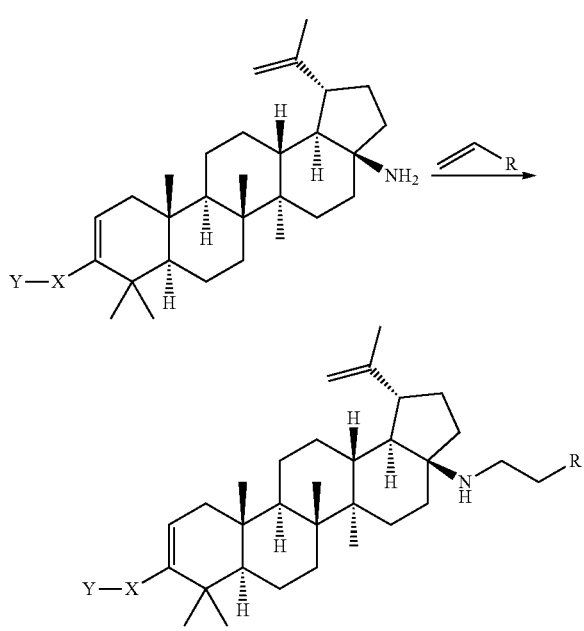

Alternatively, some C-17 amines can be prepared by 1,4-addition to Michael acceptors.

Substituents R, R' and R" may contain functional groups (i.e. COOH, COOR, OH, NHR) that can be further modified by methods know to those skilled in the art. The modification can be carried out before or after the final deprotection of the carboxylic acid is performed depending on the nature of the functional group.

Alternatively, the C-17 secondary amine can be further modified (i.e. alkylated, acylated, sulfonylated, etc.) using some of the methods described above or other standard methods known to those skilled in the art.

EXAMPLES

The following examples illustrate typical syntheses of the compounds of Formula I as described generally above. These examples are illustrative only and are not intended to limit the disclosure in any way. The reagents and starting materials are readily available to one of ordinary skill in the art.

Chemistry

Typical Procedures and Characterization of Selected Examples:

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). $^1$H NMR spectra were recorded on Bruker DRX-500f at 500 MHz (or Bruker AV 400 MHz, Bruker DPX-300B or Varian Gemini 300 at 300 MHz as stated). The chemical shifts were reported in ppm on the δ scale relative to δTMS=0. The following internal references were used for the residual protons in the following solvents: CDCl$_3$ ($\delta_H$ 7.26), CD$_3$OD ($\delta_H$ 3.30), acetic-d4 (Acetic Acid d$_4$) ($\delta_H$ 11.6, 2.07), DMSO mix or DMSO-D6-CDCl$_3$ ($\delta_H$ 2.50 and 8.25) (ratio 75%:25%), and DMSO-D6 ($\delta_H$ 2.50). Standard acronyms were employed to describe the multiplicity patterns: s (singlet), br. s (broad singlet), d (doublet), t (triplet), q (quartet), m (multiplet), b (broad), app (apparent). The coupling constant (J) is in Hertz. All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

Section 1

LC/MS Methods

Method 1
Start % B=0, Final % B=100 over 2 minute gradient, hold at 100% B
Flow Rate=1 mL/min
Wavelength=220 nm
Solvent A=90% water, 10% methanol, 0.1% TFA
Solvent B=10% water, 90% methanol, 0.1% TFA
Column=Phenomenex Luna C18, 3 μm, 2.0×30 mm Method 2
Start % B=0, Final % B=100 over 4 minute gradient, hold at 100% B
Flow Rate=0.8 mL/min
Wavelength=220 nm
Solvent A=90% water, 10% methanol, 0.1% TFA
Solvent B=10% water, 90% methanol, 0.1% TFA
Column=Phenomenex Luna C18, 3 μm, 2.0×50 mm Method 3
Start % B=0, Final % B=100 over 2 minute gradient, hold at 100% B
Flow Rate=1 mL/min
Wavelength=220 nm
Solvent A=90% water, 10% acetonitrile, 0.1% TFA
Solvent B=10% water, 90% acetonitrile, 0.1% TFA
Column=Phenomenex Luna C18, 3 μm, 2.0×30 mm Method 4
Start % B=20, Final % B=100 over 2 minute gradient, hold at 100% B

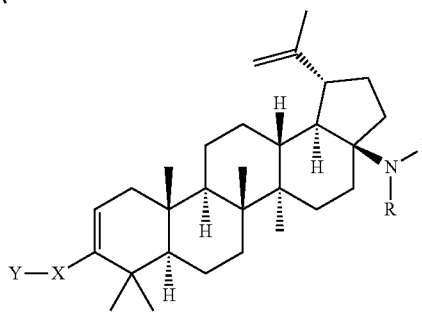

Flow Rate=0.8 mL/min
Wavelength=220 nm
Solvent A=90% water, 10% methanol, 0.1% TFA
Solvent B=10% water, 90% methanol, 0.1% TFA
Column=Waters Xbridge Phenyl, 2.5 μm, 2.1×50 mm
Method 5
Start % B=20, Final % B=100, gradient Time=1.5 min
Flow Rate=0.8 mL/min
Wavelength=220
Solvent A=10% MeOH–90% water–0.1% TFA
Solvent B=90% MeOH–10% water–0.1% TFA
Column=Waters Xbridge Phenyl 2.1×50 mm 2.5 μm
Method 6
Start % B=2, Final % B=98 over 1.5 minute gradient, hold at 98% B
Flow Rate=0.8 mL/min
Wavelength=220 nm
Solvent A=100% water, 0.05% TFA
Solvent B=100% acetonitrile, 0.05% TFA
Column=Waters Aquity UPLC BEH C18, 2.1×50 mm, 1.7 m
Method 7
Start % B=20, Final % B=100, gradient Time=3 min
Flow Rate=0.6 mL/min
Wavelength=220
Solvent A=10% MeOH–90% water–0.1% TFA
Solvent B=90% MeOH–10% water–0.1% TFA
Column=Waters Xbridge Phenyl 2.1×50 mm 2.5 μm
Method 8
Start % B=20, Final % B=100, gradient Time=2 min
Flow Rate=0.6 mL/min
Wavelength=220
Solvent A=10% MeOH–90% water–0.1% TFA
Solvent B=90% MeOH–10% water–0.1% TFA
Column=Waters Xbridge Phenyl 2.1×50 mm 2.5 μm
Method 9
Start % B=0, Final % B=100 over 2 minute gradient, hold at 100% B
Flow Rate=0.6 mL/min
Wavelength=220 nm
Solvent A=90% water, 10% methanol, 0.1% TFA
Solvent B=10% water, 90% methanol, 0.1% TFA
Column=Xbridge Phenyl, 2.5 m, 2.1×50 mm
Method 10
Start % B=30, Final % B=100 over 4 min gradient, hold at 100% B
Flow Rate=0.8 ml/min
Wavelength=220
Solvent Pair=Water-Methanol–0.1% TFA
Solvent A=90% Water–10% Methanol-0.1% TFA
Solvent B=10% Water–90% Methanol-0.1% TFA
Column 2=(2) PHENOMENEX-LUNA 2.0×50 mm 3 μm
Method 11
Start % B=40, Final % B=100 over 4 min gradient, hold at 100% B
Flow Rate=0.8 ml/min
Wavelength=220
Solvent Pair=Acetonitrile:Water: 10 mM Ammonium Acetate
Solvent A=5% Acetonitrile: 95% Water: 10 mM Ammonium Acetate
Solvent B=95% Acetonitrile:5% Water: 10 mM Ammonium Acetate
Column 2=2.) PHENOMENEX-LUNA 2.0×50 mm 3 μm
Method 12
Start % B=20, Final % B=100 over 4 min gradient, hold at 100% B
Flow Rate=0.8 ml/min
Wavelength=220
Solvent Pair=Acetonitrile:Water: 10 mM Ammonium Acetate
Solvent A=5% Acetonitrile: 95% Water: 10 mM Ammonium Acetate
Solvent B=95% Acetonitrile: 5% Water: 10 mM Ammonium Acetate
Column 2=2.) PHENOMENEX-LUNA 2.0×50 mm 3 μm
SFC Methods:
Method 1
Instrument=SFC Thar 350/A5
Flow rate=220 mL/min
Wavelength=220 nm
Mobile phase=$CO_2$/[heptane/IPA=4:1 (v:v)]=80/20 isocratic
Column=Whelko(rr) 50×5 cm, 10 μm
Injection Volume=1.0 mL [solute concentration=100 mg/mL of heptane/IPA 4:1 (v:v)]
Injection Program: Stacked injections (1.0 mL every 2 min)
Prep HPLC methods:
Prep HPLC method 1
Start % B=30, Final % B=67 over 16 minute gradient, step to 100% B for 10 minutes
Flow Rate=100 mL/min
Solvent A=90% water, 10% acetonitrile, 0.1% TFA
Solvent B=10% water, 90% acetonitrile, 0.1% TFA
Column=Waters Sunfire C18, 5 μm, 50×250 mm
Prep HPLC method 2
Start % B=0, Final % B=100 over 20 minute gradient, hold 100% B for 4 minutes
Flow Rate=50 mL/min
Solvent A=90% water, 10% acetonitrile, 0.1% TFA
Solvent B=10% water, 90% acetonitrile, 0.1% TFA
Column=Waters XBridge Phenyl, 5 μm, 30×100 mm
Prep HPLC method 3
Start % B=15, Final % B=100 over 20 minute gradient, hold 100% B for 4 minutes
Flow Rate=50 mL/min
Solvent A=90% water, 10% acetonitrile, 0.1% TFA
Solvent B=10% water, 90% acetonitrile, 0.1% TFA
Column=Waters XBridge Phenyl, 5 μm, 30×100 mm
Prep HPLC method 4
Start % B=20, Final % B=100 over 20 minute gradient, hold 100% B for 5 minutes
Flow Rate=50 mL/min
Solvent A=90% water, 10% acetonitrile, 0.1% TFA
Solvent B=10% water, 90% acetonitrile, 0.1% TFA
Column=Waters Sunfire C18, 5 μm, 30×150 mm
Prep HPLC method 5
Start % B=30, Final % B=100 over 15 minute gradient, hold 100% B for 5 minutes
Flow Rate=20 mL/min
Solvent A=90% water, 10% acetonitrile, 0.1% TFA
Solvent B=10% water, 90% acetonitrile, 0.1% TFA
Column=Waters Xbridge Phenyl, 5 μm, 19×250 mm
Prep HPLC method 6
Start % B=20, Final % B=65 over 20 minute gradient, step to 100% B for 5 minutes
Flow Rate=50 mL/min
Solvent A=90% water, 10% acetonitrile, 0.1% TFA
Solvent B=10% water, 90% acetonitrile, 0.1% TFA
Column=Waters Sunfire C18, 5 μm, 30×150 mm
Prep HPLC method 7
Start % B=20, Final % B=100 over 30 minute gradient, hold 100% B for 4 minutes Flow Rate=50 mL/min
Solvent A=90% water, 10% acetonitrile, 0.1% TFA
Solvent B=10% water, 90% acetonitrile, 0.1% TFA
Column=Waters Sunfire C18, 5 μm, 30×150 mm
Prep HPLC method 8
Start % B=30, Final % B=100 over 18 minute gradient, hold 100% B for 2 minutes
Flow Rate=25 mL/min
Collection by ELSD
Solvent A=95% water, 5% acetonitrile, 10 mM ammonium acetate
Solvent B=5% water, 95% acetonitrile, 10 mM ammonium acetate
Column=XBridge OBD Prep Shield RP18 19×100 mm 5 μm
Prep HPLC Method 9
Start % B=10, Final % B=100 over 10 minute gradient, hold 100% B for 5 minutes
Flow Rate=50 mL/min
Solvent A=90% water, 10% acetonitrile, 0.1% TFA
Solvent B=10% water, 90% acetonitrile, 0.1% TFA
Column=Waters Sunfire C18, 5 μm, 30×100 mm
Prep HPLC Method 10
Start % B=10, Final % B=100 over 10 minute gradient, hold 100% B for 5 minutes
Flow Rate=50 mL/min
Solvent A=95% water, 5% acetonitrile, 10 mM ammonium acetate
Solvent B=5% water, 95% acetonitrile, 10 mM ammonium acetate
Column=Xbridge OBD Prep Shield RP, 5 μm, 19×100 mm
Prep HPLC Method 11
Start % B=25, Final % B=100 over 15 minute gradient, hold 100% B
Flow Rate=40 mL/min
Solvent A=90% water, 10% acetonitrile, 0.1% TFA
Solvent B=10% water, 90% acetonitrile, 0.1% TFA
Column=Waters Sunfire C18, 5 μm, 30×100 mm
Prep HPLC Method 12
Start % B=20, Final % B=100 over 15 min gradient, hold at 100% B for 4 min
Flow Rate=50 ml/min
Wavelength=220
Solvent Pair=Water–acetonitrile–TFA
Solvent A=90% Water–10% acetonitrile–0.1% TFA
Solvent B=10% Water–90% acetonitrile–0.1% TFA
Column=Waters Sunfire C18, 5 μm, 30×150 mm
Prep HPLC Method 13
Start % B=30, Final % B=100 over 15 min gradient, hold at 100% B for 15 min
Flow Rate=50 ml/min
Wavelength=220
Solvent Pair=Water–acetonitrile–TFA
Solvent A=90% Water–10% acetonitrile–0.1% TFA
Solvent B=10% Water–90% acetonitrile–0.1% TFA
Column=Waters Sunfire C18, 5 μm, 30×150 mm
Prep HPLC Method 14
Start % B=30, Final % B=100 over 20 min gradient, hold at 100% B for 6 min
Flow Rate=50 ml/min
Wavelength=220
Solvent Pair=Water–acetonitrile–TFA
Solvent A=90% Water–10% acetonitrile–0.1% TFA
Solvent B=10% Water–90% acetonitrile–0.1% TFA
Column=Waters Sunfire C18, 5 μm, 30×150 mm
Prep HPLC Method 15
Start % B=30, Final % B=100 over 15 min gradient, hold at 100% B for 5 min
Flow Rate=50 ml/min
Wavelength=220
Solvent Pair=Water–acetonitrile–TFA
Solvent A=90% Water–10% acetonitrile–0.1% TFA
Solvent B=10% Water–90% acetonitrile–0.1% TFA
Column=Waters Sunfire C18, 5 μm, 30×150 mm
Prep HPLC Method 16
Start % B=20, Final % B=100 over 10 min gradient, hold at 100% B for 4 min
Flow Rate=50 ml/min
Wavelength=220
Solvent Pair=Water–acetonitrile–TFA
Solvent A=90% Water–10% acetonitrile–0.1% TFA
Solvent B=10% Water–90% acetonitrile–0.1% TFA
Column=Waters Sunfire C18, 5 μm, 30×150 mm
Prep HPLC Method 17
Start % B=30, Final % B=50 over 30 min gradient, hold at 50% B for 5 min
Flow Rate=25 ml/min
Wavelength=220
Solvent Pair=Water–acetonitrile–TFA
Solvent A=90% Water–10% acetonitrile–0.1% TFA
Solvent B=10% Water–90% acetonitrile–0.1% TFA
Column=YMC-OBD 20×100 mm S5

Preparation of ethyl 1-(fluoromethyl)-4-(4,4,5,5-tetramethyl-1,3,2-dioxaborolan-2-yl)cyclohex-3-enecarboxylate

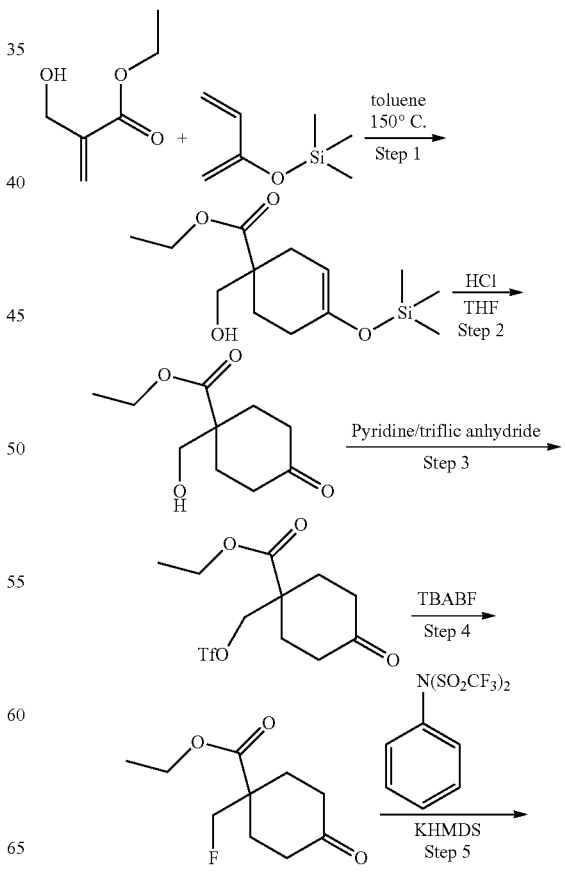

-continued

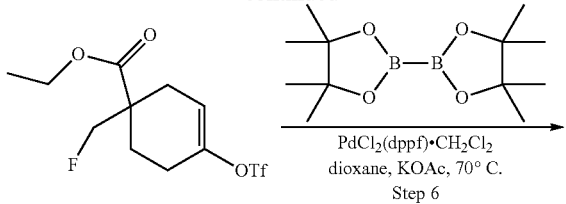

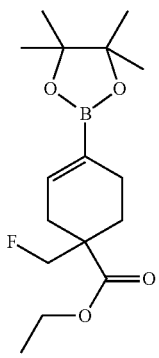

Step 1. Preparation of ethyl 1-(hydroxymethyl)-4-((trimethylsilyl)oxy)cyclohex-3-enecarboxylate

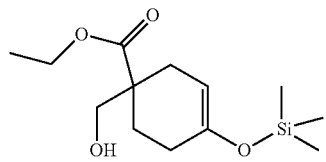 [SMILES: CCOC(=O)C1(CO)CC=C(O[Si](C)(C)C)CC1]

A solution of ethyl 2-(hydroxymethyl)acrylate (5.21 g, 40 mmol) and (buta-1,3-dien-2-yloxy)trimethylsilane (8.54 g, 60.0 mmol) in toluene (100 mL) was flushed with nitrogen, sealed and heated in a pressure flask at 150° C. for 48 h. The resulting light yellow reaction mixture was cooled to room temperature and concentrated in vacuum to give the crude product as an oil which was used for the next step without purification. MS: m/e 201.05 (M+H-silyl)$^+$, 0.839 min (method 4).

Step 2. Preparation of ethyl 1-(hydroxymethyl)-4-oxocyclohexanecarboxylate

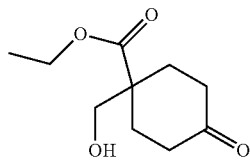

To a solution of ethyl 1-(hydroxymethyl)-4-((trimethylsilyl)oxy)cyclohex-3-enecarboxylate (10.9 g, 40.0 mmol) in THF (5 mL) was added HCl (0.005N) (1 mL, 5.00 µmol). The resulting solution was stirred at room temperature for 18 h. The reaction mixture was extracted with EtOAc (2×10 mL), washed with saturated aqueous NaHCO$_3$ (5 mL) followed by brine (10 mL). The organic extract was dried over Na$_2$SO$_4$, filtered and concentrated under reduced pressure. The crude product was purified by silica gel chromatography using ethyl acetate/hexanes to give the title compound as a colorless oil (3 g, 37.4%). MS: m/e 200.95 (M+H)$^+$, 0.853 min (method 4). $^1$H NMR (400 MHz, CHLOROFORM-d) δ 4.28 (q, J=7.3 Hz, 2H), 3.75 (s, 2H), 2.57-2.45 (m, 2H), 2.45-2.33 (m, 4H), 1.86-1.71 (m, 2H), 1.39-1.30 (m, 3H).

Step 3. Preparation of ethyl 4-oxo-1-((((trifluoromethyl)sulfonyl)oxy)methyl)cyclohexanecarboxylate

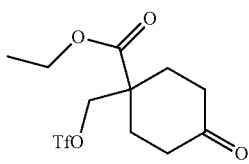 [SMILES: CCOC(=O)C1(COS(=O)(=O)C(F)(F)F)CCC(=O)CC1]

To a stirred mixture of ethyl 1-(hydroxymethyl)-4-oxocyclohexanecarboxylate (1,170 mg, 5.84 mmol) and pyridine (0.614 mL, 7.60 mmol) in DCM (10 mL) at −10° C. was added trifluoromethanesulfonic anhydride (7.60 mL, 7.60 mmol) dropwise. The resulting mixture was stirred at −10° C. for 30 min and washed with ice cold 1N HCl solution and brine. The separated organic layer was dried over sodium sulfate. The solvent was removed and the residue was used as it without purification. MS: m/e 333.05 (M+H)$^+$, 1.969 min (method 4).

Step 4. Preparation of ethyl 1-(fluoromethyl)-4-oxocyclohexanecarboxylate

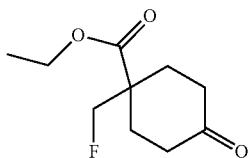

To a stirred mixture of ethyl 4-oxo-1-((((trifluoromethyl)sulfonyl)oxy)methyl)cyclohexanecarboxylate (1.941 g, 5.84 mmol) in DCM (10 mL) at 25° C. was added tetrabutylammonium bifluoride (3.63 mL, 7.01 mmol) dropwise. The resulting mixture was stirred at 25° C. for 18 hours. The reaction mixture was concentrated under vacuum. Two layers were formed upon stirring the residue obtained in 50 mL of hexanes. The top layer was decanted to a flask and dried under vacuum to yield a colorless oil. This residue was purified by flash chromatography using a 12 g silica gel column and a 0-35% EtOAc in hexanes gradient to yield the title compound as a colorless oil (0.20 g, 9.0%). MS: m/e 203.15 (M+H)$^+$, 1.470 min (method 4). $^1$H NMR (400 MHz, CHLOROFORM-d) δ 4.49-4.30 (m, 2H), 4.25-4.11 (m, 2H), 2.50-2.35 (m, 4H), 2.33-2.20 (m, 2H), 1.80-1.64 (m, 2H), 1.30-1.20 (m, 3H). $^{19}$F NMR (376 MHz, CHLOROFORM-d) δ −223.02-225.00 (m, 1F).

Step 5. Preparation of ethyl 1-(fluoromethyl)-4-(((trifluoromethyl)sulfonyl)oxy)cyclohex-3-enecarboxylate

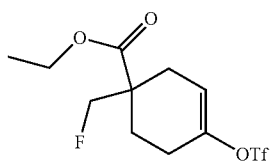 [SMILES: CCOC(=O)C1(CF)CC=C(OS(=O)(=O)C(F)(F)F)CC1]

KHMDS (1.27 ml, 1.27 mmol) was added to a pale yellow solution of ethyl 1-(fluoromethyl)-4-oxocyclohexanecarboxylate (0.20 g, 0.98 mmol) and 1,1,1-trifluoro-N-phenyl-N-((trifluoromethyl)sulfonyl)methanesulfonamide (0.38 g, 1.07 mmol) in THF (20 mL) at −78° C. The resulting yellow solution was stirred at −78° C. for 2 hr. The reaction mixture was quenched with aqueous saturated ammonium chloride and extracted once with 10 mL of EtOAc. The organic layer was washed with brine (10 mL), dried over Na$_2$SO$_4$, filtered and concentrated under reduced pressure. The crude product was purified by flash chromatography using a 12 g silica gel column and a 0-10% EtOAc in hexanes gradient to give the title compound as a colorless oil (179 mg, 54.7%). $^1$H NMR (400 MHz, CHLOROFORM-d) δ 5.84-5.69 (m, 1H), 4.60-4.37 (m, 2H), 4.30-4.15 (m, 2H), 2.89-2.70 (m, 1H), 2.56-2.33 (m, 2H), 2.32-2.14 (m, 2H), 2.07-1.81 (m, 1H), 1.34-1.22 (m, 3H). $^{19}$F NMR (376 MHz, CHLOROFORM-d) δ −225.18-−225.70 (m, 1F)

Step 6

To a flask containing ethyl 1-(fluoromethyl)-4-(((trifluoromethyl)sulfonyl)oxy)cyclohex-3-enecarboxylate (0.179 g, 0.53 mmol) was added bis(pinacolato)diboron (0.143 g, 0.56 mmol), potassium acetate (0.156 g, 1.59 mmol), and 1,1′-bis(diphenylphosphino)ferrocenepalladium(II) dichloride (0.013 g, 0.016 mmol). The mixture was diluted with dioxane (8 mL), flushed with nitrogen, and heated to 70° C. for 5 h. Upon cooling to rt, the mixture was diluted with water (25 mL) and extracted with ethyl acetate (2×20 mL). The combined organic layers were washed with brine and dried over magnesium sulfate. The drying agent was removed by filtration and the filtrate was concentrated under reduced pressure. The residue was purified by flash chromatography using a 12 g Isco silica gel column and a 0-10% EtOAc in hexanes gradient. The fractions containing the expected product were combined and concentrated under reduced pressure to give the title compound as a clear, colorless oil (91 mg, 54%). MS: m/e 313.20 (M+H)$^+$, 2.299 min (method 4). $^1$H NMR (400 MHz, CHLOROFORM-d) δ 6.50 (td, J=3.9, 2.0 Hz, 1H), 4.59-4.32 (m, 2H), 4.23-4.13 (m, 2H), 2.74-2.52 (m, 1H), 2.30-2.08 (m, 3H), 1.98-1.69 (m, 2H), 1.32-1.20 (m, 15H). $^{19}$F NMR (376 MHz, CHLOROFORM-d) δ −225.59-−226.36 (m, 1F).

Alternative method of preparation for the preparation of ethyl 1-(fluoromethyl)-4-oxocyclohexanecarboxylate

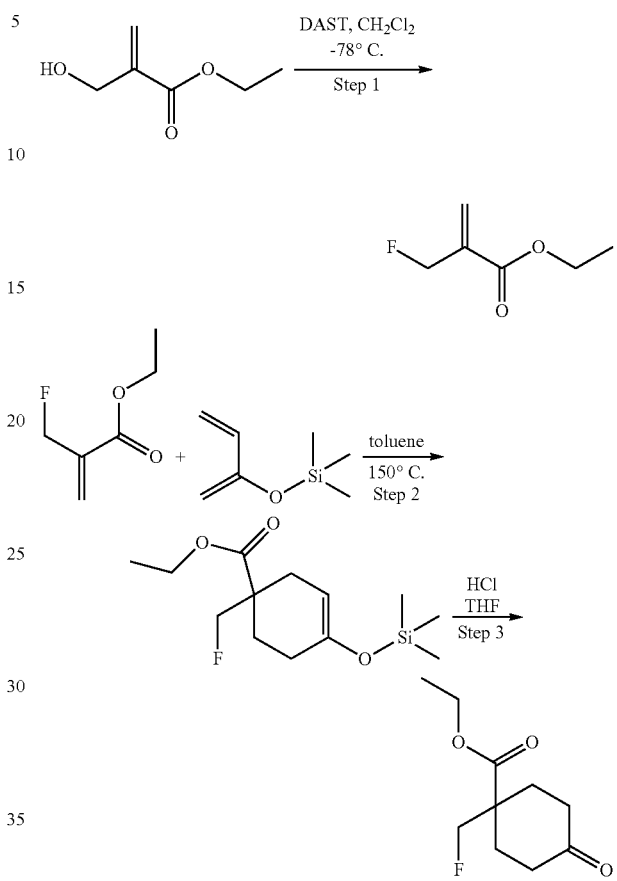

Step 1. Preparation of ethyl 2-(fluoromethyl)acrylate

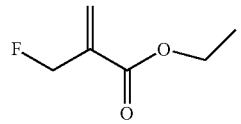

To the solution of ethyl 2-(hydroxymethyl)acrylate (5 g, 38.4 mmol) in DCM (50 mL) was added DAST (6.60 mL, 49.9 mmol) at −78° C. The reaction mixture was stirred at −78° C. for 1 hour. The mixture was warmed to 25° C. and continuously stirred for another 3 hours. The reaction mixture was quenched by the addition of CH$_2$Cl$_2$ (20 mL) and NaHCO$_3$ saturated aqueous solution (20 mL). The organic layer was separated, and the aqueous layer was extracted twice with CH$_2$Cl$_2$ (20 mL). The combined organic extracts were dried over sodium sulfate and evaporated to give a residual oil which was used in the next step without purification. $^1$H NMR (500 MHz, CHLOROFORM-d) δ 6.49-6.33 (m, 1H), 6.03-5.87 (m, 1H), 6.45-5.84 (m, 2H), 4.27 (q, J=7.1 Hz, 2H), 1.33 (t, J=7.1 Hz, 3H). $^{19}$F NMR (470 MHz, CHLOROFORM-d) δ −220.33-−221.86 (m, 1F).

Step 2. Preparation of ethyl 1-(fluoromethyl)-4-((trimethylsilyl)oxy)cyclohex-3-enecarboxylate

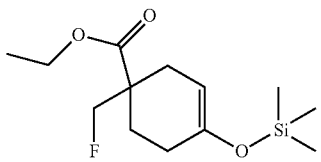 [SMILES: CCOC(=O)C1(CF)CC=C(O[Si](C)(C)C)CC1]

A solution of ethyl 2-(fluoromethyl)acrylate (4.7 g, 35.6 mmol)) and (buta-1,3-dien-2-yloxy)trimethylsilane (10.12 g, 71.1 mmol) in toluene (100 mL)) was flushed with nitrogen, sealed and heated at 150° C. in a pressure vessel for 48 h. The resulting pale yellow solution was cooled to room temperature and concentrated under reduced pressure to give the title compound as an oil which was used in the next step without further purification. $^1$H NMR (400 MHz, CHLOROFORM-d) δ 4.83 (t, J=3.3 Hz, 1H), 4.64-4.38 (m, 2H), 4.25-4.12 (m, 2H), 2.62-2.48 (m, 1H), 2.19-1.99 (m, 4H), 1.93-1.78 (m, 1H), 1.34-1.22 (m, 3H), 0.24-0.15 (m, 9H). $^{19}$F NMR (470 MHz, CHLOROFORM-d) δ -224.80--225.37 (m, 1F).

Step 3. Preparation of ethyl 1-(fluoromethyl)-4-oxocyclohexanecarboxylate

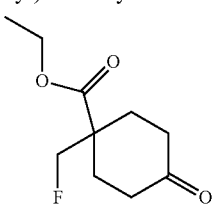

To a solution of ethyl 1-(fluoromethyl)-4-((trimethylsilyl)oxy)cyclohex-3-enecarboxylate (9.76 g, 35.6 mmol) in THF (5 ml) was added HCl (0.005N) (1 mL, 5.00 μmol). The resulting solution was stirred at room temperature overnight. The reaction mixture was extracted with EtOAc (2×10 mL), washed with aqueous saturated NaHCO$_3$ (5 mL) followed by brine (10 mL), dried over Na$_2$SO$_4$, filtered and concentrated under reduced pressure. The crude product was purified by flash chromatography using a 80 g silica gel column and a 0-25% EtOAc in hexanes gradient. The fraction containing the expected product was collected and concentrated under reduced pressure to give the title compound as a colorless oil (6.5 g, 90.2%). $^1$H NMR (400 MHz, CHLOROFORM-d) δ 4.59-4.42 (m, 2H), 4.30 (q, J=7.0 Hz, 2H), 2.58-2.34 (m, 6H), 1.88-1.73 (m, 2H), 1.33 (t, J=7.2 Hz, 3H). $^{19}$F NMR (376 MHz, CHLOROFORM-d) δ -223.54--223.99 (m, 1F).

Preparation of benzyl 1-(fluoromethyl)-4-oxocyclohexanecarboxylate

Method A.

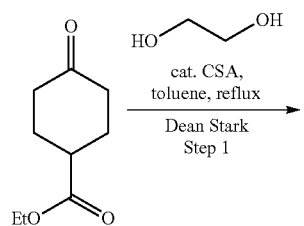

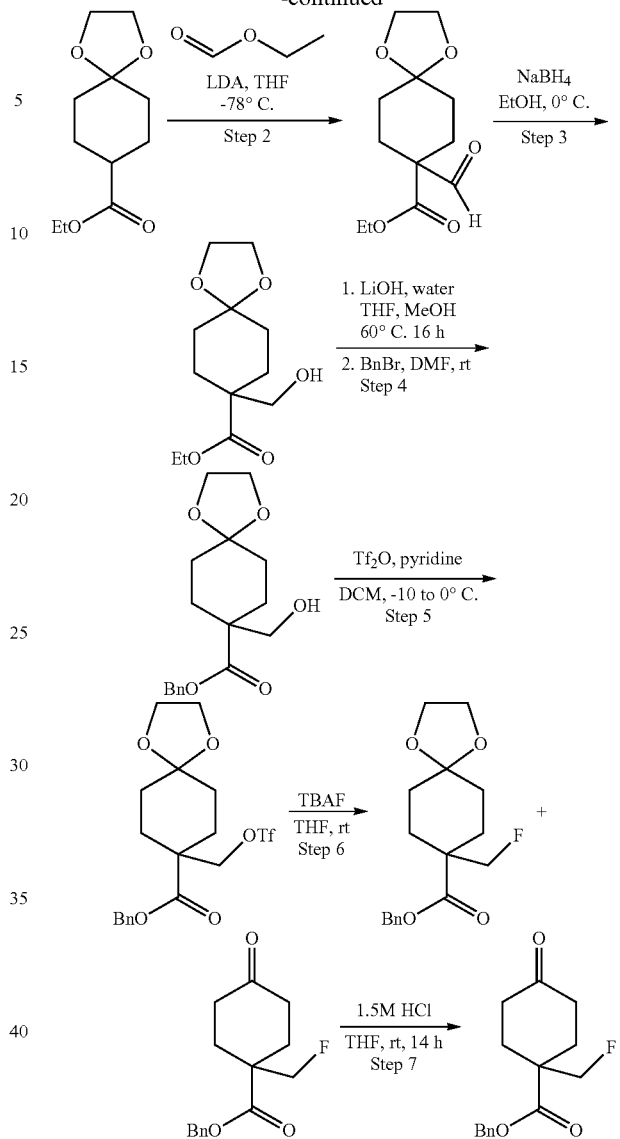

Step 1. Preparation of ethyl 1,4-dioxaspiro[4.5]decane-8-carboxylate

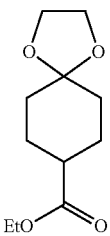

Into a 3 L, 3 neck round bottom flask was placed ethyl 4-oxocyclohexanecarboxylate (100 g, 570 mmol), ethane-1,2-diol (0.159 L, 2849 mmol), ((1S,4R)-7,7-dimethyl-2-oxo-bicyclo[2.2.1]heptan-1-yl)methanesulfonic acid (1.324 g, 5.70 mmol) and dry toluene (1.2 L). A Dean-Stark water trap and a condenser were installed and the mixture heated to reflux with stirring. Immiscible distillate was collected in the Dean-Stark trap and was periodically removed. After 28 h of total reflux time, a total of 82 mL of immiscible distillate had been removed from the Dean-Stark trap. After the mixture had cooled to approximately 40° C., sat. NaHCO$_3$ (400 mL) was added to the reaction mixture with rapid stirring. The mixture was transferred to a separatory funnel, shaken and the phases separated. The organic layer was washed with water (4×500 mL), then with 5% NaHCO$_3$ (200 mL) and then with brine (100 mL). The organic material was dried over anhydrous MgSO$_4$, filtered and concentrated under reduced pressure to give a slightly yellow viscous oil (118.50 g, 97% yield). $^1$H NMR (400 MHz, CHLOROFORM-d) δ 4.15 (q, J=7.3 Hz, 2H), 3.96 (s, 4H), 2.41-2.27 (m, 1H), 1.96 (dt, J=8.7, 4.3 Hz, 2H), 1.89-1.74 (m, 4H), 1.68-1.49 (m, 2H), 1.27 (t, J=7.1 Hz, 3H). $^{13}$C NMR (101 MHz, CHLOROFORM-d) δ 175.2, 108.1, 64.3, 60.3, 41.6, 33.8, 26.3, 14.3.

Step 2: Preparation of ethyl 8-formyl-1,4-dioxaspiro[4.5]decane-8-carboxylate

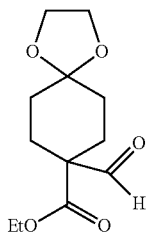

To a −78° C. solution of ethyl 1,4-dioxaspiro[4.5]decane-8-carboxylate (32.31 g, 151 mmol) in THF (250 mL) was added a solution of 2M lithium diisopropylamide (98 mL, 196 mmol) in THF via a cannula over 5 mins. The resulting brown solution was stirred at −78° C. After 1 h, the cold bath was replaced with an ice bath and the reaction mixture was stirred at 0° C. for 1 h. The reaction mixture was again chilled to −78° C. and treated with a solution of ethyl formate (18.65 mL, 226 mmol) in THF (40 mL) added dropwise over 45 min. The resulting light brown reaction mixture was stirred at −78° C. for 1 h. The cold bath was removed and to the mixture was added dropwise saturated aqueous NH$_4$Cl (250 mL) and the mixture stirred at ambient temperature for 30 min. The resulting yellow mixture was extracted with EtOAc (3×300 mL). The combined organic phase was washed with 0.5N HCl (300 mL), then with brine, dried over MgSO$_4$, filtered and concentrated to a brown viscous oil. The crude material was purified by flash column chromatography over silica gel (750 g silica, step elution 9:1 hexanes/EtOAc and 5:1 hexanes/EtOAc) to provide recovered starting material, ethyl 1,4-dioxaspiro[4.5]decane-8-carboxylate (8.6 g, 40.1 mmol, 26.6% yield) and the desired product, ethyl 8-formyl-1,4-dioxaspiro[4.5]decane-8-carboxylate (20.1 g, 83 mmol, 55.0% yield), both as viscous yellow oils. $^1$H NMR (400 MHz, CHLOROFORM-d) δ 9.50 (s, 1H), 4.17 (q, J=7.2 Hz, 2H), 3.94-3.86 (m, 4H), 2.24-2.09 (m, 2H), 2.01 (ddd, J=13.5, 8.3, 5.1 Hz, 2H), 1.75-1.48 (m, 4H), 1.23 (t, J=7.2 Hz, 3H).

Step 3: Preparation of ethyl 8-(hydroxymethyl)-1,4-dioxaspiro[4.5]decane-8-carboxylate

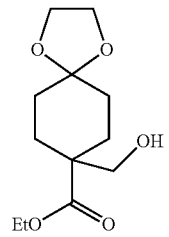

To a 0° C. solution of ethyl 8-formyl-1,4-dioxaspiro[4.5]decane-8-carboxylate (28.9 g, 119 mmol) in ethanol (300 mL) was added sodium borohydride (5.30 g, 137 mmol) and the resulting mixture was stirred at 0° C. After 3 h, the reaction mixture was quenched with saturated aqueous NH$_4$Cl (200 mL) added dropwise via a dropping funnel. The ice bath was removed and the resulting slurry was treated slowly with H$_2$O (150 mL). The resulting mixture was filtered to remove a small amount of white solid. The liquid filtrate was concentrated to remove most of the organic solvent, and the remainder was extracted with EtOAc (4×250 mL). The combined organic phase was washed with brine, dried over MgSO$_4$, filtered, concentrated and dried under reduced pressure to give ethyl 8-(hydroxymethyl)-1,4-dioxaspiro[4.5]decane-8-carboxylate (27.7 g, 113 mmol, 95% yield) as a clear viscous oil. The material from this experiment was used directly in the next step without further purification. In a separate experiment the crude material was purified by flash column chromatography (SiO$_2$, elution 3:1 hexanes:EtOAc) to give ethyl 8-(hydroxymethyl)-1,4-dioxaspiro[4.5]decane-8-carboxylate in 91% yield. $^1$H NMR (400 MHz, CHLOROFORM-d) δ 4.18 (q, J=7.1 Hz, 2H), 3.98-3.87 (m, 4H), 3.61 (d, J=6.1 Hz, 2H), 2.23 (br. s., 1H), 2.17-2.07 (m, 2H), 1.72-1.51 (m, 6H), 1.32-1.20 (m, 3H).

Step 4. Preparation of benzyl 8-(hydroxymethyl)-1,4-dioxaspiro[4.5]decane-8-carboxylate

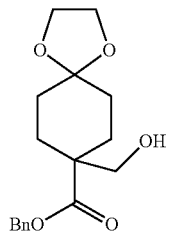

To a solution of ethyl 8-(hydroxymethyl)-1,4-dioxaspiro[4.5]decane-8-carboxylate (27.6 g, 113 mmol) in THF (150 mL) and MeOH (50 mL) was added a solution of 3N aqueous lithium hydroxide (45.2 mL, 136 mmol) and the mixture was heated to 60° C. with stirring for 17 h. Additional 3N aqueous lithium hydroxide (30.1 mL, 90 mmol) was then added and the mixture was heated to 60° C. for an additional 14 h. The reaction mixture was concentrated and dried under reduced pressure to give a residue containing the corresponding carboxylate (24.5 g, 107 mmol) which was used without further purification.

To this residue in DMF (200 mL) was added benzyl bromide (12.98 mL, 107 mmol) and the resulting mixture was stirred at rt for 17 h. The reaction mixture was concentrated to about half of the original volume, diluted with EtOAc (250 mL) and washed with 1N HCl (200 mL). The aqueous phase was extracted with 3×250 mL EtOAc. The combined organic phase was washed with H$_2$O (100 mL), brine, dried over MgSO$_4$, filtered and concentrated to a light yellow viscous oil. The crude material was purified by flash column chromatography (SiO$_2$, elution step gradient 70:30 hex:EtOAc then 1:1 hex:EtOAc) and dried under reduced pressure to give benzyl 8-(hydroxymethyl)-1,4-dioxaspiro[4.5]decane-8-carboxylate (23.1 g, 71.6 mmol, 63% yield over 3 steps). $^1$H NMR (400 MHz, CHLOROFORM-d) δ 7.40-7.28 (m, 5H), 5.16 (s, 2H), 3.91 (s, 4H), 3.64 (s, 2H), 2.34 (br. s., 1H), 2.22-2.12 (m, 2H), 1.70-1.63 (m, 4H), 1.62-1.54 (m, 2H). $^{13}$C NMR (101 MHz, CHLOROFORM-d) δ 175.3, 135.8, 128.5 (s, 2C), 128.1, 127.8, 108.3, 68.5, 66.4, 64.2, 64.1, 48.1, 31.3, 27.9.

Step 5. Preparation of benzyl 8-((((trifluoromethyl)sulfonyl)oxy)methyl)-1,4-dioxaspiro[4.5]decane-8-carboxylate

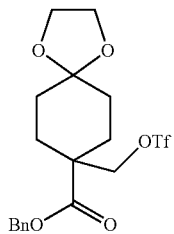

In a 500 mL round bottom flask were combined benzyl 8-(hydroxymethyl)-1,4-dioxaspiro[4.5]decane-8-carboxylate (14.9 g, 48.6 mmol) with dry DCM (250 mL). The solution was chilled in an ice/acetone bath to approx −10° C. and to it was added pyridine (5.31 mL, 65.7 mmol) followed by the dropwise addition of Tf$_2$O (11.09 mL, 65.7 mmol) over 30 min. The slightly yellow suspension was stirred at 0° C. (ice water bath) for 1.5 h. The resulting deep orange mixture with significant suspended solids was concentrated under reduced pressure to leave a residue that was put under vacuum to remove excess triflic anhydride, then the residue was redissolved in DCM (150 mL). The mixture was filtered to remove a significant quantity of white solid which was rinsed with DCM. The deep reddish/orange filtrate was concentrated and purified by flash silica gel column chromatography (330 g silica, elution 100% DCM). Product fractions were combined and concentrated to a thick orange oil which was placed under high vacuum with stirring overnight. The color turned to blue/green. Thus was obtained the desired product (20.94 g, 98% yield) as a blue/green viscous oil. $^1$H NMR (400 MHz, CHLOROFORM-d) δ 7.48-7.30 (m, 5H), 5.21 (s, 2H), 4.53 (s, 2H), 4.04-3.87 (m, 4H), 2.30-2.14 (m, 2H), 1.76-1.56 (m, 6H). $^{19}$F NMR (376 MHz, CHLOROFORM-d) δ −74.39 (s, 1F).

Step 6. Preparation of benzyl 8-(fluoromethyl)-1,4-dioxaspiro[4.5]decane-8-carboxylate

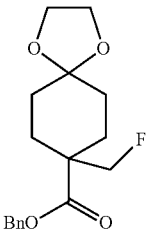 [SMILES: O=C(OCc1ccccc1)C1(CF)CCC2(CC1)OCCO2]

In a 500 mL round bottom flask under nitrogen atmosphere were combined benzyl 8-((((trifluoromethyl)sulfonyl)oxy)methyl)-1,4-dioxaspiro[4.5]decane-8-carboxylate (20.76 g, 47.4 mmol) with anhydrous THF (150 mL) which was introduced via cannula. To the blue solution was added dropwise via addition funnel TBAF, 1.0M in THF (71.0 mL, 71.0 mmol) dropwise over 15 min. The mixture immediately turned canary yellow when TBAF was added. The mixture was stirred at rt for 1 h. The crude mixture was concentrated to leave a thick oil which was diluted with ethyl acetate (700 mL) and washed with water (2×250 mL) and with brine (100 mL). The organic phase was dried over MgSO$_4$, filtered and concentrated to a thick yellow residue. Purification by flash silica gel column chromatography (330 g silica, elution gradient 100% hexanes to 2:1 hexanes:EtOAc) gave the desired product as a yellow oil (13.73 g, 94% yield). LCMS: m/e 309.2 (M+H)$^+$, 1.27 min (method 6). $^1$H NMR (400 MHz, CHLOROFORM-d) δ 7.44-7.31 (m, 5H), 5.21 (s, 2H), 4.45 (d, J=47.2 Hz, 2H), 4.01-3.89 (m, 4H), 2.28-2.16 (m, 2H), 1.75-1.55 (m, 6H). $^{19}$F NMR (376 MHz, CHLOROFORM-d) δ −223.25 (t, J=46.8 Hz, 1F).

Step 7

In a 2 L round bottom flask cooled in an ice bath were combined benzyl 8-(fluoromethyl)-1,4-dioxaspiro[4.5]decane-8-carboxylate (13.72 g, 44.5 mmol) with THF (500 mL) and then hydrochloric acid, 1.5M aqueous (534 mL, 801 mmol) was added slowly over 2 min. The ice bath was removed and the mixture was stirred at rt for 15 h. The mixture was concentrated under reduced pressure to remove the organic and the remnant was extracted with ethyl acetate (300 mL). The ethyl acetate phase was washed with water (2×200 mL) and with brine (50 mL). Concentration under reduced pressure provided the desired product (12.13 g, quantitative) as a yellow oil. LCMS: m/e 265.3 (M+H)$^+$, 1.19 min (method 6). $^1$H NMR (400 MHz, CHLOROFORM-d) δ 7.47-7.32 (m, 5H), 5.27 (s, 2H), 4.52 (d, J=47.2 Hz, 2H), 2.57-2.42 (m, 4H), 2.42-2.31 (m, 2H), 1.87-1.76 (m, 2H). $^{19}$F NMR (376 MHz, CHLOROFORM-d) δ −223.41 (t, J=46.8 Hz, 1F).

Method B

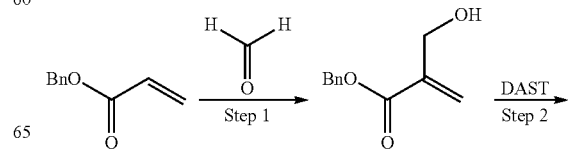

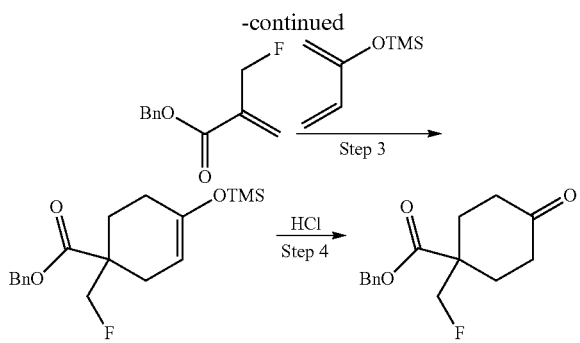

Step 1. Preparation of benzyl 2-(hydroxymethyl)acrylate

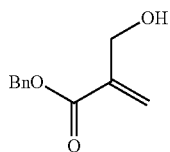

In a 1-L flask was placed benzyl acrylate (44.6 mL, 292 mmol), dioxane (290 mL), 1,4-diazabicyclo[2.2.2]octane (32.7 g, 292 mmol) and water (270 mL). The mixture was vigorously stirred at RT forming an emulsion. To the stirring mixture was added an aqueous solution of formaldehyde (37%, 23.9 mL, 321 mmol) and the stirring was continued for 14 hours at RT. The crude reaction mixture was extracted with methylene chloride (3×150 mL). The organic layers were separated, combined and washed with a 50:50 mixture of saturated aqueous ammonium chloride and HCl (0.2 N). Evaporation and concentration under reduced pressure (2 cm Hg) at 45° C. gave 49.1 g of a free flowing syrup. The crude product was purified on a silica gel column eluted with a gradient mixture of EtOAc/Hexanes to give the title compound as a clear colorless syrup (27 g, 141 mmol, 48%). LCMS: m/e 193.05 (M+H)$^+$, 1.78 min (Method 1). $^1$H NMR (500 MHz, CHLOROFORM-d) δ 7.50-7.30 (m, 5H), 6.34 (s, 1H), 5.89 (s, 1H), 5.25 (s, 2H), 4.38 (d, J=6.4 Hz, 2H), 2.20 (t, J=6.6 Hz, 1H); $^{13}$C NMR (126 MHz, CHLOROFORM-d) δ 166.1, 139.3, 135.7, 128.7, 128.4, 128.2, 126.2, 66.6, 62.7.

Step 2. Preparation of benzyl 2-(fluoromethyl)acrylate

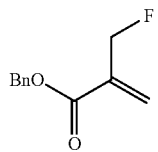

Benzyl 2-(hydroxymethyl)acrylate (13.7 g, 71.3 mmol) was dissolved in dry methylene chloride (100 mL) under nitrogen and the mixture was cooled at −78° C. To this stirring solution and using a polyethylene pipette, was added diethylaminosulfur trifluoride (DAST, 13.0 mL, 98 mmol) in 4 portions over a period of 5 minutes. A pale orange solution was formed. Once addition was complete, the dry-ice bath was removed and the reaction temperature was allowed to rise to RT. Stirring continued at RT for a total of 4 hours. The reaction mixture was transferred dropwise, into a chilled (~4° C.) 50:50 mixture of saturated aqueous sodium bicarbonate and water. Once all of the crude reaction mixture was transferred, it was extracted with BHT-stabilized ether (3×150 mL). The organic layers were combined, and washed once with water (50 mL). The solvent from the organic phase was removed under reduced pressure at sub-ambient temperature (~15° C.) to constant weight (14.2 g, quant.). The crude material was used immediately in the next step. $^1$H NMR (500 MHz, CHLOROFORM-d) δ 7.44-7.34 (m, 5H), 6.49-6.43 (m, 1H), 5.99 (dt, J=2.8, 1.5 Hz, 1H), 5.26 (s, 2H), 5.13 (d, J=46.5 Hz, 2H); $^{19}$F NMR (470 MHz, CHLOROFORM-d) δ −220.91 (t, J=46.2 Hz).

Step 3—Preparation of benzyl 1-(fluoromethyl)-4-((trimethylsilyl)oxy)cyclohex-3-enecarboxylate

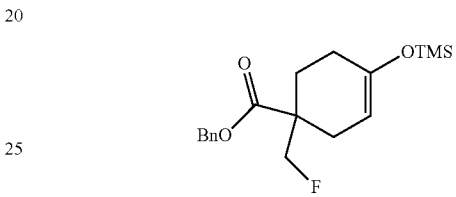

To a 500 mL resealable pressure vessel was added the crude starting material benzyl 2-(fluoromethyl)acrylate (14.2 g, 73.1 mmol) and (buta-1,3-dien-2-yloxy)trimethylsilane (Sigma Aldrich material used as supplied, 18.73 g, 132 mmol) in toluene (200 mL). The vessel was evacuated to 80 micron Hg at −78° C., followed by purging with nitrogen. The process was repeated twice. The flask was sealed, and warmed to RT before it was immersed into an oil bath at 125° C. for 22 hours. The mixture was allowed to cool to RT. A small aliquot (25 μL) was removed from the crude reaction, vacuum-dried at RT for NMR analyses in $^1$H and $^{19}$F. The NMR results were consistent with the formation of the title compound and small amount of the corresponding Diels-Alder regioisomer. $^1$H NMR (400 MHz, CHLOROFORM-d) δ 7.43-7.29 (m, 5H), 5.18 (s, 2H), 4.80 (d, J=3.0 Hz, 1H), 4.52 (dq, J=46.9, 8.4 Hz, 2H), 2.65-2.49 (m, 1H), 2.21-2.00 (m, 4H), 1.92-1.78 (m, 1H), 0.24-0.12 (m, 9H); $^{19}$F NMR (376 MHz, CHLOROFORM-d) δ −224.76 (t, J=47.7 Hz, 1F) and a minor $^{19}$F NMR (376 MHz, CHLOROFORM-d) δ −225.20 (t, J=46.8 Hz, 0.06 F). The crude material was evaporated and dried under vacuum (20 micron Hg) at ~35° C. until constant weight (24.6 g, quant.). This crude material was used in the next step as is without further purification.

Step 4

The crude material from the previous step (24.6 gm, 73 mmol) was dissolved in THF (200 mL) at RT to form a clear solution. Aqueous 1N HCl (2 mL, 2 mmol) and water 4 mL were added. The clear solution was stirred at RT for a total of 16 hours. The crude reaction mixture was quenched with 150 mL of a 50:50 mixture of saturated aqueous ammonium sodium bicarbonate and water. The organic layer was extracted with EtOAc (3×75 mL). The organic layers were combined, and evaporated to dryness to give 18.8 g of a thick syrup. The crude residue was purified using a 330 g silica gel column eluted with a gradient mixture of 0 to 25% v/v of ethyl acetate in hexanes, in ~25 column volumes to render the title compound (15.6 g, 81.0%). LCMS: m/e 265.15 (M+H)+, 1.60 min (Method 3). $^1$H NMR (400 MHz, CHLOROFORM-d) δ 7.50-7.30 (m, 5H), 5.26 (s, 2H), 4.43 (d, J=46.9 Hz, 2H), 2.54-2.29 (m, 6H), 1.90-1.71 (m, 2H); $^{19}$F NMR (376 MHz, CHLOROFORM-d) δ −223.47 (t, J=46.8 Hz, 1F).

Preparation of (R)-benzyl 1-(fluoromethyl)-4-(4,4,5,5-tetramethyl-1,3,2-dioxaborolan-2-yl)cyclohex-3-enecarboxylate and (S)-benzyl 1-(fluoromethyl)-4-(4,4,5,5-tetramethyl-1,3,2-dioxaborolan-2-yl)cyclohex-3-enecarboxylate

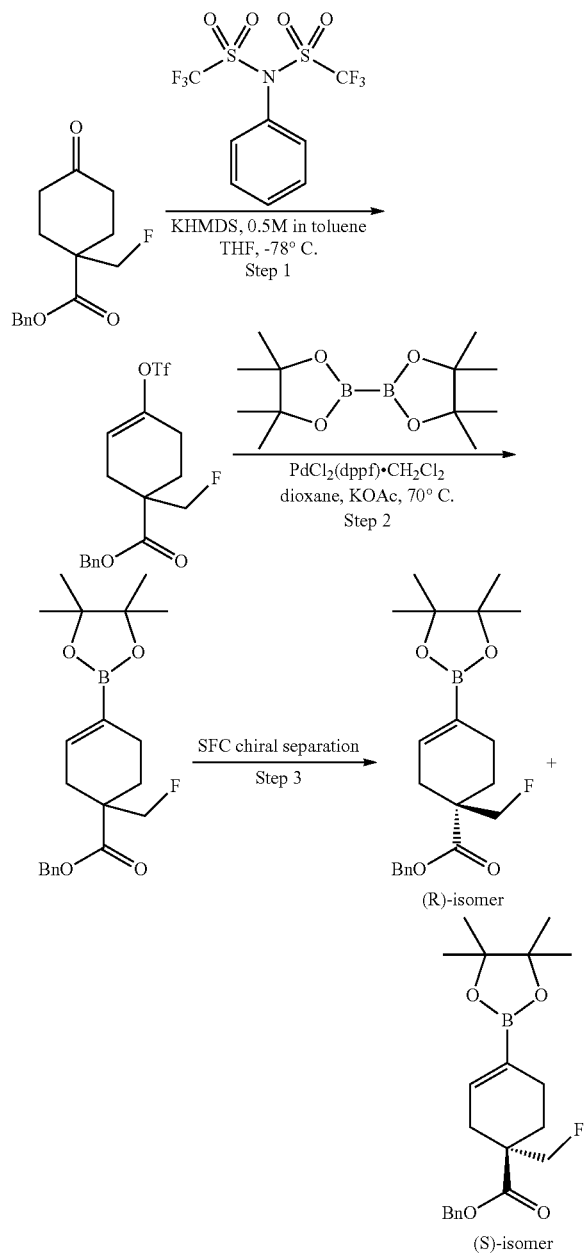

Step 1. Preparation of benzyl 1-(fluoromethyl)-4-(((trifluoromethyl)sulfonyl)oxy)cyclohex-3-enecarboxylate

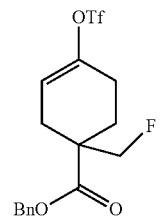 [SMILES: O=C(OCc1ccccc1)C1(CF)CC=C(OS(=O)(=O)C(F)(F)F)CC1]

In a 500 mL round bottom flask were combined benzyl 1-(fluoromethyl)-4-oxocyclohexanecarboxylate (12.65 g, 47.9 mmol) and N,N-bis(trifluoromethylsulfonyl)aniline (18.81 g, 52.7 mmol) in anhydrous tetrahydrofuran (250 mL). The solution was cooled to −78° C. in a dry ice/acetone bath. To the cold solution was added dropwise potassium hexamethyldisilazide, 0.5M in toluene (105 mL, 52.7 mmol) over 30 min. The mixture was stirred at −78° C. for a total of 2.5 h and was then lifted out of the cold bath and stirred for an additional 20 min at rt. The mixture was placed back in the −78° C. bath and to it was added with stirring 125 mL of saturated aqueous ammonium chloride. The resulting suspension was removed from the cold bath and allowed to come to rt while stirring. The mixture was concentrated under reduced pressure to remove the organic solvent, then to the mixture was added ethyl acetate (600 mL) and water (300 mL) and the mixture was shaken and the phases were separated. The organic layer was washed with water (2×200 mL) and with brine (50 mL). The organic layer was dried over MgSO$_4$, filtered and concentrated under reduced pressure to leave a yellow/orange oil. The crude residue was purified by flash silica gel column chromatography (800 g silica, elution isocratic 3:2 hexanes:DCM). Product fractions were combined and concentrated under reduced pressure to give the desired product (17.43 g, 92% yield) as a very slightly yellow oil. $^1$H NMR (400 MHz, CHLOROFORM-d) δ 7.43-7.31 (m, 5H), 5.78 (br. s., 1H), 5.26-5.15 (m, 2H), 4.52 (dm, J=46.7 Hz, 2H), 2.78 (d, J=16.9 Hz, 1H), 2.52-2.33 (m, 2H), 2.33-2.17 (m, 2H), 1.94 (dt, J=13.8, 6.9 Hz, 1H). $^{19}$F NMR (376 MHz, CHLOROFORM-d) δ −73.88 (s, 1 F), −225.02 (t, J=46.8 Hz, 1F).

Step 2. Preparation of benzyl 1-(fluoromethyl)-4-(4,4,5,5-tetramethyl-1,3,2-dioxaborolan-2-yl)cyclohex-3-enecarboxylate

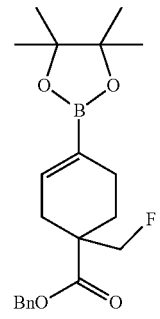 [SMILES: CC1(C)OB(C2=CCC(CF)(C(=O)OCc3ccccc3)CC2)OC1(C)C]

In a 500 mL round bottom flask were combined benzyl 1-(fluoromethyl)-4-(((trifluoromethyl)sulfonyl)oxy)cyclohex-3-enecarboxylate (17.42 g, 44.0 mmol), potassium acetate (0.030 g, 0.307 mmol), 4,4,4',4',5,5,5',5'-octamethyl-2,2'-bi(1,3,2-dioxaborolane) (11.72 g, 46.1 mmol), 1,1'-bis(diphenylphosphino)ferrocenepalladium(II) dichloride (3.03 mg, 3.69 µmol) and anhydrous dioxane (200 mL). The flask was placed under a nitrogen atmosphere and heated to 70° C. After 5 h, the mixture was allowed to cool to rt and stood overnight. The reaction mixture was concentrated under reduced pressure and the crude deep red residue was diluted with ethyl acetate (600 mL) and water (300 mL). The mixture was shaken and phases were separated. The organic was washed with water (250 mL) and then with brine (100 mL). The organic phase was dried over anhydrous MgSO$_4$, filtered and concentrated under reduced pressure to a deep red viscous oil. Purification of the crude mixture by flash silica gel column chromatography (800 g silica; step elution 1:3 hexanes:DCM for 4 L, then 100% DCM for 5 L. 2 g of material from the mixed fractions from the first purification were repurified over 80 g of silica gel, elution gradient 100% hexanes to 100% DC,) to give the desired product as a colorless thick oil (13.06 g, 79.4% yield). LCMS: m/e 375.3 (M+H)$^+$, 1.52 min (method 6). $^1$H NMR (400 MHz, CHLOROFORM-d) δ 7.44-7.30 (m, 5H), 6.54 (br. s., 1H), 5.25-5.11 (m, 2H), 4.51 (dm, J=47.4 Hz, 2H), 2.67 (d, J=19.3 Hz, 1H), 2.29-2.10 (m, 3H), 2.02-1.89 (m, 1H), 1.86-1.74 (m, 1H), 1.28 (s, 12H). $^{19}$F NMR (376 MHz, CHLOROFORM-d) δ −225.62 (t, J=45.1 Hz, 1F).

Step 3

Racemic benzyl 1-(fluoromethyl)-4-(4,4,5,5-tetramethyl-1,3,2-dioxaborolan-2-yl)cyclohex-3-enecarboxylate (11.15 g, 0.0298 mmol) was purified by supercritical fluid chromatography (SFC Method 1) to provide the separated single isomer title compounds: (R)-benzyl 1-(fluoromethyl)-4-(4,4,5,5-tetramethyl-1,3,2-dioxaborolan-2-yl)cyclohex-3-enecarboxylate. This was the first isomer to elute from the SFC chiral separation. The product was isolated as a yellow oil (5.45 g, 98% SFC recovery, 99.2% chiral purity). $^1$H NMR (400 MHz, CHLOROFORM-d) δ 7.42-7.30 (m, 5H), 6.54 (br. s., 1H), 5.24-5.12 (m, 2H), 4.51 (dm, J=47.2 Hz, 2H), 2.67 (d, J=19.3 Hz, 1H), 2.27-2.10 (m, 3H), 2.00-1.90 (m, 1H), 1.85-1.75 (m, 1H), 1.28 (s, 12H). $^{19}$F NMR (376 MHz, CHLOROFORM-d) δ −225.62 (t, J=46.8 Hz, 1F).

(S)-benzyl 1-(fluoromethyl)-4-(4,4,5,5-tetramethyl-1,3,2-dioxaborolan-2-yl)cyclohex-3-enecarboxylate. This was the second isomer to elute from the SFC chiral separation. The product was isolated as a yellow oil (4.94 g, 89% SFC recovery, 99.3% chiral purity). $^1$H NMR (400 MHz, CHLOROFORM-d) δ 7.43-7.31 (m, 5H), 6.54 (br. s., 1H), 5.24-5.13 (m, 2H), 4.52 (dm, J=47.2 Hz, 2H), 2.68 (d, J=19.3 Hz, 1H), 2.27-2.10 (m, 3H), 2.01-1.90 (m, 1H), 1.85-1.75 (m, 1H), 1.28 (s, 12H). $^{19}$F NMR (376 MHz, CHLOROFORM-d) δ −225.61 (t, J=48.6 Hz, 1F).

Preparation of 4-(2-bromoethyl)tetrahydro-2H-thiopyran 1,1-dioxide

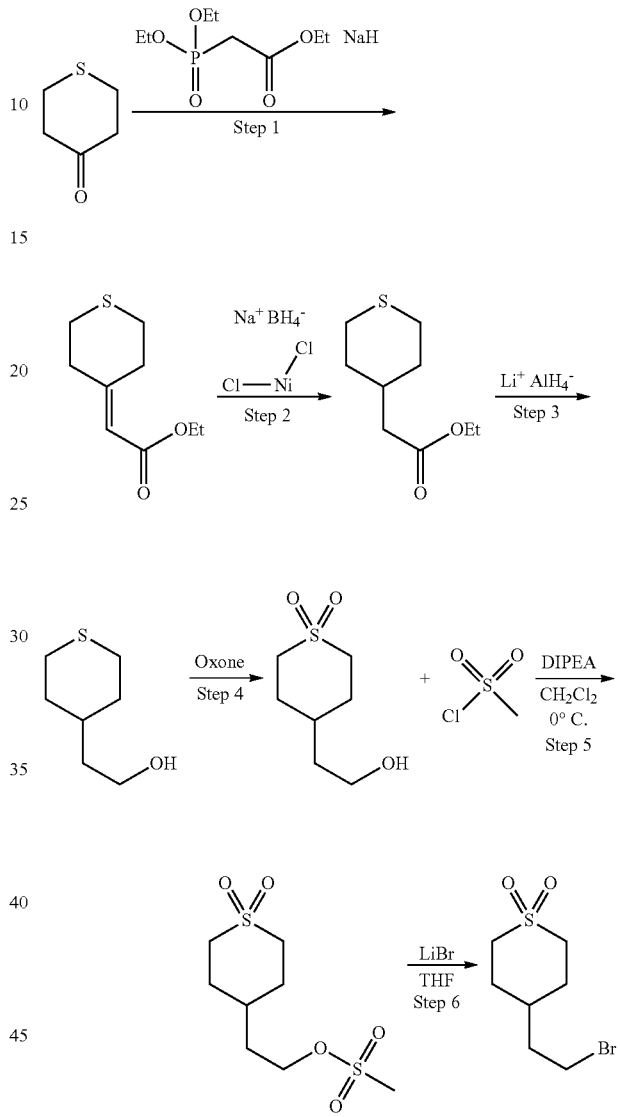

Step 1 Preparation of ethyl 2-(dihydro-2H-thiopyran-4 (3H)-ylidene)acetate

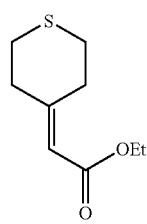 [SMILES: CCOC(=O)C=C1CCSCC1]

The title intermediate was prepared in accordance with that reported by Lammek, Derdowska and Rekowski in Polish Journal of Chemistry 64, 351 (1990).

Step 2: Preparation of ethyl 2-(tetrahydro-2H-thiopyran-4-yl)acetate

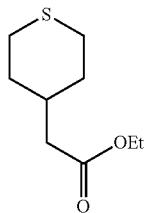 [SMILES: CCOC(=O)CC1CCSCC1]

The title intermediate was prepared in accordance with that published in PCT WO 00/44713 in 64% yield in two steps (1 and 2).

Step 3: Preparation of 2-(tetrahydro-2H-thiopyran-4-yl)ethanol

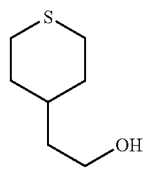

To a chilled (iced bath, 0° C.) solution of ethyl 2-(tetrahydro-2H-thiopyran-4-yl)acetate (6.4 g, 34.0 mmol) in diethyl ether (100 mL) in a 500 mL flask was added dropwise a stock, 1M solution of lithium aluminum hydride (34.0 mL, 34.0 mmol) in THF. A turbid suspension was formed initially and evolution of hydrogen gas was observed. The reaction mixture became clear when about ⅔ of the LiAlH₄ reagent was added. The iced bath was removed and the reaction mixture was allowed to warm to ambient temperature (~19-21° C.) for 4 hours. The reaction was quenched with a half-saturated NH₄Cl solution in 0.5N HCl dropwise until a freely stirred, white suspension was formed. The solid was removed by filtration and washed with additional solvent. The filtrate and the wash were combined and concentrated under vacuum to give the title intermediate (4.9 gm 99%). $^1$H NMR (400 MHz, CHLOROFORM-d) δ 3.71 (t, J=6.4 Hz, 2H), 2.78-2.53 (m, 4H), 2.03 (d, J=13.3 Hz, 2H), 1.52 (dd, J=6.8, 3.3 Hz, 3H), 1.46-1.33 (m, 2H).

Step 4: Preparation of 4-(2-hydroxyethyl)tetrahydro-2H-thiopyran 1,1-dioxide

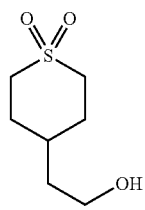 [SMILES: O=S1(=O)CCC(CCO)CC1]

To a solution of 2-(tetrahydro-2H-thiopyran-4-yl)ethanol (182 mg, 1.244 mmol) in acetone (3 mL) at room temperature, was added a suspension of Oxone® (1.53 gm, 2.5 mmol) in water (7 mL). A mild exotherm was detected and stirring was continued at room temperature for 2 hours. The crude reaction suspension was extracted with ethyl acetate (3×20 mL). The organic layers were combined and concentrated under vacuum to render a thick syrup containing the title compound (66 mg 29.8%). $^1$H NMR (400 MHz, CHLOROFORM-d) δ 3.74 (t, J=6.3 Hz, 2H), 3.12-2.92 (m, 4H), 2.15 (dd, J=13.8, 2.5 Hz, 2H), 1.96-1.84 (m, 2H), 1.84-1.73 (m, 1H), 1.61 (q, J=6.4 Hz, 2H)

Step 5: Preparation of 2-(1,1-dioxidotetrahydro-2H-thiopyran-4-yl)ethyl methanesulfonate

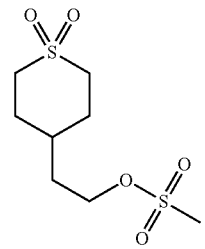

A solution of 4-(2-hydroxyethyl)tetrahydro-2H-thiopyran 1,1-dioxide (30 mg, 0.168 mmol) in DCM (1 mL) was cooled in an iced bath under nitrogen. DIPEA (0.088 ml, 0.505 mmol) was added, followed by methanesulfonyl chloride (0.020 ml, 0.252 mmol). The reaction mixture was stirred at 0° C. for 30 minutes. The reaction mixture was diluted with water (2 mL) and extracted with DCM (3×5 mL). The combined organic layers were washed with brine (5 mL), dried over Na₂SO₄ and concentrated under reduced pressure. The crude product was purified by flash chromatography on silica gel column eluted with 50-100% EtOAc/Hexane using ELS detector to give the desired compound as an oil (37 mg, 86%). LCMS m/e 257.10 (M+H)⁺, 1.086 min (method 3). $^1$H NMR (400 MHz, CHLOROFORM-d) δ 4.29 (t, J=5.9 Hz, 2H), 3.03 (s, 3H), 3.11-2.94 (m, 4H), 2.14 (dt, J=14.2, 1.2 Hz, 2H), 1.98-1.73 (m, 5H).

Step 6: Preparation of 4-(2-bromoethyl)tetrahydro-2H-thiopyran 1,1-dioxide

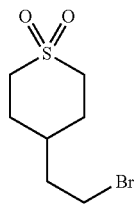 [SMILES: O=S1(=O)CCC(CCBr)CC1]

To a solution of 2-(1,1-dioxidotetrahydro-2H-thiopyran-4-yl)ethyl methanesulfonate (37 mg, 0.144 mmol) in THF (2 mL) was added lithium bromide (37.6 mg, 0.433 mmol). The mixture was stirred at room temperature for 18 h. The solvent was removed and the residue was dissolved in DCM (20 mL) and washed with brine (20 mL). The aqueous layer was extracted with DCM (2×20 mL). The combined DCM layers were dried over Na₂SO₄ and concentrated under reduced pressure. The crude product was purified by flash chromatography on silica gel column eluted with 40-75% EtOAc/Hexane using ELS detector to give the desired product as a solid (30 mg, 86%). LCMS m/e 241.05 (M+H)⁺, 1.5 minutes (method 3). ¹H NMR (400 MHz, CHLOROFORM-d) δ 3.46 (t, J=6.4 Hz, 2H), 3.12-2.94 (m, 4H), 2.17-2.07 (m, 2H), 1.96-1.80 (m, 5H).

Preparation of 4-(1-amino-2-methylpropan-2-yl)thiomorpholine 1,1-dioxide

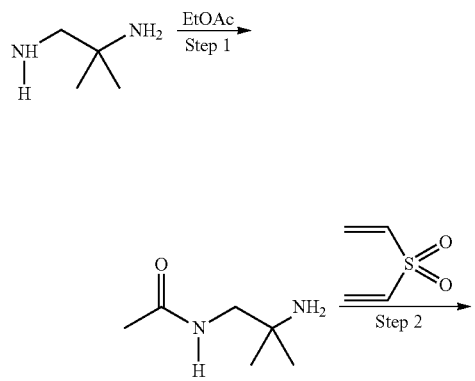

Step 1: Preparation of N-(2-amino-2-methylpropyl)acetamide

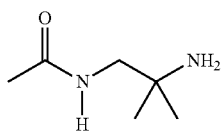

The title intermediate was prepared in accordance with the procedures published in U.S. Pat. No. 4,906,661, in 82%. ¹H NMR (500 MHz, CHLOROFORM-d) δ 6.01 (br. s., 1H), 3.15 (d, J=5.8 Hz, 2H), 2.04 (s, 3H), 1.14 (s, 6H).

Step 2: Preparation of N-(2-(1,1-dioxidothiomorpholino)-2-methylpropyl)acetamide

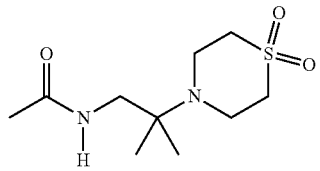 [SMILES: CC(=O)NCC(C)(C)N1CCS(=O)(=O)CC1]

To a solution of N-(2-amino-2-methylpropyl)acetamide (2.3 g, 17.67 mmol) in 2-propanol (28 mL) was added (vinylsulfonyl)ethene (2.3 g, 19.47 mmol) in a resealable pressure vessel. It was flushed with nitrogen and heated at 100° C. for 4 hours. After cooling to room temperature, a solid started to separate. The solid was filtered, washed with isopropanol and dried to give the desired product (2.7 gm, 61.5%). ¹H NMR (500 MHz, CHLOROFORM-d) δ 5.73 (br. s., 1H), 3.28 (d, J=5.2 Hz, 2H), 3.12-3.00 (m, 8H), 2.04 (s, 3H), 1.15-1.10 (m, 6H).

Step 3: Preparation of 4-(1-amino-2-methylpropan-2-yl)thiomorpholine 1,1-dioxide

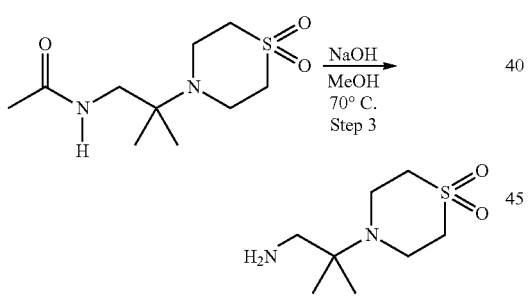

A solution of N-(2-(1,1-dioxidothiomorpholino)-2-methylpropyl)acetamide (100 mg, 0.403 mmol) in MeOH (2 mL) was added 1N NaOH (2.013 ml, 2.013 mmol) and the mixture was stirred at 70° C. for 18 h. Additional NaOH (2.013 ml, 2.013 mmol) was added and the solution was stirred at 90° C. for 24 h. The reaction mixture was concentrated under reduced pressure to remove MeOH, and the residue was extracted with EtOAc (2×20 mL). The combined organic layers were dried over Na₂SO₄, filtered and concentrated under reduced pressure. The crude product was purified by flash chromatography on silica gel column eluted with 5-10% MeOH/CH₂Cl₂ using ELS detector to give the desired product as an oil in quantitative yield. LCMS m/e 207.20 (M+H)⁺, 0.268 minutes (method 3). ¹H NMR (400 MHz, CHLOROFORM-d) δ 3.07 (s, 8H), 2.71 (s, 2H), 1.11 (s, 6H).

Example 1
Preparation of diastereomeric (1R)- and (1S)-1-(fluoromethyl)-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid
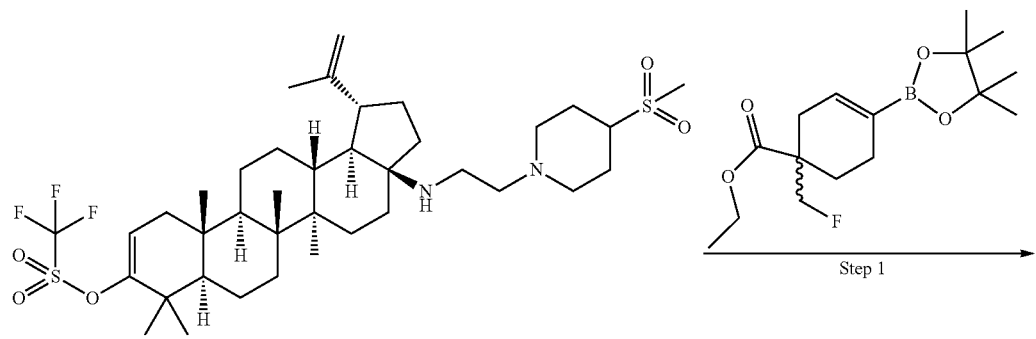
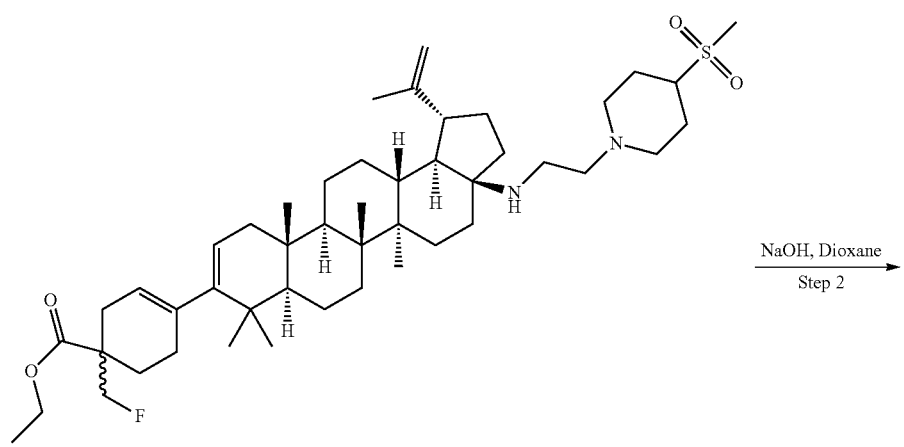
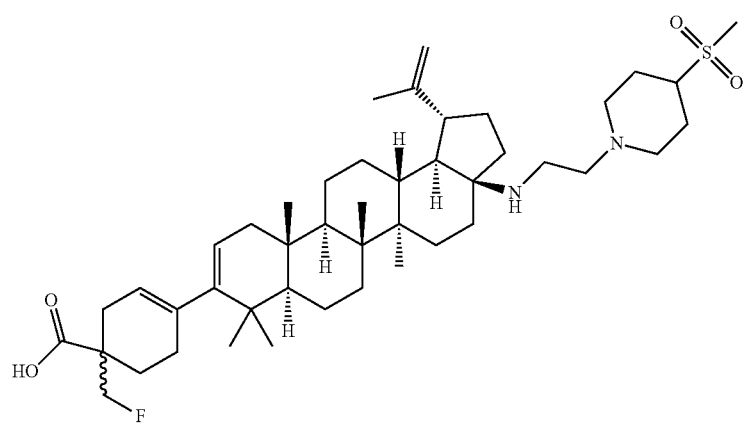
Example 1

Step 1. Preparation of ethyl 1-(fluoromethyl)-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate A mixture of (1R,3aS,5aR,5bR,7aR,11aR,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate (240 mg, 0.321 mmol) (prepared as described in WO2013123019), racemic ethyl 1-(fluoromethyl)-4-(4,4,5,5-tetramethyl-1,3,2-dioxaborolan-2-yl)cyclohex-3-enecarboxylate (91 mg, 0.291 mmol), sodium carbonate hydrate (108 mg, 0.874 mmol) and palladium tetrakis (20.21 mg, 0.017 mmol) was dissolved in dioxane (4 mL) under nitrogen. An orange solution was formed, which upon addition of water (1 mL) turned into a very pale yellow suspension. The mixture was chilled to −78° C. and evacuation/purging cycles were performed 3 times. The flask was immersed in an oil bath heated at 85° C. for a total of two hours. The resulting black suspension was diluted with ethyl acetate (20 mL) and washed with water (30 mL). The organic phase was collected and dried over sodium sulfate, filtered and concentrated under reduced pressure. The crude product was purified by flash chromatography to yield a white solid (180 mg, 79%). MS: m/e 783.47 (M+H)$^+$, 2.36 min (method 1)$^1$H NMR (400 MHz, CHLOROFORM-d) δ 5.32 (d, J=3.5 Hz, 1H), 5.18 (d, J=5.5 Hz, 1H), 4.75 (d, J=1.5 Hz, 1H), 4.62 (s, 1H), 4.58-4.37 (m, 2H), 4.25-4.15 (m, 2H), 3.24-2.41 (m, 14H), 2.27-1.76 (m, 20H), 1.70 (s, 3H), 1.64-1.31 (m, 13H), 1.10-1.04 (m, 5H), 1.00-0.88 (m, 8H), 0.85 (s, 3H). $^{19}$F NMR (376 MHz, CHLOROFORM-d) δ −225.42 (s, 1F)

Step 2

NaOH (1N, 2 mL, 2.0 mmol) was added to a solution of ethyl 1-(fluoromethyl)-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (180 mg, 0.230 mmol) in 1,4-dioxane (4 mL) and MeOH (2 mL). The mixture was stirred at 66° C. for 2 h, forming a clear solution. The crude reaction mixture was purified by preparative HPLC (Xbridge OBD prep shield RP C18 19×100 mm) (MeCN/H$_2$O/AcONH$_4$) to give 1-(fluoromethyl)-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid as a white solid (29 mg, 16.7%). MS: m/e 755.50 (M+H)$^+$, 2.548 min (method 4)$^1$H NMR (400 MHz, CHLOROFORM-d) δ 5.34 (br. s., 1H), 5.19 (br. s., 1H), 4.74 (br. s., 1H), 4.61-4.49 (m, 3H), 3.18 (d, J=10.5 Hz, 2H), 2.97-2.40 (m, 12H), 2.35-1.78 (m, 14H), 1.73-1.60 (m, 6H), 1.58-1.17 (m, 11H), 1.13 (br. s., 3H), 1.08 (m, 4H), 1.01-0.90 (m, 8H), 0.86 (br. s., 3H). $^{19}$F NMR (376 MHz, CHLOROFORM-d) δ −217.84-−231.26 (m, 1F)

Preparation of Examples 1a and 1b

HPLC separation of example 1 into (S)-1-(fluoromethyl)-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid (Example 1a) and (R)-1-(fluoromethyl)-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid (Example 1b

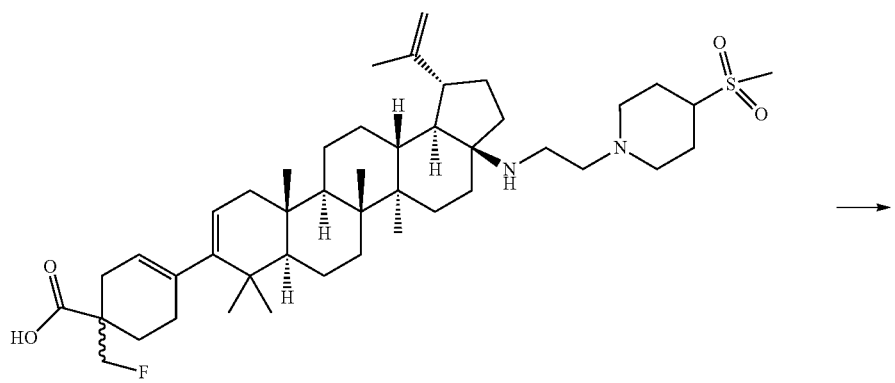

Example 1

-continued

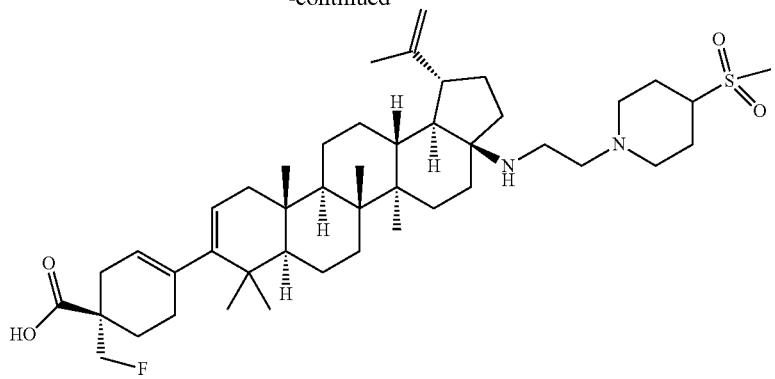

Example 1a

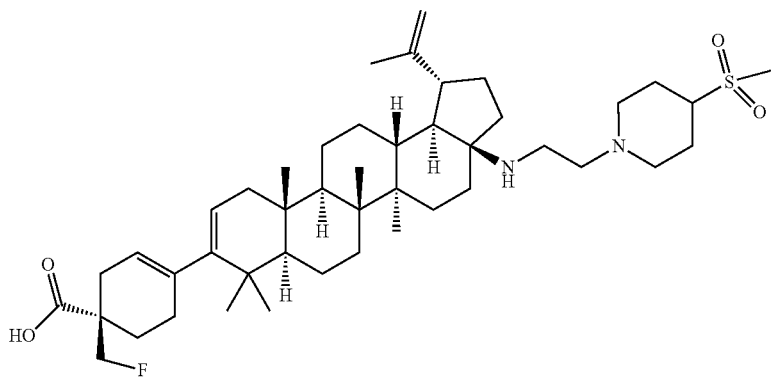

Example 1b

The two diasteroisomers were separated using preparative HPLC (method 17). The first product to elute was identified as (S)-1-(fluoromethyl)-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid (Example 1a) (white solid, 18 mg, 29.6%). MS: m/e 755.55 (M+H)$^+$, 2.620 min (method 4). $^1$H NMR (400 MHz, METHANOL-d$_4$) δ 5.35 (br. s., 1H), 5.21 (d, J=4.8 Hz, 1H), 4.85 (s, 1H), 4.74 (s, 1H), 4.63-4.39 (m, 2H), 3.51-3.43 (m, 1H), 3.41-3.37 (m, 3H), 3.28 (d, J=4.0 Hz, 1H), 3.20 (d, J=10.0 Hz, 1H), 3.10 (br. s., 1H), 3.02-2.96 (m, 3H), 2.85-2.68 (m, 2H), 2.63-2.51 (m, 2H), 2.35-1.78 (m, 16H), 1.77 (s, 3H), 1.74-1.28 (m, 15H), 1.21 (s, 3H), 1.11 (s, 3H), 0.99 (s, 3H), 0.97 (s, 3H), 0.93 (s, 3H). $^{19}$F NMR (376 MHz, METHANOL-d$_4$) δ −227.00 (s, 1F).

The second compound isolated was identified as: (R)-1-(fluoromethyl)-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, (Example 1b), (white solid, 20 mg, 32.8%) MS: m/e 755.55 (M+H)$^+$, 2.626 min (method 4)$^1$H NMR (400 MHz, METHANOL-d$_4$) δ 5.35 (br. s., 1H), 5.21 (d, J=4.5 Hz, 1H), 4.85 (br. s., 1H), 4.75 (s, 1H), 4.61-4.36 (m, 2H), 3.38-3.19 (m, 6H), 3.05 (m, 1H), 2.98 (s, 3H), 2.89 (d, J=7.8 Hz, 1H), 2.82-2.70 (m, 1H), 2.67-2.50 (m, 2H), 2.45-1.97 (m, 14H), 1.92-1.80 (m, 3H), 1.78 (s, 3H), 1.73-1.28 (m, 14H), 1.21 (br. s., 3H), 1.14-1.08 (m, 3H), 1.01-0.99 (m, 3H), 0.97-0.94 (m, 3H), 0.93 (s, 3H). $^{19}$F NMR (376 MHz, METHANOL-d$_4$) δ −227.04 (s, 1F).

Alternative preparation method for Example 1a:
(S)-1-(fluoromethyl)-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid bis hydrochloride salt
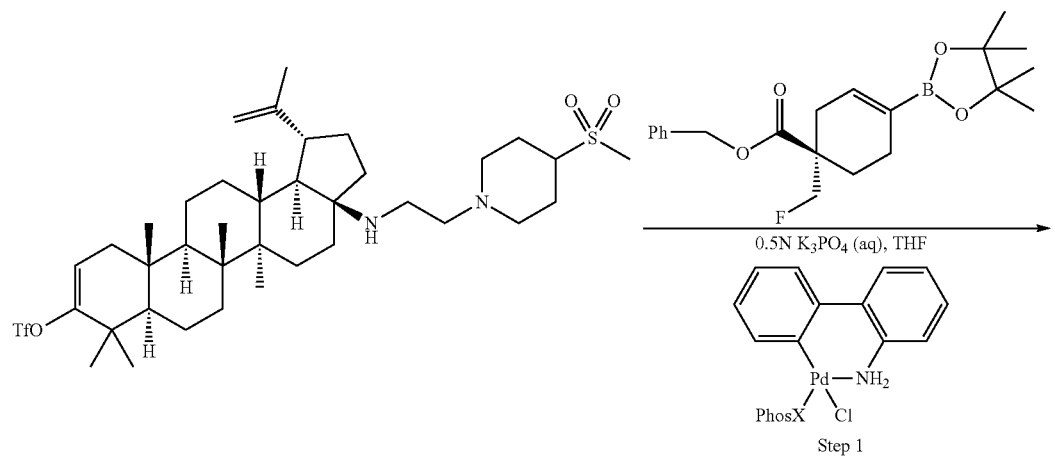
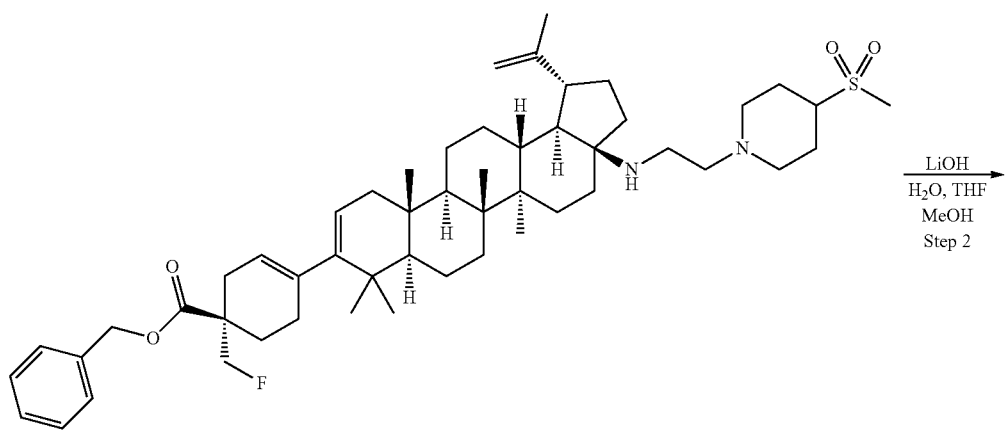
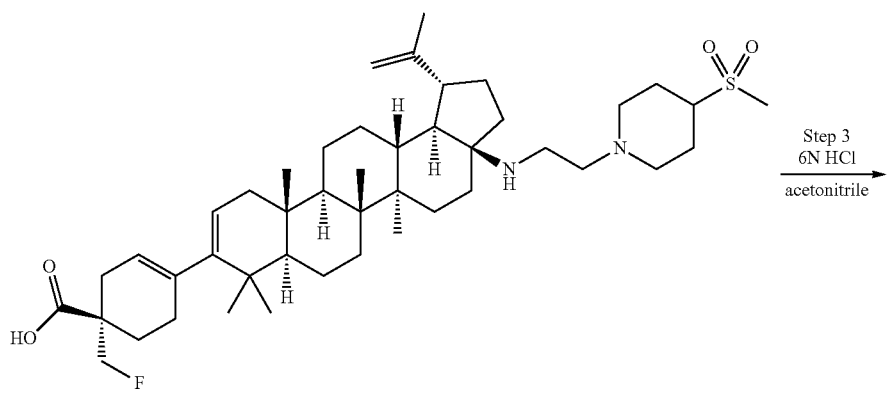

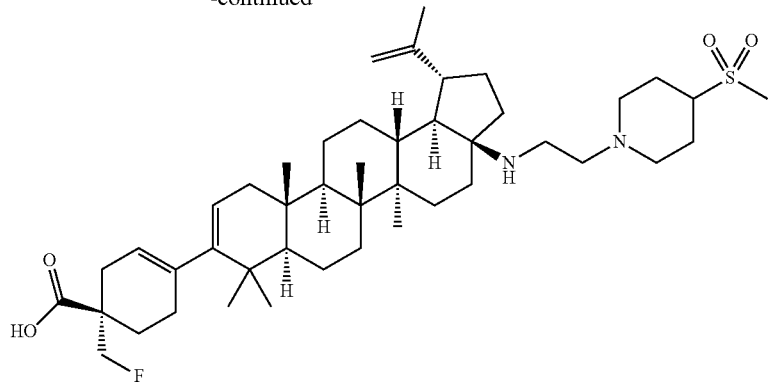

Example 1b

Step 1. Preparation of (S)-benzyl 1-(fluoromethyl)-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) cyclohex-3-enecarboxylate

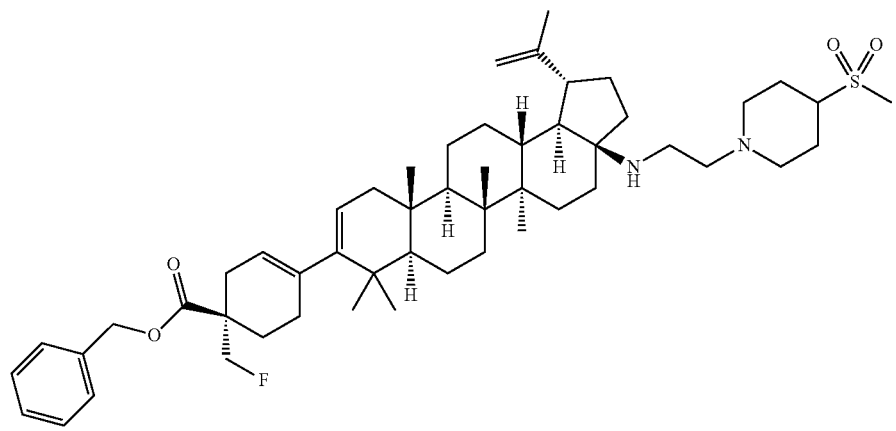

In a 350 mL glass pressure vessel with threaded stopper were combined (1R,3aS,5aR,5bR,7aR,11aR,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate (9.00 g, 12.05 mmol), (S)-benzyl 1-(fluoromethyl)-4-(4,4,5,5-tetramethyl-1,3,2-dioxaborolan-2-yl)cyclohex-3-enecarboxylate (4.96 g, 13.25 mmol) and chloro(2-dicyclohexylphosphino-2',4',6'-triisopropyl-1,1'-biphenyl)[2-(2'-amino-1,1'-biphenyl)]palladium(II) (X-Phos aminobiphenyl palladium chloride precatalyst, XPhos-Pd-G2, 0.569 g, 0.723 mmol). The vessel was purged with nitrogen, and to the reaction flask was added anhydrous THF (180 mL). A freshly prepared aqueous 0.5 M $K_3PO_4$ solution was purged with nitrogen gas and added to the vessel (60.2 mL, 30.1 mmol). The vessel was sealed and the resulting yellow solution was stirred at 80° C. The color of the mixture darkened to a very deep green over 30 min. The mixture was heated for 18 h. The olive green colored reaction mixture was diluted with EtOAc (700 mL) and washed with 5% aqueous sodium bicarbonate (250 mL×2) and then with brine (100 mL). The aqueous phase was extracted with 2×100 mL of chloroform and the organic phases were combined, dried over $MgSO_4$, filtered and concentrated to a yellow foam solid. The crude material was purified by flash column chromatography (800 g silica, step elution 3:1 hexanes:acetone for 8 L, then 1:1 hexanes:acetone for 4 L). Mixed fractions from the first chromatography (1.0 g of material) were repurified by flash silica chromatography (80 g silica, elution gradient 100% hexanes to 3:1 hexanes:acetone over 8 column volumes, hold 3:1 hexanes:acetone for 10 column volumes). Thus was obtained the desired material (7.18 g, 70.5% yield) as a yellow foamy solid. LCMS: m/e 845.6 (M+H)+, 1.57 min (method 6). $^1$H NMR (400 MHz, CHLOROFORM-d) δ 7.41-7.31 (m, 5H), 5.32 (s, 2H), 5.23-5.15 (m, 2H), 5.13 (dd, J=6.0, 1.6 Hz, 1H), 4.73 (d, J=2.2 Hz, 1H), 4.64-4.44 (m, 3H), 3.13 (dd, J=15.4, 13.0 Hz, 2H), 2.89-2.78 (m, 4H), 2.68-2.53 (m, 4H), 2.52-2.41 (m, 2H), 2.21-1.16 (m, 31H), 1.13-0.99 (m, 7H), 0.97 (s, 3H), 0.91 (s, 3H), 0.90 (s, 3H), 0.85 (s, 3H). $^{19}$F NMR (376 MHz, CHLOROFORM-d) δ −225.07 (t, J=46.8 Hz, 1F).

Step 2. Preparation of (S)-1-(fluoromethyl)-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) cyclohex-3-enecarboxylic acid

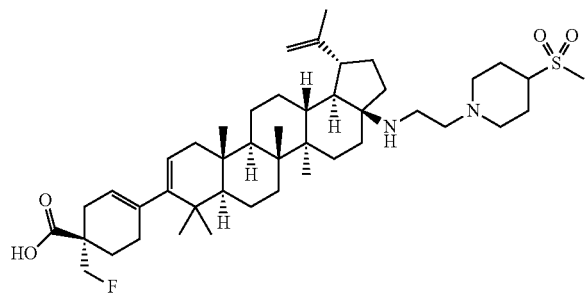

In a 500 mL round bottom flask were combined (S)-benzyl 1-(fluoromethyl)-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (7.17 g, 8.48 mmol) with lithium hydroxide, 1.0 M aqueous (42.4 mL, 42.4 mmol) and tetrahydrofuran (50 mL) and MeOH (50 mL). The mixture was heated to 75° C. for 2.5 h. The nearly black mixture was concentrated under reduced pressure to leave a solid residue. The residue was redissolved in a mixture of acetonitrile (50 mL) and chloroform (50 mL) and the black solution was treated dropwise with trifluoroacetic acid (6.54 mL, 85 mmol). The mixture was then concentrated under reduced pressure to leave a two-phase mixture (black oil with clear liquid floating above). This mixture was diluted with acetonitrile:chloroform (150 mL) and concentrated under reduced pressure again. This dissolution/reconcentration was repeated once more to give a black oil which was placed under high vacuum overnight. The black oil solidified overnight to a foam. The crude black solid was dissolved in a mixture of chloroform (20 mL) and acetone (5 mL) and was loaded onto a short column composed of silica (approx 60 g) with celite on top (approx 25 g). Elution with 1:1 acetone:chloroform (500 mL) followed by 3:1 acetone:chloroform (1000 mL) removed the black color, and product eluted as a yellow band. Product fractions were combined and concentrated under reduced pressure to a leave hygroscopic yellow foam solid (16 g). A portion of this solid (approx 1.4 g) was readily dissolved in 5 mL of 80:20 acetonitrile:water and loaded onto a 130 g Isco Redisep Rf Gold C18 cartridge. Solvent A=90% water, 10% acetonitrile, 0.1% TFA. Solvent B=10% water, 90% acetonitrile, 0.1% TFA. Elution gradient 30-100% B over 8 column volumes, then hold 100% B for 8 column volumes. Concentration under reduced pressure of the product-containing fractions afforded a clean white powder. This pure material was set aside as Batch 1. The remainder of the crude material (approx 14.5 g) was readily dissolved in 20 mL of an 80:20 mixture of acetonitrile:water. This crude material was purified by reverse phase preparative HPLC in 9 injections using prep HPLC method 1. The pure material obtained in this manner was combined with the previously obtained Batch 1 pure material to give 6.32 g of clean white powder (Batch 2) along with slightly impure material (1.40 g) from mixed fractions. The mixed fractions material (1.40 g) was loaded in minimum 80:20 acetonitrile:water onto a 130 g Isco Redisep Rf Gold C18 cartridge. Solvent A=90% water, 10% acetonitrile, 0.1% TFA. Solvent B=10% water, 90% acetonitrile, 0.1% TFA. Elution gradient 30-100% B over 10 column volumes, then hold 100% B for 4 column volumes. Concentration under reduced pressure of the product-containing fractions afforded a clean white foam (1.17 g). This material was combined with the clean Batch 2 material to provide the title compound as the TFA salt (7.41 g, 89% yield, white foam). LCMS: m/e 755.6 (M+H)$^+$, 1.29 min (method 6). $^1$H NMR (400 MHz, Acetic) δ 5.39 (br. s., 1H), 5.24 (d, J=4.6 Hz, 1H), 4.85 (s, 1H), 4.74 (s, 1H), 4.56 (dm, J=47.2 Hz, 2H), 3.93-3.65 (m, 6H), 3.43 (tt, J=11.3, 3.9 Hz, 1H), 3.26 (t, J=12.3 Hz, 2H), 3.02 (s, 3H), 2.86-2.73 (m, 1H), 2.61 (d, J=16.6 Hz, 1H), 2.43 (d, J=13.0 Hz, 2H), 2.35-2.13 (m, 7H), 2.13-2.09 (m, 1H), 2.01-1.78 (m, 4H), 1.78-1.70 (m, 4H), 1.69-1.45 (m, 9H), 1.45-1.27 (m, 3H), 1.24-1.12 (m, 5H), 1.10 (s, 3H), 1.01 (s, 3H), 0.99 (s, 3H), 0.95 (s, 3H). $^{19}$F NMR (376 MHz, Acetic) δ −76.46 (s, 1F), −225.82 (t, J=46.8 Hz, 1F).

Step 3

In a 500 mL round bottom flask with magnetic stir bar were combined acetonitrile (150 mL) with hydrochloric acid, 6.0M aqueous (37.1 mL, 223 mmol). To the rapidly stirred mixture was added via a dropping funnel a solution of (S)-1-(fluoromethyl)-4-((1R,3aS,5 aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA salt (7.30 g, 7.42 mmol) dissolved in acetonitrile (60 mL). Almost immediately a white precipitate formed and became heavier as the addition progressed. Addition was completed over 20 min total. The milky white suspension was stirred at rt for 1.25 h. The suspension was chilled in an ice bath and the very fine white solid thus produced was isolated by filtration, rinsed with ice cold acetonitrile, allowed to air dry and then dried under high vacuum at rt. Thus was isolated the desired product as a white powder (5.857 g, 95% yield). LCMS: m/e 755.5 (M+H)$^+$, 1.27 min (method 6). $^1$H NMR (400 MHz, Acetic) δ 5.39 (br. s., 1H), 5.25 (d, J=4.6 Hz, 1H), 4.89 (s, 1H), 4.75 (s, 1H), 4.55 (dm, J=47.2 Hz, 2H), 4.13-3.87 (m, 4H), 3.82 (br. s., 2H), 3.55-3.42 (m, 2H), 3.39 (br. s., 1H), 3.03 (s, 3H), 3.01-2.90 (m, 1H), 2.62 (d, J=17.9 Hz, 1H), 2.55-2.43 (m, 2H), 2.43-2.14 (m, 8H), 1.95-1.79 (m, 3H), 1.79-1.71 (m,4H), 1.69-1.47 (m, 9H), 1.47-1.28 (m, 4H), 1.22 (s, 3H), 1.19-1.12 (m, 3H), 1.10 (s, 3H), 1.01 (s, 3H), 0.99 (s, 3H), 0.96 (s, 3H). $^{19}$F NMR (376 MHz, Acetic) δ −225.81 (t, J=45.1 Hz, 1F).

Alternative method of preparation for Example 1b
Preparation of (R)-1-(fluoromethyl)-4-((1R,3aS, 5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b, 6,7,7a,8,11,11a,11b,12,13,13a,13b-octadecahydro-1H-cyclopenta[a]chrysen-9-yl)cyclohex-3-enecarboxylic acid
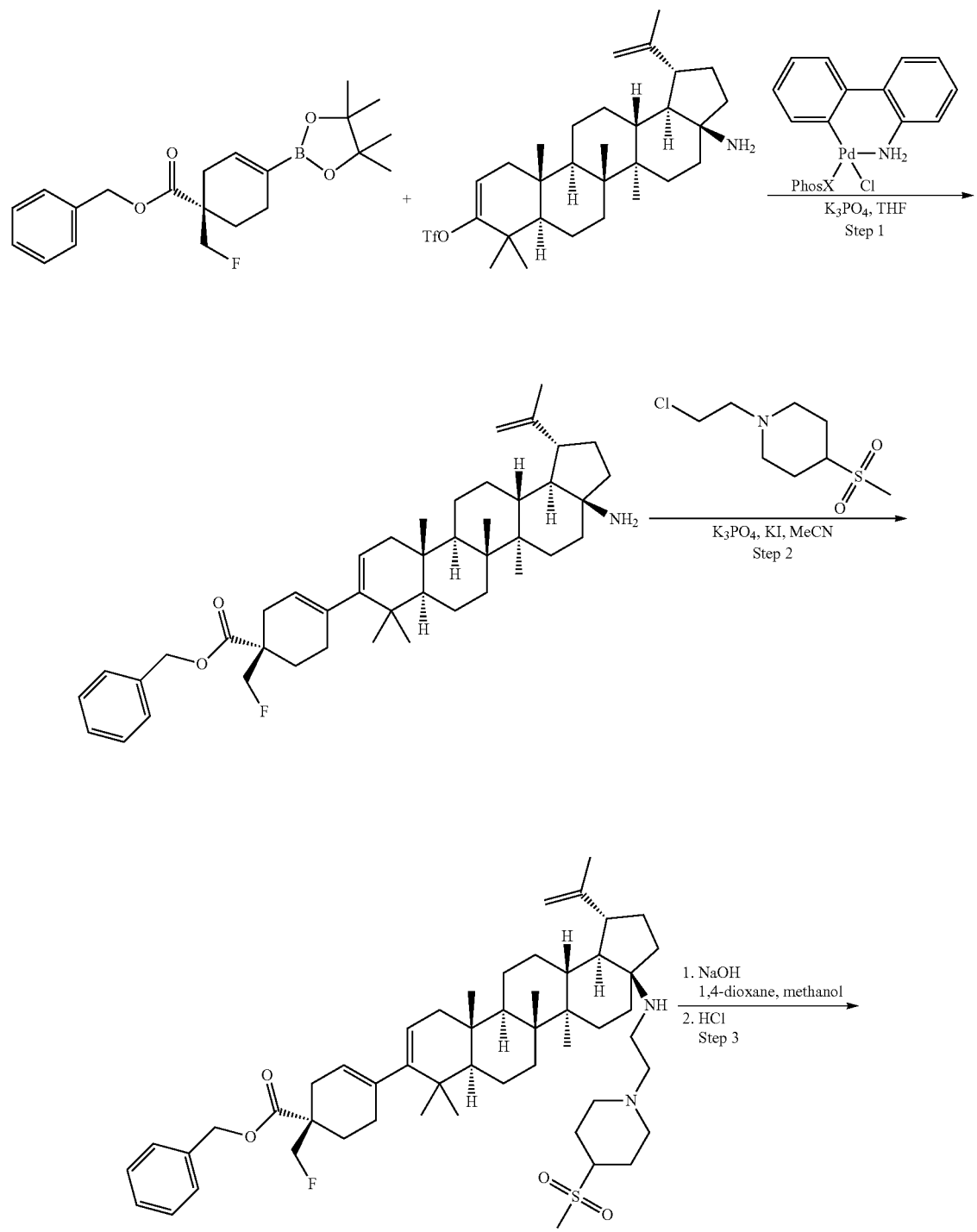

Step 1. Preparation of (R)-benzyl 4-((1R,3aS,5aR, 5bR,7aR,11aS,11bR,13aR,13bR)-3a-amino-5a,5b,8, 8,11a-pentamethyl-1-(prop-1-en-2-yl)-2,3,3a,4,5,5a, 5b,6,7,7a,8,11,11a,11b,12,13,13a,13b- octadecahydro-1H-cyclopenta[a]chrysen-9-yl)-1- (fluoromethyl)cyclohex-3-enecarboxylate

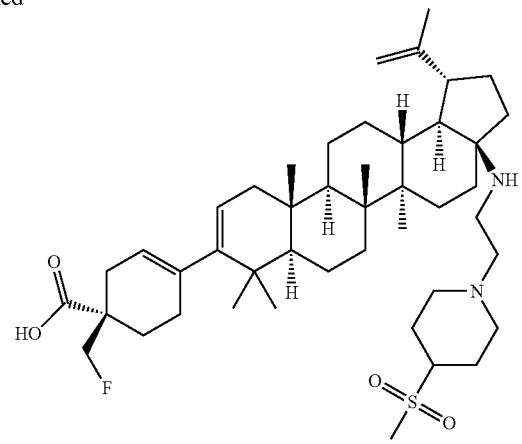

Example 1b

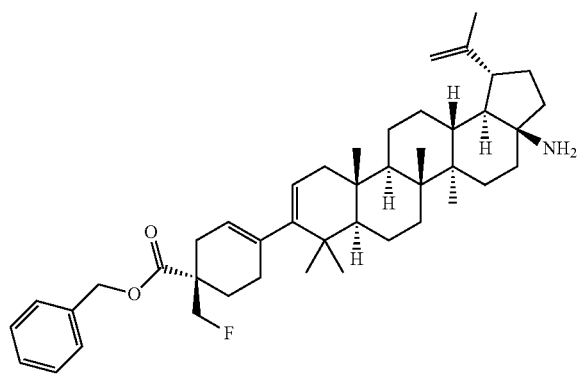

To a flask containing (1R,3aS,5aR,5bR,7aR,11aR,11bR, 13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl trifluoromethanesulfonate (3.0 g, 5.38 mmol), (R)-benzyl 1-(fluoromethyl)-4-(4,4,5,5-tetramethyl-1,3,2-dioxaborolan-2-yl)cyclohex-3-enecarboxylate (2.013 g, 5.38 mmol) (prepared as described in WO2013169578, and potassium phosphate tribasic (3.43 g, 16.14 mmol) was added the second generation Buchwald X-Phos precatalyst (0.042 g, 0.134 mmol). The mixture was diluted with THF (20 mL) and water (4 mL), flushed with nitrogen and heated to 50° C. After heating the mixture for 15.5 h, it was cooled to rt and partially concentrated under reduced pressure. The mixture was diluted with water (75 mL) and extracted with ethyl acetate (3×75 mL). The organic layers were dried over magnesium sulfate, filtered, and concentrated under reduced pressure. The residue was purified by flash chromatography using a 0-10% methanol in dichloromethane gradient and a 220 g silica gel column to give the title product (3.34 g, 95% yield) as an off-white foam. LCMS: m/e: 656.6 (M+H)+, 2.30 min (method 1). $^1$H NMR (500 MHz, CHLOROFORM-d) δ=7.39-7.30 (m, 5H), 5.32 (br. s., 1H), 5.21-5.15 (m, 2H), 5.11 (dd, J=6.1, 1.9 Hz, 1H), 4.73 (d, J=2.0 Hz, 1H), 4.61 (dd, J=2.1, 1.3 Hz, 1H), 4.53 (dm, J=47.3 Hz, 2H), 2.64-2.51 (m, 2H), 2.23-1.93 (m, 7H), 1.70 (s, 3H), 1.07 (s, 3H), 0.96 (s, 3H), 0.93 (s, 3H), 0.87 (s, 3H), 0.85 (s, 3H), 1.85-0.83 (m, 22H).

Step 2. Preparation of (R)-benzyl 1-(fluoromethyl)- 4-((1R,3aS,5aR,5bR,7aR,11aS,11bR,13aR,13bR)-5a, 5b,8,8,11a-pentamethyl-3a-((2-(4-(methylsulfonyl) piperidin-1-yl)ethyl)amino)-1-(prop-1-en-2-yl)-2,3, 3a,4,5,5a,5b,6,7,7a,8,11,11a,11b,12,13,13a,13b- octadecahydro-1H-cyclopenta[a]chrysen-9-yl) cyclohex-3-enecarboxylate

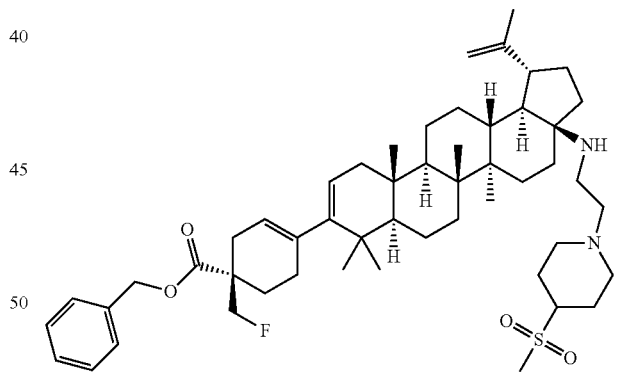

To a sealable flask containing benzyl 4-((1R,3aS,5aR, 5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)-1-(fluoromethyl)cyclohex-3-enecarboxylate (3.34 g, 5.09 mmol) was added phosphoric acid, potassium salt (5.40 g, 25.5 mmol), potassium iodide (0.930 g, 5.60 mmol), and 1-(2-chloroethyl)-4-(methylsulfonyl)piperidine- .HCl (4.01 g, 15.28 mmol). The mixture was diluted with acetonitrile (50 mL), flushed with nitrogen, then the flask was sealed and heated to 100° C. After 4 h of heating, the mixture was cooled to rt and stirred overnight at rt. The mixture was diluted with 50 mL of acetonitrile and an additional 1 g of 1-(2-chloroethyl)-4-(methylsulfonyl)piperidine.HCl was added. The flask was sealed and the mixture was heated to 100° C. for 2 h. The mixture was cooled to rt and concentrated under reduced pressure. The residue was diluted with water (75 mL) and extracted with dichloromethane (3×75 mL). The combined organic layers were dried over sodium sulfate, filtered, and concentrated under reduced pressure. The residue was purified by flash chromatography using a 0-8% MeOH in dichloromethane gradient and a 220 g silica gel column. The fractions containing the product were combined and concentrated under reduced pressure. The residue was repurified by reverse phase chromatography (150 g C18 column, 30-90% acetonitrile in water gradient with 0.1% TFA added) to give the TFA salt of the title product (3.17 g, 3.30 mmol, 64.9% yield) as a white foam. LCMS: m/e: 845.6 (M+H)$^+$, 2.10 min (method 1). $^1$H NMR (500 MHz, CHLOROFORM-d) δ=7.39-7.30 (m, 5H), 5.32 (br. s., 1H), 5.21-5.15 (m, 2H), 5.11 (dd, J=6.1, 1.7 Hz, 1H), 4.78 (s, 1H), 4.70 (s, 1H), 4.53 (dm, J=47.1 Hz, 2H), 3.44-3.21 (m, 6H), 3.17-3.08 (m, 1H), 3.05-2.97 (m, 1H), 2.90 (s, 3H), 2.79-2.57 (m, 4H), 1.69 (s, 3H), 1.12 (s, 3H), 1.02 (s, 3H), 0.92 (s, 3H), 0.87 (s, 3H), 0.86 (s, 3H), 2.37-0.83 (m, 31H).

Step 3

To a solution of (R)-benzyl 1-(fluoromethyl)-4-((1R,3aS, 5aR,5bR,7aR,11aS,11bR,13aR,13bR)-5a,5b,8,8,11a-pentamethyl-3a-((2-(4-(methylsulfonyl)piperidin-1-yl)ethyl) amino)-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)cyclohex-3-enecarboxylate (3.17 g, 3.75 mmol) in 1,4-dioxane (30 mL) and methanol (10 mL) was added NaOH (3N) (7.50 mL, 22.50 mmol) and the mixture was heated to 80° C. for 17 h. The mixture was cooled to rt and partially concentrated under reduced pressure. The mixture was made acidic by adding 1N HCl, and the solids that formed were collected by filtration. To the collected solid material was added 20 mL of water and 1N NaOH solution (9.38 mL, 9.38 mmol). The mixture was stirred for ten minutes, then concentrated under reduced pressure. The residue was diluted with water (20 mL) and acetonitrile (30 mL) and treated with TFA (1.445 mL, 18.75 mmol). The mixture was then concentrated under reduced pressure and was adsorbed to silica gel and purified using a 20-30% chloroform in acetone gradient and a 220 g silica gel column. The fractions containing the expected product were combined and concentrated under reduced pressure to give the product as the TFA salt. To convert to the HCl salt, the residue was diluted with 200 mL acetonitrile and 6N HCl solution (6.66 mL, 40.0 mmol) was added. Solids formed and the mixture was diluted with 20 mL of chloroform. The solids did not dissolve, so the mixture was concentrated under reduced pressure. The residue was diluted again with acetonitrile and chloroform and 6N HCl (6.66 mL, 40.0 mmol) was added. The mixture was concentrated under reduced pressure and the procedure was repeated a third time. The solids were then diluted with acetonitrile and heated to reflux, then were cooled to rt and collected by filtration to give the HCl salt of the expected product. Since an impurity of ~1.5% was still present, the mixture was reconverted to the TFA salt for purification by adding 20 mL of water and 1N NaOH (8.26 mL, 8.26 mmol), stirring for several minutes, then concentrated under reduced pressure. The residue was then diluted with water (20 mL) and acetonitrile (30 mL) and was treated with TFA (1.273 mL, 16.52 mmol). The mixture was concentrated under reduced pressure and was adsorbed to silica gel and purified using a 20-30% chloroform in acetone gradient and a 220 g silica gel column. The fractions containing the title compound were combined and concentrated under reduced pressure to give the product as the TFA salt. HPLC of the residue still showed minor impurities present. The mixture was purified again using a 150 g C18 column and a 30-90% acetonitrile in water gradient with 0.1% TFA added. The fractions containing the expected product were combined and concentrated under reduced pressure to give the product as a white solid, the TFA salt of the title product. To convert to the HCl salt, the residue was dissolved in acetonitrile and was treated with 6N HCl solution (6.66 mL, 40.0 mmol), then was concentrated under reduced pressure. This process was repeated two additional times, then the solids were diluted with acetonitrile, heated to reflux, cooled, and collected by filtration to give (R)-1-(fluoromethyl)-4-((1R,3aS,5aR,5bR, 7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) cyclohex-3-enecarboxylic acid, bis HCl salt (1.6 g, 1.859 mmol, 49.6% yield) as a white solid. LCMS: m/e: 755.5 (M+H)$^+$, 1.69 min (method 1). $^1$H NMR (400 MHz, Acetic acid-d$_4$) δ=5.37 (br. s., 1H), 5.22 (d, J=4.8 Hz, 1H), 4.86 (s, 1H), 4.72 (s, 1H), 4.53 (dm, J=47.0 Hz, 2H), 4.09-3.72 (m, 6H), 3.51-3.27 (m, 3H), 3.01 (s, 3H), 2.98-2.88 (m, 1H), 2.59 (d, J=17.6 Hz, 1H), 2.52-2.40 (m, 2H), 1.74 (s, 3H), 1.19 (s, 3H), 1.08 (s, 3H), 2.39-1.04 (m, 29H), 1.00 (s, 3H), 0.95 (s, 3H), 0.93 (s, 3H). C45H71FN2O4S.2.0 HCl.1.530 H2O.

Example 2

Preparation of diasteromeric (1R)- and (1S)-4-((1R, 3aS,5aR,5bR,7aR,11aS,11bR,13aR,13bR)-3a-((2-(1, 1-dioxidothiomorpholino)ethyl)amino)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)-1-(fluoromethyl)cyclohex-3-enecarboxylic acid

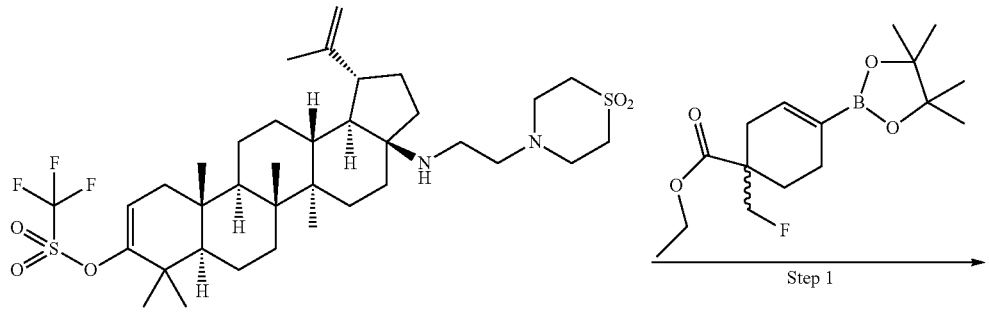

Step 1

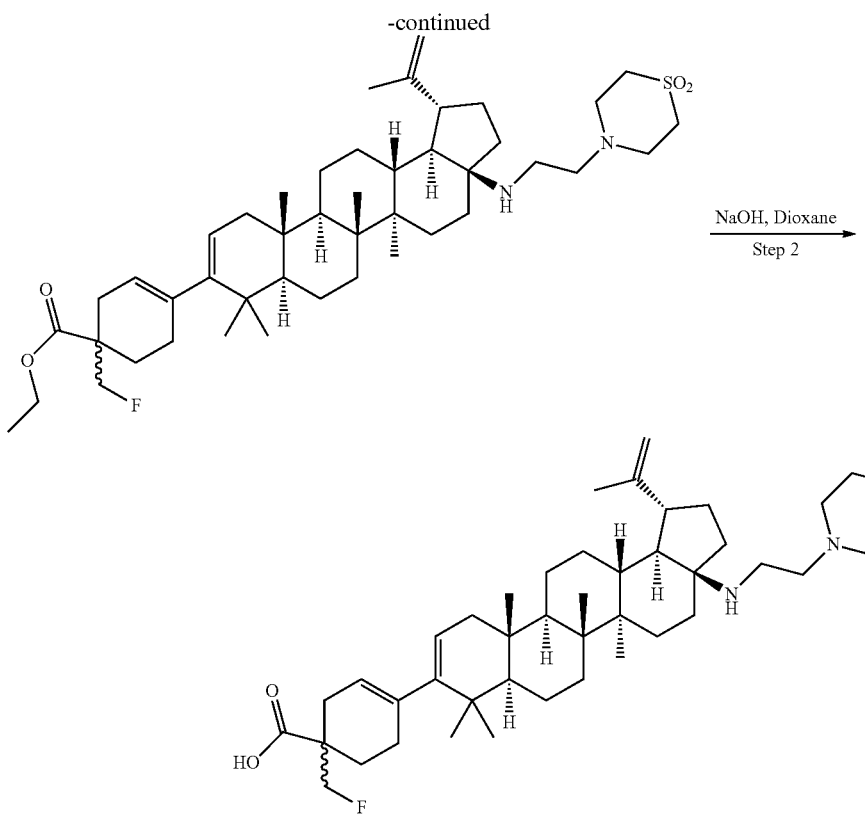

Example 2

Step 1. Preparation of ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate The title compound was prepared in 82% yield following the procedure described above for preparation of ethyl 1-(fluoromethyl)-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate, using (1R,3aS,5aR,5bR,7aR,11aR,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate (prepared as described in WO2013123019) instead of (1R,3aS,5aR,5bR,7aR,11aR,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate as the reactant. MS: m/e 755.55 (M+H)$^+$, 2.706 min (method 4) $^1$H NMR (400 MHz, CHLOROFORM-d) δ 5.32 (d, J=3.5 Hz, 1H), 5.18 (d, J=5.8 Hz, 1H), 4.73 (d, J=1.8 Hz, 1H), 4.66-4.58 (m, 1H), 4.56-4.39 (m, 2H), 4.26-4.15 (m, 2H), 3.17-2.92 (m, 8H), 2.83-2.45 (m, 6H), 2.22-2.05 (m, 3H), 2.03-1.72 (m, 5H), 1.69 (s, 3H), 1.65-1.26 (m, 16H), 1.23 (br. s., 3H), 1.18-1.02 (m, 7H), 1.01-0.89 (m, 8H), 0.86 (s, 3H), $^{19}$F NMR (376 MHz, CHLOROFORM-d) δ −225.41 (s, 1F).

Step 2

The title compound was prepared in 11.5% yield following the procedure described above in step 2 for the preparation of ethyl 1-(fluoromethyl)-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate, using ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate instead of ethyl 1-(fluoromethyl)-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate as the reactant. MS: m/e 727.55 (M+H)$^+$, 2.527 min (method 4) $^1$H NMR (400 MHz, CHLOROFORM-d) δ 5.34 (br. s., 1H), 5.18 (br. s., 1H), 4.76 (br. s., 1H), 4.64-4.56 (m, 2H), 4.48 (br. s., 1H), 3.26-2.94 (m, 8H), 2.90-2.38 (m, 6H), 2.32-1.77 (m, 10H), 1.70 (m, 6H), 1.61-1.17 (m, 12H), 1.15-1.03 (m, 6H), 1.01-0.91 (m, 8H), 0.87 (br. s., 3H), $^{19}$F NMR (470 MHz, CHLOROFORM-d) δ −225.02 (br. s., 1F).

Preparation of Examples 2a and 2b

HPLC separation of Example 2 into (S)-4-((1R,3aS, 5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid (Example 2a) and (R)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid (Example 2b)

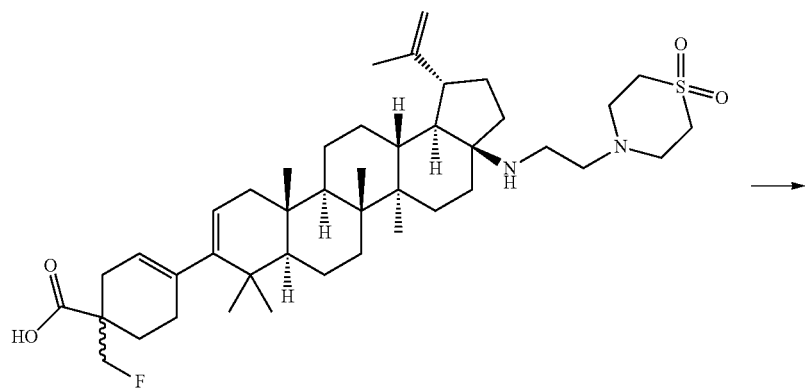

Example 2

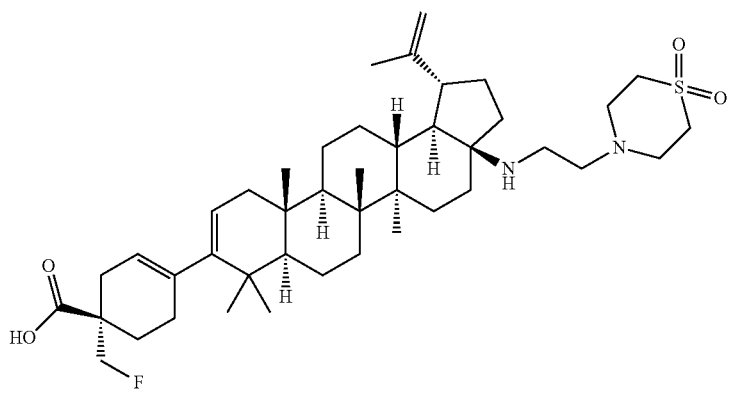

Example 2a

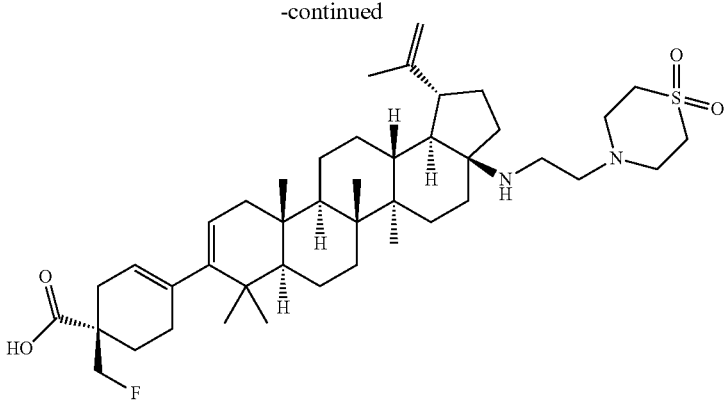

Example 2b

The two diasteroisomers were separated using preparative HPLC (method 17). The first product to elute was identified as (S)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid, (Example 2a) (white solid, 7 mg, 33%). MS: m/e 727.55 (M+H)+, 2.650 min (method 4) $^1$H NMR (400 MHz, METHANOL-d4) δ 5.35 (br. s., 1H), 5.27-5.15 (m, 1H), 4.87-4.80 (m, 1H), 4.73 (br. s., 1H), 4.62-4.37 (m, 2H), 3.29-3.17 (m, 8H), 3.16-3.05 (m, 3H), 3.02-2.86 (m, 1H), 2.80 (td, J=11.0, 5.5 Hz, 1H), 2.63-2.46 (m, 1H), 2.36-1.80 (m, 12H), 1.76 (br. s., 3H), 1.75-1.29 (m, 15H), 1.20 (s, 3H), 1.13 (s, 3H), 1.00 (s, 3H), 0.98 (s, 3H), 0.95 (s, 3H). $^{19}$F NMR (376 MHz, METHANOL-d4) δ −227.04 (s, 1F).

The second eluting compound isolated was identified as (R)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid, (Example 2b) (white solid, 7 mg, 33%). MS: m/e 727.55 (M+H)+, 2.644 min (method 4). $^1$H NMR (400 MHz, METHANOL-d4) δ 5.36 (br. s., 1H), 5.22 (d, J=4.5 Hz, 1H), 4.88-4.81 (m, 1H), 4.78-4.68 (m, 1H), 4.64-4.36 (m, 2H), 3.30-3.15 (m, 8H), 3.17-3.03 (m, 3H), 2.99-2.88 (m, 1H), 2.86-2.72 (m, 1H), 2.63-2.50 (m, 1H), 2.37-1.97 (m, 8H), 1.92-1.80 (m, 4H), 1.78 (s, 3H), 1.74-1.28 (m, 15H), 1.22-1.19 (m, 3H), 1.15-1.11 (m, 3H), 0.99 (br. s., 3H), 0.97 (s, 3H), 0.95-0.92 (m, 3H). $^{19}$F NMR (376 MHz, METHANOL-d4) δ −227.05 (br. s., 1F).

Alternative methods of preparation for Example 2b

Method A: (R)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid via chiral (R)-benzyl 1-(fluoromethyl)-4-(4,4,5,5-tetramethyl-1,3,2-dioxaborolan-2-yl)cyclohex-3-enecarboxylate

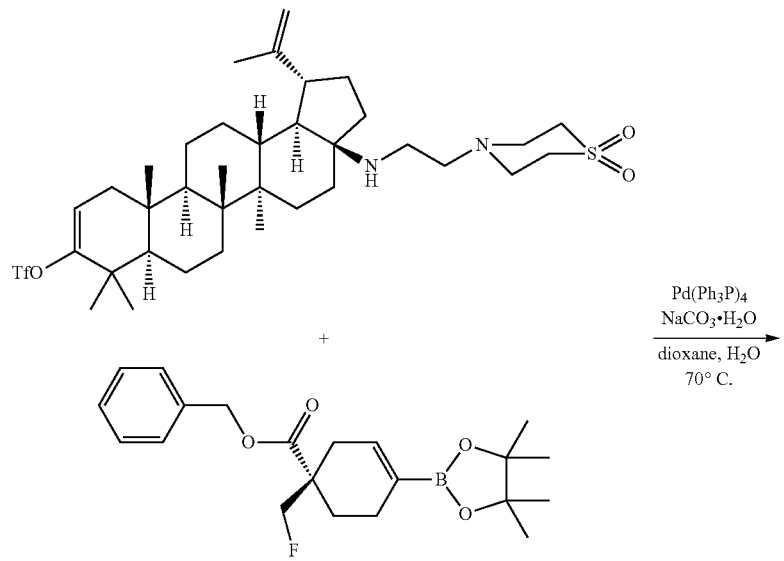

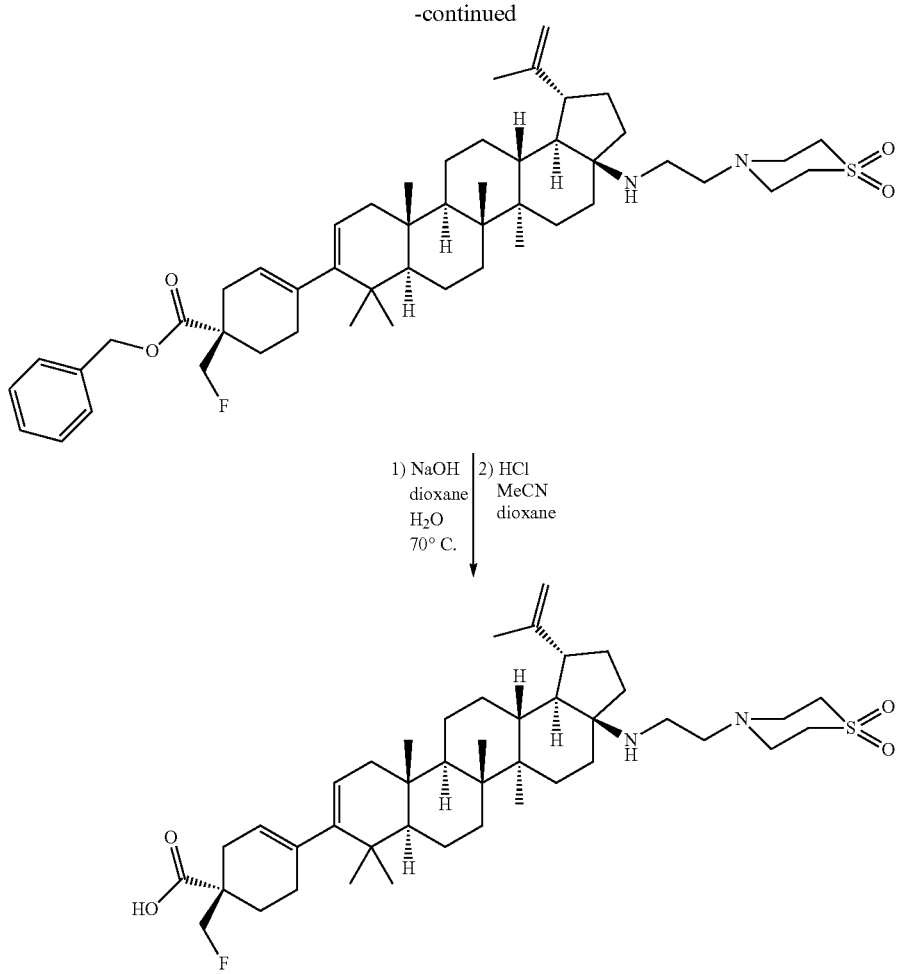

Example 2b

Step 1: Preparation of (R)-benzyl 4-((1R,3aS,5aR, 5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)-1-(fluoromethyl) cyclohex-3-enecarboxylate A mixture of (1R,3aS,5aR,5bR,7aR,11aR,11bR,13aR, 13bR)-3a-((2-(1,1-dioxidothiomorpholino)ethyl)amino)-5a, 5b,8,8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl trifluoromethanesulfonate (1.75 g, 2.434 mmol), (R)-benzyl 1-(fluoromethyl)-4-(4,4,5,5-tetramethyl-1,3,2-dioxaborolan-2-yl)cyclohex-3-enecarboxylate (1.00 g, 2.68 mmol), $Na_2CO_3 \cdot H_2O$ (0.91 g, 7.30 mmol) and $Pd(Ph_3P)_4$ (0.17 g, 0.15 mmol) in dioxane (40 mL) and water (10.00 mL) under $N_2$ was cooled to −78° C. The solution turned into a solid. Vacuuming/purging with $N_2$ cycles were performed three times. The mixture was stirred at 70° C. for 1 h. The color changed to dark brownish. The reaction mixture was concentrated under reduced pressure. The residue was diluted with $H_2O$ (100 mL) and extracted with EtOAc (3×100 mL). The combined organic layers were washed with brine (50 mL), dried over $Na_2SO_4$, filtered and concentrated under reduced pressure. The crude product was purified on silica gel column eluted with 0-35% EtOAc/Hexane to give the title compound as a solid (1.12 g, 56%). $^1H$ NMR (500 MHz, CHLOROFORM-d) δ 7.39-7.30 (m, 5H), 5.32 (s, 1H), 5.22-5.14 (m, 2H), 5.11 (d, J=5.0 Hz, 1H), 4.71 (s, 1H), 4.60 (s, 1H), 4.60-4.45 (m, 2H), 3.13-2.98 (m, 8H), 2.72-2.54 (m, 5H), 2.51-2.43 (m, 1H), 2.23-1.00 (m, 27H), 1.69 (s, 3H), 1.06 (s, 3H), 0.96 (s, 3H), 0.93 (s, 3H), 0.87 (s, 3H), 0.85 (s, 3H). $^{13}C$ NMR (126 MHz, CHLOROFORM-d) δ 174.30, 150.72, 147.90, 139.10, 135.94, 128.52, 128.13, 127.97, 121.41, 121.30, 109.41, 87.60, 86.21, 66.62, 62.72, 57.21, 52.91, 51.29, 51.00, 49.71, 49.39, 47.38, 45.84, 45.70, 41.98, 41.64, 40.64, 38.71, 37.46, 36.80, 36.09, 34.14, 33.61, 30.05, 29.74, 29.18, 29.14, 29.06, 28.66, 26.79, 26.43, 26.39, 25.24, 21.52, 21.36, 19.66, 19.56, 16.30, 16.04, 14.34. $^{19}F$ NMR (470 MHz, CHLOROFORM-d) δ −225.09 (t, J=47.3 Hz, 1F). MS m/e 817.50 $(M+H)^+$, 2.32 min (method 5).

Step 2

A solution of (R)-benzyl 4-((1R,3aS,5aR,5bR,7aR,11aS, 11bR,13aR,13bR)-3a-((2-(1,1-dioxidothiomorpholino) ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (2.3 g, 2.81 mmol) in 1,4-dioxane (60 mL) and $H_2O$ (30 mL) was cooled in an ice bath, and 1N NaOH (28 mL, 28 mmol) was added. The resulted cloudy mixture was warmed to RT then stirred at 70° C. for 2 h. The reaction mixture was cooled to RT and then placed in an ice bath before it was neutralized with 0.5N HCl. The mixture was stirred overnight. The precipitated solid was collected by filtration, washed with MeOH—H$_2$O and dried under vacuum. The solid was dissolved in MeCN (80 mL) and dioxane (20 mL), and 6 N HCl (50 mL) was added dropwise. The mixture was stirred for 1 h. The precipitated solid was collected by filtration, washed with MeCN and dried under vacuum to give (R)-benzyl 4-((1R, 3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)-1-(fluoromethyl)cyclohex-3-enecarboxylate as the bis-HCl salt (1.95 g, 90%). $^1$H NMR (400 MHz, METHANOL-d$_4$) δ 5.34 (s, 1H), 5.20 (dd, J=6.1, 1.6 Hz, 1H), 4.87 (s, 1H), 4.74 (s, 1H), 4.58-4.39 (m, 2H), 3.45-3.11 (m, 12H), 2.87 (td, J=11.0, 5.5 Hz, 1H), 2.55 (d, J=16.6 Hz, 1H), 2.34-1.08 (m, 27H), 1.77 (s, 3H), 1.19 (s, 3H), 1.11 (s, 3H), 0.99 (s, 3H), 0.95 (s, 3H), 0.93 (s, 3H). $^{13}$C NMR (126 MHz, METHANOL-d$_4$) δ 178.20, 149.71, 149.37, 140.47, 123.31, 122.51, 112.28, 89.36, 87.98, 73.56, 54.52, 51.90, 50.64, 50.43, 49.82, 47.03, 46.91, 46.76, 43.44, 42.95, 42.13, 40.78, 38.87, 38.77, 37.41, 34.96, 33.19, 30.55, 30.46, 30.42, 30.38, 29.37, 27.91, 27.72, 27.67, 27.54, 26.53, 22.26, 20.82, 19.41, 17.33, 17.09, 14.85. $^{19}$F NMR (470 MHz, METHANOL-d$_4$) δ −227.03 (s, 1F). MS m/e 727.45 (M+H)$^+$, 2.55 min (method 4).

Method B

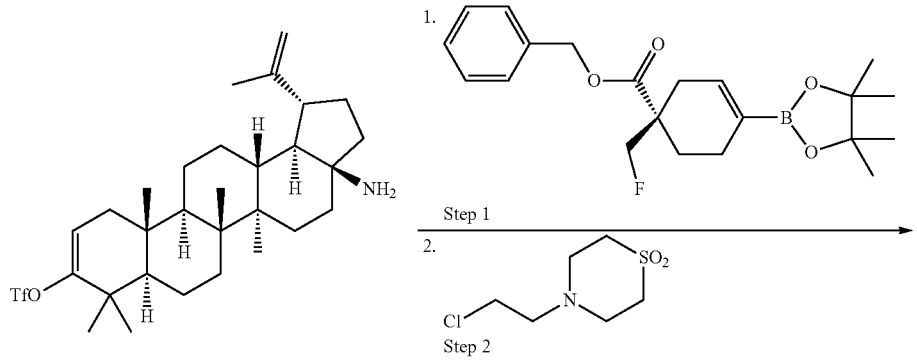

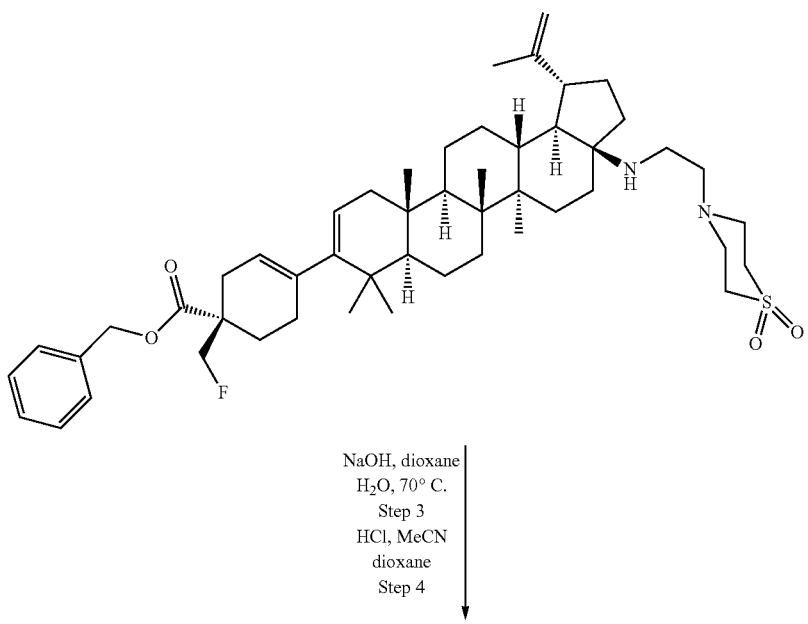

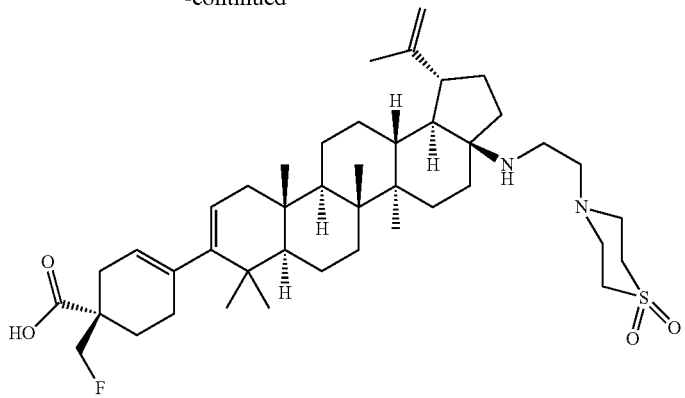

Step 1. Preparation of (R)-benzyl 4-((1R,3aS,5aR, 5bR,7aR,11aS,11bR,13aR,13bR)-3a-((2-(1,1-dioxi-dothiomorpholino)ethyl)amino)-5a,5b,8,8,11a-pen-tamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)-1-(fluoromethyl) cyclohex-3-enecarboxylate To a flask containing (1R,3aS,5aR,5bR,7aR,11aR,11bR, 13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl trifluoromethanesulfonate (8.9 g, 15.96 mmol), (R)-benzyl 1-(fluoromethyl)-4-(4,4,5,5-tetramethyl-1,3,2-dioxaboro-lan-2-yl)cyclohex-3-enecarboxylate (6.57 g, 17.55 mmol), and potassium phosphate tribasic (10.16 g, 47.9 mmol) was added Buchwald 2$^{nd}$ generation Xphos precatalyst (0.313 g, 0.399 mmol). The mixture was diluted with THF (50 mL) and water (10 mL), flushed with nitrogen and then heated to 50° C. for 22 h. The mixture was cooled to rt, partially concentrated and diluted with water (150 mL), extracted with ethyl acetate (3×150 mL) (some solids were noticed between the layers on the first extraction so excess ethyl acetate was added to make sure the product was dissolved), dried over magnesium sulfate, filtered, and concentrated under reduced pressure. The residue was purified by flash chromatography using a 0-10% methanol in dichloromethane gradient and a 220 g silica gel column. The fractions containing the product were combined and concentrated under reduced pressure to give the product as a yellow solid with minor impurities present that will be carried to the next step.

Step 2

To a sealable flask containing (R)-benzyl 4-((1R,3aS,5aR, 5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)-1-(fluoromethyl)cyclohex-3-enecarboxylate (10.5 g, 16.0 mmol) was added potassium phosphate tribasic (13.59 g, 64.0 mmol), potassium iodide (3.99 g, 24.01 mmol), and 4-(2-chloroethyl)thiomorpholine 1,1-dioxide, HCl (9.37 g, 40.0 mmol). The mixture was diluted with acetonitrile (200 mL), flushed with nitrogen, sealed, and heated to 100° C. After heating the mixture for 16 h, it was cooled to rt, transferred to a rb flask using dichloromethane and then concentrated under reduced pressure. The residue was diluted with water (200 mL) and extracted with ethyl acetate (200 mL then 2×150 mL). The organic layers were washed with brine, dried over sodium sulfate, filtered, and concentrated under reduced pressure. The residue was purified by flash chromatography using a 0-6% methanol in dichloromethane gradient and a 330 g silica gel column. The fractions containing the expected product were combined and concentrated under reduced pressure to give the product along with other impurities as a thick red oil. The residue was dissolved in acetonitrile and split into three fractions and was repurified using a 25-100% A to B gradient (A=9:1 water: acetonitrile with 0.1% TFA added, B=1:9 water: acetonitrile with 0.1% TFA added) and a 275 g C18 column. The fractions containing the product were combined and concentrated under reduced pressure to give the TFA salt of the product. Less pure fractions were combined and concentrated then were purified again using the same reverse phase method above. The TFA salt of the products was diluted with sat. aq. NaHCO$_3$ (150 mL) and was extracted with dichloromethane (150 mL then 3×75 mL). The combined organic layers were dried over sodium sulfate, filtered and concentrated under reduced pressure to give the product (7.52 g, 9.2 mmol, 57.5% yield over two steps) as a white solid.

Step 3

To a solution of (R)-benzyl 4-((1R,3aS,5aR,5bR,7aR, 11aS,11bR,13aR,13bR)-3a-((2-(1,1-dioxidothiomor-pholino)ethyl)amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)-1-(fluoromethyl)cyclohex-3-enecarboxylate (0.6 g, 0.734 mmol) in 1,4-dioxane (10 mL) and methanol (2 mL) was added NaOH (1N) (2.94 mL, 2.94 mmol). The mixture was heated to 60° C. for 2.5 h, then cooled to rt. Step 4. 1N HCl solution (5 mL, 5.00 mmol) was added to the mixture and it was partially concentrated under reduced pressure until solids began to form, then the mixture was put in the refrigerator overnight.

The solids that formed were collected by filtration and were washed with water to give the HCl salt of (R)-benzyl 4-((1R,3aS,5aR,5bR,7aR,11aS,11bR,13aR,13bR)-3a-((2-(1, 1-dioxidothiomorpholino)ethyl)amino)-5a,5b,8,8,11a-pen-tamethyl-1-(prop-1-en-2-yl)-2,3,3a,4,5,5a,5b,6,7,7a,8,11, 11a,11b,12,13,13a,13b-octadecahydro-1H-cyclopenta[a]chrysen-9-yl)-1-(fluoromethyl)cyclohex-3-enecarboxylate (0.55 g, 0.706 mmol, 96% yield) as a white solid. The new analytical data for the title compound matched the data previously acquired data for the same compound prepared using different methods.

Example 3
Preparation of (S)-1-(fluoromethyl)-4-((1R,3aS,5aR,5bR,7aR,11aS,11bR,13aR,13bR)-5a,5b,8,8,11a-pentamethyl-3a-((2-morpholinoethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid
5
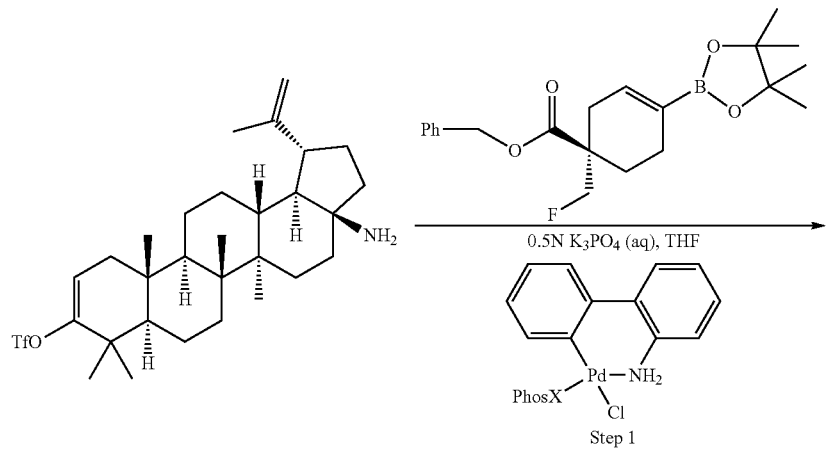
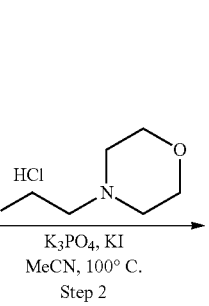

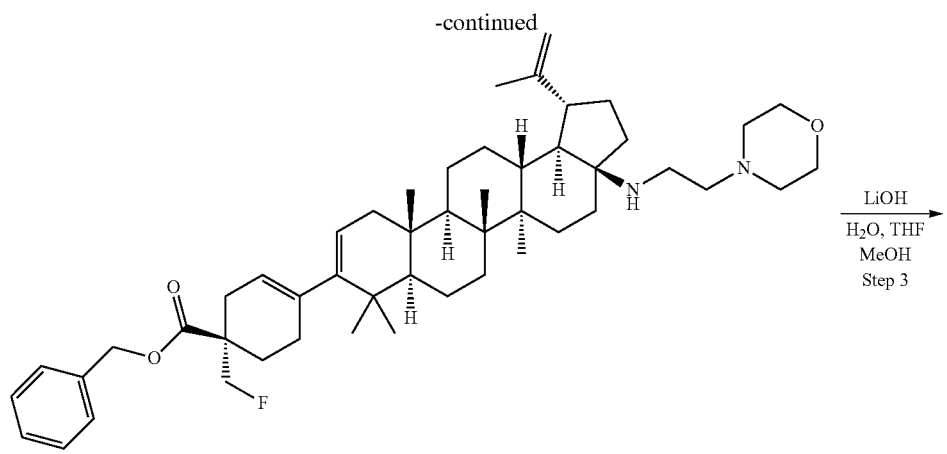

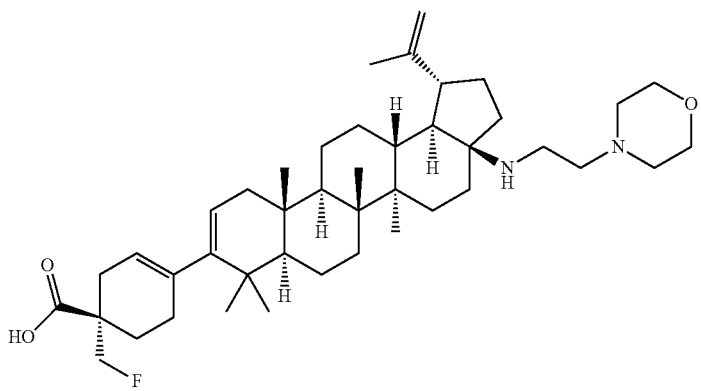

Example 3

Step 1. Preparation of (S)-benzyl 4-((1R,3aS,5aR, 5bR,7aR,11aS,11bR,13aR,13bR)-3a-amino-5a,5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)-1-(fluoromethyl)cyclohex-3-enecarboxylate

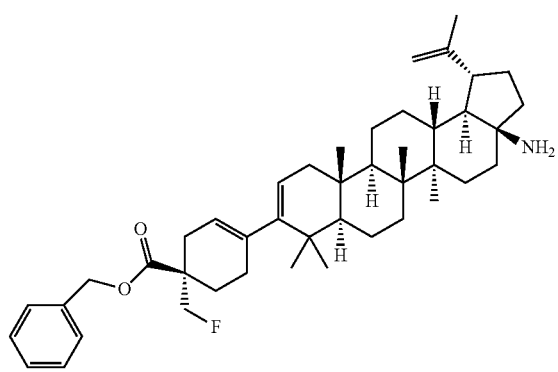

In a 75 mL glass pressure vessel were combined (1R,3aS, 5aR,5bR,7aR,11aR,11bR,13aR,13bR)-3a-amino-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl trifluoromethanesulfonate (0.850 g, 1.524 mmol), (S)-benzyl 1-(fluoromethyl)-4-(4,4,5,5-tetramethyl-1,3,2-dioxaborolan-2-yl)cyclohex-3-enecarboxylate (0.599 g, 1.600 mmol) and XPhos-Pd-G2 (0.036 g, 0.046 mmol). The vessel was sealed with a rubber septum. A needle was inserted into the septum and the vessel was iteratively evacuated and then purged with nitrogen in a vacuum oven at rt four times over a 10 min period. To the nitrogen-flushed reaction vessel was added anhydrous THF (20 mL) and freshly prepared, nitrogen sparged aqueous 0.5 M $K_3PO_4$ (7.62 mL, 3.81 mmol). The vessel was sealed with a PTFE stopper and the resulting yellow solution stirred at 80° C. The color darkened to a very deep green over 30 min. The mixture was heated for 20 h. The reaction mixture was diluted with EtOAc (70 mL) and washed with 5% aqueous sodium bicarbonate (25 mL×2) and then with brine (10 mL). The aqueous layer was extracted with 2×10 mL of chloroform and the organic phases were combined, dried over $MgSO_4$, filtered and concentrated to a yellow foamy solid. The crude yellow material was purified by flash column chromatography (40 g silica, elution gradient 100% DCM to 20:1 DCM:MeOH). Product fractions were combined and concentrated to a yellow thick oil which became a foam when placed under high vacuum. Total recovery of a slightly yellow foam=0.493 g (49% yield). LCMS: m/e 656.5 (M+H)+, 1.59 min (method 6). $^1$H NMR (400 MHz, 1:1 mixture of CDCl$_3$ and CD$_3$OD, CD$_3$OD lock) δ 7.38-7.26 (m, 5H), 5.31 (br. s., 1H), 5.21-5.12 (m, 2H), 5.12-5.06 (m, 1H), 4.77-4.71 (m, 1H), 4.63 (s, 1H), 4.57 (dm, J=47.4 Hz, 2H), 2.59 (d, J=17.6 Hz, 1H), 2.50 (td, J=10.6, 5.3 Hz, 1H), 2.16-1.93 (m, 6H), 1.78-1.65 (m, 7H), 1.60 (dd, J=12.0, 9.0Hz, 5H), 1.55-1.39 (m, 8H), 1.38-1.22 (m, 4H), 1.11-1.03 (m, 4H), 1.03-0.93 (m, 4H), 0.89 (s, 3H), 0.88 (s, 3H), 0.86 (s, 3H).

Step 2. Preparation of (S)-benzyl 1-(fluoromethyl)-4-((1R,3aS,5aR,5bR,7aR,11aS,11bR,13aR,13bR)-5a,5b,8,8,11a-pentamethyl-3a-((2-morpholinoethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate combined and concentrated under reduced pressure. The crude residue thus obtained was carried directly into the next step. LCMS: m/e 769.6 (M+H)+, 2.47 min (method 1).

Step 3

In a 1 dram vial with PTFE screw cap were combined the crude mixture from Step 2 containing (S)-benzyl 1-(fluoromethyl)-4-((1R,3aS,5aR,5bR,7aR,11aS,11bR,13aR,13bR)-5a,5b,8,8,11a-pentamethyl-3a-((2-morpholinoethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate with lithium hydroxide, 1.0M aqueous (0.973 mL, 0.973 mmol), MeOH (1 mL) and tetrahydrofuran (1 mL). The vial was capped and heated to 75° C. for 45 min. The crude mixture was purified by reverse phase preparative HPLC (prep HPLC method 2). The material thus obtained was then repurified by reverse phase preparative HPLC (prep HPLC method 3) to provide

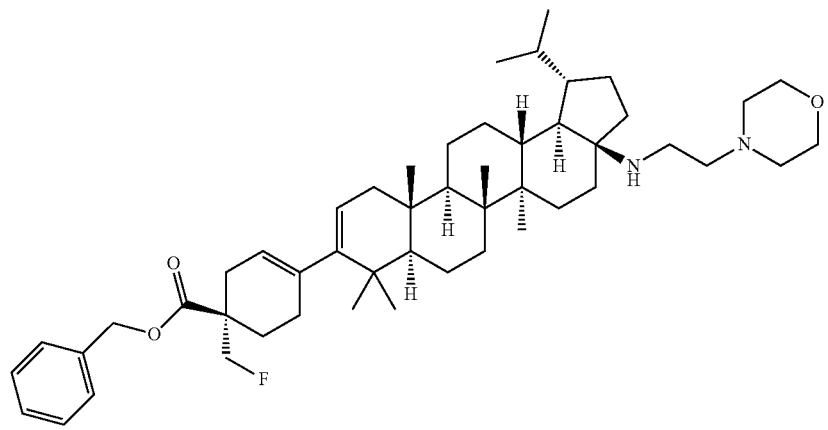

In a 15 mL glass pressure vessel were combined (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (0.091 g, 0.139 mmol) with 4-(2-chloroethyl)morpholine hydrochloride (0.077 g, 0.416 mmol), potassium phosphate tribasic (0.147 g, 0.694 mmol) and potassium iodide (0.046 g, 0.277 mmol) in dry acetonitrile (5 mL). The vessel was sealed and heated to 120° C. in an oil bath with stirring for 19 h. The crude mixture was concentrated under a nitrogen stream, taken up in EtOAc (30 mL) and washed with water (3×10 mL) and brine (5 mL). The combined aqueous phases were extracted with chloroform (10 mL) and the organic phases were (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate as a white solid TFA salt (0.0191 g, 17.3% yield over 2 steps). LCMS: m/e 679.5 (M+H)+, 4.26 min (method 2). $^1$H NMR (400 MHz, 1:1 mixture of CDCl$_3$ and CD$_3$OD, CD$_3$OD lock) δ 5.33 (br. s., 1H), 5.23-5.15 (m, 1H), 4.80 (s, 1H), 4.72 (s, 1H), 4.49 dm, J=47.4 Hz, 2H), 3.84-3.68 (m, 4H), 3.18-3.09 (m, 2H), 2.98-2.85 (m, 1H), 2.82-2.76 (m, 1H), 2.71 (dd, J=13.7, 3.4 Hz, 3H), 2.63-2.50 (m, 3H), 2.30-2.11 (m, 2H), 2.11-1.91 (m, 7H), 1.83-1.75 (m, 3H), 1.73 (s, 4H), 1.67-1.30 (m, 12H), 1.19 (s, 3H), 1.17-1.09 (m, 2H), 1.07 (s, 3H), 0.97 (s,3H), 0.94 (s, 3H), 0.90 (s, 3H).

Example 4
Preparation of (S)-4-((1R,3aS,5aR,5bR,7aR,11aS,11bR,13aR,13bR)-3a-((2-((1S,4S)-2,2-dioxido-2-thia-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid
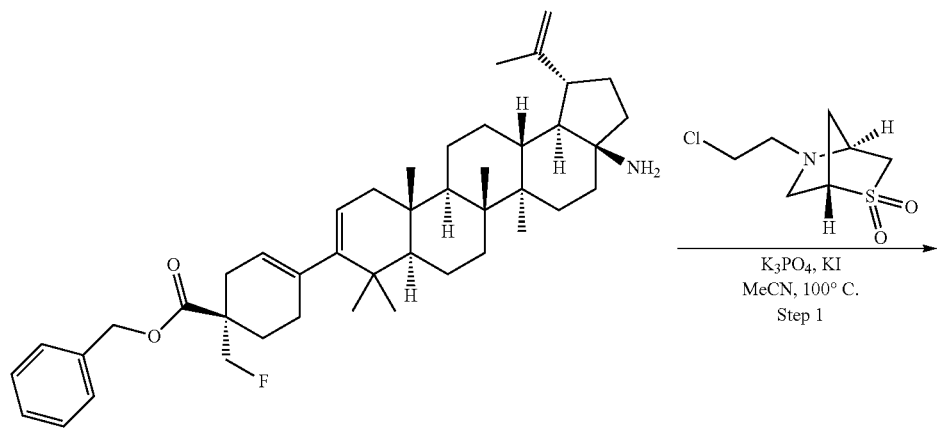
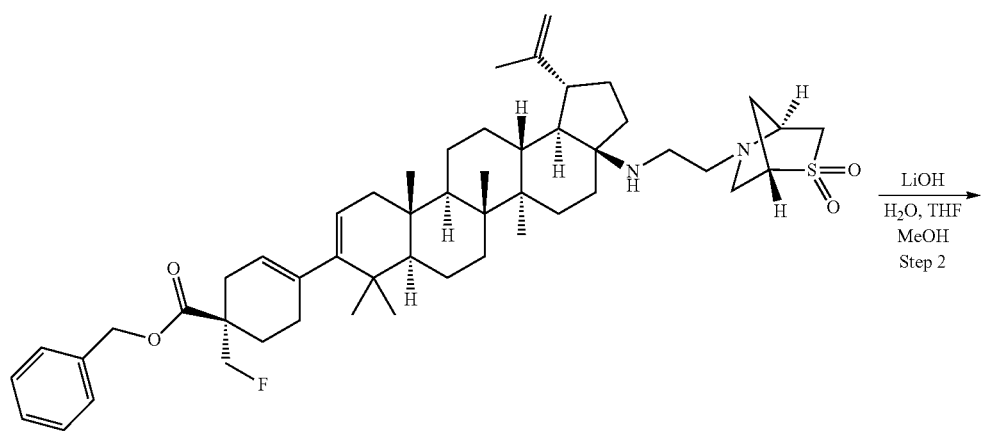
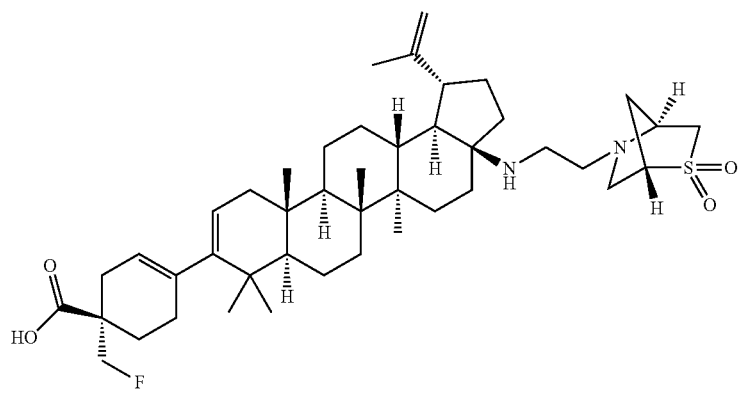
Example 4

Step 1

Preparation of (S)-benzyl 4-((1R,3aS,5aR,5bR,7aR,11aS,11bR,13aR,13bR)-3a-((2-((1S,4S)-2,2-dioxido-2-thia-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate.

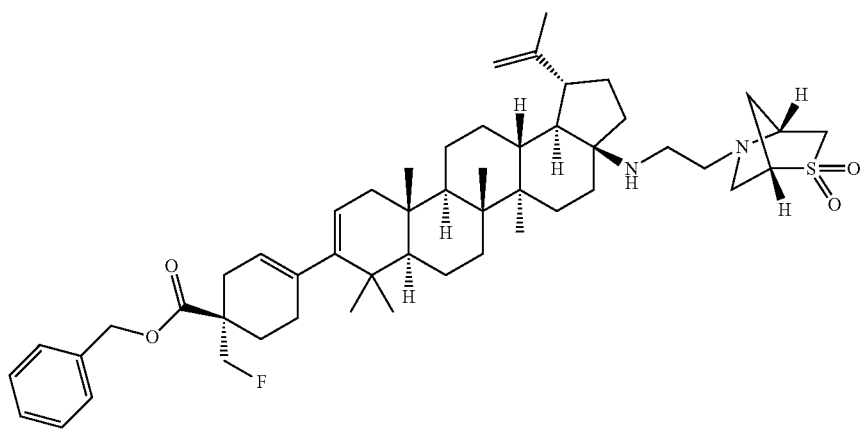

In a 15 mL glass pressure vessel were combined (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (0.091 g, 0.139 mmol) with (1S,4S)-5-(2-chloroethyl)-2-thia-5-azabicyclo[2.2.1]heptane 2,2-dioxide (0.075 g, 0.358 mmol) (prepared as described in WO2013169578), potassium phosphate tribasic (0.147 g, 0.694 mmol) and potassium iodide (0.046 g, 0.277 mmol) in dry acetonitrile (5 mL). The vessel was sealed and heated to 120° C. in an oil bath with stirring for 19 h. The crude mixture was concentrated under a nitrogen stream, taken up in EtOAc (30 mL) and washed with water (3×10 mL) and then with brine (5 mL). The combined aqueous phases were extracted with chloroform (10 mL) and the organic phases were combined and concentrated under reduced pressure. The crude residue thus obtained was carried directly into the next step. LCMS: m/e 829.6 (M+H)⁺, 2.44 min (method 1).

Step 2

In a 1 dram vial with PTFE screw cap were combined the crude mixture from Step 1 containing (S)-benzyl 4-((1R,3aS,5aR,5bR,7aR,11aS,11bR,13aR,13bR)-3a-((2-((1S,4S)-2,2-dioxido-2-thia-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (0.115 g, 0.139 mmol) with lithium hydroxide, 1.0M aqueous (0.695 mL, 0.695 mmol), MeOH (0.7 mL) and tetrahydrofuran (0.7 mL). The vial was capped and heated to 75° C. for 45 min.

The crude mixture was purified by reverse phase preparative HPLC (Prep HPLC method 4) and the yellow solid thus obtained was then repurified by reverse phase preparative HPLC (Prep HPLC method 5), followed by a third and final reverse phase preparative HPLC purification (Prep HPLC method 6) to provide 47.4 mg (39.2% yield over 2 steps) of (S)-benzyl 4-((1R,3aS,5aR,5bR,7aR,11aS,11bR,13aR,13bR)-3a-((2-((1S,4S)-2,2-dioxido-2-thia-5-azabicyclo[2.2.1]heptan-5-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate as a white powder TFA salt. LCMS: m/e 739.5 (M+H)⁺, 4.22 min (method 2). $^1$H NMR (400 MHz, 1:1 mixture of CDCl$_3$ and CD$_3$OD, CD$_3$OD lock) δ 5.33 (br. s., 1H), 5.19 (d, J=4.6 Hz, 1H), 4.79 (s, 1H), 4.71 (s, 1H), 4.48 (dm, J=47.2 Hz, 2H), 4.00 (br. s., 1H), 3.69-3.63 (m, 1H), 3.23-3.13 (m, 2H), 3.13-2.95 (m, 4H), 2.79 (td, J=11.1, 5.0 Hz, 1H), 2.63-2.55 (m, 1H), 2.53 (br. s., 1H), 2.42 (d, J=12.5 Hz, 1H), 2.28-2.06 (m, 4H), 2.06-1.91 (m, 6H), 1.86-1.74 (m, 3H), 1.73 (s, 4H), 1.69-1.55 (m, 4H), 1.54-1.38 (m, 7H), 1.38-1.23 (m, 3H), 1.20-1.14 (m, 1H), 1.13-1.08 (m, 4H), 1.07 (s, 3H), 0.96 (s, 3H), 0.93 (s, 3H), 0.89 (s, 3H).

Example 5
Preparation of (S)-4-(((1R,3aS,5aR,5bR,7aR,11aS,11bR,13aR,13bR)-3a-((2-(1,1-dioxido-1,4-thiazepan-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid
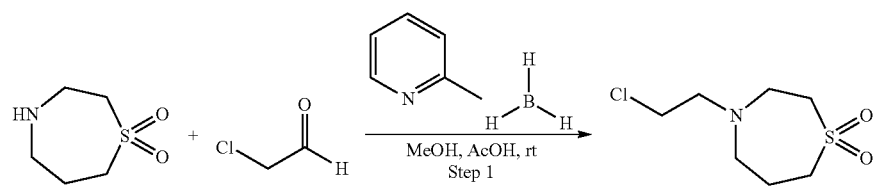
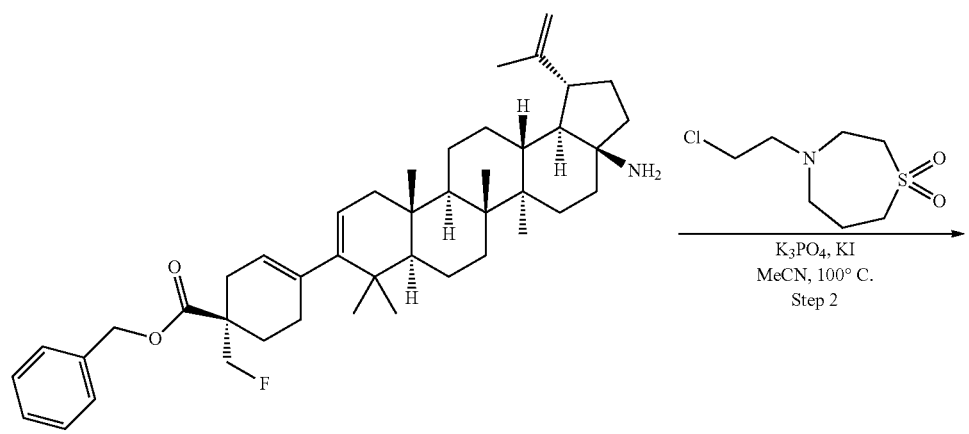
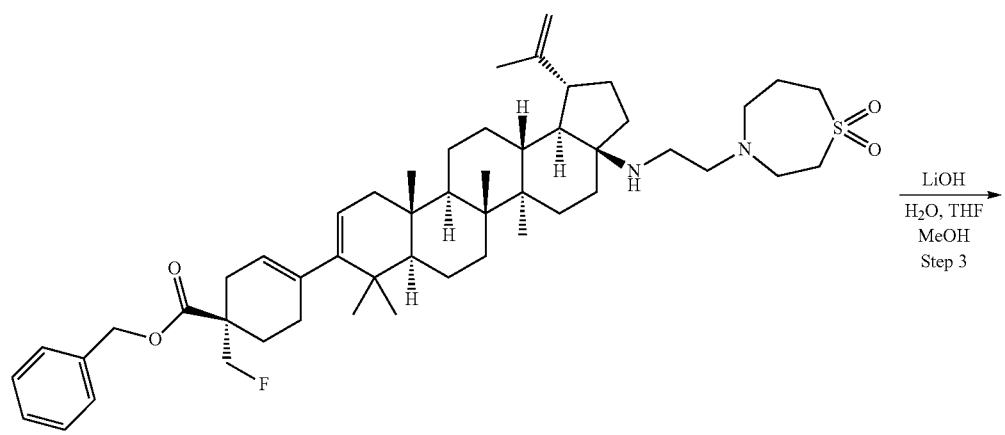

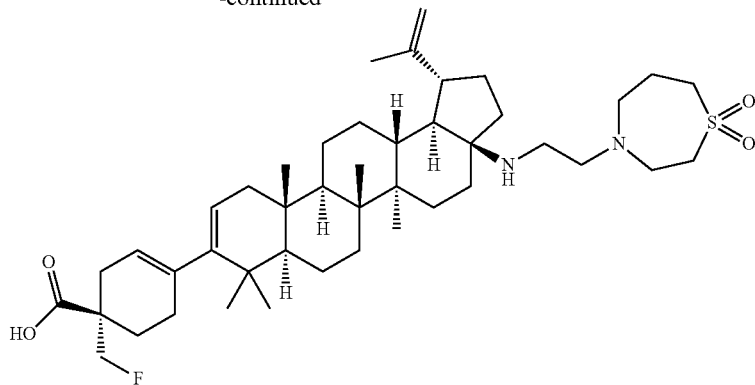

Example 5

Step 1. Preparation of 4-(2-chloroethyl)-1,4-thiazepane 1,1-dioxide

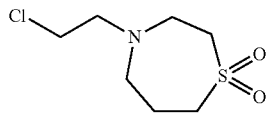 [SMILES: O=S1(=O)CCCN(CCCl)CC1]

To a mixture of 1,4-thiazepane 1,1-dioxide (200 mg, 1.340 mmol) and 2-chloroacetaldehyde, 50 wt % solution in water (0.234 mL, 1.877 mmol) in methanol (5 mL) and acetic acid (1 mL) was added 2-picoline borane-complex (158 mg, 1.474 mmol). The resulting mixture was stirred at rt overnight. The reaction mixture was concentrated under reduced pressure to a residue that was washed with saturated Na$_2$CO$_3$ (10 mL) and extracted with ethyl acetate (3×10 mL). The aqueous phase was extracted with chloroform (10 mL). The combined organic phases were dried over anhydrous MgSO$_4$, filtered and concentrated under reduced pressure to provide 334 mg (quant.) of the desired product as crude reddish-brown oil that partially solidified upon standing. This crude material was used as-is directly in the next step. LCMS: m/e 212.0 (M+H)$^+$, 0.18 min (method 1).

Step 2. Preparation of (S)-benzyl 4-((1R,3aS,5aR, 5bR,7aR,11aS,11bR,13aR,13bR)-3a-((2-(1,1-dioxido-1,4-thiazepan-4-yl)ethyl)amino)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)-1-(fluoromethyl)cyclohex-3-enecarboxylate

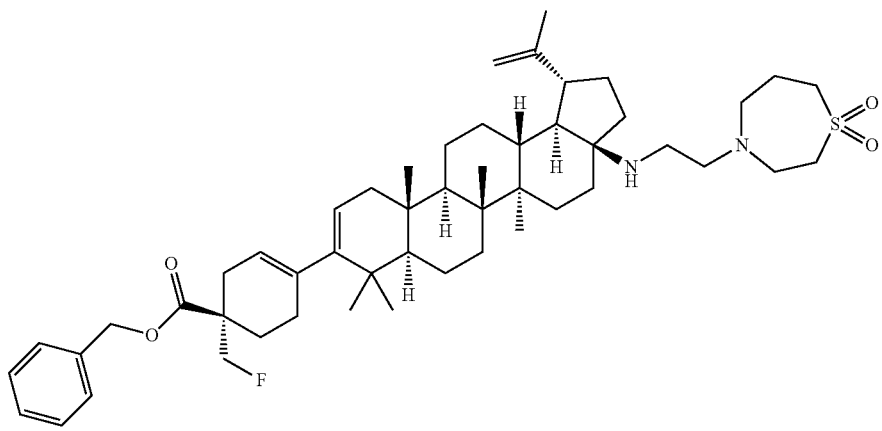

In a 15 mL glass pressure vessel were combined the crude material from Step 1 containing 4-(2-chloroethyl)-1,4-thiazepane 1,1-dioxide (0.065 g, 0.305 mmol) with (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (0.100 g, 0.152 mmol), potassium phosphate tribasic (0.162 g, 0.762 mmol) and potassium iodide (0.051 g, 0.305 mmol) in dry acetonitrile (5 mL). The vessel was sealed and heated to 120° C. in an oil bath with stirring for 17 h. The reaction mixture was concentrated under reduced pressure, taken up in EtOAc (30 mL) and washed with water (3×10 mL) and with brine (5 mL). The combined aqueous phases were extracted with chloroform (10 mL) and the organic phases were combined and concentrated under reduced pressure. The crude residue thus obtained was carried into the saponification step as-is with no further purification. LCMS: m/e 831.6 (M+H)$^+$, 2.39 min (method 1).

Step 3

In a 1 dram vial with PTFE screw cap were combined the crude mixture from Step 2 containing (S)-benzyl 4-((1R,3aS,5aR,5bR,7aR,11aS,11bR,13aR,13bR)-3a-((2-(1,1-dioxido-1,4-thiazepan-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (0.126 g, 0.152 mmol) with lithium hydroxide, 1.0M aqueous (1.064 mL, 1.064 mmol), MeOH (1 mL) and tetrahydrofuran (1 mL). The vial was capped and the mixture heated to 75° C. for 45 min. The mixture was filtered and purified by reverse phase preparative HPLC (Prep HPLC method 7) to provide (S)-4-((1R,3aS,5aR,5bR,7aR,11aS,11bR,13aR,13bR)-3a-((2-(1,1-dioxido-1,4-thiazepan-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid as a white solid TFA salt (36.7 mg, 28.2% yield over 2 steps). LCMS: m/e 741.5 (M+H)$^+$, 2.26 min (method 1). $^1$H NMR (400 MHz, 1:1 mixture of CDCl$_3$ and CD$_3$OD, CD$_3$OD lock) δ 5.33 (br. s., 1H), 5.19 (d, J=4.6 Hz, 1H), 4.80 (s, 1H), 4.71 (s, 1H), 4.49 (dm, J=47.4 Hz, 1H), 3.47-3.37 (m, 1H), 3.35 (br. s., 1H), 3.28-3.17 (m, 2H), 3.15-3.02 (m, 5H), 3.02-2.93 (m, 1H), 2.79 (td, J=11.0, 4.6 Hz, 1H), 2.55 (d, J=17.1 Hz, 1H), 2.29-2.14 (m, 2H), 2.13-1.91 (m, 9H), 1.86-1.74 (m, 3H), 1.73 (s, 4H), 1.68-1.55 (m, 4H), 1.55-1.42 (m, 6H), 1.41-1.24 (m, 3H), 1.19-1.09 (m, 5H), 1.07 (s, 3H), 0.97 (s, 3H), 0.94 (s, 3H), 0.90 (s, 3H).

Example 6

Preparation of (S)-1-(fluoromethyl)-4-((1R,3aS,5aR,5bR,7aR,11aS,11bR,13aR,13bR)-5a,5b,8,8,11a-pentamethyl-3a-((2-(4-(methylsulfonyl)piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid

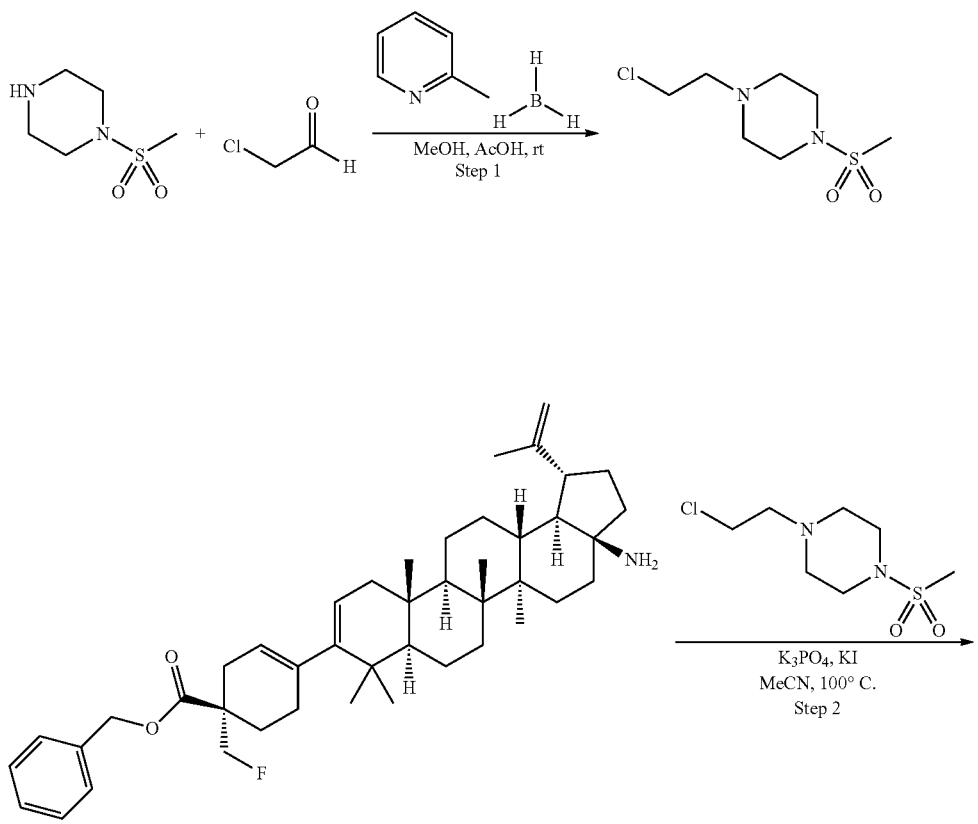

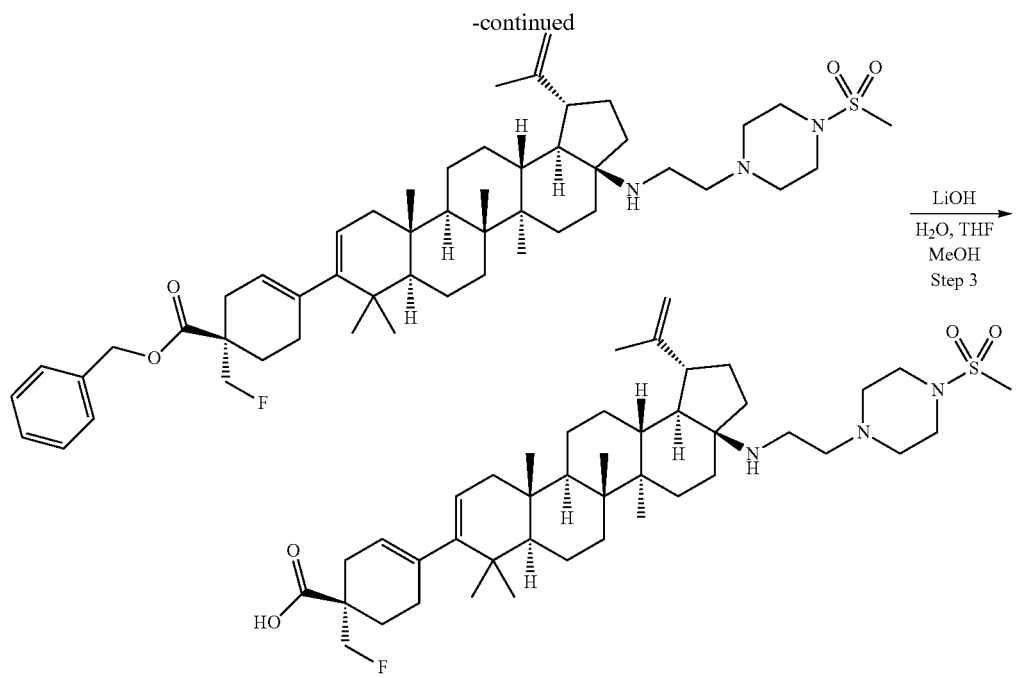

Example 6

Step 1. Preparation of 1-(2-chloroethyl)-4-(methylsulfonyl)piperazine

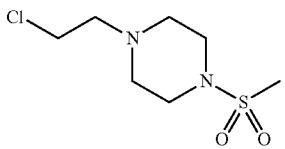

To a mixture of 1-(methylsulfonyl)piperazine (0.200 g, 1.218 mmol) and 2-chloroacetaldehyde, 50 wt % solution in water (0.212 mL, 1.705 mmol) in methanol (5 mL) and acetic acid (1 mL) was added 2-picoline-borane-complex (0.143 g, 1.340 mmol). The resulting mixture was stirred at rt overnight. The reaction mixture was concentrated under reduced pressure to a leave a residue that was washed with saturated Na$_2$CO$_3$ (10 mL) and extracted with ethyl acetate (3×10 mL). The aqueous phase was extracted with chloroform (10 mL). The combined organic phases were dried over anhydrous MgSO$_4$, filtered and concentrated under reduced pressure to provide 394 mg (>100% yield) of the desired product as colorless oil that solidified upon standing to a waxy, slightly yellow solid. This crude material was used as-is directly in the next step. LCMS: m/e 227.0 (M+H)$^+$, 0.19 min (method 1).

Step 2. Preparation of (S)-benzyl 1-(fluoromethyl)-4-((1R,3aS,5aR,5bR,7aR,11aS,11bR,13aR,13bR)-5a,5b,8,8,11a-pentamethyl-3a-((2-(4-(methylsulfonyl)piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate

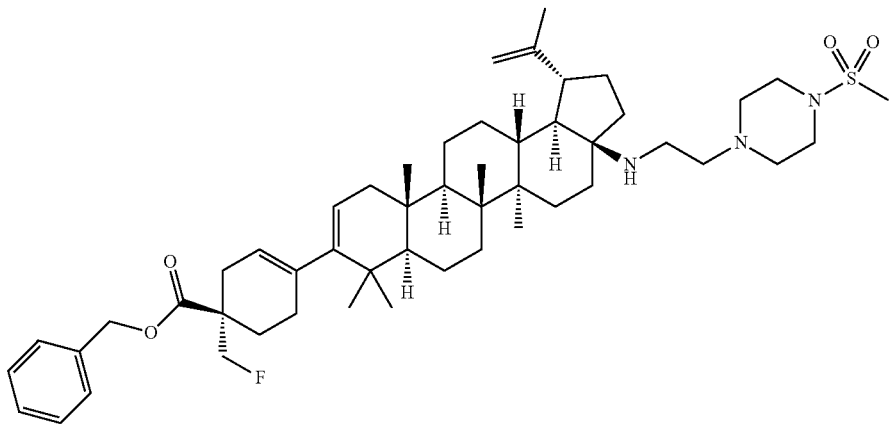

In a 15 mL glass pressure vessel were combined the crude material from Step 1 containing 1-(2-chloroethyl)-4-(methylsulfonyl)piperazine (0.069 g, 0.305 mmol) with (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (0.100 g, 0.152 mmol), potassium phosphate tribasic (0.162 g, 0.762 mmol) and potassium iodide (0.051 g, 0.305 mmol) in dry acetonitrile (5 mL). The vessel was sealed and heated to 120° C. in an oil bath with stirring for 15 h. The reaction mixture was concentrated under reduced pressure, the residue taken up in EtOAc (30 mL) and washed with water (3×10 mL) and with brine (5 mL). The combined aqueous phases were extracted with chloroform (10 mL) and the organic phases were combined and concentrated under reduced pressure. The crude residue thus obtained was carried into the saponification step as-is with no further purification. LCMS: m/e 846.7 (M+H)$^+$, 2.43 min (method 1).

Step 3. In a 1 dram vial with PTFE screw cap were combined the crude mixture from Step 2 containing (S)-benzyl 1-(fluoromethyl)-4-((1R,3aS,5aR,5bR,7aR,11aS,11bR,13aR,13bR)-5a,5b,8,8,11a-pentamethyl-3a-((2-(4-(methylsulfonyl)piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (0.129 g, 0.152 mmol) with 1.0M aqueous lithium hydroxide (1.064 mL, 1.064 mmol), MeOH (1 mL) and tetrahydrofuran (1 mL). The vial was capped and the mixture heated to 75° C. for 45 min. The mixture was filtered and purified by reverse phase preparative HPLC (Prep HPLC method 7) to provide (S)-1-(fluoromethyl)-4-((1R,3aS,5aR,5bR,7aR,11aS,11bR,13aR,13bR)-5a,5b,8,8,11a-pentamethyl-3a-((2-(4-(methylsulfonyl)piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid as a white solid TFA salt (47.4 mg, 35.8% yield over 2 steps). LCMS: m/e 756.5 (M+H)$^+$, 4.21 min (method 2). $^1$H NMR (400 MHz, 1:1 mixture of CDCl$_3$ and CD$_3$OD, CD$_3$OD lock) δ 5.33 (br. s., 1H), 5.19 (d, J=4.6 Hz, 1H), 4.79 (s, 1H), 4.71 (s, 1H), 4.48 (dm, J=47.2 Hz, 1H), 3.30-3.22 (m, 2H), 3.19-3.09 (m, 2H), 3.00-2.90 (m, 1H), 2.87 (s, 3H), 2.84-2.64 (m, 6H), 2.55 (d, J=17.6 Hz, 1H), 2.29-2.14 (m, 2H), 2.14-1.91 (m, 7H), 1.86-1.75 (m, 3H), 1.73 (s, 4H), 1.65-1.47 (m, 7H), 1.45-1.34 (m, 4H), 1.29 (dd, J=17.7, 5.0 Hz, 1H), 1.17 (s, 3H), 1.16-1.08 (m, 2H), 1.07 (s, 3H), 0.96 (s, 3H), 0.93 (s, 3H), 0.89 (s, 3H).

Example 7

Preparation of (S)-4-((1R,3aS,5aR,5bR,7aR,11aS,11bR,13aR,13bR)-3a-((2-(1,1-dioxidotetrahydro-2H-thiopyran-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid

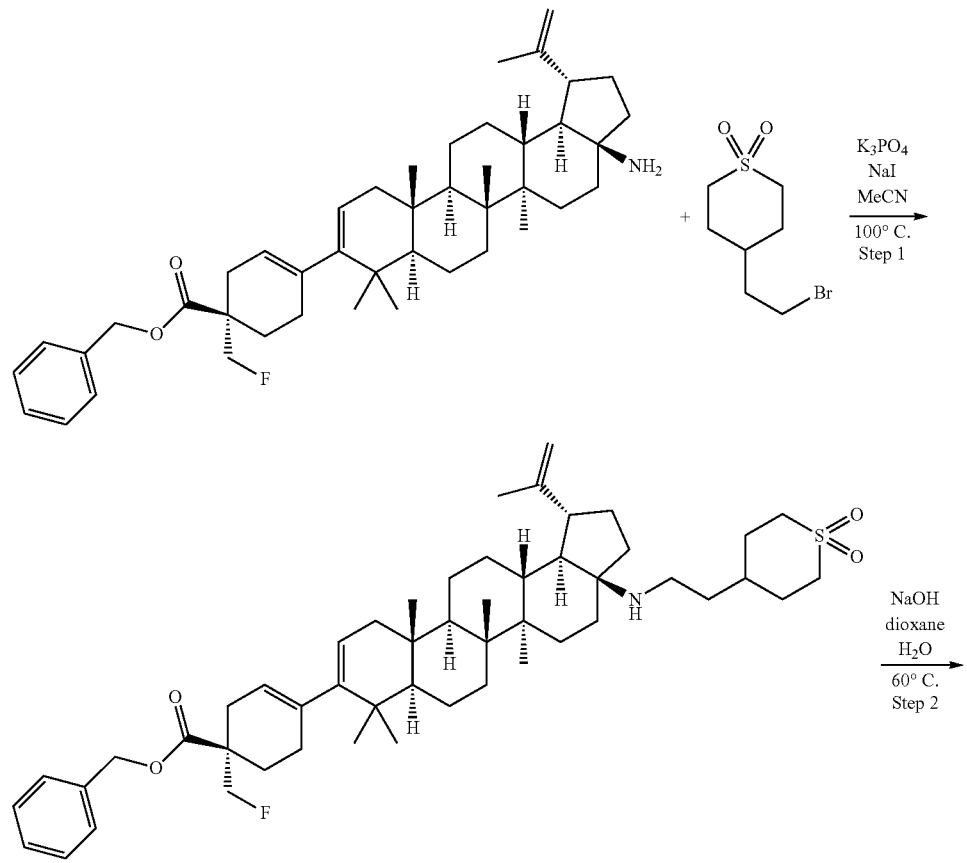

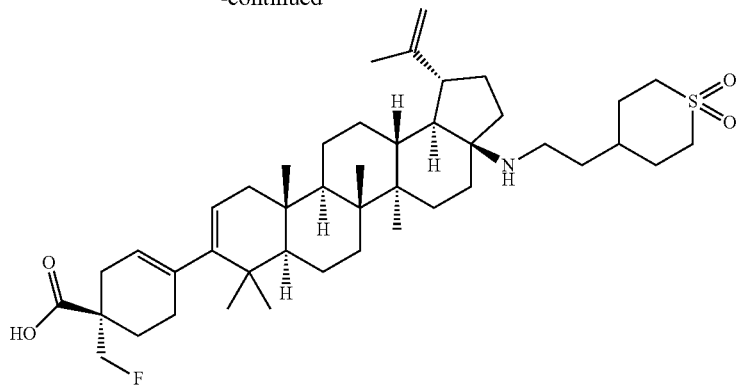

Example 7

Step 1: Preparation of (S)-benzyl 4-((1R,3aS,5aR, 5bR,7aR,11aS,11bR,13aR,13bR)-3a-((2-(1,1-dioxidotetrahydro-2H-thiopyran-4-yl)ethyl)amino)-5a,5b, 8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl)-1-(fluoromethyl)cyclohex-3-enecarboxylate A suspension of (S)-benzyl 4-((1R,3aS,5aR,5bR,7aR, 11aS,11bR,13aR,13bR)-3a-amino-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)-1-(fluoromethyl)cyclohex-3-enecarboxylate (45 mg, 0.069 mmol), 4-(2-bromoethyl)tetrahydro-2H-thiopyran 1,1-dioxide (17 mg, 0.069 mmol), $K_3PO_4$ (44 mg, 0.206 mmol) and NaI (17 mg, 0.103 mmol) in MeCN (1 mL) was flushed with nitrogen, sealed, and stirred at 100° C. for 18 h. The reaction mixture was filtered and the filtrate was concentrated under reduced pressure. The crude product was purified by flash chromatography on silica gel column (0-40% EtOAc/Hexane) using ELS detector to give the title product as a solid (28 mg, 50%). LCMS m/e 816.45 (M+H)$^+$, 3.864 minutes (Method 7). $^1$H NMR (400 MHz, CHLOROFORM-d) δ 7.40-7.28 (m, 5H), 5.32 (s., 1H), 5.17 (d, J=1.3 Hz, 2H), 5.15-5.09 (m, 1H), 4.70 (d, J=1.8 Hz, 1H), 4.63-4.55 (m, 2H), 4.50-4.43 (m, 1H), 3.13-2.90 (m, 4H), 2.64-2.41 (m, 4H), 2.21-0.80 (m, 34H), 1.69 (s, 3H), 1.03 (s, 3H), 0.95 (s, 3H), 0.90 (s, 3H), 0.89 (s, 3H), 0.85 (s, 3H).

Step 2

To a solution of (S)-benzyl 4-((1R,3aS,5aR,5bR,7aR, 11aS,11bR,13aR,13bR)-3a-((2-(1,1-dioxidotetrahydro-2H-thiopyran-4-yl)ethyl)amino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)-1-(fluoromethyl)cyclohex-3-enecarboxylate (28 mg, 0.034 mmol) in 1,4-dioxane (2 mL) and MeOH (1 mL) was added 1N NaOH (1 mL, 1.0 mmol). The mixture was stirred at 60° C. for 3 h. The reaction mixture was purified by Prep HPLC (Method 8) to give (S)-4-((1R,3aS,5aR,5bR,7aR,11aS, 11bR,13aR,13bR)-3a-((2-(1,1-dioxidotetrahydro-2H-thiopyran-4-yl)ethyl)amino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)-1-(fluoromethyl)cyclohex-3-enecarboxylic acid as a solid (16 mg, 64%). LCMS m/e 726.50 (M+H)$^+$, 3.528 minutes (Method 7). $^1$H NMR (400 MHz, CHLOROFORM-d) δ 5.34 (s, 1H), 5.18 (d, J=4.5 Hz, 1H), 4.71 (s, 1H), 4.60 (s, 2H), 4.48 (s, 1H), 3.10-2.89 (m, 4H), 2.66-2.48 (m, 4H), 2.27-0.91 (m, 34H), 1.68 (s, 3H), 1.06 (s, 3H), 0.96 (s, 3H), 0.95 (s, 3H), 0.93 (s, 3H), 0.86 (s, 3H). $^{19}$F NMR (376 MHz, CHLOROFORM-d) δ −224.87 (s, 1F).

Example 8

Preparation of (S)-1-(fluoromethyl)-4-((1R,3aS,5aR, 5bR,7aR,11aS,11bR,13aR,13bR)-5a,5b,8,8,11a-pentamethyl-1-(prop-1-en-2-yl)-3a-(2-(tetrahydro-2H-pyran-4-yl)acetamido)-2,3,3a,4,5,5a,5b,6,7,7a,8,11, 11a,11b,12,13,13a,13b-octadecahydro-1H-cyclopenta[a]chrysen-9-yl)cyclohex-3-enecarboxylic acid

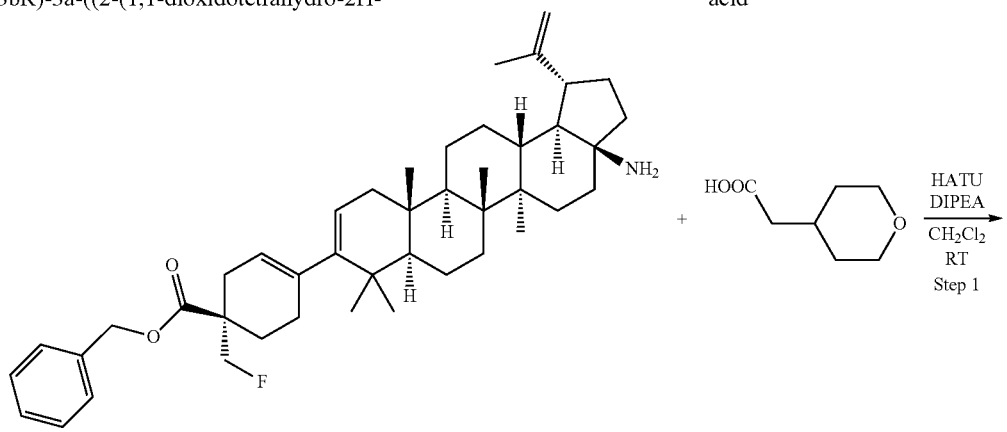

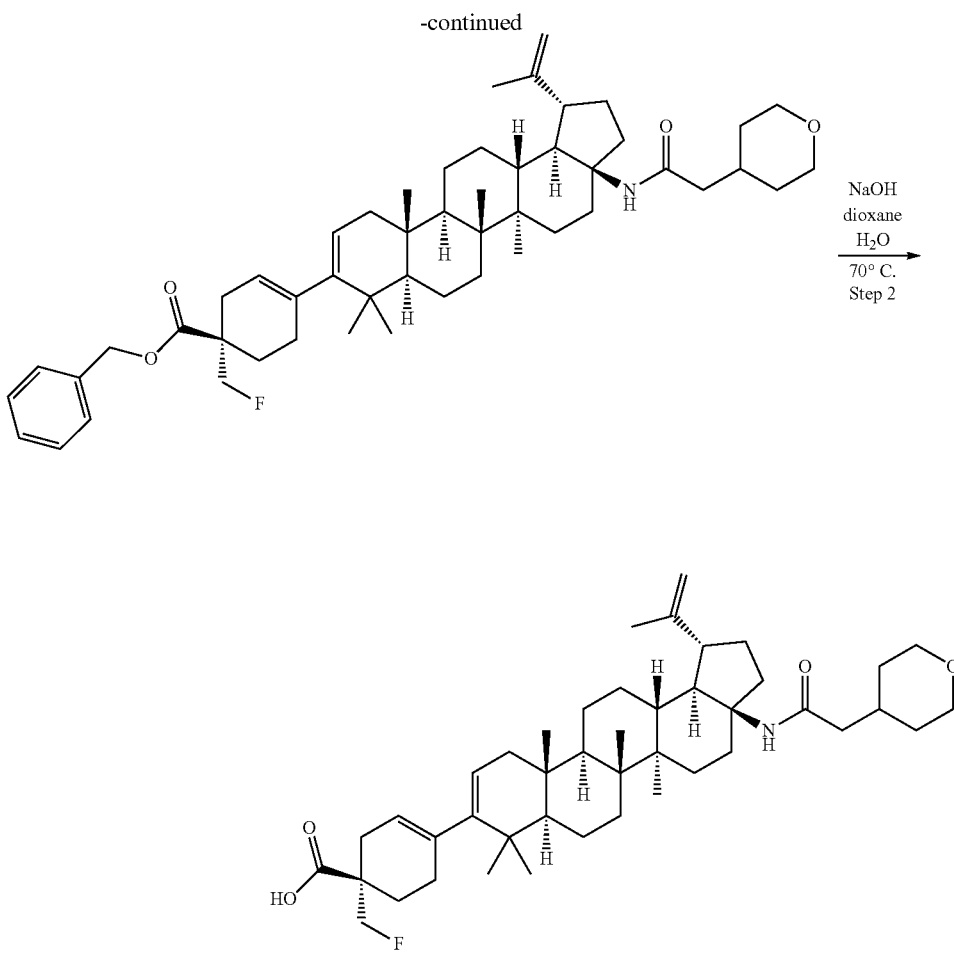

Example 8

Step 1: Preparation of (S)-benzyl 1-(fluoromethyl)-4-((1R,3aS,5aR,5bR,7aR,11aS,11bR,13aR,13bR)-5a,5b,8,8,11a-pentamethyl-1-(prop-1-en-2-yl)-3a-(2-(tetrahydro-2H-pyran-4-yl)acetamido)-2,3,3a,4,5,5a,5b,6,7,7a,8,11,11a,11b,12,13,13a,13b-octadecahydro-1H-cyclopenta[a]chrysen-9-yl) cyclohex-3-enecarboxylate To a mixture of (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (50 mg, 0.076 mmol) and 2-(tetrahydro-2H-pyran-4-yl)acetic acid (13 mg, 0.091 mmol) in $CH_2Cl_2$ (1 mL) was added DIPEA (0.05 ml, 0.305 mmol) followed by HATU (44 mg, 0.114 mmol). The solution was stirred at room temperature for 1 h. The reaction mixture was concentrated under reduced pressure. The crude product was purified by flash chromatography on silica gel column (20-45% EtOAc/Hexane) using ELS detector to give the desired product as a solid (quantitative yield). LCMS m/e 782.55 (M+H)+, 4.346 minutes (Method 8). $^1$H NMR (400 MHz, CHLOROFORM-d) δ 7.39-7.29 (m, 5H), 5.32 (s, 1H), 5.21-5.14 (m,2H), 5.12 (d, J=4.5 Hz, 1H), 5.10 (s, 1H), 4.73 (d, J=1.3 Hz, 1H), 4.63 (s, 1H), 4.61-4.56 (m, 1H), 4.50-4.44 (m, 1H), 3.96 (dd, J=11.3, 3.5 Hz, 2H), 3.47-3.38 (m, 2H), 2.73-2.65 (m, 1H), 2.60 (d, J=17.3 Hz, 1H), 2.51 (dd, J=12.4, 8.2 Hz, 1H), 2.42 (td, J=10.5, 5.3 Hz, 1H), 2.19-0.92 (m, 32H), 1.70 (s, 3H), 1.01 (s, 3H), 0.97 (s, 3H), 0.90 (s, 3H), 0.88 (s, 3H), 0.85 (s, 3H).

Step 2

To a solution of (S)-benzyl 1-(fluoromethyl)-4-((1R,3aS,5aR,5bR,7aR,11aS,11bR,13aR,13bR)-5a,5b,8,8,11a-pentamethyl-1-(prop-1-en-2-yl)-3a-(2-(tetrahydro-2H-pyran-4-yl)acetamido)-2,3,3a,4,5,5a,5b,6,7,7a,8,11,11a,11b,12,13,13a,13b-octadecahydro-1H-cyclopenta[a]chrysen-9-yl) cyclohex-3-enecarboxylate (60 mg, 0.077 mmol) in 1,4-dioxane (3 mL) and MeOH (1.5 mL) was added 1N NaOH (1.5 mL, 1.5 mmol). The mixture was stirred at 60° C. for 3 h. The reaction mixture was purified by Prep HPLC (Method 8) to give (S)-1-(fluoromethyl)-4-((1R,3aS,5aR,5bR,7aR,11aS,11bR,13aR,13bR)-5a,5b,8,8,11a-pentamethyl-1-(prop-1-en-2-yl)-3a-(2-(tetrahydro-2H-pyran-4-yl) acetamido)-2,3,3a,4,5,5a,5b,6,7,7a,8,11,11a,11b,12,13,13a, 13b-octadecahydro-1H-cyclopenta[a]chrysen-9-yl) cyclohex-3-enecarboxylic acid as a solid (45 mg, 85%) .LCMS m/e 692.55 (M+H)+, 3.141 minutes (Method 8). $^1$H NMR (400 MHz, CHLOROFORM-d) δ 5.33 (s, 1H), 5.18 (d, J=4.5 Hz, 1H), 5.13 (s, 1H), 4.73 (s, 1H), 4.63 (s, 1H), 4.59 (s, 1H), 4.48 (s, 1H), 3.97 (d, J=8.5 Hz, 2H), 3.43 (t, J=11.8 Hz, 2H), 2.70 (d, J=12.8 Hz, 1H), 2.63-2.36 (m, 3H), 2.28-0.95 (m, 32H), 1.70 (s, 3H), 1.02 (s, 3H), 0.97 (s, 3H), 0.94 (s, 3H), 0.92 (s, 3H), 0.86 (s, 3H). $^{19}$F NMR (376 MHz, CHLOROFORM-d) δ −225.31 (s, 1F).

Example 9

Preparation of (S)-1-(fluoromethyl)-4-((1R,3aS,5aR, 5bR,7aR,11aS,11bR,13aR,13bR)-5a,5b,8,8,11a-pentamethyl-1-(prop-1-en-2-yl)-3a-((2-(tetrahydro-2H-pyran-4-yl)ethyl)amino)-2,3,3a,4,5,5a,5b,6,7,7a,8, 11,11a,11b,12,13,13a,13b-octadecahydro-1H-cyclopenta[a]chrysen-9-yl)cyclohex-3-enecarboxylic acid

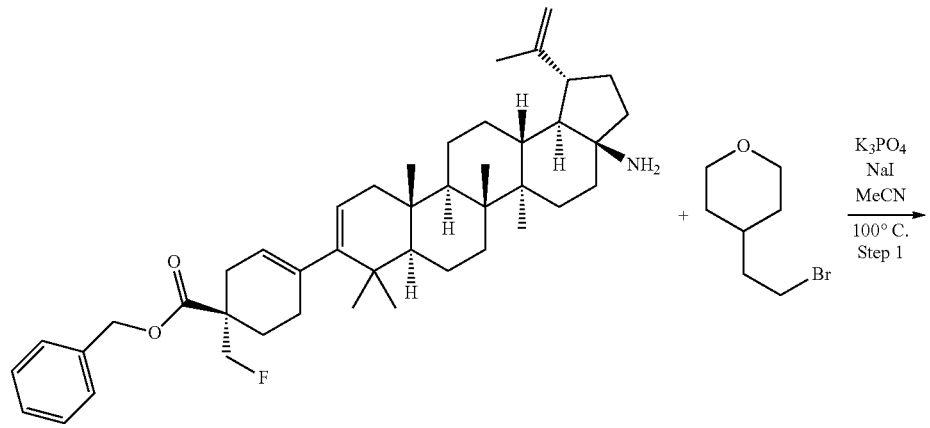

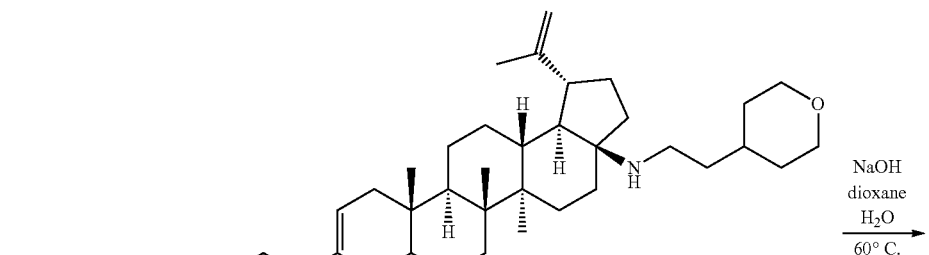

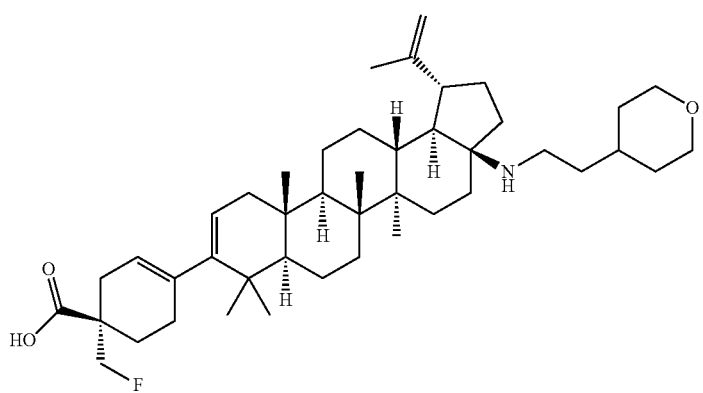

Example 9

Step 1: Preparation of (S)-benzyl 1-(fluoromethyl)-4-((1R,3aS,5aR,5bR,7aR,11aS,11bR,13aR,13bR)-5a,5b,8,8,11a-pentamethyl-1-(prop-1-en-2-yl)-3a-((2-(tetrahydro-2H-pyran-4-yl)ethyl)amino)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate A suspension of (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (50 mg, 0.076 mmol), 4-(2-bromoethyl)tetrahydro-2H-pyran (15 mg, 0.076 mmol), K₃PO₄ (49 mg, 0.229 mmol) and NaI (19 mg, 0.114 mmol) in MeCN (1 mL) was flushed with nitrogen, sealed, and stirred at 90° C. for 18 h. The reaction mixture was filtered and the filtrate was concentrated under reduced pressure. The crude product was purified by flash chromatography on silica gel column (0-40% EtOAc/Hexane) using ELS detector to give the desired product as a solid (30 mg, 51%). LCMS m/e 768.55 (M+H)⁺, 3.033 minutes (Method 8). ¹H NMR (400 MHz, CHLOROFORM-d) δ 7.39-7.29 (m, 5H), 5.32 (s, 1H), 5.22-5.14 (m, 2H), 5.14-5.10 (m, 1H), 4.71 (d, J=2.0 Hz, 1H), 4.62-4.55 (m, 1H), 4.58 (s, 1H), 4.51-4.43 (m, 1H), 4.01-3.93 (m, 4H), 2.65-2.52 (m, 2H), 2.50-2.36 (m, 2H), 2.18-0.87 (m, 34H), 1.69 (s, 3H), 1.05 (s, 3H), 0.95 (s, 3H), 0.90 (s, 3H), 0.89 (s, 3H), 0.85 (s, 3H). ¹⁹F NMR (376 MHz, CHLOROFORM-d) δ -225.06 (s, 1F).

Step 2

To a solution of (S)-benzyl 1-(fluoromethyl)-4-((1R,3aS,5aR,5bR,7aR,11aS,11bR,13aR,13bR)-5a,5b,8,8,11a-pentamethyl-1-(prop-1-en-2-yl)-3a-((2-(tetrahydro-2H-pyran-4-yl)ethyl)amino)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (30 mg, 0.039 mmol) in 1,4-dioxane (2 mL) and MeOH (1 mL) was added 1N NaOH (1 mL, 1.0 mmol). The mixture was stirred at 60° C. for 2 h. The reaction mixture was purified by Prep HPLC (Method 8) to give (S)-1-(fluoromethyl)-4-((1R,3aS,5aR,5bR,7aR,11aS,11bR,13aR,13bR)-5a,5b,8,8,11a-pentamethyl-1-(prop-1-en-2-yl)-3a-((2-(tetrahydro-2H-pyran-4-yl)ethyl)amino)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid as a solid (12 mg, 45%). LCMS m/e 678.50 (M+H)⁺, 2.968 minutes (Method 8). ¹H NMR (400 MHz, CHLOROFORM-d) δ 5.34 (s, 1H), 5.18 (d, J=4.5 Hz, 1H), 4.72 (d, J=2.0 Hz, 1H), 4.60 (s, 2H), 4.48 (s, 1H), 3.97 (d, J=11.3 Hz, 2H), 3.39 (tdd, J=11.8, 4.5, 2.1 Hz, 2H), 2.67-2.48 (m, 4H), 2.19-0.89 (m, 34H), 1.69 (s, 3H), 1.07 (s, 3H), 0.96 (s, 3H), 0.95 (s, 3H), 0.93 (s, 3H), 0.86 (s, 3H). ¹⁹F NMR (376 MHz, CHLOROFORM-d) δ -225.04 (s, 1F).

Example 10

Preparation of (S)-4-((1R,3aS,5aR,5bR,7aR,11aS,11bR,13aR,13bR)-3a-(((2-(1,1-dioxidothiomorpholino)-2-methylpropyl)amino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid

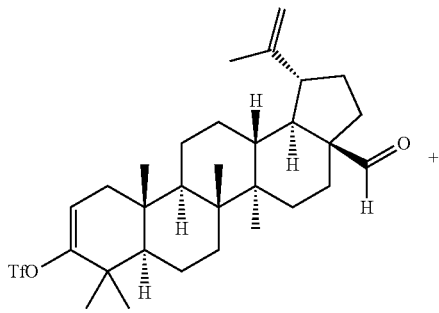

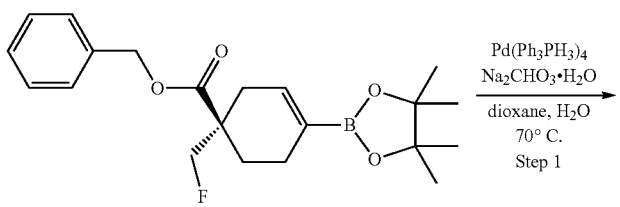

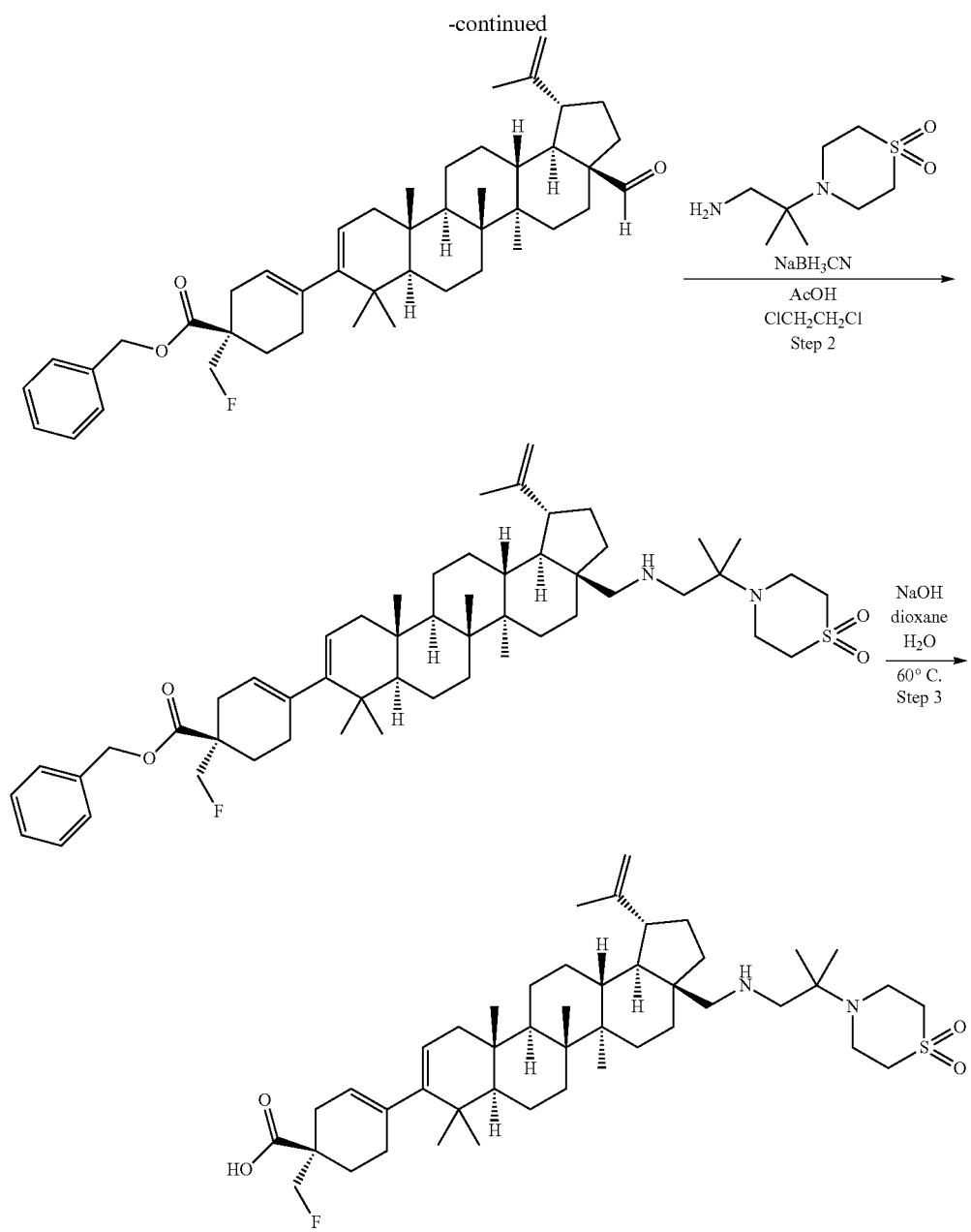

Example 10

Step 1: Preparation of (S)-benzyl 1-(fluoromethyl)-4-((1R,3aS,5aR,5bR,7aR,11aS,11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate A mixture of (1R,3aS,5aR,5bR,7aR,11aR,11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate (2.0 g, 3.50 mmol), (S)-benzyl 1-(fluoromethyl)-4-(4,4,5,5-tetramethyl-1,3,2-dioxaborolan-2-yl)cyclohex-3-enecarboxylate (1.44 g, 3.85 mmol), $Na_2CO_3 \cdot H_2O$ (1.3 g, 10.5 mmol) and $Pd(Ph_3P)_4$ (0.24 g, 0.21 mmol) in dioxane (40 mL) was flushed with nitrogen, sealed, and stirred at 70° C. for 1 h. The mixture was cooled to room temperature and concentrated under reduced pressure. The residue was diluted with $H_2O$ (100 mL) and extracted with EtOAc (3×100 mL). The combined organic layers were washed with brine (50 mL), dried over $Na_2SO_4$, filtered and concentrated under reduced pressure. The crude product was purified by flash chromatography on silica gel column eluted (0-15% EtOAc/Hexane) using ELS detector to give the desired product as a solid (1.85 g, 79%). $^1$H NMR (400 MHz, CHLOROFORM-d) δ 9.69 (d, J=1.5 Hz, 1H), 7.39-7.31 (m, 5H), 5.31 (br. s., 1H), 5.21-5.14 (m, 2H), 5.12 (dd, J=6.3, 1.8 Hz, 1H), 4.77 (d, J=2.0 Hz, 1H), 4.65-4.62 (m, 1H), 4.62-4.55 (m, 1H), 4.50-4.44 (m, 1H), 2.89 (td, J=11.1, 5.9 Hz, 1H), 2.60 (d, J=16.3 Hz, 1H), 2.17-1.72 (m, 11H), 1.71 (s, 3H), 1.53-1.19 (m, 14H), 1.11-1.01 (m, 2H), 0.98 (s, 3H), 0.94 (s, 3H), 0.90 (s, 3H), 0.88 (s, 3H), 0.84 (s, 3H). $^{19}$F NMR (376 MHz, CHLOROFORM-d) δ −225.07 (s, 1F)

Step 2: Preparation of (S)-benzyl 4-((1R,3aS,5aR,5bR,7aR,11aS,11bR,13aR,13bR)-3a-(((2-(1,1-dioxidothiomorpholino)-2-methylpropyl)amino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate A suspension of (S)-benzyl 1-(fluoromethyl)-4-((1R,3aS,5aR,5bR,7aR,11aS,11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (70 mg, 0.105 mmol) and 4-(1-amino-2-methylpropan-2-yl)thiomorpholine 1,1-dioxide (32 mg, 0.157 mmol) in DCE (1 mL) was stirred at rt for 1 h. To the resulting solution were added sodium cyanoborohydride (20 mg, 0.314 mmol) and AcOH (0.012 mL, 0.209 mmol). The mixture was stirred at rt for 18 h. The mixture was diluted with saturated NaHCO$_3$ (5 mL) and extracted with CH$_2$Cl$_2$ (3×10 mL). The combined organic layers were dried over Na$_2$SO$_4$, filtered and concentrated under reduced pressure. The crude product was purified by flash chromatography on silica gel column (20-80% EtOAc/Hexane) using ELS detector to give the desired product as a solid (18 mg, 20%). LCMS m/e 859.55 (M+H)$^+$, 3.113 minutes (Method 8). $^1$H NMR (400 MHz, CHLOROFORM-d) δ 7.40-7.29 (m, 5H), 5.32 (s, 1H), 5.21-5.14 (m, 2H), 5.12 (d, J=4.5 Hz, 1H), 4.69 (d, J=1.5 Hz, 1H), 4.63-4.55 (m, 1H), 4.59 (s, 1H), 4.51-4.44 (m, 1H), 3.07 (m, 8H), 2.73-2.55 (m, 3H), 2.42 (td, J=11.0, 5.6 Hz, 1H), 2.18-0.92 (m, 29H), 1.69 (s, 3H), 1.16 (s, 3H), 1.15 (s, 3H), 1.04 (s, 3H), 0.98 (s, 3H), 0.90 (s, 3H), 0.89 (s, 3H), 0.84 (s, 3H). $^{19}$F NMR (376 MHz, CHLOROFORM-d) δ −225.06 (s, 1F).

Step 3

To a solution of (S)-benzyl 4-((1R,3aS,5aR,5bR,7aR,11aS,11bR,13aR,13bR)-3a-(((2-(1,1-dioxidothiomorpholino)-2-methylpropyl)amino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (18 mg, 0.021 mmol) in 1,4-dioxane (1 mL) and MeOH (0.5 mL) was added 1N NaOH (0.5 mL, 0.5 mmol)). The mixture was stirred at 60° C. for 2 h. The reaction mixture was purified by Prep HPLC (Method 8) to give (S)-4-((1R,3aS,5aR,5bR,7aR,11aS,11bR,13aR,13bR)-3a-(((2-(1,1-dioxidothiomorpholino)-2-methylpropyl)amino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid as solid (6 mg, 37%). LCMS m/e 769.55 (M+H)$^+$, 2.816 minutes (Method 8). $^1$H NMR (400 MHz, CHLOROFORM-d) δ 5.33 (s, 1H), 5.17 (d, J=4.3 Hz, 1H), 4.69 (s, 1H), 4.60 (s, 1H), 4.56 (s, 1H), 4.44 (s, 1H), 3.13-3.01 (m, 8H), 3.01-0.89 (m, 33H), 1.68 (s, 3H), 1.15 (s, 6H), 1.03 (s, 3H), 0.97 (s, 3H), 0.96 (s, 3H), 0.92 (s, 3H), 0.85 (s, 3H). $^{19}$F NMR (376 MHz, CHLOROFORM-d) δ −224.76 (s, 1F).

Example 11

Preparation of (R)-4-((1R,3aS,5aR,5bR,7aR,11aS,11bR,13aR,13bR)-3a-(((3-(1,1-dioxidothiomorpholino)propyl)amino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid

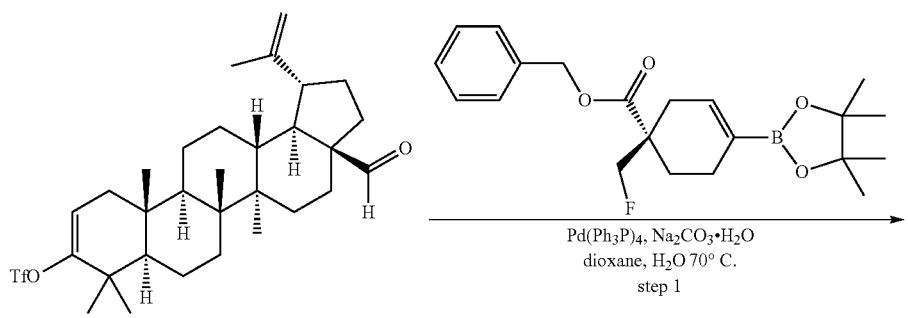

-continued

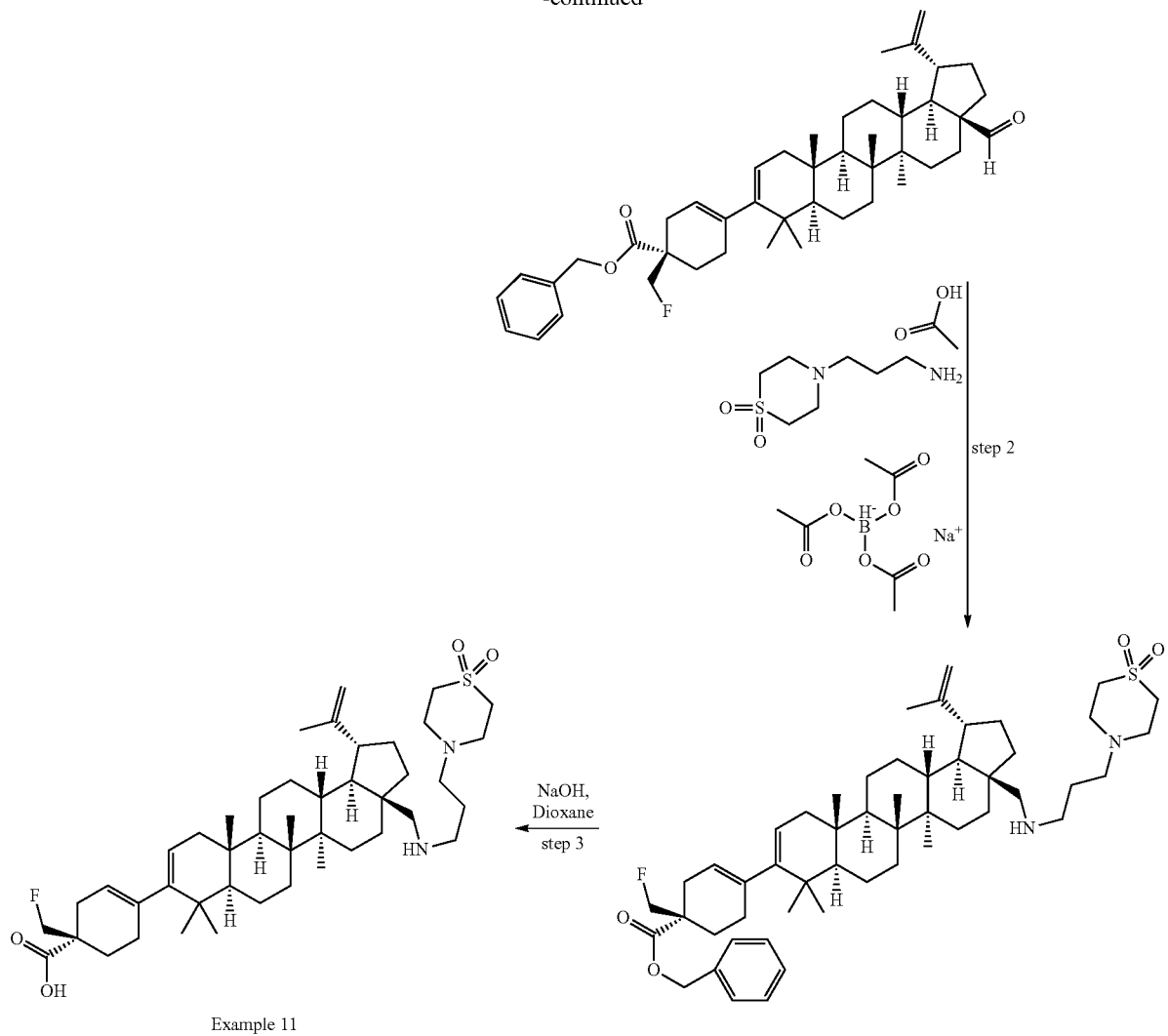

Example 11

Step 1. Preparation of (R)-benzyl 1-(fluoromethyl)-4-((1R,3aS,5aR,5bR,7aR,11aS,11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate In a 25 mL pressure vessel, a mixture of (1R,3aS,5aR,5bR,7aR,11aR,11bR,13aR,13bR)-3a-formyl-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate (164 mg, 0.287 mmol), (R)-benzyl 1-(fluoromethyl)-4-(4,4,5,5-tetramethyl-1,3,2-dioxaborolan-2-yl)cyclohex-3-enecarboxylate (118 mg, 0.316 mmol), $Na_2CO_3 \cdot H_2O$ (107 mg, 0.862 mmol) and $Pd(Ph_3P)_4$ (19.92 mg, 0.017 mmol) in dioxane (2 mL) and water (0.500 mL) under $N_2$ was cooled to $-78°$ C. The mixture solidified and vacuuming/purging with $N_2$ cycles were performed three times. The mixture was stirred at 70° C. for 1 h and the color turned dark brownish. The reaction mixture was diluted with $H_2O$ (100 mL) and extracted with EtOAc (3×100 mL). The combined organic layers were washed with brine (50 mL), dried over $Na_2SO_4$, filtered and concentrated under reduced pressure. The crude product was purified (24 g silica gel column; 0-25%, 25% EtOAc/Hexane; ELS detector) to give the title compound as a white solid (122 mg, 63.5%). LCMS: m/e 691.45 (M+Na)$^+$, 4.428 min (Method 9). $^1$H NMR (400 MHz, CHLOROFORM-d) δ 9.73 (d, J=1.5 Hz, 1H), 7.47-7.25 (m, 5H), 5.35 (br. s., 1H), 5.20 (d, J=1.8 Hz, 2H), 5.16-5.09 (m, 1H), 4.79 (d, J=1.8 Hz, 1H), 4.71-4.64 (m, 1H), 4.61-4.53 (m, 1H), 4.51-4.41 (m, 1H), 2.89 (td, J=11.1, 5.9 Hz, 1H), 2.63 (d, J=18.3 Hz, 1H), 2.31-1.85 (m, 8H), 1.85-1.76 (m, 3H), 1.73 (s, 3H), 1.61-1.20 (m, 14H), 1.15-1.05 (m, 2H), 1.04-1.00 (m, 3H), 0.99 (br. s., 3H), 0.96 (s, 3H), 0.90 (s, 3H), 0.87 (s, 3H).

Step 2. Preparation of (R)-benzyl 4-((1R,3aS,5aR,5bR,7aR,11aS,11bR,13aR,13bR)-3a-(((3-(1,1-dioxidothiomorpholino)propyl)amino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate To a solution of (R)-benzyl 1-(fluoromethyl)-4-((1R,3aS,5aR,5bR,7aR,11aS,11bR,13aR,13bR)-3a-formyl-5a,5b,8,8, 11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (122 mg, 0.182 mmol) in DCE (2 mL) was added acetic acid (0.021 mL, 0.365 mmol) and 4-(3-aminopropyl)thiomorpholine 1,1-dioxide (70.1 mg, 0.365 mmol). The solution turned to cloudy first and clear 10 minutes later. The mixture was stirred at RT for 2 h. Sodium triacetoxyborohydride (193 mg, 0.912 mmol) was added and the resulting mixture was stirred for 18 h. Acidic acid (0.2 mL) and sodium triacetoxyborohydride (193 mg, 0.912 mmol) were added and mixture was stirred for 18 h. The mixture was then diluted with sat. NaHCO$_3$ (7 mL) and was extracted with dichloromethane (3×7 mL). The combined organic layers were dried with Na$_2$SO$_4$. The drying agent was removed by filtration and the filtrate was concentrated under reduced pressure. The crude product was purified (silica gel). The fractions containing the expected product were collected and concentrated under reduced pressure to yield the title compound as a white solid (130 mg, 84%). LCMS: m/e 845.60 (M+H)$^+$, 3.116 min (Method 9). $^1$H NMR (400 MHz, CHLOROFORM-d) δ 7.41-7.29 (m, 5H), 5.34-5.29 (m, 1H), 5.18 (d, J=2.3 Hz, 2H), 5.11 (s, 1H), 4.70 (s, 1H), 4.63-4.53 (m, 2H), 4.47 (d, J=4.5 Hz, 1H), 3.14-2.97 (m, 12H), 2.95-2.82 (m, 3H), 2.68-2.51 (m, 4H), 2.48-2.33 (m, 2H), 2.24-2.07 (m, 3H), 2.03-1.91 (m, 4H), 1.91-1.73 (m, 6H), 1.71 (br. s., 3H), 1.63-1.30 (m, 11H), 1.08 (br. s., 3H), 0.98 (s, 3H), 0.92 (s, 3H), 0.87 (s, 3H), 0.84 (s, 3H).

Step 3

To a solution of (R)-benzyl 4-((1R,3aS,5aR,5bR,7aR,11aS,11bR,13aR,13bR)-3a-(((3-(1,1-dioxidothiomorpholino)propyl)amino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (130 mg, 0.154 mmol) in 1,4-dioxane (6 mL) and MeOH (3 mL) was added 1N NaOH (3 mL, 3.00 mmol). The mixture was stirred at 66° C. for 2 h and a clear solution was obtained. The reaction mixture was purified by prep HPLC (method 9) to give (R)-4-((1R,3aS,5aR,5bR,7aR,11aS,11bR,13aR,13bR)-3a-(((3-(1,1-dioxidothiomorpholino)propyl)amino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid as a white solid (55 mg, 45%). LCMS: m/e 755.50 (M+H)$^+$, 2.837 min (Method 9). $^1$H NMR (400 MHz, CHLOROFORM-d) δ 5.29 (br. s., 1H), 5.15 (d, J=4.5 Hz, 1H), 4.71 (s, 1H), 4.60 (s, 1H), 4.50 (q, J=8.8 Hz, 1H), 4.39 (q, J=8.6 Hz, 1H), 3.36 (d, J=6.0 Hz, 4H), 3.33-3.28 (m, 4H), 3.23-3.10 (m, 3H), 2.95 (t, J=7.2 Hz, 2H), 2.82 (d, J=13.1 Hz, 1H), 2.56-2.40 (m, 2H), 2.31-2.17 (m, 1H), 2.14-1.89 (m, 7H), 1.85-1.61 (m, 10H), 1.60-1.13 (m, 13H), 1.12-1.04 (m, 4H), 1.01 (s, 3H), 0.94 (s, 3H), 0.90 (s, 3H), 0.87 (s, 3H). $^{19}$F NMR (376 MHz, CHLOROFORM-d) δ −222.66−−223.63 (m, 1F).

Example 12

Preparation of (R)-4-((1R,3aS,5aR,5bR,7aR,11aS,11bR,13aR,13bR)-3a4N-(3-(1,1-dioxidothiomorpholino)propyl)acetamido)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid

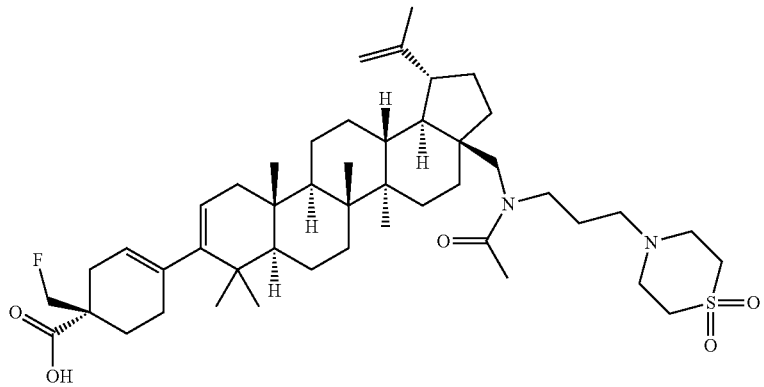

To a solution of (R)-4-((1R,3aS,5aR,5bR,7aR,11aS,11bR,13aR,13bR)-3a-(((3-(1,1-dioxidothiomorpholino)propyl)amino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid (20 mg, 0.026 mmol) in CH$_2$Cl$_2$ (1 mL) was added acetic anhydride (0.012 mL, 0.132 mmol) and DMAP (0.324 mg, 2.65 μmol). The resulting mixture was heated at 50° C. for 24 h. The reaction mixture was concentrated under reduced pressure. The residue was redissolved MeOH (4 mL) and purified by prep. HPLC (method 10) to give the title compound as a white solid (3 mg, 13.5%). LCMS: m/e 797.55 (M+H)$^+$, 3.103 min (Method 9). $^1$H NMR (400 MHz, METHANOL-d$_4$) δ 5.35 (br. s., 1H), 5.21 (d, J=4.8 Hz, 1H), 4.76 (d, J=2.0 Hz, 1H), 4.82-4.72 (m, 1H), 4.62 (s, 1H), 4.60-4.52 (m, 1H), 4.50-4.36 (m, 1H), 3.64 (d, J=13.8 Hz, 1H), 3.49 (t, J=7.4 Hz, 2H), 3.27 (m, 1H), 3.18-3.08 (m, 4H), 3.03 (d, J=5.5 Hz, 4H), 2.68-2.47 (m, 4H), 2.27 (d, J=6.0 Hz, 1H), 2.22-1.93 (m, 9H), 1.89-1.23 (m, 21H), 1.17 (s, 3H), 1.16-1.07 (m, 3H), 1.05 (s, 3H), 1.00 (s, 3H), 0.96 (s, 3H), 0.92 (s, 3H). $^{19}$F NMR (376 MHz, METHANOL-d$_4$) δ −226.56−−227.82 (m, 1F).

Example 13
Preparation of (R)-4-((1R,3aS,5aR,5bR,7aR,11aS,11bR,13aR,13bR)-3a-((2-(4,4-bis(ethoxycarbonyl)piperidin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid
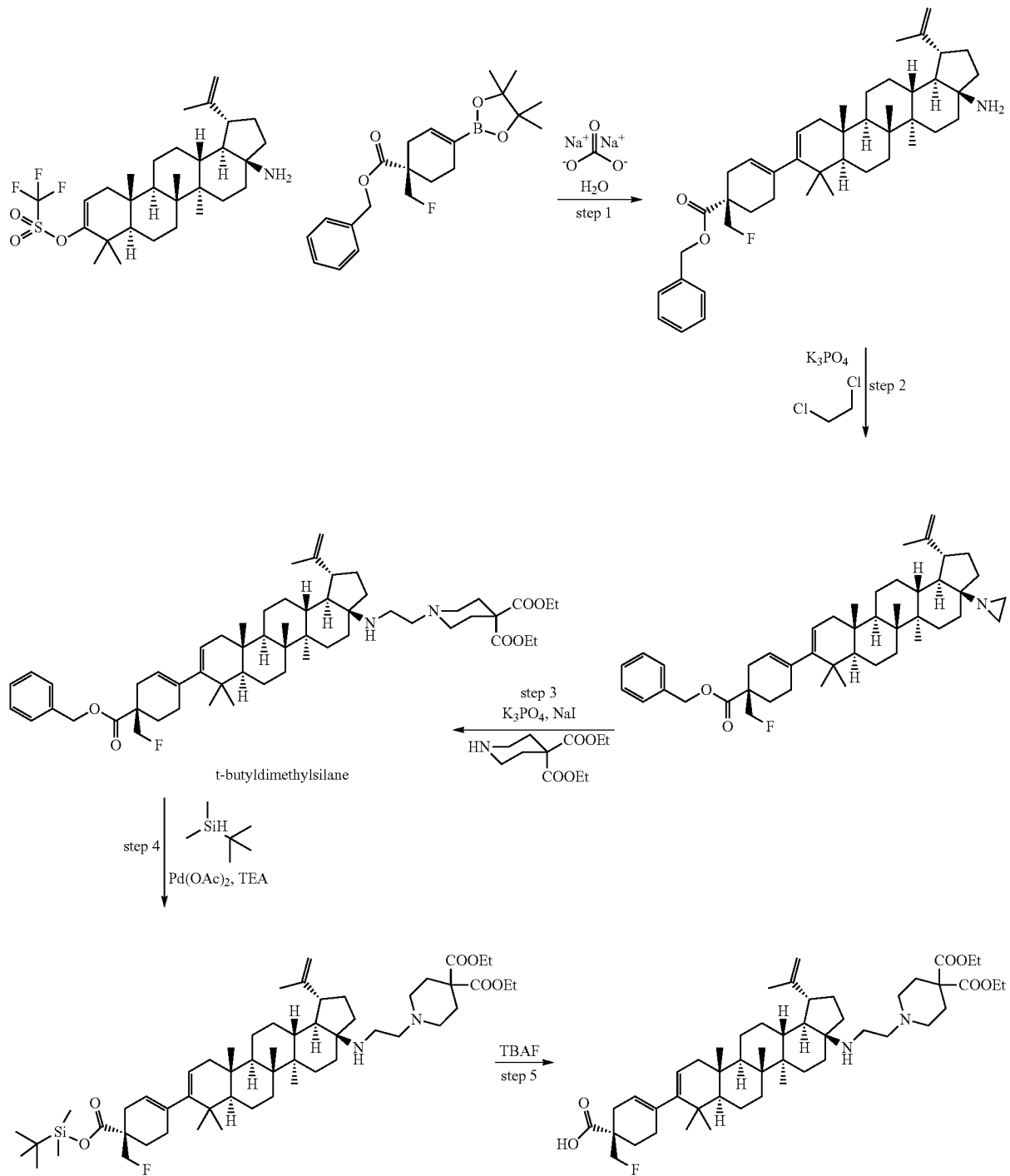
Example 13

Step 1. Preparation of ((R)-benzyl 4-((1R,3aS,5aR, 5bR,7aR,11aS,11bR,13aR,13bR)-3a-amino-5a,5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)-1-(fluoromethyl)cyclohex-3-enecarboxylate A mixture of (R)-benzyl 1-(fluoromethyl)-4-(4,4,5,5-tetramethyl-1,3,2-dioxaborolan-2-yl)cyclohex-3-enecarboxylate (669 mg, 1.788 mmol), (1R,3aS,5aR,5bR,7aR,11aR, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl trifluoromethanesulfonate (950 mg, 1.703 mmol), sodium carbonate hydrate (634 mg, 5.11 mmol) and palladium tetrakis (118 mg, 0.102 mmol) was placed under nitrogen atmosphere. Dioxane (16 mL) was added and an orange solution was formed. Water (4 mL) was added and a very pale yellow suspension formed. The entire mixture was chilled to −78° C. and evacuation/purging cycles were performed three times and finally a nitrogen purge was performed. The flask was immersed into an oil bath at 65-85° C. The color of the mixture changed from pale yellow suspension to dark brown over a 10 min period. Heating was allowed to proceed at 85° C. for a total of 5 hours. The reaction mixture was diluted with $H_2O$ (100 mL) and extracted with EtOAc (3×100 mL). The combined organic layers were washed with brine (50 mL), dried over $Na_2SO_4$, filtered and concentrated under reduced pressure. The crude material was purified by silica gel chromatography to afford the title compound as a white solid (0.78 g, 69.8%). LCMS: m/e 656.50 (M+H)$^+$, 3.003 min (Method 9). $^1$H NMR (400 MHz, CHLOROFORM-d) δ 7.46-7.29 (m, 5H), 5.43-5.28 (m, 1H), 5.24-5.16 (m, 2H), 5.13 (dd, J=6.1, 2.0 Hz, 1H), 4.75 (d, J=2.0 Hz, 1H), 4.62 (s, 1H), 4.61-4.56 (m, 1H), 4.52-4.44 (m, 1H), 2.68-2.51 (m, 2H), 2.26-1.94 (m, 6H), 1.84-1.72 (m, 4H), 1.72 (s, 3H), 1.65-1.28 (m, 12H), 1.27 (s, 3H), 1.14 (d, J=13.9 Hz, 2H), 1.09 (s, 3H), 1.06 (m, 2H), 0.98 (s, 3H), 0.95 (s, 3H), 0.89 (s, 3H), 0.87 (s, 3H).

Step 2. Preparation of (R)-benzyl 4-((1R,3aS,5aR, 5bR,7aR,11aS,11bR,13aR,13bR)-3a-(aziridin-1-yl)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate In a flame dried 75 mL thick-walled resealable vessel was placed (R)-benzyl 4-((1R,3aS,5aR,5bR,7aR,11aS,11bR, 13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)-1-(fluoromethyl)cyclohex-3-enecarboxylate (0.78 g, 1.189 mmol) and flame dried potassium phosphate (1.262 g, 5.95 mmol), followed by 1,2-dichloroethane (20 mL) and acetonitrile (10 mL). The reaction mixture was flushed with nitrogen, sealed, and warmed to 130° C. for 36 h. The crude reaction mixture was filtered through a short pad of silica gel and washed with ethyl acetate to obtain a very pale orange solution. The solution was concentrated under reduced pressure to obtain the title compound as a off-white solid. The compound was used as it, without further purification. LCMS: m/e 682.50 (M+H)$^+$, 700.55 (M+H$_2$O)$^+$, 714.55 (M+MeOH)$^+$, 3.053 min (Method 9).

Step 3

Preparation of diethyl 1-(2-((1R,3aS,5aR,5bR,7aR,11aS, 11bR,13aR,13bR)-9-((R)-4-((benzyloxy)carbonyl)-4-(fluoromethyl)cyclohex-1-en-1-yl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-3a-yl) amino)ethyl)piperidine-4,4-dicarboxylate (R)-benzyl 4-((1R,3aS,5aR,5bR,7aR,11aS,11bR,13aR,13bR)-3a-(aziridin-1-yl)-5a,5b,8,8,11a-pentamethyl-1-(prop-1-en-2-yl)-2, 3,3a,4,5,5a,5b,6,7,7a,8,11,11a,11b,12,13,13a,13b-octadecahydro-1H-cyclopenta[a]chrysen-9-yl)-1-(fluoromethyl) cyclohex-3-enecarboxylate (100 mg, 0.147 mmol) was placed in a 15 mL sealed tube. CH$_3$CN (2 mL) was added followed by diethyl piperidine-4,4-dicarboxylate (67.2 mg, 0.293 mmol). To this suspension was added sodium iodide (24.18 mg, 0.161 mmol) and potassium phosphate (93 mg, 0.440 mmol). The resulting mixture was heated up at 125° C. for 15 h. The reaction mixture was diluted with ethyl acetate (50 mL) and washed by sodium bicarbonate and brine. The organic layer was collected, dried over sodium sulfate and concentrated under reduced pressure. The crude material was purified on silica gel (0-25% ethyl acetate/hexanes) to yield the title compound as a white solid (60 mg, 48%). LCMS: m/e 911.65 (M+H)$^+$, 3.213 min (Method 9). $^1$H NMR (400 MHz, CHLOROFORM-d) δ 7.41-7.31 (m, 5H), 5.31 (br. s., 1H), 5.22-5.14 (m, 2H), 5.10 (d, J=4.5 Hz, 1H), 4.71 (d, J=2.5 Hz, 1H), 4.63-4.53 (m, 2H), 4.50-4.41 (m, 1H), 4.28-4.20 (m, 4H), 3.01-2.79 (m, 2H), 2.69-2.55 (m, 2H), 2.54-2.29 (m, 2H), 2.20-2.10 (m, 6H), 2.00-1.73 (m, 15H), 1.70-1.67 (s, 3H), 1.67-1.49 (m, 10H), 1.26 (t, J=7.2 Hz, 11H), 1.07 (s, 3H), 0.97-0.93 (m, 3H), 0.92 (s, 3H), 0.86 (s, 3H), 0.84 (s, 3H).

Step 4. Preparation of diethyl 1-(2-(((1R,3aS,5aR, 5bR,7aR,11aS,11bR,13aR,13bR)-9-((R)-4-(((tert-butyldimethylsilyl)oxy)carbonyl)-4-(fluoromethyl) cyclohex-1-en-1-yl)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-3a-yl)amino)ethyl)piperidine-4,4-dicarboxylate To a solution of diethyl 1-(2-(((1R,3aS,5aR,5bR,7aR, 11aS,11bR,13aR,13bR)-9-((R)-4-((benzyloxy)carbonyl)-4-(fluoromethyl)cyclohex-1-en-1-yl)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-3a-yl)amino)ethyl)piperidine-4,4-dicarboxylate (60 mg, 0.066 mmol) in DCE (3 mL) was added TEA (0.015 mL, 0.105 mmol), t-butyldimethylsilane (0.022 mL, 0.132 mmol), and palladium(II) acetate (3.70 mg, 0.016 mmol). The mixture was flushed with N$_2$ and was heated to 60° C. After 3 h of heating the mixture was cooled to RT and filtered through a pad of celite and silica gel (washed with 50% EtOAc in hexanes, then dichloromethane). The filtrate was concentrated under reduced pressure to yield the title compound as a solid (61 mg, 100%). The crude product was used in the next step with no additional purification. LCMS: m/e 935.70 (M+H)$^+$, 3.247 min (Method 9).

Step 5

To a solution of diethyl 1-(2-(((1R,3aS,5aR,5bR,7aR,11aS,11bR,13aR,13bR)-9-((R)-4-(((tert-butyldimethylsilyl)oxy)carbonyl)-4-(fluoromethyl)cyclohex-1-en-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)amino)ethyl)piperidine-4,4-dicarboxylate (15 mg, 0.016 mmol) in THF (4 mL) was added TBAF (1M in THF) (0.024 mL, 0.024 mmol). The mixture was stirred at rt for 30 min. The mixture was purified by Prep HPLC (method 9) to give (R)-4-((1R,3aS,5aR,5bR,7aR,11aS,11bR,13aR,13bR)-3a-((2-(4,4-bis(ethoxycarbonyl)piperidin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid as a white solid (7 mg, 53.2%). LCMS: m/e 821.60 (M+H)$^+$, 2.901 min (Method 9). $^1$H NMR (400 MHz, CHLOROFORM-d) δ 5.38-5.32 (m, 1H), 5.17 (d, J=4.8 Hz, 1H), 4.79 (s, 1H), 4.72-4.40 (m, 3H), 4.32-4.21 (m, 4H), 3.54-3.24 (m, 4H), 3.10 (br. s., 3H), 2.90-2.60 (m, 2H), 2.36 (br. s., 4H), 2.28-1.73 (m, 12H), 1.69 (s, 3H), 1.66-1.50 (m, 6H), 1.44 (br. s., 3H), 1.38-1.33 (m, 3H), 1.32-1.24 (m, 9H), 1.12 (s, 3H), 1.08 (d, J=8.3 Hz, 2H), 1.02 (s, 3H), 0.97 (s, 3H), 0.92 (s, 3H), 0.87 (s, 3H).

Example 14 and Example 15

Preparation of (1R)-4-((1R,3aS,5aR,5bR,7aR,11aS,11bR,13aR,13bR)-3a-((2-(3-(ethoxycarbonyl)-1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid (isomer 1) and
Preparation of (1R)-4-((1R,3aS,5aR,5bR,7aR,11aS,11bR,13aR,13bR)-3a-((2-(3-(ethoxycarbonyl)-1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid (isomer 2)

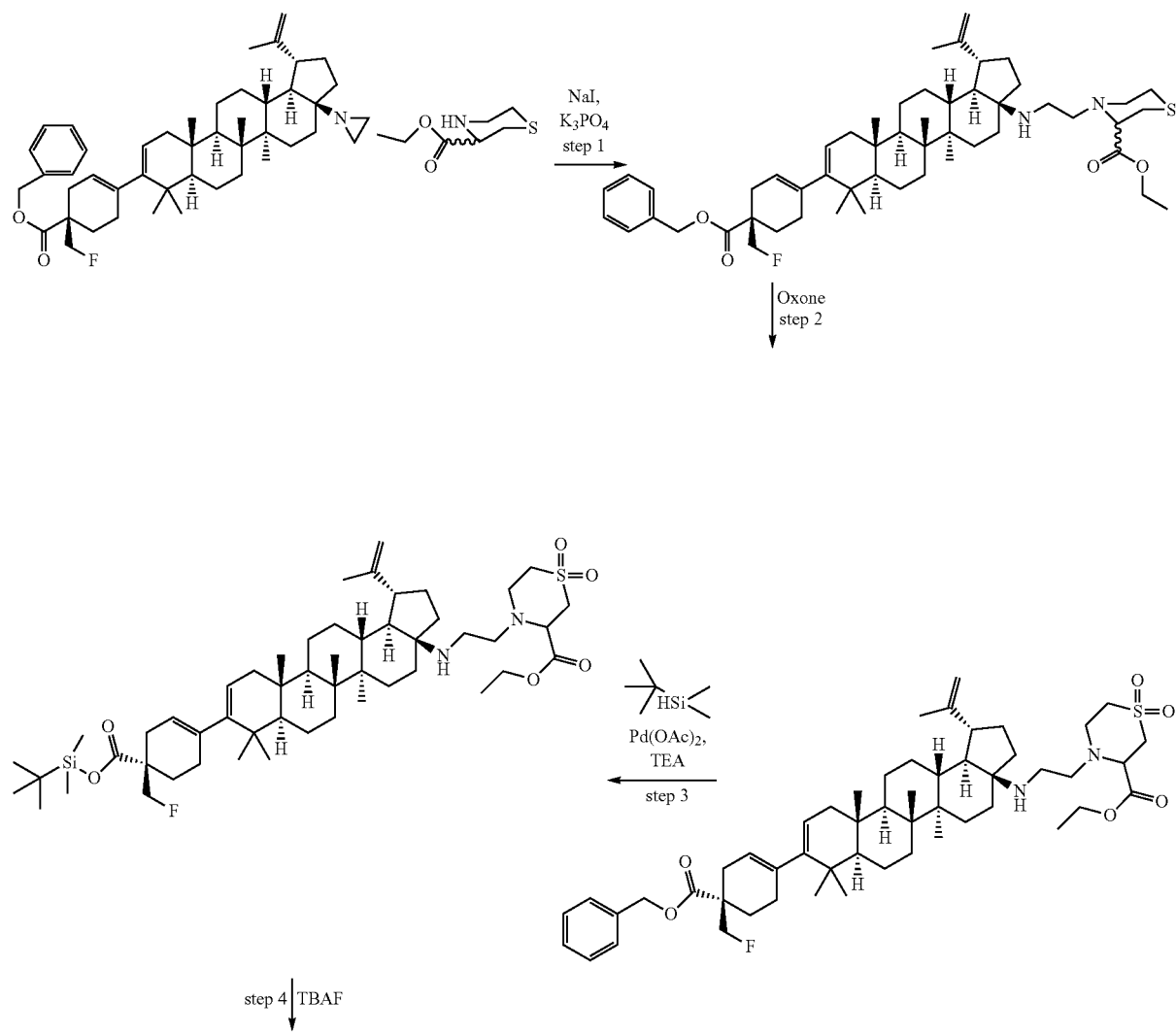

-continued

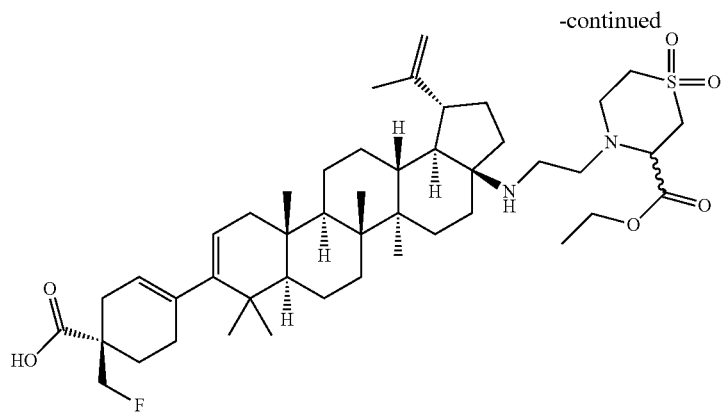

Isomer 1, Example 14
and
Isomer 2, Example 15

Step 1. Preparation of ethyl 4-(2-((1R,3aS,5aR,5bR, 7aR,11aS,11bR,13aR,13bR)-9-((R)-4-((benzyloxy) carbonyl)-4-(fluoromethyl)cyclohex-1-en-1-yl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-3a-yl) amino)ethyl)thiomorpholine-3-carboxylate The title compound was prepared in 26.3% yield following the procedure described above for the preparation of diethyl 1-(2-(((1R,3aS,5aR,5bR,7aR,11aS,11bR,13aR, 13bR)-9-((R)-4-((benzyloxy)carbonyl)-4-(fluoromethyl)cyclohex-1-en-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)amino) ethyl)piperidine-4,4-dicarboxylate, using thiomorpholine-3-carboxylic acid ethyl ester hydrochloride instead of diethyl piperidine-4,4-dicarboxylate as starting material. MS: m/e 857.65. (M+H)$^+$, 3.876 min (Method 9) $^1$H NMR (400 MHz, CHLOROFORM-d) δ 7.38-7.31 (m, 5H), 5.31 (d, J=3.8 Hz, 1H), 5.23-5.13 (m, 2H), 5.10 (d, J=4.5 Hz, 1H), 4.70 (d, J=2.0 Hz, 1H), 4.62-4.54 (m, 2H), 4.51-4.40 (m, 1H), 4.28-4.22 (m, 2H), 3.81-3.67 (m, 1H), 3.63 (ddd, J=12.5, 5.8, 3.5 Hz, 1H), 3.37 (ddd, J=12.4, 9.9, 2.9 Hz, 1H), 3.21 (ddd, J=12.4, 8.5, 5.8 Hz, 1H), 3.09 (ddd, J=9.9, 6.0, 3.5 Hz, 1H), 3.03-2.95 (m, 1H), 2.93-2.66 (m, 5H), 2.64-2.32 (m, 5H), 2.17-2.08 (m, 3H), 2.00-1.77 (m, 8H), 1.69 (s, 3H), 1.64-1.48 (m, 8H), 1.18-1.01 (m, 8H), 0.99-0.80 (m, 16H).

Step 2. Preparation of ethyl 4-(2-((1R,3aS,5aR,5bR, 7aR,11aS,11bR,13aR,13bR)-9-((R)-4-((benzyloxy) carbonyl)-4-(fluoromethyl)cyclohex-1-en-1-yl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-3a-yl) amino)ethyl)thiomorpholine-3-carboxylate 1,1-dioxide To a solution of mixture of ethyl 4-(2-((1R,3aS,5aR,5bR, 7aR,11aS,11bR,13aR,13bR)-9-((R)-4-((benzyloxy)carbonyl)-4-(fluoromethyl)cyclohex-1-en-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)amino)ethyl)thiomorpholine-3-carboxylate (32 mg, 0.037 mmol) in MeOH (2 mL) was added a suspension of OXONE® (34.4 mg, 0.056 mmol) in water (2.00 mL) at 0° C., followed by acetone (5 mL). The resulting mixture was stirred at 0° C. for 12 h. The reaction mixture was diluted with water (10 mL) and extracted with ethyl acetate. The organic layer was washed with sodium hydrosulfite and then dried over sodium sulfate, filtered and concentrated under reduced pressure to yield the title compound as a solid. The 30 mg of crude product was used in the next step without further purification. MS: m/e 889.55. (M+H)$^+$, 3.26 min (Method 9)

Step 3. Preparation of ethyl 4-(2-(((1R,3aS,5aR, 5bR,7aR,11aS,11bR,13aR,13bR)-9-((R)-4-(((tert-butyldimethylsilyl)oxy)carbonyl)-4-(fluoromethyl) cyclohex-1-en-1-yl)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-3a-yl)amino)ethyl)thiomorpholine-3-carboxylate 1,1-dioxide The title compound was prepared in 97% yield following the procedure described above for the preparation of diethyl 1-(2-(((1R,3aS,5aR,5bR,7aR,11aS,11bR,13aR,13bR)-9-((R)-4-(((tert-butyldimethylsilyl)oxy)carbonyl)-4-(fluoromethyl)cyclohex-1-en-1-yl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-3a-yl) amino)ethyl)piperidine-4,4-dicarboxylate, using ethyl 4-(2-(((1R,3aS,5aR,5bR,7aR,11aS,11bR,13aR,13bR)-9-((R)-4-((benzyloxy)carbonyl)-4-(fluoromethyl)cyclohex-1-en-1-yl)-5a,5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-3a-yl)amino)ethyl) thiomorpholine-3-carboxylate 1,1-dioxide instead of diethyl 1-(2-(((1R,3aS,5aR,5bR,7aR,11aS,11bR,13aR,13bR)-9-((R)-4-((benzyloxy)carbonyl)-4-(fluoromethyl)cyclohex-1-en-1-yl)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-3a-yl)amino) ethyl)piperidine-4,4-dicarboxylate as starting material. MS: m/e 913.65. (M+H)$^+$, 3.204 min (Method 9)

Step 4

To a solution of ethyl 4-(2-(((1R,3aS,5aR,5bR,7aR,11aS, 11bR,13aR,13bR)-9-((R)-4-(((tert-butyldimethylsilyl)oxy)

carbonyl)-4-(fluoromethyl)cyclohex-1-en-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)amino)ethyl)thiomorpholine-3-carboxylate 1,1-dioxide (20 mg, 0.022 mmol) in THF (4 mL) was added TBAF (1M in THF) (0.032 mL, 0.032 mmol). The mixture was stirred at RT for 30 minutes. The mixture was purified by Prep HPLC (method 9) to give two products:

Example 14: (1R)-4-((1R,3aS,5aR,5bR,7aR,11aS,11bR,13aR,13bR)-3a-((2-(3-(ethoxycarbonyl)-1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid (Isomer 1) as a white solid (2 mg, 11.43%). LCMS: m/e 799.50 (M+H)$^+$, 2.866 min (Method 9). $^1$H NMR (400 MHz, CHLOROFORM-d) δ 5.40-5.29 (m, 1H), 5.19 (d, J=4.8 Hz, 1H), 4.83 (s, 1H), 4.71 (s, 1H), 4.64-4.55 (m, 1H), 4.49 (q, J=8.6 Hz, 1H), 4.37-4.25 (m, 2H), 3.74-3.62 (m, 1H), 3.46-2.85 (m, 10H), 2.68-2.53 (m, 2H), 2.26-2.06 (m, 5H), 2.02-1.75 (m, 7H), 1.72 (s, 3H), 1.67-1.50 (m, 7H), 1.37-1.27 (m, 8H), 1.13 (s, 3H), 1.09-1.01 (m, 4H), 1.04 (s, 3H), 0.97 (s, 3H), 0.94-0.91 (m, 3H), 0.88 (s, 3H) and Example 15: (1R)-4-((1R,3aS,5aR,5bR,7aR,11aS,11bR,13aR,13bR)-3a-((2-(3-(ethoxycarbonyl)-1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid Isomer 2 as white solid (2 mg, 11.43%) as isomer 2. LCMS: m/e 799.55 (M+H)$^+$, 2.778 min (Method 9). $^1$H NMR (400 MHz, CHLOROFORM-d) δ 5.44-5.31 (m, 1H), 5.20 (d, J=4.5 Hz, 1H), 4.83 (s, 1H), 4.75-4.69 (m, 1H), 4.67-4.56 (m, 1H), 4.55-4.43 (m, 1H), 4.37-4.29 (m, 2H), 4.28-4.22 (m, 1H), 3.67 (br. s., 1H), 3.51-3.42 (m, 2H), 3.34-3.09 (m, 5H), 3.05-2.86 (m, 3H), 2.61 (d, J=5.8 Hz, 1H), 2.33-2.22 (m, 2H), 2.19-2.15 (m, 2H), 2.14-2.09 (m, 1H), 2.05-1.76 (m, 14H), 1.73 (s, 3H), 1.64-1.01 (m, 12H), 1.12 (s, 3H), 1.06 (s, 3H), 0.98 (s, 3H), 0.93 (s, 3H), 0.88 (s, 3H). $^{19}$F NMR (376 MHz, CHLOROFORM-d) δ −224.87−−225.57 (m, 1F).

Example 16

Preparation of 1-(2-(((1R,3aS,5aR,5bR,7aR,11aS,11bR,13aR,13bR)-9-((R)-4-carboxy-4-(fluoromethyl)cyclohex-1-en-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)amino)ethyl)piperidine-4,4-dicarboxylic acid

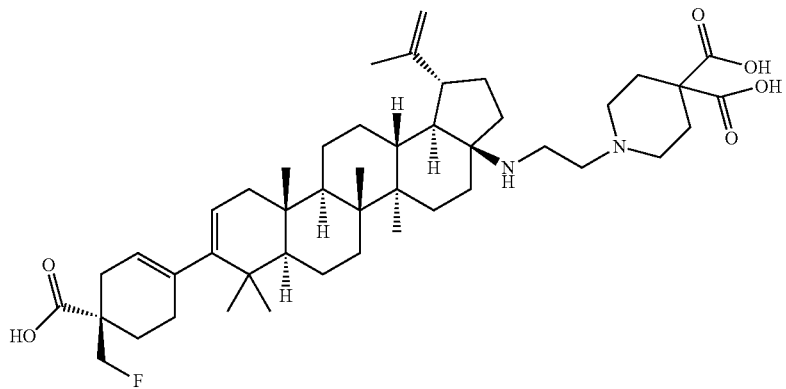

To a solution of (R)-4-(((1R,3aS,5aR,5bR,7aR,11aS,11bR, 13aR,13bR)-3a-((2-(4,4-bis(ethoxycarbonyl)piperidin-1-yl) ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid (5 mg, 6.09 μmol)) in 1,4-dioxane (2 mL) and MeOH (1 mL) was added sodium hydroxide (1 mL, 1.000 mmol). The mixture was stirred at 66° C. for 2 h, and then cooled to room temperature. The reaction mixture was purified by Prep HPLC (method 9) to give the title compound as a film (0.8 mg, 15.46%). LCMS: m/e 765.60 (M+H)$^+$, 2.928 min (Method 9).

Example 17

Preparation of 1-(2-(((1R,3aS,5aR,5bR,7aR,11aS, 11bR,13aR,13bR)-9-((R)-4-carboxy-4-(fluoromethyl)cyclohex-1-en-1-yl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-3a-yl)amino)ethyl)piperidine-4,4-dicarboxylic acid

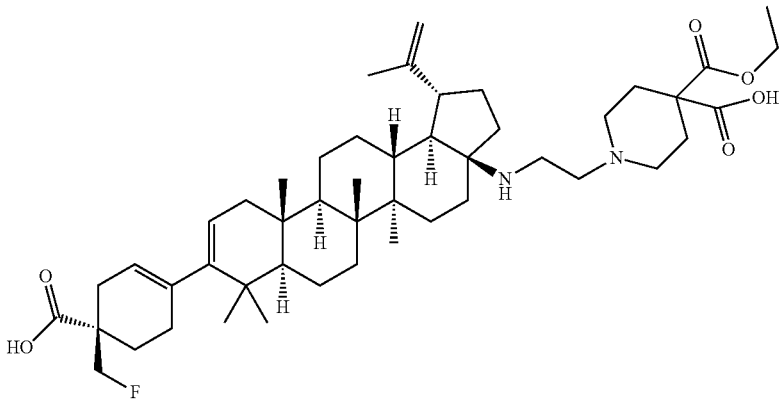

The title compound was isolated during the purification of 1-(2-(((1R,3aS,5 aR,5bR,7aR,11aS,11bR,13aR,13bR)-9-((R)-4-carboxy-4-(fluoromethyl)cyclohex-1-en-1-yl)-5a,5b, 8,8,11a-pentamethyl-1-(prop-1-en-2-yl)-2,3,3a,4,5,5a,5b,6, 7,7a,8,11,11a,11b,12,13,13a,13b-octadecahydro-1H-cyclopenta[a]chrysen-3a-yl)amino)ethyl)piperidine-4,4-dicarboxylic acid. (white solid, 1.2 mg, 22.36%). LCMS: m/e 793.60 (M+H)$^+$, 2.992 min (Method 9). $^1$H NMR (400 MHz, CHLOROFORM-d) δ 5.37 (br. s., 1H), 5.18 (d, J=6.0 Hz, 1H), 4.77 (s, 1H), 4.69 (s, 1H), 4.63-4.37 (m, 2H), 4.31-4.18 (m, 2H), 3.80-3.71 (m, 1H), 3.69-3.61 (m, 1H), 3.58-3.53 (m, 1H), 3.52-3.47 (m, 2H), 3.46-3.41 (m, 1H), 3.24-3.09 (m, 2H), 2.65-2.60 (m, 1H), 2.56-1.17 (m, 40H), 1.10 (s, 3H), 1.02 (s, 3H), 0.97 (s, 3H), 0.9 (s, 3H), 0.87 (s, 3H).

Example 18

Preparation of 4-(2-(((1R,3aS,5aR,5bR,7aR,11aS, 11bR,13aR,13bR)-9-((R)-4-carboxy-4-(fluoromethyl)cyclohex-1-en-1-yl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-3a-yl)amino)ethyl) thiomorpholine-3-carboxylic acid

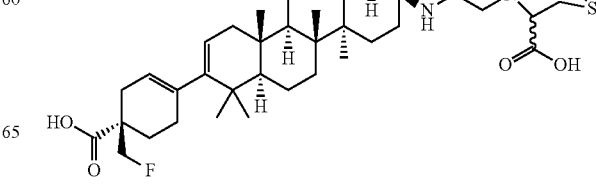

To a solution of ethyl 4-(2-(((1R,3aS,5aR,5bR,7aR,11aS, 11bR,13aR,13bR)-9-((R)-4-((benzyloxy)carbonyl)-4-(fluoromethyl)cyclohex-1-en-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)amino)ethyl)thiomorpholine-3-carboxylate (0.030 g, 0.035 mmol) in 1,4-dioxane (2 mL) and MeOH (1 mL) was added sodium hydroxide (1 ml, 1.000 mmol). The mixture was stirred at 66° C. for 2 h and a clear solution was formed. The crude reaction mixture was purified by Prep HPLC (method 10) to give the title compound as a white solid (4.5 mg, 16.53%). LCMS: m/e 739.55 (M+H)$^+$, 2.838 min (Method 9). $^1$H NMR (400 MHz, METHANOL-d$_4$) δ 5.35 (br. s., 1H), 5.21 (d, J=5.8 Hz, 1H), 4.85-4.80 (m, 1H), 4.75-4.68 (m, 1H), 4.63-4.51 (m, 1H), 4.49-4.37 (m, 1H), 3.44-3.36 (m, 1H), 3.22-2.90 (m, 4H), 2.89-2.68 (m, 4H), 2.66-2.48 (m, 3H), 2.44-2.23 (m, 2H), 2.18-1.98 (m, 8H), 1.85 (d, J=12.5 Hz, 2H), 1.77 (d, J=4.0 Hz, 3H), 1.74-1.28 (m, 14H), 1.25-1.17 (m, 3H), 1.14 (d, J=11.3 Hz, 2H), 1.11-1.08 (m, 3H), 1.00 (s, 3H), 0.96 (s, 3H), 0.94-0.89 (m, 3H). $^{19}$F NMR (376 MHz, METHANOL-d$_4$) δ −226.92 (m, 1F).

Example 19

Preparation of (R)-1-(fluoromethyl)-4-((1R,3aS, 5aR,5bR,7aR,11aS,11bR,13aR,13bR)-3a-((2-hydroxyethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid

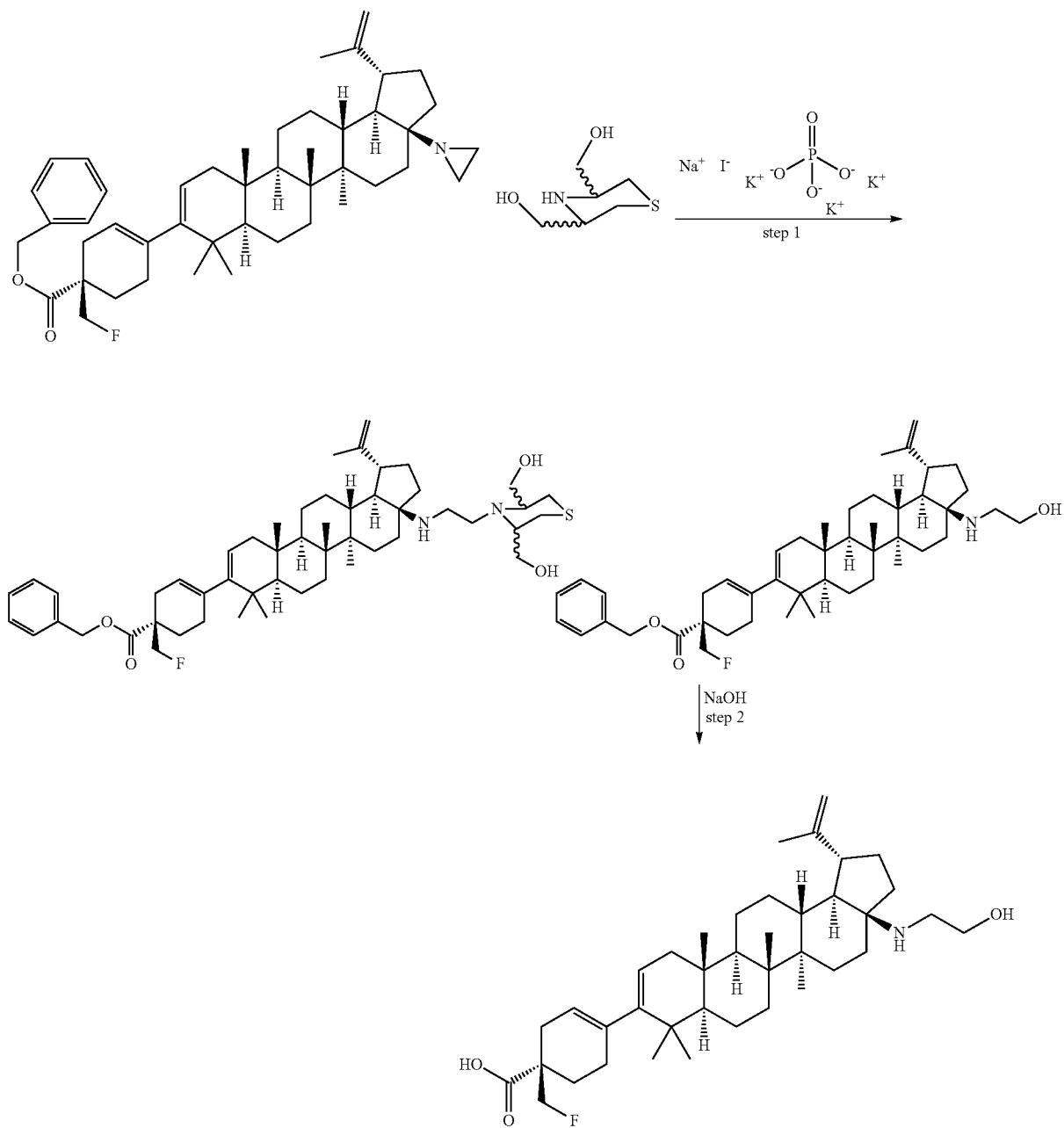

Example 19

Step 1. Preparation of (R)-benzyl 1-(fluoromethyl)-4-((1R,3aS,5aR,5bR,7aR,11aS,11bR,13aR,13bR)-3a-((2-hydroxyethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate To (R)-benzyl 4-((1R,3aS,5aR,5bR,7aR,11aS,11bR,13aR,13bR)-3a-(aziridin-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (230 mg, 0.337 mmol) in CH₃CN (6 mL) was added thiomorpholine-3,5-diyldimethanol (77 mg, 0.472 mmol), sodium iodide (55.6 mg, 0.371 mmol) and potassium phosphate (215 mg, 1.012 mmol). The resulting suspension was heated up at 125° C. for 15 h. The reaction mixture was diluted with ethyl acetate, washed with an aqueous solution of sodium bicarbonate and brine. The organic layer was dried over sodium sulfate and concentrated to dryness. The crude material was purified using silica gel to obtain an off-white solid (6 mg, 2.5%). LCMS: m/e 700.55 (M+H)⁺, 2.925 min (Method 9).

Step 2

(R)-benzyl 1-(fluoromethyl)-4-((1R,3aS,5aR,5bR,7aR,11aS,11bR,13aR,13bR)-3a-((2-hydroxyethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (6 mg, 8.57 µmol) was dissolved in a mixture of MeOH (2 mL) and dioxane (2 mL). Sodium hydroxide (1 ml, 1.000 mmol) was added. The resulting mixture was stirred at 25° C. for 15 h and purified by Prep HPLC (method 9) to give (R)-1-(fluoromethyl)-4-((1R,3aS,5aR,5bR,7aR,11aS,11bR,13aR,13bR)-3a-((2-hydroxyethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid as a white solid (2.0 mg, 36.3%). LCMS: m/e 610.55 (M+H)⁺, 2.928 min (Method 9).

General scheme for the preparation of Examples 20 and 21

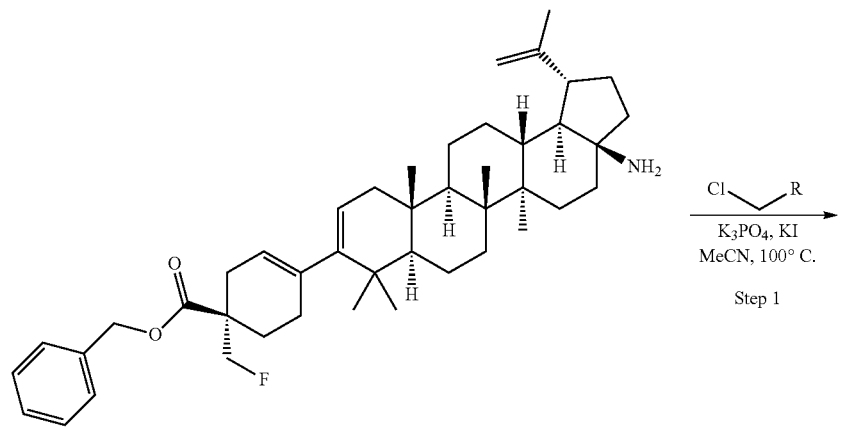

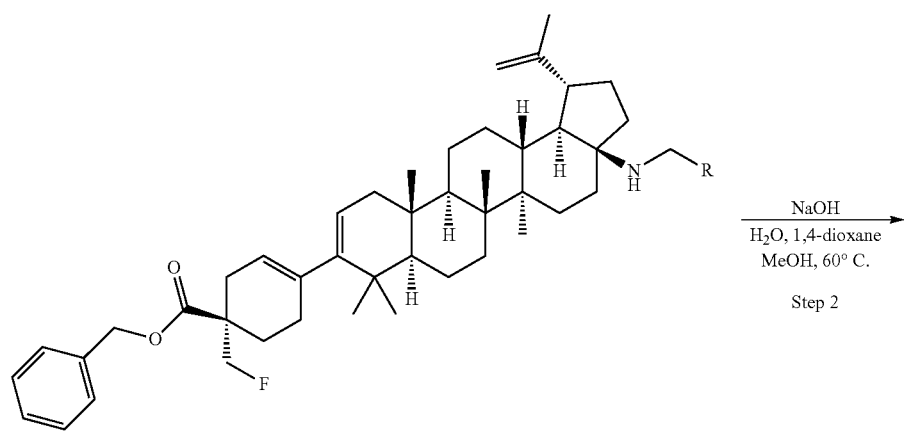

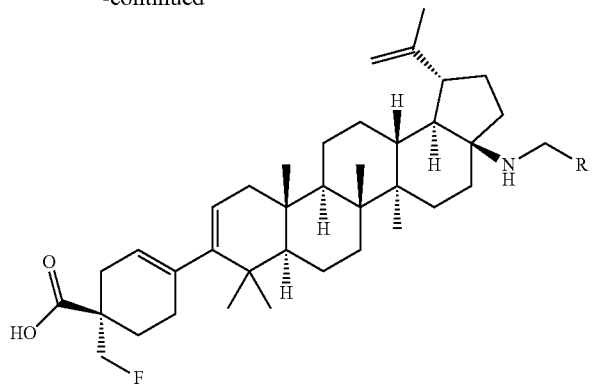

Example 20

Preparation of (S)-1-(fluoromethyl)-4-((1R,3aS,5aR, 5bR,7aR,11aS,11bR,13aR,13bR)-5a,5b,8,8,11a-pentamethyl-3a-((2-(2-oxopyrrolidin-1-yl)ethyl)amino)-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)cyclohex-3-enecarboxylic acid

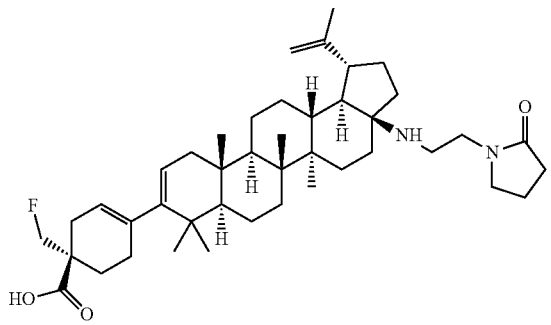

Step 1. Preparation of (S)-benzyl 1-(fluoromethyl)-4-((1R,3aS,5aR,5bR,7aR,11aS,11bR,13aR,13bR)-5a, 5b,8,8,11a-pentamethyl-3a-((2-(2-oxopyaolidin-1-yl) ethyl)amino)-1-(prop-1-en-2-yl)-2,3,3a,4,5,5a,5b,6, 7,7a,8,11,11a,11b,12,13,13a,13b-octadecahydro-1H-cyclopenta[a]chrysen-9-yl)cyclohex-3-enecarboxylate To a sealable flask containing (S)-benzyl 4-((1R,3aS,5aR, 5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)-1-(fluoromethyl)cyclohex-3-enecarboxylate (0.1 g, 0.152 mmol) and 1-(2-chloroethyl)pyrrolidin-2-one (0.056 g, 0.381 mmol) was added phosphoric acid, potassium salt (0.129 g, 0.610 mmol) and potassium iodide (0.038 g, 0.229 mmol). The mixture was diluted with acetonitrile (2 mL), flushed with nitrogen, then the vial was sealed and heated to 100° C. for 21 h. The mixture was cooled to rt, diluted with water (10 mL) and extracted with dichloromethane (3×10 mL). The organic layers were dried over sodium sulfate, filtered and concentrated under reduced pressure. The residue was purified by flash chromatography using a 0-5% methanol in dichloromethane gradient and a 12 g silica gel column to give the title compound (0.104 g, 0.136 mmol, 89% yield) as a clear film. LCMS: m/e 767.6 (M+H)+, 2.20 min (method 3).

Step 2

To a solution of (S)-benzyl 1-(fluoromethyl)-4-((1R,3aS, 5aR,5bR,7aR,11aS,11bR,13aR,13bR)-5a,5b,8,8,11a-pentamethyl-3a-((2-(2-oxopyrrolidin-1-yl)ethyl)amino)-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) cyclohex-3-enecarboxylate (0.104 g, 0.136 mmol) in 1,4-dioxane (2 mL) and MeOH (0.5 mL) was added NaOH (1N) (0.542 mL, 0.542 mmol). The mixture was heated to 60° C. After 4.5 h of heating, the mixture was cooled to rt and was purified by reverse phase chromatography using a 25-100% A to B gradient (A=9:1 water:acetonitrile with 0.1% TFA added, B=1:9 water:acetonitrile with 0.1% TFA added) and a 50 g C18 column. The fractions containing the product were combined and concentrated under reduced pressure to give the TFA salt of the title compound (0.076 g, 0.096 mmol, 71% yield) as a white solid. LCMS: m/e 677.4 (M+H)+, 1.73 min (method 3). $^1$H NMR (500 MHz, Acetic Acid $d_4$) δ 5.37 (br. s., 1H), 5.22 (d, J=4.4 Hz, 1H), 4.87 (s, 1H), 4.73 (s, 1H), 4.63-4.45 (m, 2H), 3.81-3.68 (m, 2H), 3.66-3.54 (m, 3H), 3.51-3.44 (m, 1H), 2.83-2.74 (m, 1H), 2.63-2.48 (m, 3H), 1.74 (s, 3H), 1.15 (s, 3H), 1.07 (s, 3H), 2.34-1.04 (m, 29H), 0.98 (s, 3H), 0.97 (s, 3H), 0.93 (s, 3H).

Example 21

Preparation of (S)-1-(fluoromethyl)-4-((1R,3aS,5aR, 5bR,7aR,11aS,11bR,13aR,13bR)-5a,5b,8,8,11a-pentamethyl-3 a#3-(2-oxopyrrolidin-1-yl)propyl) amino)-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)cyclohex-3-enecarboxylic acid

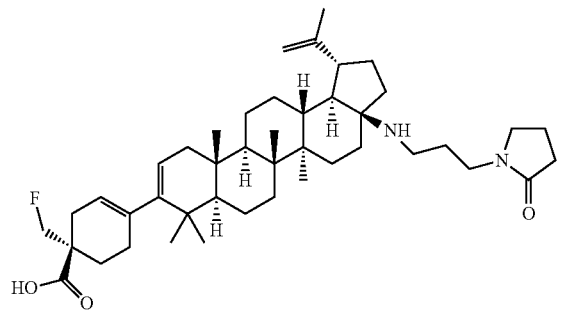

Step 1. Preparation of (S)-benzyl 1-(fluoromethyl)-4-((1R,3aS,5aR,5bR,7aR,11aS,11bR,13aR,13bR)-5a,5b,8,8,11a-pentamethyl-3a-((3-(2-oxopyaolidin-1-yl)propyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate To a sealable flask containing (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (0.1 g, 0.152 mmol) and 1-(3-chloropropyl)pyrrolidin-2-one (0.074 g, 0.457 mmol) was added phosphoric acid, potassium salt (0.129 g, 0.610 mmol) and potassium iodide (0.038 g, 0.229 mmol). The mixture was diluted with acetonitrile (2 mL), flushed with nitrogen, then the vial was sealed and heated to 100° C. for 16 h. The mixture was cooled to rt, diluted with water (10 mL) and extracted with dichloromethane (3×10 mL). The organic layers were dried over sodium sulfate, filtered and concentrated under reduced pressure. The residue was purified by flash chromatography using a 0-5% MeOH in DCM gradient and a 12 g silica gel column. The fractions containing the product were combined and concentrated under reduced pressure to give the title compound (0.074 g, 0.095 mmol, 62% yield) as a clear film. LCMS: m/e 781 (M+H)$^+$, 2.20 min (method 3).

Step 2

To a solution of (S)-benzyl 1-(fluoromethyl)-4-((1R,3aS,5aR,5bR,7aR,11aS,11bR,13aR,13bR)-5a,5b,8,8,11a-pentamethyl-3a-((3-(2-oxopyrrolidin-1-yl)propyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (0.074 g, 0.095 mmol) in 1,4-dioxane (2 mL) and Methanol (0.4 mL) was added 1N NaOH (0.379 mL, 0.379 mmol) and the mixture was warmed to 60° C. After 4 h of heating, the mixture was cooled to rt and was purified by prep HPLC (method 11). The fractions containing the product were combined and concentrated under reduced pressure to give the TFA salt of the title product (0.042 g, 0.052 mmol, 55% yield) as a white solid. LCMS: m/e 691.5 (M+H)$^+$, 1.73 min (method 3). $^1$H NMR (500 MHz, Acetic acid d$_4$) δ 5.39 (br. s., 1H), 5.25 (d, J=4.6 Hz, 1H), 4.85 (s, 1H), 4.73 (s, 1H), 4.65-4.47 (m, 2H), 3.56-3.41 (m, 4H), 3.28-3.16 (m, 2H), 2.90-2.81 (m, 1H), 2.65-2.58 (m, 1H), 2.52 (t, J=8.1 Hz, 2H), 1.75 (s, 3H), 1.18 (s, 3H), 1.10 (s, 3H), 2.36-1.06 (m, 31H), 1.01 (s, 3H), 0.99 (s, 3H), 0.95 (s, 3H).

Example 22

Preparation of (R)-4-((1S,3aS,5aR,5bR,7aR,11aS,11bR,13aR,13bR)-3a-((2-(1,1-dioxidothiomorpholino)ethyl)amino)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid

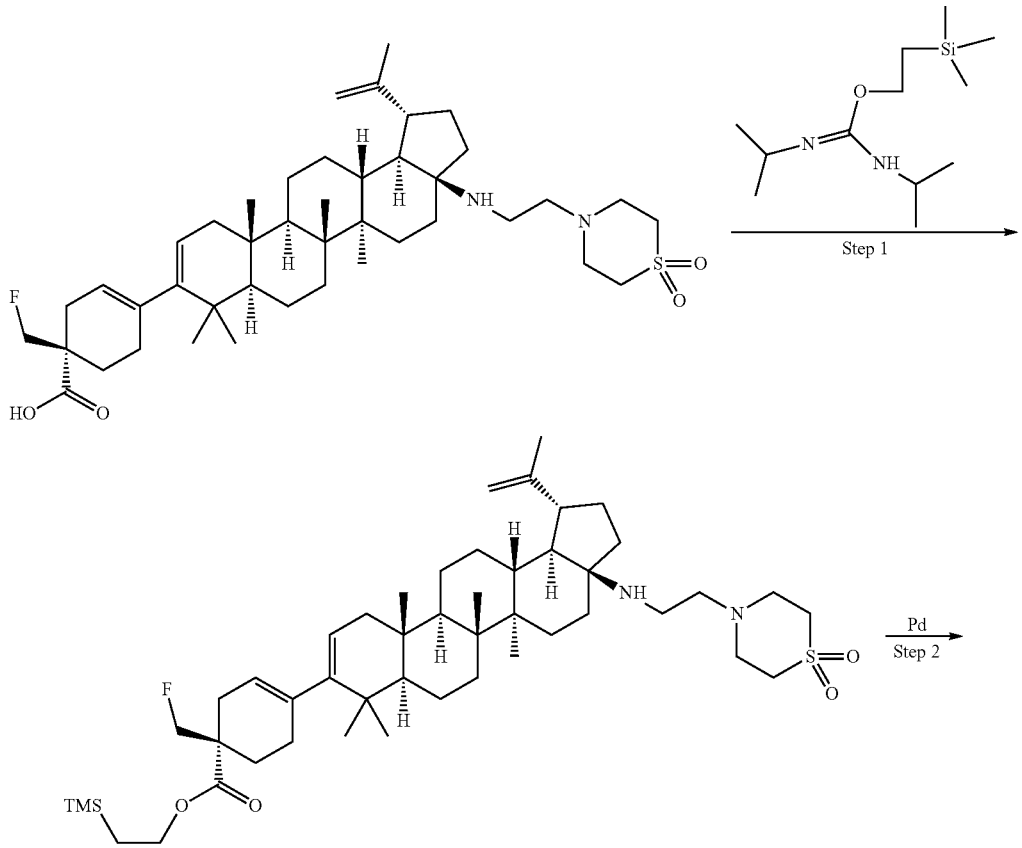

-continued

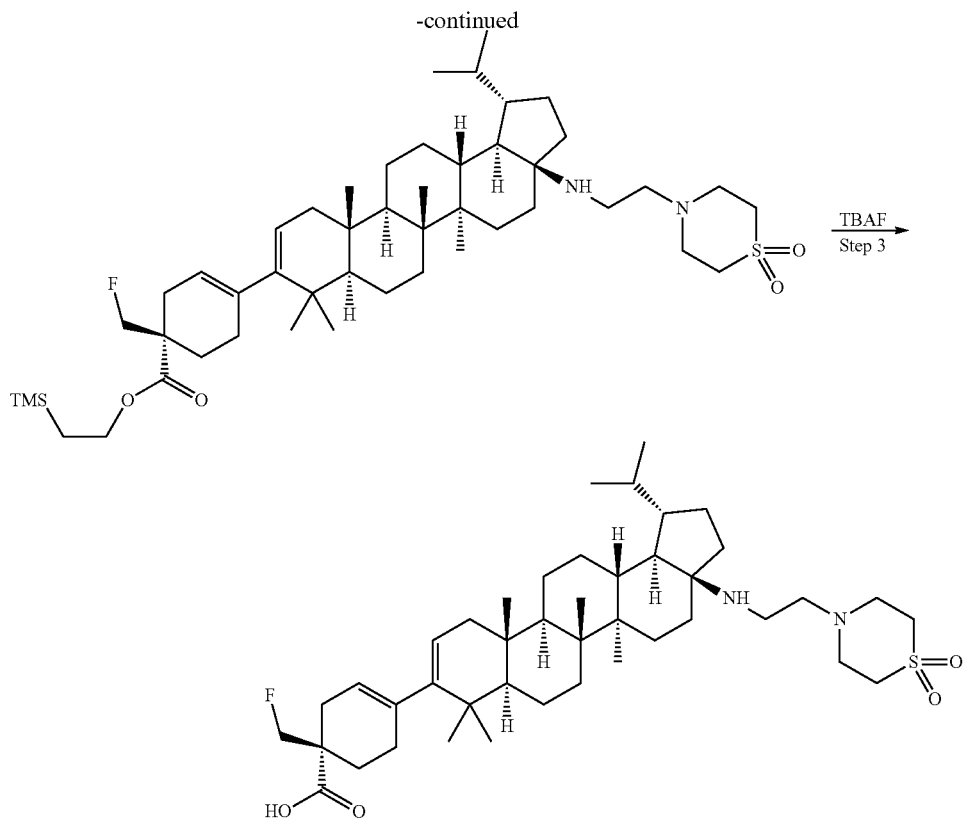

Example 22

Step 1. Preparation of (R)-2-(trimethylsilyl)ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate A mixture of (R)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid (180 mg, 0.248 mmol) and 2-(trimethylsilyl)ethyl N,N'-diisopropylcarbamimidate (91 mg, 0.371 mmol) in tetrahydrofuran (10 mL) was refluxed at 80° C. for 4 hours. The reaction mixture was concentrated under reduced pressure and the residue was diluted with methanol (3 mL) and tetrahydrofuran (4 mL). The resulting mixture was left at room temperature for 14 h. A white solid was formed and removed by filtration. The filtrate was concentrated under reduced pressure. This residue was treated with methanol (2 mL) and water (5 mL) to afford a white precipitate. The solid was collected by filtration and washed with diethyl ether (4 mL) to provide the title compound as a white solid (130 mg, 60%). LCMS: m/e 827.8 (M+H)$^+$, 2.39 min (method 3).

Step 2. Preparation of (R)-2-(trimethylsilyl)ethyl 4-((1S,3aS,5aR,5bR,7aR,11aS,11bR,13aR,13bR)-3a-((2-(1,1-dioxidothiomorpholino)ethyl)amino)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate A mixture of (R)-2-(trimethylsilyl)ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (50 mg, 0.060 mmol) and Pd-C (6.43 mg, 6.04 μmol) in tetrahydrofuran (2 mL) and methanol (1 mL) was stirred under hydrogen atmosphere at 20° C. for 31 hours. The reaction mixture was filtered through a pad of celite to remove the Palladium catalyst and washed with tetrahydrofuran (10 mL). The filtrates were concentrated under reduced pressure to provide the title compound as a white solid (40 mg, 64%, 80% pure). LCMS: m/e 829.8 (M+H)$^+$, 2.43 min (method 3).

Step 3

A mixture of (R)-2-(trimethylsilyl)ethyl 4-((1S,3aS,5aR,5bR,7aR,11aS,11bR,13aR,13bR)-3a-((2-(1,1-dioxidothiomorpholino)ethyl)amino)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (15 mg, 0.014 mmol) and tetra-N-butylammonium fluoride (101 mg, 0.289 mmol) in dioxane (1 mL) was stirred at 20° C. for 5 hours. The reaction mixture was filtered and purified by prep HPLC with 0-70 acetonitrile/water/TFA to provide the desired product as colorless oil (6 mg, 54%). LCMS: m/e 729.7 (M+H)⁺, 1.90 min (method 3). ¹H NMR (500 MHz, Acetic) δ 5.40 (br. s., 1H), 5.31-5.17 (m, 1H), 4.73-4.56 (m, 1H), 4.55-4.40 (m, 1H), 3.58-3.02 (m, 12H), 2.62 (d, J=16.9 Hz, 1H), 2.35-2.30 (m, 1H), 2.25-1.13 (m, 28H), 1.26 (s, 3H), 1.10 (s, 3H), 1.03 (s, 3H), 0.99 (s, 3H), 0.99 (s, 3H), 0.93 (d, J=6.8 Hz, 3H), 0.85 (d, J=6.8 Hz, 3H).

Example 23

Preparation of 4-((1S,3aS,5aR,5bR,7aR,11aS,11bR,13aR,13bR)-3a-((2-(1,1-dioxidothiomorpholino)ethyl)amino)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohexanecarboxylic acid

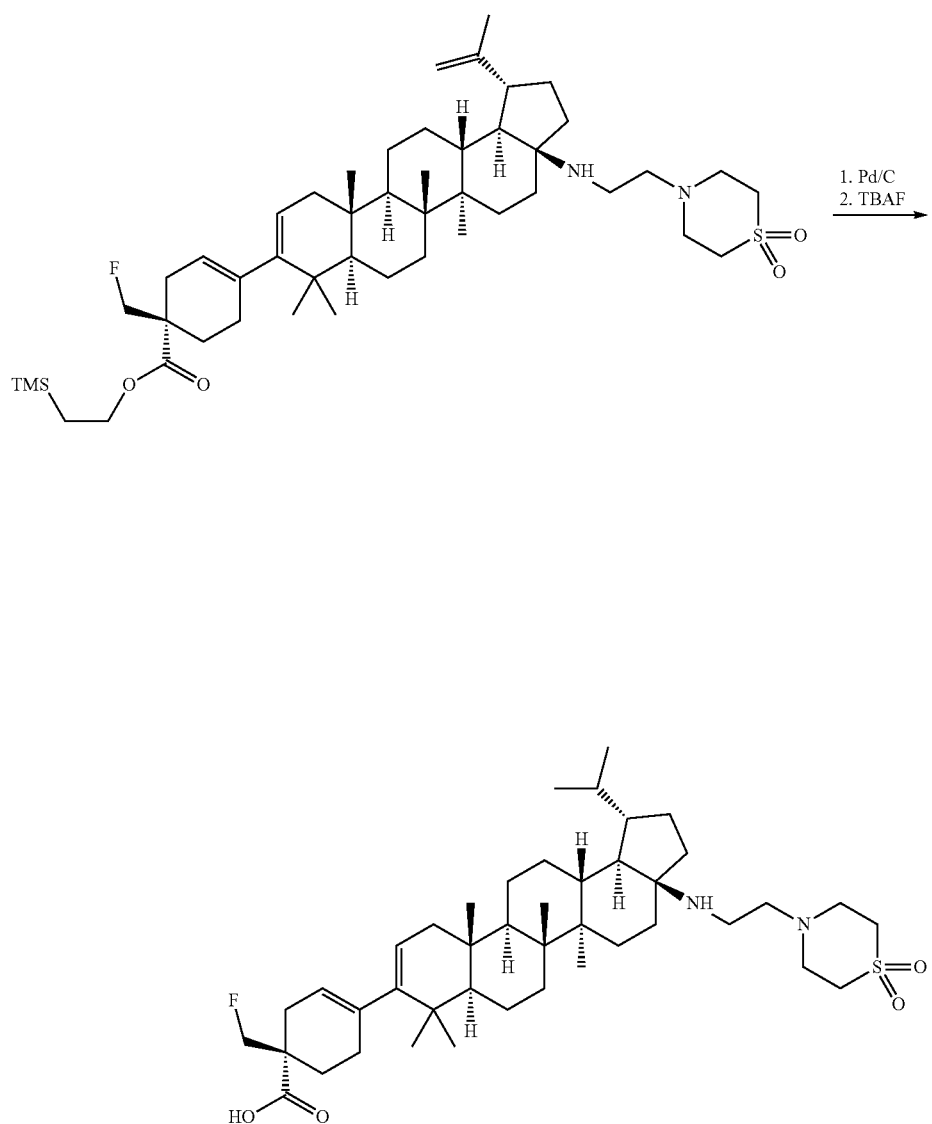

A mixture of (R)-2-(trimethylsilyl)ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (18 mg, 0.022 mmol) and Pd-C (4.63 mg, 4.35 μmol) in tetrahydrofuran (2 mL) and methanol (2 mL) was stirred at 20° C. for 3 days. The reaction mixture was filtered through a pad of celite and then washed with tetrahydrofuran (2 mL), the filtrates were concentrated under reduced pressure to provide a solid. The solid was dissolved in tetrahydrofuran (2 mL) and tetra-N-butylammonium fluoride (152 mg, 0.435 mmol) was added and the reaction. The mixture was stirred at 20° C. for 2 days. The reaction mixture was filtered and purified by prep HPLC with 0-70 acetonitrile/water/TFA to provide the title compound as a white solid (4 mg, 24%). LCMS: m/e 731.8 (M+H)$^+$, 1.87 min (method 3). $^1$H NMR (500 MHz, ACETONITRILE-d$_3$) δ 5.28 (dd, J=6.5, 1.6 Hz, 1H), 4.41 (s, 1H), 4.31 (s, 1H), 3.27-2.97 (m, 11H), 2.94-2.83 (m, 1H), 2.20-1.24 (m, 32H), 1.16 (s, 3H), 1.13-1.11 (m, 1H), 1.05 (s, 3H), 1.01 (s, 3H), 0.94 (s, 3H), 0.92 (d, J=6.9 Hz, 3H), 0.88 (s, 3H), 0.84 (d, J=6.6 Hz, 3H).

Example 24

Preparation of (1R)-4-((1R,3aS,5aR,5bR,7aR,11aS,11bR,13aR,13bR)-3a-((2-(2,6-dimethyl-1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid

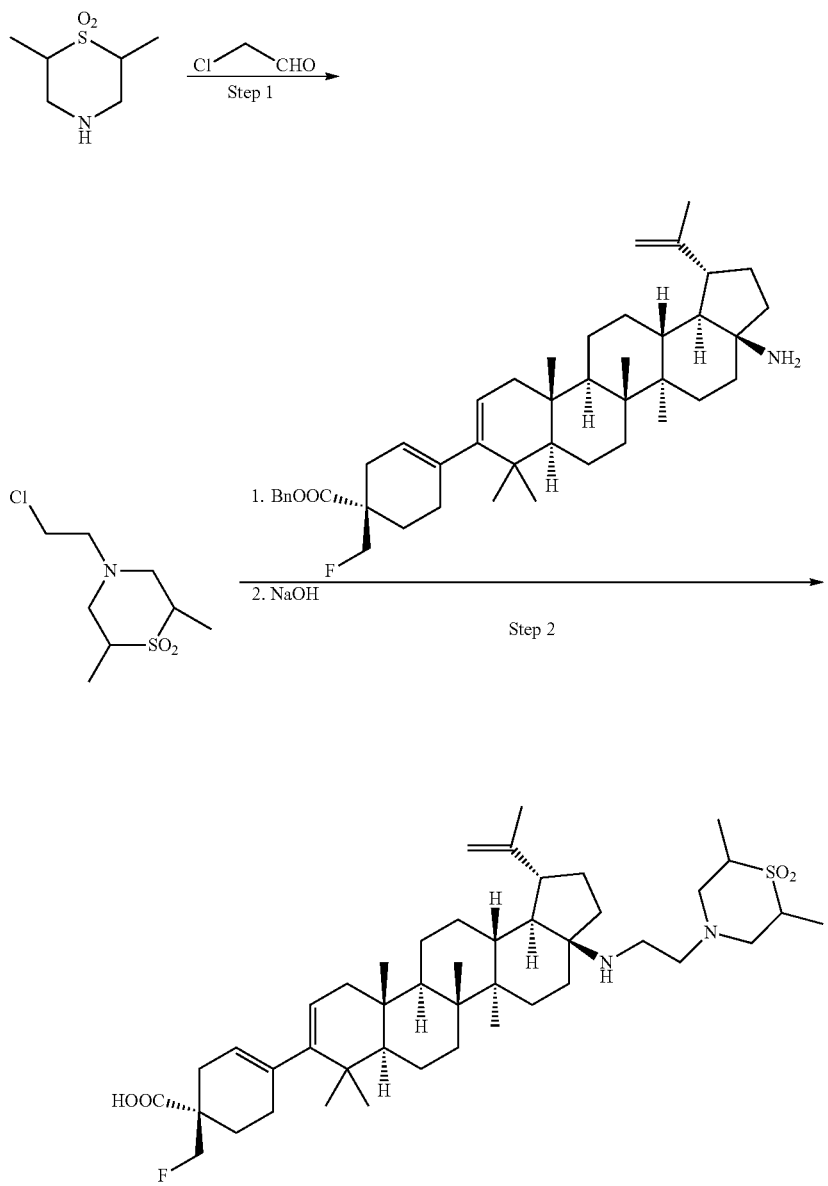

Example 24

Step 1. Preparation of 4-(2-chloroethyl)-2,6-dimethylthiomorpholine 1,1-dioxide A mixture of 2,6-dimethylthiomorpholine 1,1-dioxide (100 mg, 0.613 mmol), 2-chloroacetaldehyde (135 mg, 0.858 mmol) and borane-2-picolin complex (72.1 mg, 0.674 mmol) in methanol (2 mL) and acetic acid (1 mL) was stirred at rt for 17 hours. The reaction mixture was washed with sat. sodium carbonate (10 mL) and extracted with ethyl acetate (3×10 mL). The combined organic phases were dried over sodium sulfate, filtered and concentrated under reduced pressure to provide the title compound as colorless oil (90 mg, 65%). LCMS: m/e 226.2 (M+H)$^+$, 0.54 min (method 3).

Step 2

A mixture of 4-(2-chloroethyl)-2,6-dimethylthiomorpholine 1,1-dioxide (20.65 mg, 0.091 mmol), (R)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (30 mg, 0.046 mmol), potassium iodide (8.35 mg, 0.050 mmol) and potassium phosphate (48.5 mg, 0.229 mmol) in acetonitrile (1 mL) was heated up at 120° C. for 16 hours. The reaction mixture was cooled to rt, quenched with distilled water (3 mL) and extracted with dichloromethane (3×3 mL). The combined organic phases were washed with brine (3 mL), dried over sodium sulfate, filtered and concentrated under reduced pressure to provide a white solid. This solid was dissolved in acetonitrile (1 mL) and sodium hydroxide (0.457 mL, 0.457 mmol) was added. The mixture was heated at 80° C. for 3 h and then it was filtered and purified by prep HPLC with acteonitrile/water/TFA to provide (1R)-4-((1R,3aS,5aR,5bR,7aR,11aS,11bR,13aR,13bR)-3a-((2-(2,6-dimethyl-1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid as a white solid (12 mg, 33%). LCMS: m/e 755.8 (M+H)$^+$, 1.96 min (method 3). $^1$H NMR (500 MHz, METHANOL-d$_4$) δ 5.36 (br. s., 1H), 5.22 (dd, J=6.1, 1.7 Hz, 1H), 4.86 (br. s., 1H), 4.76 (s, 1H), 4.62-4.51 (m, 1H), 4.50-4.39 (m, 1H), 3.39-3.11 (m, 7H), 3.01-2.73 (m, 4H), 2.57 (d, J=17.7 Hz, 1H), 2.38-1.15 (m, 27H), 1.79 (s, 3H), 1.30 (dd, J=6.8, 3.3 Hz, 6H), 1.17 (s, 3H), 1.13 (s, 3H), 1.02 (s, 3H), 0.98 (s, 3H), 0.95 (s, 3H).

Example 25

Preparation of (1S)-4-((1R,3aS,5aR,5bR,7aR,11aS,11bR,13aR,13bR)-3a-((2-(2,6-dimethyl-1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid

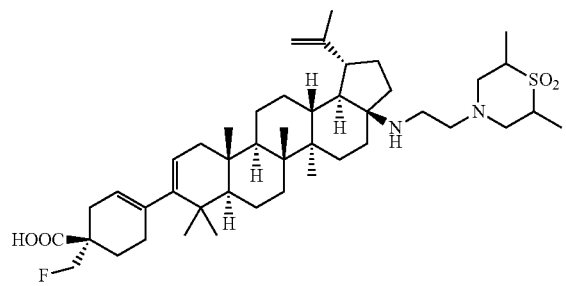

A mixture of (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (30 mg, 0.046 mmol), 4-(2-chloroethyl)-2,6-dimethylthiomorpholine 1,1-dioxide (20.65 mg, 0.091 mmol), potassium iodide (8.35 mg, 0.050 mmol) and potassium phosphate (48.5 mg, 0.229 mmol) in acetonitrile (1 mL) was heated at 120° C. for 16 h. The reaction mixture was cooled to rt, quenched with distilled water (3 mL) and extracted with dichloromethane (3×3 mL). The combined organic phases were washed with brine (3 mL), dried over sodium sulfate, filtered and concentrated under reduced pressure to provide the a white solid. This white solid was dissolved in acetonitrile (1 mL) and sodium hydroxide (0.457 mL, 0.457 mmol) was added. The mixture was heated at 80° C. for 3 h, filtered and purified by prep HPLC with acteonitrile/water/TFA to provide the title compound as a white solid (12 mg, 33%). LCMS: m/e 755.8 (M+H)$^+$, 1.92 min (method 3). $^1$H NMR (500 MHz, METHANOL-d$_4$) δ 5.35 (br. s., 1H), 5.22 (dd, J=6.1, 1.6 Hz, 1H), 4.86 (s, 1H), 4.76 (d, J=1.3 Hz, 1H), 4.61-4.51 (m, 1H), 4.50-4.38 (m, 1H), 3.39-3.07 (m, 7H), 3.01-2.73 (m, 4H), 2.57 (d, J=16.6 Hz, 1H), 2.37-1.20 (m, 27H), 1.78 (s, 3H), 1.30 (dd, J=6.7, 3.1 Hz, 6H), 1.17 (s, 3H), 1.13 (s, 3H), 1.00 (s, 3H), 0.98 (s, 3H), 0.95 (s, 3H).

Example 26

Preparation of (1R)-1-(fluoromethyl)-4-((1R,3aS, 5aR,5bR,7aR,11aS,11bR,13aR,13bR)-5a,5b,8,8,11a-pentamethyl-3a-((2-(6-methyl-1,1-dioxido-1,4-thiaz-epan-4-yl)ethyl)amino)-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) cyclohex-3-enecarboxylic acid

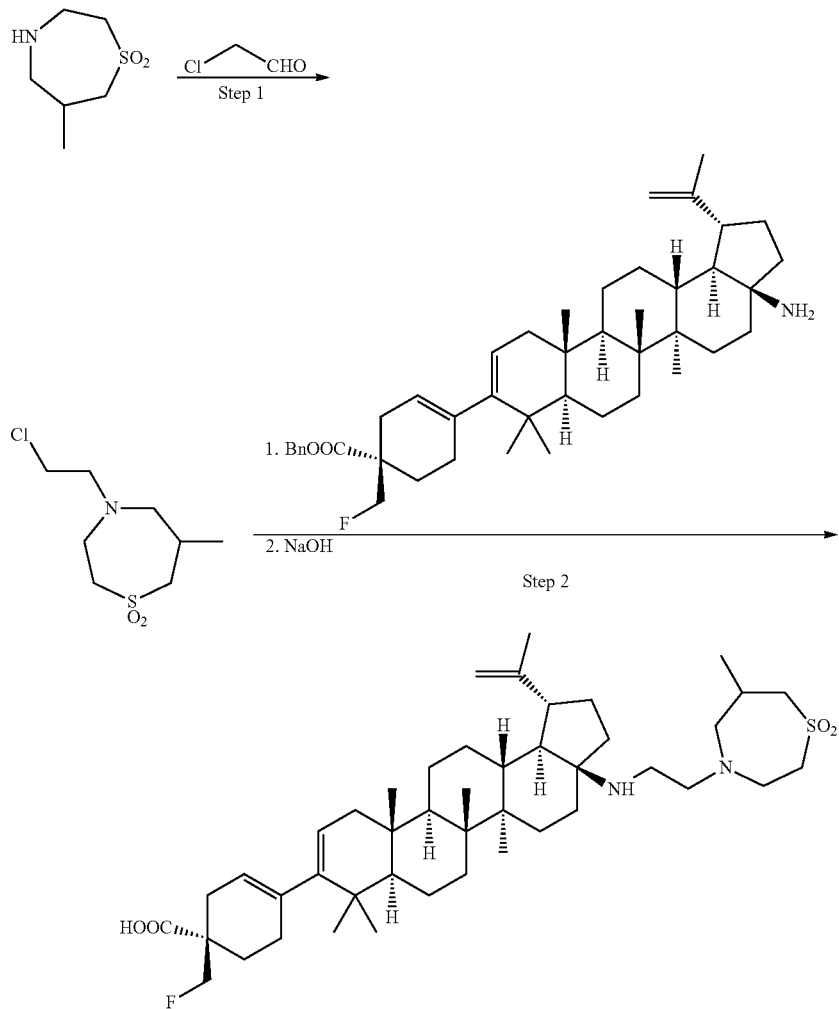

Example 26

Step 1

Preparation of 4-(2-chloroethyl)-6-methyl-1,4-thiazepane 1,1-dioxide A mixture of 6-methyl-1,4-thiazepane 1,1-dioxide (100 mg, 0.613 mmol), 2-chloroacetaldehyde (0.107 mL, 0.858 mmol) and borane-2-picolin complex (72.1 mg, 0.674 mmol) in methanol (1 mL) and acetic acid (0.5 mL) was stirred at rt for 17 hours. The reaction mixture was washed with sat. sodium carbonate (3 mL) and extracted with ethyl acetate (3×2 mL). The combined organic phases were dried over sodium sulfate, filtered and concentrated under reduced pressure to provide the title compound as colorless oil (105 mg, 76%). LCMS: m/e 226.2 (M+H)$^+$, 0.33 min (method 3).

Step 2

A mixture of (R)-benzyl 4-((1R,3aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)-1-(fluoromethyl)cyclohex-3-enecarboxylate (20 mg, 0.030 mmol), 4-(2-chloroethyl)-6-methyl-1,4-thiazepane 1,1-dioxide (27.5 mg, 0.122 mmol), potassium iodide (5.57 mg, 0.034 mmol) and potassium phosphate (32.4 mg, 0.152 mmol) in acetonitrile (1 mL) was heated at 120° C. for 16 h. The reaction mixture was cooled to rt, quenched with distilled water (3 mL) and extracted with dichloromethane (3×2 mL). The combined organic phases were washed with brine (3 mL), dried over sodium sulfate, filtered and concentrated under reduced pressure to provide the desired intermediate a white solid. This solid was dissolved in dioxane (1 mL) and sodium hydroxide (0.305 mL, 0.305 mmol) was added. The mixture was heated at 80° C. for 3 h.

The reaction mixture was filtered and purified by prep HPLC with 0-70 acteonitrile/water/TFA to provide (1R)-1-(fluoromethyl)-4-((1R,3aS,5aR,5bR,7aR,11aS,11bR,13aR,13bR)-5a,5b,8,8,11a-pentamethyl-3a-((2-(6-methyl-1,1-dioxido-1,4-thiazepan-4-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid as a colorless oil (9.8 mg, 40%). LCMS: m/e 755.9 (M+H)$^+$, 1.93 min (method 3). $^1$H NMR (500 MHz, METHANOL-d$_4$) δ 5.36 (br. s., 1H), 5.22 (dd, J=6.1, 1.7 Hz, 1H), 4.86 (br. s., 1H), 4.76 (s, 1H), 4.61-4.51 (m, 1H), 4.50-4.40 (m, 1H), 3.69-3.14 (m, 9H), 3.11-2.75 (m, 4H), 2.57 (d, J=17.2 Hz, 1H), 2.49-2.24 (m, 2H), 2.22-1.15 (m, 26H), 1.78 (s, 3H), 1.19 (d, J=3.0 Hz, 3H), 1.13 (s, 3H), 1.09 (dd, J=7.0, 4.8 Hz, 3H), 1.01 (s, 3H), 0.97 (s, 3H), 0.95 (d, J=2.0 Hz, 3H).

Example 27

Preparation of (1S)-1-(fluoromethyl)-4-((1R,3aS,5aR,5bR,7aR,11aS,11bR,13aR,13bR)-5a,5b,8,8,11a-pentamethyl-3a-((2-(6-methyl-1,1-dioxido-1,4-thiazepan-4-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid A mixture of (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (20 mg, 0.030 mmol), 4-(2-chloroethyl)-6-methyl-1,4-thiazepane 1,1-dioxide (34.4 mg, 0.152 mmol), potassium iodide (5.57 mg, 0.034 mmol) and potassium phosphate (32.4 mg, 0.152 mmol) in acetonitrile (1 mL) was heated at 120° C. for 16 h. The reaction mixture was cooled to rt, quenched with distilled water (3 mL) and extracted with dichloromethane (3×2 mL). The combined organic phases were washed with brine (3 mL), dried over sodium sulfate, filtered and concentrated under reduced pressure to provide a white solid. This solid was dissolved in dioxane (1 mL) and sodium hydroxide (0.305 mL, 0.305 mmol) was added. The mixture was heated at 80° C. for 3 h. The reaction mixture was filtered and purified by prep HPLC with 0-70 acteonitrile/water/TFA to provide the title compound as a colorless oil (6 mg, 25%). LCMS: m/e 755.9 (M+H)$^+$, 1.90 min (method 3). $^1$H NMR (500 MHz, METHANOL-d$_4$) δ 5.35 (br. s., 1H), 5.22 (dd, J=6.1, 1.7 Hz, 1H), 4.86 (br. s., 1H), 4.76 (s, 1H), 4.62-4.51 (m, 1H), 4.51-4.40 (m, 1H), 3.67-3.15 (m, 9H), 3.10-2.75 (m, 4H), 2.57 (d, J=18.1 Hz, 1H), 2.49-2.23 (m, 2H), 2.21-1.14 (m, 26H), 1.78 (s, 3H), 1.22-1.17 (m, 3H), 1.13 (s, 3H), 1.10-1.06 (m, 3H), 1.00 (s, 3H), 0.98 (s, 3H), 0.96 (s, 3H).

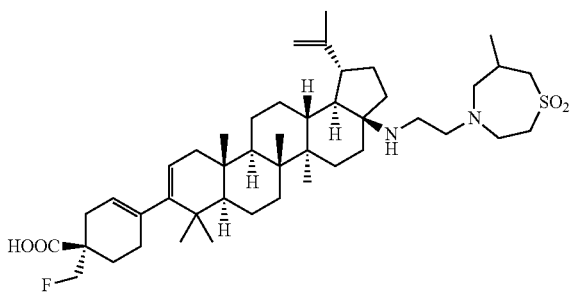

Example 28

Preparation of (S)-4-((1R,3aS,5aR,5bR,7aR,11aS,11bR,13aR,13bR)-3a-((carboxymethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid

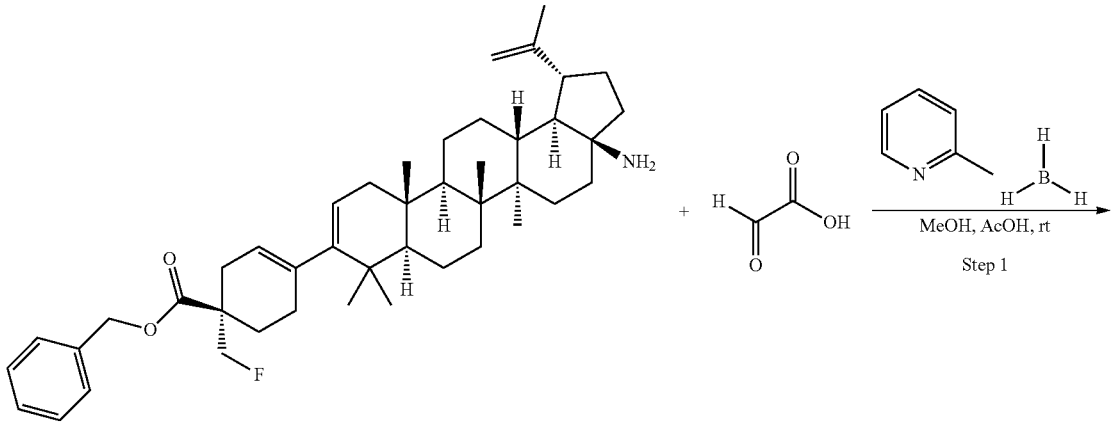

Step 1

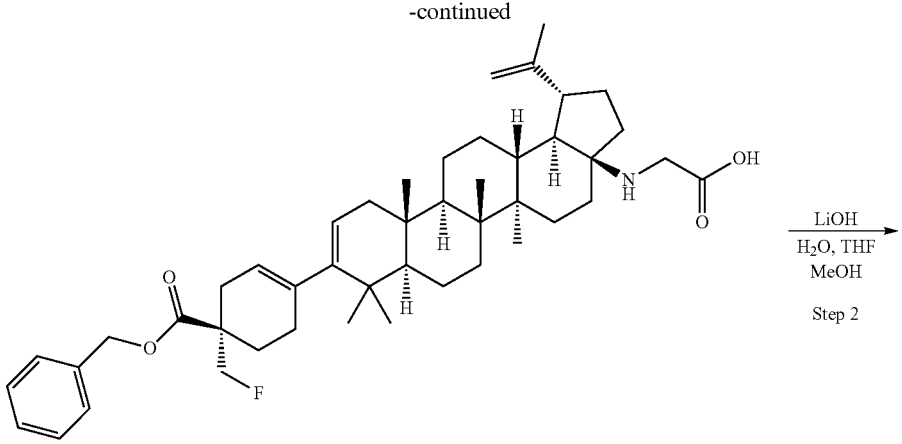

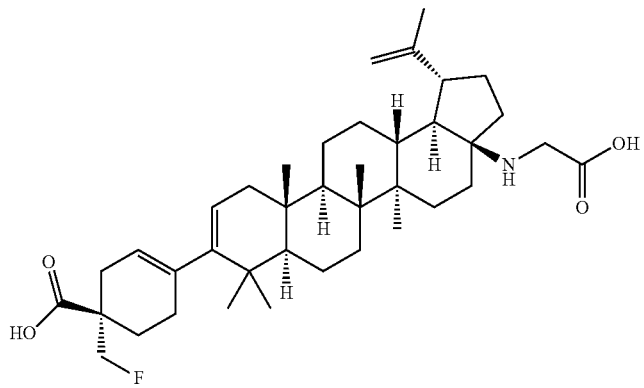

Example 28

Step 1. Preparation of 2-((1R,3aS,5aR,5bR,7aR, 11aS,11bR,13aR,13bR)-9-((S)-4-((benzyloxy)carbonyl)-4-(fluoromethyl)cyclohex-1-en-1-yl)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-3a-yl) amino)acetic acid A mixture of (S)-benzyl 4-((1R,3aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)-1-(fluoromethyl)cyclohex-3-enecarboxylate (0.250 g, 0.381 mmol) and 2-oxoacetic acid monohydrate (0.053 g, 0.572 mmol) in methanol (1 mL), THF (1 mL) and acetic acid (0.5 mL) was treated with borane 2-picolin complex (0.061 g, 0.572 mmol). The mixture immediately effervesced upon addition and was stirred at rt. After stirring 2.5 h, the mixture was treated with additional borane 2-picolin complex (0.061 g, 0.572 mmol) and 2-oxoacetic acid monohydrate (0.053 g, 0.572 mmol) and the resulting solution was stirred at rt for an additional 96 h. The crude mixture was purified by reverse phase preparative HPLC (Prep HPLC Method 14) to provide the desired material (0.213 g, 78% yield) as a colorless glassy solid TFA salt. LCMS: m/z 714.4 (M+H)$^+$, 2.63 min (method 1). $^1$H NMR (400 MHz, 1:1 mixture of CDCl$_3$ and CD$_3$OD, CD$_3$OD lock) δ 7.59 (s, 2H), 7.38-7.26 (m, 3H), 5.31 (br. s., 1H), 5.21-5.12 (m, 2H), 5.10 (d, J=4.9 Hz, 1H), 4.81 (s, 1H), 4.73 (s, 1H), 4.61-4.38 (dm, J=47.2 Hz, 2H), 3.50 (s, 2H), 2.70-2.54 (m, 2H), 2.12 (d, J=7.8 Hz, 3H), 2.08-1.87 (m, 6H), 1.84-1.67 (m, 8H), 1.67-1.57 (m, 3H), 1.56-1.40 (m, 6H), 1.40-1.28 (m, 3H), 1.28-1.21 (m, 1H), 1.17 (s, 3H), 1.11-1.00 (m, 4H), 0.93-0.82 (m, 9H).

Step 2.

2-(((1R,3aS,5aR,5bR,7aR,11aS,11bR,13aR,13bR)-9-((S)-4-((benzyloxy)carbonyl)-4-(fluoromethyl)cyclohex-1-en-1-yl)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-3a-yl)amino) acetic acid TFA salt (0.050 g, 0.060 mmol) was combined with LiOH, 1M aqueous (0.483 mL, 0.483 mmol) and a mixture of THF (0.5 mL) and MeOH (0.5 mL). The resulting mixture was stirred at 80° C. for 30 min. The crude mixture was purified by reverse phase preparative HPLC (Prep HPLC Method 15) to provide the title compound (0.0318 g, 71% yield) as a white solid TFA salt. LCMS: m/z 624.4 (M+H)$^+$, 2.43 min (method 1). $^1$H NMR (400 MHz, 1:1 mixture of CDCl$_3$ and CD$_3$OD, CD$_3$OD lock) δ 5.33 (br. s., 1H), 5.18 (d, J=4.4 Hz, 1H), 4.81 (s, 1H), 4.73 (s, 1H), 4.60-4.39 (dm, J=47.2 Hz, 2H), 3.43 (s, 2H), 2.65 (td, J=11.0, 5.1 Hz, 1H), 2.55 (d, J=17.9 Hz, 1H), 2.29-2.11 (m, 2H), 2.11-1.86 (m, 7H), 1.85-1.66 (m, 8H), 1.66-1.43 (m, 8H), 1.43-1.24 (m, 4H), 1.18 (s, 4H), 1.14-1.01 (m, 4H), 0.96 (s, 3H), 0.93 (s, 3H), 0.89 (s, 3H).

Example 29
Preparation of (S)-4-((1R,3aS,5aR,5bR,7aR,11aS,11bR,13aR,13bR)-3a-((2-(1,1-dioxidothiomorpholino)-2-oxoethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid
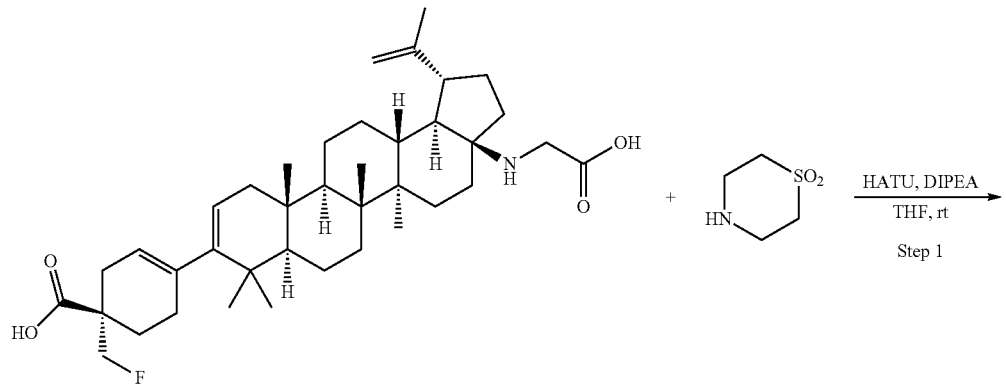
Step 1
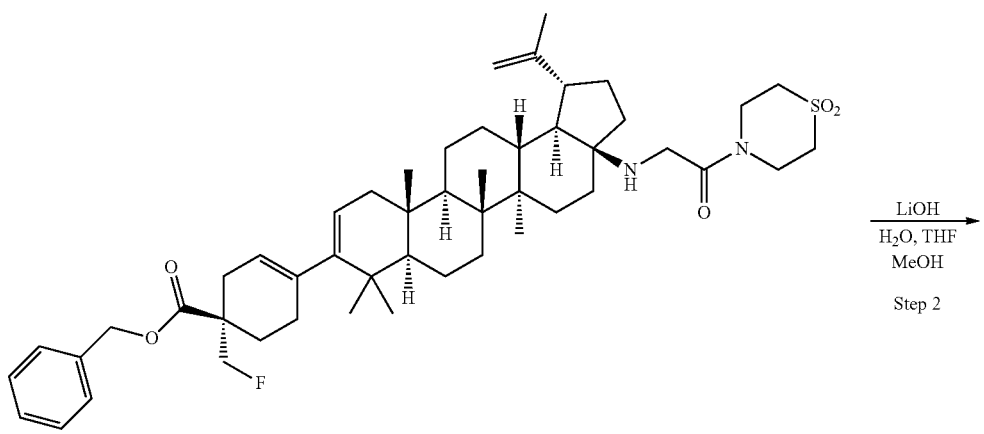
Step 2
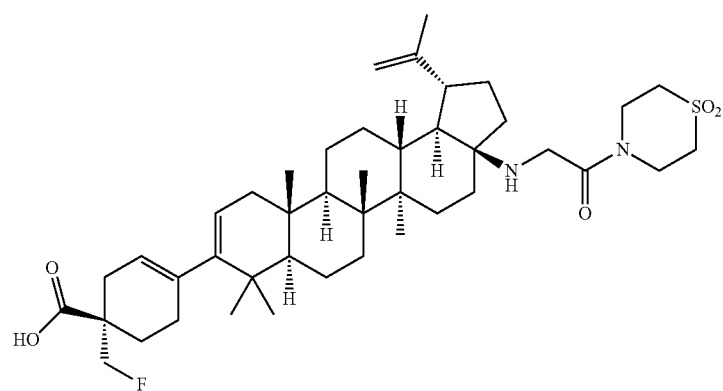
Example 29

Step 1. Preparation of (S)-benzyl 4-((1R,3aS,5aR, 5bR,7aR,11aS,11bR,13aR,13bR)-3a-((2-(1,1-dioxidothiomorpholino)-2-oxoethyl)amino)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)-1-(fluoromethyl)cyclohex-3-enecarboxylate In a 1 dram vial with PTFE lined screw cap were combined 2-(((1R,3aS,5 aR,5bR,7aR,11aS,11bR,13aR, 13bR)-9-((S)-4-((benzyloxy)carbonyl)-4-(fluoromethyl)cyclohex-1-en-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)amino) acetic acid, TFA (0.025 g, 0.030 mmol) with thiomorpholine 1,1-dioxide (10.20 mg, 0.075 mmol) and HATU (0.029 g, 0.075 mmol) in THF (1 mL). To the mixture was added DIPEA (0.026 mL, 0.151 mmol), and the resulting solution was agitated overnight at rt. The crude mixture was purified by reverse phase preparative HPLC (Prep HPLC Method 16) to give the product (0.0269 g, 94% yield) as a white powder TFA salt. LCMS: m/z 831.5 (M+H)$^+$, 2.50 min (method 1).

Step 2

In a 1 dram vial with PTFE lined screw cap were combined (S)-benzyl 4-((1R,3aS,5aR,5bR,7aR,11aS,11bR, 13aR,13bR)-3a-((2-(1,1-dioxidothiomorpholino)-2-oxoethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate, TFA (0.0269 g, 0.028 mmol) with LiOH, 1M aqueous (0.063 mL, 0.063 mmol) and a mixture of THF (0.5 mL) and MeOH (0.5 mL). The resulting mixture was stirred at 70° C. for 30 min and then to 80° C. for 1 h. Additional LiOH, 1M aqueous (0.080 mL, 0.080 mmol) was added and the mixture was heated to 70° C. for 20 min and then to 80° C. for 30 min. The crude mixture was purified by reverse phase preparative HPLC (Prep HPLC Method 4) to give the title compound (0.0178 g, 66% yield) as a white glassy solid TFA salt. LCMS: m/z 741.5 (M+H)$^+$, 2.34 min (method 1). $^1$H NMR (400 MHz, 1:1 mixture of CDCl$_3$ and CD$_3$OD, CD$_3$OD lock) δ 5.33 (br. s., 1H), 5.19 (d, J=4.4 Hz, 1H), 4.82 (s, 1H), 4.74 (s, 1H), 4.59-4.40 (dm, J=47.2 Hz, 2H), 4.33-4.21 (m, 2H), 4.13-3.86 (m, 4H), 3.25 (t, J=4.9 Hz, 2H), 3.18 (t, J=4.9 Hz, 2H), 2.76-2.65 (m, 1H), 2.55 (d, J=16.4 Hz, 1H), 2.29-2.13 (m, 2H), 2.13-2.07 (m, 2H), 2.07-1.91 (m, 5H), 1.91-1.71 (m, 7H), 1.71-1.20 (m, 14H), 1.18 (s, 3H), 1.15-1.02 (m, 4H), 0.96 (s, 3H), 0.93 (s, 3H), 0.90 (s, 3H).

Example 30

Preparation of (S)-1-(fluoromethyl)-4-((1R,3aS,5aR, 5bR,7aR,11aS,11bR,13aR,13bR)-3a-((2-(4-hydroxy-4-methylpiperidin-1-yl)-2-oxoethyl)amino)-5a,5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) cyclohex-3-enecarboxylic acid

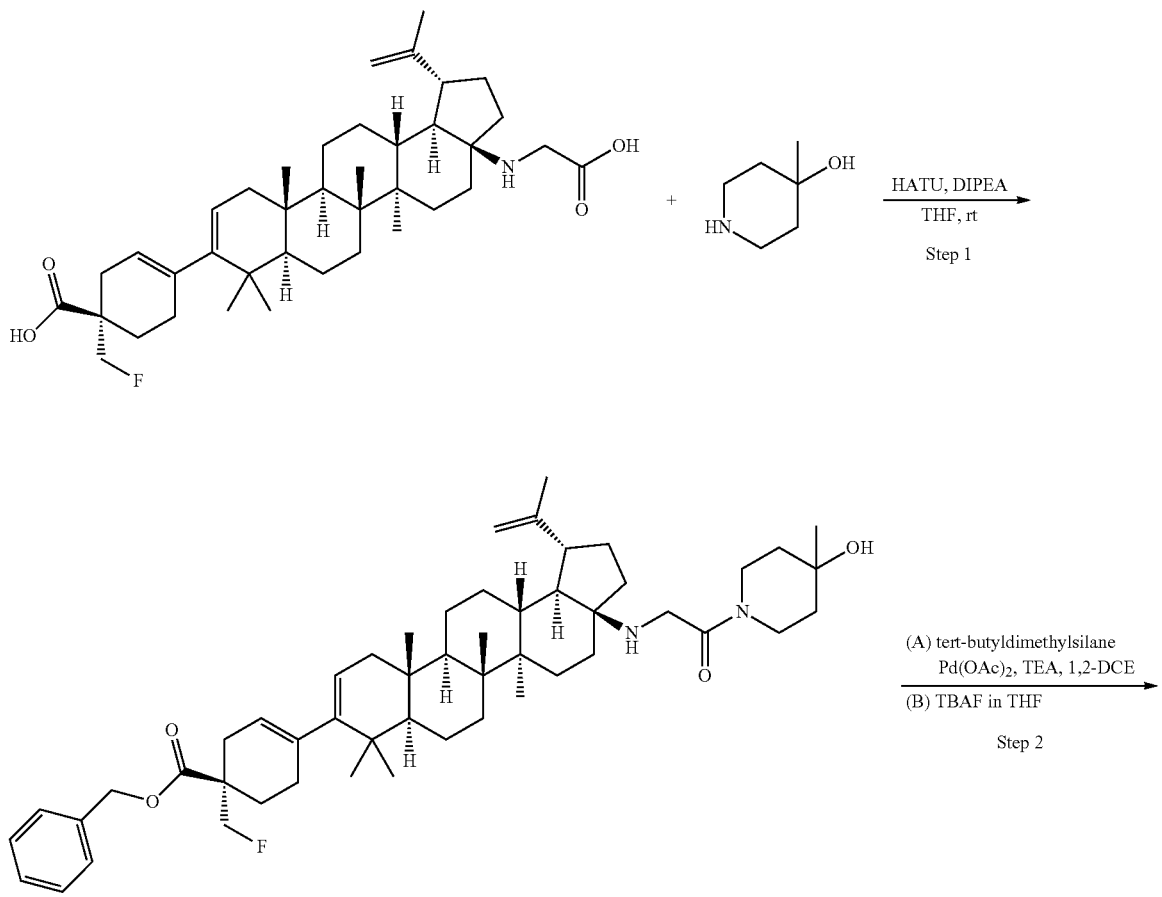

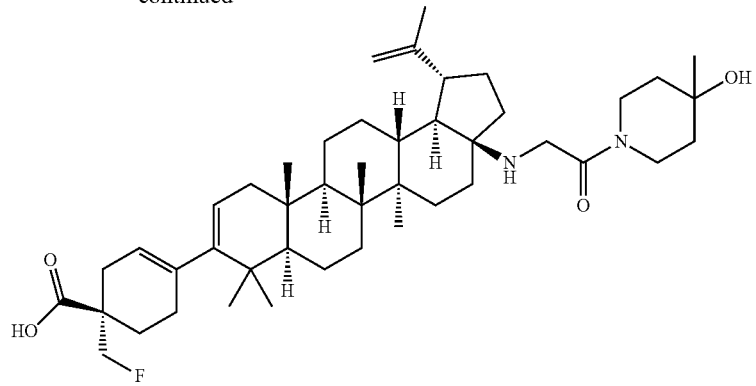

Example 30

Step 1. Preparation of (S)-benzyl 1-(fluoromethyl)-4-((1R,3aS,5aR,5bR,7aR,11aS,11bR,13aR,13bR)-3a-((2-(4-hydroxy-4-methylpiperidin-1-yl)-2-oxoethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate In a 1 dram vial with PTFE lined screw cap were combined 2-(((1R,3aS,5aR,5bR,7aR,11aS,11bR,13aR,13bR)-9-((S)-4-((benzyloxy)carbonyl)-4-(fluoromethyl)cyclohex-1-en-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-3a-yl)amino)acetic acid, TFA (0.025 g, 0.030 mmol) with 4-methylpiperidin-4-ol (8.69 mg, 0.075 mmol) and HATU (0.029 g, 0.075 mmol) in THF (1 mL). To the mixture was added DIPEA (0.026 mL, 0.151 mmol), and the resulting solution was agitated overnight at rt. The crude mixture was purified by reverse phase preparative HPLC (Prep HPLC Method 16) to give the product (0.0280 g, 100% yield) as a glassy solid TFA salt. LCMS: m/z 811.6 (M+H)$^+$, 2.54 min (method 1).

Step 2

(S)-benzyl 1-(fluoromethyl)-4-((1R,3aS,5aR,5bR,7aR,11aS,11bR,13aR,13bR)-3a-((2-(4-hydroxy-4-methylpiperidin-1-yl)-2-oxoethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate, TFA (0.028 g, 0.030 mmol) was dissolved in 1,2-dichloroethane (1 mL) and to the resulting solution was added triethylamine (10.97 µl, 0.079 mmol), tert-butyldimethylsilane (0.015 mL, 0.091 mmol) and palladium(II) acetate (1.699 mg, 7.57 µmol). The mixture was flushed with nitrogen and heated to 60° C. for 1 h. The mixture was then concentrated via nitrogen stream to a residue and then redissolved in THF (0.8 mL). To the mixture was added TBAF, 1.0M in THF (0.106 mL, 0.106 mmol) and the resulting mixture was stirred at rt for 30 min. The crude mixture was purified by reverse phase preparative HPLC (Prep HPLC Method 16) to give the title compound (0.0204 g, 79% yield) as a white solid TFA salt. LCMS: m/z 721.5 (M+H)$^+$, 2.16 min (method 1). $^1$H NMR (400 MHz, 1:1 mixture of CDCl$_3$ and CD$_3$OD, CD$_3$OD lock) δ 5.33 (br. s., 1H), 5.19 (d, J=4.9 Hz, 1H), 4.82 (s, 1H), 4.74 (s, 1H), 4.44 (d, J=4.4 Hz, 1H), 4.25-4.13 (m, 1H), 4.13-3.96 (m, 1H), 3.96-3.80 (m, 1H), 3.53-3.45 (m, 2H), 2.73-2.60 (m, 1H), 2.60-2.49 (m, 1H), 2.28-2.13 (m, 2H), 2.13-1.92 (m, 7H), 1.90-1.71 (m, 7H), 1.71-1.45 (m, 13H), 1.45-1.30 (m, 4H), 1.28 (d, J=4.2 Hz, 3H), 1.20 (s, 3H), 1.10 (d, J=6.8 Hz, 1H), 1.07 (s, 3H), 0.96 (s, 3H), 0.94 (s, 3H), 0.90 (s, 3H).

Example 31

Preparation of (S)-1-(fluoromethyl)-4-((1R,3aS,5aR,5bR,7aR,11aS,11bR,13aR,13bR)-5a,5b,8,8,11a-pentamethyl-3a-((2-(4-(methylsulfonyl)piperidin-1-yl)-2-oxoethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid

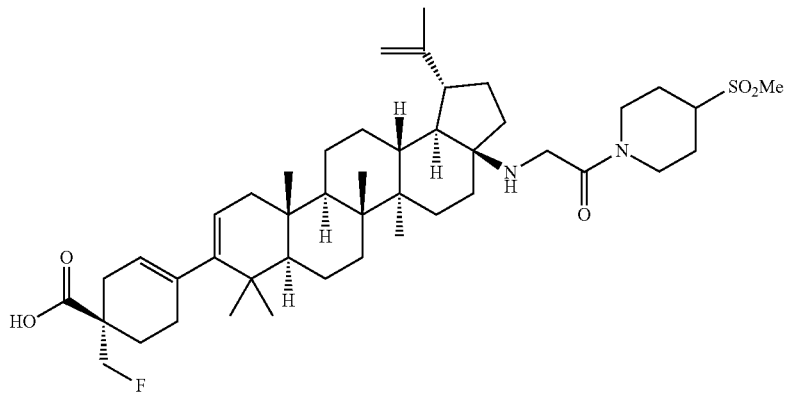

The title compound was prepared by the same procedure used for the preparation of (S)-1-(fluoromethyl)-4-((1R,3aS,5aR,5bR,7aR,11aS,11bR,13aR,13bR)-3a-((2-(4-hydroxy-4-methylpiperidin-1-yl)-2-oxoethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, except 4-(methylsulfonyl)piperidine (0.012 g, 0.075 mmol) was used instead of 4-methylpiperidin-4-ol in Step 1. Purification of the crude Step 2 mixture by reverse phase preparative HPLC (Prep HPLC Method 12) provided the title compound (0.0205 g, 70% yield over 2 steps) as a white solid TFA salt. LCMS: m/z 769.4 (M+H)$^+$, 2.33 min (method 1). $^1$H NMR (400 MHz, 1:1 mixture of CDCl$_3$ and CD$_3$OD, CD$_3$OD lock) δ 5.33 (br. s., 1H), 5.22-5.16 (m, 1H), 4.82 (s, 1H), 4.74 (s, 1H), 4.72-4.61 (m, 2H), 4.48-4.40 (m, 1H), 4.22-4.06 (m, 1H), 4.02-3.87 (m, 2H), 3.29-3.13 (m, 1H), 3.00-2.87 (m, 4H), 2.73-2.62 (m, 1H), 2.55 (d, J=17.4 Hz, 1H), 2.28-2.19 (m, 3H), 2.19-2.11 (m, 1H), 2.11-1.92 (m, 7H), 1.89-1.75 (m, 5H), 1.74 (s, 3H), 1.71-1.60 (m, 4H), 1.58 (br. s., 1H), 1.55-1.41 (m, 5H), 1.40-1.25 (m, 3H), 1.19 (s, 3H), 1.13-1.08 (m, 1H), 1.07 (s, 3H), 0.96 (s, 3H), 0.94 (s, 3H), 0.90 (s, 3H).

Example 32

Preparation of (S)-1-(fluoromethyl)-4-((1R,3aS,5aR,5bR,7aR,11aS,11bR,13aR,13bR)-5a,5b,8,8,11a-pentamethyl-3a-((2-morpholino-2-oxoethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid The title compound was prepared by the same procedure used for the preparation of (S)-1-(fluoromethyl)-4-((1R,3aS,5aR,5bR,7aR,11aS,11bR,13aR,13bR)-3a-((2-(4-hydroxy-4-methylpiperidin-1-yl)-2-oxoethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, except morpholine (6.58 μl, 0.075 mmol) was used instead of 4-methylpiperidin-4-ol in Step 1. Purification of the crude Step 2 mixture by reverse phase preparative HPLC (Prep HPLC Method 12) provided the title compound (0.0185 g, 74% yield over 2 steps) as a white solid TFA salt. LCMS: m/z 693.4 (M+H)$^+$, 2.35 min (method 1). $^1$H NMR (400 MHz, 1:1 mixture of CDCl$_3$ and CD$_3$OD, CD$_3$OD lock) d 5.33 (br. s., 1H), 5.22-5.16 (m, 1H), 4.81 (s, 1H), 4.73 (s, 1H), 4.48-4.39 (m, 1H), 4.05 (d, J=15.2 Hz, 1H), 3.88 (d, J=15.9 Hz, 1H), 3.78-3.71 (m, 4H), 3.71-3.64 (m, 2H), 3.53-3.45 (m, 2H), 2.72-2.61 (m, 1H), 2.55 (d, J=16.4 Hz, 1H), 2.19 (d, J=19.3 Hz, 2H), 2.13-2.07 (m, 1H), 2.07-1.90 (m, 6H), 1.88-1.75 (m, 3H), 1.74 (s, 3H), 1.72-1.56 (m, 5H), 1.56-1.42 (m, 5H), 1.42-1.25 (m, 4H), 1.19 (s, 4H), 1.15-1.08 (m, 1H), 1.07 (s, 3H), 0.96 (s, 3H), 0.93 (s, 3H), 0.90 (s, 3H).

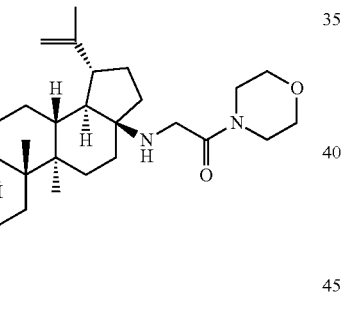

Example 33

Preparation of (S)-1-(fluoromethyl)-4-((1R,3aS,5aR,5bR,7aR,11aS,11bR,13aR,13bR)-5a,5b,8,8,11a-pentamethyl-3a-((2-(4-(methylsulfonyl)piperazin-1-yl)-2-oxoethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid

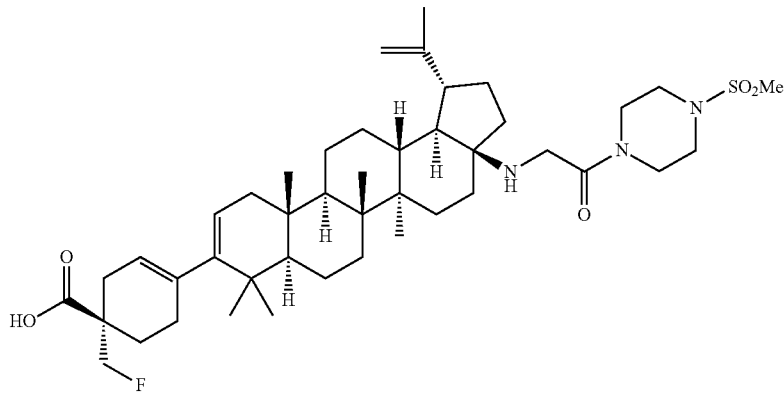

The title compound was prepared by the same procedure used for the preparation of (S)-1-(fluoromethyl)-4-((1R,3aS,5aR,5bR,7aR,11aS,11bR,13aR,13bR)-3a-((2-(4-hydroxy-4-methylpiperidin-1-yl)-2-oxoethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, except 1-(methylsulfonyl)piperazine (0.012 g, 0.075 mmol) was used instead of 4-methylpiperidin-4-ol in Step 1. Purification of the crude Step 2 mixture by reverse phase preparative HPLC (Prep HPLC Method 12) provided the title compound (0.0210 g, 77% yield over 2 steps) as a white solid TFA salt. LCMS: m/z 770.5 (M+H)$^+$, 2.33 min (method 1). $^1$H NMR (400 MHz, 1:1 mixture of CDCl$_3$ and CD$_3$OD, CD$_3$OD lock) δ 5.33 (br. s., 1H), 5.22-5.16 (m, 1H), 4.82 (s, 1H), 4.74 (s, 1H), 4.48-4.40 (m, 1H), 4.21 (d, J=16.1 Hz, 1H), 3.96 (d, J=15.9 Hz, 1H), 3.92-3.83 (m, 1H), 3.73 (ddd, J=13.6, 7.3, 3.3 Hz, 1H), 3.67-3.52 (m, 2H), 3.31-3.20 (m, 2H), 2.88 (s, 3H), 2.71 (td, J=11.1, 4.9 Hz, 1H), 2.55 (d, J=15.9 Hz, 1H), 2.29-2.13 (m, 2H), 2.13-1.91 (m, 7H), 1.89-1.71 (m, 7H), 1.71-1.60 (m, 4H), 1.60-1.41 (m, 6H), 1.41-1.21 (m, 4H), 1.19 (s, 4H), 1.13-1.08 (m, 1H), 1.07 (s, 3H), 0.96 (s, 3H), 0.94 (s, 3H), 0.90 (s, 3H).

Example 34

Preparation of (S)-4-((1R,3aS,5aR,5bR,7aR,11aS,11bR,13aR,13bR)-3a-((2-(1,1-dioxido-1,4-thiazepan-4-yl)-2-oxoethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid

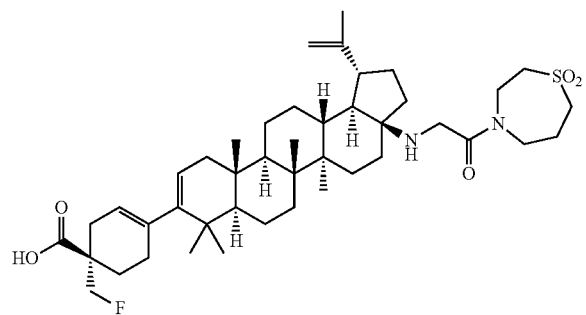

The title compound was prepared by the same procedure used for the preparation of (S)-1-(fluoromethyl)-4-((1R,3aS,5aR,5bR,7aR,11aS,11bR,13aR,13bR)-3a-((2-(4-hydroxy-4-methylpiperidin-1-yl)-2-oxoethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, except 1,4-thiazepane 1,1-dioxide (0.011 g, 0.075 mmol) was used instead of 4-methylpiperidin-4-ol in Step 1. Purification of the crude Step 2 mixture by reverse phase preparative HPLC (Prep HPLC Method 12) provided the title compound (0.0188 g, 70% yield over 2 steps) as a white solid TFA salt. LCMS: m/z 755.4 (M+H)$^+$, 2.32 min (method 1). $^1$H NMR (400 MHz, 1:1 mixture of CDCl$_3$ and CD$_3$OD, CD$_3$OD lock) δ 5.33 (br. s., 1H), 5.19 (d, J=4.9 Hz, 1H), 4.82 (s, 1H), 4.74 (s, 1H), 4.49-4.39 (m, 1H), 4.25-4.10 (m, 1H), 4.04-3.91 (m, 2H), 3.91-3.81 (m, 1H), 3.81-3.66 (m, 3H), 3.66-3.48 (m, 1H), 3.41 (t, J=5.9 Hz, 1H), 3.30-3.23 (m, 1H), 2.77-2.64 (m, 1H), 2.55 (d, J=17.9 Hz, 1H), 2.32-2.13 (m, 3H), 2.13-1.91 (m, 8H), 1.90-1.75 (m, 3H), 1.74 (s, 3H), 1.71-1.60 (m, 4H), 1.59-1.44 (m, 5H), 1.44-1.29 (m, 4H), 1.19 (d, J=2.2 Hz, 4H), 1.10 (d, J=7.1 Hz, 1H), 1.07 (s, 3H), 0.97 (s, 3H), 0.94 (s, 3H), 0.90 (s, 3H).

Example 35

Preparation of (S)-4-((1R,3aS,5aR,5bR,7aR,11aS,11bR,13aR,13bR)-3a-((2-(1,1-dioxidothiazolidin-3-yl)-2-oxoethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid The title compound was prepared by the same procedure used for the preparation of (S)-1-(fluoromethyl)-4-((1R,3aS,5aR,5bR,7aR,11aS,11bR,13aR,13bR)-3a-((2-(4-hydroxy-4-methylpiperidin-1-yl)-2-oxoethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, except thiazolidine 1,1-dioxide (9.15 mg, 0.075 mmol) was used instead of 4-methylpiperidin-4-ol in Step 1. Purification of the crude Step 2 mixture by reverse phase preparative HPLC (Prep HPLC Method 12) provided the title compound (0.0117 g, 45% yield over 2 steps) as a white solid TFA salt. LCMS: m/z 727.4 (M+H)$^+$, 2.31 min (method 1). $^1$H NMR (400 MHz, 1:1 mixture of CDCl$_3$ and CD$_3$OD, CD$_3$OD lock) δ 5.33 (br. s., 1H), 5.19 (d, J=6.1 Hz, 1H), 4.81 (s, 1H), 4.72 (br. s., 1H), 4.64 (br. s., 1H), 4.47-4.40 (m, 1H), 4.19-4.08 (m, 2H), 4.01-3.84 (m, 1H), 3.49 (t, J=6.1 Hz, 1H), 3.41 (t, J=7.2 Hz, 1H), 2.74-2.63 (m, 1H), 2.55 (d, J=17.1 Hz, 1H), 2.30-2.12 (m, 2H), 2.09 (br. s., 1H), 2.07-1.92 (m, 5H), 1.92-1.75 (m, 4H), 1.73 (s, 3H), 1.69-1.44 (m, 9H), 1.44-1.36 (m, 2H), 1.36-1.24 (m, 2H), 1.17 (d, J=4.6 Hz, 3H), 1.14-1.01 (m, 4H), 0.96 (s, 3H), 0.93 (s, 3H), 0.90 (s, 3H).

Example 36

Preparation of (1S)-1-(fluoromethyl)-4-((1R,3aS,5aR,5bR,7aR,11aS,11bR,13aR,13bR)-5a,5b,8,8,11a-pentamethyl-3a-((2-(3-(methylsulfonyl)pyrrolidin-1-yl)-2-oxoethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid

Example 37

Preparation of (S)-4-((1R,3aS,5aR,5bR,7aR,11aS,11bR,13aR,13bR)-3a-((2-((1S,4S)-2,2-dioxido-2-thia-5-azabicyclo[2.2.1]heptan-5-yl)-2-oxoethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid

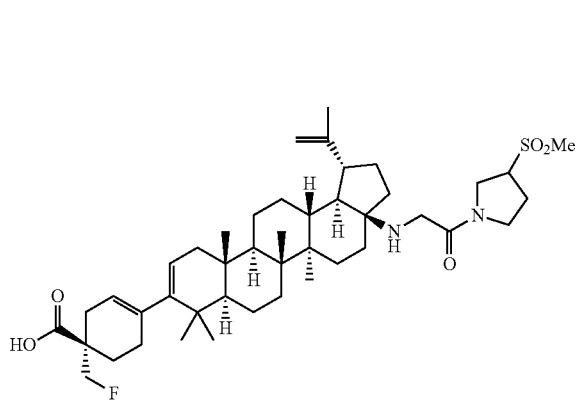

The title compound was prepared by the same procedure used for the preparation of (S)-1-(fluoromethyl)-4-((1R,3aS,5aR,5bR,7aR,11aS,11bR,13aR,13bR)-3a-((2-(4-hydroxy-4-methylpiperidin-1-yl)-2-oxoethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, except 3-(methylsulfonyl)pyrrolidine (0.011 g, 0.075 mmol) was used instead of 4-methylpiperidin-4-ol in Step 1. Purification of the crude Step 2 mixture by reverse phase preparative HPLC (Prep HPLC Method 12) provided the title compound (0.0117 g, 57% yield over 2 steps) as a white solid TFA salt. LCMS: m/z 755.4 (M+H)$^+$, 2.31 min (method 1). $^1$H NMR (400 MHz, 1:1 mixture of CDCl$_3$ and CD$_3$OD, CD$_3$OD lock) δ 5.33 (br. s., 1H), 5.19 (d, J=5.4 Hz, 1H), 4.82 (s, 1H), 4.74 (br. s., 1H), 4.47-4.39 (m, 1H), 4.19-3.97 (m, 2H), 3.97-3.81 (m, 3H), 3.81-3.61 (m, 2H), 3.09-3.01 (m, 3H), 2.75-2.46 (m, 4H), 2.30-2.12 (m, 2H), 2.12-1.91 (m, 7H), 1.88-1.75 (m, 3H), 1.74 (s, 3H), 1.71-1.61 (m, 4H), 1.59-1.42 (m, 6H), 1.41-1.29 (m, 3H), 1.26 (br. s., 1H), 1.19 (s, 4H), 1.10 (d, J=8.6 Hz, 1H), 1.07 (s, 3H), 0.97 (s, 3H), 0.94 (s, 3H), 0.90 (s, 3H).

The title compound was prepared by the same procedure used for the preparation of (S)-1-(fluoromethyl)-4-((1R,3aS,5aR,5bR,7aR,11aS,11bR,13aR,13bR)-3a-((2-(4-hydroxy-4-methylpiperidin-1-yl)-2-oxoethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, except (1S,4S)-2-thia-5-azabicyclo[2.2.1]heptane 2,2-dioxide, hydrobromide (0.017 g, 0.075 mmol) was used instead of 4-methylpiperidin-4-ol in Step 1. Purification of the crude Step 2 mixture by reverse phase preparative HPLC (Prep HPLC Method 12) provided the title compound (0.0154 g, 57% yield over 2 steps) as a white solid TFA salt. LCMS: m/z 753.4 (M+H)$^+$, 2.31 min (method 1). $^1$H NMR (400 MHz, 1:1 mixture of CDCl$_3$ and CD$_3$OD, CD$_3$OD lock) δ 5.33 (br. s., 1H), 5.22-5.16 (m, 1H), 5.11 (d, J=3.4 Hz, 1H), 4.82 (s, 1H), 4.76-4.70 (m, 1H), 4.48-4.39 (m, 1H), 4.17-4.07 (m, 1H), 3.99-3.84 (m, 2H), 3.84-3.69 (m, 1H), 3.30-3.13 (m, 2H), 2.75-2.60 (m, 2H), 2.60-2.42 (m, 2H), 2.29-2.12 (m, 2H), 2.12-1.90 (m, 7H), 1.87-1.75 (m, 3H), 1.74 (s, 3H), 1.72-1.59 (m, 4H), 1.59-1.41 (m, 6H), 1.41-1.21 (m, 4H), 1.21-1.15 (m, 4H), 1.10 (d, J=7.6 Hz, 1H), 1.07 (s, 3H), 0.96 (s, 3H), 0.93 (s, 3H), 0.89 (s, 3H).

Example 38
Preparation of (R)-4-((1R,3aS,5aR,5bR,7aR,11aS, 11bR,13aR,13bR)-3a-((2-(1,1-dioxidothiomorpholino)ethyl)carbamoyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)-1-(fluoromethyl) cyclohex-3-enecarboxylic acid, TFA
5
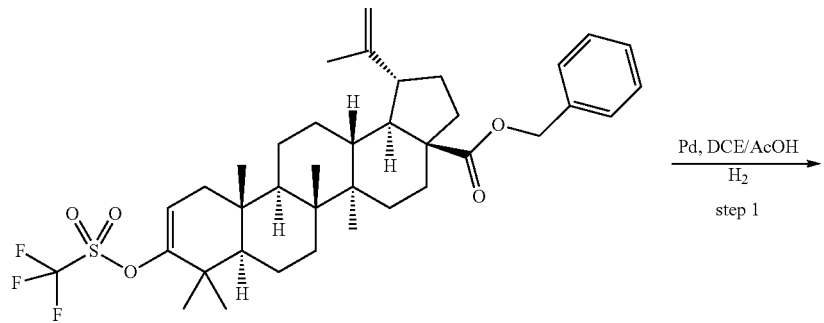
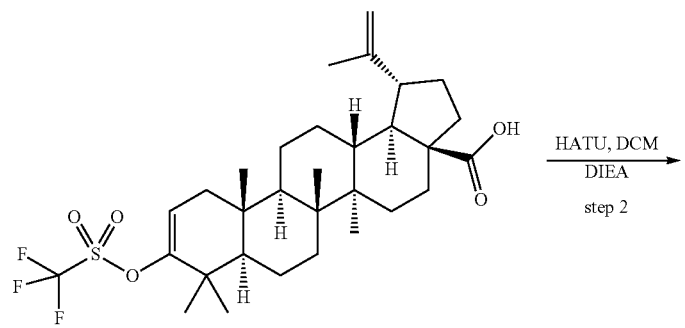
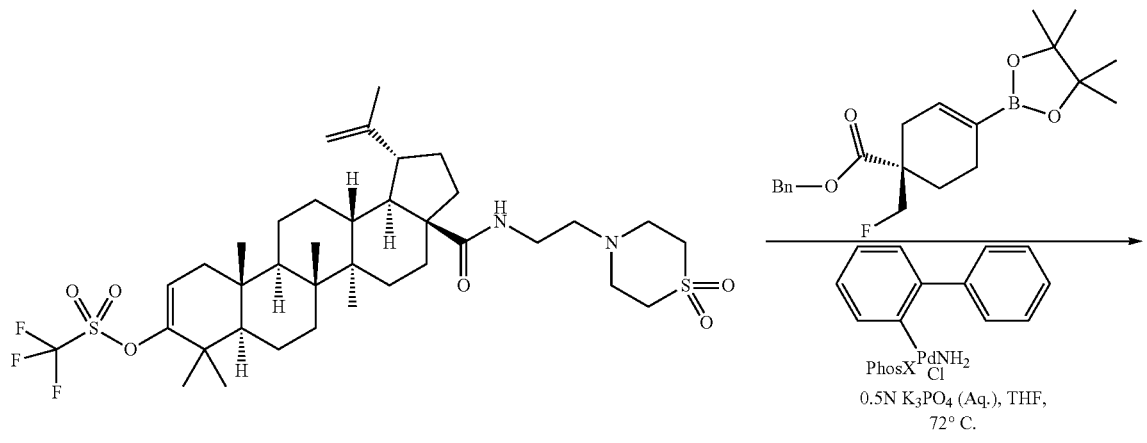

Example 38

Step 1. Preparation of (1R,3aS,5aR,5bR,7aR,11aR, 11bR,13aR,13bR)-5a,5b,8,8,11a-pentamethyl-1-(prop-1-en-2-yl)-9-(((trifluoromethyl)sulfonyl)oxy)-2,3,3a,4,5,5a,5b,6,7,7a,8,11,11a,11b,12,13,13a,13b-octadecahydro-1H-cyclopenta[a]chrysene-3a-carboxylic acid To a solution of (1R,3aS,5aR,5bR,7aR,11aR,11bR,13aR,13bR)-benzyl 5a,5b,8,8,11a-pentamethyl-1-(prop-1-en-2-yl)-9-(((trifluoromethyl)sulfonyl)oxy)-2,3,3a,4,5,5a,5b,6,7,7a,8,11,11a,11b,12,13,13a,13b-octadecahydro-1H-cyclopenta[a]chrysene-3a-carboxylate (1.500 g, 2.216 mmol) in DCE (20 mL) and acetic acid (5 mL) under a $N_2$ (g) atmosphere was added palladium black (0.047 g, 0.443 mmol). The reaction vessel was purged with $H_2$ (g) and stirred under a $H_2$ (g) atmosphere for 5 h, filtered, washed with DCM (50 mL) and concentrated to white solid. Crude material was triturated with minimal DCM and hexanes, concentrated to white slurry, filtered and washed with hexanes to give 1$^{st}$ crop of desired product. The liquid filtrate was further concentrated to white slurry, filtered and washed with hexanes to give a second crop. Both crops were combined and dried under vacuum to give (1R,3aS,5aR,5bR,7aR,11aR,11bR,13aR,13bR)-5a,5b,8,8,11a-pentamethyl-1-(prop-1-en-2-yl)-9-(((trifluoromethyl)sulfonyl)oxy)-2,3,3a,4,5,5a,5b,6,7,7a,8,11,11a,11b,12,13,13a,13b-octadecahydro-1H-cyclopenta[a]chrysene-3a-carboxylic acid (1.1 g, 1.875 mmol, 85% yield) as white solid. LCMS: m/e 587.2 (M+H)$^+$, 3.23 min (method 1). $^1$H NMR (400 MHz, CHLOROFORM-d) δ 5.57 (d, J=3.9 Hz, 1H), 4.76 (br. s., 1H), 4.63 (br. s., 1H), 3.03 (br. s., 1H), 2.46-2.10 (m, 3H), 2.00 (d, J=6.8 Hz, 2H), 1.81-1.63 (m, 6H), 1.59-1.32 (m, 12H), 1.25 (br. s., 3H), 1.13 (br. s., 3H), 1.02 (br. s., 3H), 1.00 (br. s., 6H), 0.93 (br. s., 3H). $^{13}$C NMR (101 MHz, CHLOROFORM-d) δ 182.0, 155.4, 150.3, 113.7, 109.8, 56.4, 53.3, 49.2, 48.9, 46.9, 42.5, 40.6, 40.3, 38.5, 37.9, 37.1, 36.4, 33.3, 32.1, 30.6, 29.7, 27.5, 25.5, 21.4, 19.4, 19.39-19.33, 18.9, 16.2, 15.7, 14.6. $^{19}$F NMR (376 MHz, CHLOROFORM-d) δ −74.82 (br. s., 3F).

Step 2. Preparation of (1R,3aS,5aR,5bR,7aR,11aR, 11bR,13aR,13bR)-3a-((2-(1,1-dioxidothiomorpholino)ethyl)carbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate To a solution of (1R,3aS,5aR,5bR,7aR,11aR,11bR,13aR,13bR)-5a,5b,8,8,11a-pentamethyl-1-(prop-1-en-2-yl)-9-(((trifluoromethyl)sulfonyl)oxy)-2,3,3a,4,5,5a,5b,6,7,7a,8,11,11a,11b,12,13,13a,13b-octadecahydro-1H-cyclopenta[a]chrysene-3a-carboxylic acid (0.500 g, 0.852 mmol) and N,N-diisopropylethylamine (0.520 mL, 2.98 mmol) in DCM (10 mL) was added HATU (0.389 g, 1.023 mmol) and 4-(2-aminoethyl)thiomorpholine 1,1-dioxide (0.182 g, 1.023 mmol). The reaction was stirred at rt (10:25 am). After 2 h, the reaction was diluted with DCM and washed with 20 mL 5% aqueous citric acid. The aqueous layer was extracted with DCM (25 mL). The combined organic was washed with 10% $Na_2CO_3$, brine, dried over $MgSO_4$, filtered and concentrated to clear viscous oil. Crude material was purified by column chromatography (SiO$_2$, 24 g Isco cartridge, eluted with 97:3 DCM:MeOH) and dried under vacuum to give (1R,3aS,5aR,5bR,7aR,11aR,11bR,13aR,13bR)-3a-((2-(1,1-dioxidothiomorpholino)ethyl)carbamoyl)-5a,5b,8,8,11a- pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate (394 mg, 0.527 mmol, 61.9% yield) as white solid. LCMS: m/e 747.5 (M+H)+, 2.75 min (method 1). $^1$H NMR (400 MHz, CHLOROFORM-d) δ 5.87 (t, J=5.4 Hz, 1H), 5.56 (dd, J=6.6, 1.7 Hz, 1H), 4.74 (d, J=1.5 Hz, 1H), 4.61 (s, 1H), 3.37 (q, J=6.0 Hz, 2H), 3.15-3.07 (m, 1H), 3.05 (s, 7H), 2.66 (t, J=6.2 Hz, 2H), 2.56-2.46 (m, 1H), 2.16 (dd, J=17.1, 6.8 Hz, 1H), 1.97-1.88 (m, 2H), 1.79-1.71 (m, 3H), 1.69 (s, 3H), 1.66-1.54 (m, 3H), 1.52-1.30 (m, 10H), 1.25-1.16 (m, 2H), 1.12 (s, 3H), 1.10-1.06 (m, 1H), 1.01 (s, 3H), 0.98 (s, 3H), 0.97 (s, 3H), 0.91 (s, 3H). $^{13}$C NMR (101 MHz, CHLOROFORM-d) δ 176.3, 155.3, 150.6, 113.7, 109.6, 55.7, 55.6, 53.3, 51.3, 50.7, 50.0, 49.0, 46.8, 42.5, 40.6, 40.2, 38.6, 38.4, 37.9, 37.8, 36.3, 36.3, 33.8, 33.5, 30.8, 29.4, 27.4, 25.5, 21.5, 19.5, 19.4, 19.0, 16.2, 15.9, 14.6. $^{19}$F NMR (376 MHz, CHLOROFORM-d) δ −74.83 (s, 3F).

Step 3

Preparation of (R)-benzyl 4-((1R,3aS,5aR,5bR,7aR,11aS,11bR,13aR,13bR)-3a-((2-(1,1-dioxidothiomorpholino)ethyl)carbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate, TFA. (1R,3aS,5aR,5bR,7aR,11aR,11bR,13aR,13bR)-3a-((2-(1,1-dioxidothiomorpholino)ethyl)carbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate (250 mg, 0.335 mmol), (R)-benzyl 1-(fluoromethyl)-4-(4,4,5,5-tetramethyl-1,3,2-dioxaborolan-2-yl)cyclohex-3-enecarboxylate (150 mg, 0.402 mmol) and Buchwald precatalyst 13 (92371-003-01) (10.53 mg, 0.013 mmol) were combined. The reaction vessel was evacuated for 15 mins in a vacuum oven then refilled back with a N$_2$ (g). To the reaction flask was charged with pre-sparged with N$_2$ (g) THF (4 mL) and aqueous 0.5 M K$_3$PO$_4$ (1.673 mL, 0.837 mmol). The reaction mixture was sparged with N$_2$ (g) and stirred at 72° C. for 15 h and let cooled to rt overnight. The reaction was diluted with EtOAc (50 mL) and washed with 1.5N K$_3$PO$_4$. The aqueous layer was extracted with EtOAc (50 mL). The combined organic layer was washed with brine, dried over MgSO$_4$, filtered and concentrated to brown viscous oil. Crude material was purified by flash column chromatography (silica gel, 12 g, eluted with 97:3 DCM:MeOH) and dried to give product but still contaminated with a couple impurities. This material was further purified by reverse phase prep-HPLC (prep-HPLC methods 8) and dried under vacuum to give (R)-benzyl 4-((1R,3aS,5aR,5bR,7aR,11aS,11bR,13aR,13bR)-3a-((2-(1,1-dioxidothiomorpholino)ethyl)carbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate, TFA (161 mg, 0.166 mmol, 49.6% yield) as white solid. LCMS: m/e 845.7 (M+H)+, 3.25 min (method 1). $^1$H NMR (400 MHz, CHLOROFORM-d) δ 7.39-7.30 (m, 5H), 6.78 (br. s., 1H), 5.32 (br. s., 1H), 5.24-5.14 (m, 2H), 5.11 (d, J=4.6 Hz, 1H), 4.74 (s, 1H), 4.62 (s, 1H), 4.60-4.54 (m, 1H), 4.50-4.40 (m, 1H), 3.82-3.57 (m, 6H), 3.46 (br. s., 4H), 3.25 (t, J=5.6 Hz, 2H), 3.05 (td, J=11.0, 3.9 Hz, 1H), 2.60 (d, J=17.1 Hz, 1H), 2.41-2.31 (m, 1H), 2.24-2.03 (m, 4H), 2.02-1.90 (m, 3H), 1.88-1.72 (m, 3H), 1.69 (s, 3H), 1.66-1.61 (m, 1H), 1.60-1.46 (m, 4H), 1.46-1.18 (m, 10H), 1.05 (d, J=8.8 Hz, 2H), 0.97 (s, 3H), 0.92 (s, 6H), 0.87 (s, 3H), 0.84 (s, 3H).

Step 4

To a solution of (R)-benzyl 4-((1R,3aS,5aR,5bR,7aR,11aS,11bR,13aR,13bR)-3a-((2-(1,1-dioxidothiomorpholino)ethyl)carbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate, TFA (96 mg, 0.100 mmol) in THF (1.0 mL) and MeOH (0.5 mL) was added a solution of 1N lithium hydroxide (0.500 mL, 0.500 mmol) and stirred at 60° C. (11:25 AM). After 2 h, LC/MS showed reaction completed and it was let cooled to rt. The reaction mixture was purified by reverse phase prep-HPLC (prep-HPLC method 12) and dried under vacuum to give (R)-4-((1R,3aS,5aR,5bR,7aR,11aS,11bR,13aR,13bR)-3a-((2-(1,1-dioxidothiomorpholino)ethyl)carbamoyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid, TFA (66.1 mg, 0.075 mmol, 75% yield) as white solid. LCMS: m/e 755.5 (M+H)+, 2.69 min (method 1). $^1$H NMR (400 MHz, 1:1 CDCl$_3$:METHANOL-d$_4$) δ 5.30 (br. s., 1H), 5.16 (d, J=4.6 Hz, 1H), 4.69 (d, J=1.7 Hz, 1H), 4.45-4.36 (m, 1H), 3.09 (s, 6H), 3.06-3.01 (m, 1H), 2.67 (t, J=6.4 Hz, 2H), 2.57-2.45 (m, 2H), 2.30-2.19 (m, 1H), 2.12 (br. s., 1H), 2.08-2.04 (m, 1H), 2.02 (br. s., 1H), 2.00-1.92 (m, 2H), 1.91-1.81 (m, 1H), 1.80-1.69 (m, 3H), 1.67 (s, 3H), 1.63-1.52 (m, 3H), 1.50-1.30 (m, 10H), 1.29-1.14 (m, 5H), 1.09-0.99 (m, 2H), 0.97 (s, 3H), 0.95 (s, 3H), 0.94 (br. s., 3H), 0.89 (s, 3H), 0.84 (s, 3H).). $^{13}$C NMR (101 MHz, 1:1 CD3Cl$_3$:METHANOL-d$_4$) δ 178.7, 178.0, 151.6, 148.9, 140.0, 122.3, 122.2, 110.0, 78.6, 56.6, 56.2, 53.9, 51.7, 51.5, 50.9, 50.4, 47.6, 46.2, 46.1, 43.2, 42.6, 41.4, 39.0, 38.7, 38.3, 37.1, 36.9, 34.57-34.44, 33.9, 31.6, 30.3, 30.2, 29.9, 29.8, 27.1, 26.6, 22.2, 22.1, 20.45-20.36 (m, 1C), 19.8, 16.9, 16.5, 15.1. $^{19}$F NMR (376 MHz, 1:1 CDCl$_3$:METHANOL-d$_4$) δ −76.79 (s, 3F), −226.23 (t, J=47.7 Hz, 1F).

Example 39 and Example 40

Preparation of (1S)-4-((1R,3aS,5aR,5bR,7aR,11aS, 11bR,13aR,13bR)-3a-((3-amino-1,1,1-trifluoropropan-2-yl)amino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a] chrysen-9-yl)-1-(fluoromethyl)cyclohex-3-enecarboxylic acid, TFA (isomer A) and (1S)-4-((1R,3aS,5aR,5bR,7aR,11aS,11bR,13aR,13bR)-3a-((3-amino-1,1,1-trifluoropropan-2-yl)amino)-5a,5b, 8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid, TFA isomer B)

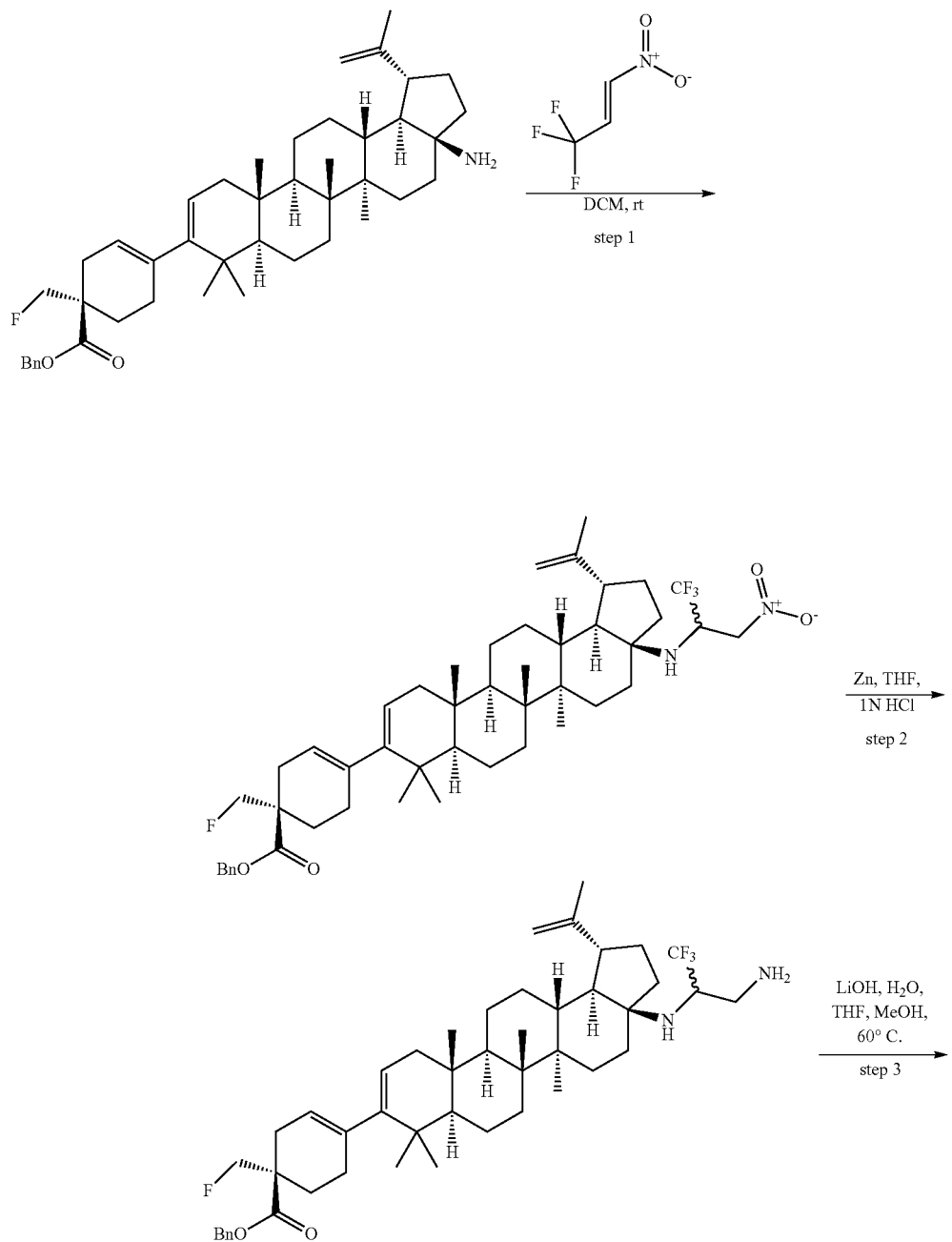

Isomer A
Example 39

Isomer B
Example 40

Step 1. (1S)-benzyl 1-(fluoromethyl)-4-((1R,3aS, 5aR,5bR,7aR,11aS,11bR,13aR,13bR)-5a,5b,8,8,11a-pentamethyl-1-(prop-1-en-2-yl)-3a-((1,1,1-trifluoro-3-nitropropan-2-yl)amino)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate To a solution of (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (190 mg, 0.290 mmol) in DCM (2 mL) was added (1E)-3,3,3-trifluoro-1-nitropro-lene (64.5 mg, 0.434 mmol) and stirred at rt. After 16 h, the reaction was concentrated to brown viscous oil and was purified by flash column chromatography (SiO$_2$, 24 g Isco cartridge, eluted with 9:1 Hex:EtOAc) and dried under vacuum to give (1S)-benzyl 1-(fluoromethyl)-4-((1R,3aS,5aR,5bR,7aR,11aS,11bR,13aR,13bR)-5a,5b,8,8,11a-pentamethyl-1-(prop-1-en-2-yl)-3a-((1,1,1-trifluoro-3-nitropropan-2-yl)amino)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (171.2 mg, 0.215 mmol, 74.2% yield) as white solid. LCMS: m/e 797.5 (M+H)$^+$, 4.55 min (method 10).

Step 2. (1 S)-benzyl 4-((1R,3aS,5aR,5bR,7aR,11aS,11bR,13aR,13bR)-3a-((3-amino-1,1,1-trifluoropropan-2-yl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate To a solution of (1S)-benzyl 1-(fluoromethyl)-4-((1R,3aS,5aR,5bR,7aR,11aS,11bR,13aR,13bR)-5a,5b,8,8,11a-pentamethyl-1-(prop-1-en-2-yl)-3a-((1,1,1-trifluoro-3-nitropropan-2-yl)amino)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (26 mg, 0.033 mmol) in THF (1 mL) was added 1N HCl (0.489 mL, 0.489 mmol). To the resulting slurry was added 1.5N Rieke zinc solution in THF (0.217 mL, 0.326 mmol). To the resulting grey slurry was added MeOH (1 mL). The reaction became homogeneous solution and was stirred at rt overnight. After 15 h, the reaction was concentrated. The resulting residue was dissolved with THF (5 mL), neutralized with 1.5 K$_3$PO$_4$ (5 mL) and the mixture was extracted with 2×25 mL EtOAc. The combined organic layer was washed with brine, dried over MgSO$_4$, filtered and concentrated to white foam. The material was used as crude in the next step. LCMS: m/e 767.6 (M+H)$^+$, 4.96 min (method 10).

Step 3. (1S)-4-((1R,3aS,5aR,5bR,7aR,11aS,11bR,13aR,13bR)-3a-((3-amino-1,1,1-trifluoropropan-2-yl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid, TFA (isomer A) and (1S)-4-((1R,3aS,5aR,5bR,7aR,11aS,11bR,13aR,13bR)-3a-((3-amino-1,1,1-trifluoropropan-2-yl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid, TFA isomer B)

To a solution of crude material, (1S)-benzyl 4-((1R,3aS,5aR,5bR,7aR,11aS,11bR,13aR,13bR)-3a-((3-amino-1,1,1-trifluoropropan-2-yl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (25 mg, 0.033 mmol), from experiments 99699-178 in THF (1 mL) and MeOH (0.5 mL) was added a solution of 1N lithium hydroxide (0.114 mL, 0.114 mmol). The reaction was stirred at 65° C. After 4 h, the reaction was let cooled to rt and was purified by reverse phase prep-HPLC (prep-method 13) and dried under vacuum to give isomer A, (1S)-4-((1R,3aS,5aR,5bR,7aR,11aS,11bR,13aR,13bR)-3a-((3-amino-1,1,1-trifluoropropan-2-yl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid, TFA and isomer B, (1S)-4-((1R,3aS,5aR,5bR,7aR,11aS,11bR,13aR,13bR)-3a-((3-amino-1,1,1-trifluoropropan-2-yl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid, TFA; both as white solid.

Example 39: Isomer A: LCMS: m/e 675.8 (M+H)$^+$, 4.29 min (method 11). $^1$H NMR (400 MHz, 1:1 CHLORO- FORM-d:METHANOL-d$_4$) δ 5.31 (br. s., 1H), 5.16 (d, J=4.9 Hz, 1H), 4.72 (br. s., 1H), 4.67 (br. s., 1H), 4.54-4.49 (m, 2H), 4.45-4.38 (m, 2H), 4.25 (br. s., 2H), 3.73 (t, J=6.5 Hz, 2H), 3.59 (br. s., 1H), 3.15-3.05 (m, 1H), 3.03-2.96 (m, 1H), 2.69 (td, J=11.0, 5.6 Hz, 1H), 2.53 (d, J=18.3 Hz, 1H), 2.17 (d, J=18.6 Hz, 2H), 2.05 (d, J=18.1 Hz, 1H), 2.01-1.90 (m, 2H), 1.89-1.84 (m, 2H), 1.82-1.71 (m, 4H), 1.68 (s, 3H), 1.66-1.61 (m, 1H), 1.56 (d, J=16.4 Hz, 1H), 1.44 (d, J=6.4 Hz, 6H), 1.38-1.22 (m, 5H), 1.20 (s, 1H), 1.07 (br. s., 2H), 1.04 (s, 3H), 0.97 (s, 3H), 0.94 (s, 3H), 0.91 (s, 2H), 0.85 (s, 3H). $^{19}$F NMR-1H Decoupled (376 MHz, 1:1 CHLOROFORM-d:METHANOL-d$_4$) δ −73.36 (s, 3F), −76.38 (s, 3F), −226.33 (s, 1F). $^{19}$F NMR (376 MHz, 1:1 CHLOROFORM-d:METHANOL-d$_4$) δ −73.37 (d, J=6.9 Hz, 3F), −76.39 (s, 3F), −226.14-226.54 (m, 1F).

Example 40: Isomer B: LCMS: m/e 675.7 (M+H)$^+$, 4.63 min (method 11). $^1$H NMR (400 MHz, 1:1 CHLOROFORM-d:METHANOL-d$_4$) δ 5.30 (br. s., 1H), 5.16 (d, J=4.6 Hz, 1H), 4.70 (s, 1H), 4.46-4.36 (m, 2H), 3.72 (t, J=6.6 Hz, 1H), 3.64 (dd, J=7.2, 3.5 Hz, 1H), 3.24-3.15 (m, 1H), 3.14-3.04 (m, 1H), 2.62-2.46 (m, 2H), 2.30-2.11 (m, 2H), 2.10-2.00 (m, 2H), 1.99-1.89 (m, 4H), 1.86 (dt, J=6.7, 3.2 Hz, 1H), 1.80-1.70 (m, 3H), 1.68 (s, 3H), 1.66 (br. s., 1H), 1.64-1.57 (m, 1H), 1.55-1.48 (m, 3H), 1.47-1.38 (m, 5H), 1.38-1.29 (m, 2H), 1.28-1.18 (m, 2H), 1.12 (br. s., 2H), 1.07 (s, 3H), 1.04 (br. s., 1H), 0.97 (s, 3H), 0.94 (s, 3H), 0.91 (s, 3H), 0.86 (s, 3H). $^{19}$F NMR (376 MHz, 1:1 CHLOROFORM-d:METHANOL-d$_4$) δ −73.84 (s, 3 F), −76.35 (s, 5 F), −226.26 (s, 1F).

Example 41 and Example 42

Preparation of (1S)-4-((1R,3aS,5aR,5bR,7aR,11aS,11bR,13aR,13bR)-3a-((3-(1,1-dioxidothiomorpholino)-1,1,1-trifluoropropan-2-yl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid, TFA (Isomer A) and (1S)-4-((1R,3aS,5aR,5bR,7aR,11aS,11bR,13aR,13bR)-3a-((3-(1,1-dioxidothiomorpholino)-1,1,1-trifluoropropan-2-yl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid, TFA (Isomer B)

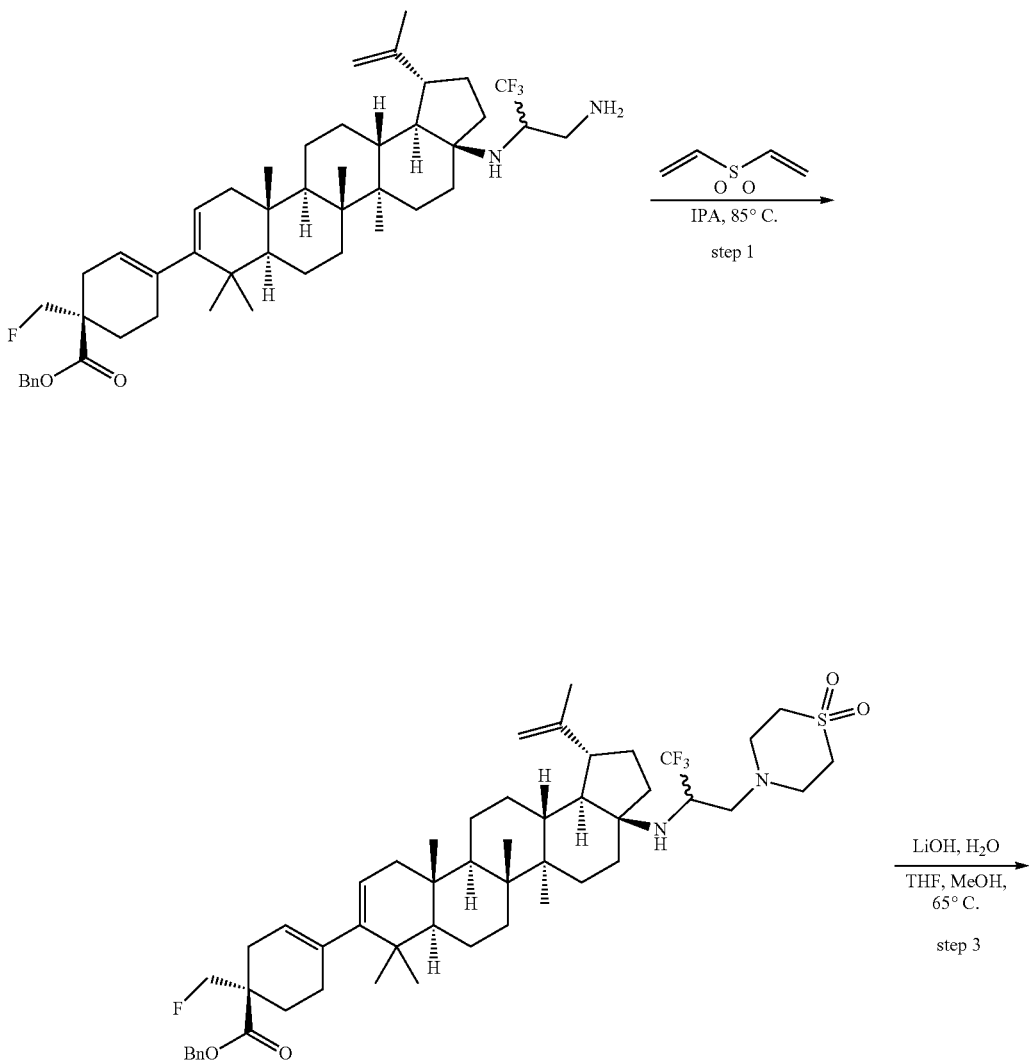

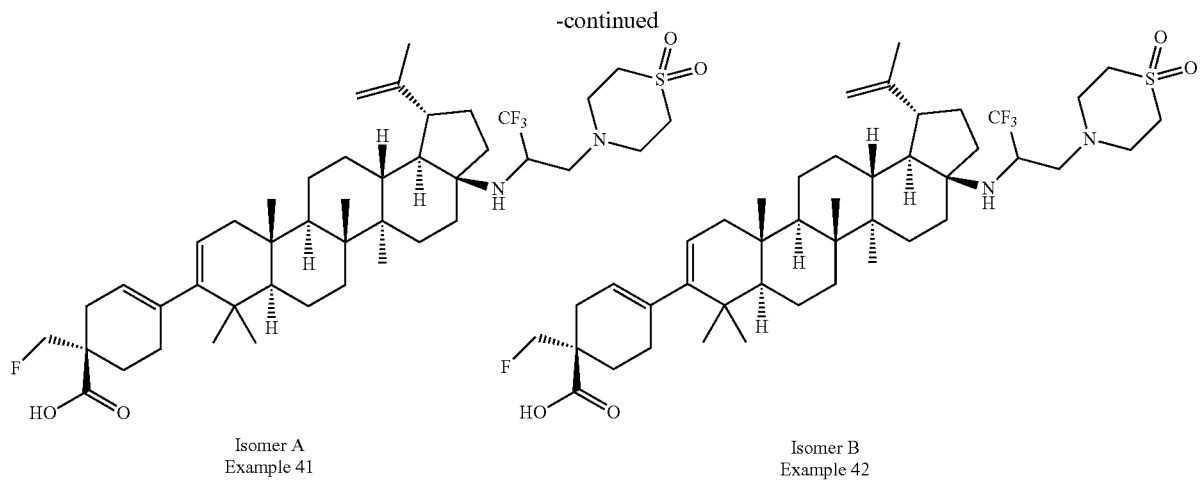

Isomer A
Example 41

Isomer B
Example 42

Step 1. Preparation of (1S)-benzyl 4-((1R,3aS,5aR, 5bR,7aR,11aS,11bR,13aR,13bR)-3a-((3-(1,1-dioxidothiomorpholino)-1,1,1-trifluoropropan-2-yl) amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)-1-(fluoromethyl)cyclohex-3-enecarboxylate To a solution of (1S)-benzyl 4-((1R,3aS,5aR,5bR,7aR, 11aS,11bR,13aR,13bR)-3a-((3-amino-1,1,1-trifluoropropan-2-yl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (107 mg, 0.139 mmol) in 2-Propanol (3 mL) was added divinyl sulfone (0.020 mL, 0.167 mmol) and stirred at 85° C. After 22 h, the reaction was cooled to rt and concentrated to give (1S)-benzyl 4-((1R,3aS,5aR,5bR,7aR,11aS,11bR,13aR,13bR)-3a-((3-(1,1-dioxidothiomorpholino)-1,1,1-trifluoropropan-2-yl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate as viscous brown oil and it was used directly in the next step.

Step 2. Preparation of (1S)-4-((1R,3aS,5aR,5bR, 7aR,11aS,11bR,13aR,13bR)-3a-((3-(1,1-dioxidothiomorpholino)-1,1,1-trifluoropropan-2-yl)amino)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid, TFA (Isomer A) and (1S)-4-((1R,3aS,5aR,5bR,7aR,11aS, 11bR,13aR,13bR)-3a-((3-(1,1-dioxidothiomorpholino)-1,1,1-trifluoropropan-2-yl)amino)-5a,5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)-1-(fluoromethyl)cyclohex-3-enecarboxylic acid, TFA (Isomer B)

To (1 S)-benzyl 4-((1R,3aS,5aR,5bR,7aR,11aS,11bR, 13aR,13bR)-3a-((3-(1,1-dioxidothiomorpholino)-1,1,1-trifluoropropan-2-yl)amino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)-1-(fluoromethyl)cyclohex-3-enecarboxylate was dissolved in THF (1 mL) and MeOH (1 mL) and treated with a solution of 1N lithium hydroxide (0.697 mL, 0.697 mmol), heated to 65° C. for 4 h and let cooled to rt. The reaction content was subjected to reverse phase HPLC purification using prep-Method below and dried under vacuum to give isomer A as (1S)-4-((1R,3aS,5aR,5bR,7aR,11aS,11bR,13aR,13bR)-3a-((3-(1,1-dioxidothiomorpholino)-1,1,1-trifluoropropan-2-yl)amino)-5a,5b,8,8,11a-pentamethyl-1-(prop-1-en-2-yl)-2, 3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid, TFA (32 mg, 0.035 mmol, 24.98% yield) and isomer B as (1S)-4-((1R, 3aS,5aR,5bR,7aR,11aS,11bR,13aR,13bR)-3a-((3-(1,1-dioxidothiomorpholino)-1,1,1-trifluoropropan-2-yl)amino)-5a,5b,8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid, TFA (24.3 mg, 0.026 mmol, 18.97% yield), both as white solid.

Example 41: Isomer A: LCMS: m/e 795.6 (M+H)+, 4.11 min (method 11). $^1$H NMR (400 MHz, 1:1 CDCl3:METHANOL-$d_4$) 5.30 (br. s., 1H), 5.16 (t, J=4.0 Hz, 1H), 5.12 (s, 1H), 4.70 (d, J=9.5 Hz, 1H), 4.46-4.36 (m, 2H), 4.21-4.06 (m, 1H), 3.23-2.94 (m, 10H), 2.88-2.76 (m, 1H), 2.70-2.46 (m, 3H), 2.44-2.27 (m, 1H), 2.26-2.12 (m, 3H), 2.11-2.01 (m, 2H), 2.00-1.85 (m, 4H), 1.81-1.69 (m, 3H), 1.68 (s, 1H), 1.66 (s, 2H), 1.61 (d, J=11.7 Hz, 1H), 1.58-1.51 (m, 1H), 1.51-1.34 (m, 7H), 1.34-1.18 (m, 4H), 1.11-1.05 (m, 1H), 1.04 (s, 2H), 0.98 (s, 1.5H), 0.96 (s, 1.5H), 0.94 (s, 6H), 0.91 (s, 3H), 0.86 (s, 1.5H), 0.85 (br. s., 1.5H).

Example 42: Isomer B: LCMS: m/e 795.6 (M+H)+, 4.19 min (method 11). $^1$H NMR (400 MHz, 1:1 CDCl3:METHANOL-$d_4$) δ 5.30 (br. s., 1H), 5.20-5.14 (m, 1H), 5.12 (s, 1H), 4.77-4.67 (m, 1H), 4.60-4.48 (m, 3H), 3.86 (d, J=3.4 Hz, 1H), 3.21-2.99 (m, 9H), 2.96-2.71 (m, 2H), 2.70-2.57 (m, 2H), 2.52 (d, J=17.4 Hz, 1H), 2.34-2.12 (m, 3H), 2.05 (d, J=19.1 Hz, 2H), 2.01-1.89 (m, 3H), 1.81-1.67 (m, 4H), 1.66 (s, 3H), 1.62-1.54 (m, 2H), 1.54-1.36 (m, 7H), 1.35-1.12 (m, 5H), 1.07 (br. s., 1H), 1.05 (s, 3H), 0.97 (s, 3H), 0.95 (s, 1H), 0.93 (s, 3H), 0.90 (s, 3H), 0.84 (s, 3H).

Example 43
Preparation of (S)-4-((1R,3aS,5aR,5bR,7aR,11aS,11bR,13aR,13bR)-3a-((2-((2-(1,1-dioxidothiomorpholino)ethyl)sulfonyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid, 2 TFA
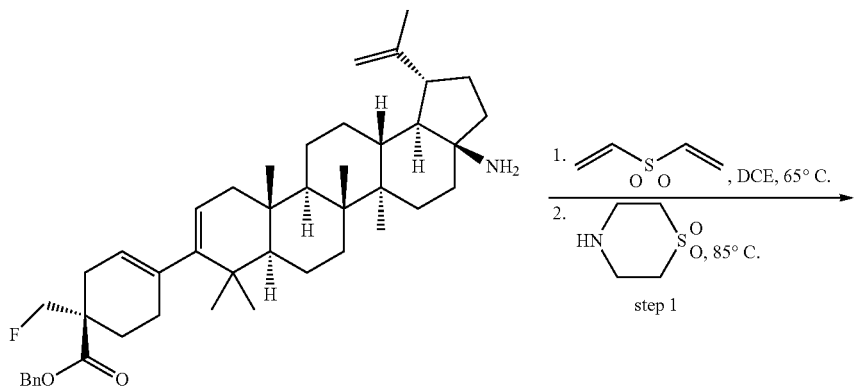
step 1
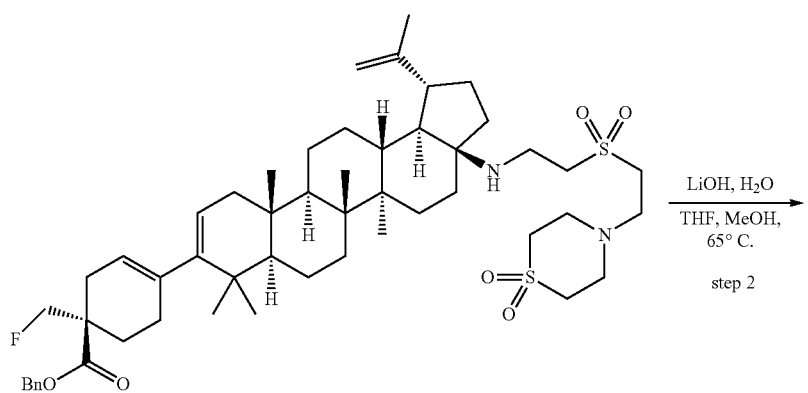
step 2
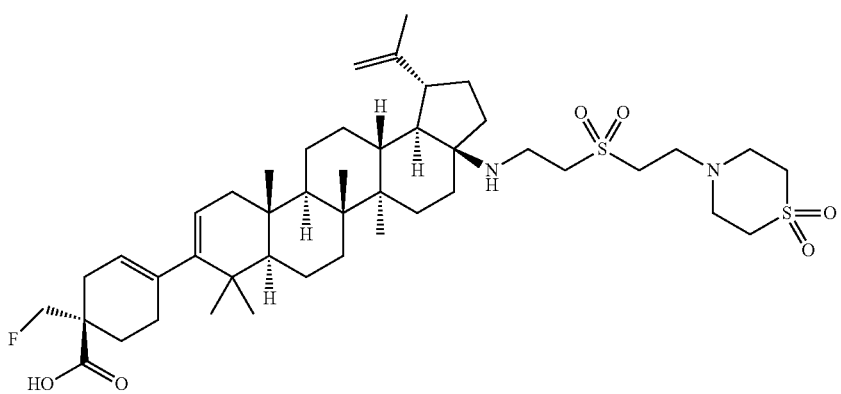
Example 43

Step 1. (S)-benzyl 4-((1R,3aS,5aR,5bR,7aR,11aS, 11bR,13aR,13bR)-3a-((2-((2-(1,1-dioxidothiomorpholino)ethyl)sulfonyl)ethyl)amino)-5a,5b,8,8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)-1-(fluoromethyl) cyclohex-3-enecarboxylate To a solution of (S)-benzyl 4-((1R,3aS,5aR,5bR,7aR, 11aS,11bR,13aR,13bR)-3a-amino-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)-1-(fluoromethyl)cyclohex-3-enecarboxylate (0.100 g, 0.152 mmol) in DCE (1 mL) was added divinyl sulfone (0.037 mL, 0.305 mmol) and stirred at 65° C. for 15 h and cooled to rt. LCMS: m/e 774.5 (M+H)$^+$, 4.53 min (method 10). To the reaction mixture above was added thiomorpholine 1,1-dioxide (0.041 g, 0.305 mmol) stirred at 85° C. for 8 h and let cooled back to rt. The reaction was concentrated and dried under vacuum to give crude (S)-benzyl 4-((1R,3aS,5aR,5bR,7aR,11aS,11bR,13aR,13bR)-3a-((2-((2-(1,1-dioxidothiomorpholino)ethyl)sulfonyl) ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate as viscous dark brown oil which was used as crude in the next step. LCMS: m/e 909.8 (M+H)$^+$, 4.79 min (method 10).

Step 2. Preparation of (S)-4-((1R,3aS,5aR,5bR,7aR, 11aS,11bR,13aR,13bR)-3a-((2-((2-(1,1-dioxidothiomorpholino)ethyl)sulfonyl)ethyl)amino)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)-1-(fluoromethyl)cyclohex-3-enecarboxylic acid, 2 TFA To a solution of crude (S)-benzyl 4-((1R,3aS,5aR,5bR, 7aR,11aS,11bR,13aR,13bR)-3a-((2-((2-(1,1-dioxidothiomorpholino)ethyl)sulfonyl)ethyl)amino)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a]chrysen-9-yl)-1-(fluoromethyl)cyclohex-3-enecarboxylate (139 mg, 0.153 mmol) in THF (1 mL) and MeOH (0.5 mL) was added a solution of 1N lithium hydroxide (0.535 mL, 0.535 mmol). The reaction was stirred at 65° C. for 3 h and cooled to rt. The reaction content was purified by reverse phase prep-HPLC (prep-method 12) and dried under vacuum to give (S)-4-((1R,3aS,5aR,5bR,7aR,11aS,11bR, 13aR,13bR)-3a-((2-((2-(1,1-dioxidothiomorpholino)ethyl) sulfonyl)ethyl)amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)-1-(fluoromethyl)cyclohex-3-enecarboxylic acid, 2 TFA (66.7 mg, 0.061 mmol, 39.6% yield for the three reaction steps) as white solid. LCMS: m/e 819.7 (M+H)$^+$, 3.90 min (method 12). $^1$H NMR (400 MHz, CHLOROFORM-d) δ 5.34 (br. s., 1H), 5.19 (d, J=4.6 Hz, 1H), 4.80 (s, 1H), 4.71 (s, 1H), 4.60 (s, 1H), 4.48 (s, 1H), 4.35-4.24 (m, 1H), 4.07 (br. s., 3H), 3.78 (t, J=6.6 Hz, 1H), 3.67-3.47 (m, 4H), 3.32 (dt, J=14.7, 5.6 Hz, 1H), 3.20-3.00 (m, 10H), 2.86-2.76 (m, 1H), 2.56 (d, J=17.4 Hz, 1H), 2.26-2.16 (m, 3H), 2.15-2.05 (m, 3H), 2.03-1.92 (m, 3H), 1.70 (s, 3H), 1.69 (br. s., 1H), 1.63-1.49 (m, 4H), 1.44 (br. s., 4H), 1.37 (d, J=11.0 Hz, 1H), 1.30 (br. s., 2H), 1.10 (s, 3H), 1.06 (d, J=7.6 Hz, 2H), 1.03 (s, 3H), 0.95 (s, 3H), 0.92 (s, 3H), 0.88 (s, 3H). $^{19}$F NMR (376 MHz, CHLOROFORM-d) δ −75.76 (s, 6F), −224.87 (s, 1F).

Section 2
LC/MS Methods
LC/MS Method 2-1
Conditions: 0% B→100% B over 2 minute gradient; hold at 100% B for 1 min
Solvent A: 90% water, 10% methanol, 0.1% TFA
Solvent B: 10% water, 90% methanol, 0.1% TFA
Column: Phenomenex Luna C18, 2.0×50 mm, 3 nm
Flow Rate: 1 mL/min
Detector Wavelength: 220 nm
LC/MS Method 2-2
Conditions: 0% B→100% B over 4 minute gradient; hold at 100% B for 1 min
Solvent A: 90% water, 10% methanol, 0.1% TFA
Solvent B: 10% water, 90% methanol, 0.1% TFA
Column: Phenomenex Luna C18, 3 mm, 2.0×50 mm
Flow Rate: 1 mL/min
Detector Wavelength: 220 nm
LC/MS Method 2-3
Conditions: 0% B→100% B over 4 minute gradient; hold at 100% B for 2 min
Solvent A: 90% water, 10% methanol, 0.1% TFA
Solvent B: 10% water, 90% methanol, 0.1% TFA
Column: Phenomenex Luna C18, 3 mm, 2.0×50 mm
Flow Rate: 0.8 mL/min
Detector Wavelength: 220 nm
Prep HPLC Methods
Prep HPLC Method 2-1
Conditions: 30% B→100% B over 20 minute gradient; hold at 100% B for 4 min
Solvent A: 5% acetonitrile, 95% water, 0.1% TFA
Solvent B: 95% acetonitrile, 5% water 0.1% TFA
Column: Waters Xbridge 30×100 mm, 5 μm
Flow Rate: 40 mL/min
Detector Wavelength: 220 nm
Prep HPLC Method 2-2
Conditions: see experimental section
Solvent A: 5:95 acetonitrile: water with 10-mM ammonium acetate
Solvent B: 95:5 acetonitrile: water with 10-mM ammonium acetate
Column: Waters Xbridge C18, 19×200 mm, 5 μm
Flow Rate: 20 mL/min
Detector Wavelength: 220 nm
Prep HPLC Method 2-3
Conditions: 50 B→100% B over 20 minutes gradient; hold at 100% B for 5 min
Solvent A: 5:95 acetonitrile: water with 0.1% trifluoroacetic acid
Solvent B: 95:5 acetonitrile: water with 0.1% trifluoroacetic acid
Column: Xbridge C18, 19×200 mm, 5 μm particles
Flow Rate: 20 mL/min
Detector Wavelength: 220 nm
Prep HPLC Method 2-4
Conditions: 10% B→100% B over 20 minute gradient; hold at 100% B for 5 min Solvent A: 5% acetonitrile, 95% water, 0.1% TFA
Solvent B: 95% acetonitrile, 5% water 0.1% TFA
Column: Waters Sunfire 30×150 mm, 5 um
Flow Rate: 40 mL/min
Detector Wavelength: 220 nm
Prep HPLC Method 2-5
Conditions: 30% B→100% B over 20 minute gradient; hold at 100% B for 5 min
Solvent A: 5% acetonitrile, 95% water, 0.1% TFA
Solvent B: 95% acetonitrile, 5% water 0.1% TFA
Column: Waters Sunfire 30×150 mm, 5 um
Flow Rate: 40 mL/min
Detector Wavelength: 220 nm
Prep HPLC Method 2-6
Conditions: 10% B→100% B over 20 minute gradient; hold at 100% B for 2 min
Solvent A: 10% methanol, 90% water, 0.1% TFA
Solvent B: 90% methanol, 10% water 0.1% TFA
Column: Waters Sunfire 30×100 mm, 5 μm
Flow Rate: 40 mL/min
Detector Wavelength: 220 nm
Analytical HPLC Methods
Analytical HPLC Method 2-1
Conditions: 10% B→100% B over 15 min gradient; hold at 100% B for 10 min
Solvent A: 10% methanol, 90% water, 0.1% TFA
Solvent B: 90% methanol, 10% water, 0.1% TFA
Column: Waters Sunfire C18, 4.6×150 mm, 3.5 mm
Flow Rate: 1 mL/min
Detector Wavelength: 220 nm
Analytical HPLC Method 2-2
Conditions: 10% B→100% B over 15 min gradient; hold at 100% B for 10 min
Solvent A: 10% methanol, 90% water, 0.1% TFA
Solvent B: 90% methanol, 10% water, 0.1% TFA
Column: Waters Xbridge phenyl, 4.6×150 mm, 3.5 mm
Flow Rate: 1 mL/min
Detector Wavelength: 220 nm
Analytical HPLC Method 2-3
Gradient: 0→100% B over 3 minutes, then a 0.5-minute hold at 100% B
Solvent A: 5:95 acetonitrile:water with 10 mM ammonium acetate
Solvent B: 95:5 acetonitrile:water with 10 mM ammonium acetate
Column: Waters BEH C18, 2.0×50 mm, 1.7-μm particles
Flow Rate: 1 mL/min
Detector Wavelength: 220 nm
Temperature: 50° C.
Analytical HPLC Method 2-4
Gradient: 0→100% B over 3 minutes, then a 0.5-minute hold at 100% B
Solvent A: 5:95 acetonitrile:water with 10 mM ammonium acetate
Solvent B: 95:5 acetonitrile:water with 10 mM ammonium acetate
Column: Waters BEH C18, 2.0×50 mm, 1.7-μm particles
Flow Rate: 1 mL/min
Detector Wavelength: 220 nm
Temperature: 50° C.
Analytical HPLC Method 2-5
Conditions: 10% B→100% B over 15 min gradient; hold at 100% B for 10 min
Solvent A: 5% acetonitrile, 95% water, 0.1% TFA
Solvent B: 95% acetonitrile, 5% water, 0.1% TFA
Column: Waters Sunfire C18, 3.0×150 mm, 3.5 um
Flow Rate: 0.5 mL/min
Detector Wavelength: 220 nm
Analytical HPLC Method 2-6
Conditions: 10% B→100% B over 15 min gradient; hold at 100% B for 10 min
Solvent A: 5% acetonitrile, 95% water, 0.1% TFA
Solvent B: 95% acetonitrile, 5% water, 0.1% TFA
Column: Waters Xbridge phenyl, 3.0×150 mm, 3.5 um
Flow Rate: 0.5 mL/min
Detector Wavelength: 220 nm Example 2-1

Preparation of (S)-1-(fluoromethyl)-4-((1R,3aS,5aR,5bR,7aR,11aS,11bR,13aR,13bR)-3a-((3-hydroxy-3-methylbutyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid

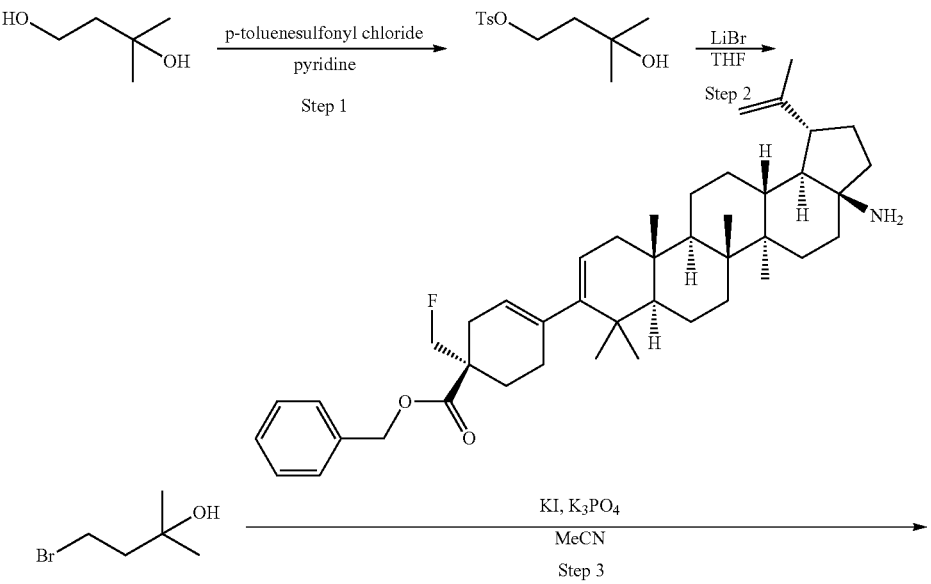

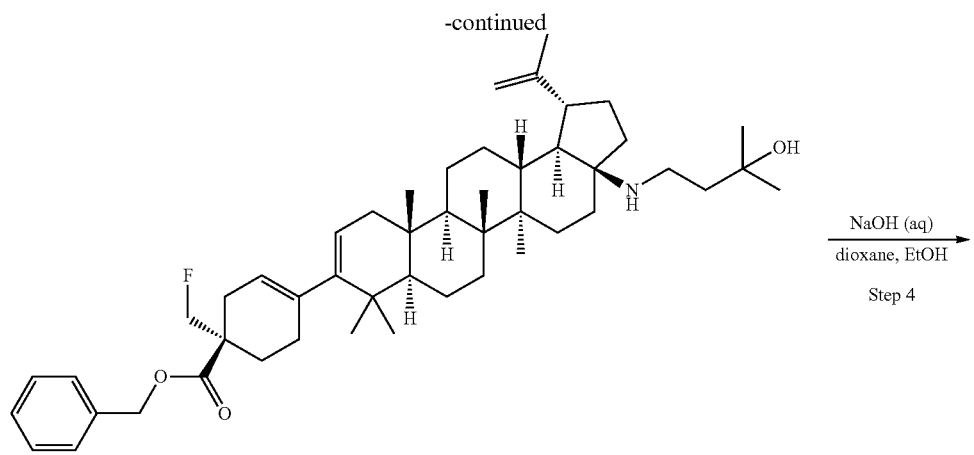

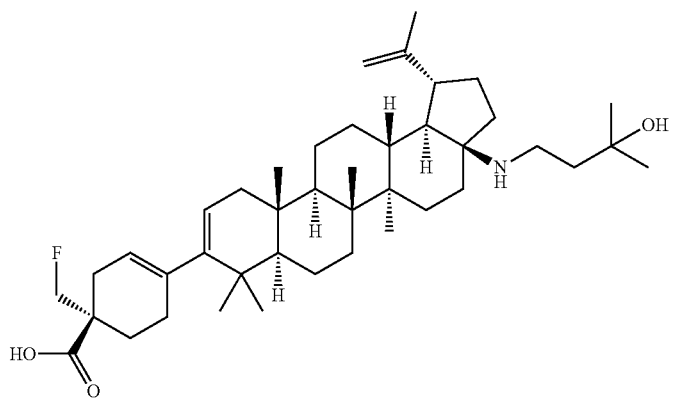

Example 2-1

Step 1. Preparation of 3-hydroxy-3-methylbutyl 4-methylbenzenesulfonate

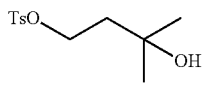

To a solution of 3-methylbutane-1,3-diol (1.00 g, 9.60 mmol) in pyridine (10 mL) at 0° C. was added p-toluenesulfonyl chloride (2.014 g, 10.56 mmol). The reaction mixture was stirred for 16 h while allowing the reaction mixture to slowly warm up to room temperature by dissipation of the ice-water bath. The mixture was transferred to a separatory funnel containing ethyl acetate (100 mL). The organic layer was washed with 1 N HCl (3×50 mL). The organic layer was then washed with saturated NaHCO$_3$ solution (50 mL), brine (50 mL), dried over MgSO$_4$, filtered, and concentrated. The product was purified by column chromatography on silica gel (30%→50% ethyl acetate in hexanes; 220 g column) to afford 3-hydroxy-3-methylbutyl 4-methylbenzenesulfonate (2.03 g, 7.86 mmol, 82% yield) as a colorless oil: $^1$H NMR (400 MHz, CHLOROFORM-d) δ 7.85-7.78 (m, 2H), 7.37 (dd, J=8.5, 0.8 Hz, 2H), 4.23 (t, J=6.9 Hz, 2H), 2.47 (s, 3H), 1.88 (t, J=6.9 Hz, 2H), 1.24 (s, 6H); LC/MS: The product did not ionize, $t_R$=1.78 min (method 2-1).

Step 2. Preparation of 4-bromo-2-methylbutan-2-ol

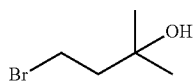

To a solution of 3-hydroxy-3-methylbutyl 4-methylbenzenesulfonate (400 mg, 1.548 mmol) in THF (15 mL) at room temperature was added lithium bromide (403 mg, 4.65 mmol). The reaction mixture was stirred at room temperature overnight. The mixture was transferred to a separatory funnel containing saturated aqueous NaHCO$_3$ solution (10 mL) and water (10 mL). The aqueous layer was extracted with ether (3×20 mL). The combined organic layers were washed with brine (10 mL), dried over MgSO$_4$, filtered, and concentrated. The product was purified by column chromatography on silica gel (20%→40% ethyl acetate in hexanes; 80 g column) to afford 4-bromo-2-methylbutan-2-ol (231 mg, 1.383 mmol, 89% yield) as a colorless oil: $^1$H NMR (500 MHz, CHLOROFORM-d) δ 3.55-3.49 (m, 2H), 2.15-2.09 (m, 2H), 1.28 (s, 6H).

Step 3. Preparation of (S)-benzyl 1-(fluoromethyl)-4-((1R,3aS,5aR,5bR,7aR,11aS,11bR,13aR,13bR)-3a-((3-hydroxy-3-methylbutyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (56.6 mg, 0.076 mmol, 72% yield) as a colorless foam: $^1$H NMR (500 MHz, CHLOROFORM-d) δ 7.42-7.31 (m, 5H), 5.33 (br. s., 1H), 5.23-5.16 (m, 2H), 5.13 (dd, J=6.2, 1.8 Hz, 1H), 4.72 (s, 1H), 4.63-4.55 (m, 2H), 4.52-4.45 (m, 1H), 2.86-2.78 (m, 1H), 2.77-2.68 (m, 1H), 2.65-2.53 (m, 2H), 2.18-0.86 (m, 29H), 1.69 (s, 3H), 1.27 (s,

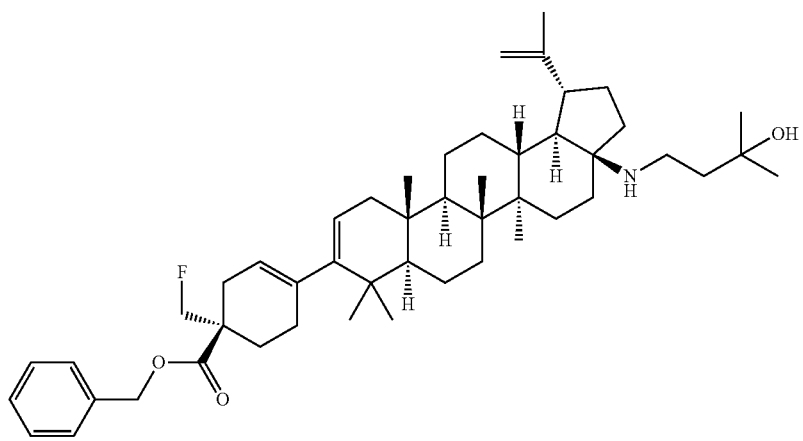

To a mixture of (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (70 mg, 0.107 mmol), 4-bromo-2-methylbutan-2-ol (24.96 mg, 0.149 mmol), potassium phosphate tribasic (68.0 mg, 0.320 mmol), and potassium iodide (24.80 mg, 0.149 mmol) in an oven-dried vial was added acetonitrile (0.8 mL). The cap was sealed and the reaction mixture was heated at 120° C. for 2 h. During this time the solvent evaporated. Additional acetonitrile (0.8 mL) was added and the reaction mixture was heated for 1 h at 120° C. The mixture was transferred to a separatory funnel containing water (5 mL). The aqueous layer was extracted with dichloromethane (3×10 mL). The combined organic layers were washed with brine (5 mL), dried over MgSO$_4$, filtered, and concentrated. The product was purified by column chromatography on silica gel (10% 9:1 acetone:methanol/90% hexanes→30% 9:1 acetone:methanol/70% hexanes; 24 g column, λ=220 nm) to afford (S)-benzyl 1-(fluoromethyl)-4-((1R,3aS,5aR,5bR,7aR,11aS,11bR,13aR,13bR)-3a-((3-hydroxy-3-methylbutyl)amino)-5a,5b,8,8,11a-pentamethyl-1-(prop-1-en-2-

6H), 1.07 (s, 3H), 0.98 (s, 3H), 0.91 (s, 3H), 0.90 (s, 3H), 0.86 (s, 3H); LC/MS m/e 742.6 [(M+H)$^+$, calcd for C$_{49}$H$_{73}$FNO$_3$ 742.6], t$_R$=4.86 min (method 2-3).

Step 4. A solution of (S)-benzyl 1-(fluoromethyl)-4-((1R,3aS,5aR,5bR,7aR,11aS,11bR,13aR,13bR)-3a-((3-hydroxy-3-methylbutyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (72 mg, 0.097 mmol) in 1,4-dioxane (1.4 mL) and EtOH (0.7 mL) was treated with sodium hydroxide (2M aq) (0.243 mL, 0.485 mmol). The reaction mixture was heated at 70° C. for 2 h. The mixture was cooled to room temperature, was filtered through a syringe filter, and was purified by reverse phase preparative HPLC (Method 2-1). The organic solvent was evaporated on the rotovapor and the aqueous mixture was lyophilized to afford (S)-1-(fluoromethyl)-4-((1R,3aS,5aR,5bR,7aR,11aS,11bR,13aR,13bR)-3a-((3-hydroxy-3-methylbutyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid.TFA (55.4 mg, 74% yield) as a white amorphous solid:

¹H NMR (500 MHz, Acetic Acid-d₄) δ 5.39 (br. s., 1H), 5.27-5.21 (m, 1H), 4.82 (s, 1H), 4.72 (s, 1H), 4.61 (dt, J=10.8, 9.0 Hz, 1H), 4.51 (dt, J=10.8, 9.2 Hz, 1H), 3.46-3.38 (m, 1H), 3.38-3.30 (m, 1H), 2.91-2.83 (m, 1H), 2.61 (d, J=17.1 Hz, 1H), 2.32-1.09 (m, 29H), 1.75 (s, 3H), 1.36 (s, 3H), 1.33 (s, 3H), 1.13 (s, 3H), 1.09 (s, 3H), 1.00 (s, 3H), 0.99 (s, 3H), 0.94 (s, 3H); LC/MS m/e 652.5 [(M+H)⁺, calcd for $C_{42}H_{67}FNO_3$ 652.5], $t_R$=4.40 min (method 2-2); HPLC (method 2-1): $t_R$=18.97 min; HPLC (method 2-2): $t_R$=20.16 min.

Example 2-2

Preparation of (S)-1-(fluoromethyl)-4-((1R,3aS,5aR, 5bR,7aR,11aS,11bR,13aR,13bR)-3a-((2-hydroxy-2-methylpropyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)cyclohex-3-enecarboxylic acid

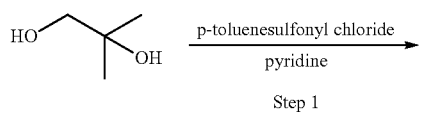

Step 1

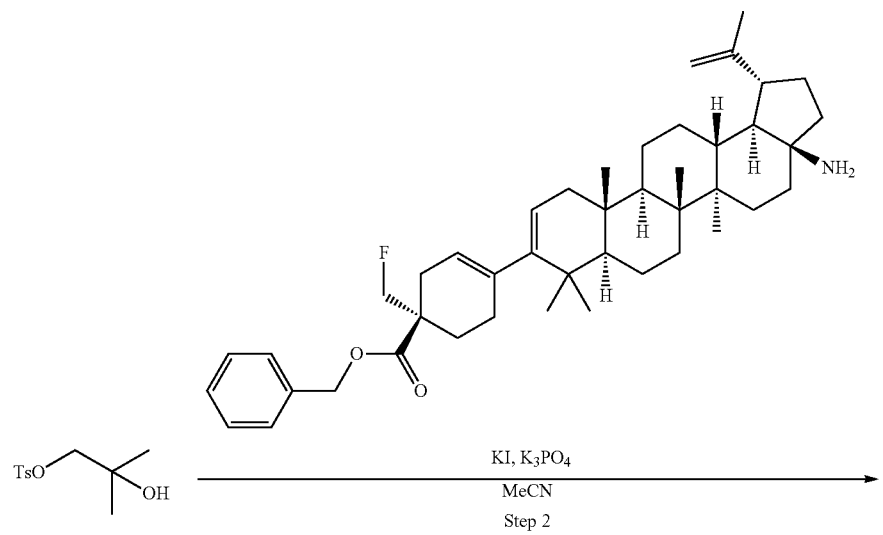

Step 2

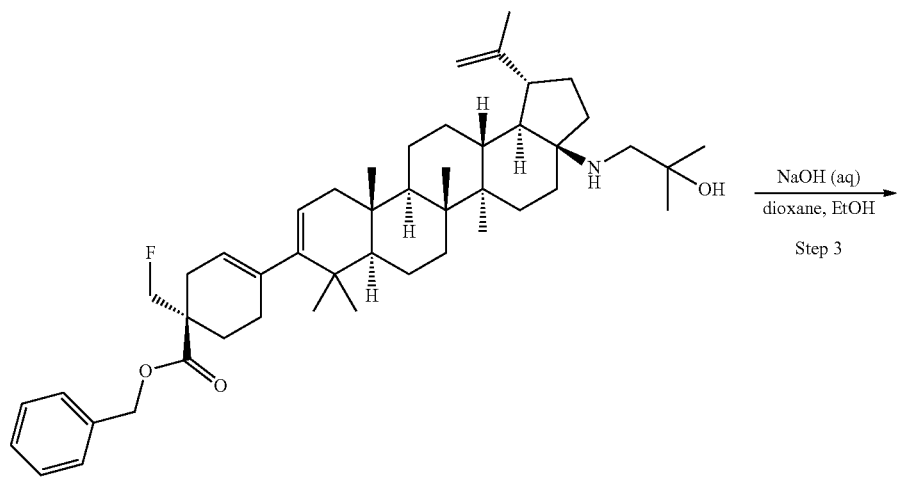

Step 3

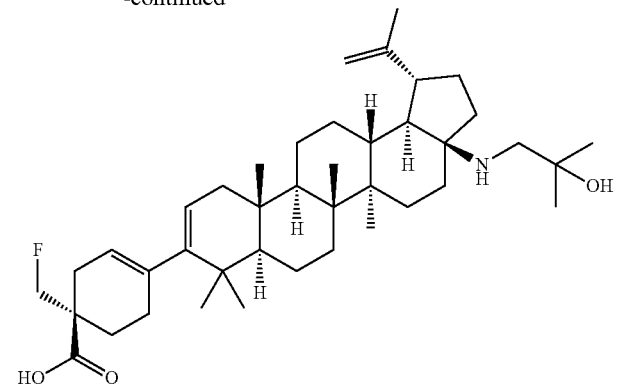

Example 2-2

Step 1. Preparation of 2-hydroxy-2-methylpropyl 4-methylbenzenesulfonate

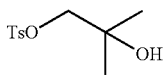 [SMILES: Cc1ccc(S(=O)(=O)OCC(C)(C)O)cc1]

To a solution of 2-methylpropane-1,2-diol (415 mg, 4.60 mmol) in pyridine (5 mL) at 0° C. was added p-toluenesulfonyl chloride (966 mg, 5.07 mmol). The reaction mixture was stirred for 16 h while allowing the reaction mixture to slowly warm up to room temperature by dissipation of the ice-water bath. The mixture was transferred to a separatory funnel containing ethyl acetate (50 mL). The organic layer was washed with 1 N HCl (3×25 mL). The organic layer was then washed with saturated NaHCO$_3$ solution (25 mL), brine (25 mL), dried over MgSO$_4$, filtered, and concentrated. The product was purified by column chromatography on silica gel (30%→50% ethyl acetate in hexanes; 120 g column) to afford 2-hydroxy-2-methylpropyl 4-methylbenzenesulfonate (1.01 g, 4.13 mmol, 90% yield) as a colorless oil: $^1$H NMR (400 MHz, CHLOROFORM-d) δ 7.86-7.78 (m, 2H), 7.38 (d, J=8.0 Hz, 2H), 3.86 (s, 2H), 2.48 (s, 3H), 1.24 (s, 6H); LC/MS: The product did not ionize, $t_R$=1.70 min (method 2-1).

Step 2. Preparation of (S)-benzyl 1-(fluoromethyl)-4-((1R,3aS,5aR,5bR,7aR,11aS,11bR,13aR,13bR)-3a-((2-hydroxy-2-methylpropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate

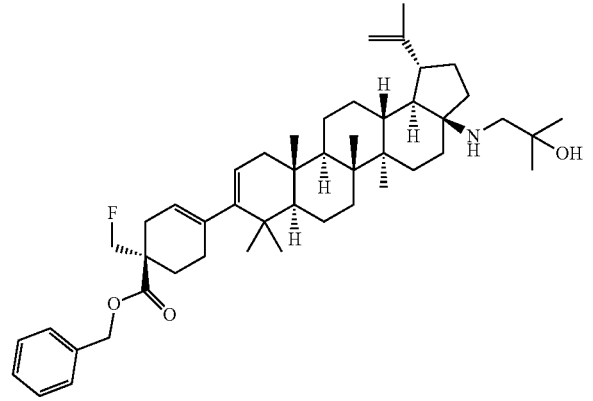

To a solution of 2-hydroxy-2-methylpropyl 4-methylbenzenesulfonate (22.35 mg, 0.091 mmol) in acetonitrile (0.7 mL) was added (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (50 mg, 0.076 mmol), potassium phosphate tribasic (32.4 mg, 0.152 mmol, 2 eq), and potassium iodide (63.27 mg, 0.381 mmol). The reaction mixture was heated at 100° C. for 6 h. Additional 2-hydroxy-2-methylpropyl 4-methylbenzenesulfonate (56 mg, 0.229 mmol, 3 eq) and potassium phosphate tribasic (16 mg, 0.076 mmol, 1 eq) was then added and the reaction mixture was heated at 120° C. for 22 h. Additional 2-hydroxy-2-methylpropyl 4-methylbenzenesulfonate (37 mg, 0.153 mmol, 2 eq), potassium phosphate tribasic (32 mg, 0.152 mmol, 2 eq), and potassium iodide (28 mg, 0.168 mmol, 2.2 eq) was then added and the reaction mixture was heated at 120° C. for an additional 18 h. The reaction mixture was cooled to room temperature. The mixture was transferred to a separatory funnel containing water (10 mL). The aqueous layer was extracted with dichloromethane (3×10 mL). The combined organic layers were washed with brine (10 mL), dried over MgSO$_4$, filtered, and concentrated. The product was used directly in the next step without further purification: LC/MS m/e 728.6 [(M+H)$^+$, calcd for C$_{48}$H$_{71}$FNO$_3$ 728.5], $t_R$=4.72 min (method 2-2).

Step 3

A solution of (S)-benzyl 1-(fluoromethyl)-4-((1R,3aS,5aR,5bR,7aR,11aS,11bR,13aR,13bR)-3a-((2-hydroxy-2-methylpropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (55 mg, 0.076 mmol) in 1,4-dioxane (0.5 mL) and EtOH (0.25 mL) was treated with sodium hydroxide (0.189 mL, 0.378 mmol). The reaction mixture was heated at 70° C. for 2 h. The mixture was cooled to room temperature, was filtered through a syringe filter, and was purified by reverse phase preparative HPLC (Method 2-1). The organic solvent was evaporated on the rotovapor and the aqueous mixture was lyophilized to afford (S)-1-(fluoromethyl)-4-((1R,3aS,5aR,5bR,7aR,11aS,11bR,13aR,13bR)-3a-((2-hydroxy-2-methylpropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid•TFA (2.7 mg, 5% yield) as a white amorphous solid: $^1$H NMR (500 MHz, Acetic Acid-d$_4$) δ 5.39 (br. s., 1H), 5.25 (d, J=4.6 Hz, 1H), 4.83 (s, 1H), 4.72 (s, 1H), 4.65-4.57 (m, 1H), 4.55-4.46 (m, 1H), 3.51 (d, J=12.7 Hz, 1H), 3.06 (d, J=12.4 Hz, 1H), 3.03-2.95 (m, 1H), 2.61 (d, J=16.9 Hz, 1H), 2.32-1.07 (m, 27H), 1.75 (s, 3H), 1.43 (s, 3H), 1.41 (s, 3H), 1.18 (s, 3H), 1.10 (s, 3H), 1.00 (s, 3H), 0.99 (s, 3H), 0.95 (s, 3H); LC/MS m/e 738.6 [(M+H)$^+$, calcd for C$_{41}$H$_{65}$FNO$_3$ 738.5], $t_R$=4.29 min (method 2-2). HPLC (method 2-1): $t_R$=18.88 min; HPLC (method 2-2): $t_R$=20.24 min.

Example 2-3
Preparation of (S)-1-(fluoromethyl)-4-((1R,3aS,5aR, 5bR,7aR,11aS,11bR,13aR,13bR)-3a-((4-hydroxy-4-methylpentyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)cyclohex-3-enecarboxylic acid
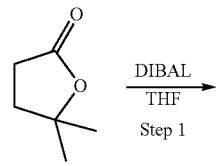
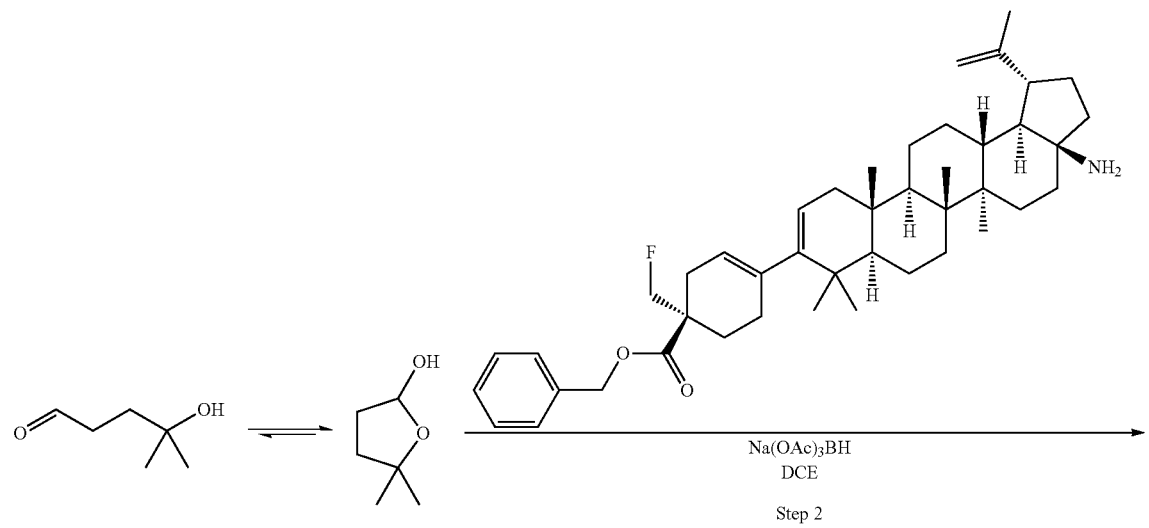
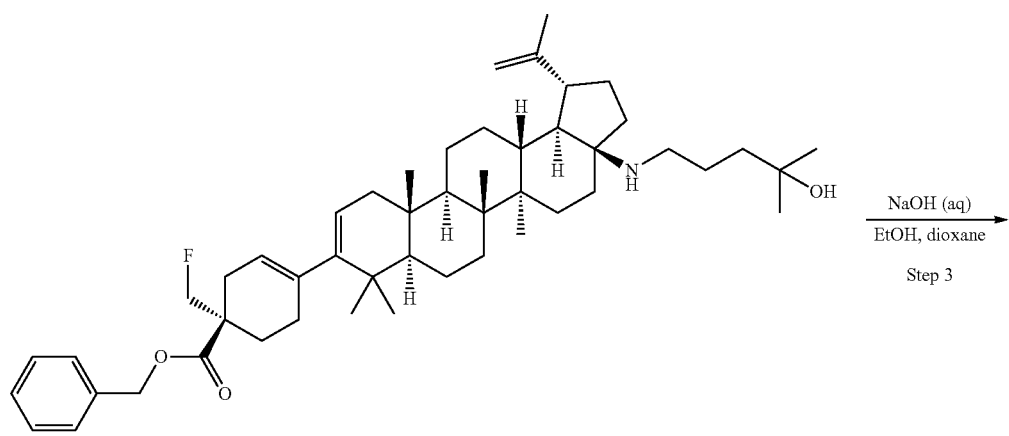

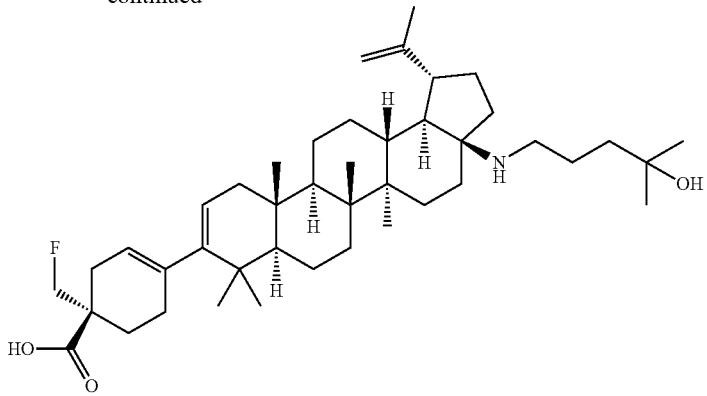

Example 2-3

Step 1. Preparation of 5,5-dimethyltetrahydrofuran-2-ol

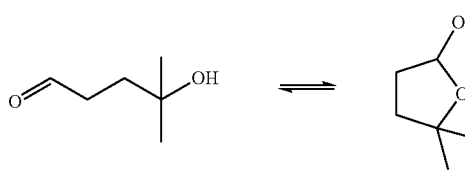

DIBAL (1.314 mL, 1.314 mmol) was added to a solution of 5,5-dimethyldihydrofuran-2 (3H)-one (100 mg, 0.876 mmol) in THF (10 mL) under nitrogen at −78° C. The reaction mixture was stirred at −78° C. for 3 h. A solution of Rochelle's salt was added to the reaction mixture, which was stirred at rt for 30 min. The reaction mixture was partitioned between EtOAc and water. The organic layer was washed with brine, dried over magnesium sulfate and concentrated under vacuum to afford the crude product (35 mg, 0.301 mmol, 34% yield). $^1$H-NMR of the crude product showed that it was in equilibrium between 4-hydroxy-4-methylpentanal and 5,5-dimethyltetrahydrofuran-2-ol with 5,5-dimethyltetrahydrofuran-2-ol (35 mg, 0.301 mmol, 34% yield) being the predominant form. $^1$H NMR (400 MHz, CHLOROFORM-d) δ 5.51 (d, J=4.8 Hz, 1H), 2.90 (br. s., 1H), 2.03-1.94 (m, 2H), 1.82-1.64 (m, 2H), 1.43 (s, 3H), 1.22 (s, 3H).

Step 2. Preparation of (S)-benzyl 1-(fluoromethyl)-4-((1R,3aS,5aR,5bR,7aR,11aS,11bR,13aR,13bR)-3a-((4-hydroxy-4-methylpentyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) cyclohex-3-enecarboxylate

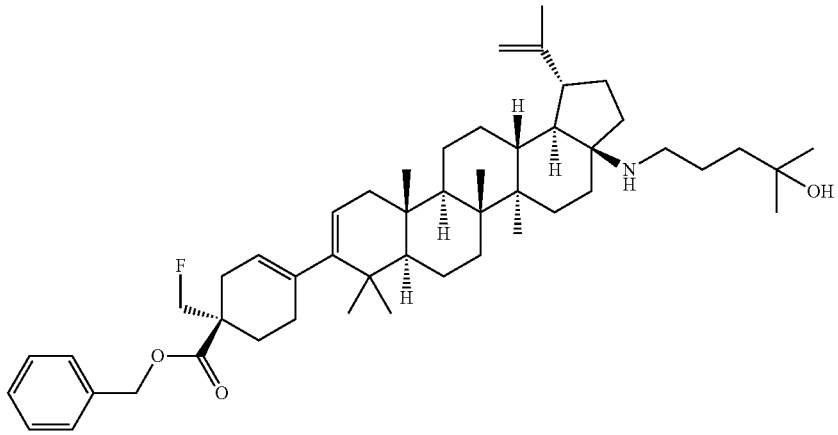

To a solution of (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (25 mg, 0.038 mmol) and 5,5-dimethyltetrahydrofuran-2-ol (13.28 mg, 0.114 mmol) in DCE (0.6 mL) was added titanium(IV) isopropoxide (0.018 mL, 0.061 mmol). The mixture was stirred at room temperature for 1 h. Sodium triacetoxyborohydride (16.15 mg, 0.076 mmol) was added and the mixture was stirred at rt for 16 h. The reaction mixture was partitioned between DCM and sat. aq. sodium bicarbonate solution. The organic layer was washed with brine, dried over magnesium sulfate and concentrated under vacuum to afford (S)-benzyl 1-(fluoromethyl)-4-((1R,3aS,5aR,5bR,7aR,11aS,11bR,13aR,13bR)-3a-((4-hydroxy-4-methylpentyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (28.8 mg, 0.038 mmol, 100% yield). The crude product was used in the next step without further purification. LC/MS m/e 756.7 [(M+H)$^+$, calcd for $C_{50}H_{74}FNO_3$ 756.6] $t_R$=2.66 min (method 2-1).

Step 3

Sodium hydroxide (0.048 mL, 0.190 mmol, 4 N aq) was added to a solution of crude (S)-benzyl 1-(fluoromethyl)-4-((1R,3aS,5aR,5bR,7aR,11aS,11bR,13aR,13bR)-3a-((4-hydroxy-4-methylpentyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (28.7 mg, 0.038 mmol) in dioxane (1 mL) and ethanol (0.500 mL). The reaction mixture was stirred at 70° C. for 2 h. The mixture was cooled to room temperature and the crude material was purified by reverse phase preparative HPLC (method 2-2, gradient: 60-100% B over 10 minutes, then a 15-minute hold at 100%) to afford (S)-1-(fluoromethyl)-4-((1R,3aS,5aR,5bR,7aR,11aS,11bR,13aR,13bR)-3a-((4-hydroxy-4-methylpentyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid (2.8 mg, 4.08 μmol, 11% yield); LC/MS m/e 666.6 [(M+H)$^+$, calcd for $C_{43}H_{68}FNO_3$ 666.5] $t_R$=2.40 min (method 2-1); HPLC (method 2-3): $t_R$=2.76 min; HPLC (method 2-4): $t_R$=2.11 min.

Example 2-4

Preparation of (S)-4-((1R,3aS,5aR,5bR,7aR,11aS,11bR,13aR,13bR)-3a-((3-ethyl-3-hydroxypentyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid

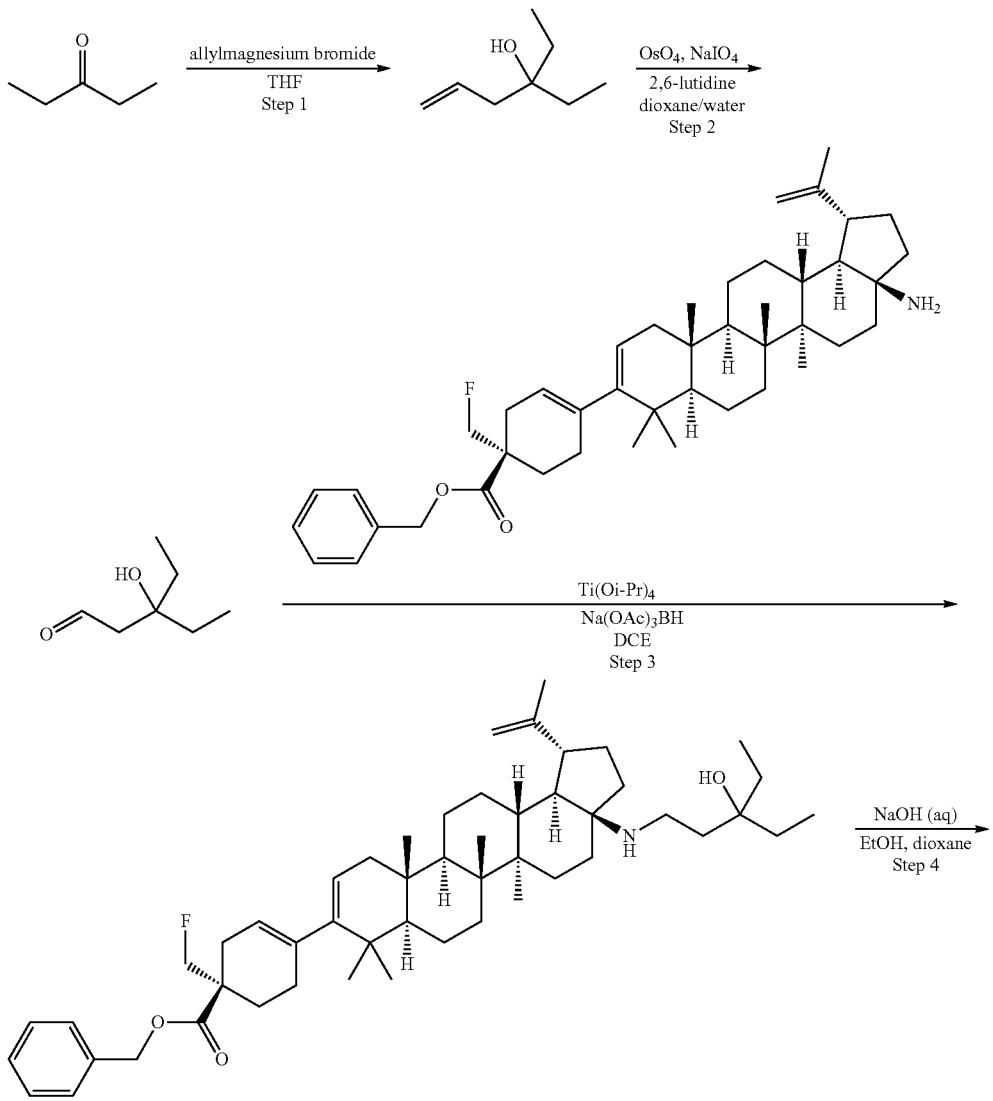

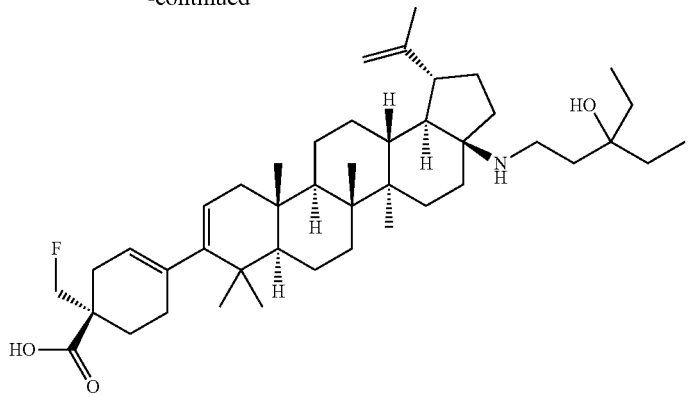

Example 2-4

Step 1. Preparation of 3-ethylhex-5-en-3-ol

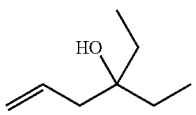

To a solution of allylmagnesium bromide (13.93 mL, 13.93 mmol) in THF (10 mL) at 0° C. was added pentan-3-one (400 mg, 4.64 mmol). The cooling bath was removed and the reaction mixture was stirred at room temperature for 1 h. The reaction mixture was cooled in an ice-water bath and was quenched by the addition of saturated aqueous NH₄Cl solution (20 mL). The mixture was transferred to a separatory funnel and the aqueous layer was extracted with ethyl acetate (4×25 mL). The combined organic layers were washed with brine (25 mL), dried over MgSO₄, filtered, and concentrated to afford 3-ethylhex-5-en-3-ol (595 mg, 4.64 mmol, 100% yield) as a colorless oil. The product was used directly in the next step without further purification. ¹H NMR (400 MHz, CHLOROFORM-d) δ 5.86 (ddt, J=16.7, 10.6, 7.5 Hz, 1H), 5.21-5.07 (m, 2H), 2.23 (dt, J=7.4, 1.2 Hz, 2H), 1.57-1.43 (m, 4H), 0.90 (t, J=7.5 Hz, 6H)

Step 2. Preparation of 3-ethyl-3-hydroxypentanal

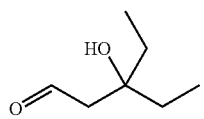

To a solution of 3-ethylhex-5-en-3-ol (595 mg, 4.64 mmol) in dioxane (30 mL) and water (7.50 mL) at 0° C. was added 2,6-lutidine (1.081 mL, 9.28 mmol), osmium tetroxide (2.5% in t-BuOH) (1.165 mL, 0.093 mmol), and sodium periodate (3970 mg, 18.56 mmol). The reaction mixture was allowed to warm up to room temperature as the ice-water bath melted while stirring for 16 h. The mixture was transferred to a separatory funnel containing water (20 mL) and saturated aqueous NaHCO₃ solution (30 mL). The aqueous layer was extracted with ethyl acetate (3×30 mL). The combined organic layers were washed with brine (20 mL), dried over MgSO₄, filtered, and concentrated. The product was purified by column chromatography on silica gel (0%→8% methanol in CH₂Cl₂; 40 g column) to afford 3-ethyl-3-hydroxypentanal (217 mg, 1.667 mmol, 36% yield) as a colorless oil: ¹H NMR (400 MHz, CHLOROFORM-d) δ 9.85 (t, J=2.4 Hz, 1H), 3.66 (s, 2H), 1.65-1.41 (m, 4H), 0.86 (t, J=7.5 Hz, 6H).

Step 3. Preparation of (S)-benzyl 4-((1R,3aS,5aR, 5bR,7aR,11aS,11bR,13aR,13bR)-3a-((3-ethyl-3-hydroxypentyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)-1-(fluoromethyl)cyclohex-3-enecarboxylate

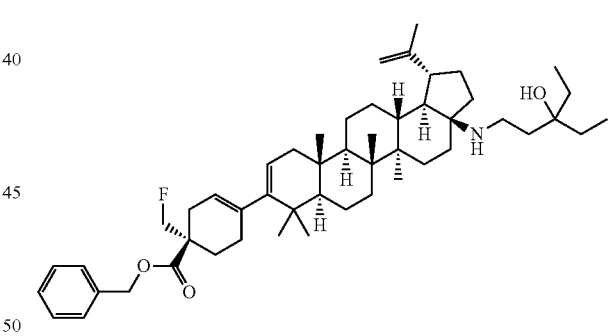

Titanium(IV) isopropoxide (0.036 mL, 0.122 mmol) was added to a solution of (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (50 mg, 0.076 mmol) and 3-ethyl-3-hydroxypentanal (15.88 mg, 0.122 mmol) in DCE (0.6 mL). The reaction mixture was stirred at rt for 1 h. Sodium triacetoxyborohydride (32.3 mg, 0.152 mmol) was added and the reaction mixture was stirred for 3 days. The reaction mixture was partitioned between sat. aq. sodium bicarbonate and CH₂Cl₂. The aq layer was extracted with CH₂Cl₂ (3×10 mL). The combined organic layers were washed with brine, dried over magnesium sulfate and concentrated. The product was purified by column chromatography on silica gel (0% 9:1 acetone/methanol/100% hexanes→40% 9:1 acetone/methanol/60% hexanes; 24 g column, λ=220 nm) to afford (S)-benzyl 4-((1R,3aS,5aR,5bR,7aR,11aS,11bR,13aR,13bR)-3a-((3-ethyl-3-hydroxypentyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (14 mg, 0.018 mmol, 24% yield) as a colorless oil: LC/MS (ESI) m/e 770.6 [(M+H)$^+$, calcd for $C_{51}H_{76}FNO_3$ 770.6] $t_R$=2.61 min (method 2-1).

Step 4

Sodium hydroxide (0.023 mL, 0.091 mmol) was added to a solution of (S)-benzyl 4-((1R,3aS,5aR,5bR,7aR,11aS,11bR,13aR,13bR)-3a-((3-ethyl-3-hydroxypentyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (14 mg, 0.018 mmol) in dioxane (1 mL) and ethanol (0.500 mL). The reaction mixture was stirred at 70° C. for 2 h. The mixture was cooled to room temperature. The crude material was purified by reverse phase preparative HPLC (method 2-2, gradient 60-100% B over 15 minutes, then a 6-minute hold at 100% B) to afford (S)-4-((1R,3aS,5aR,5bR,7aR,11aS,11bR,13aR,13bR)-3a-((3-ethyl-3-hydroxypentyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid (5.9 mg, 8.5 μmol, 47% yield); $^1$H NMR (500 MHz, DMSO-d$_6$) δ 5.25 (br. s., 1H), 5.12 (d, J=5.1 Hz, 1H), 4.67 (br. s., 1H), 4.55 (br. s., 1H), 4.48 (s, 1H), 4.38 (s, 1H), 2.61-2.53 (m, 1H), 2.48-2.38 (m, 3H), 2.23-2.08 (m, 1H), 2.07-0.93 (m, 32H), 1.65 (s, 3H), 1.02 (s, 3H), 0.92 (s, 3H), 0.91 (s, 3H), 0.88 (s, 3H), 0.82 (s, 3H), 0.80-0.77 (m, 6H); LC/MS (ESI) m/e 680.5 [(M+H)$^+$, calcd for $C_{44}H_{70}FNO_3$ 680.5] $t_R$=2.38 min (method 2-1); HPLC (method 2-3): $t_R$=2.29 min; HPLC (method 2-4): $t_R$=2.40 min.

Example 2-5

Preparation of (S)-4-((1R,3aS,5aR,5bR,7aR,11aS,11bR,13aR,13bR)-3a-((3,3-dicyclopropyl-3-hydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid

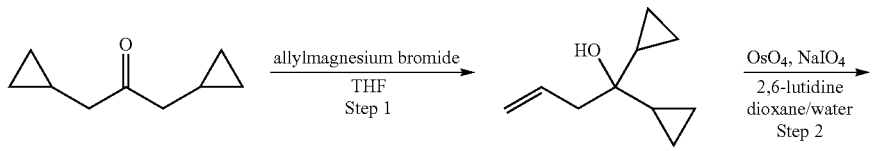

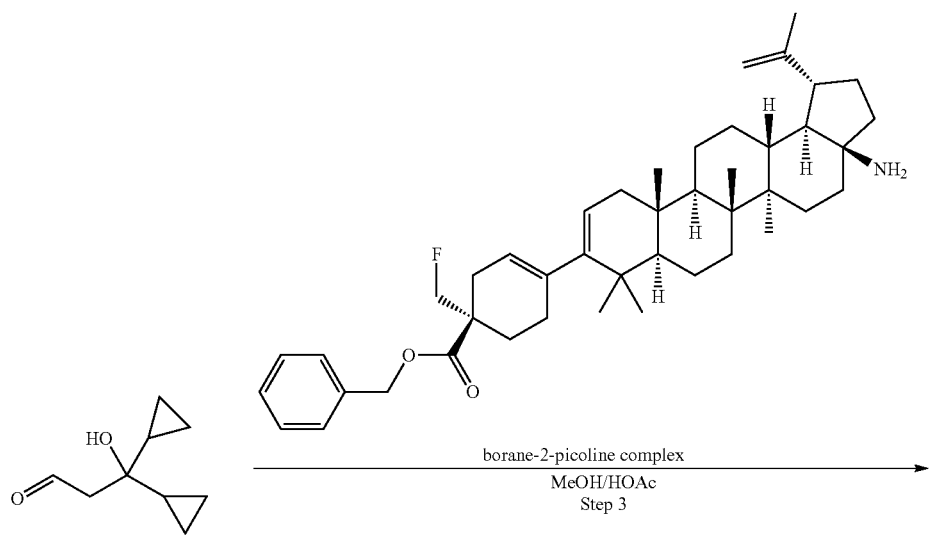

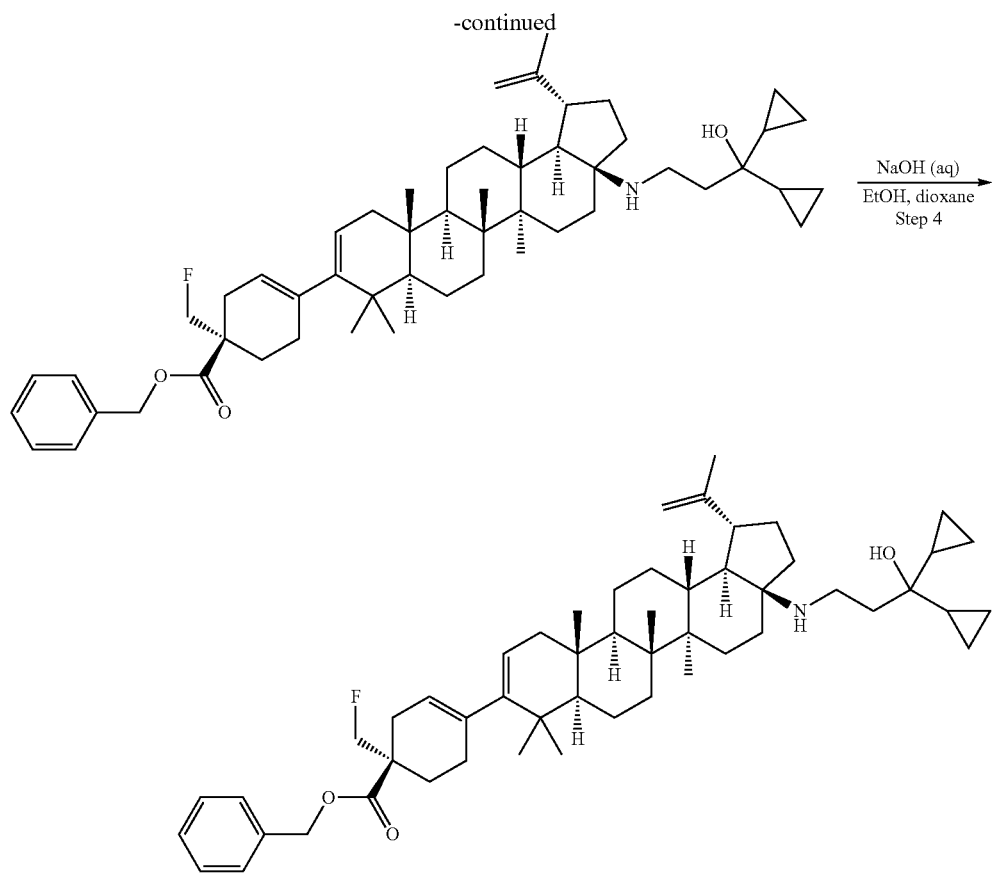

Example 2-5

Step 1. Preparation of
1,1-dicyclopropylbut-3-en-1-ol

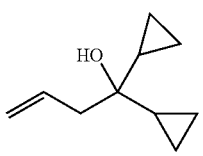

To a solution of allylmagnesium bromide (10.89 mL, 10.89 mmol) in THF (10 mL) at 0° C. was added dicyclopropylmethanone (400 mg, 3.63 mmol). The cooling bath was removed and the reaction mixture was stirred at room temperature for 1 h. The reaction was cooled in an ice-water bath and was quenched by the addition of saturated aqueous NH$_4$Cl solution (20 mL). The mixture was transferred to a separatory funnel and the aqueous layer was extracted with ethyl acetate (4×25 mL). The combined organic layers were washed with brine (25 mL), dried over MgSO$_4$, filtered, and concentrated to afford 1,1-dicyclopropylbut-3-en-1-ol (553 mg, 3.63 mmol, 100% yield) as a colorless oil. The product was used directly in the next step without further purification. $^1$H NMR (400 MHz, CHLOROFORM-d) δ 6.16-5.98 (m, 1H), 5.21-5.08 (m, 2H), 2.37 (dt, J=7.5, 1.1 Hz, 2H), 0.94-0.79 (m, 2H), 0.49-0.25 (m, 8H).

Step 2. Preparation of
3,3-dicyclopropyl-3-hydroxypropanal

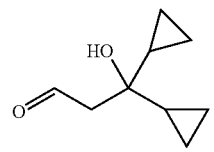 [SMILES: O=CCC(O)(C1CC1)C1CC1]

To a solution of 1,1-dicyclopropylbut-3-en-1-ol (553 mg, 3.63 mmol) in dioxane (12 mL) and water (3 mL) at 0° C. was added 2,6-lutidine (0.846 mL, 7.26 mmol), osmium tetroxide (4% in water) (0.444 mL, 0.073 mmol), and sodium periodate (3,106 mg, 14.52 mmol). The reaction mixture was allowed to warm up to room temperature as the ice-water bath melted while stirring for 16 h. The mixture was transferred to a separatory funnel containing water (20 mL) and saturated aqueous NaHCO$_3$ solution (30 mL). The aqueous layer was extracted with ethyl acetate (3×30 mL). The combined organic layers were washed with brine (20 mL), dried over MgSO$_4$, filtered, and concentrated. The product was purified by column chromatography on silica gel (0%→8% methanol in CH$_2$Cl$_2$; 40 g column) to afford 3,3-dicyclopropyl-3-hydroxypropanal (152 mg, 0.986 mmol, 27% yield) as a colorless oil: $^1$H NMR (400 MHz, CHLOROFORM-d) δ 9.96 (t, J=2.8 Hz, 1H), 2.63 (d, J=2.8 Hz, 2H), 0.94 (tt, J=8.2, 5.8 Hz, 2H), 0.51-0.38 (m, 8H).

Step 3. (S)-benzyl 4-((1R,3aS,5aR,5bR,7aR,11aS, 11bR,13aR,13bR)-3a-((3,3-dicyclopropyl-3-hydroxypropyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)-1-(fluoromethyl)cyclohex-3-enecarboxylate

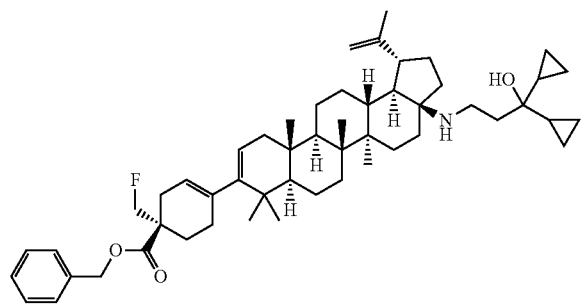

To a solution of (S)-benzyl 4-((1R,3aS,5aR,5bR,7aR, 11aS,11bR,13aR,13bR)-3a-amino-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)-1-(fluoromethyl)cyclohex-3-enecarboxylate (40 mg, 0.061 mmol) and 3,3-dicyclopropyl-3-hydroxypropanal (14.10 mg, 0.091 mmol) in MeOH (0.5 mL) and acetic acid (0.1 mL) was added borane-2-picoline complex (9.78 mg, 0.091 mmol). The reaction mixture was stirred for 16 h at rt. The mixture was transferred to a separatory funnel containing saturated aqueous sodium bicarbonate solution (5 mL). The aqueous layer was extracted with dichloromethane (3×10 mL). The combined organic layers were washed with brine (5 mL), dried over MgSO₄, filtered, and concentrated. The product was purified by column chromatography on silica gel (0% 9:1 acetone:methanol/90% hexanes→40% 9:1 acetone:methanol/60% hexanes; 24 g column, λ=220 nm) to afford (S)-benzyl 4-((1R,3aS,5aR,5bR,7aR,11aS,11bR, 13aR,13bR)-3a-((3,3-dicyclopropyl-3-hydroxypropyl) amino)-5a,5b,8,8,11a-pentamethyl-1-(prop-1-en-2-yl) -2,3, 3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (11 mg, 0.014 mmol, 23% yield) as a colorless oil: LC/MS (ESI) m/e 794.6 [(M+H)⁺, calcd for $C_{53}H_{76}FNO_3$ 794.6] $t_R$=2.66 min (method 2-1).

Step 4. Sodium hydroxide (0.017 mL, 0.069 mmol) was added to a solution of (S)-benzyl 4-((1R,3aS,5aR,5bR,7aR, 11aS,11bR,13aR,13bR)-3a-((3,3-dicyclopropyl-3-hydroxypropyl)amino)-5a,5b,8, 8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (11 mg, 0.014 mmol) in dioxane (1 mL) and ethanol (0.500 mL). The reaction mixture was stirred at 70° C. for 2 h. The reaction mixture was cooled to room temperature. The crude material was purified by reverse phase preparative HPLC (method 2-2, 70-100% B over 10 minutes, then a 15-minute hold at 100% B) to afford (S)-4-((1R,3aS,5aR,5bR,7aR,11aS,11bR, 13aR,13bR)-3a-((3,3-dicyclopropyl-3-hydroxypropyl) amino)-5a,5b,8, 8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid (1.0 mg, 1.37 μmol, 10% yield); ¹H NMR (500 MHz, Acetic Acid-d₄) δ 5.39 (br. s., 1H), 5.25 (dd, J=6.1, 1.7 Hz, 1H), 4.82 (s, 1H), 4.72 (s, 1H), 4.65-4.57 (m, 1H), 4.56-4.47 (m, 1H), 3.53-3.41 (m, 2H), 2.97-2.87 (m, 1H), 2.62 (d, J=16.7 Hz, 1H), 2.31-2.32 (m, 28H), 1.14-1.10 (m, 1H), 1.75 (s, 3H), 1.11 (s, 3H), 1.09 (s, 3H), 1.01 (s, 3H), 0.99 (s, 3H), 0.95 (s, 3H), 0.87-0.76 (m, 2H), 0.65-0.35 (m, 8H); LC/MS (ESI) m/e 704.6 [(M+H)⁺, calcd for $C_{46}H_{70}FNO_3$ 704.5] $t_R$=2.44 min (method 2-1); HPLC (method 2-3): $t_R$=2.43 min; HPLC (method 2-4): $t_R$=2.46 min.

Example 2-6

Preparation of (S)-4-((1R,3aS,5aR,5bR,7aR,11aS, 11bR,13aR,13bR)-3a-((3,3-dicyclopropylallyl) amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)-1-(fluoromethyl)cyclohex-3-enecarboxylic acid

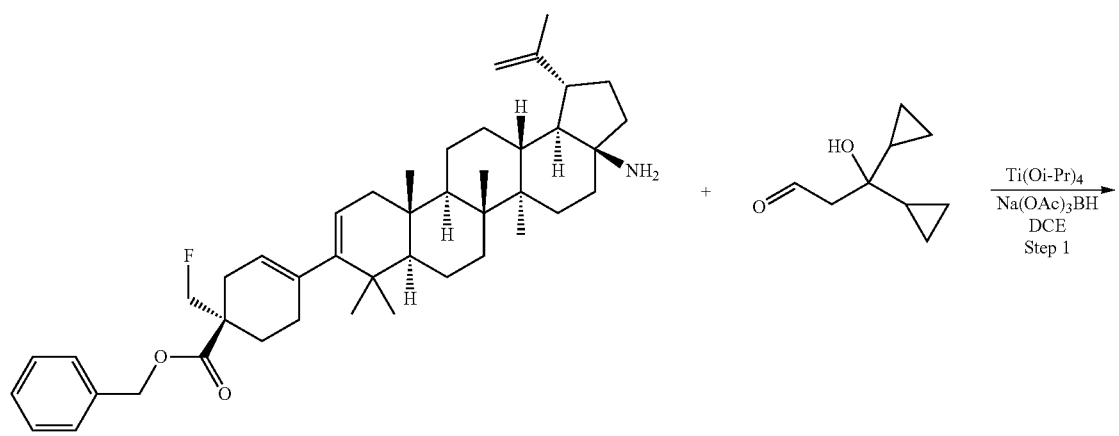

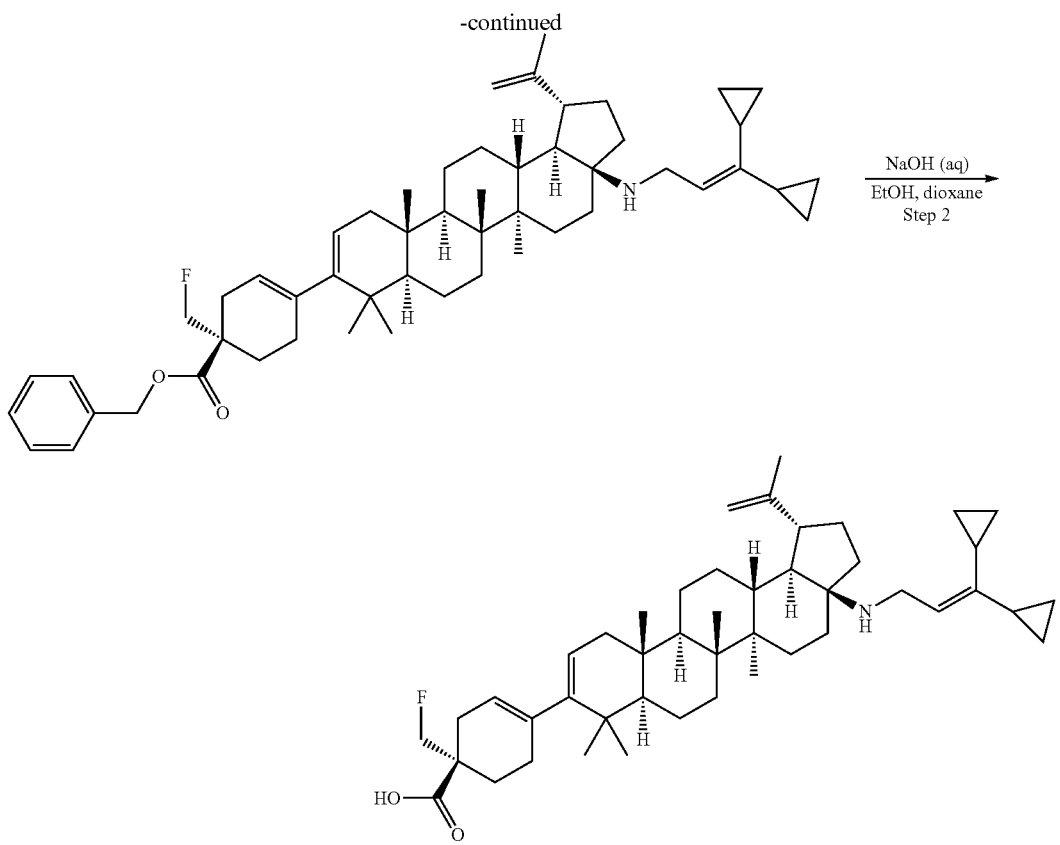

Example 2-6

Step 1. (S)-benzyl 4-((1R,3aS,5aR,5bR,7aR,11aS, 11bR,13aR,13bR)-3a-((3,3-dicyclopropylallyl) amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)-1-(fluoromethyl)cyclohex-3-enecarboxylate

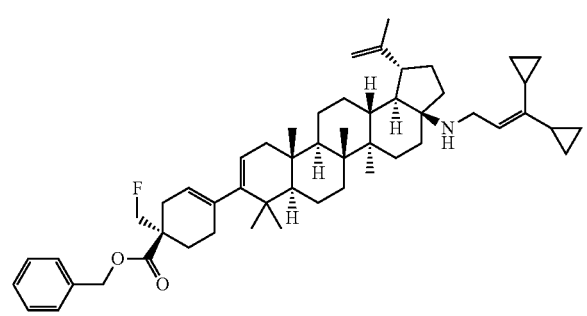

Titanium(IV) isopropoxide (0.036 mL, 0.122 mmol) was added to a solution of (S)-benzyl 4-((1R,3aS,5aR,5bR,7aR, 11aS,11bR,13aR,13bR)-3a-amino-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)-1-(fluoromethyl)cyclohex-3-enecarboxylate (50 mg, 0.076 mmol) and 3,3-dicyclopropyl-3-hydroxypropanal (18.81 mg, 0.122 mmol) in DCE (0.6 mL). The reaction mixture was stirred at rt for 1 h.

Sodium triacetoxyborohydride (32.3 mg, 0.152 mmol) was added and the reaction mixture was stirred for 3 days. The reaction mixture was partitioned between sat. aq. sodium bicarbonate (10 mL) and $CH_2Cl_2$ (10 mL). The aq layer was extracted with $CH_2Cl_2$ (3×10 mL). The combined organic layers was washed with brine, dried over magnesium sulfate and concentrated. The crude product, (S)-benzyl 4-((1R,3aS,5aR,5bR,7aR,11aS,11bR,13aR,13bR)-3a-((3,3-dicyclopropylallyl)amino)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)-1-(fluoromethyl)cyclohex-3-enecarboxylate (32 mg, 0.041 mmol, 54% yield), was used in the next step without further purification. LC/MS (ESI) m/e 776.6 [(M+H)$^+$, calcd for $C_{53}H_{74}FNO_2$ 776.6], $t_R$=2.67 min (method 2-1).

Step 2. Sodium hydroxide (0.052 mL, 0.206 mmol) was added to a solution of (S)-benzyl 4-((1R,3aS,5aR,5bR,7aR, 11aS,11bR,13aR,13bR)-3a-((3,3-dicyclopropylallyl) amino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (32 mg, 0.041 mmol) in dioxane (1 mL) and ethanol (0.500 mL). The reaction mixture was stirred at 70° C. for 2 h. The mixture was cooled to room temperature. The crude material was purified by reverse phase preparative HPLC (method 2-2, 90-100% B over 20 minutes, then a 25-minute hold at 100% B) to afford (S)-4-((1R,3aS,5aR,5bR,7aR,11aS,11bR,13aR, 13bR)-3a-((3,3-dicyclopropylallyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid (1.0 mg, 1.34 μmol, 3.3% yield); $^1$H NMR (500 MHz, Acetic Acid-$d_4$) δ 5.39 (br. s., 2H), 5.27-5.22 (m, 1H), 4.84 (s, 1H), 4.72 (s, 1H), 4.65-4.57 (m, 1H), 4.56-4.48 (m, 1H), 4.01 (t, J=6.9 Hz, 2H), 2.89 (br. s., 1H), 2.62 (d, J=16.7 Hz, 1H), 2.30-0.85 (m, 31H), 1.75 (s, 3H), 1.18 (s, 3H), 1.10 (s, 3H), 1.01 (s, 3H), 0.99 (s, 3H), 0.96 (s, 3H), 0.80 (d, J=8.4 Hz, 2H), 0.66-0.60 (m, 2H), 0.47-0.36 (m, 2H); LC/MS (ESI) m/e 686.6 [(M+H)$^+$, calcd for $C_{46}H_{68}FNO_2$ 686.5] $t_R$=2.44 min (method 2-1); HPLC (method 2-3): $t_R$=2.62 min; HPLC (method 2-4): $t_R$=1.96 min.

Example 2-7

Preparation of (S)-1-(fluoromethyl)-4-((1R,3aS,5aR,5bR,7aR,11aS,11bR,13aR,13bR)-3a-(isopentylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid

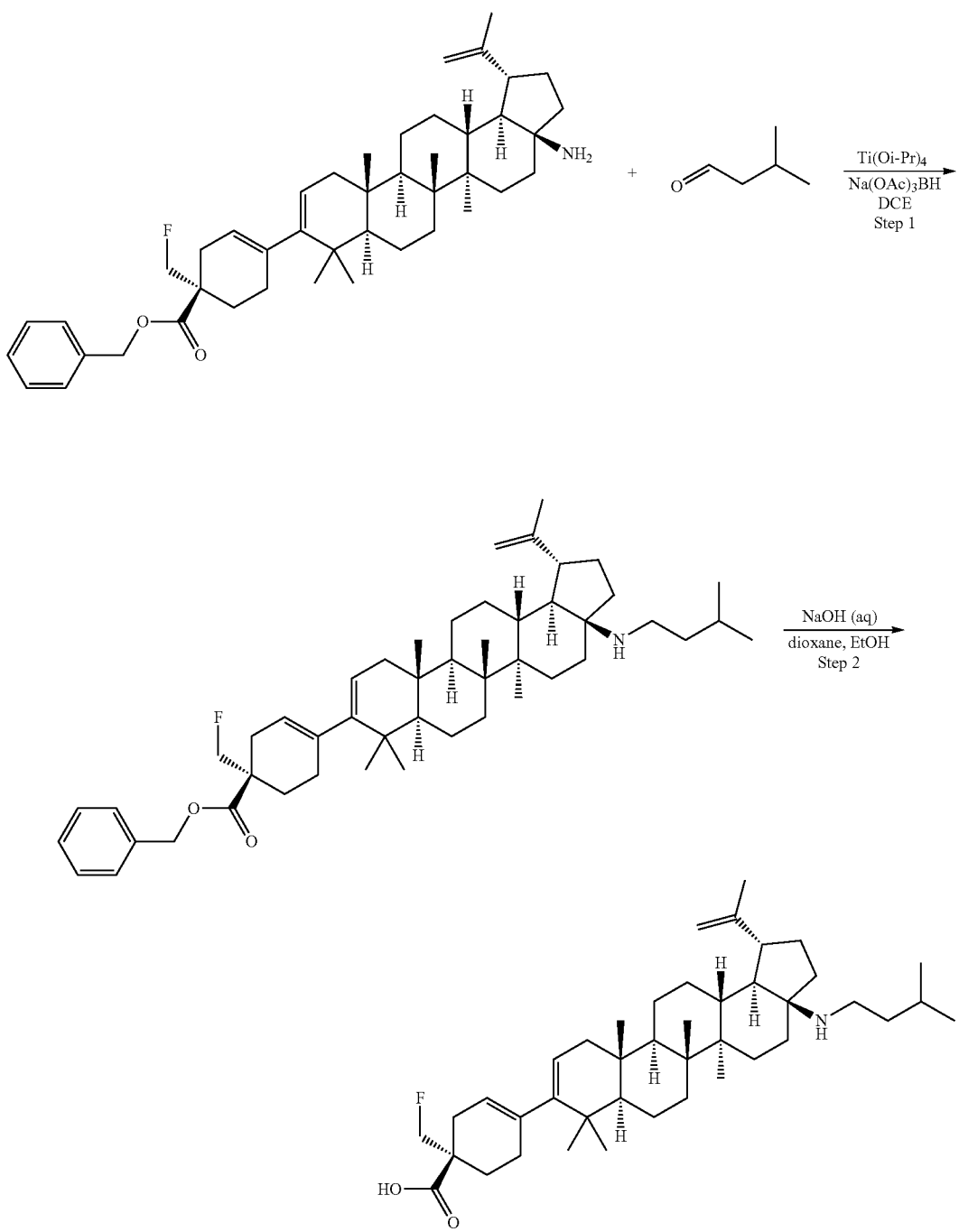

Example 2-7

Step 1. Preparation of (S)-benzyl 1-(fluoromethyl)-4-((1R,3aS,5aR,5bR,7aR,11aS,11bR,13aR,13bR)-3a-(isopentylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate

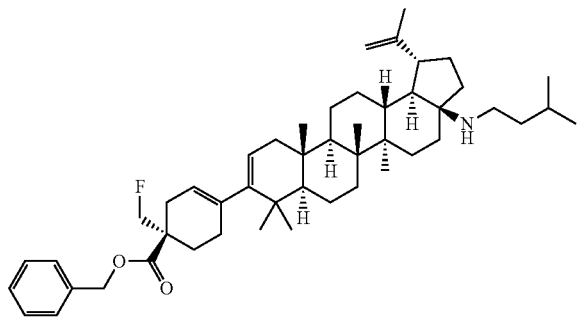

To a solution of (S)-benzyl 4-((1R,3aS,5aR,5bR,7aR,11aS,11bR,13aR,13bR)-3a-amino-5a,5b,8,8,11a-pentamethyl-1-(prop-1-en-2-yl) -2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (35 mg, 0.053 mmol) and 3-methylbutanal (7.35 mg, 0.085 mmol) in DCE (0.6 mL) was added titanium(IV) isopropoxide (0.025 mL, 0.085 mmol). The mixture was stirred at room temperature for 1 h. Sodium triacetoxyborohydride (22.62 mg, 0.107 mmol) was added and the mixture was stirred at room temperature overnight. The mixture was transferred to a separatory funnel containing saturated aqueous sodium bicarbonate solution (5 mL). The aqueous layer was extracted with dichloromethane (3×10 mL). The combined organic layers were washed with brine (5 mL), dried over MgSO$_4$, filtered, and concentrated. The product was purified by column chromatography on silica gel (10% 9:1 acetone:methanol/90% hexanes→30% 9:1 acetone:methanol/70% hexanes; 24 g column, λ=220 nm) to afford (S)-benzyl 1-(fluoromethyl)-4-((1R,3aS,5aR,5bR,7aR,11aS,11bR,13aR,13bR)-3a-(isopentylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (20 mg, 0.028 mmol, 52% yield) as a colorless foam: LC/MS m/e 726.6 [(M+H)$^+$, calcd for $C_{49}H_{73}FNO_2$ 726.6], $t_R$=5.10 min (method 2-3).

Step 2. A solution of (S)-benzyl 1-(fluoromethyl)-4-((1R,3aS,5aR,5bR,7aR,11aS,11bR,13aR,13bR)-3a-(isopentylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (20 mg, 0.028 mmol) in 1,4-dioxane (0.5 mL) and EtOH (0.25 mL) was treated with sodium hydroxide (2M aq) (0.069 mL, 0.138 mmol). The reaction mixture was heated at 70° C. for 2 h. The mixture was cooled to room temperature, filtered through a syringe filter, and was purified by reverse phase preparative HPLC (method 2-3) to afford (S)-1-(fluoromethyl)-4-((1R,3aS,5aR,5bR,7aR,11aS,11bR,13aR,13bR)-3a-(isopentylamino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid•TFA (9.9 mg, 48% yield): $^1$H NMR (500 MHz, Acetic Acid-d$_4$) δ 5.39 (br. s., 1H), 5.28-5.22 (m, 1H), 4.84 (s, 1H), 4.73 (s, 1H), 4.61 (dt, J=10.9, 8.8 Hz, 1H), 4.52 (dt, J=11.0, 8.8 Hz, 1H), 3.29-3.15 (m, 2H), 2.92-2.84 (m, 1H), 2.62 (d, J=16.6 Hz, 1H), 2.30-1.10 (m, 30H), 1.75 (s, 3H), 1.19 (s, 3H), 1.10 (s, 3H), 1.01 (s, 3H), 0.99 (s, 3H), 0.97 (s, 3H), 0.95 (s, 6H); LC/MS m/e 636.3 [(M+H)$^+$, calcd for $C_{42}H_{67}FNO_2$ 636.5], $t_R$=4.49 min (method 2-2); HPLC (method 2-3): $t_R$=2.54 min; HPLC (method 2-4): $t_R$=2.59 min.

Example 2-8

Preparation of (1S)-4-((1R,3aS,5aR,5bR,7aR,11aS,11bR,13aR,13bR)-3a-((3-(1,1-dioxidothiomorpholino)-2-hydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid

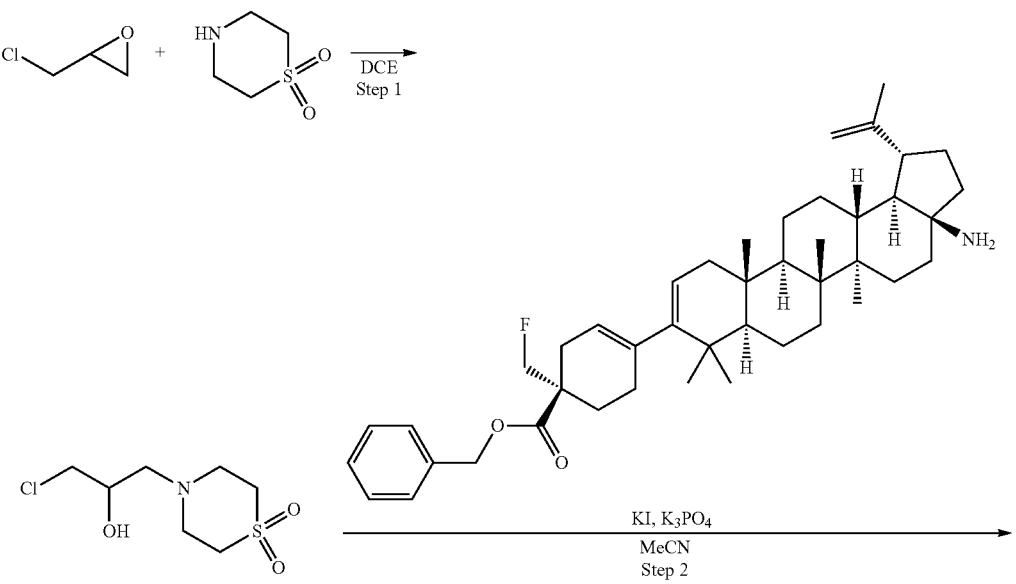

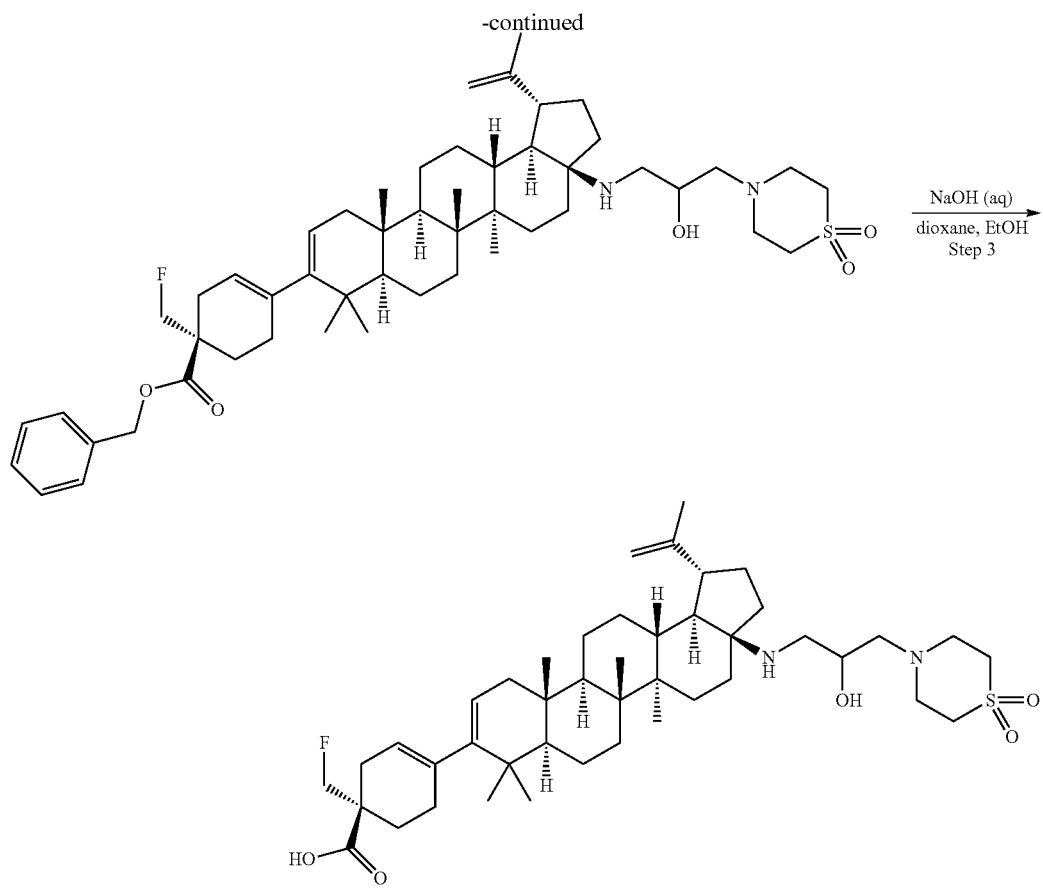

Example 2-8

Step 1. Preparation of 4-(3-Chloro-2-hydroxypropyl)thiomorpholine 1,1-dioxide

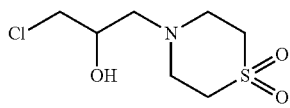 [SMILES: O=S1(=O)CCN(CC(O)CCl)CC1]

To a solution of thiomorpholine 1,1-dioxide (2.40 g, 17.75 mmol) in DCE (4.4 mL) was added slowly via syringe 2-(chloromethyl)oxirane (1.392 mL, 17.75 mmol). The reaction mixture was stirred at 50° C. for 48 h. The white solid (4,4'-(2-hydroxypropane-1,3-diyl)bis(thiomorpholine 1,1-dioxide) that formed was removed by filtration. The filtrate was concentrated and was purified by column chromatography on silica gel (3%→5% methanol in $CH_2Cl_2$; 120 g column) to afford 4-(3-chloro-2-hydroxypropyl)thiomorpholine 1,1-dioxide (2.57 g, 11.29 mmol, 64% yield) as a colorless oil that solidified upon standing: $^1$H NMR (400 MHz, CHLOROFORM-d) δ 3.95 (dq, J=8.9, 4.6 Hz, 1H), 3.69-3.55 (m, 2H), 3.26-3.15 (m, 2H), 3.14-3.03 (m, 6H), 2.75 (dd, J=13.1, 4.3 Hz, 1H), 2.65 (dd, J=13.1, 8.5 Hz, 1H); LC/MS m/e 228.1 [(M+H)$^+$, calcd for $C_7H_{15}ClNO_3S$ 228.0], $t_R$=0.26 min, (ionization peak, no UV) (method 2-1).

Step 2. Preparation of (1 S)-benzyl 4-((1R,3aS,5aR,5bR,7aR,11aS,11bR,13aR,13bR)-3a-((3-(1,1-dioxidothiomorpholino)-2-hydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (S)-Benzyl 4-((1R,3aS,5 aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (120 mg, 0.183 mmol), 4-(3-chloro-2-hydroxypropyl)thiomorpholine 1,1-dioxide (146 mg, 0.640 mmol), potassium phosphate tribasic (175 mg, 0.823 mmol), and potassium iodide (137 mg, 0.823 mmol) were combined in an oven-dried vial. Acetonitrile (2 mL) was added, the vial was sealed, and the reaction mixture was heated at 120° C. for 20 h. Additional 4-(3-chloro-2-hydroxypropyl)thiomorpholine 1,1-dioxide (83 mg, 0.366 mmol, 2 eq), potassium phosphate tribasic (78 mg, 0.366 mmol, 2 eq), and potassium iodide (60.7 mg, 0.366 mmol, 2 eq) was added and the reaction mixture was heated for an additional 16 h. The mixture was cooled to room temperature. The mixture was transferred to a separatory funnel containing water (10 mL). The aqueous layer was extracted with dichloromethane (3×10 mL). The combined organic layers were washed with brine (10 mL), dried over MgSO$_4$, filtered, and concentrated. The product was purified by column chromatography on silica gel (10% 9:1 acetone:methanol/90% hexanes→30% 9:1 acetone:methanol/70% hexanes; 40 g column, λ=220 nm) to afford (1 S)-benzyl 4-((1R,3aS,5aR,5bR,7aR,11aS,11bR,13aR,13bR)-3a-((3-(1,1-dioxidothiomorpholino)-2-hydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (71.4 mg, 0.084 mmol, 46% yield) as a pale-blue foam: $^1$H NMR (500 MHz, CHLOROFORM-d) δ 7.39-7.31 (m, 5H), 5.33 (br. s., 1H), 5.23-5.15 (m, 2H), 5.15-5.10 (m, 1H), 4.72 (s, 1H), 4.61 (d, J=1.4 Hz, 1H), 4.60-4.54 (m, 1H), 4.52-4.45 (m, 1H), 3.80-3.67 (m, 1H), 3.23-3.03 (m, 8H), 2.73-2.53 (m, 5H), 2.37 (dd, J=11.7, 7.2 Hz, 1H, diasteroisomer A), 2.29 (dd, J=11.7, 8.1 Hz, 1H, diasteroisomer B), 2.19-0.83 (m, 47H) (Mixture of diasteroisomers); LC/MS m/e 847.6 [(M+H)$^+$, calcd for C$_{51}$H$_{76}$FN$_2$O$_5$S 847.5], t$_R$=4.58 min (method 2-2).

Step 3. A solution of (1S)-benzyl 4-((1R,3aS,5aR,5bR,7aR,11aS,11bR,13aR,13bR)-3a-((3-(1,1-dioxidothiomorpholino)-2-hydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (30 mg, 0.035 mmol) in 1,4-dioxane (0.5 mL) and EtOH (0.2 mL) was treated with sodium hydroxide (0.089 mL, 0.177 mmol). The reaction mixture was heated at 70° C. for 2 h. The mixture was filtered through a syringe filter, and was purified by reverse phase preparative HPLC (method 2-1). The organic solvent was evaporated on the rotovapor and the aqueous mixture was lyophilized to afford (1 S)-4-((1R,3aS,5aR,5bR,7aR,11aS,11bR,13aR,13bR)-3a-((3-(1,1-dioxidothiomorpholino)-2-hydroxypropyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid•TFA (13.6 mg, 43% yield) as a white amorphous solid: $^1$H NMR (500 MHz, Acetic Acid-d$_4$) δ 5.39 (br. s., 1H), 5.24 (d, J=4.9 Hz, 1H), 4.85 (d, J=5.3 Hz, 1H), 4.75 (br. s., 1H), 4.73-4.67 (m, 1H), 4.64-4.56 (m, 1H), 4.54-4.47 (m, 1H), 3.98-3.89 (m, 3H), 3.65-3.51 (m, 6H), 3.49-3.43 (m, 2H), 3.23 (dd, J=12.4, 8.5 Hz, 1H, diasteroisomer A), 3.07 (t, J=11.4 Hz, 1H, diasteroisomer B), 2.94-2.79 (m, 1H), 2.61 (d, J=17.1 Hz, 1H), 2.32-1.09 (m, 27H), 1.76 (s, 3H, diasteroisomer A), 1.76 (s, 3H, diasteroisomer B), 1.15 (s, 3H), 1.11 (s, 3H, diasteroisomer A), 1.10 (s, 3H, diasteroisomer B), 1.00 (s, 3H), 0.99 (s, 3H), 0.95 (s, 3H) (Mixture of diasteroisomer; LC/MS m/e 757.6 [(M+H)$^+$, calcd for C$_{44}$H$_{70}$FN$_2$O$_5$S 757.5], t$_R$=4.24 min (method 2-2); HPLC (method 2-1): t$_R$=18.72 min; HPLC (method 2-2): t$_R$=20.02 min.

Example 2-9

Preparation of (S)-1-(fluoromethyl)-4-((1R,3aS,5aR,5bR,7aR,11aS,11bR,13aR,13bR)-3a-((2-(1-hydroxycyclobutyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid

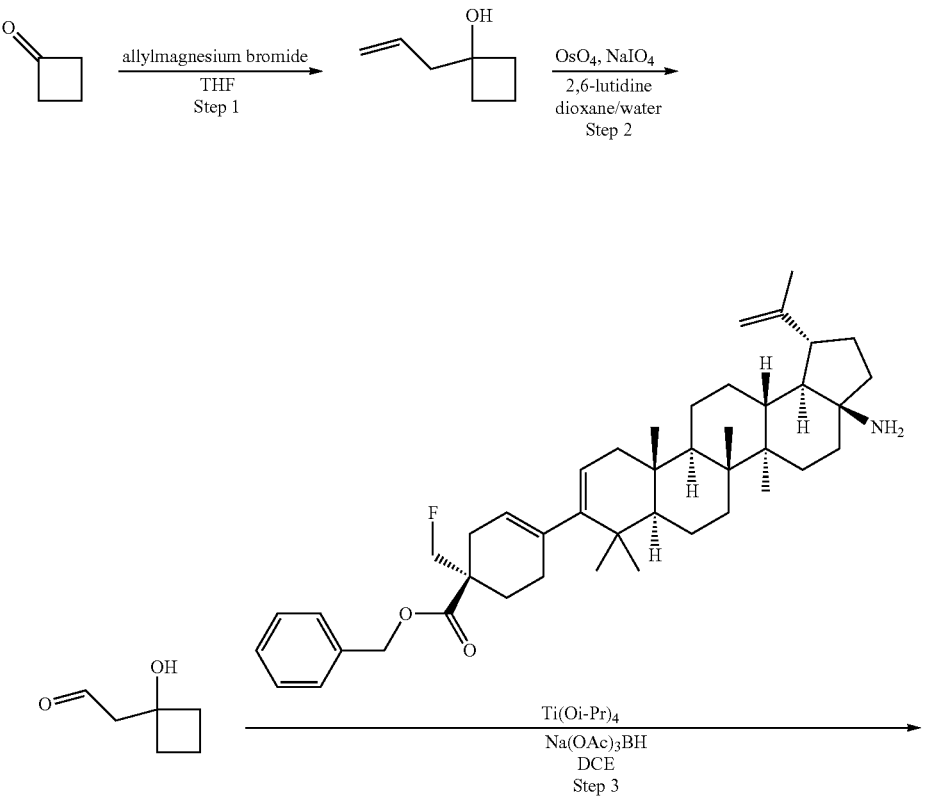

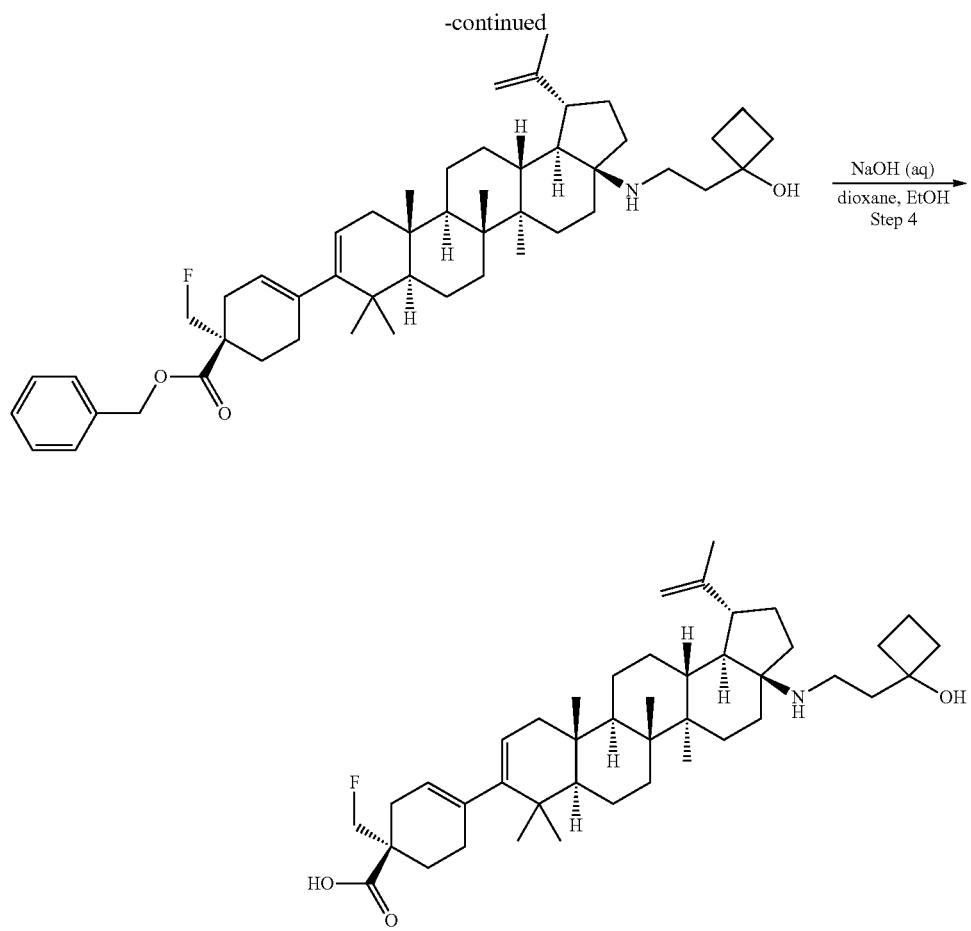

Example 2-9

Step 1. Preparation of 1-allylcyclobutanol

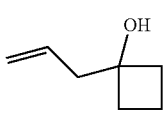

To a solution of allylmagnesium bromide (12.8 mL, 12.8 mmol) in THF (10 mL) at 0° C. was added a solution of cyclobutanone (300 mg, 4.28 mmol) in THF (5 mL). The cooling bath was removed and the reaction mixture was stirred at room temperature for 16 h. The reaction was cooled in an ice-water bath and was quenched by the addition of saturated $NH_4Cl$ solution (20 mL). The mixture was transferred to a separatory funnel and the aqueous layer was extracted with ethyl acetate (4×25 mL). The combined organic layers were washed with brine (25 mL), dried over $MgSO_4$, filtered, and concentrated to afford 1-allylcyclobutanol (377 mg, 3.36 mmol, 79% yield) as a colorless oil. The product was used directly in the next step without further purification: $^1$H NMR (400 MHz, CHLOROFORM-d) δ 5.90 (ddt, J=16.4, 10.7, 7.3 Hz, 1H), 5.27-5.16 (m, 2H), 2.41 (d, J=7.3 Hz, 2H), 2.13-2.05 (m, 4H), 1.93 (s, 1H), 1.83-1.71 (m, 1H), 1.65-1.51 (m, 1H).

Step 2. Preparation of 2-(1-hydroxycyclobutyl)acetaldehyde

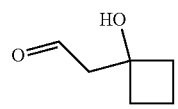

To a solution of 1-allylcyclobutanol (350 mg, 3.12 mmol) in dioxane (30 mL) and water (7.50 mL) was added 2,6-lutidine (0.727 mL, 6.24 mmol), osmium tetroxide (4% in water) (0.490 mL, 0.062 mmol), and sodium periodate (2670 mg, 12.48 mmol) at 0° C. The reaction mixture was allowed to warm up to rt and was stirred for 16 h. The reaction mixture was partitioned between EtOAc (25 mL) and aq sat sodium bicarbonate solution (25 mL). The aq layer was extracted with ethyl acetate (3×25 mL). The combined organic layers were washed with brine, dried over magnesium sulfate and concentrated under vacuum. The product was purified by column chromatography on silica gel (0%→8% methanol in $CH_2Cl_2$; 40 g column) to afford 2-(1-hydroxycyclobutyl)acetaldehyde (187 mg, 1.638 mmol, 53% yield) as an oil: $^1$H NMR (400 MHz, CHLOROFORM-d) δ 9.86 (t, J=1.8 Hz, 1H), 2.32-1.95 (m, 4H), 1.92-1.73 (m, 2H), 1.69-1.43 (m, 2H).

Step 3. Preparation of (S)-benzyl 1-(fluoromethyl)-4-((1R,3aS,5aR,5bR,7aR,11aS,11bR,13aR,13bR)-3a-((2-(1-hydroxycyclobutyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate

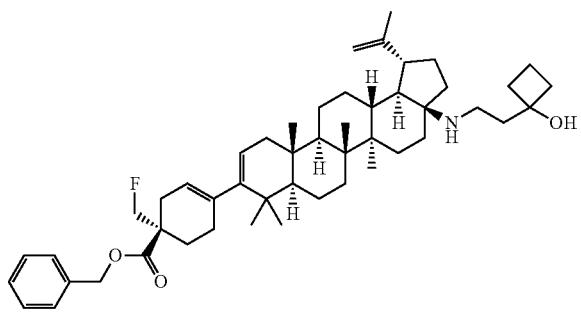

To a solution of (S)-benzyl 4-((1R,3aS,5aR,5bR,7aR,11aS,11bR,13aR,13bR)-3a-amino-5a,5b,8,8,11a-pentamethyl-1-(prop-1-en-2-yl) 2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (50 mg, 0.076 mmol) and 2-(1-hydroxycyclobutyl)acetaldehyde (13.92 mg, 0.122 mmol) in dichloroethane (0.6 mL) in a vial was added titanium(IV) isopropoxide (0.036 mL, 0.122 mmol). The reaction mixture was stirred at rt for 1 h. Sodium triacetoxyborohydride (32.3 mg, 0.152 mmol) was added and the reaction mixture was stirred for 4 days. The reaction mixture was partitioned between sat. aq. sodium bicarbonate (10 mL) and $CH_2Cl_2$ (10 mL). The aq layer was extracted with $CH_2Cl_2$ (3×10 mL). The combined organic layers were washed with brine, dried over magnesium sulfate and concentrated. The product was purified by column chromatography on silica gel (100% hexanes→40% acetone containing 10% methanol/60% hexanes; 24 g column, λ=220 nm) to afford (S)-benzyl 1-(fluoromethyl)-4-((1R,3aS,5aR,5bR,7aR,11aS,11bR,13aR,13bR)-3a#2-(1-hydroxycyclobutyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (51 mg, 0.068 mmol, 89% yield) as an oil: LC/MS (ESI) m/e 754.6 [(M+H)$^+$, calcd for $C_{50}H_{72}FNO_3$ 754.6], $t_R$=2.74 min (method 2-1).

Step 4. A solution of (S)-benzyl 1-(fluoromethyl)-4-((1R,3aS,5aR,5bR,7aR,11aS,11bR,13aR,13bR)-3a-((2-(1-hydroxycyclobutyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (51 mg, 0.068 mmol) in dioxane (1 mL) and ethanol (0.500 mL) was treated with sodium hydroxide (0.085 mL, 0.338 mmol). The reaction mixture was heated at 70° C. for 2 h. The mixture was cooled to room temperature, was filtered through a syringe filter, and was purified by reverse phase preparative HPLC (method 2-1). The organic solvent was evaporated on the rotovapor and the aqueous mixture was lyophilized to afford, (S)-1-(fluoromethyl)-4-((1R,3aS,5aR,5bR,7aR,11aS,11bR,13aR,13bR)-3a-((2-(1-hydroxycyclobutyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid•TFA (12.9 mg, 0.016 mmol, 24% yield) as a white amorphous solid: $^1$H NMR (500 MHz, Acetic Acid-d$_4$) δ 5.39 (br. s., 1H), 5.29-5.21 (m, 1H), 4.84 (s, 1H), 4.72 (s, 1H), 4.65-4.57 (m, 1H), 4.55-4.47 (m, 1H), 3.44-3.36 (m, 1H), 3.28 (t, J=9.9 Hz, 1H), 2.94-2.84 (m, 1H), 2.61 (d, J=16.8 Hz, 1H), 2.31-0.83 (m, 35H), 1.75 (s, 3H), 1.14 (s, 3H), 1.08 (s, 3H), 1.00 (s, 3H), 0.99 (s, 3H), 0.94 (s, 3H); LC/MS (ESI) m/e 664.6 [(M+H)$^+$, calcd for $C_{43}H_{66}FNO_3$ 664.5], $t_R$=2.43 min (method 2-1). HPLC (method 2-1): $t_R$=19.00 min; HPLC (method 2-2): $t_R$=20.57 min.

Example 2-10

Preparation of (S)-1-(fluoromethyl)-4-((1R,3aS,5aR,5bR,7aR,11aS,11bR,13aR,13bR)-3a-((2-(3-hydroxyoxetan-3-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid

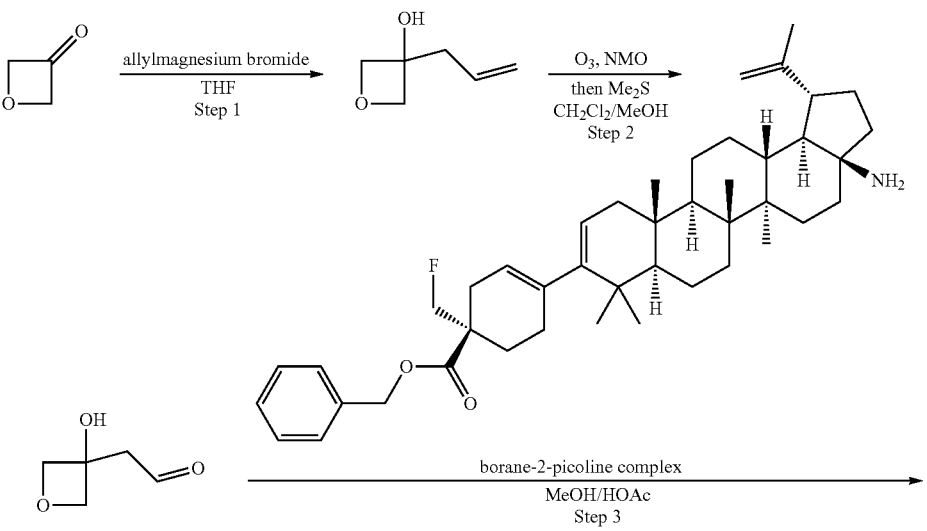

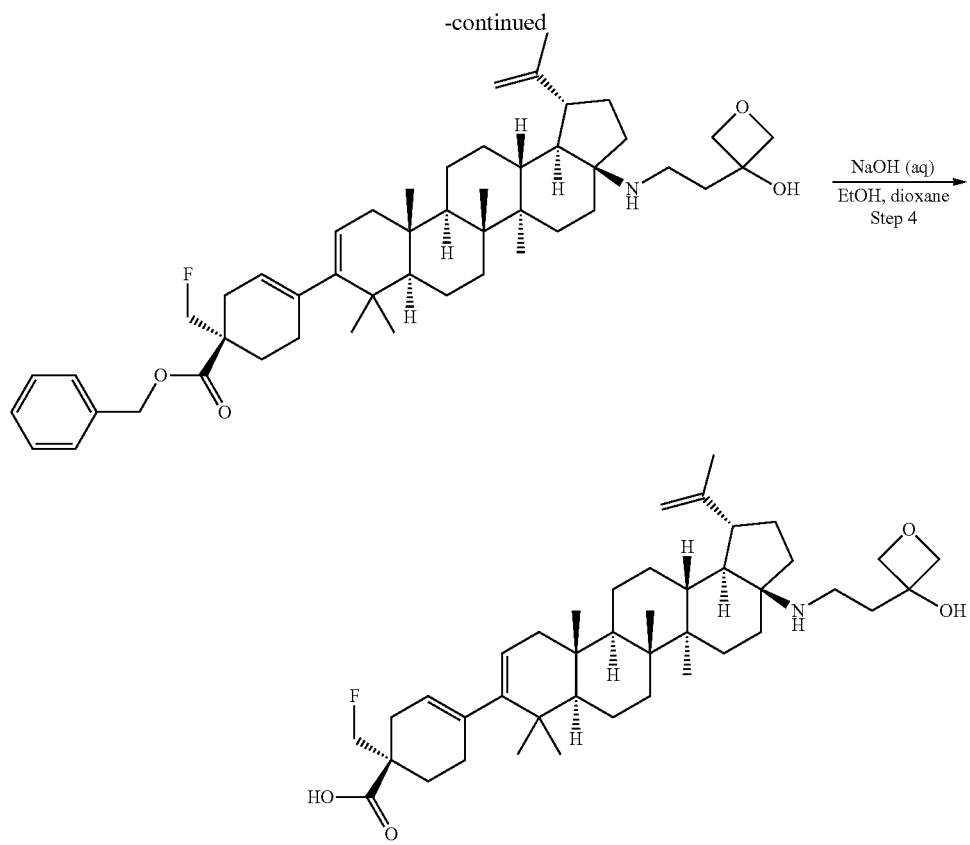

Example 2-10

Step 1. Preparation of 3-allyloxetan-3-ol

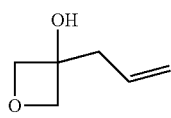

Step 2. Preparation of 2-(3-hydroxyoxetan-3-yl)acetaldehyde

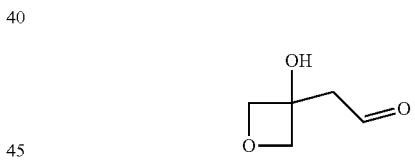

To a solution of allylmagnesium bromide (7.29 mL, 7.29 mmol) in THF (40 mL) at −78° C. was added a solution of oxetan-3-one (500 mg, 6.94 mmol) in THF (10 mL). The reaction mixture was stirred at −78° C. for 30 min. The reaction was quenched by the addition of saturated NH$_4$Cl solution (40 mL). The mixture was transferred to a separatory funnel and the layers were separated. The aqueous layer was extracted with ether (3×50 mL). The combined organic layers were washed with brine (50 mL), dried over MgSO$_4$, filtered, and concentrated to afford 3-allyloxetan-3-ol (735 mg, 6.44 mmol, 93% yield) as a colorless oil. The product was used in the next step without further purification: $^1$H NMR (400 MHz, CHLOROFORM-d) δ 5.97-5.78 (m, 1H), 5.28 (t, J=1.0 Hz, 1H), 5.27-5.22 (m, 1H), 4.64 (d, J=7.3 Hz, 2H), 4.55-4.50 (m, 2H), 2.65 (d, J=7.0 Hz, 2H); $^{13}$C NMR (101 MHz, CHLOROFORM-d) δ 131.8, 120.1, 83.2, 73.3, 42.4.

3-Allyloxetan-3-ol (508 mg, 4.45 mmol) was dissolved in CH$_2$Cl$_2$ (35 mL) and MeOH (3.5 mL) in a 100 mL round bottom flask. N-methylmorpholine-N-oxide (NMO) (626 mg, 5.34 mmol) was added and the mixture was cooled to −78° C. [Schwartz, C., Raible, J., Mott, K., Dussault, P. H. Org. Leu. 2006, 8, 3199-3201]. Ozone was bubbled through the reaction mixture until the solution was saturated with ozone (turned into a blue color) and several minutes thereafter (total time 10 min) Nitrogen was then bubbled through the reaction mixture until the disappearance of the blue color. Dimethyl sulfide (3.29 mL, 44.5 mmol) was then added and the reaction mixture was stirred at 0° C. for 14 h. The mixture was concentrated under vacuum. The product was purified by column chromatography on silica gel (50% ethyl acetate with 1% methanol/50% hexanes→100% ethyl acetate with 1% methanol; 80 g column) to afford 2-(3-hydroxyoxetan-3-yl)acetaldehyde (287 mg, 2.472 mmol, 56% yield) as a colorless oil: $^1$H NMR (400 MHz, CHLOROFORM-d) δ 9.85 (s, 1H), 4.71 (d, J=7.5 Hz, 2H), 4.52-4.47 (m, 2H), 3.14 (d, J=0.5 Hz, 2H); $^{13}$C NMR (100 MHz, CHLOROFORM-d) δ 201.1, 83.0, 71.4, 50.7.

Step 3. Preparation of (S)-benzyl 1-(fluoromethyl)-4-((1R,3aS,5aR,5bR,7aR,11aS,11bR,13aR,13bR)-3a-((2-(3-hydroxyoxetan-3-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate

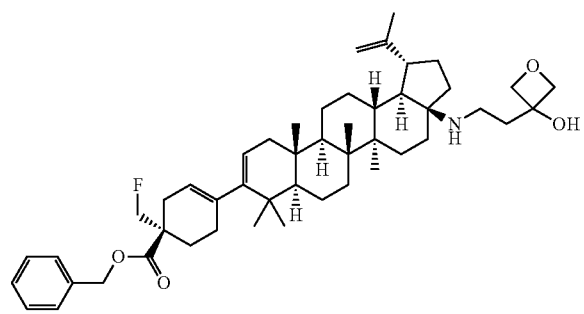

In a vial, a mixture of (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (500 mg, 0.762 mmol), borane-2-picoline complex (163 mg, 1.524 mmol) and 2-(3-hydroxyoxetan-3-yl)acetaldehyde (177 mg, 1.524 mmol) in MeOH (8 mL) and acetic acid (1.6 mL) was stirred at rt for 16 h. The mixture was transferred to a separatory funnel containing saturated aqueous sodium bicarbonate solution (50 mL). The aqueous layer was extracted with dichloromethane (3×50 mL). The combined organic layers were washed with brine (50 mL), dried over MgSO$_4$, filtered, and concentrated. The product was purified by column chromatography on silica gel (10% 9:1 acetone:methanol/90% hexanes→40% 9:1 acetone:methanol/60% hexanes; 80 g column, λ=220 nm) to afford (S)-benzyl 1-(fluoromethyl)-4-((1R,3aS,5aR,5bR,7aR,11aS,11bR,13aR,13bR)-3a-((2-(3-hydroxyoxetan-3-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (320 mg, 0.423 mmol, 56% yield) as a colorless oil: LC/MS (ESI) m/e 756.6 [(M+H)$^+$, calcd for C$_{49}$H$_{70}$FNO$_4$ 756.5], t$_R$=2.59 min (method 2-1).

Step 4. A solution of (S)-benzyl 1-(fluoromethyl)-4-((1R,3aS,5aR,5bR,7aR,11aS,11bR,13aR,13bR)-3a-((2-(3-hydroxyoxetan-3-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (320 mg, 0.423 mmol) in dioxane (4 mL) and ethanol (2 mL) was treated with sodium hydroxide (0.529 mL, 2.116 mmol). The reaction mixture was heated at 70° C. for 2.5 h. LC/MS showed the formation of the desired product. The mixture was filtered through a syringe filter, and was purified by reverse phase preparative HPLC (method 2-5). The organic solvent was removed on the rotovapor and the aqueous mixture was frozen and placed on the lyophilizer to afford (S)-1-(fluoromethyl)-4-((1R,3aS,5aR,5bR,7aR,11aS,11bR,13aR,13bR)-3a-((2-(3-hydroxyoxetan-3-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid•TFA (220 mg, 0.282 mmol, 67% yield) as a white amorphous solid: $^1$H NMR (500 MHz, Acetic Acid-d$_4$) δ 5.39 (br. s., 1H), 5.25 (d, J=4.6 Hz, 1H), 4.83 (s, 1H), 4.81-4.77 (m, 2H), 4.75-4.68 (m, 2H), 4.67-4.57 (m, 2H), 4.55-4.46 (m, 1H), 3.52-3.42 (m, 1H), 3.33-3.23 (m, 1H), 2.92-2.81 (m, 1H), 2.61 (d, J=16.8 Hz, 1H), 2.57-2.42 (m, 2H), 2.31-1.32 (m, 25H), 1.14-1.12 (m, 2H), 1.75 (s, 3H), 1.15 (s, 3H), 1.09 (s, 3H), 1.01 (s, 3H), 0.99 (s, 3H), 0.95 (s, 3H); LC/MS m/e 666.5 [(M+H)$^+$, calcd for C$_{42}$H$_{67}$FNO$_4$ 666.5], t$_R$=2.44 min (method 2-1); HPLC (method 2-1): t$_R$=18.63 min; HPLC (method 2-2): t$_R$=19.94 min.

Example 2-11

Preparation of (R)-1-(fluoromethyl)-4-((1R,3aS,5aR,5bR,7aR,11aS,11bR,13aR,13bR)-3a-((2-(3-hydroxyoxetan-3-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid

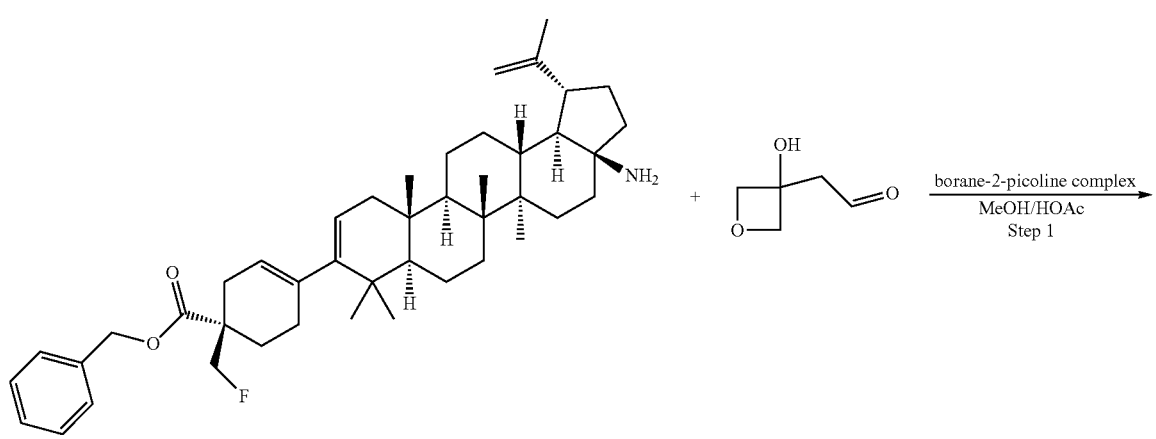

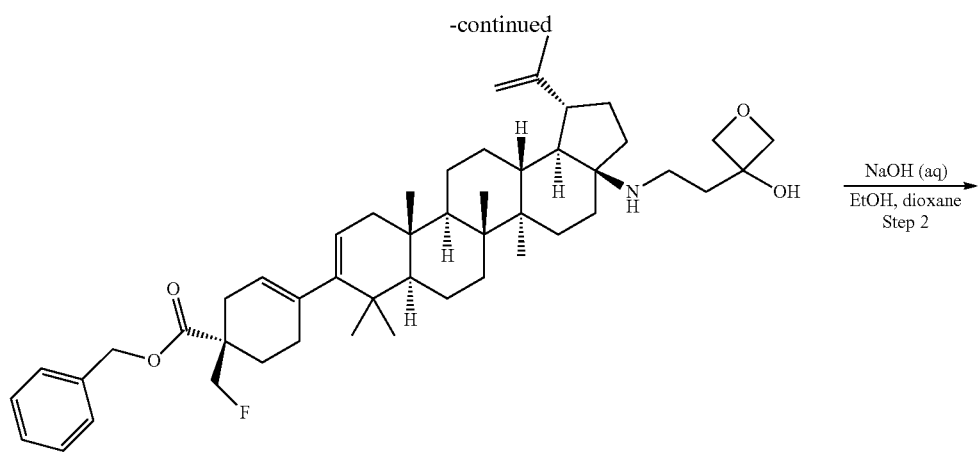
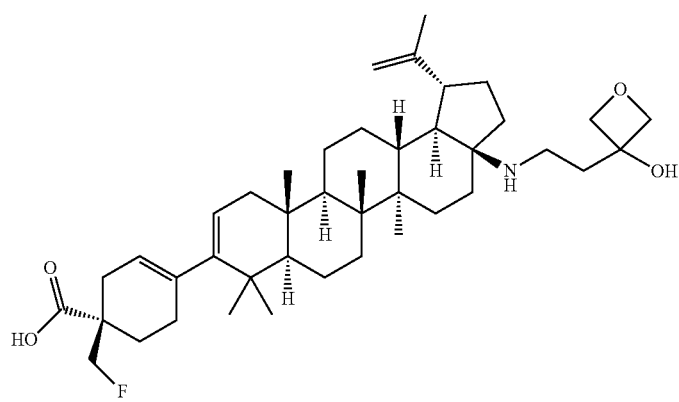
Example 2-11
Step 1. Preparation of (R)-benzyl 1-(fluoromethyl)-4-((1R,3aS,5aR,5bR,7aR,11aS,11bR,13aR,13bR)-3a-((2-(3-hydroxyoxetan-3-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate
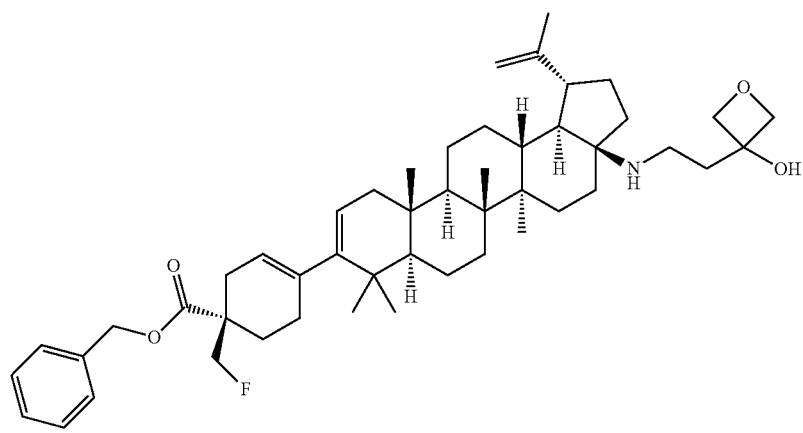

(R)-Benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (100 mg, 0.152 mmol) and 2-(3-hydroxyoxetan-3-yl)acetaldehyde (31.9 mg, 0.274 mmol) were suspended in MeOH (1.2 mL). Borane-2-picoline complex (29.4 mg, 0.274 mmol) was added followed by acetic acid (0.24 mL) and the mixture was stirred at room temperature for 16 h. The mixture was transferred to a separatory funnel containing saturated aqueous sodium bicarbonate solution (5 mL) and saturated aqueous sodium carbonate solution (1 mL). The aqueous layer was extracted with dichloromethane (4×5 mL). The combined organic layers were washed with brine (5 mL), dried over MgSO$_4$, filtered, and concentrated. The product was purified by column chromatography on silica gel (20% ethyl acetate with 5% methanol/80% hexanes→90% ethyl acetate with 5% methanol/10% hexanes; 24 g column) to afford (R)-benzyl 1-(fluoromethyl)-4-((1R,3aS,5aR,5bR,7aR,11aS,11bR,13aR,13bR)-3a-((2-(3-hydroxyoxetan-3-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (110 mg, 0.145 mmol, 95% yield) as a colorless oil: $^1$H NMR (500 MHz, CHLOROFORM-d) δ 7.42-7.31 (m, 5H), 5.34 (br. s., 1H), 5.24-5.16 (m, 2H), 5.12 (d, J=5.7 Hz, 1H), 4.73 (br. s., 1H), 4.69 (t, J=5.3 Hz, 2H), 4.64-4.55 (m, 2H), 4.53-4.46 (m, 2H), 4.43 (d, J=6.0 Hz, 1H), 2.90-2.83 (m, 1H), 2.72-2.48 (m, 3H), 2.26-1.87 (m, 8H), 1.82-0.91 (m, 21H), 1.69 (s, 3H), 1.06 (s, 3H), 0.98 (s, 3H), 0.94 (s, 3H), 0.89 (s, 3H), 0.86 (s, 3H); LC/MS m/e 756.6 [(M+H)$^+$, calcd for $C_{49}H_{71}FNO_4$ 756.6], $t_R$=4.59 min (method 2-3).

Step 2. A solution of (R)-benzyl 1-(fluoromethyl)-4-((1R,3aS,5aR,5bR,7aR,11aS,11bR,13aR,13bR)-3a-((2-(3-hydroxyoxetan-3-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (105 mg, 0.139 mmol) in 1,4-dioxane (1.5 mL) and MeOH (0.5 mL) was treated with sodium hydroxide (2M aq) (0.347 mL, 0.694 mmol). The reaction mixture was heated at 70° C. for 4 h. The mixture was cooled to room temperature and was partially neutralized by the addition of 6 N HCl (70 µL). The mixture was then filtered through a syringe filter, and was purified by reverse phase preparative HPLC (method 2-5). The organic solvent was evaporated on the rotovapor and the aqueous mixture was lyophilized to afford (R)-1-(fluoromethyl)-4-((1R,3aS,5aR,5bR,7aR,11aS,11bR,13aR,13bR)-3a-((2-(3-hydroxyoxetan-3-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid•TFA (38.0 mg, 0.048 mmol, 35% yield) as a white amorphous solid: $^1$H NMR (500 MHz, Acetic Acid-d$_4$) δ 5.39 (br. s., 1H), 5.24 (d, J=4.7 Hz, 1H), 4.83 (s, 1H), 4.80 (d, J=7.3 Hz, 2H), 4.74-4.69 (m, 2H), 4.66-4.57 (m, 2H), 4.55-4.46 (m, 1H), 3.47 (ddd, J=12.7, 6.1, 3.2 Hz, 1H), 3.28 (ddd, J=12.5, 9.2, 2.9 Hz, 1H), 2.90-2.83 (m, 1H), 2.61 (d, J=17.2 Hz, 1H), 2.56-2.44 (m, 2H), 2.37-2.28 (m, 1H), 2.22-1.32 (m, 24H), 1.75 (s, 3H), 1.15 (s, 3H), 1.14-1.12 (m, 2H), 1.09 (s, 3H), 1.02 (s, 3H), 0.98 (s, 3H), 0.95 (s, 3H); LC/MS m/e 666.5 [(M+H)$^+$, calcd for $C_{42}H_{65}FNO_4$ 666.5], $t_R$=4.31 min (method 2-2); HPLC (method 2-5): $t_R$=10.94 min; HPLC (method 2-6): $t_R$=10.82 min.

Example 2-12

Preparation of (S)-1-(fluoromethyl)-4-((1R,3aS,5aR,5bR,7aR,11aS,11bR,13aR,13bR)-3a-((2-(4-hydroxytetrahydro-2H-pyran-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid

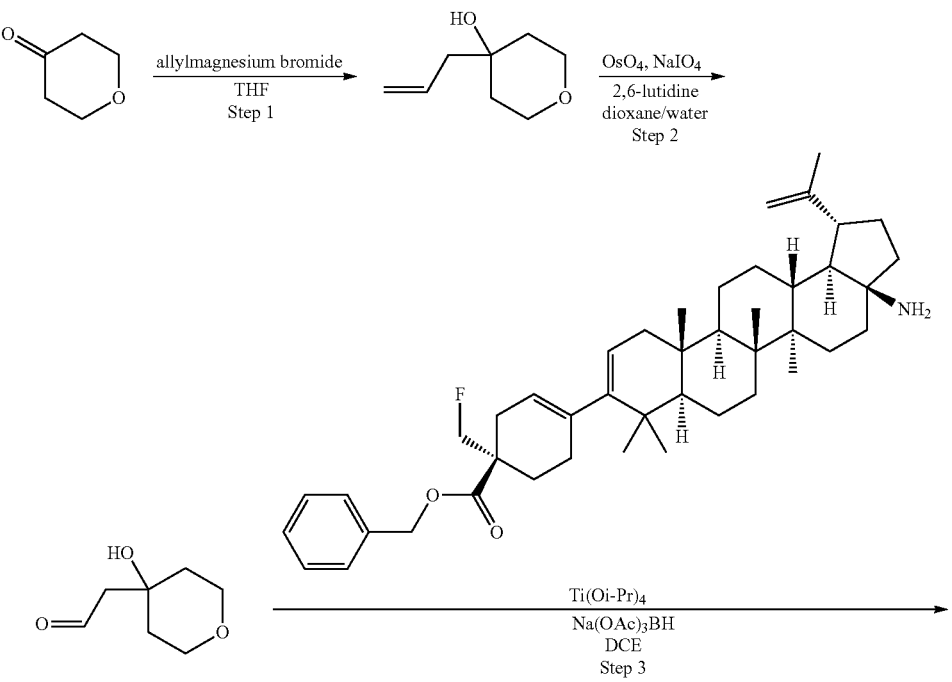

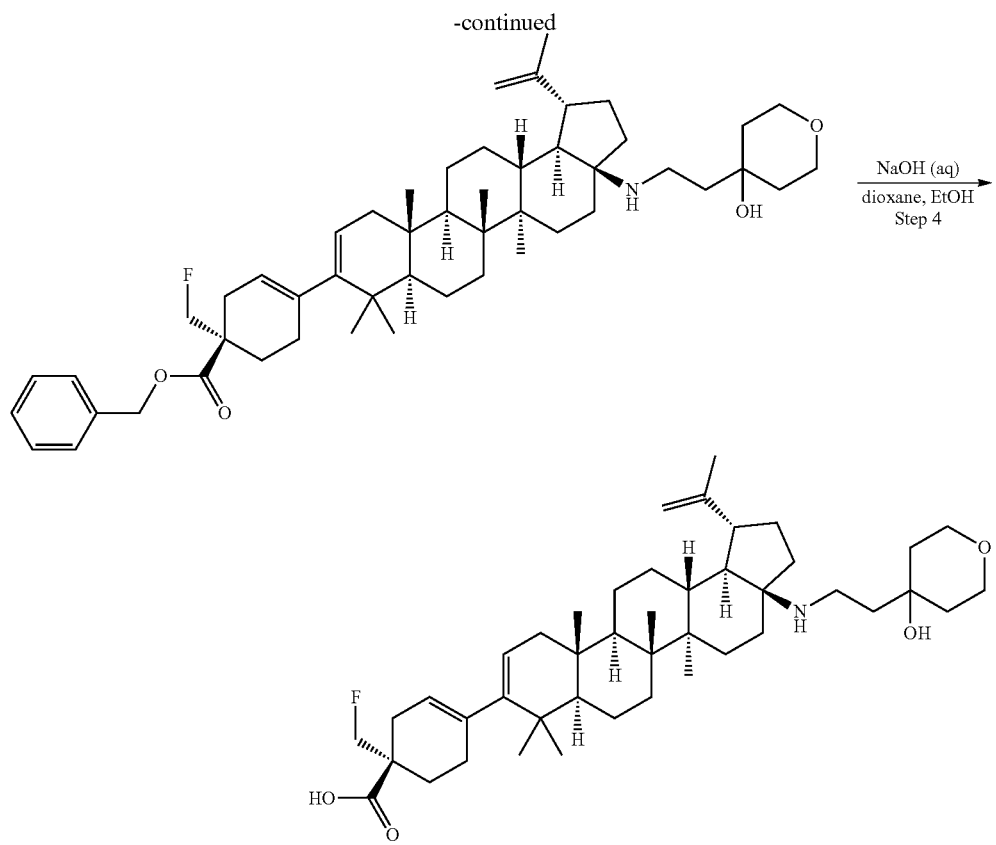

Example 2-12

Step 1. Preparation of 4-allyltetrahydro-2H-pyran-4-ol

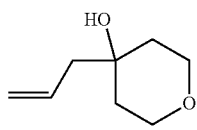

To a solution of allylmagnesium bromide (20.98 mL, 20.98 mmol) in THF (40 mL) at 0° C. was added via cannula a solution of dihydro-2H-pyran-4 (3H)-one (700 mg, 6.99 mmol) in THF (10 mL). The cooling bath was removed and the reaction mixture was stirred at room temperature for 2 h. The reaction was cooled in an ice-water bath and was quenched by the addition of saturated NH$_4$Cl solution (40 mL). The mixture was transferred to a separatory funnel and the layers were separated. The aqueous layer was extracted with ethyl acetate (3×50 mL). The combined organic layers were washed with brine (50 mL), dried over MgSO$_4$, filtered, and concentrated. The product was purified by column chromatography on silica gel (20%→60% ethyl acetate in hexanes; 80 g column) to afford 4-allyltetrahydro-2H-pyran-4-ol (818 mg, 5.75 mmol, 82% yield) as a colorless oil: $^1$H NMR (400 MHz, CHLOROFORM-d) δ 5.90 (ddt, J=17.2, 9.9, 7.5 Hz, 1H), 5.28-5.14 (m, 2H), 3.85-3.74 (m, 4H), 2.28 (d, J=7.5 Hz, 2H), 1.80-1.68 (m, 2H), 1.51 (dq, J=14.0, 2.5 Hz, 3H).

Step 2. Preparation of 2-(4-hydroxytetrahydro-2H-pyran-4-yl)acetaldehyde

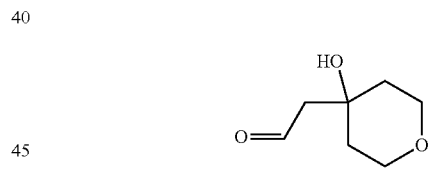

To a solution of 4-allyltetrahydro-2H-pyran-4-ol (150 mg, 1.055 mmol) in dioxane (12 mL) and water (3 mL) at 0° C. was added 2,6-lutidine (0.246 mL, 2.110 mmol), osmium tetroxide (0.265 mL, 0.021 mmol), and sodium periodate (903 mg, 4.22 mmol). The reaction mixture was allowed to warm up to room temperature as the ice-water bath melted while stirring for 14 h. The mixture was transferred to a separatory funnel containing water (10 mL) and saturated aqueous NaHCO$_3$ solution (10 mL). The aqueous layer was extracted with ethyl acetate (3×20 mL). The combined organic layers were washed with brine (20 mL), dried over MgSO$_4$, filtered, and concentrated. The product was purified by column chromatography on silica gel (3%→6% methanol in CH$_2$Cl$_2$; 40 g column) to afford 2-(4-hydroxytetrahydro-2H-pyran-4-yl)acetaldehyde (67 mg, 0.465 mmol, 44% yield) as a colorless oil: $^1$H NMR (400 MHz, CHLOROFORM-d) δ 9.89 (t, J=1.3 Hz, 1H), 3.90-3.80 (m, 2H), 3.78-3.69 (m, 2H), 3.50 (s, 1H), 2.70 (d, J=1.3 Hz, 2H), 1.75-1.66 (m, 4H).

Step 3. Preparation of (S)-benzyl 1-(fluoromethyl)-4-((1R,3aS,5aR,5bR,7aR,11aS,11bR,13aR,13bR)-3a-((2-(4-hydroxytetrahydro-2H-pyran-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (33.2 mg, 0.042 mmol, 69% yield) as a colorless foam: $^1$H NMR (400 MHz, CHLOROFORM-d) δ 7.43-7.32 (m, 5H), 5.36-5.31 (m, 1H), 5.23-5.16 (m, 2H), 5.14 (dd, J=6.0, 1.8 Hz, 1H), 4.75 (d, J=1.8 Hz, 1H), 4.64-4.57 (m, 2H), 4.53-4.45 (m, 1H), 3.94-3.82 (m, 2H),

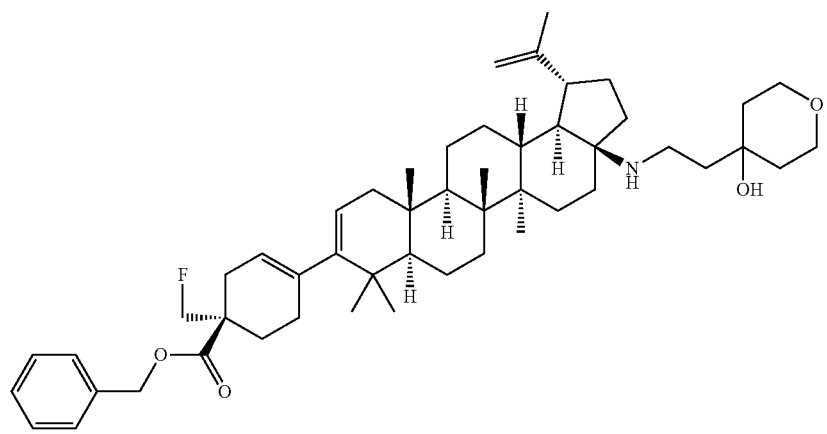

To a solution of (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (40 mg, 0.061 mmol) and 2-(4-hydroxytetrahydro-2H-pyran-4-yl)acetaldehyde (13.19 mg, 0.091 mmol) in DCE (0.5 mL) was added titanium(IV) isopropoxide (0.027 mL, 0.091 mmol). The mixture was stirred at room temperature for 1 h. Sodium triacetoxyborohydride (25.8 mg, 0.122 mmol) was added and the mixture was stirred at room temperature overnight. The mixture was transferred to a separatory funnel containing saturated aqueous sodium bicarbonate solution (5 mL). The aqueous layer was extracted with dichloromethane (3×10 mL). The combined organic layers were washed with brine (5 mL), dried over MgSO$_4$, filtered, and concentrated. The product was purified by column chromatography on silica gel (10% 9:1 acetone:methanol/90% hexanes→40% 9:1 acetone:methanol/60% hexanes; 24 g column, λ=220 nm) to afford (S)-benzyl 1-(fluoromethyl)-4-((1R,3aS,5aR,5bR,7aR,11aS,11bR,13aR,13bR)-3a-((2-(4-hydroxytetrahydro-2H-pyran-4-yl)

3.80-3.70 (m, 2H), 2.86-2.69 (m, 2H), 2.67-2.51 (m, 2H), 2.19-0.86 (m, 33H), 1.70 (s, 3H), 1.06 (s, 3H), 0.98 (s, 3H), 0.92 (s, 3H), 0.91 (s, 3H), 0.86 (s, 3H); LC/MS m/e 784.6 [(M+H)$^+$, calcd for C$_{51}$H$_{75}$FNO$_4$ 784.6], $t_R$=4.69 min (method 2-2).

Step 4. A solution of (S)-benzyl 1-(fluoromethyl)-4-((1R,3aS,5aR,5bR,7aR,11aS,11bR,13aR,13bR)-3a-((2-(4-hydroxytetrahydro-2H-pyran-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (56 mg, 0.071 mmol) in 1,4-dioxane (0.7 mL) and EtOH (0.35 mL) was treated with sodium hydroxide (2M aq) (0.179 mL, 0.357 mmol). The reaction mixture was heated at 70° C. for 2 h. The mixture was cooled to room temperature, filtered through a syringe filter, and was purified by reverse phase preparative HPLC (method 2-1). The organic solvent was evaporated on the rotovapor and the aqueous mixture was lyophilized to afford (S)-1-(fluoromethyl)-4-((1R,3aS,5aR,5bR,7aR,11aS,11bR,13aR,13bR)-3a-((2-(4-hydroxytetrahydro-2H-pyran-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid•TFA (37.1 mg, 64% yield) as a white amorphous solid:

$^1$H NMR (500 MHz, Acetic Acid-d$_4$) δ 5.39 (br. s., 1H), 5.28-5.21 (m, 1H), 4.83 (s, 1H), 4.72 (s, 1H), 4.65-4.57 (m, 1H), 4.55-4.46 (m, 1H), 3.97-3.79 (m, 4H), 3.46-3.31 (m, 2H), 2.92-2.83 (m, 1H), 2.61 (d, J=16.8 Hz, 1H), 2.34-1.09 (m, 33H), 1.75 (s, 3H), 1.18 (s, 3H), 1.09 (s, 3H), 1.00 (s, 3H), 0.99 (s, 3H), 0.96 (s, 3H); LC/MS m/e 694.6 [(M+H)$^+$, calcd for C$_{44}$H$_{69}$FNO$_4$ 694.5], t$_R$=4.27 min (method 2-2);

HPLC (method 2-1): t$_R$=18.95 min; HPLC (method 2-2): t$_R$=20.14 min.

Example 2-13

Preparation of (S)-1-(fluoromethyl)-4-((1R,3aS,5aR,5bR,7aR,11aS,11bR,13aR,13bR)-3a-((2-(4-hydroxy-1,1-dioxidotetrahydro-2H-thiopyran-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid

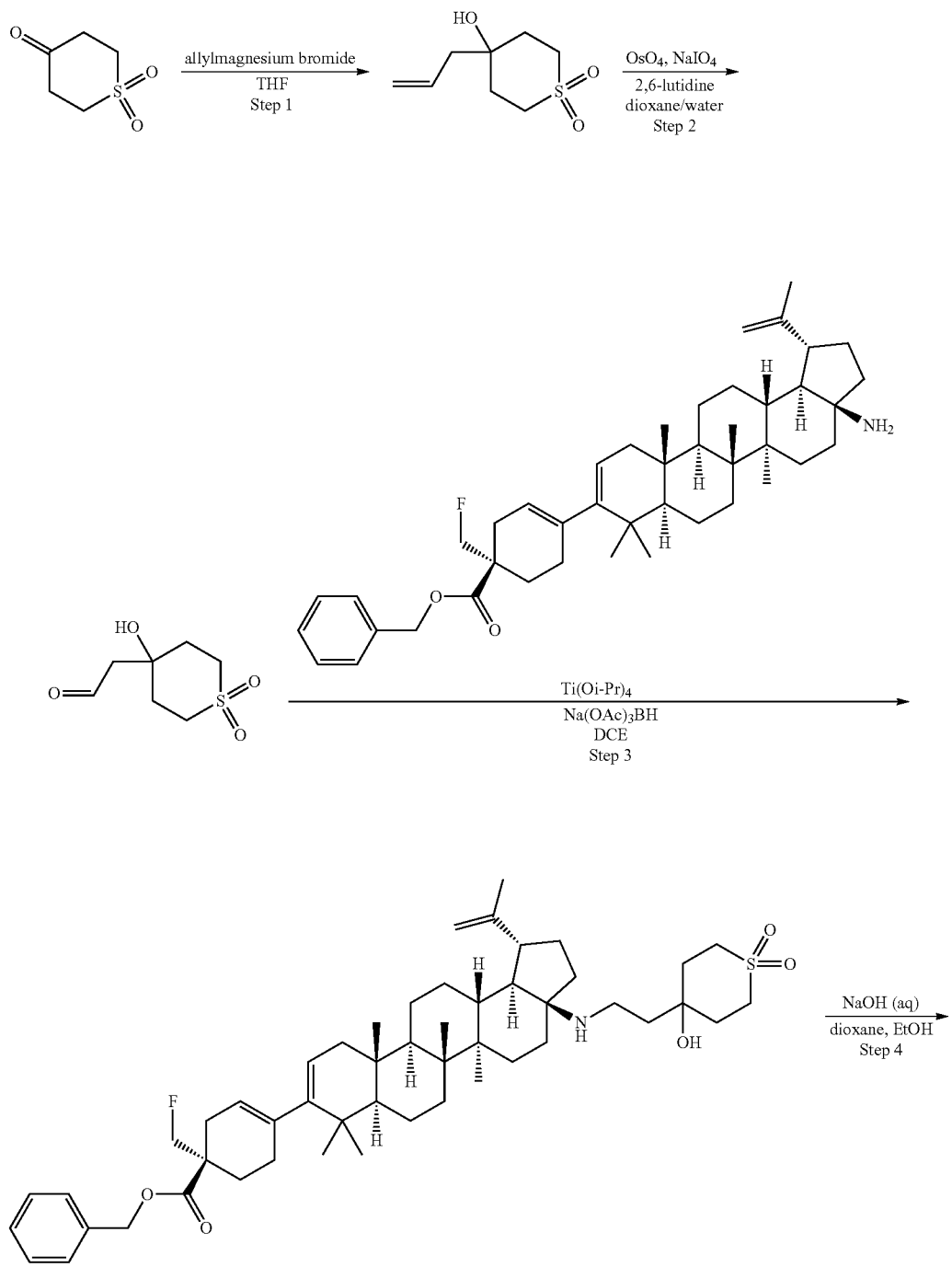

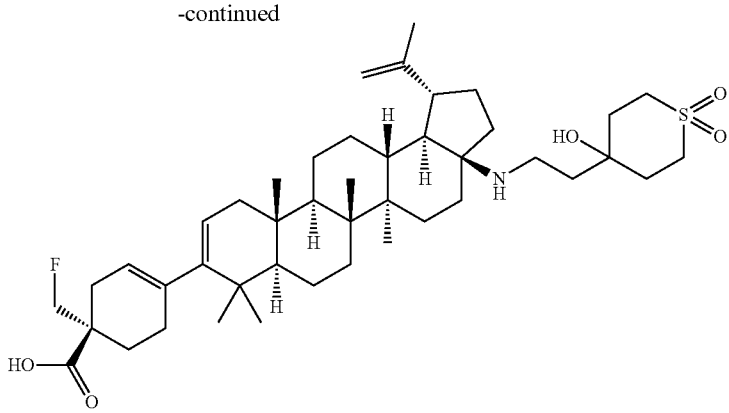

Example 2-13

Step 1. Preparation of 4-allyl-4-hydroxytetrahydro-2H-thiopyran 1,1-dioxide

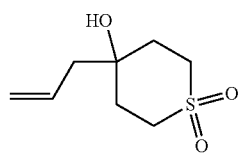

To a solution of allylmagnesium bromide (10.83 mL, 10.83 mmol) in THF (15 mL) at 0° C. was added via cannula a solution of dihydro-2H-thiopyran-4 (3H)-one 1,1-dioxide (1.07 g, 7.22 mmol) in THF (50 mL) (dissolved by warming in an oil bath to 70° C.). The cooling bath was removed and the reaction mixture was stirred at room temperature for 30 min. The reaction was cooled in an ice-water bath and was quenched by the addition of saturated NH$_4$Cl solution (50 mL). The mixture was transferred to a separatory funnel and the aqueous layer was extracted with ethyl acetate (4×50 mL). The combined organic layers were washed with brine (50 mL), dried over MgSO$_4$, filtered, and concentrated to afford 4-allyl-4-hydroxytetrahydro-2H-thiopyran 1,1-dioxide (1.42 g, 7.46 mmol, 103% yield) as a colorless solid. The product was used directly in the next step without further purification: $^1$H NMR (400 MHz, CHLOROFORM-d) δ 5.85 (ddt, J=17.2, 9.9, 7.6 Hz, 1H), 5.34-5.28 (m, 1H), 5.23 (dq, J=17.1, 1.4 Hz, 1H), 3.43 (td, J=13.6, 3.8 Hz, 2H), 2.92-2.84 (m, 2H), 2.32 (d, J=7.5 Hz, 2H), 2.23 (td, J=13.8, 3.3 Hz, 2H), 2.05-1.97 (m, 2H).

Step 2. Preparation of 2-(4-hydroxy-1,1-dioxidotetrahydro-2H-thiopyran-4-yl)acetaldehyde

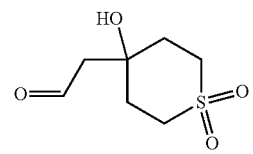 [SMILES: O=CCC1(O)CCS(=O)(=O)CC1]

To a solution of 4-allyl-4-hydroxytetrahydro-2H-thiopyran 1,1-dioxide (1.52 g, 7.99 mmol) in dioxane (80 mL) and water (20 mL) at 0° C. was added 2,6-lutidine (1.861 mL, 15.98 mmol), osmium tetroxide (4% in water) (1.254 mL, 0.160 mmol), and sodium periodate (6.84 g, 32.0 mmol). The reaction mixture was allowed to warm up to room temperature as the ice-water bath melted while stirring for 14 h. The mixture was transferred to a separatory funnel containing 1 N HCl solution (50 mL). The aqueous layer was extracted with ethyl acetate (12×50 mL). The combined organic layers were washed with 1 N HCl solution (10 mL), saturated aqueous NaHCO$_3$ solution (10 mL), brine (10 mL), dried over MgSO$_4$, filtered, and concentrated. The product was purified by column chromatography on silica gel (3%→10% methanol in CH$_2$Cl$_2$; 80 g column) to afford 2-(4-hydroxy-1,1-dioxidotetrahydro-2H-thiopyran-4-yl)acetaldehyde (821 mg, 4.27 mmol, 54% yield) as a colorless oil: $^1$H NMR (400 MHz, CHLOROFORM-d) δ 9.86 (s, 1H), 3.54-3.43 (m, 3H), 2.91-2.83 (m, 2H), 2.80 (s, 2H), 2.28-2.14 (m, 4H).

Step 3. Preparation of (S)-benzyl 1-(fluoromethyl)-4-((1R,3aS,5aR,5bR,7aR,11aS,11bR,13aR,13bR)-3a-((2-(4-hydroxy-1,1-dioxidotetrahydro-2H-thiopyran-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate

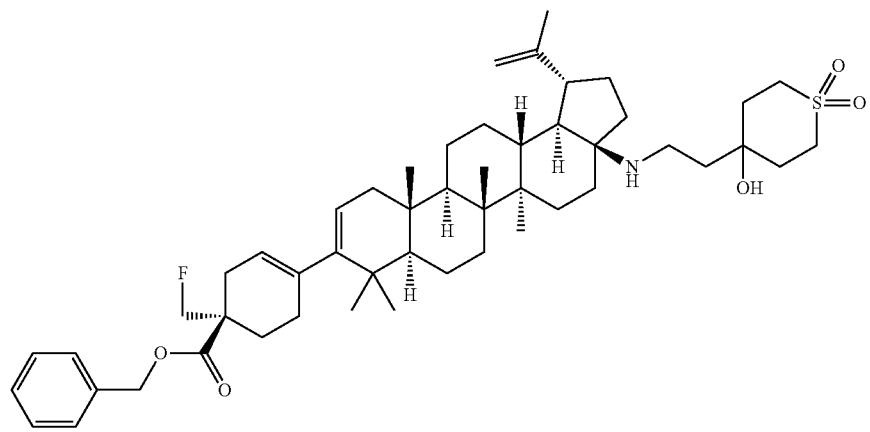

To a solution of (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (632 mg, 0.963 mmol) and 2-(4-hydroxy-1,1-dioxidotetrahydro-2H-thiopyran-4-yl)acetaldehyde (296 mg, 1.542 mmol) in DCE (7.5 mL) was added titanium(IV) isopropoxide (0.452 mL, 1.542 mmol). The mixture was stirred at room temperature for 1 h. Sodium triacetoxyborohydride (408 mg, 1.927 mmol) was added and the mixture was stirred at room temperature overnight. The mixture was transferred to a separatory funnel containing saturated aqueous sodium bicarbonate solution (25 mL). The aqueous layer was extracted with dichloromethane (4×50 mL). The combined organic layers were washed with brine (25 mL), dried over MgSO$_4$, filtered, and concentrated. The product was purified by column chromatography on silica gel (10% 9:1 acetone:methanol/90% hexanes→40% 9:1 acetone:methanol/60% hexanes; 80 g column, λ=220 nm) to afford (S)-benzyl 1-(fluoromethyl)-4-((1R,3aS,5aR,5bR,7aR,11aS,11bR,13aR,13bR)-3a-((2-(4-hydroxy-1,1-dioxidotetrahydro-2H-thiopyran-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (591 mg, 0.710 mmol, 74% yield) as a colorless foam: $^1$H NMR (500 MHz, CHLOROFORM-d) δ 7.40-7.32 (m, 5H), 5.34 (br. s., 1H), 5.23-5.16 (m, 2H), 5.14 (dd, J=6.2, 1.8 Hz, 1H), 4.75 (d, J=1.5 Hz, 1H), 4.63 (s, 1H), 4.61-4.55 (m, 1H), 4.53-4.46 (m, 1H), 3.58-3.46 (m, 2H), 2.91-2.81 (m, 3H), 2.78-2.70 (m, 1H), 2.62 (d, J=16.6 Hz, 1H), 2.53 (td, J=10.8, 5.6 Hz, 1H), 2.17-1.06 (m, 33H), 1.70 (s, 3H), 1.06 (s, 3H), 0.99 (s, 3H), 0.92 (s, 3H), 0.91 (s, 3H), 0.87 (s, 3H); LC/MS m/e 832.6 [(M+H)$^+$, calcd for C$_{51}$H$_{75}$FNO$_5$S 832.5], $t_R$=4.64 min (method 2-2).

Step 4. A solution of (S)-benzyl 1-(fluoromethyl)-4-((1R,3aS,5aR,5bR,7aR,11aS,11bR,13aR,13bR)-3a-((2-(4-hydroxy-1,1-dioxidotetrahydro-2H-thiopyran-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (500 mg, 0.601 mmol) in 1,4-dioxane (6 mL) and EtOH (3 mL) was treated with sodium hydroxide (2M aq) (1.502 mL, 3.00 mmol). The reaction mixture was heated at 70° C. for 2.5 h. The mixture was cooled to room temperature and 6 N HCl (0.20 mL, 2 eq) was added to partially neutralize the reaction mixture. The mixture was filtered through a syringe filter, and was purified by reverse phase preparative HPLC (method 2-1). The organic solvent was evaporated on the rotovapor and the aqueous mixture was lyophilized to afford (S)-1-(fluoromethyl)-4-((1R,3aS,5aR,5bR,7aR,11aS,11bR,13aR,13bR)-3a-((2-(4-hydroxy-1,1-dioxidotetrahydro-2H-thiopyran-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid·TFA (435 mg, 84% yield) as a white amorphous solid: $^1$H NMR (500 MHz, Acetic Acid-d$_4$) δ 5.39 (br. s., 1H), 5.24 (d, J=4.6 Hz, 1H), 4.82 (s, 1H), 4.73 (s, 1H), 4.65-4.56 (m, 1H), 4.55-4.47 (m, 1H), 3.59-3.33 (m, 4H), 3.10-2.97 (m, 2H), 2.88-2.78 (m, 1H), 2.61 (d, J=16.6 Hz, 1H), 2.42-1.12 (m, 33H), 1.75 (s, 3H), 1.18 (s, 3H), 1.10 (s, 3H), 1.00 (s, 3H), 0.99 (s, 3H), 0.95 (s, 3H); LC/MS m/e 742.6 [(M+H)$^+$, calcd for C$_{44}$H$_{69}$FNO$_5$S 742.5], $t_R$=4.19 min (method 2-2); HPLC (method 2-1): $t_R$=18.71 min; HPLC (method 2-2): $t_R$=19.66 min.

Example 2-14
Preparation of (S)-1-(fluoromethyl)-4-((1R,3aS,5aR, 5bR,7aR,11aS,11bR,13aR,13bR)-3a-((2-(4-hydroxy-1-(methylsulfonyl)piperidin-4-yl)ethyl)amino)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) cyclohex-3-enecarboxylic acid
5
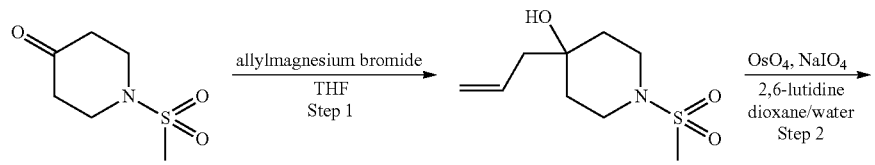
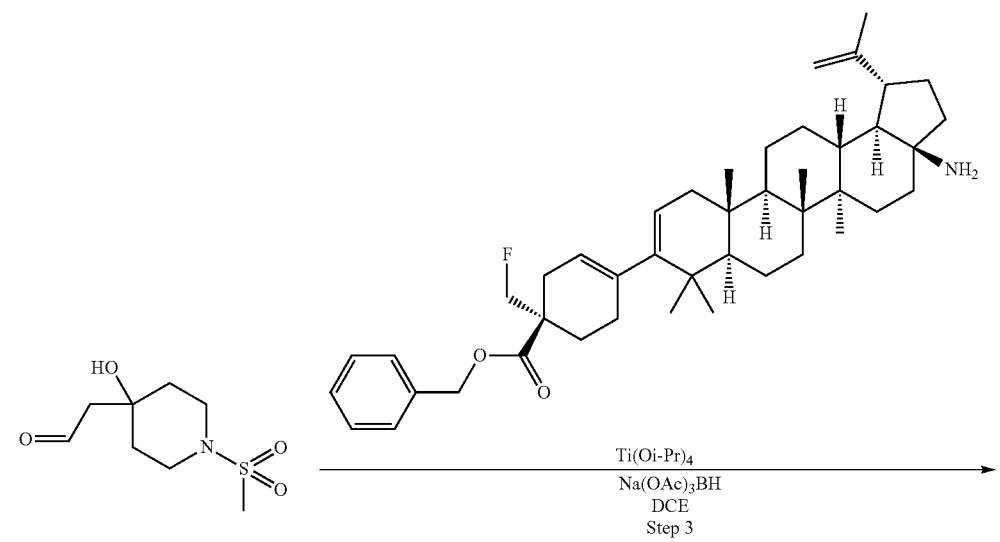

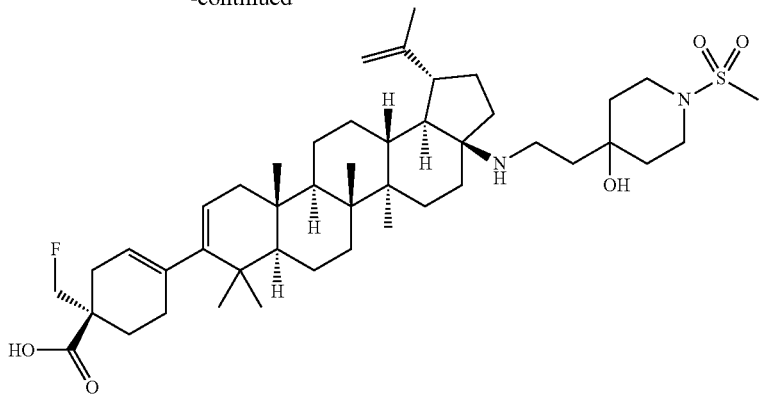

Example 2-14

Step 1. Preparation of 4-allyl-1-(methylsulfonyl)piperidin-4-ol

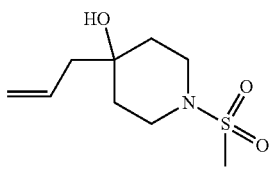

To a solution of allylmagnesium bromide (5.08 mL, 5.08 mmol) in THF (15 mL) at 0° C. was added via cannula a solution of 1-(methylsulfonyl)piperidin-4-one (300 mg, 1.693 mmol) in THF (5 mL). The cooling bath was removed and the reaction mixture was stirred at room temperature for 30 min. The reaction was cooled in an ice-water bath and was quenched by the addition of saturated NH$_4$Cl solution (20 mL). The mixture was transferred to a separatory funnel and the aqueous layer was extracted with ethyl acetate (4×25 mL). The combined organic layers were washed with brine (25 mL), dried over MgSO$_4$, filtered, and concentrated to afford 4-allyl-1-(methylsulfonyl)piperidin-4-ol (423 mg, 1.929 mmol, 114% yield (impure)) as a colorless solid, which was used directly in the next step without further purification. $^1$H NMR (500 MHz, CHLOROFORM-d) δ 5.87 (ddt, J=17.2, 10.0, 7.6 Hz, 1H), 5.28-5.24 (m, 1H), 5.23-5.17 (m, 1H), 3.61 (dt, J=11.4, 2.4 Hz, 2H), 3.05 (td, J=11.9, 3.0 Hz, 2H), 2.80 (s, 3H), 2.27 (d, J=7.5 Hz, 2H), 1.80-1.71 (m, 2H), 1.70-1.61 (m, 2H).

Step 2. Preparation of 2-(4-hydroxy-1-(methylsulfonyl)piperidin-4-yl)acetaldehyde

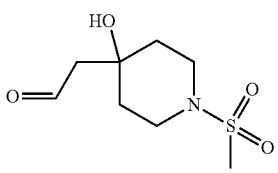

To a solution of 4-allyl-1-(methylsulfonyl)piperidin-4-ol (210 mg, 0.958 mmol) in dioxane (12 mL) and water (3 mL) at 0° C. was added 2,6-lutidine (0.223 mL, 1.915 mmol), osmium tetroxide (4% in water) (0.150 mL, 0.019 mmol), and sodium periodate (819 mg, 3.83 mmol). The reaction mixture was allowed to warm up to room temperature as the ice-water bath melted while stirring for 14 h. The mixture was transferred to a separatory funnel containing water (10 mL) and saturated aqueous NaHCO$_3$ solution (10 mL). The aqueous layer was extracted with ethyl acetate (5×20 mL). The combined organic layers were washed with brine (20 mL), dried over MgSO$_4$, filtered, and concentrated. The product was purified by column chromatography on silica gel (3%→8% methanol in CH$_2$Cl$_2$; 40 g column) to afford 2-(4-hydroxy-1-(methylsulfonyl)piperidin-4-yl)acetaldehyde (101 mg, 0.456 mmol, 48% yield) as a colorless oil: $^1$H NMR (400 MHz, CHLOROFORM-d) δ 9.87 (s, 1H), 3.64-3.55 (m, 2H), 3.15-3.05 (m, 3H), 2.81 (s, 3H), 2.73 (d, J=0.8 Hz, 2H), 1.93-1.85 (m, 2H), 1.73 (dd, J=12.8, 4.5 Hz, 2H).

Step 3. Preparation of (S)-benzyl 1-(fluoromethyl)-4-((1R,3aS,5aR,5bR,7aR,11aS,11bR,13aR,13bR)-3a-((2-(4-hydroxy-1-(methylsulfonyl)piperidin-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate

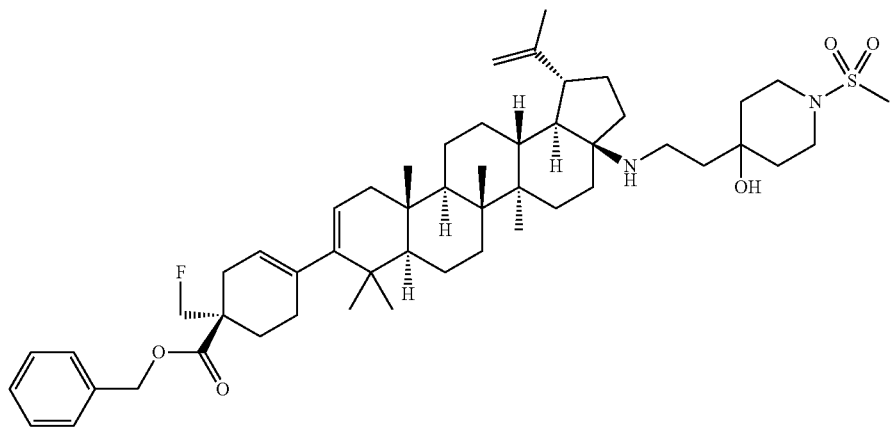

To a solution of (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (50 mg, 0.076 mmol) and 2-(4-hydroxy-1-(methylsulfonyl)piperidin-4-yl)acetaldehyde (25.3 mg, 0.114 mmol) in DCE (0.6 mL) was added titanium(IV) isopropoxide (0.034 mL, 0.114 mmol). The mixture was stirred at room temperature for 1 h. Sodium triacetoxyborohydride (32.3 mg, 0.152 mmol) was added and the mixture was stirred at room temperature overnight. The mixture was transferred to a separatory funnel containing saturated aqueous sodium bicarbonate solution (5 mL). The aqueous layer was extracted with dichloromethane (3×10 mL). The combined organic layers were washed with brine (5 mL), dried over MgSO$_4$, filtered, and concentrated. The product was purified by column chromatography on silica gel (10% 9:1 acetone:methanol/90% hexanes→30% 9:1 acetone:methanol/70% hexanes; 24 g column, λ=220 nm) to afford (S)-benzyl 1-(fluoromethyl)-4-((1R,3aS,5aR,5bR,7aR,11aS,11bR,13aR,13bR)-3a-((2-(4-hydroxy-1-(methylsulfonyl)piperidin-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (49 mg, 0.057 mmol, 75% yield) as a colorless foam: $^1$H NMR (500 MHz, CHLOROFORM-d) δ 7.41-7.31 (m, 5H), 5.33 (br. s., 1H), 5.22-5.16 (m, 2H), 5.13 (dd, J=6.2, 1.8 Hz, 1H), 4.75 (d, J=1.5 Hz, 1H), 4.62 (s, 1H), 4.61-4.55 (m, 1H), 4.49 (td, J=8.9, 5.5 Hz, 1H), 3.67-3.58 (m, 2H), 3.16-3.05 (m, 2H), 2.86-2.79 (m, 1H), 2.82 (s, 3H), 2.77-2.69 (m, 1H), 2.62 (d, J=16.8 Hz, 1H), 2.55 (td, J=10.9, 5.6 Hz, 1H), 2.18-0.86 (m, 33H), 1.70 (s, 3H), 1.05 (s, 3H), 0.98 (s, 3H), 0.92 (s, 3H), 0.91 (s, 3H), 0.86 (s, 3H); LC/MS m/e 861.6 [(M+H)$^+$, calcd for C$_{52}$H$_{78}$FN$_2$O$_5$S 861.6], t$_R$=4.63 min (method 2-2).

Step 4. A solution of (S)-benzyl 1-(fluoromethyl)-4-((1R,3aS,5aR,5bR,7aR,11aS,11bR,13aR,13bR)-3 a-((2-(4-hydroxy-1-(methylsulfonyl)piperidin-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (48 mg, 0.056 mmol) in 1,4-dioxane (0.7 mL) and EtOH (0.35 mL) was treated with sodium hydroxide (2M aq) (0.139 mL, 0.279 mmol). The reaction mixture was heated at 70° C. for 2 h. The mixture was cooled to room temperature, was filtered through a syringe filter, and was purified by reverse phase preparative HPLC (method 2-1). The organic solvent was evaporated on the rotovapor and the aqueous mixture was lyophilized to afford (S)-1-(fluoromethyl)-4-((1R,3aS,5aR,5bR,7aR,11aS,11bR,13aR,13bR)-3a-((2-(4-hydroxy-1-(methylsulfonyl)piperidin-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid•TFA (38.6 mg, 77% yield) as a white amorphous solid: $^1$H NMR (500 MHz, Acetic Acid-d$_4$) δ 5.39 (br. s., 1H), 5.25 (d, J=4.6 Hz, 1H), 4.83 (s, 1H), 4.73 (s, 1H), 4.66-4.57 (m, 1H), 4.55-4.47 (m, 1H), 3.65-3.50 (m, 2H), 3.47-3.34 (m, 2H), 3.25-3.12 (m, 2H), 2.88 (s, 3H), 2.87-2.79 (m, 1H), 2.61 (d, J=17.5 Hz, 1H), 2.33-1.09 (m, 33H), 1.75 (s, 3H), 1.17 (s, 3H), 1.09 (s, 3H), 1.00 (s, 3H), 0.99 (s, 3H), 0.95 (s, 3H); LC/MS m/e 771.6 [(M+H)$^+$, calcd for C$_{45}$H$_{72}$FN$_2$O$_5$S 771.5], t$_R$=4.43 min (method 2-2); HPLC (method 2-1): t$_R$=18.97 min; HPLC (method 2-2): t$_R$=20.11 min.

Example 2-15

Preparation of (S)-4-((1R,3aS,5aR,5bR,7aR,11aS,11bR,13aR,13bR)-3a-((2-(1-acetyl-4-hydroxypiperidin-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid

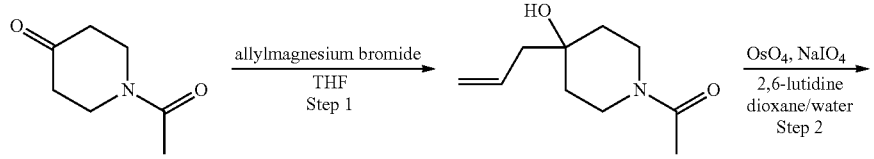

-continued
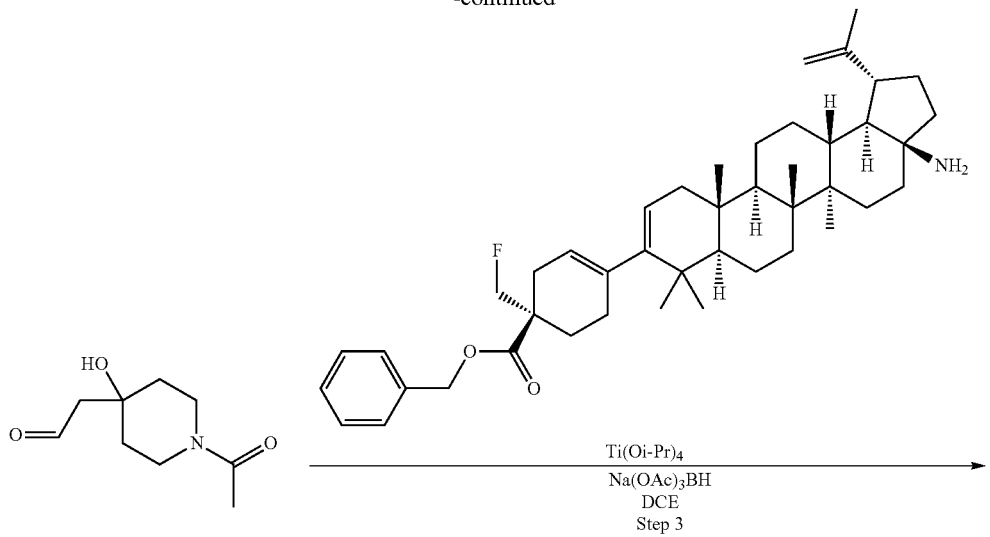
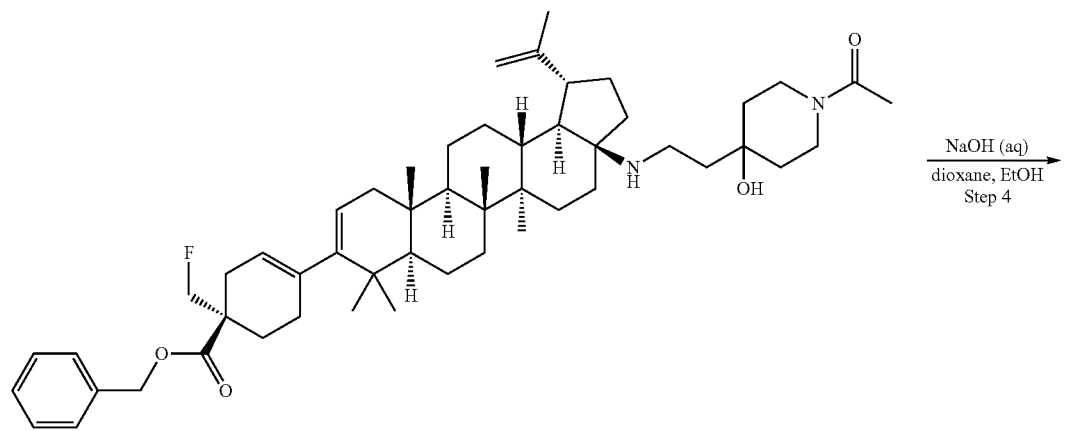
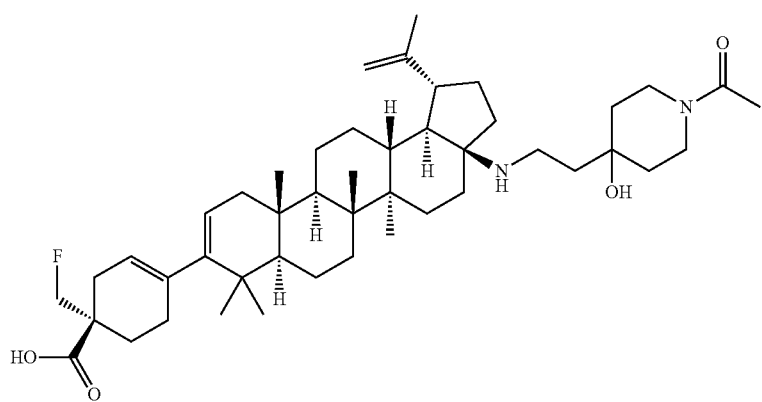
Example 2-15

Step 1. Preparation of 1-(4-allyl-4-hydroxypiperidin-1-yl)ethanone

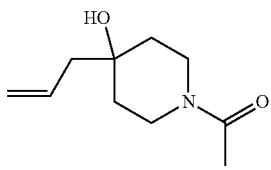

To a solution of 1-acetylpiperidin-4-one (1.00 g, 7.08 mmol) in THF (50 mL) at −10° C. (acetone/ice bath) was added allylmagnesium bromide (1 M in diethyl ether) (7.44 mL, 7.44 mmol). The reaction mixture was stirred at −10° C. for 30 min. The reaction was quenched by the addition of saturated NH$_4$Cl solution (50 mL). The mixture was transferred to a separatory funnel and the aqueous layer was extracted with ethyl acetate (3×50 mL). The combined organic layers were washed with brine (50 mL), dried over MgSO$_4$, filtered, and concentrated to afford 1-(4-allyl-4-hydroxypiperidin-1-yl)ethanone (836 mg, 4.56 mmol, 64% yield) as a brown oil. The product was used directly in the next step without further purification. $^1$H NMR (400 MHz, CHLOROFORM-d) δ 5.88 (ddt, J=17.2, 10.1, 7.6 Hz, 1H), 5.28-5.22 (m, 1H), 5.19 (ddt, J=17.1, 2.1, 1.2 Hz, 1H), 4.41-4.33 (m, 1H), 3.65-3.56 (m, 1H), 3.52-3.43 (m, 1H), 3.04 (ddd, J=13.4, 9.3, 6.1 Hz, 1H), 2.26 (d, J=7.8 Hz, 2H), 2.12 (s, 3H), 1.63-1.55 (m, 4H).

Step 2. Preparation of 2-(1-acetyl-4-hydroxypiperidin-4-yl)acetaldehyde

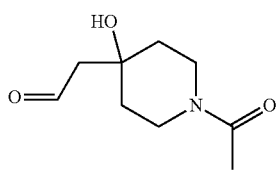

To a solution of 1-(4-allyl-4-hydroxypiperidin-1-yl)ethanone (280 mg, 1.528 mmol) in dioxane (12 mL) and water (3 mL) at 0° C. was added 2,6-lutidine (0.356 mL, 3.06 mmol), osmium tetroxide (2.5% in t-BuOH) (0.384 mL, 0.031 mmol), and sodium periodate (1307 mg, 6.11 mmol). The cooling bath was removed and the reaction mixture was stirred at room temperature for 2.5 h. The mixture was transferred to a separatory funnel containing water (10 mL) and saturated aqueous NaHCO$_3$ solution (10 mL). The aqueous layer was extracted with 5% methanol in chloroform (8×20 mL). The combined organic layers were washed with brine (20 mL), dried over MgSO$_4$, filtered, and concentrated. The product was purified by column chromatography on silica gel (4%→10% methanol in CH$_2$Cl$_2$; 24 g column) to afford 2-(1-acetyl-4-hydroxypiperidin-4-yl)acetaldehyde (48.6 mg, 0.262 mmol, 17% yield) as a colorless oil. $^1$H NMR showed that the product was not completely pure. The product was used directly in the next step. $^1$H NMR (400 MHz, CHLOROFORM-d) δ 9.88 (t, J=1.0 Hz, 1H), 4.41-4.33 (m, 1H), 3.61-3.56 (m, 1H), 3.56-3.45 (m, 3H), 3.12-3.00 (m, 1H), 2.11 (s, 3H), 1.87-1.76 (m, 2H), 1.54 (tdd, J=12.8, 8.0, 4.9 Hz, 2H).

Step 3. Preparation of (S)-benzyl 4-((1R,3aS,5aR,5bR,7aR,11aS,11bR,13aR,13bR)-3a-((2-(1-acetyl-4-hydroxypiperidin-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate

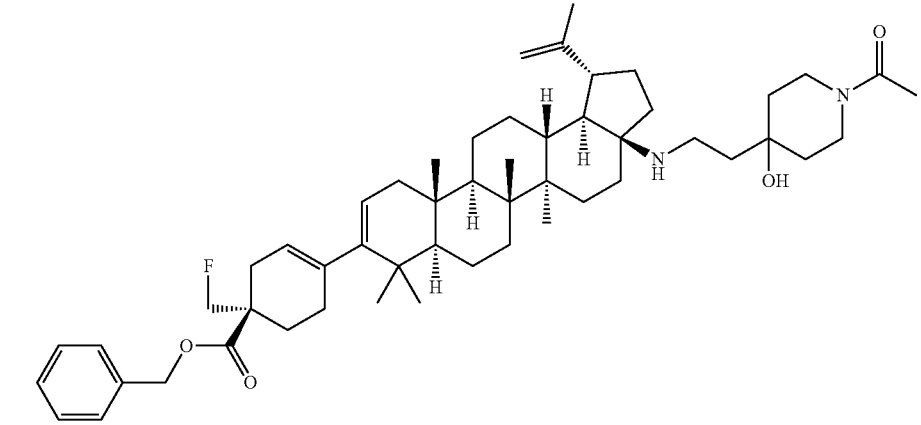

To a solution of (S)-benzyl 4-((1R,3aS,5aR,5bR,7aR,11aS,11bR,13aR,13bR)-3a-amino-5a,5b,8,8,11a-pentamethyl-1-(prop-1-en-2-yl) 2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (50 mg, 0.076 mmol) and 2-(1-acetyl-4-hydroxypiperidin-4-yl)acetaldehyde (42.4 mg, 0.229 mmol) in DCE (0.6 mL) was added titanium(IV) isopropoxide (0.067 mL, 0.229 mmol). The mixture was stirred at room temperature for 1 h. Sodium triacetoxyborohydride (48.5 mg, 0.229 mmol) was added and the mixture was stirred at room temperature overnight. The mixture was transferred to a separatory funnel containing saturated aqueous sodium bicarbonate solution (5 mL). The aqueous layer was extracted with dichloromethane (3×10 mL). The combined organic layers were washed with brine (5 mL), dried over MgSO$_4$, filtered, and concentrated. The product was purified by column chromatography on silica gel (10% 9:1 acetone:methanol/ 90% hexanes→40% 9:1 acetone:methanol/60% hexanes; 24 g column, λ=220 nm) to afford (S)-benzyl 4-((1R,3aS,5aR, 5bR,7aR,11aS,11bR,13aR,13bR)-3a-((2-(1-acetyl-4-hydroxypiperidin-4-yl)ethyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)-1-(fluoromethyl)cyclohex-3-enecarboxylate (46 mg, 0.056 mmol, 73% yield) as a colorless foam: $^1$H NMR (500 MHz, CHLOROFORM-d) δ 7.40-7.31 (m, 5H), 5.33 (br. s., 1H), 5.22-5.16 (m, 2H), 5.15-5.10 (m, 1H), 4.74 (s, 1H), 4.62 (d, J=1.2 Hz, 1H), 4.60-4.55 (m, 1H), 4.52-4.46 (m, 1H), 4.38 (d, J=13.1 Hz, 1H), 3.64-3.49 (m, 2H), 3.15-3.05 (m, 1H), 2.87-2.70 (m, 2H), 2.64-2.52 (m, 2H), 2.19-0.87 (m, 33H), 2.11 (s, 3H), 1.70 (s, 3H), 1.07 (s, 3H), 0.98 (s, 3H), 0.92 (s, 3H), 0.90 (s, 3H), 0.86 (s, 3H); LC/MS m/e 825.6 [(M+H)$^+$, calcd for $C_{53}R_{78}FN_2O_4$ 825.6], $t_R$=4.74 min (method 2-3).

Step 4. A solution of (S)-benzyl 4-((1R,3aS,5aR,5bR,7aR, 11aS,11bR,13aR,13bR)-3a-((2-(1-acetyl-4-hydroxypiperidin-4-yl)ethyl)amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)-1-(fluoromethyl)cyclohex-3-enecarboxylate (45 mg, 0.055 mmol) in 1,4-dioxane (0.7 mL) and EtOH (0.35 mL) was treated with sodium hydroxide (2M aq) (0.136 mL, 0.273 mmol). The reaction mixture was heated at 50° C. for 2 h then at 65° C. for 1 h. The mixture was cooled to room temperature, was filtered through a syringe filter, and was purified by reverse phase preparative HPLC (method 2-1). The organic solvent was evaporated on the rotovapor and the aqueous mixture was lyophilized to afford (S)-4-((1R,3aS, 5aR,5bR,7aR,11aS,11bR,13aR,13bR)-3a-((2-(1-acetyl-4-hydroxypiperidin-4-yl)ethyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)-1-(fluoromethyl)cyclohex-3-enecarboxylic acid•TFA (34 mg, 73% yield) as a white amorphous solid: $^1$H NMR (500 MHz, Acetic Acid-d$_4$) δ 5.39 (br. s., 1H), 5.25 (d, J=5.0 Hz, 1H), 4.83 (br. s., 1H), 4.73 (s, 1H), 4.64-4.57 (m, 1H), 4.55-4.47 (m, 1H), 4.43-4.28 (m, 1H), 3.78-3.67 (m, 1H), 3.66-3.52 (m, 1H), 3.47-3.35 (m, 2H), 3.26-3.10 (m, 1H), 2.92-2.77 (m, 1H), 2.61 (d, J=17.2 Hz, 1H), 2.39-1.10 (m, 33H), 2.18 (s, 3H), 1.75 (s, 3H), 1.17 (s, 3H), 1.10 (s, 3H), 1.00 (s, 3H), 0.99 (s, 3H), 0.95 (s, 3H); LC/MS m/e 735.6 [(M+H)$^+$, calcd for $C_{46}H_{76}FN_2O_4$ 739.6], $t_R$=4.27 min (method 2-2); HPLC (method 2-1): $t_R$=18.86 min; HPLC (method 2-2): $t_R$=19.90 min.

Preparation of 2-((trans)-1,4-dihydroxy-4-methylcyclohexyl)acetaldehyde and 2-((cis)-1,4-dihydroxy-4-methylcyclohexyl)acetaldehyde

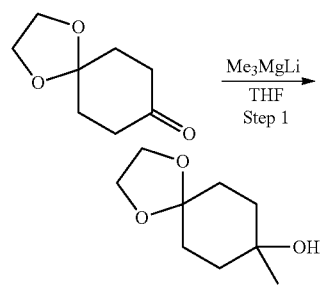

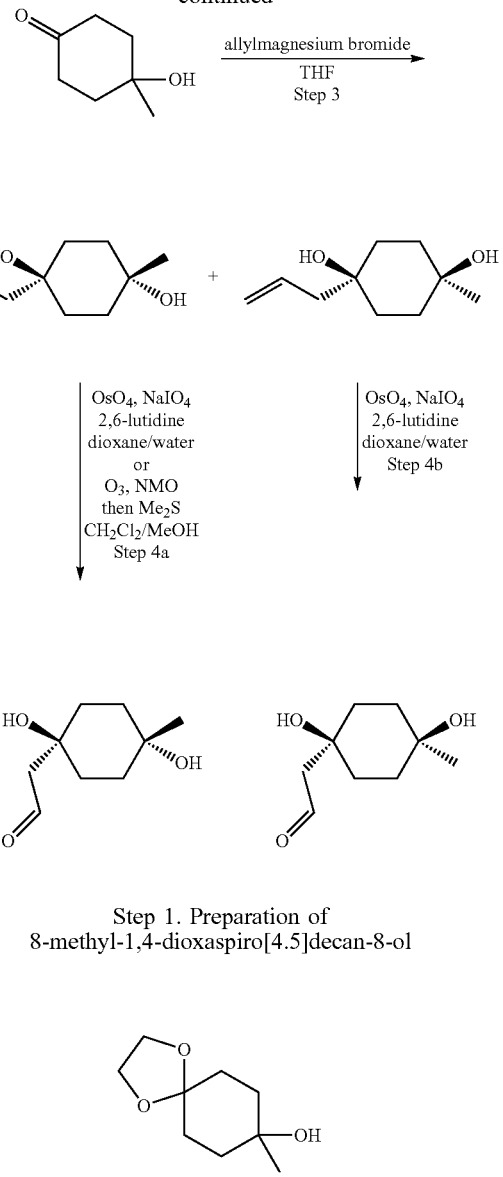

Step 1. Preparation of 8-methyl-1,4-dioxaspiro[4.5]decan-8-ol

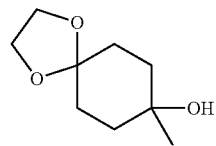

To THF (100 mL) in a round bottom flask at −78° C. under N$_2$ was added methyllithium (48.0 mL, 77 mmol) and methylmagnesium bromide (12.81 mL, 38.4 mmol) via syringe. After stirring at −78° C. for 1 h, 1,4-dioxaspiro[4.5]decan-8-one (5.00 g, 32.0 mmol) in THF (50 mL) was added via cannula. The reaction mixture was stirred at −78° C. for 1.5 h. The reaction was quenched by the addition of saturated aqueous NH$_4$Cl solution (100 mL). The mixture was transferred to a separatory funnel containing water (50 mL) and the aqueous layer was extracted with ethyl acetate (3×150 mL). The combined organic layers were washed with brine (100 mL), dried over MgSO$_4$, filtered, and concentrated to afford 8-methyl-1,4-dioxaspiro[4.5]decan-8-ol (5.47 g, 99% yield). The product was used in the next step without further purification. $^1$H NMR (400 MHz, CHLOROFORM-d) δ 4.03-3.91 (m, 4H), 1.97-1.84 (m, 2H), 1.79-1.56 (m, 6H), 1.28 (s, 3H), 1.17 (s, 1H); $^{13}$C NMR (100 MHz, CHLOROFORM-d) δ 108.27, 68.52, 63.87, 63.81, 36.33, 30.47, 29.39.

Step 2. Preparation of 4-hydroxy-4-methylcyclohexanone

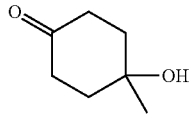

To a solution of 8-methyl-1,4-dioxaspiro[4.5]decan-8-ol (5.26 g, 30.5 mmol) in acetone (40 mL) and water (60 mL) at room temperature was added 4 M HCl (22.91 mL, 92 mmol). The reaction mixture was heated at 40° C. for 14 h. The mixture was cooled to room temperature and was neutralized by the addition of solid sodium carbonate. The acetone was removed on the rotovapor and the aqueous layer was extracted with ethyl acetate (7×150 mL). The combined organic layers were dried over MgSO$_4$, filtered, and concentrated. The product was purified by column chromatography on silica gel (70% ethyl acetate in hexanes) to afford 4-hydroxy-4-methylcyclohexanone (3.27 g, 25.5 mmol, 84% yield) as a white solid: $^1$H NMR (400 MHz, CHLOROFORM-d) δ 2.80-2.68 (m, 2H), 2.30-2.20 (m, 2H), 2.04-1.94 (m, 2H), 1.92-1.80 (m, 2H), 1.56 (s, 1H), 1.39 (s, 3H); $^{13}$C NMR (100 MHz, CHLOROFORM-d) δ 211.55, 68.14, 38.40, 36.80, 29.51.

Step 3. Preparation of (trans)-1-allyl-4-methylcyclohexane-1,4-diol and (cis)-1-allyl-4-methylcyclohexane-1,4-diol

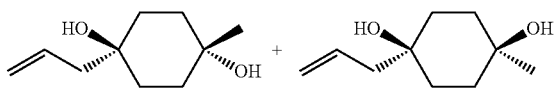

To a solution of 4-hydroxy-4-methylcyclohexanone (3.20 g, 24.97 mmol) in THF (200 mL) at 0° C. was added allylmagnesium bromide (1 M in diethyl ether) (62.4 mL, 62.4 mmol). The reaction mixture was stirred at 0° C. for 30 min. The reaction was quenched by the addition of saturated NH$_4$Cl solution (70 mL). The mixture was transferred to a separatory funnel and the aqueous layer was extracted with ethyl acetate (3×150 mL). The combined organic layers were washed with brine (50 mL), dried over MgSO$_4$, filtered, and concentrated. The product was purified by column chromatography on silica gel (30%→90% ethyl acetate in hexanes; 330 g column, 35 min gradient) to afford (trans)-1-allyl-4-methylcyclohexane-1,4-diol (1.90 g, 11.16 mmol, 45% yield) as a white solid and (cis)-1-allyl-4-methylcyclohexane-1,4-diol (2.35 g, 13.80 mmol, 55% yield) as a colorless oil, which solidified upon standing.

(trans)-1-allyl-4-methylcyclohexane-1,4-diol:
$^1$H NMR (400 MHz, CHLOROFORM-d) δ 5.92 (ddt, J=17.3, 10.1, 7.5 Hz, 1H), 5.23-5.12 (m, 2H), 2.26 (d, J=7.5 Hz, 2H), 1.85-1.71 (m, 4H), 1.55-1.43 (m, 4H), 1.28 (s, 3H); $^{13}$C NMR (100 MHz, CHLOROFORM-d) δ 133.08, 118.72, 69.66, 68.77, 47.59, 33.87, 32.29, 30.80.

The structure of (trans)-1-allyl-4-methylcyclohexane-1,4-diol was confirmed by X-ray crystallography.

(cis)-1-allyl-4-methylcyclohexane-1,4-diol $^1$H NMR (400 MHz, CHLOROFORM-d) δ 5.90 (ddt, J=17.2, 10.0, 7.5 Hz, 1H), 5.21-5.10 (m, 2H), 2.25 (dt, J=7.5, 1.0 Hz, 2H), 1.81-1.66 (m, 4H), 1.57-1.47 (m, 4H), 1.24 (s, 3H); $^{13}$C NMR (100 MHz, CHLOROFORM-d) δ 133.12, 118.59, 70.01, 69.34, 44.54, 35.55, 33.99, 26.76.

Step 4a. Preparation of 2-((trans)-1,4-dihydroxy-4-methylcyclohexyl)acetaldehyde (Method A)

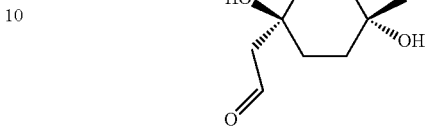

To a solution of (trans)-1-allyl-4-methylcyclohexane-1,4-diol (0.98 g, 5.76 mmol) in dioxane (40 mL) and water (10 mL) at 0° C. was added 2,6-lutidine (1.341 mL, 11.51 mmol), osmium tetroxide (4% in water) (0.704 mL, 0.115 mmol), and sodium periodate (4.92 g, 23.03 mmol). The reaction mixture was allowed to warm up to room temperature as the ice-water bath melted while stirring for 14 h. The mixture was transferred to a separatory funnel containing 1 N HCl (aq) (25 mL). The aqueous layer was extracted with ethyl acetate (20×50 mL). (It was difficult to extract the product from the aqueous layer.) The combined organic layers were washed with saturated NaHCO$_3$ solution (8 mL), dried over MgSO$_4$, filtered, and concentrated. TLC of the bicarbonate wash showed that some product went into the aqueous layer. This layer was concentrated. The residue was suspended in dichloromethane and, along with the residue from the organic extract, was purified by column chromatography on silica gel (70% ethyl acetate with 3% methanol/30% hexanes→100% ethyl acetate with 3% methanol; 120 g column) to afford 2-((trans)-1,4-dihydroxy-4-methylcyclohexyl)acetaldehyde (0.78 g, 4.53 mmol, 79% yield) as a white solid: $^1$H NMR (400 MHz, CHLOROFORM-d) δ 9.91 (t, J=1.6 Hz, 1H), 2.65 (d, J=1.8 Hz, 2H), 1.91-1.73 (m, 4H), 1.69-1.62 (m, 2H), 1.53-1.46 (m, 2H), 1.28 (s, 3H).

Step 4a. Alternate method for the preparation of 2-((trans)-1,4-dihydroxy-4-methylcyclohexyl)acetaldehyde (Method B)

(trans)-1-Allyl-4-methylcyclohexane-1,4-diol (1.00 g, 5.87 mmol) was dissolved in CH$_2$Cl$_2$ (50 mL) and MeOH (10 mL) in a 250 mL round bottom flask. N-methylmorpholine-N-oxide (NMO) (0.826 g, 7.05 mmol) was added and the mixture was cooled to −78° C. [Schwartz, C., Raible, J., Mott, K., Dussault, P. H. *Org. Lett.* 2006, 8, 3199-3201]. Ozone was bubbled through the reaction mixture until the solution was saturated with ozone (turned into a blue color) and several minutes thereafter (total time 10 min) Nitrogen was then bubbled through the reaction mixture until the disappearance of the blue color. Dimethyl sulfide (4.34 mL, 58.7 mmol) was then added and the reaction mixture was stirred at 0° C. for 2.5 h. The mixture was concentrated under vacuum. The product was purified by column chromatography on silica gel (50% ethyl acetate with 1% methanol/50% hexanes→95% ethyl acetate with 1% methanol/5% hexanes; 80 g column) to afford 2-((trans)-1,4-dihydroxy-4-methylcyclohexyl)acetaldehyde (937 mg, 5.44 mmol, 93% yield) as a white solid: $^1$H NMR (400 MHz, CHLOROFORM-d) δ 9.90 (s, 1H), 2.65 (s, 2H), 1.89-1.74 (m, 4H), 1.69-1.62 (m, 2H), 1.52-1.46 (m, 2H), 1.28 (s, 3H); $^{13}$C NMR (100 MHz, CHLOROFORM-d) δ 203.02, 69.65, 68.45, 55.15, 33.34, 32.46, 30.90.

Step 4b. Preparation of 2-((cis)-1,4-dihydroxy-4-methylcyclohexyl)acetaldehyde

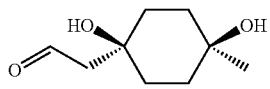

To a solution of (cis)-1-allyl-4-methylcyclohexane-1,4-diol (185 mg, 1.087 mmol) in dioxane (8 mL) and water (2 mL) at 0° C. was added 2,6-lutidine (0.253 mL, 2.173 mmol), osmium tetroxide (4% in water) (0.133 mL, 0.022 mmol), and sodium periodate (930 mg, 4.35 mmol). The reaction mixture was allowed to warm up to room temperature as the ice-water bath melted while stirring for 14 h. The mixture was transferred to a separatory funnel containing 1N HCl (aq) (15 mL). The aqueous layer was extracted with ethyl acetate (10 mL). After the first extraction, the aqueous layer was saturated with sodium chloride and the aqueous layer was extracted with ethyl acetate (17×10 mL). The combined organic layers were washed with saturated aqueous NaHCO$_3$ (2 mL), dried over MgSO$_4$, filtered, and concentrated. The product was purified by column chromatography on silica gel (8%→12% methanol in CH$_2$Cl$_2$; 40 g column) to afford 2-((cis)-1,4-dihydroxy-4-methylcyclohexyl)acetaldehyde (146 mg, 0.848 mmol, 78% yield) as a colorless oil: $^1$H NMR (400 MHz, CHLOROFORM-d) δ 9.91 (t, J=1.8 Hz, 1H), 2.65 (d, J=2.0 Hz, 2H), 1.91-1.76 (m, 4H), 1.63-1.46 (m, 4H), 1.26 (s, 3H).

Example 2-16

Preparation of (S)-4-((1R,3aS,5aR,5bR,7aR,11aS,11bR,13aR,13bR)-3a-((2-((trans)-1,4-dihydroxy-4-methylcyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid

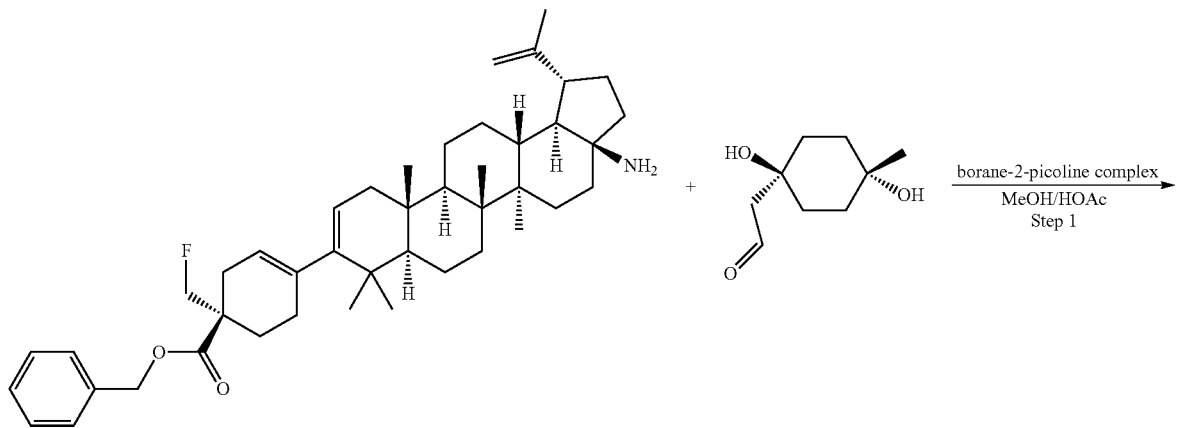

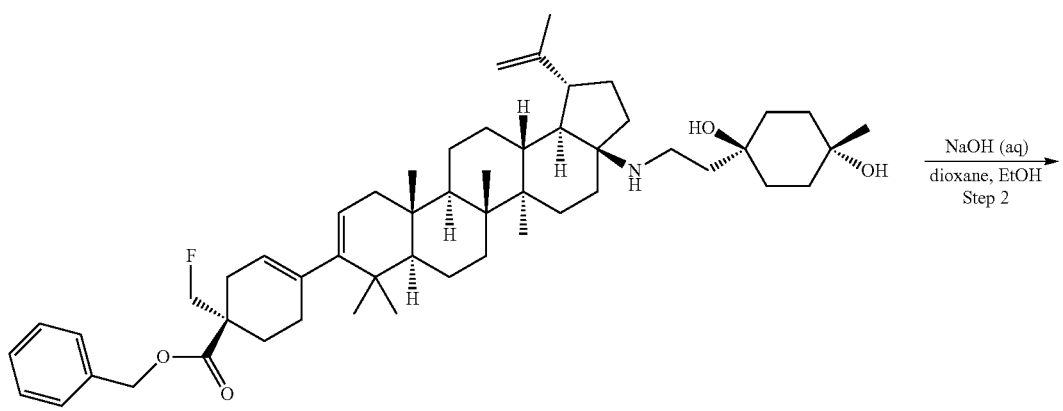

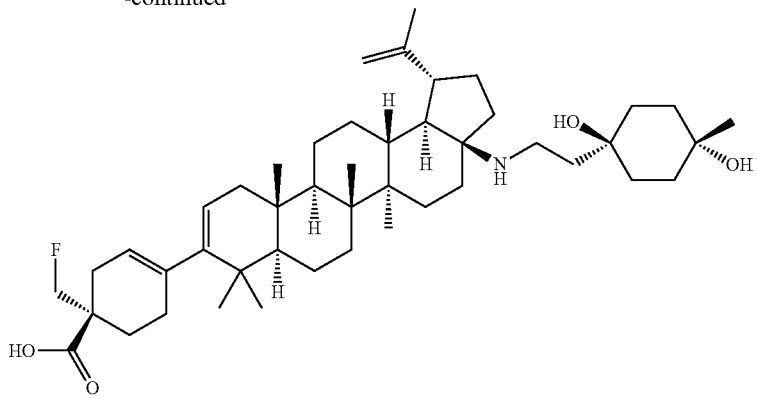

Example 2-16

Step 1. Preparation of (S)-benzyl 4-((1R,3aS,5aR, 5bR,7aR,11aS,11bR,13aR,13bR)-3a-((2-((trans)-1,4-dihydroxy-4-methylcyclohexyl)ethyl)amino)-5a,5b, 8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl)-1-(fluoromethyl)cyclohex-3-enecarboxylate

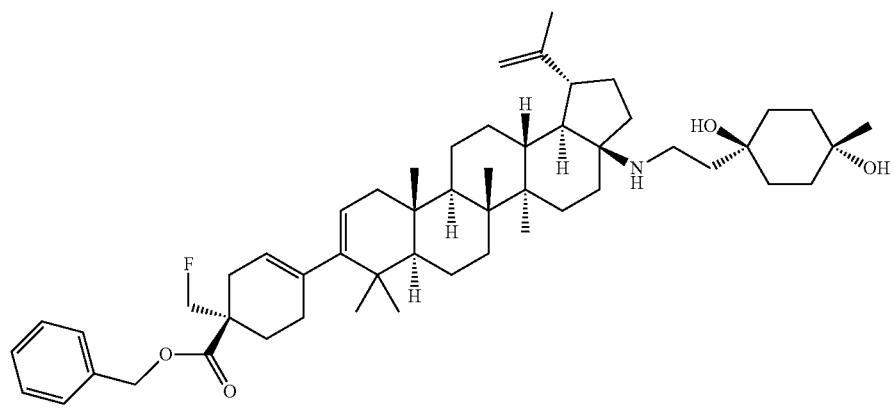

(S)-Benzyl 4-((1R,3aS,5aR,5bR,7aR,11aS,11bR,13aR, 13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (1.00 g, 1.524 mmol) and 2-((trans)-1,4-dihydroxy-4-methylcyclohexyl)acetaldehyde (0.420 g, 2.439 mmol) were dissolved in MeOH (12.5 mL) and acetic acid (2.5 mL). Borane-2-picoline complex (0.261 g, 2.439 mmol) was added and the mixture was stirred at room temperature for 14 h. Additional 2-((trans)-1,4-dihydroxy-4-methylcyclohexyl)acetaldehyde (0.131 g, 0.762 mmol, 0.5 eq) and borane-2-picoline complex (0.082 g, 0.762 mmol, 0.5 eq) were added to the reaction mixture and stirring was continued for 1 h. The reaction mixture was neutralized by the addition of water (5 mL) and solid sodium carbonate. The mixture was transferred to a separatory funnel containing saturated aqueous sodium bicarbonate solution (50 mL). The aqueous layer was extracted with ethyl acetate (7×50 mL). The combined organic layers were washed with brine (15 mL), dried over MgSO$_4$, filtered, and concentrated. The product was purified by column chromatography on silica gel (20% ethyl acetate with 5% methanol/80% hexanes→90% ethyl acetate with 5% methanol/10% hexanes; 120 g column, 25 min gradient) to afford (S)-benzyl 4-((1R,3aS,5aR,5bR,7aR,11aS,11bR, 13aR,13bR)-3a-((2-((trans)-1,4-dihydroxy-4-methylcyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)-1-(fluoromethyl)cyclohex-3-enecarboxylate (856 mg, 1.054 mmol, 69% yield) as a colorless foam: $^1$H NMR (500 MHz, CHLOROFORM-d) δ 7.40-7.31 (m, 5H), 5.33 (br. s., 1H), 5.23-5.16 (m, 2H), 5.13 (dd, J=6.2, 1.8 Hz, 1H), 4.74 (d, J=1.5 Hz, 1H), 4.62-4.56 (m, 2H), 4.53-4.46 (m, 1H), 2.85-2.78 (m, 1H), 2.77-2.70 (m, 1H), 2.66-2.55 (m, 2H), 2.18-1.02 (m, 37H), 1.69 (s, 3H), 1.30 (s, 3H), 1.06 (s, 3H), 0.98 (s, 3H), 0.91 (s, 3H), 0.91 (s, 3H), 0.86 (s, 3H); LC/MS m/e 812.6 [(M+H)$^+$, calcd for C$_{53}$H$_{79}$FNO$_4$ 812.6], $t_R$=4.89 min (method 2-3).

Step 2. A solution of (S)-benzyl 4-((1R,3aS,5aR,5bR,7aR, 11aS,11bR,13aR,13bR)-3a-((2-((trans)-1,4-dihydroxy-4-methylcyclohexyl)ethyl)amino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)-1-(fluoromethyl)cyclohex-3-enecarboxylate (401 mg, 0.494 mmol) in 1,4-dioxane (7.5 mL) and EtOH (2.5 mL) was treated with sodium hydroxide (2M aq) (1.234 mL, 2.469 mmol). The reaction mixture was heated at 70° C. for 2.5 h. The mixture was cooled to room temperature, was diluted with methanol (4 mL) (to dissolve the precipitate), was filtered through a syringe filter, and was purified by reverse phase preparative HPLC (method 2-4). The organic solvent was evaporated on the rotovapor and the aqueous mixture was lyophilized to afford (S)-4-((1R,3aS,5aR,5bR,7aR,11aS,11bR,13aR,13bR)-3a-((2-((trans)-1,4-dihydroxy-4-methylcyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid•TFA (267 mg, 0.316 mmol, 64% yield) as a white amorphous solid: $^1$H NMR (500 MHz, Acetic Acid-$d_4$) δ 5.39 (br. s., 1H), 5.27-5.22 (m, 1H), 4.82 (s, 1H), 4.72 (s, 1H), 4.66-4.57 (m, 1H), 4.55-4.44 (m, 1H), 3.42-3.35 (m, 2H), 2.89-2.81 (m, 1H), 2.61 (d, J=16.9 Hz, 1H), 2.31-1.34 (m, 35H), 1.75 (s, 3H), 1.30 (s, 3H), 1.17 (s, 3H), 1.15-1.11 (m, 2H), 1.09 (s, 3H), 1.00 (s, 3H), 0.99 (s, 3H), 0.95 (s, 3H); LC/MS m/e 722.6 [(M+H)$^+$, calcd for $C_{46}H_{73}FNO_4$ 722.6], $t_R$=4.36 min (method 2-2); HPLC (method 2-1): $t_R$=19.03 min; HPLC (method 2-2): $t_R$=20.26 min.

Example 2-17

Preparation of (R)-4-((1R,3aS,5aR,5bR,7aR,11aS,11bR,13aR,13bR)-3a-((2-((trans)-1,4-dihydroxy-4-methylcyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid

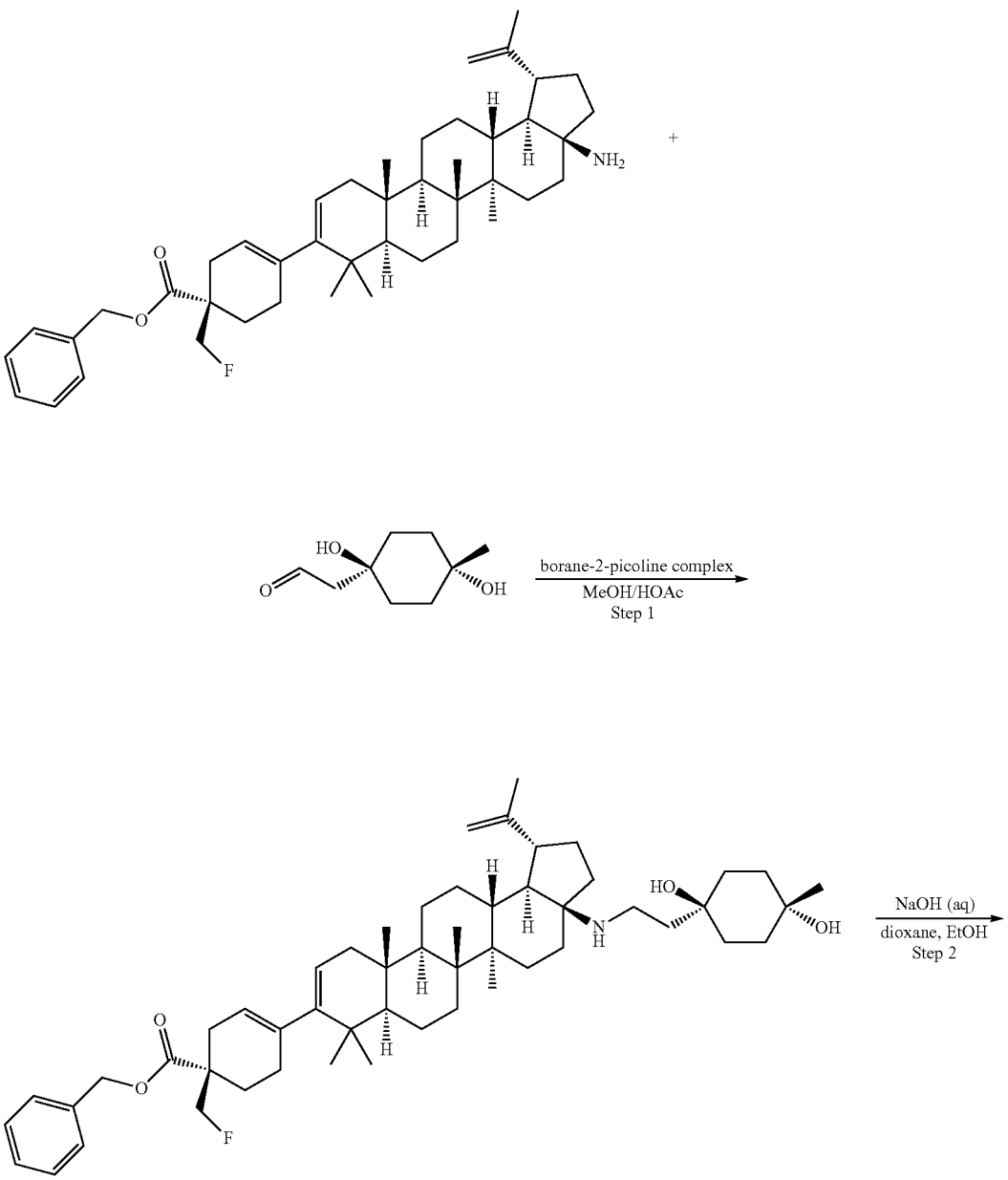

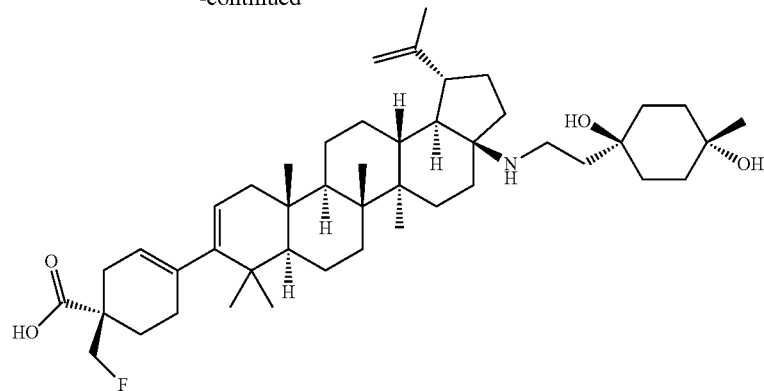

Example 2-17

Step 1. Preparation of (R)-benzyl 4-((1R,3aS,5aR, 5bR,7aR,11aS,11bR,13aR,13bR)-3a-((2-((trans)-1,4-dihydroxy-4-methylcyclohexyl)ethyl)amino)-5a,5b, 8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl)-1-(fluoromethyl)cyclohex-3-enecarboxylate

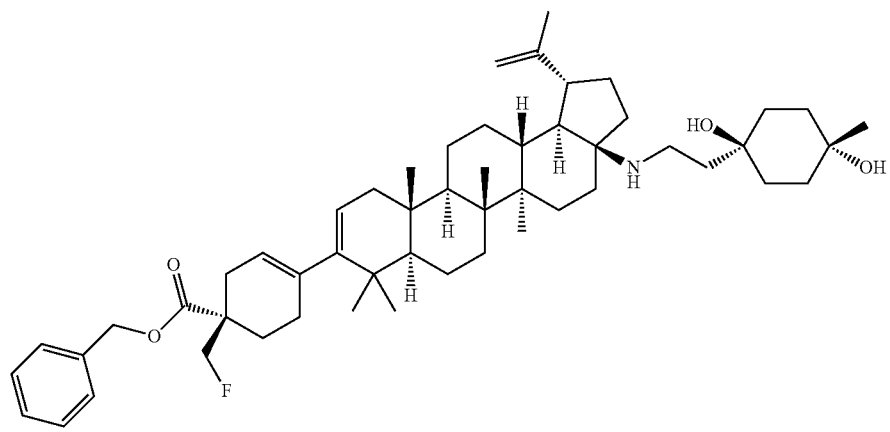

(R)-Benzyl 4-((1R,3aS,5aR,5bR,7aR,11aS,11bR,13aR, 13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (120 mg, 0.183 mmol) and 2-((trans)-1,4-dihydroxy-4-methylcyclohexyl) acetaldehyde (56.7 mg, 0.329 mmol) were dissolved in MeOH (1.5 mL) and acetic acid (0.3 mL). Borane-2-picoline complex (35.2 mg, 0.329 mmol) was added and the mixture was stirred at room temperature for 16 h. The mixture was transferred to a separatory funnel containing saturated aqueous sodium bicarbonate solution (20 mL) and saturated aqueous sodium carbonate solution (2 mL). The aqueous layer was extracted with dichloromethane (4×25 mL). The combined organic layers were washed with brine (15 mL), dried over MgSO$_4$, filtered, and concentrated. The product was purified by column chromatography on silica gel (20% ethyl acetate with 5% methanol/80% hexanes→90% ethyl acetate with 5% methanol/10% hexanes; 80 g column, 20 min gradient) to afford (R)-benzyl 4-((1R,3aS,5aR,5bR,7aR, 11aS,11bR,13aR,13bR)-3a-((2-((trans)-1,4-dihydroxy-4-methylcyclohexyl)ethyl)amino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)-1-(fluoromethyl)cyclohex-3-enecarboxylate (96.7 mg, 0.119 mmol, 65% yield) as a colorless foam: $^1$H NMR (500 MHz, CHLOROFORM-d) δ 7.39-7.31 (m, 5H), 5.33 (br. s., 1H), 5.22-5.15 (m, 2H), 5.11 (dd, J=6.1, 1.5 Hz, 1H), 4.73 (s, 1H), 4.62-4.55 (m, 2H), 4.52-4.45 (m, 1H), 2.83-2.69 (m, 2H), 2.65-2.53 (m, 2H), 2.21-0.87 (m, 37H), 1.69 (s, 3H), 1.29 (s, 3H), 1.05 (s, 3H), 0.97 (s, 3H), 0.93 (s, 3H), 0.88 (s, 3H), 0.86 (s, 3H); LC/MS m/e 812.6 [(M+H)$^+$, calcd for C$_{53}$H$_{79}$FNO$_4$ 812.6], t$_R$=4.58 min (method 2-3).

Step 2. A solution of (R)-benzyl 4-((1R,3aS,5aR,5bR, 7aR,11aS,11bR,13aR,13bR)-3a-((2-((trans)-1,4-dihydroxy-4-methylcyclohexyl)ethyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)-1-(fluoromethyl)cyclohex-3-enecarboxylate (95 mg, 0.117 mmol) in 1,4-dioxane (1.5 mL) and MeOH (0.5 mL) was treated with sodium hydroxide (2M aq) (0.292 mL, 0.585 mmol). The reaction mixture was heated at 70° C. for 4 h. The reaction was complete. The mixture was cooled to room temperature, was filtered through a syringe filter, and was purified by reverse phase preparative HPLC (method 2-4). The organic solvent was evaporated on the rotovapor and the aqueous mixture was lyophilized to afford (R)-4-((1R,3aS,5aR,5bR,7aR,11aS,11bR,13aR,13bR)-3a-((2-((trans)-1,4-dihydroxy-4-methylcyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid•TFA (40.8 mg, 0.049 mmol, 42% yield) as a white amorphous solid: $^1$H NMR (500 MHz, Acetic Acid-$d_4$) δ 5.39 (br. s., 1H), 5.25 (d, J=5.4 Hz, 1H), 4.83 (s, 1H), 4.72 (s, 1H), 4.66-4.57 (m, 1H), 4.55-4.47 (m, 1H), 3.43-3.36 (m, 2H), 2.90-2.82 (m, 1H), 2.62 (d, J=16.9 Hz, 1H), 2.38-2.28 (m, 1H), 2.26-1.35 (m, 34H), 1.75 (s, 3H), 1.31 (s, 3H), 1.17 (s, 3H), 1.14 (d, J=9.5 Hz, 2H), 1.10 (s, 3H), 1.02 (s, 3H), 0.98 (s, 3H), 0.95 (s, 3H); LC/MS m/e 722.6 [(M+H)$^+$, calcd for $C_{46}H_{73}FNO_4$ 722.6], $t_R$=4.34 min (method 2-2); HPLC (method 2-5): $t_R$=11.74 min; HPLC (method 2-6): $t_R$=11.29 min.

Example 2-18

Preparation of (S)-4-((1R,3aS,5aR,5bR,7aR,11aS,11bR,13aR,13bR)-3a-((2-((cis)-1,4-dihydroxy-4-methylcyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid

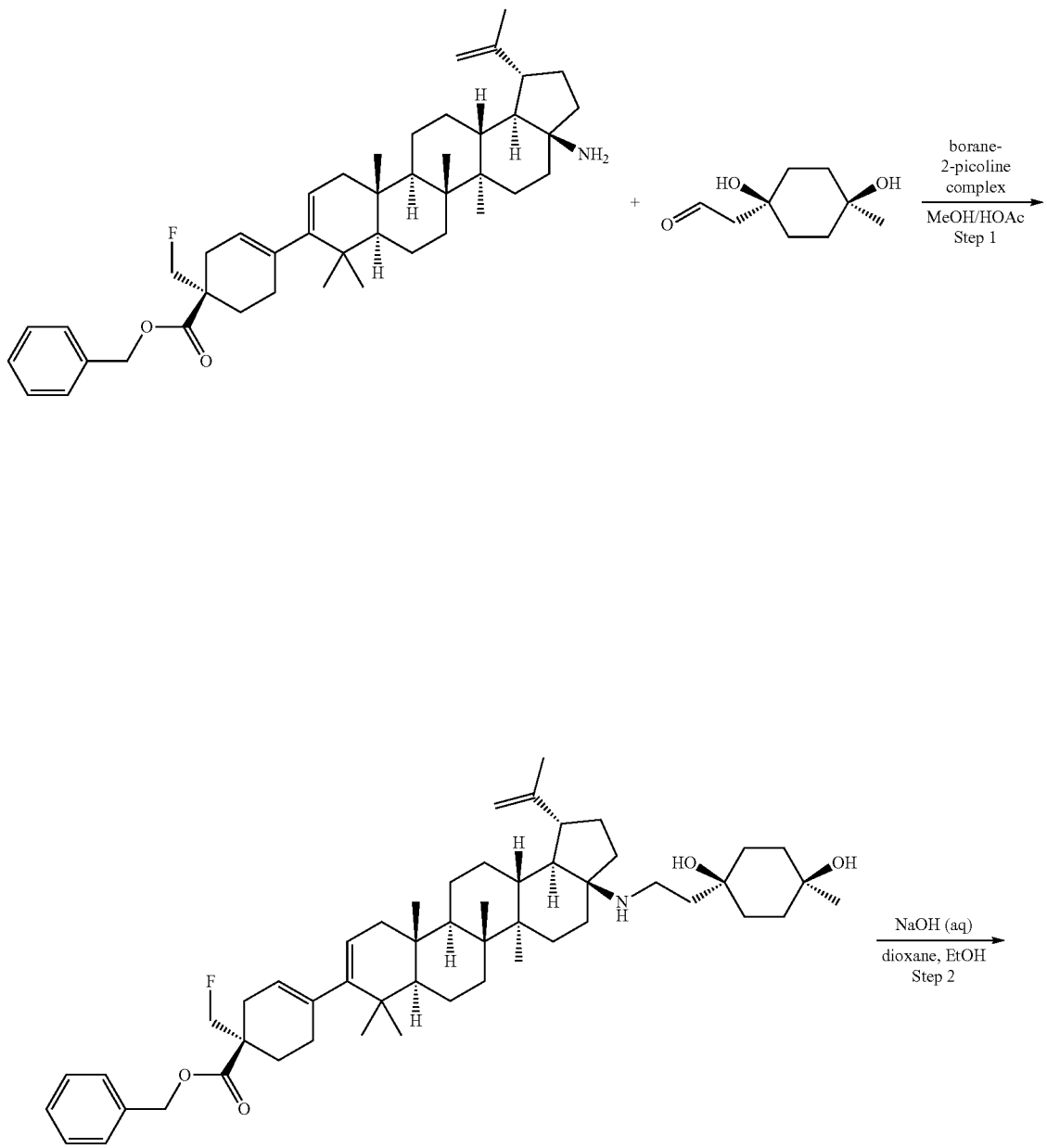

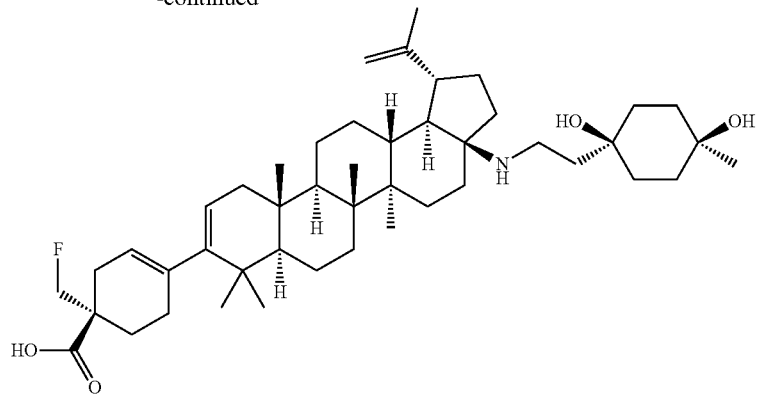

Example 2-18

Step 1. Preparation of (S)-benzyl 4-((1R,3aS,5aR, 5bR,7aR,11aS,11bR,13aR,13bR)-3a-((2-((cis)-1,4-dihydroxy-4-methylcyclohexyl)ethyl)amino)-5a,5b, 8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl)-1-(fluoromethyl)cyclohex-3-enecarboxylate 13aR,13bR)-3a-((2-((cis)-1,4-dihydroxy-4-methylcyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)-1-(fluoromethyl)cyclohex-3-enecarboxylate (72.5 mg, 0.089 mmol, 59% yield) as a white foam: $^1$H NMR (500 MHz, CHLOROFORM-d) δ 7.38-7.34 (m, 5H), 5.33 (br. s., 1H), 5.23-5.16 (m, 2H), 5.13 (dd, J=6.1, 1.5 Hz, 1H), 4.73 (d, J=1.7 Hz, 1H), 4.62-4.56 (m, 2H), 4.53-4.46 (m, 1H),

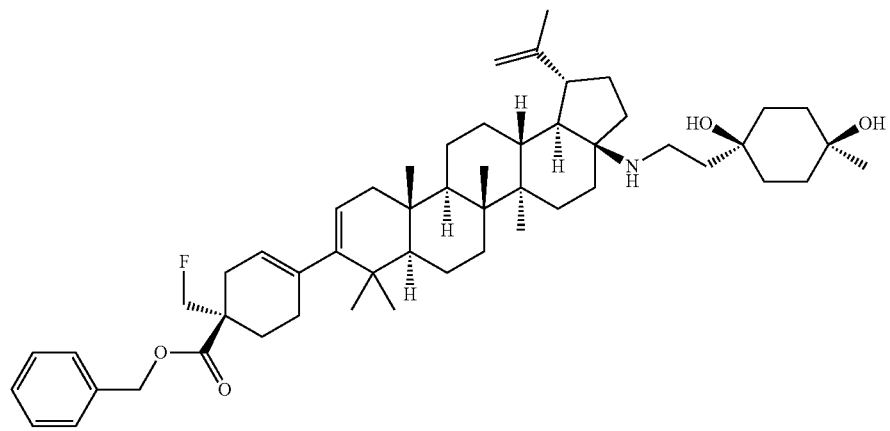

A mixture of (S)-benzyl 4-((1R,3aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)-1-(fluoromethyl)cyclohex-3-enecarboxylate (100 mg, 0.152 mmol), 2-((cis) 1,4-dihydroxy-4-methylcyclohexyl)acetaldehyde (52.5 mg, 0.305 mmol), and borane-2-picoline complex (32.6 mg, 0.305 mmol) in MeOH (1.4 mL) and acetic acid (0.35 mL) was stirred at room temperature for 18 h. The mixture was transferred to a separatory funnel containing saturated aqueous sodium bicarbonate solution (5 mL). The aqueous layer was extracted with dichloromethane (3×10 mL). The combined organic layers were washed with brine (5 mL), dried over MgSO$_4$, filtered, and concentrated. The product was purified by column chromatography on silica gel (10% 9:1 acetone:methanol/90% hexanes→30% 9:1 acetone:methanol/70% hexanes; 40 g column, λ=220 nm) to afford (S)-benzyl 4-((1R,3aS,5aR,5bR,7aR,11aS,11bR, 2.83-2.75 (m, 1H), 2.73-2.66 (m, 1H), 2.64-2.52 (m, 2H), 2.18-1.00 (m, 37H), 1.69 (s, 3H), 1.24 (s, 3H), 1.07 (s, 3H), 0.98 (s, 3H), 0.91 (s, 3H), 0.90 (s, 3H), 0.86 (s, 3H); LC/MS m/e 812.7 [(M+H)$^+$, calcd for C$_{53}$H$_{79}$FNO$_4$ 812.6], t$_R$=4.78 min (method 2-3).

Step 2. A solution of (S)-benzyl 4-((1R,3aS,5aR,5bR,7aR, 11aS,11bR,13aR,13bR)-3a-((2-((cis)-1,4-dihydroxy-4-methylcyclohexyl)ethyl)amino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)-1-(fluoromethyl)cyclohex-3-enecarboxylate (65 mg, 0.080 mmol) in 1,4-dioxane (1.0 mL) and EtOH (0.5 mL) was treated with sodium hydroxide (2M aq) (0.200 mL, 0.400 mmol). The reaction mixture was heated at 70° C. for 2 h. The mixture was cooled to room temperature, was filtered through a syringe filter, and was purified by reverse phase preparative HPLC (method 2-1). The product (37 mg)

contained a significant amount of an impurity (ca. 10%). The product was then repurified by reverse phase preparative HPLC (method 2-5) to afford (S)-4-((1R,3aS,5aR,5bR,7aR,11aS,11bR,13aR,13bR)-3a-((2-(((cis)-1,4-dihydroxy-4-methylcyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid•TFA (22.1 mg, 33% yield) as a white amorphous solid: $^1$H NMR (500 MHz, Acetic Acid-$d_4$) δ 5.39 (br. s., 1H), 5.25 (d, J=4.6 Hz, 1H), 4.83 (s, 1H), 4.72 (s, 1H), 4.64-4.56 (m, 1H), 4.55-4.46 (m, 1H), 3.44-3.37 (m, 1H), 3.36-3.28 (m, 1H), 2.91-2.82 (m, 1H), 2.61 (d, J=16.6 Hz, 1H), 2.31-1.11 (m, 37H), 1.75 (s, 3H), 1.27 (s, 3H), 1.17 (s, 3H), 1.09 (s, 3H), 1.00 (s, 3H), 0.99 (s, 3H), 0.95 (s, 3H); LC/MS m/e 722.6 [(M+H)$^+$, calcd for $C_{46}H_{73}FNO_4$ 722.6], $t_R$=4.34 min (method 2-2); HPLC (method 2-1): $t_R$=18.87 min; HPLC (method 2-2): $t_R$=20.20 min.

Preparation of 4-(methylsulfonyl)cyclohexanone (Route 1)

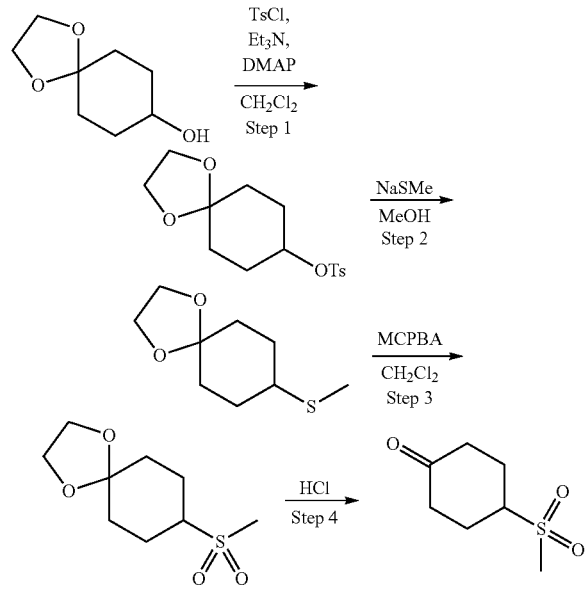

Step 1. Preparation of 1,4-dioxaspiro[4.5]decan-8-yl 4-methylbenzenesulfonate

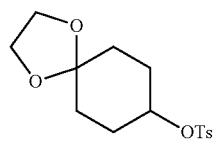 [SMILES: Cc1ccc(S(=O)(=O)OC2CCC3(CC2)OCCO3)cc1]

To a 0° C. solution of 1,4-dioxaspiro[4.5]decan-8-ol (10 g, 63.2 mmol), triethylamine (13.22 mL, 95.0 mmol), and N,N-dimethylpyridin-4-amine (0.772 g, 6.32 mmol) in $CH_2Cl_2$ (400 mL) was added portion wise 4-methylbenzene-1-sulfonyl chloride (13.26 g, 69.5 mmol). The reaction mixture was allowed to warm to room temperature while stirring for 16 hours. The reaction mixture was diluted with $CH_2Cl_2$ (400 mL) and was washed with water (2×400 mL). The combined organic layers were dried over $MgSO_4$, filtered and concentrated. The product was purified by column chromatography on silica gel (0%→30% ethyl acetate in hexanes; the crude product was divided in half and purified on two 330 g columns) to afford 1,4-dioxaspiro[4.5] decan-8-yl4-methylbenzenesulfonate (19.6 g, 62.7 mmol, 99% yield): $^1$H NMR (400 MHz, CDCl$_3$) δ 7.82 (d, J=8.3 Hz, 2H), 7.35 (d, J=8.0 Hz, 2H), 4.66 (tt, J=6.0, 3.0 Hz, 1H), 3.98-3.88 (m, 4H), 2.47 (s, 3H), 1.95-1.74 (m, 5H), 1.63-1.51 (m, 3H); LC/MS (ESI) m/e 335.2 [(M+Na)$^+$, calcd for $C_{15}H_{20}O_5SNa$ 335.1], $t_R$=2.06 min (method 2-1).

Step 2. Preparation of 8-(methylthio)-1,4-dioxaspiro[4.5]decane

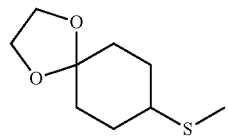

1,4-dioxaspiro[4.5]decan-8-yl4-methylbenzenesulfonate (19.6 g, 62.7 mmol) in ethanol (26.7 mL) was added to a solution of sodium thiomethoxide (13.19 g, 188 mmol) in MeOH (80 mL). The reaction mixture was heated at 80° C. for 16 h in a sealed pressure vessel. LC-MS showed the formation of the desired product. The reaction mixture was partitioned between ethyl acetate and water. The aqueous layer was extracted with ethyl acetate (3×250 mL) and the combined organic layers were concentrated under vacuum. The residue was partitioned between $CH_2Cl_2$ and sat. aq. sodium bicarbonate solution. The aq layer was extracted with additional $CH_2Cl_2$. The combined organic layers were dried over sodium sulfate, concentrated under vacuum and purified by column chromatography on silica gel (100% hexanes→25% ethyl acetate with 5% methanol/75% hexanes; 330 g column) to afford 8-(methylthio)-1,4-dioxaspiro[4.5]decane (9.6 g, 51.0 mmol, 81% yield) as a colorless oil: $^1$H NMR (400 MHz, CDCl$_3$) δ 3.93 (s, 4H), 2.62 (tt, J=9.9, 3.8 Hz, 1H), 2.08 (s, 3H), 2.02-1.93 (m, 2H), 1.87-1.78 (m, 2H), 1.72-1.52 (m, 4H); LC/MS (ESI) m/e 189.2 [(M+H)$^+$, calcd for $C_9H_{16}O_2S$ 189.1], $t_R$=1.91 min (method 2-1).

Step 3. Preparation of 8-(methylsulfonyl)-1,4-dioxaspiro[4.5]decane

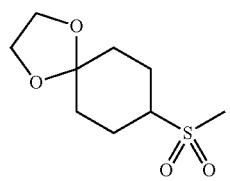

To a solution of 8-(methylthio)-1,4-dioxaspiro[4.5]decane (9.6 g, 51.0 mmol) in $CH_2Cl_2$ (400 mL) was added mCPBA (22.85 g, 102 mmol) at 0° C. The solution was warmed to room temperature and was stirred for 15 h. The reaction mixture was transferred to a separatory funnel containing 1 N aqueous sodium hydroxide (200 mL) and was extracted with ethyl acetate (3×200 mL). The combined organic layers were washed with brine, dried over Na$_2$SO$_4$, filtered and concentrated to afford 8-(methylsulfonyl)-1,4-dioxaspiro [4.5]decane (9.42 g, 42.8 mmol, 84% yield). The product was used in the next step without further purification. $^1$H NMR (400 MHz, CDCl$_3$) δ 3.99-3.95 (m, 4H), 2.90-2.80 (m, 1H), 2.85 (s, 3H), 2.29-2.19 (m, 2H), 1.98-1.83 (m, 4H), 1.67-1.56 (m, 2H).

Step 4. Preparation of 4-(methylsulfonyl)cyclohexanone

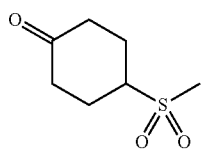

In a round bottom flask, HCl (71.1 mL, 427 mmol) was added to a solution of 8-(methylsulfonyl)-1,4-dioxaspiro [4.5]decane (9.4 g, 42.7 mmol). The reaction mixture was stirred overnight at rt for 16 h. The reaction mixture was partially concentrated in vacuum and was partitioned between EtOAc (200 mL) and water (200 mL). The aq layer was extracted with EtOAc (3×200 mL). The combined organic layers were washed with saturated aqueous sodium bicarbonate solution, brine, dried over MgSO$_4$, filtered, and concentrated under vacuum. The crude product was purified by column chromatography on silica gel (70% ethyl acetate with 1% methanol/30% hexanes→100% ethyl acetate with 1% methanol; 330 g column) to afford 4-(methylsulfonyl) cyclohexanone (4.7 g, 26.7 mmol, 63% yield): $^1$H NMR (400 MHz, CDCl$_3$) δ 3.35-3.21 (m, 1H), 2.92 (s, 3H), 2.65-2.56 (m, 2H), 2.54-2.35 (m, 4H), 2.16-2.01 (m, 2H).

Alternate method for the preparation of 4-(methylsulfonyl)cyclohexanone (Route 2)

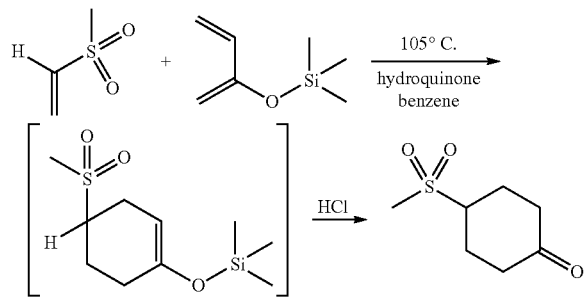

To a solution of (methylsulfonyl)ethene (10.0 g, 94 mmol) in benzene (50 mL) was added (buta-1,3-dien-2-yloxy) trimethylsilane (14.07 g, 99 mmol) and hydroquinone (20 mg, 0.182 mmol). The mixture was degassed several times at −78° C. prior to heating. The contents were sealed and heated at 105° C. for 48 hours. The reaction was analyzed by NMR in CDCl$_3$ that showed about 10% of the vinyl sulfone residue. Additional (buta-1,3-dien-2-yloxy)trimethylsilane (4 mL) was added and heating resumed for another 48 hours. The reaction mixture was evaporated to a thick gum under vacuum at room temperature (−19° C.). The mixture was rediluted with acetone (250 mL) resulting in the formation of a clear solution. The mixture was chilled in an ice bath until cold. 4 mL of 0.25 N HCl (pre-chilled in the same ice-bath) was added resulting in the formation a cloudy mixture, which became clear after 15 minutes of stirring at 0° C., and then returned to a cloudy state in another 10 minutes, it remained turbid for the rest of stirring period. The acetone solution was filtered through a short bed of silica gel type-H after a total reaction time of about one hour, and was then washed with more acetone. The filtrate was concentrated on the rotovapor at 19° C. bath temperature. The crude product was sub-divided into two parts, 7.75 gm each, for purification. The product was purified by column chromatography on silica gel (30% ethyl acetate→100% ethyl acetate in hexanes; two 330 g columns) to afford 4-(methylsulfonyl)cyclohexanone (16.7 g, 100% yield) as a white solid: $^1$H NMR (400 MHz, CHLOROFORM-d) δ 3.29 (tt, J=11.0, 3.9 Hz, 1H), 2.94 (s, 3H), 2.73-2.62 (m, 2H), 2.58-2.37 (m, 4H), 2.15 (qd, J=11.9, 4.5 Hz, 2H).

Preparation of 2-(cis-1-hydroxy-4-(methylsulfonyl) cyclohexyl)acetaldehyde and 2-(trans-1-hydroxy-4-(methylsulfonyl)cyclohexyl)acetaldehyde

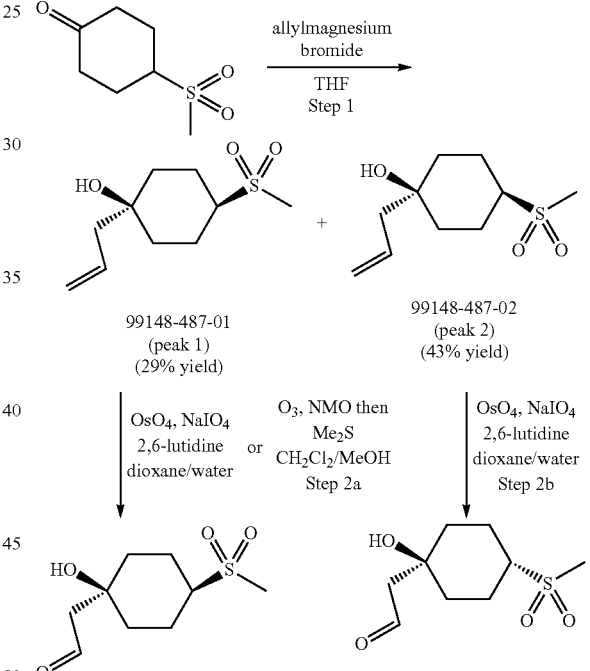

Step 1. Preparation of (cis)-1-allyl-4-(methylsulfonyl)cyclohexanol and (trans)-1-allyl-4-(methylsulfonyl)cyclohexanol

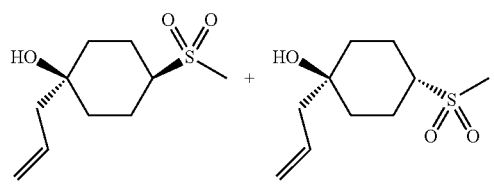

To a solution of 4-(methylsulfonyl)cyclohexanone (1.03 g, 5.84 mmol) in THF (40 mL) at 0° C. was added via cannula allylmagnesium bromide (7.60 mL, 7.60 mmol). The reaction mixture was stirred at 0° C. for 30 min. The reaction was quenched by the addition of saturated NH$_4$Cl solution (25 mL). The mixture was transferred to a separatory funnel and the aqueous layer was extracted with ethyl acetate (5×50 mL). The combined organic layers were washed with brine (20 mL), dried over MgSO$_4$, filtered, and concentrated. The product was purified by column chromatography on silica gel (70% ethyl acetate with 1% methanol/30% hexanes→100% ethyl acetate with 1% methanol; 40 g column) to afford (cis)-1-allyl-4-(methylsulfonyl)cyclohexanol (374 mg, 1.713 mmol, 29% yield) as a white solid and (trans)-1-allyl-4-(methylsulfonyl)cyclohexanol (551 mg, 2.52 mmol, 43% yield) as a colorless oil.

(cis)-1-allyl-4-(methylsulfonyl)cyclohexanol $^1$H NMR (400 MHz, CDCl$_3$) δ 5.96-5.79 (m, 1H), 5.26-5.21 (m, 1H), 5.18 (ddt, J=17.1, 2.1, 1.2 Hz, 1H), 2.85 (s, 3H), 2.80 (tt, J=12.5, 3.6 Hz, 1H), 2.25 (d, J=7.5 Hz, 2H), 2.15-2.07 (m, 2H), 1.97 (qd, J=13.0, 3.8 Hz, 2H), 1.88-1.81 (m, 2H), 1.52-1.42 (m, 2H); $^{13}$C NMR (100 MHz, CDCl$_3$) δ 132.50, 120.02, 69.06, 62.26, 47.86, 36.85, 35.67, 21.13.

The structure of (cis)-1-allyl-4-(methylsulfonyl)cyclohexanol was confirmed by X-ray crystallography.

(trans)-1-allyl-4-(methylsulfonyl)cyclohexanol $^1$H NMR (400 MHz, CDCl$_3$) δ 5.88 (ddt, J=17.2, 10.1, 7.4 Hz, 1H), 5.28-5.16 (m, 2H), 2.98-2.91 (m, 1H), 2.90 (s, 3H), 2.35 (d, J=7.0.5 Hz, 2H), 2.23-2.14 (m, 2H), 2.02-1.93 (m, 2H), 1.90-1.78 (m, 2H), 1.57-1.46 (m, 2H); $^{13}$C NMR (100 MHz, CDCl$_3$) δ 132.62, 120.19, 69.20, 62.41, 48.00, 36.98, 35.83, 21.29.

Step 2a. Preparation of 2-((cis)-1-hydroxy-4-(methylsulfonyl)cyclohexyl)acetaldehyde (Method A)

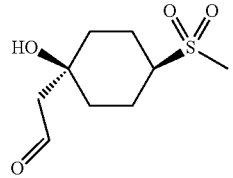

To a solution of (cis)-1-allyl-4-(methylsulfonyl)cyclohexanol (125 mg, 0.573 mmol) in dioxane (4.4 mL) and water (1.1 mL) at 0° C. was added 2,6-lutidine (0.133 mL, 1.145 mmol), osmium tetroxide (4% in water) (0.070 mL, 0.011 mmol), and sodium periodate (490 mg, 2.290 mmol). The reaction mixture was allowed to warm up to room temperature as the ice-water bath melted while stirring for 14 h. The mixture was transferred to a separatory funnel containing 1 N HCl(aq) (10 mL). The aqueous layer was extracted with ethyl acetate (20×15 mL). (It was difficult to extract the product from the aqueous layer.) The combined organic layers were washed with saturated NaHCO$_3$ solution (8 mL), dried over MgSO$_4$, filtered, and concentrated. TLC of the bicarbonate wash showed that some product went into the aqueous layer. This layer was concentrated. The residue was suspended in dichloromethane and, along with the residue from the organic extract, was purified by column chromatography on silica gel (80% ethyl acetate with 3% methanol/20% hexanes→100% ethyl acetate with 3% methanol; 40 g column) to afford 2-((cis)-1-hydroxy-4-(methylsulfonyl)cyclohexyl)acetaldehyde (94.4 mg, 0.429 mmol, 75% yield) as a colorless oil which solidified upon standing: $^1$H NMR (400 MHz, CDCl$_3$) δ 9.87 (t, J=1.3 Hz, 1H), 2.85 (s, 3H), 2.82-2.75 (m, 1H), 2.68 (d, J=1.0 Hz, 2H), 2.13-1.98 (m, 6H), 1.50-1.39 (m, 2H).

Step 2a. Preparation of 2-((cis)-1-hydroxy-4-(methylsulfonyl)cyclohexyl)acetaldehyde (Method B)

(trans)-1-Allyl-4-(methylsulfonyl)cyclohexanol (3.4 g, 15.57 mmol) was dissolved in CH$_2$Cl$_2$ (160 mL) and MeOH (32.0 mL) in a 500 mL round bottom flask. N-Methylmorpholine-N-oxide (NMO) (2.189 g, 18.69 mmol) was added and the mixture was cooled to −78° C. [Schwartz, C., Raible, J., Mott, K., Dussault, P. H. Org. Lett. 2006, 8, 3199-3201]. Ozone was bubbled through the reaction mixture until the solution was saturated with ozone (turned into a blue color) and several minutes thereafter (total time 25 min) Nitrogen was then bubbled through the reaction mixture until the disappearance of the blue color. Dimethyl sulfide (11.52 mL, 156 mmol) was then added and the reaction mixture was stirred at 0° C. for 16 h. The mixture was concentrated under vacuum. The product was purified by column chromatography on silica gel (50% ethyl acetate with 1% methanol/50% hexanes→95% ethyl acetate with 1% methanol/5% hexanes; 330 g column) to afford 2-((1s,4s)-1-hydroxy-4-(methylsulfonyl)cyclohexyl)acetaldehyde (3.31 g, 15.03 mmol, 96% yield) as a white solid: $^1$H NMR (400 MHz, CHLOROFORM-d) δ 9.87 (t, J=1.1 Hz, 1H), 2.85 (s, 3H), 2.82-2.76 (m, 1H), 2.67 (d, J=1.3 Hz, 2H), 2.13-1.98 (m, 6H), 1.50-1.38 (m, 2H); $^{13}$C NMR (101 MHz, CHLOROFORM-d) δ 202.5, 68.9, 61.9, 54.9, 36.8, 35.9, 20.8.

Step 2b. Preparation of 2-((trans)-1-hydroxy-4-(methylsulfonyl)cyclohexyl)acetaldehyde

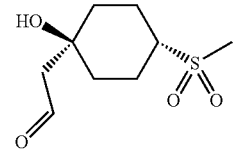

To a solution of (trans)-1-allyl-4-(methylsulfonyl)cyclohexanol (242 mg, 1.108 mmol) in dioxane (10 mL) and water (2.5 mL) at 0° C. was added 2,6-lutidine (0.258 mL, 2.217 mmol), osmium tetroxide (4% in water) (0.135 mL, 0.022 mmol), and sodium periodate (948 mg, 4.43 mmol). The reaction mixture was allowed to warm up to room temperature as the ice-water bath melted while stirring for 14 h. The mixture was transferred to a separatory funnel containing 1 N HCl (aq) (10 mL). The aqueous layer was extracted with ethyl acetate (20×20 mL). (It was difficult to extract the product from the aqueous layer.) The combined organic layers were washed with saturated NaHCO$_3$ solution (8 mL), dried over MgSO$_4$, filtered, and concentrated. TLC of the bicarbonate wash showed that some product went into the aqueous layer. This layer was concentrated. The residue was suspended in dichloromethane and, along with the residue from the organic extract, was purified by column chromatography on silica gel (80% ethyl acetate with 3% methanol/20% hexanes→100% ethyl acetate with 3% methanol; 40 g column) to afford 2-((trans)-1-hydroxy-4-(methylsulfonyl)cyclohexyl)acetaldehyde (191 mg, 0.867 mmol, 78% yield) as a colorless oil: $^1$H NMR (400 MHz, CDCl$_3$) δ 9.89 (t, J=1.3 Hz, 1H), 3.13 (br. s., 1H), 3.02-2.93 (m, 1H), 2.91 (s, 3H), 2.79 (d, J=1.3 Hz, 2H), 2.29-2.17 (m, 2H), 2.13-2.04 (m, 2H), 1.92-1.78 (m, 2H), 1.68-1.57 (m, 2H).

Example 2-19

Preparation of (S)-1-(fluoromethyl)-4-((1R,3aS,5aR,5bR,7aR,11aS,11bR,13aR,13bR)-3a-((2-((cis)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid

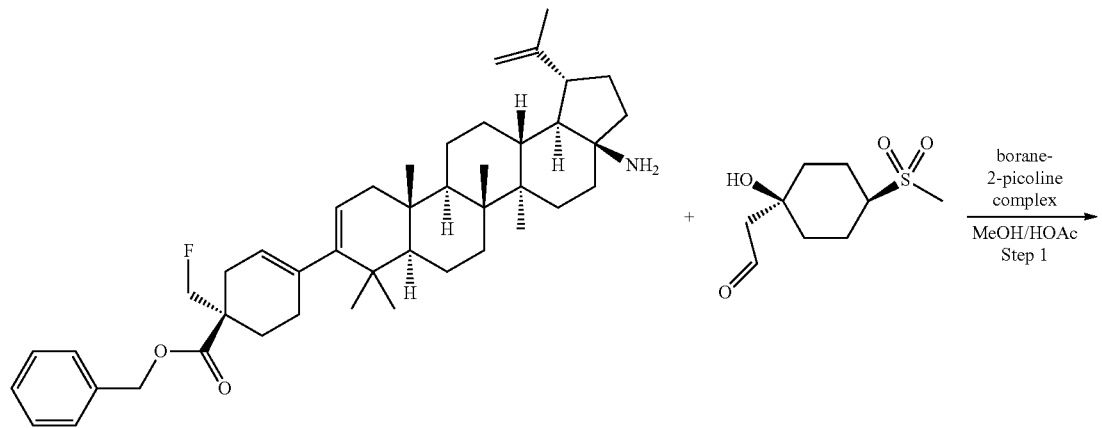

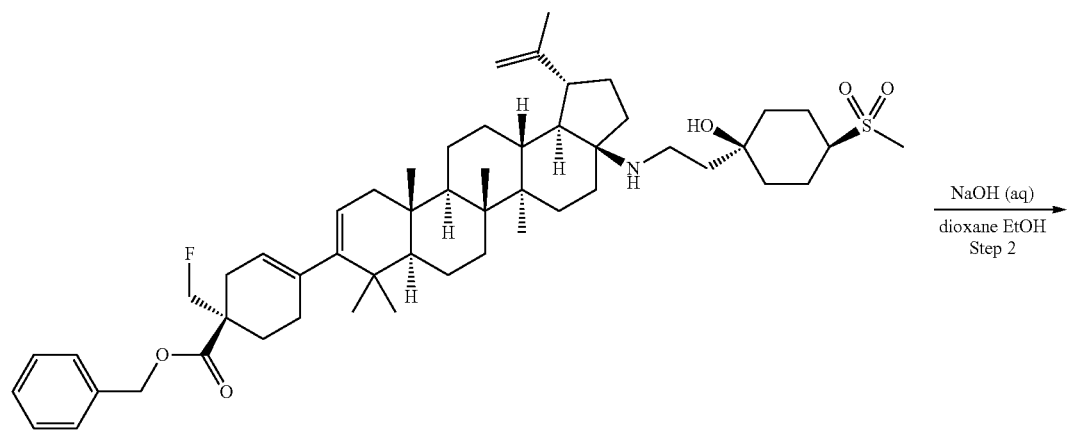

-continued

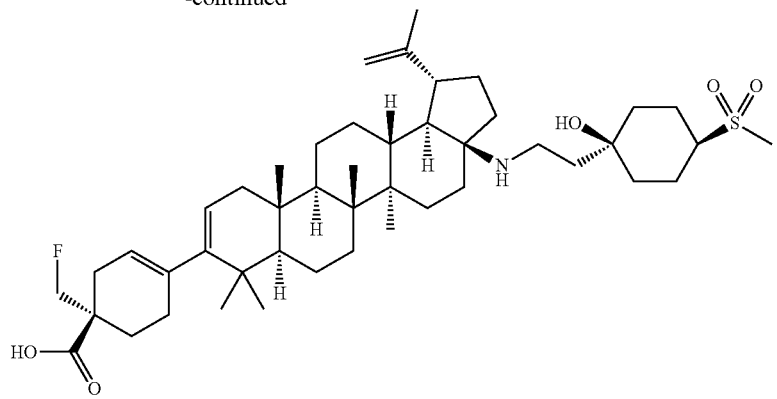

Example 2-19

Step 1. Preparation of (S)-benzyl 1-(fluoromethyl)-4-((1R,3aS,5aR,5bR,7aR,11aS,11bR,13aR,13bR)-3a-((2-((cis)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate

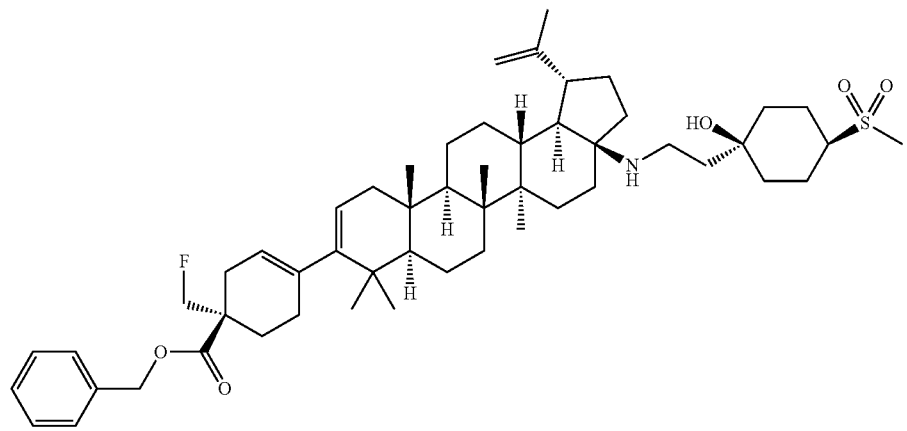

A mixture of (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (550 mg, 0.838 mmol), 2-((cis)-1-hydroxy-4-(methylsulfonyl)cyclohexyl)acetaldehyde (406 mg, 1.845 mmol), and borane-2-picoline complex (197 mg, 1.845 mmol) in MeOH (8 mL) and acetic acid (1.6 mL) was stirred at room temperature for 14 h. LC/MS showed a peak with the desired mass along with some remaining starting material. Additional 2-((cis)-1-hydroxy-4-(methylsulfonyl)cyclohexyl)acetaldehyde (56 mg, 0.254 mmol, 0.3 eq) and borane-2-picoline complex (27 mg, 0.252 mmol, 0.3 eq) was added and stirring was continued for 3 h. The mixture was transferred to a separatory funnel containing saturated aqueous sodium bicarbonate solution (20 mL) and saturated aqueous sodium carbonate solution (2 mL). The aqueous layer was extracted with dichloromethane (4×50 mL). The combined organic layers were washed with brine (25 mL), dried over $MgSO_4$, filtered, and concentrated. The product was purified by column chromatography on silica gel (10% 9:1 acetone:methanol/90% hexanes→70% 9:1 acetone:methanol/30% hexanes, 20 min gradient; 80 g column, λ=220 nm) to afford (S)-benzyl 1-(fluoromethyl)-4-((1R,3aS,5aR,5bR,7aR,11aS,11bR,13aR,13bR)-3a-((2-((cis)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (566 mg, 0.658 mmol, 78% yield) as a white solid: $^1$H NMR (500 MHz, CHLOROFORM-d) δ 7.41-7.31 (m, 5H), 5.33 (br. s., 1H), 5.23-5.16 (m, 2H), 5.13 (dd, J=6.2, 1.8 Hz, 1H), 4.75 (d, J=1.8 Hz, 1H), 4.64-4.55 (m, 2H), 4.53-4.46 (m, 1H), 2.85 (s, 3H), 2.83-2.69 (m, 3H), 2.64-2.51 (m, 2H), 2.19-1.02 (m, 36H), 1.70 (s, 3H), 1.06 (s, 3H), 0.98 (s, 3H), 0.92 (s, 3H), 0.91 (s, 3H), 0.86 (s, 3H); LC/MS m/e 860.6 [(M+H)$^+$, calcd for $C_{53}H_{79}FNO_5S$ 860.6], $t_R$=4.63 min (method 2-3).

Step 2. A solution of (S)-benzyl 1-(fluoromethyl)-4-((1R,3aS,5aR,5bR,7aR,11aS,11bR,13aR,13bR)-3a-((2-((cis)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (537 mg, 0.624 mmol) in 1,4-dioxane (9 mL) and EtOH (3 mL)

was treated with sodium hydroxide (2M aq) (1.561 mL, 3.12 mmol). The reaction mixture was heated at 70° C. for 2.5 h. The mixture was cooled to room temperature, was diluted with methanol (4 mL) (to dissolve the precipitate), was filtered through a syringe filter, and was purified by reverse phase preparative HPLC (method 2-1). The organic solvent was evaporated on the rotovapor and the aqueous mixture was lyophilized to afford (S)-1-(fluoromethyl)-4-((1R,3aS, 5aR,5bR,7aR,11aS,11bR,13aR,13bR)-3a-((2-((cis)-1-hydroxy-4-(methylsulfonyl)cyclohexyl)ethyl)amino)-5a,5b,8, 8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)cyclohex-3-enecarboxylic acid•TFA (438 mg, 0.495 mmol, 79% yield) as a white amorphous solid: $^1$H NMR (500 MHz, Acetic Acid-$d_4$) δ 5.39 (br. s., 1H), 5.27-5.21 (m, 1H), 4.83 (s, 1H), 4.73 (s, 1H), 4.65-4.56 (m, 1H), 4.55-4.47 (m, 1H), 3.47-3.33 (m, 2H), 3.08-2.99 (m, 1H), 2.96 (s, 3H), 2.89-2.80 (m, 1H), 2.61 (d, J=16.8 Hz, 1H), 2.31-1.11 (m, 37H), 1.75 (s, 3H), 1.18 (s, 3H), 1.10 (s, 3H), 1.00 (s, 3H), 0.99 (s, 3H), 0.95 (s, 3H); LC/MS m/e 770.5 [(M+H)$^+$, calcd for $C_{46}H_{73}FNO_5S$ 770.5], $t_R$=4.22 min (method 2-2); HPLC (method 2-1): $t_R$=18.75 min; HPLC (method 2-2): $t_R$=19.89 min.

Example 2-20

Preparation of (R)-1-(fluoromethyl)-4-((1R,3aS, 5aR,5bR,7aR,11aS,11bR,13aR,13bR)-3a-((2-((cis)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)cyclohex-3-enecarboxylic acid

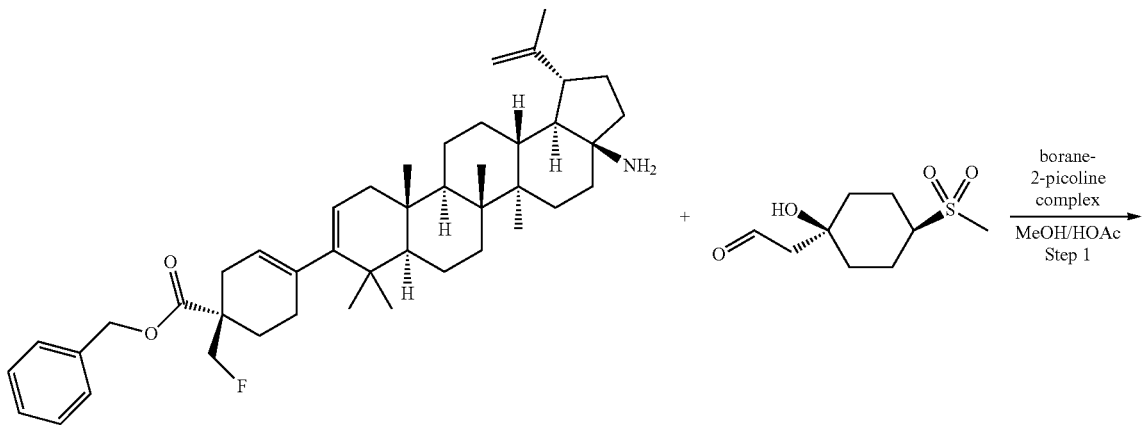

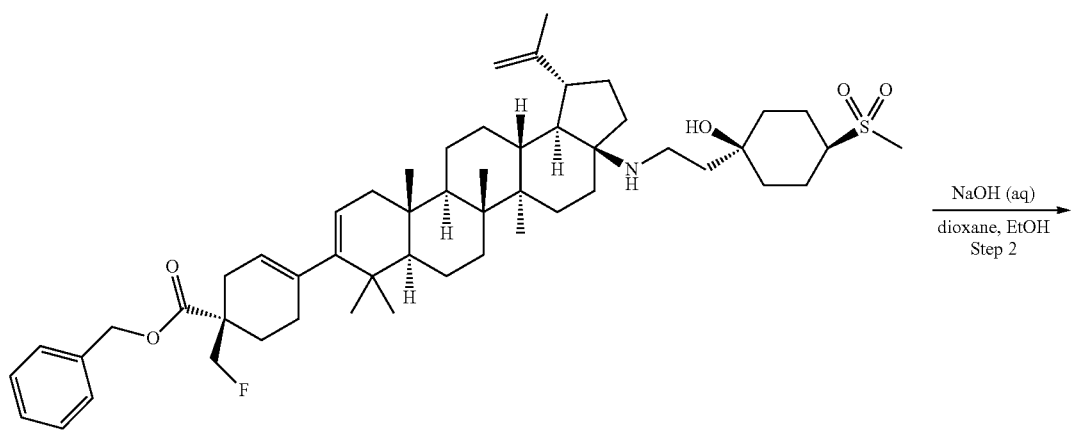

-continued

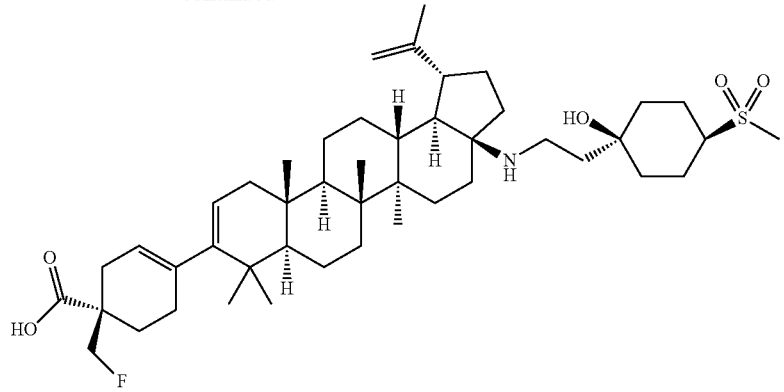

Example 2-20

Step 1. Preparation of (R)-benzyl 1-(fluoromethyl)-4-((1R,3aS,5aR,5bR,7aR,11aS,11bR,13aR,13bR)-3a-((2-((cis)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate

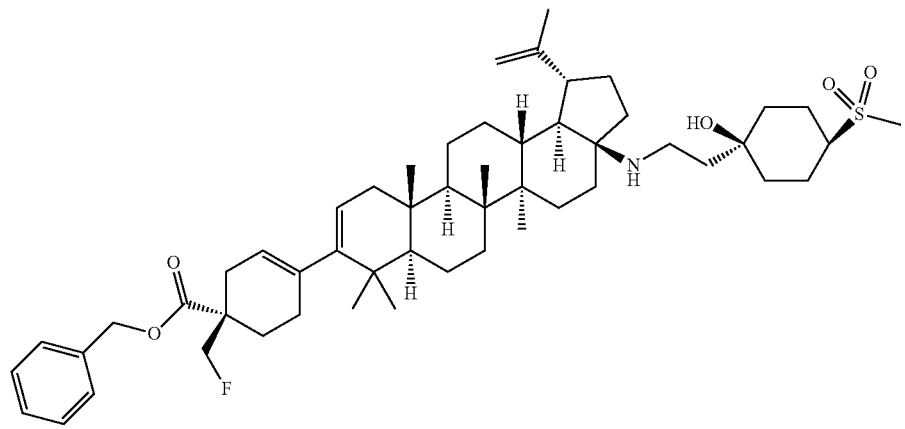

To a suspension of (R)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (100 mg, 0.152 mmol) and 2-((cis)-1-hydroxy-4-(methylsulfonyl)cyclohexyl)acetaldehyde (60.4 mg, 0.274 mmol) in MeOH (1.2 mL) was added borane-2-picoline complex (29.4 mg, 0.274 mmol) followed by acetic acid (0.24 mL) and the mixture was stirred at room temperature for 16 h. The mixture was transferred to a separatory funnel containing saturated aqueous sodium bicarbonate solution (5 mL) and saturated aqueous sodium carbonate solution (1 mL). The aqueous layer was extracted with dichloromethane (4×5 mL). The combined organic layers were washed with brine (5 mL), dried over MgSO$_4$, filtered, and concentrated. The product was purified by column chromatography on silica gel (20% ethyl acetate with 5% methanol/80% hexanes→90% ethyl acetate with 5% methanol/10% hexanes; 24 g column) to afford (R)-benzyl 1-(fluoromethyl)-4-((1R,3aS,5aR,5bR,7aR,11aS,11bR,13aR,13bR)-3a-((2-((cis)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (120 mg, 0.139 mmol, 92% yield) as a colorless foam: $^1$H NMR (500 MHz, CHLOROFORM-d) δ 7.41-7.30 (m, 5H), 5.33 (br. s., 1H), 5.23-5.15 (m, 2H), 5.11 (d, J=5.7 Hz, 1H), 4.74 (s, 1H), 4.64-4.55 (m, 2H), 4.51-4.45 (m, 1H), 2.85 (s, 3H), 2.83-2.69 (m, 4H), 2.64-2.49 (m, 2H), 2.21-0.90 (m, 36H), 1.70 (s, 3H), 1.05 (s, 3H), 0.98 (s, 3H), 0.93 (s, 3H), 0.88 (s, 3H), 0.85 (s, 3H); LC/MS m/e 860.6 [(M+H)$^+$, calcd for $C_{53}H_{79}FNO_4$ 812.6], $t_R$=4.62 min (method 2-3).

Step 2. A solution of (R)-benzyl 1-(fluoromethyl)-4-((1R,3aS,5aR,5bR,7aR,11aS,11bR,13aR,13bR)-3a-((2-((cis)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (115 mg, 0.134 mmol) in 1,4-dioxane (1.5 mL) and MeOH (0.5 mL) was treated with sodium hydroxide (2M aq) (0.334 mL, 0.668 mmol). The reaction mixture was heated at 70° C. for 4 h. The reaction was complete. The mixture was cooled to room temperature. The mixture was cooled to room temperature and was partially neutralized by the addition of 6 N HCl (70 μL). The mixture was then filtered through a syringe filter, and was purified by reverse phase preparative HPLC (method 2-5). The organic solvent was evaporated on the rotovapor and the aqueous mixture was lyophilized to afford (R)-1-(fluoromethyl)-4-((1R,3aS,5aR,5bR,7aR,11aS,11bR,13aR,13bR)-3a-((2-((cis)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) cyclohex-3-enecarboxylic acid•TFA (72.6 mg, 0.082 mmol, 61% yield) as a white amorphous solid: $^1$H NMR (500 MHz, Acetic Acid-d$_4$) δ 5.39 (br. s., 1H), 5.24 (d, J=4.7 Hz, 1H), 4.83 (s, 1H), 4.72 (s, 1H), 4.65-4.57 (m, 1H), 4.54-4.46 (m, 1H), 3.47-3.34 (m, 2H), 3.09-2.99 (m, 1H), 2.96 (s, 3H), 2.90-2.81 (m, 1H), 2.61 (d, J=16.8 Hz, 1H), 2.35-1.71 (m, 21H), 1.75 (s, 3H), 1.65-1.32 (m, 14H), 1.17 (s, 3H), 1.13 (d, J=6.0 Hz, 2H), 1.09 (s, 3H), 1.02 (s, 3H), 0.97 (s, 3H), 0.95 (s, 3H); LC/MS m/e 770.5 [(M+H)$^+$, calcd for C$_{46}$H$_{73}$FNO$_5$S 770.5], t$_R$=4.33 min (method 2-2); HPLC (method 2-5): t$_R$=11.55 min; HPLC (method 2-6): t$_R$=11.20 min.

Example 2-21

Preparation of (S)-1-(fluoromethyl)-4-((1R,3aS,5aR,5bR,7aR,11aS,11bR,13aR,13bR)-3a-((2-((trans)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) cyclohex-3-enecarboxylic acid

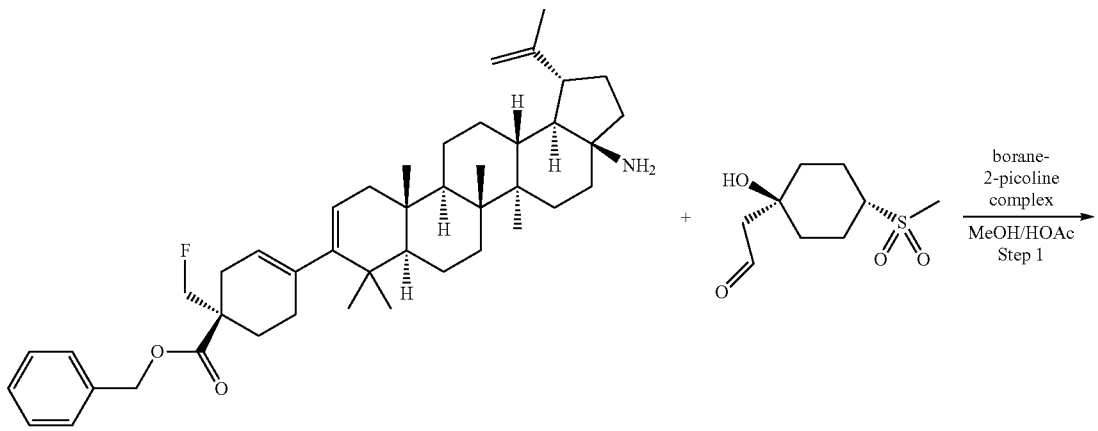

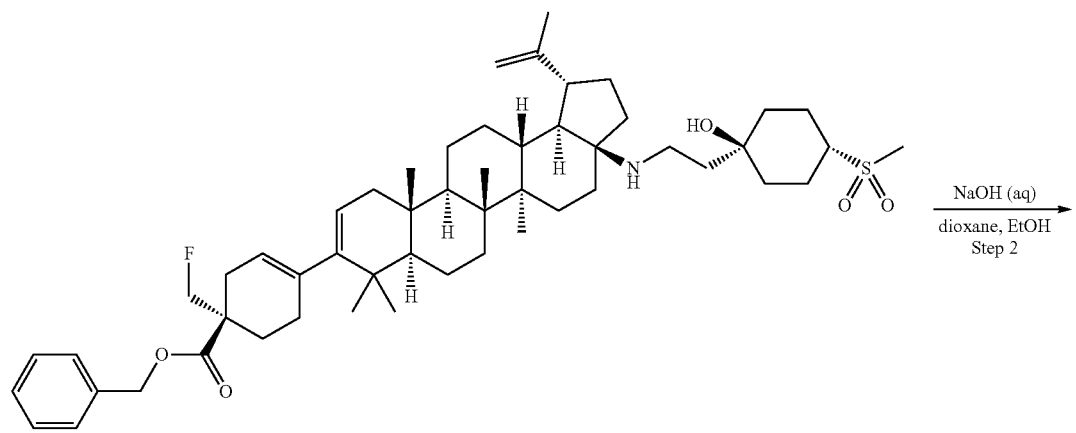

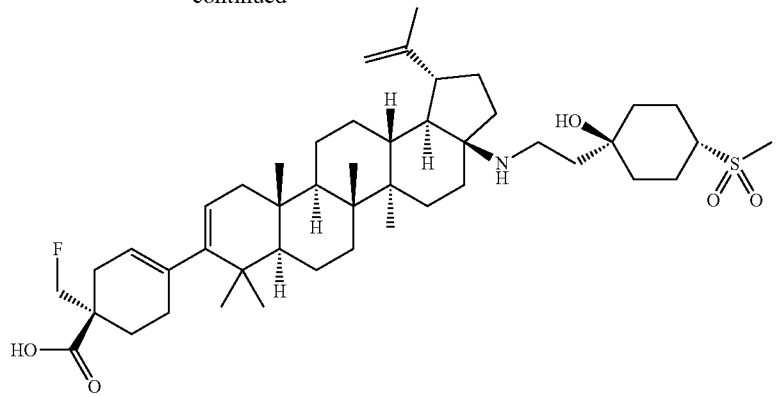

Example 2-21

Step 1. Preparation of (S)-benzyl 1-(fluoromethyl)-4-((1R,3aS,5aR,5bR,7aR,11aS,11bR,13aR,13bR)-3a-((2-((trans)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate

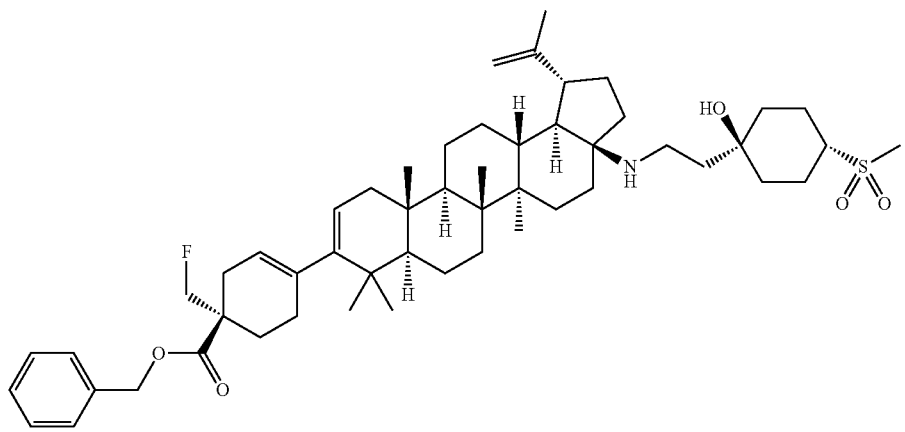

A mixture of (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (150 mg, 0.229 mmol), 2-((trans)-1-hydroxy-4-(methylsulfonyl)cyclohexyl)acetaldehyde (126 mg, 0.572 mmol), and borane-2-picoline complex (61.1 mg, 0.572 mmol) in methanol (2.5 mL) and acetic acid (0.5 mL) was stirred at room temperature for 16 h. The mixture was transferred to a separatory funnel containing saturated aqueous sodium bicarbonate solution (10 mL) and saturated aqueous sodium carbonate solution (2 mL). The aqueous layer was extracted with dichloromethane (4×20 mL). The combined organic layers were washed with brine (10 mL), dried over MgSO$_4$, filtered, and concentrated. The product was purified by column chromatography on silica gel (10% 9:1 acetone:methanol/90% hexanes→50% 9:1 acetone:methanol/50% hexanes; 24 g column, λ=220 nm) to afford (S)-benzyl 1-(fluoromethyl)-4-((1R,3aS,5aR, 5bR,7aR,11aS,11bR,13aR,13bR)-3a-((2-((1r,4S)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (143 mg, 0.166 mmol, 73% yield) as a colorless film: $^1$H NMR (500 MHz, CHLOROFORM-d) δ 7.40-7.32 (m, 5H), 5.33 (br. s., 1H), 5.23-5.16 (m, 2H), 5.13 (dd, J=6.1, 1.7 Hz, 1H), 4.73 (d, J=1.7 Hz, 1H), 4.63-4.56 (m, 2H), 4.52-4.46 (m, 1H), 2.99-2.91 (m, 1H), 2.89 (s, 3H), 2.83-2.76 (m, 1H), 2.71-2.50 (m, 3H), 2.19-1.04 (m, 36H), 1.69 (s, 3H), 1.06 (s, 3H), 0.98 (s, 3H), 0.92 (s, 3H), 0.90 (s, 3H), 0.86 (s, 3H); LC/MS m/e 860.6 [(M+H)$^+$, calcd for C$_{53}$H$_{79}$FNO$_5$S 860.6], t$_R$=4.61 min (method 2-3).

Step 2. A solution of (S)-benzyl 1-(fluoromethyl)-4-((1R,3aS,5aR,5bR,7aR,11aS,11bR,13aR,13bR)-3a-((2-((trans)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (80 mg, 0.093 mmol) in 1,4-dioxane (1 mL) and EtOH (0.5 mL) was treated with sodium hydroxide (2M aq) (0.232 mL, 0.465 mmol). The reaction mixture was heated at 70° C. for 2 h. The mixture was cooled to room temperature, was filtered through a syringe filter, and was purified by reverse phase preparative HPLC (method 2-1). The product (59 mg)

contained a significant amount of an impurity (ca. 5-10%). The product was then repurified by reverse phase preparative HPLC (method 2-6). The organic solvent was evaporated on the rotovapor and the aqueous mixture was lyophilized to afford (S)-1-(fluoromethyl)-4-((1R,3aS,5aR, 5bR,7aR,11aS,11bR,13aR,13bR)-3a-((2-((trans)-1-hydroxy-4-(methylsulfonyl)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid•TFA (27.2 mg, 33% yield) as a white amorphous solid: $^1$H NMR (500 MHz, Acetic Acid-$d_4$) δ 5.39 (br. s., 1H), 5.25 (d, J=4.6 Hz, 1H), 4.83 (s, 1H), 4.72 (s, 1H), 4.66-4.57 (m, 1H), 4.54-4.47 (m, 1H), 3.42 (dd, J=8.2, 4.7 Hz, 1H), 3.36-3.28 (m, 1H), 3.18-3.10 (m, 1H), 2.98 (s, 3H), 2.91-2.83 (m, 1H), 2.61 (d, J=16.6 Hz, 1H), 2.31-1.11 (m, 37H), 1.75 (s, 3H), 1.14 (s, 3H), 1.09 (s, 3H), 1.00 (s, 3H), 0.99 (s, 3H), 0.94 (s, 3H); LC/MS m/e 770.5 [(M+H)$^+$, calcd for $C_{46}H_{73}FNO_5S$ 770.5], $t_R$=4.20 min (method 2-2); HPLC (method 2-1): $t_R$=18.74 min; HPLC (method 2-2): $t_R$=20.05 min.

Example 2-22

Preparation of (S)-1-(fluoromethyl)-4-((1R,3aS,5aR, 5bR,7aR,11aS,11bR,13aR,13bR)-3a-((2-(1-hydroxy-4-((methylsulfonyl)oxy)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid

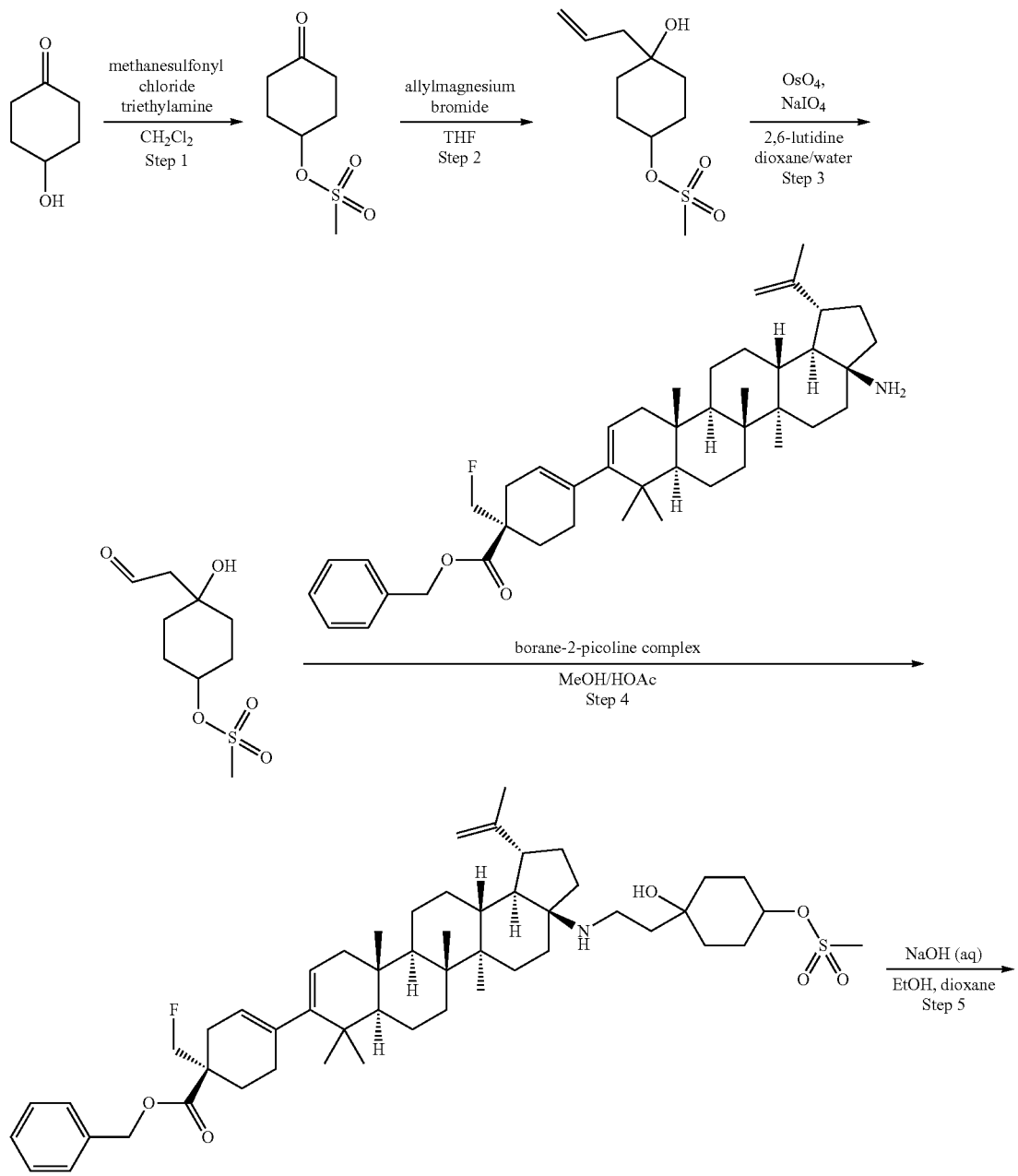

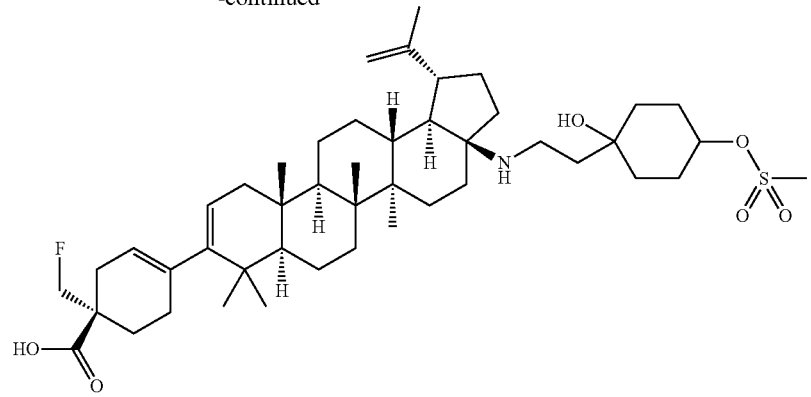

Example 2-22

Step 1. Preparation of 4-oxocyclohexyl methanesulfonate

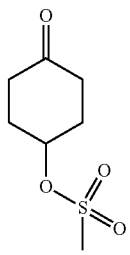

Methanesulfonyl chloride (0.746 mL, 9.64 mmol) and triethylamine (1.343 mL, 9.64 mmol) were added to a solution of 4-hydroxycyclohexanone (1 g, 8.76 mmol) in dichloromethane (10 mL). The reaction mixture was stirred at rt for 16 h. The mixture was concentrated and the product was purified by column chromatography on silica gel (0% hexanes→60% 9:1 acetone:methanol/40% hexanes, 80 g column, λ=220 nm) to afford 4-oxocyclohexyl methanesulfonate (1.65 g, 8.58 mmol, 98% yield) as a colorless oil: $^1$H NMR (400 MHz, CHLOROFORM-d) δ 5.14 (tt, J=5.5, 2.8 Hz, 1H), 3.11 (s, 3H), 2.75-2.59 (m, 2H), 2.49-2.28 (m, 4H), 2.24-2.06 (m, 2H).

Step 2. Preparation of 4-allyl-4-hydroxycyclohexyl methanesulfonate

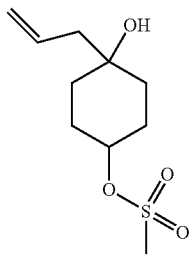

To a solution of allylmagnesium bromide (9.83 mL, 9.83 mmol) in THF (75 mL) at −78° C. was added 4-oxocyclohexyl methanesulfonate (1.8 g, 9.36 mmol). The mixture was stirred at −78° C. for 2 h. The reaction was quenched by the addition of saturated NH$_4$Cl solution (60 mL). The mixture was transferred to a separatory funnel and the layers were separated. The aqueous layer was extracted with ether (5×50 mL). The combined organic layers were washed with brine (50 mL), dried over MgSO$_4$, filtered, and concentrated to afford 4-allyl-4-hydroxycyclohexyl methanesulfonate (1.15 g, 4.91 mmol, 52% yield) as a colorless oil. The product was purified by column chromatography on silica gel (10% hexanes:ethyl acetate:MeOH (4:4:1)/90% hexanes→50% hexanes:ethyl acetate:MeOH (4:4:1)/50% hexanes; 120 g column) to afford 4-allyl-4-hydroxycyclohexyl methanesulfonate (1.15 g, 4.91 mmol, 52% yield): $^1$H NMR (400 MHz, CHLOROFORM-d) δ 5.83 (ddt, J=17.2, 9.9, 7.5 Hz, 1H), 5.20-5.04 (m, 2H), 4.68-4.53 (m, 1H), 2.99 (s, 3H), 2.18 (d, J=7.3 Hz, 2H), 1.99-1.87 (m, 4H), 1.71 (s, 2H), 1.53-1.37 (m, 2H).

Step 3. Preparation of 4-hydroxy-4-(2-oxoethyl)cyclohexyl methanesulfonate

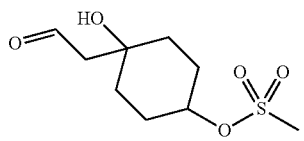

To a solution of 4-allyl-4-hydroxycyclohexyl methanesulfonate (182 mg, 0.777 mmol) in dioxane (12 mL) and water (3.00 mL) at 0° C. was added 2,6-lutidine (0.181 mL, 1.553 mmol), osmium tetroxide (2.5% in t-BuOH) (0.195 mL, 0.016 mmol), and sodium periodate (665 mg, 3.11 mmol). The reaction mixture was allowed to warm up to room temperature as the ice-water bath melted while stirring for 14 h. The reaction mixture was transferred to a separatory funnel containing water (50 mL) and saturated aqueous NaHCO$_3$ solution (50 mL). The aqueous layer was extracted with ethyl acetate (3×50 mL). The combined organic layers were washed with brine (50 mL), dried over MgSO$_4$, filtered, and concentrated. The product was purified by column chromatography on silica gel (0%→8% methanol in CH$_2$Cl$_2$; 40 g column) to afford 4-hydroxy-4-(2-oxoethyl)

cyclohexyl methanesulfonate (91 mg, 0.385 mmol, 50% yield) as a colorless oil: $^1$H NMR (400 MHz, CHLOROFORM-d) δ 9.86 (t, J=1.3 Hz, 1H), 4.66 (tt, J=10.5, 4.2 Hz, 1H), 3.03 (s, 3H), 2.65 (d, J=1.3 Hz, 2H), 2.12-2.00 (m, 2H), 2.00-1.89 (m, 4H), 1.54-1.43 (m, 2H).

Step 4. Preparation of (S)-benzyl 1-(fluoromethyl)-4-((1R,3aS,5aR,5bR,7aR,11aS,11bR,13aR,13bR)-3a-((2-(1-hydroxy-4-((methylsulfonyl)oxy)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate 7aR,11aS,11bR,13aR,13bR)-3a-((2-(1-hydroxy-4-((methylsulfonyl)oxy)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (15 mg, 17% yield). The crude product was used in the next step without further purification. LC/MS m/e 876.6 [(M+H)$^+$, calcd for $C_{53}H_{78}FNO_6S$ 876.6], $t_R$=2.66 min (method 2-1).

Step 5. Sodium hydroxide (0.038 mL, 0.150 mmol) was added to a solution of (S)-benzyl 1-(fluoromethyl)-4-((1R,3aS,5aR,5bR,7aR,11aS,11bR,13aR,13bR)-3a-((2-(1-hydroxy-4-((methylsulfonyl)oxy)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-

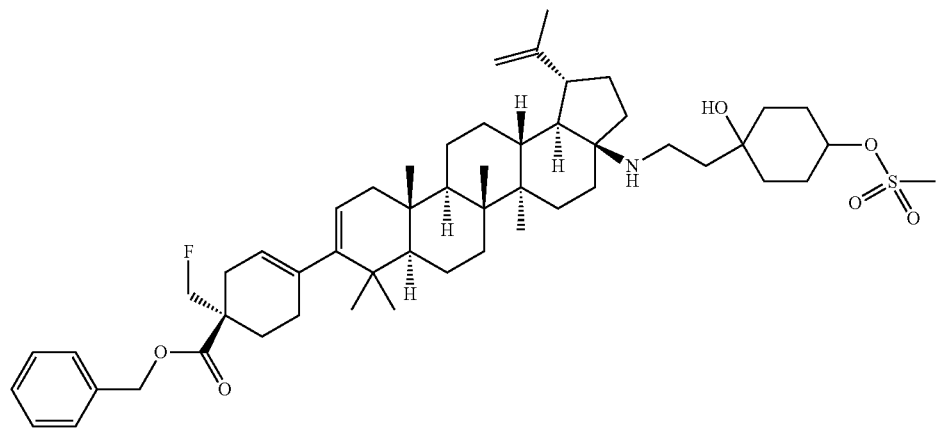

A mixture of (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (60 mg, 0.091 mmol), 4-hydroxy-4-(2-oxoethyl)cyclohexyl methanesulfonate (32.4 mg, 0.137 mmol), and borane-2-picoline complex (14.68 mg, 0.137 mmol) in MeOH (1 mL) and acetic acid (0.200 mL) was stirred at room temperature for 16 h. The mixture was transferred to a separatory funnel containing saturated aqueous sodium bicarbonate solution (5 mL). The aqueous layer was extracted with dichloromethane (3×10 mL). The combined organic layers were washed with brine (5 mL), dried over MgSO$_4$, filtered, and concentrated to afford (S)-benzyl 1-(fluoromethyl)-4-((1R,3aS,5aR,5bR, cyclopenta[a]chrysen-9-yl)cyclohex-3-enecarboxylate (13.14 mg, 0.015 mmol) in dioxane (0.5 mL) and ethanol (0.125 mL). The reaction mixture was stirred at 70° C. for 16 h. The crude material was filtered through a syringe filter, and was purified by reverse phase preparative HPLC (method 2-2, gradient 50-100% B over 10 minutes, then a 15-minute hold at 100% B) to afford the purified product, (S)-1-(fluoromethyl)-4-((1R,3aS,5aR,5bR,7aR,11aS,11bR,13aR,13bR)-3a-((2-(1-hydroxy-4-((methylsulfonyl)oxy)cyclohexyl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid (3.2 mg, 3.87 µmol, 26% yield): $^1$H NMR (500 MHz, Acetic Acid-d$_4$) δ 5.39 (br. s., 1H), 5.25 (d, J=5.2 Hz, 1H), 4.84 (s, 1H), 4.76-4.67 (m, 2H), 4.65-4.57 (m, 1H), 4.56-4.47 (m, 1H), 3.79 (s, 1H), 3.40 (d, J=12.0 Hz, 1H), 3.35-3.25 (m, 1H), 3.15 (q, J=7.1 Hz, 1H), 3.10 (s, 3H), 2.90 (br. s., 1H), 2.62 (d, J=17.2 Hz, 1H), 2.35-0.91 (m, 35H), 1.75 (s, 3H), 1.20 (s, 3H), 1.10 (s, 3H), 1.01 (s, 3H), 0.99 (s, 3H), 0.97 (s, 3H); LC/MS m/e 786.8 [(M+H)$^+$, calcd for $C_{46}H_{72}FNO_6S$ 786.5], $t_R$=2.46 min (method 2.1); HPLC (method 2-3): $t_R$=2.54 min; HPLC (method 2-4): $t_R$=2.29 min.

Example 2-23

Preparation of (S)-1-(fluoromethyl)-4-((1R,3aS,5aR, 5bR,7aR,11aS,11bR,13aR,13bR)-3a-((2-(4-hydroxy-4-methylpiperidin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid

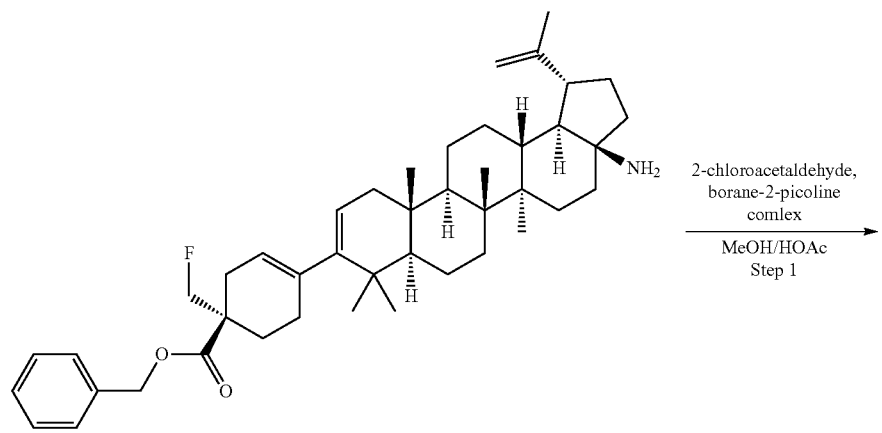

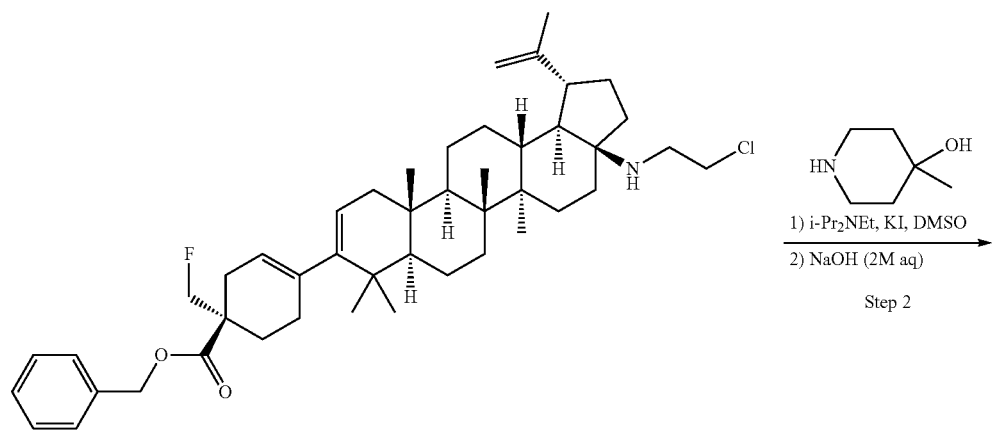

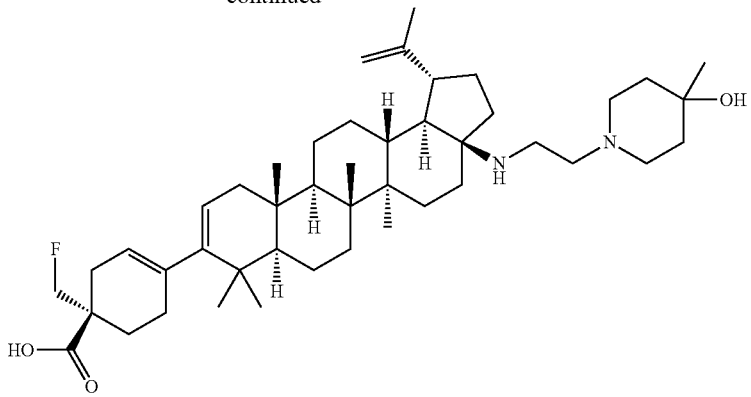

Example 2-23

Step 1. Preparation of (S)-benzyl 4-((1R,3aS,5aR, 5bR,7aR,11aS,11bR,13aR,13bR)-3a-((2-chloroethyl) amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)-1-(fluoromethyl)cyclohex-3-enecarboxylate

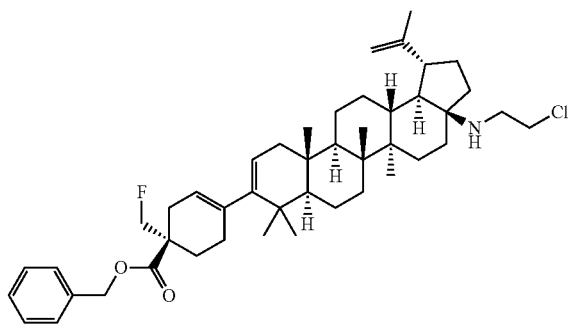

A mixture of (S)-benzyl 4-((1R,3aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)-1-(fluoromethyl)cyclohex-3-enecarboxylate (100 mg, 0.152 mmol), 2-chloroacetaldehyde (0.028 mL, 0.229 mmol), and borane-2-picoline complex (24.46 mg, 0.229 mmol) in MeOH (1 mL) and acetic acid (0.2 mL) was stirred at room temperature for 18 h. The mixture was transferred to a separatory funnel containing saturated aqueous sodium bicarbonate solution (10 mL). The aqueous layer was extracted with dichloromethane (4×15 mL). The combined organic layers were washed with brine (10 mL), dried over MgSO$_4$, filtered, and concentrated. The product was purified by column chromatography on silica gel (10% 9:1 acetone: methanol/90% hexanes→50% 9:1 acetone:methanol/50% hexanes; 40 g column, λ=220 nm) to afford (S)-benzyl 4-((1R,3aS,5aR,5bR,7aR,11aS,11bR,13aR,13bR)-3a-((2-chloroethyl)amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)-1-(fluoromethyl)cyclohex-3-enecarboxylate (57 mg, 0.079 mmol, 52% yield) as a white foam: $^1$H NMR (500 MHz, CHLOROFORM-d) δ 7.40-7.31 (m, 5H), 5.33 (br. s., 1H), 5.23-5.16 (m, 2H), 5.14 (dd, J=6.1, 1.7 Hz, 1H), 4.73 (d, J=2.0 Hz, 1H), 4.63-4.56 (m, 2H), 4.53-4.46 (m, 1H), 3.72-3.65 (m, 2H), 2.85-2.72 (m, 2H), 2.67-2.57 (m, 2H), 2.17-1.02 (m, 27H), 1.71 (s, 3H), 1.08 (s, 3H), 0.97 (s, 3H), 0.92 (s, 3H), 0.90 (s, 3H), 0.86 (s, 3H); LC/MS m/e 718.6 [(M+H)$^+$, calcd for C$_{46}$H$_{66}$ClFNO$_2$ 718.5], t$_R$=4.82 min (method 2-3).

Step 2. A mixture of (S)-benzyl 4-((1R,3aS,5aR,5bR,7aR, 11aS,11bR,13aR,13bR)-3a-((2-chloroethyl)amino)-5a,5b,8, 8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)-1-(fluoromethyl)cyclohex-3-enecarboxylate (15 mg, 0.021 mmol), 4-methylpiperidin-4-ol (7.21 mg, 0.063 mmol), Hunig's base (0.018 mL, 0.104 mmol), and potassium iodide (4.16 mg, 0.025 mmol) in DMSO (0.4 mL) was heated at 80° C. for 14 hours. The reaction mixture was then cooled to rt and NaOH (0.052 mL, 0.104 mmol) was added. The reaction mixture was heated at 70° C. for 2 h. The reaction mixture was filtered and purified by reverse phase preparative HPLC (method 2-1) to afford (S)-1-(fluoromethyl)-4-((1R,3aS,5aR,5bR,7aR,11aS,11bR, 13aR,13bR)-3a-((2-(4-hydroxy-4-methylpiperidin-1-yl) ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid.2 TFA (9.5 mg, 48% yield) as a white amorphous solid: $^1$H NMR (500 MHz, Acetic Acid-d$_4$) δ 5.39 (br. s., 1H), 5.24 (d, J=4.6 Hz, 1H), 4.85 (s, 1H), 4.74 (s, 1H), 4.65-4.56 (m, 1H), 4.55-4.47 (m, 1H), 3.85-3.70 (m, 4H), 3.56 (br. s., 2H), 3.43 (br. s., 2H), 2.85-2.76 (m, 1H), 2.61 (d, J=16.9 Hz, 1H), 2.31-1.11 (m, 32H), 1.75 (s, 3H), 1.35 (s, 3H), 1.15 (s, 3H), 1.10 (s, 3H), 1.01 (s, 3H), 0.99 (s, 3H), 0.95 (s, 3H); LC/MS (ESI) m/e 707.6 [(M+H)$^+$, calcd for C$_{45}$H$_{72}$FN$_2$O$_3$ 707.6], t$_R$=4.31 min (method 2-2); HPLC (method 2-1): t$_R$=18.63 min; HPLC (method 2-2): t$_R$=19.58 min.

Example 2-24
Preparation of (S)-1-(fluoromethyl)-4-((1R,3aS,5aR, 5bR,7aR,11aS,11bR,13aR,13bR)-5a,5b,8,8,11a-pentamethyl-3a-((2-(2-oxooxazolidin-3-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid
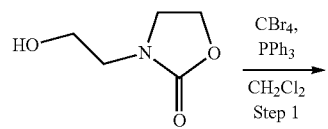
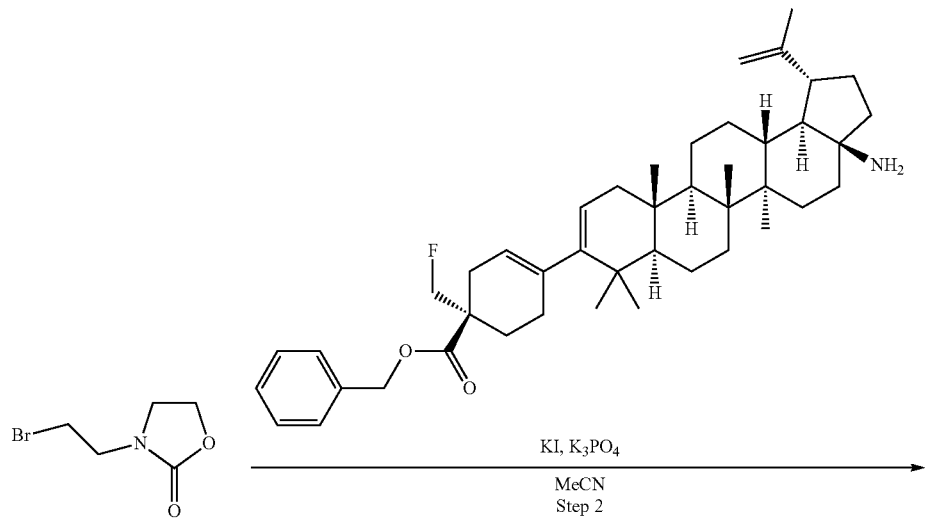
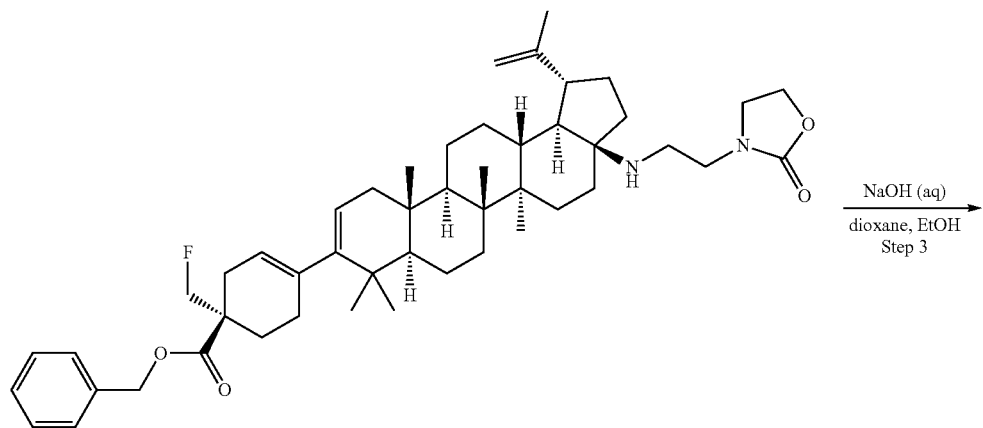

Example 2-24

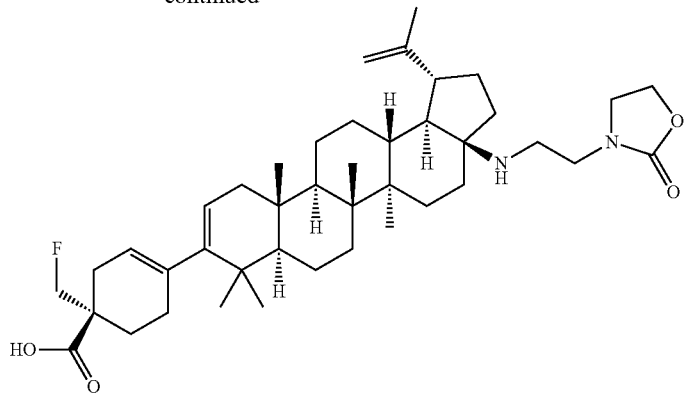

Step 1. Preparation of 3-(2-bromoethyl)oxazolidin-2-one

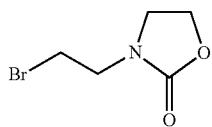

To a solution of 3-(2-hydroxyethyl)oxazolidin-2-one (1.0 g, 7.63 mmol) in $CH_2Cl_2$ (30 mL) was added carbon tetrabromide (3.03 g, 9.15 mmol). After cooling the solution to 0° C., triphenylphosphine (2.80 g, 10.68 mmol) was added in portions. The resulting solution was stirred at room temperature for 18 h. The mixture was concentrated. The residue was suspended in ether (75 mL), and was stirred for 30 min. The solid was removed by filtration and the filtrate was concentrated. The product was purified by column chromatography on silica gel (1%→4% methanol in dichloromethane; 220 g column) The first compound isolated from the chromatography was primarily the product (1.01 g) as a colorless oil, which solidified upon standing (due to the presence of triphenylphosphine oxide). The product was repurified by column chromatography on silica gel (0.5%→3% methanol in $CH_2Cl_2$; 120 g column) to afford 3-(2-bromoethyl)oxazolidin-2-one (785 mg, 4.05 mmol, 53% yield) as a colorless oil. $^1$H NMR indicated that the product was contaminated with triphenylphosphine oxide. The triphenylphosphine oxide was present as a 7:1 molar ratio of product to triphenylphosphine oxide. The product was used in the next step without further purification. $^1$H NMR (400 MHz, CHLOROFORM-d) δ 4.46-4.35 (m, 2H), 3.82-3.67 (m, 4H), 3.58-3.52 (m, 2H).

Step 2. Preparation of (S)-benzyl 1-(fluoromethyl)-4-((1R,3aS,5aR,5bR,7aR,11aS,11bR,13aR,13bR)-5a,5b,8,8,11a-pentamethyl-3a-((2-(2-oxooxazolidin-3-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate

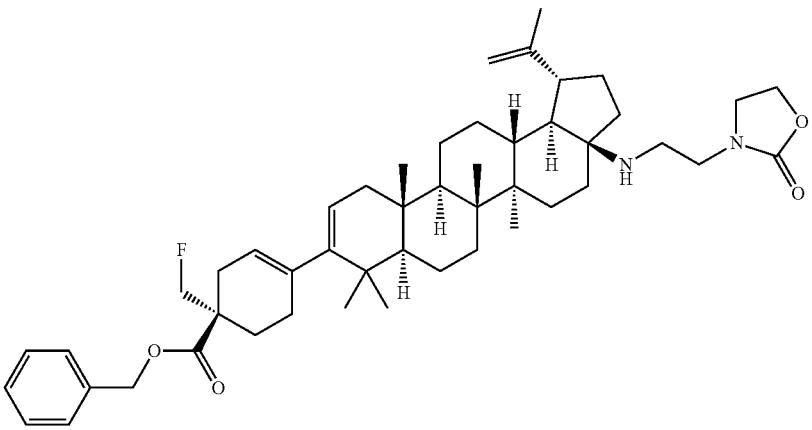

To a mixture of (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (70 mg, 0.107 mmol), 3-(2-bromoethyl)oxazolidin-2-one (72.5 mg, 0.373 mmol), potassium phosphate tribasic (91 mg, 0.427 mmol), and potassium iodide (62.0 mg, 0.373 mmol) in an oven-dried pressure vessel was added acetonitrile (1.0 mL). The cap was sealed and the reaction mixture was heated at 120° C. for 14 h. The mixture was transferred to a separatory funnel containing water (10 mL). The aqueous layer was extracted with dichloromethane (3×15 mL). The combined organic layers were washed with brine (10 mL), dried over MgSO$_4$, filtered, and concentrated. The product was purified by column chromatography on silica gel (10% 9:1 acetone:methanol/90% hexanes→30% 9:1 acetone:methanol/70% hexanes; 24 g column, λ=220 nm) to afford (S)-benzyl 1-(fluoromethyl)-4-((1R,3aS,5aR,5bR,7aR,11aS,11bR,13aR,13bR)-5a,5b,8,8,11a-pentamethyl-3a-((2-(2-oxooxazolidin-3-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (54.5 mg, 0.071 mmol, 66% yield) as a colorless foam: $^1$H NMR (500 MHz, CHLOROFORM-d) δ 7.41-7.32 (m, 5H), 5.33 (br. s., 1H), 5.23-5.16 (m, 2H), 5.13 (dd, J=6.1, 1.7 Hz, 1H), 4.72 (d, J=2.0 Hz, 1H), 4.63-4.55 (m, 2H), 4.53-4.44 (m, 1H), 4.38-4.32 (m, 2H), 3.77-3.62 (m, 2H), 3.49-3.41 (m, 1H), 3.33 (dt, J=14.1, 5.5 Hz, 1H), 2.70 (ddd, J=12.0, 7.3, 5.0 Hz, 1H), 2.65-2.52 (m, 3H), 2.19-1.10 (m, 27H), 1.70 (s, 3H), 1.06 (s, 3H), 0.96 (s, 3H), 0.91 (s, 3H), 0.90 (s, 3H), 0.86 (s, 3H); LC/MS m/e 769.6 [(M+H)$^+$, calcd for C$_{49}$H$_{70}$FN$_2$O$_4$ 769.5], t$_R$=4.65 min (method 2-2).

Step 3. A solution of (S)-benzyl 1-(fluoromethyl)-4-((1R,3aS,5aR,5bR,7aR,11aS,11bR,13aR,13bR)-5a,5b,8,8,11a-pentamethyl-3a-((2-(2-oxooxazolidin-3-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (53 mg, 0.069 mmol) in 1,4-dioxane (0.7 mL) and EtOH (0.35 mL) was treated with sodium hydroxide (2M aq) (0.172 mL, 0.345 mmol). The reaction mixture was heated at 70° C. for 2 h. The mixture was cooled to room temperature, was filtered through a syringe filter, and was purified by reverse phase preparative HPLC (method 2-1) to afford (S)-1-(fluoromethyl)-4-((1R,3aS,5aR,5bR,7aR,11aS,11bR,13aR,13bR)-5a,5b,8,8,11a-pentamethyl-3a-((2-(2-oxooxazolidin-3-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid•TFA (31.4 mg, 62% yield) as a white amorphous solid: $^1$H NMR (500 MHz, Acetic Acid-d$_4$) δ 5.39 (br. s., 1H), 5.24 (d, J=4.7 Hz, 1H), 4.86 (s, 1H), 4.74 (s, 1H), 4.64-4.57 (m, 1H), 4.55-4.43 (m, 3H), 3.84 (q, J=8.2 Hz, 1H), 3.80-3.72 (m, 3H), 3.65-3.58 (m, 1H), 3.57-3.51 (m, 1H), 2.85-2.77 (m, 1H), 2.61 (d, J=16.6 Hz, 1H), 2.32-1.11 (m, 27H), 1.76 (s, 3H), 1.17 (s, 3H), 1.10 (s, 3H), 1.01 (s, 3H), 0.99 (s, 3H), 0.95 (s, 3H); LC/MS m/e 679.5 [(M+H)$^+$, calcd for C$_{42}$H$_{64}$FN$_2$O$_4$ 679.5], t$_R$=4.18 min (method 2-2); HPLC (method 2-1): t$_R$=18.68 min; HPLC (method 2-2): t$_R$=19.92 min.

Example 2-25

Preparation of (S)-1-(fluoromethyl)-4-((1R,3aS,5aR,5bR,7aR,11aS,11bR,13aR,13bR)-5a,5b,8,8,11a-pentamethyl-3a-((2-(2-oxoimidazolidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid

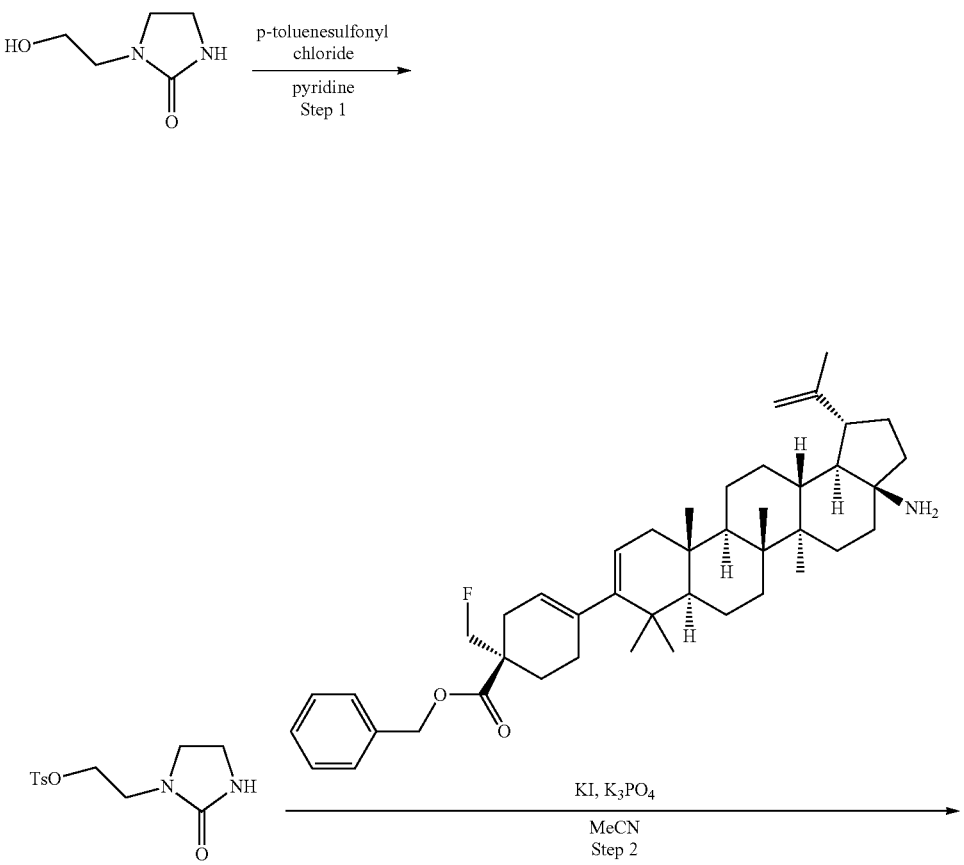

-continued

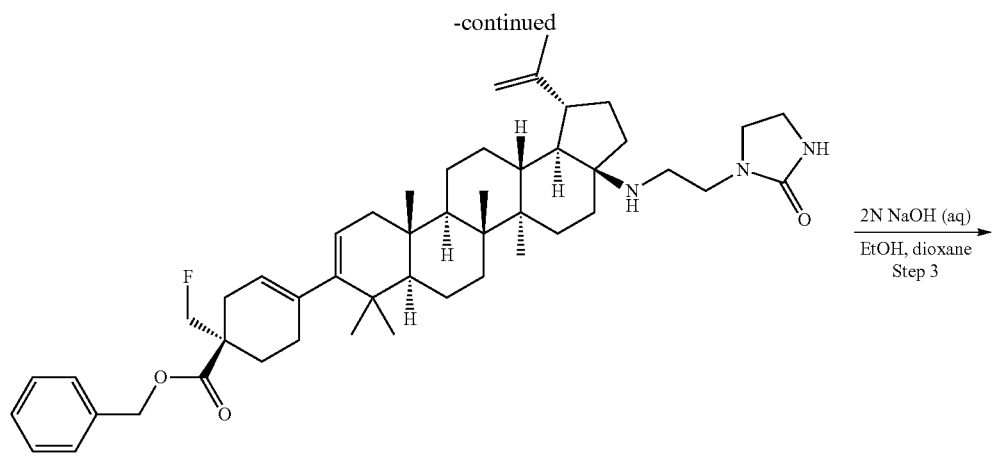

2N NaOH (aq)
EtOH, dioxane
Step 3

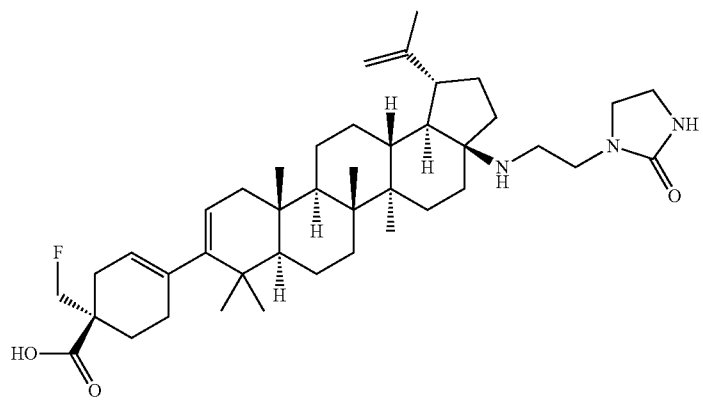

Example 2-25

Step 1. Preparation of 2-(2-oxoimidazolidin-1-yl)ethyl 4-methylbenzenesulfonate

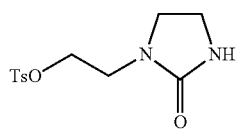 [SMILES: Cc1ccc(S(=O)(=O)OCCN2CCNC2=O)cc1]

To a solution of 1-(2-hydroxyethyl)imidazolidin-2-one (500 mg, 3.84 mmol) in pyridine (5 mL) at 0° C. was added p-toluenesulfonyl chloride (806 mg, 4.23 mmol). The reaction mixture was stirred for 16 h while allowing the reaction mixture to slowly warm up to room temperature by dissipation of the ice-water bath. The mixture was transferred to a separatory funnel containing ethyl acetate (50 mL). The aqueous layer was washed with 1N HCl (2×25 mL). The combined organic layers were washed with saturated NaHCO$_3$ (25 mL), brine (25 mL), dried over MgSO$_4$, filtered, and concentrated. The product was purified by column chromatography on silica gel (3%→7% methanol in dichloromethane; 120 g column) to afford 2-(2-oxoimidazolidin-1-yl)ethyl 4-methylbenzenesulfonate (356 mg, 1.252 mmol, 33% yield) as a yellow solid: $^1$H NMR (400 MHz, CHLOROFORM-d) δ 7.86-7.77 (m, 2H), 7.38 (d, J=8.0 Hz, 2H), 4.51 (br. s., 1H), 4.17 (t, J=5.0 Hz, 2H), 3.59-3.52 (m, 2H), 3.47 (t, J=5.0 Hz, 2H), 3.43-3.35 (m, 2H), 2.48 (s, 3H); LC/MS m/e 285.1 [(M+H)$^+$, calcd for C$_{12}$H$_{17}$N$_2$O$_4$S 285.1], t$_R$=1.58 min (method 2-1).

Step 2. Preparation of (S)-benzyl 1-(fluoromethyl)-4-((1R,3aS,5aR,5bR,7aR,11aS,11bR,13aR,13bR)-5a,5b,8,8,11a-pentamethyl-3a-((2-(2-oxoimidazolidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate

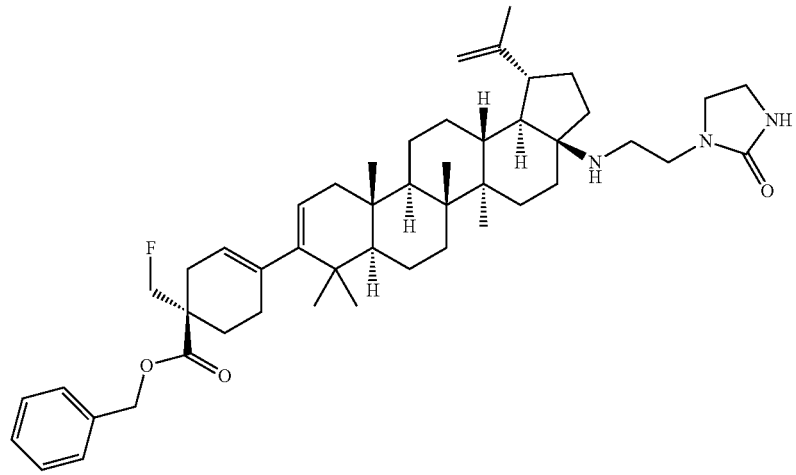

(S)-Benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (40 mg, 0.061 mmol), 2-(2-oxoimidazolidin-1-yl)ethyl 4-methylbenzenesulfonate (69.4 mg, 0.244 mmol), potassium phosphate tribasic (64.7 mg, 0.305 mmol), and potassium iodide (50.6 mg, 0.305 mmol) were combined in a vial. Acetonitrile (1 mL) was added, the vial was sealed, and the reaction mixture was heated at 120° C. for 16 h. The mixture was transferred to a separatory funnel containing water (10 mL). The aqueous layer was extracted with dichloromethane (3×10 mL). The combined organic layers were washed with brine (10 mL), dried over MgSO$_4$, filtered, and concentrated. The product was purified by column chromatography on silica gel (10% 9:1 acetone:methanol/90% hexanes→40% 9:1 acetone:methanol/60% hexanes; 40 g column, λ=220 nm) to afford (S)-benzyl 1-(fluoromethyl)-4-((1R,3aS,5aR,5bR,7aR,11aS,11bR,13aR,13bR)-5a,5b,8,8,11a-pentamethyl-3a-((2-(2-oxoimidazolidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (31 mg, 0.040 mmol, 66% yield) as a colorless foam: $^1$H NMR (500 MHz, CHLOROFORM-d) δ 7.38-7.33 (m, 5H), 5.33 (br. s., 1H), 5.19 (d, J=2.4 Hz, 2H), 5.13 (dd, J=6.1, 1.7 Hz, 1H), 4.72 (d, J=1.8 Hz, 1H), 4.63-4.55 (m, 2H), 4.53-4.45 (m, 1H), 4.32 (s, 1H), 3.61-3.47 (m, 3H), 3.46-3.35 (m, 4H), 3.24 (dt, J=13.8, 5.3 Hz, 1H), 2.70-2.52 (m, 4H), 2.20-0.85 (m, 26H), 1.70 (s, 3H), 1.05 (s, 3H), 0.96 (s, 3H), 0.91 (s, 3H), 0.90 (s, 3H), 0.85 (s, 3H); LC/MS m/e 768.6 [(M+H)$^+$, calcd for C$_{49}$H$_{71}$FN$_3$O$_3$ 768.5], $t_R$=4.61 min (method 2-2).

Step 3. A solution of (S)-benzyl 1-(fluoromethyl)-4-((1R,3aS,5aR,5bR,7aR,11aS,11bR,13aR,13bR)-5a,5b,8,8,11a-pentamethyl-3a-((2-(2-oxoimidazolidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (31 mg, 0.040 mmol) in 1,4-dioxane (0.5 mL) and EtOH (0.25 mL) was treated with sodium hydroxide (0.101 mL, 0.202 mmol). The reaction mixture was heated at 70° C. for 2 h. The mixture was cooled to room temperature, was filtered through a syringe filter, and was purified by reverse phase preparative HPLC (method 2-1) to afford (S)-1-(fluoromethyl)-4-((1R,3aS,5aR,5bR,7aR,11aS,11bR,13aR,13bR)-5a,5b,8,8,11a-pentamethyl-3a-((2-(2-oxoimidazolidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid•TFA (19.0 mg, 58% yield) as a white amorphous solid.

$^1$H NMR (500 MHz, Acetic Acid-d$_4$) δ 5.39 (br. s., 1H), 5.24 (d, J=4.6 Hz, 1H), 4.89 (s, 1H), 4.75 (s, 1H), 4.65-4.56 (m, 1H), 4.55-4.46 (m, 1H), 3.73-3.66 (m, 1H), 3.65-3.51 (m, 6H), 3.47-3.43 (m, 2H), 2.84-2.75 (m, 1H), 2.61 (d, J=17.5 Hz, 1H), 2.32-1.08 (m, 26H), 1.76 (s, 3H), 1.15 (s, 3H), 1.10 (s, 3H), 1.00 (s, 3H), 0.99 (s, 3H), 0.94 (s, 3H); LC/MS m/e 678.5 [(M+H)$^+$, calcd for C$_{42}$H$_{65}$FN$_3$O$_3$ 678.5], $t_R$=4.30 min (method 2-2); HPLC (method 2-1): $t_R$=18.88 min; HPLC (method 2-2): $t_R$=20.30 min.

Example 2-26
Preparation of (S)-1-(fluoromethyl)-4-(((1R,3aS,5aR, 5bR,7aR,11aS,11bR,13aR,13bR)-5a,5b,8,8,11a-pentamethyl-3a-((2-(3-methyl-2-oxoimidazolidin-1-yl) ethyl)amino)-1-(prop-1-en-2-yl)-2,3,3a,4,5,5a,5b,6, 7,7a,8,11,11a,11b,12,13,13a, 13b-octadecahydro-1H-cyclopenta[a]chrysen-9-yl)cyclohex-3-enecarboxylic acid
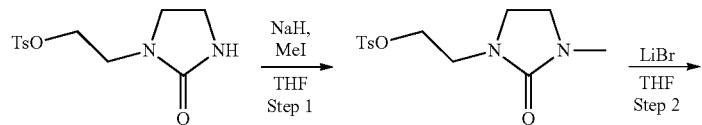

-continued

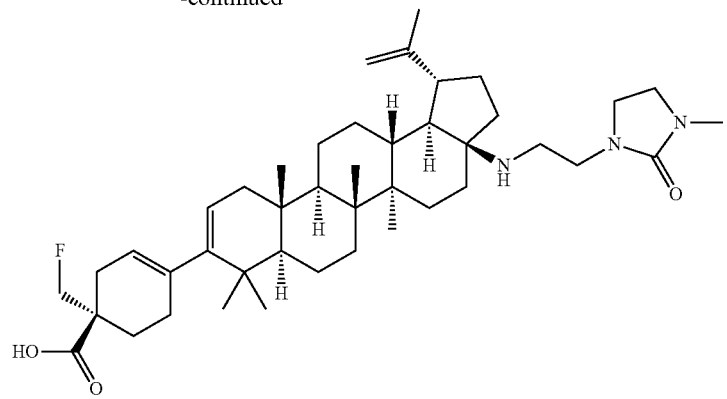

Example 2-26

Step 1. Preparation of 2-(3-methyl-2-oxoimidazolidin-1-yl)ethyl 4-methylbenzenesulfonate

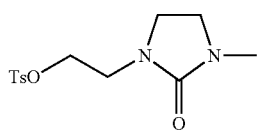 [SMILES: Cc1ccc(S(=O)(=O)OCCN2CCN(C)C2=O)cc1]

To a solution of 2-(2-oxoimidazolidin-1-yl)ethyl 4-methylbenzenesulfonate (135 mg, 0.475 mmol) in THF (4 mL) at 0° C. was added sodium bis(trimethylsilyl)amide (0.522 mL, 0.522 mmol). After stirring for 5 min, iodomethane (0.119 mL, 1.899 mmol) was added via syringe. The cooling bath was removed and the mixture was allowed to warm up to room temperature and was stirred for 2 h. The mixture was transferred to a separatory funnel containing saturated aqueous NaHCO$_3$ solution (10 mL). The aqueous layer was extracted with ethyl acetate (4×10 mL). The combined organic layers were washed with brine (10 mL), dried over MgSO$_4$, filtered, and concentrated. The product was purified by column chromatography on silica gel (1%→5% methanol in CH$_2$Cl$_2$; 40 g column) to afford 2-(3-methyl-2-oxoimidazolidin-1-yl)ethyl 4-methylbenzenesulfonate (91.3 mg, 0.306 mmol, 65% yield) as a pale-green oil: $^1$H NMR (400 MHz, CHLOROFORM-d) δ 7.83-7.77 (m, 2H), 7.37 (d, J=8.0 Hz, 2H), 4.15 (t, J=5.1 Hz, 2H), 3.45 (t, J=5.0 Hz, 2H), 3.43-3.37 (m, 2H), 3.29-3.23 (m, 2H), 2.77 (s, 3H), 2.47 (s, 3H); LC/MS (ESI) m/e 299.2 [(M+H)$^+$, calcd for C$_{13}$H$_{19}$N$_2$O$_4$S 299.1], t$_R$=1.61 min (method 2-1).

Step 2. Preparation of 1-(2-bromoethyl)-3-methylimidazolidin-2-one

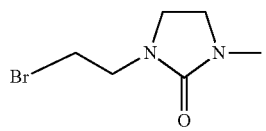

To a solution of 2-(3-methyl-2-oxoimidazolidin-1-yl) ethyl 4-methylbenzenesulfonate (158 mg, 0.530 mmol) in THF (5 mL) at room temperature was added lithium bromide (138 mg, 1.589 mmol). The reaction mixture was stirred at room temperature overnight. The reaction mixture was then heated at 60° C. for 3 h. The mixture was transferred to a separatory funnel containing saturated aqueous NaHCO$_3$ solution (5 mL) and water (5 mL). The aqueous layer was extracted with ethyl acetate (4×10 mL). The combined organic layers were washed with brine (10 mL), dried over MgSO$_4$, filtered, and concentrated. The product was purified by column chromatography on silica gel (2%→5% methanol in CH$_2$Cl$_2$; 40 g column) to afford 1-(2-bromoethyl)-3-methylimidazolidin-2-one (92.3 mg, 0.446 mmol, 84% yield) as a yellow oil: $^1$H NMR (400 MHz, CHLOROFORM-d) δ 3.65-3.60 (m, 2H), 3.52-3.44 (m, 4H), 3.38-3.32 (m, 2H), 2.82 (s, 3H); LC/MS (ESI) m/e 207.2 [(M+H)$^+$, calcd for C$_6$H$_{12}$BrN$_2$O 207.0], t$_R$=1.70 min (method 2-1).

Step 3. Preparation of (S)-benzyl 1-(fluoromethyl)-4-((1R,3aS,5aR,5bR,7aR,11aS,11bR,13aR,13bR)-5a,5b,8,8,11a-pentamethyl-3a-((2-(3-methyl-2-oxoimidazolidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate

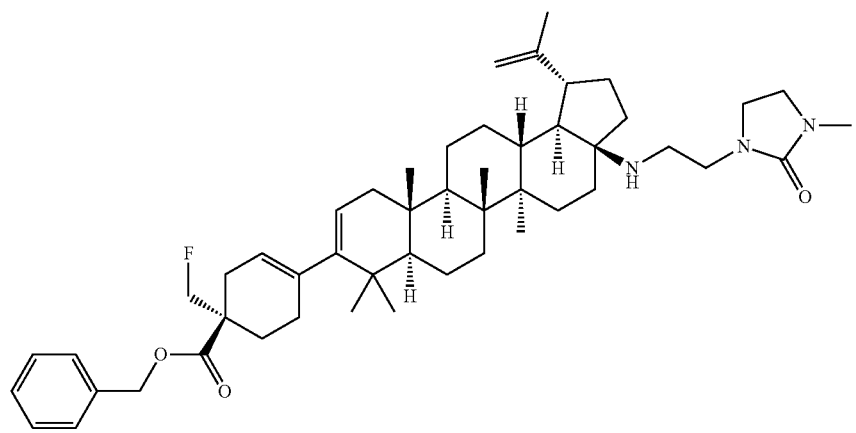

To a mixture of (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (60 mg, 0.091 mmol), 1-(2-bromoethyl)-3-methylimidazolidin-2-one (56.8 mg, 0.274 mmol), potassium phosphate tribasic (78 mg, 0.366 mmol), and potassium iodide (45.6 mg, 0.274 mmol) in an oven-dried pressure vessel was added acetonitrile (1.0 mL). The cap was sealed and the reaction mixture was heated at 120° C. for 14 h. The mixture was transferred to a separatory funnel containing water (5 mL). The aqueous layer was extracted with dichloromethane (3×10 mL). The combined organic layers were washed with brine (5 mL), dried over MgSO$_4$, filtered, and concentrated. The product was purified by column chromatography on silica gel (10% 9:1 acetone:methanol/90% hexanes→50% 9:1 acetone:methanol/50% hexanes; 24 g column, λ=220 nm) to afford (S)-benzyl 1-(fluoromethyl)-4-((1R,3aS,5aR,5bR,7aR,11aS,11bR,13aR,13bR)-5a,5b,8,8,11a-pentamethyl-3a-((2-(3-methyl-2-oxoimidazolidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (47.7 mg, 0.061 mmol, 66% yield) as a white foam: $^1$H NMR (500 MHz, CHLOROFORM-d) δ 7.40-7.33 (m, 5H), 5.33 (br. s., 1H), 5.23-5.16 (m, 2H), 5.14 (dd, J=6.2, 1.6 Hz, 1H), 4.72 (d, J=2.0 Hz, 1H), 4.63-4.56 (m, 2H), 4.53-4.47 (m, 1H), 3.45-3.20 (m, 6H), 2.82 (s, 3H), 2.68-2.51 (m, 4H), 2.19-0.87 (m 27H), 1.70 (s, 3H), 1.03 (s, 3H), 0.96 (s, 3H), 0.91 (s, 3H), 0.90 (s, 3H), 0.85 (s, 3H); LC/MS m/e 782.6 [(M+H)$^+$, calcd for C$_{50}$H$_{73}$FN$_3$O$_3$ 782.6], $t_R$=4.56 min (method 2-3).

Step 4. A solution of (S)-benzyl 1-(fluoromethyl)-4-((1R,3aS,5aR,5bR,7aR,11aS,11bR,13aR,13bR)-5a,5b,8,8,11a-pentamethyl-3a-((2-(3-methyl-2-oxoimidazolidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (46 mg, 0.059 mmol) in 1,4-dioxane (0.7 mL) and EtOH (0.35 mL) was treated with sodium hydroxide (2M aq) (0.147 mL, 0.294 mmol). The reaction mixture was heated at 70° C. for 2 h. The mixture was cooled to room temperature, was filtered through a syringe filter, and was purified by reverse phase preparative HPLC (method 2-1) to afford (S)-1-(fluoromethyl)-4-((1R,3aS,5aR,5bR,7aR,11aS,11bR,13aR,13bR)-5a,5b,8,8,11a-pentamethyl-3a-((2-(3-methyl-2-oxoimidazolidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid•TFA (35.6 mg, 74% yield) as a white amorphous solid:
$^1$H NMR (500 MHz, Acetic Acid-d$_4$) δ 5.39 (br. s., 1H), 5.25 (d, J=4.7 Hz, 1H), 4.88 (s, 1H), 4.75 (s, 1H), 4.64-4.57 (m, 1H), 4.55-4.47 (m, 1H), 3.63-3.40 (m, 8H), 2.84 (s, 3H), 2.85-2.81 (m, 1H), 2.61 (d, J=16.5 Hz, 1H), 2.31-1.12 (m, 27H), 1.76 (s, 3H), 1.15 (s, 3H), 1.10 (s, 3H), 1.01 (s, 3H), 0.99 (s, 3H), 0.95 (s, 3H); LC/MS m/e 692.6 [(M±H)$^+$, calcd for C$_{43}$H$_{67}$FN$_3$O$_3$ 692.5], t$_R$=4.19 min (method 2-2); HPLC (method 2-1): t$_R$=18.80 min; HPLC (method 2-2): t$_R$=20.44 min.
Example 2-27
Preparation of (S)-4-(((1R,3aS,5aR,5bR,7aR,11aS,11bR,13aR,13bR)-3a-((2-(4-acetyl-3,3-dimethyl-2-oxopiperazin-1-yl)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylic acid
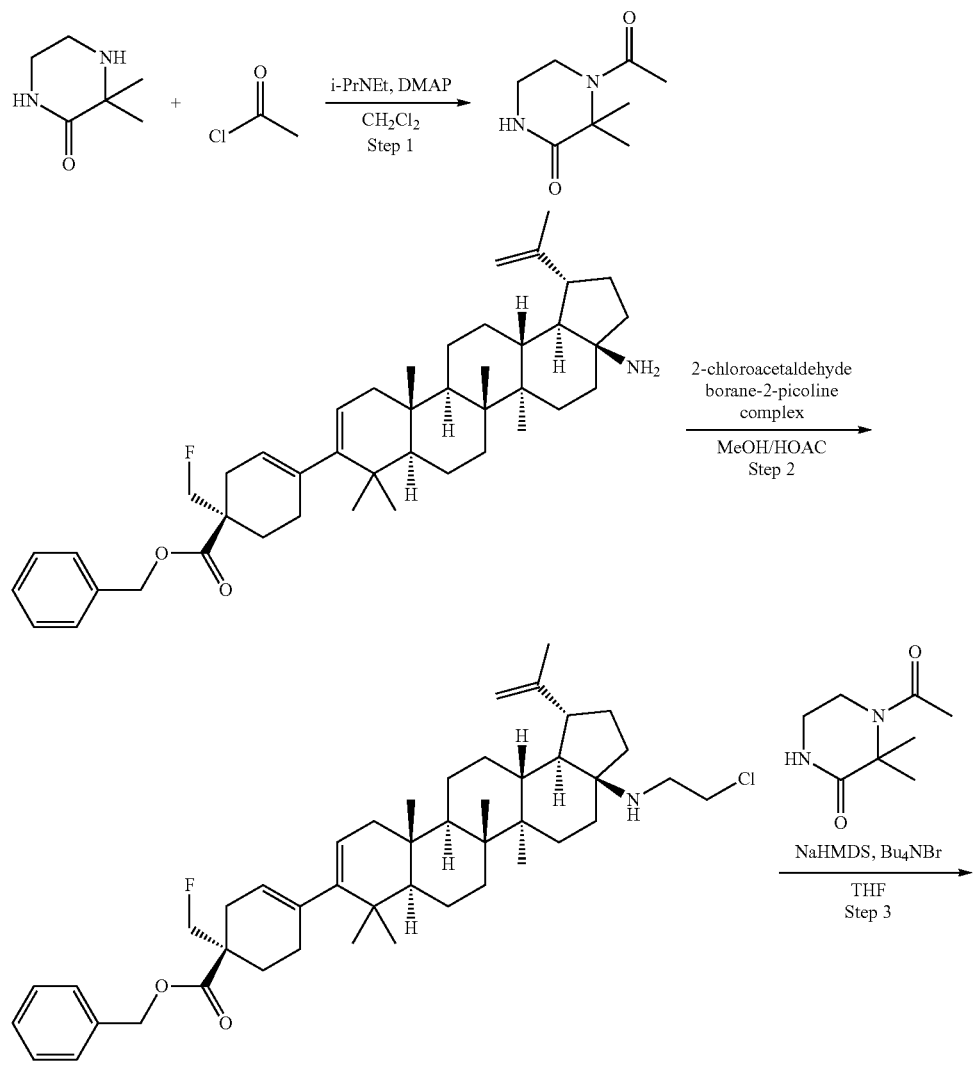

-continued

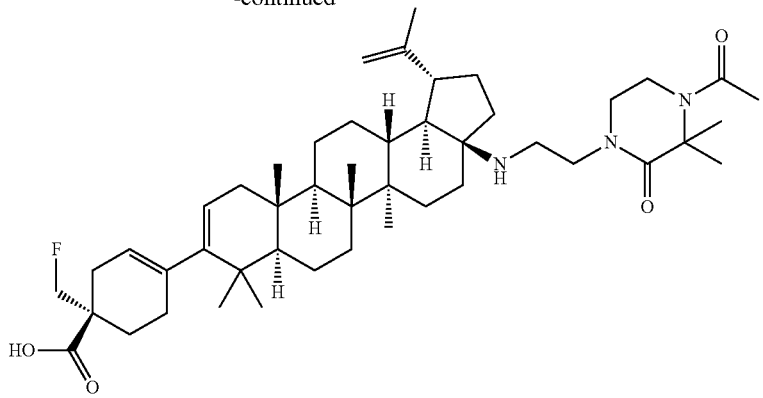

Example 2-27

Step 1. Preparation of 4-acetyl-3,3-dimethylpiperazin-2-one

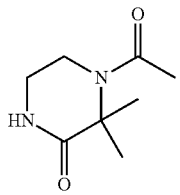

To a solution of 3,3-dimethylpiperazin-2-one (50 mg, 0.390 mmol) in $CH_2Cl_2$ (1.2 mL) at 0° C. was added N,N-diisopropylethylamine (0.204 mL, 1.170 mmol) followed by the slow addition of acetyl chloride (0.031 mL, 0.429 mmol). The reaction mixture was stirred at 0° C. for 4 h. The mixture was then concentrated. The product was purified by column chromatography on silica gel (25% 4:1 $CH_2Cl_2$:MeOH with 0.2% $NH_4OH$/75% $CH_2Cl_2 \rightarrow 100\%$ 4:1 $CH_2Cl_2$:MeOH with 0.2% $NH_4OH$; 40 g column, λ=220 nm) to afford 4-acetyl-3,3-dimethylpiperazin-2-one (59.6 mg, 0.350 mmol, 90% yield) as a colorless solid: $^1$H NMR (400 MHz, CHLOROFORM-d) δ 3.64-3.57 (m, 2H), 3.46-3.39 (m, 2H), 2.16 (s, 3H), 1.77 (s, 6H); LC/MS (ESI) m/e 171.3 [(M+H)$^+$, calcd for $C_8H_{15}N_2O_2$ 171.2], $t_R$=0.43 min (method 2-1).

Step 2. Preparation of (S)-benzyl 4-((1R,3aS,5aR,5bR,7aR,11aS,11bR,13aR,13bR)-3a-((2-chloroethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate

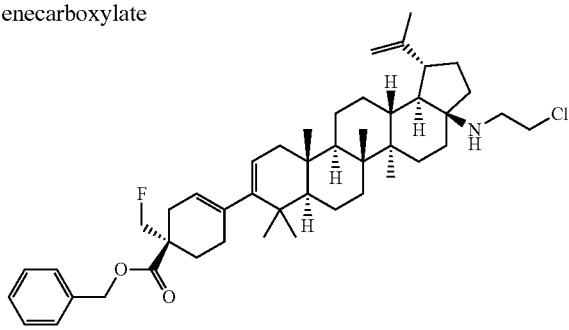

A mixture of (S)-benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (100 mg, 0.152 mmol), 2-chloroacetaldehyde (0.028 mL, 0.229 mmol), and borane-2-picoline complex (24.46 mg, 0.229 mmol) in MeOH (1 mL) and acetic acid (0.2 mL) was stirred at room temperature for 18 h. The mixture was transferred to a separatory funnel containing saturated aqueous sodium bicarbonate solution (10 mL). The aqueous layer was extracted with dichloromethane (4×15 mL). The combined organic layers were washed with brine (10 mL), dried over $MgSO_4$, filtered, and concentrated. The product was purified by column chromatography on silica gel (10% 9:1 acetone:methanol/90% hexanes→50% 9:1 acetone:methanol/50% hexanes; 40 g column, λ=220 nm) to afford (S)-benzyl 4-((1R,3aS,5aR,5bR,7aR,11aS,11bR,13aR,13bR)-3a-((2-chloroethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (57 mg, 0.079 mmol, 52% yield) as a colorless foam: $^1$H NMR (500 MHz, CHLOROFORM-d) δ 7.40-7.31 (m, 5H), 5.33 (br. s., 1H), 5.23-5.16 (m, 2H), 5.14 (dd, J=6.1, 1.7 Hz, 1H), 4.73 (d, J=2.0 Hz, 1H), 4.63-4.56 (m, 2H), 4.53-4.46 (m, 1H), 3.72-3.65 (m, 2H), 2.85-2.72 (m, 2H), 2.67-2.57 (m, 2H), 2.17-1.02 (m, 27H), 1.71 (s, 3H), 1.08 (s, 3H), 0.97 (s, 3H), 0.92 (s, 3H), 0.90 (s, 3H), 0.86 (s, 3H); LC/MS m/e 718.6 [(M+H)$^+$, calcd for $C_{46}H_{66}ClFNO_2$ 718.5], $t_R$=4.82 min (method 2-3).

Step 3. To a mixture of (S)-benzyl 4-((1R,3aS,5aR,5bR,7aR,11aS,11bR,13aR,13bR)-3a-((2-chloroethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(fluoromethyl)cyclohex-3-enecarboxylate (22 mg, 0.031 mmol), 4-acetyl-3,3-dimethylpiperazin-2-one (15.64 mg, 0.092 mmol), and tetrabutylammonium bromide (9.87 mg, 0.031 mmol) in THF (0.6 mL) at 0° C. under nitrogen was added sodium bis(trimethylsilyl)amide (0.092 mL, 0.092 mmol). The mixture was stirred at 0° C. for 5 min. The cooling bath was removed and the reaction mixture was then heated at 75° C. for 14 hours. The mixture was concentrated and the residue was dissolved in dioxane/methanol/water and was neutralized by the addition of 2 N HCl (0.10 mL). The solution was filtered and purified by reverse phase preparative HPLC (method 2-1) to afford (S)-4-((1R,3aS,5aR,5bR,7aR,11aS, 11bR,13aR,13bR)-3a-((2-(4-acetyl-3,3-dimethyl-2-oxopiperazin-1-yl)ethyl)amino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl)-1-(fluoromethyl)cyclohex-3-enecarboxylic acid•TFA (9.6 mg, 34% yield) as a white amorphous solid: $^1$H NMR (500 MHz, Acetic Acid-d$_4$) δ 5.39 (br. s., 1H), 5.25 (d, J=4.7 Hz, 1H), 4.88 (s, 1H), 4.76 (s, 1H), 4.65-4.57 (m, 1H), 4.55-4.47 (m, 1H), 3.96-3.76 (m, 3H), 3.73-3.64 (m, 3H), 3.53 (t, J=4.1 Hz, 2H), 2.82 (t, J=11.1 Hz, 1H), 2.61 (d, J=16.6 Hz, 1H), 2.31-1.12 (s, 27H), 2.22 (s, 3H), 1.79 (s, 3H), 1.77 (s, 6H), 1.22 (s, 3H), 1.10 (s, 3H), 1.01 (s, 3H), 0.99 (s, 3H), 0.96 (s, 3H); LC/MS (ESI) m/e 762.6 [(M+H)$^+$, calcd for C$_{47}$H$_{73}$FN$_3$O$_4$ 762.6], t$_R$=4.29 min (method 2-2); HPLC (method 2-1): t$_R$=19.04 min; HPLC (method 2-2): t$_R$=20.23 min.

HIV Cell Culture Assay—

MT-2 cells and 293T cells were obtained from the NIH AIDS Research and Reference Reagent Program. MT-2 cells were propagated in RPMI 1640 media supplemented with 10% heat-inactivated fetal bovine serum, 100 μg/mL penicillin G and up to 100 units/mL streptomycin. The 293T cells were propagated in DMEM media supplemented with 10% heat-inactivated fetal bovine serum (FBS), 100 units/mL penicillin G and 100 μg/mL streptomycin. The proviral DNA clone of NL$_{4-3}$ was obtained from the NIH AIDS Research and Reference Reagent Program. A recombinant NL$_{4-3}$ virus, in which a section of the nef gene from NL4-3 was replaced with the *Renilla* luciferase gene, was used as a reference virus. In addition, residue Gag P373 was converted to P373S. Briefly, the recombinant virus was prepared by transfection of the altered proviral clone of NL$_{4-3}$. Transfections were performed in 293T cells using LipofectAMINE PLUS from Invitrogen (Carlsbad, Calif.), according to manufacturer's instruction. The virus was titered in MT-2 cells using luciferase enzyme activity as a marker. Luciferase was quantitated using the Dual Luciferase kit from Promega (Madison, Wis.), with modifications to the manufacturer's protocol. The diluted Passive Lysis solution was pre-mixed with the re-suspended Luciferase Assay Reagent and the re-suspended Stop & Glo Substrate (2:1:1 ratio). Fifty (50) μL, of the mixture was added to each aspirated well on assay plates and luciferase activity was measured immediately on a Wallac TriLux (Perkin-Elmer). Antiviral activities of inhibitors toward the recombinant virus were quantified by measuring luciferase activity in cells infected for 4-5 days with NLRluc recombinants in the presence serial dilutions of the inhibitor. The EC$_{50}$ data for the compounds is shown in Table 1 below.

Determination of EC$_{50}$ for WT, EC$_{50}$ for A364V, and EC$_{50}$ for 92UG029 viruses:

WT refers to wild-type HIV virus.

HIV-1 NL$_{4-3}$ expressing *Renilla* luciferase gene was converted to the gag A364V virus by site directed mutagenesis. A364V is a site directed mutant.

HIV-1 92UG029 was obtained from the NIH (Catalog Number: 1650). This is a subtype A Gag and subtype A Env, X4 (SI) virus from Uganda. Reference: WHO Network for HIV Isolation and Characterization. *AIDS Res Hum Retroviruses* 10:1359, 1994. The Gag/Pr region from 92UG029 was used to replace that in an HIV-1 NL$_{4-3}$ virus expressing *Renilla* luciferase gene.

Both recombinant viruses were used as described above in the HIV cell culture assay for the NL$_{4-3}$ virus. The EC$_{50}$ WT, EC$_{50}$ A364V and EC$_{50}$ 92 UG029 data for the compounds is shown in Table 1 and Table 2.

Table 2 data was generated with a 3x higher viral input that the data generated for the regular screen data reported in Table 1.

| Biological Data Key for EC$_{50}$s | |
|---|---|
| Compounds with EC$_{50}$ > 0.05 μM | Compounds with EC$_{50}$ < 0.0.5 μM |
| Group "B" | Group "A" |

TABLE 1

| Example # | Structure | WT(EC50, uM) | A364V (EC50, uM) | 92UG029 A Clade T332S/V3 62I/V370 A (EC50, uM) |
|---|---|---|---|---|
| 1 | 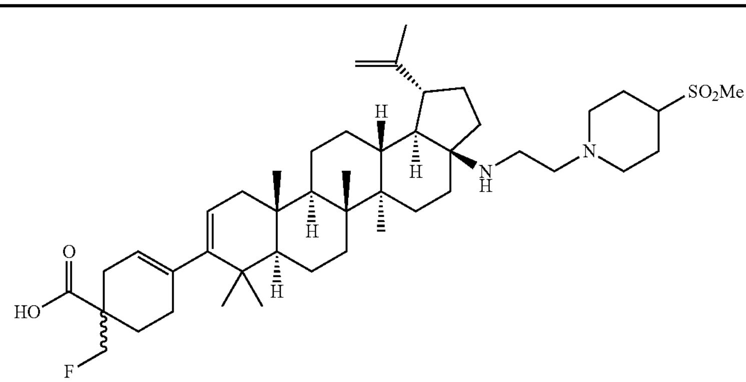 | 0.00175 | 0.123 | 0.00293 |

TABLE 1-continued

| Example # | Structure | WT(EC50, uM) | A364V (EC50, uM) | 92UG029 A Clade T332S/V362I/V370A (EC50, uM) |
|---|---|---|---|---|
| 1a | 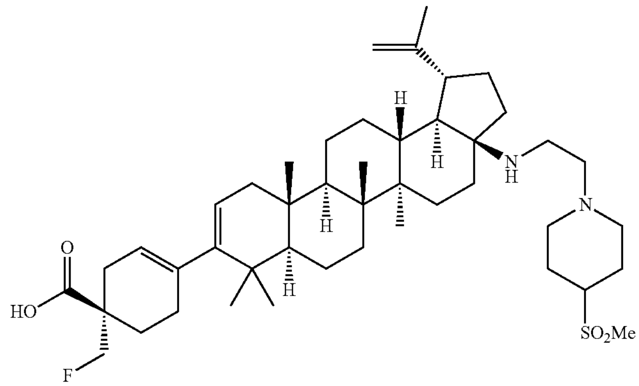 | 0.00225 | 0.109 | 0.00532 |
| 1b | 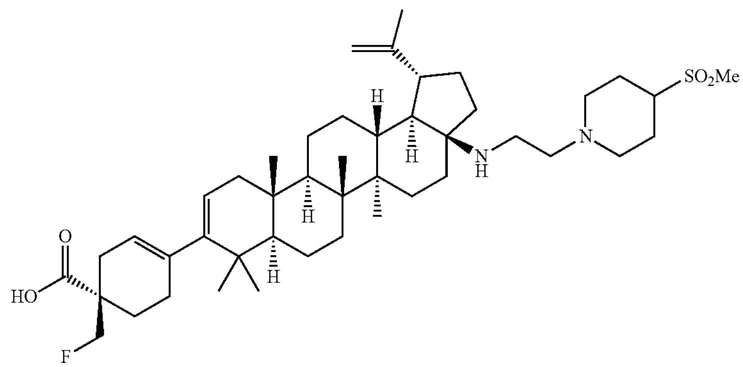 | 0.00193 | 0.176 | 0.00348 |
| 2 | 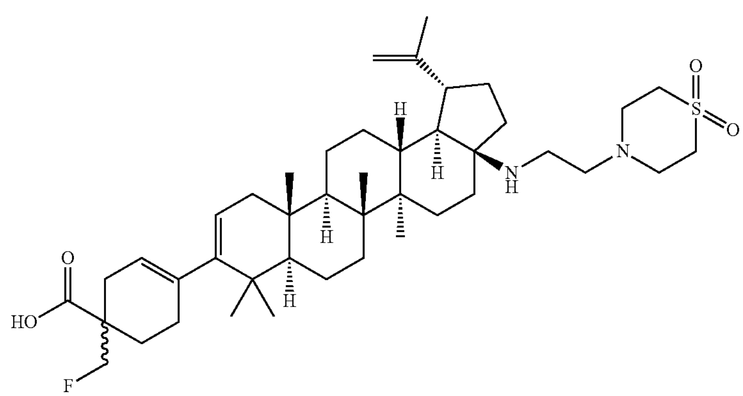 | 0.00129 | 0.0847 | 0.00461 |

TABLE 1-continued

| Example # | Structure | WT(EC50, uM) | A364V (EC50, uM) | 92UG029 A Clade T332S/V362I/V370A (EC50, uM) |
|---|---|---|---|---|
| 2a | 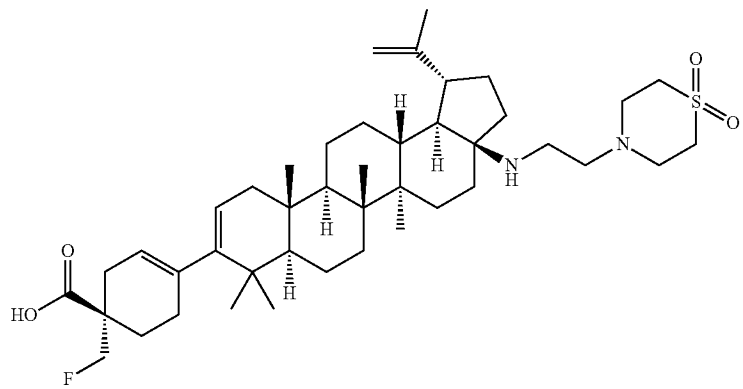 | 0.00198 | 0.160 | 0.00706 |
| 2b | 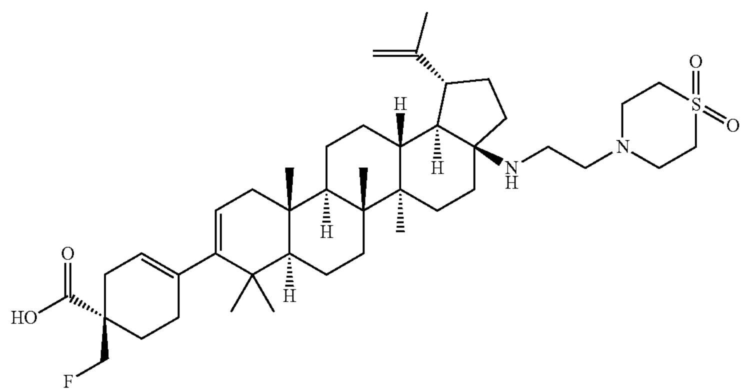 | 0.00148 | 0.201 | 0.00618 |
| 3 | 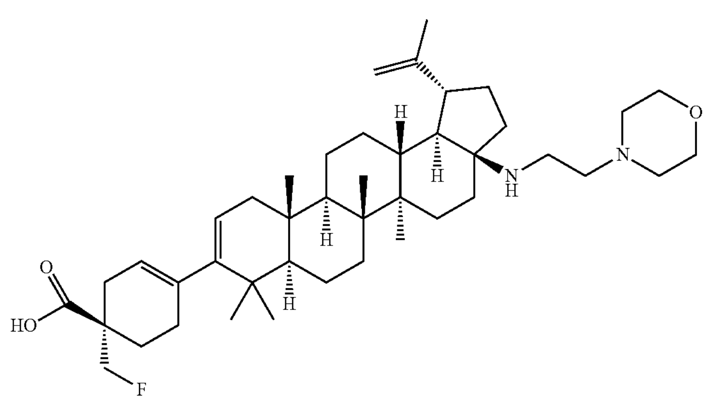 | 0.00453 | 0.679 | |

TABLE 1-continued

| Example # | Structure | WT(EC50, uM) | A364V (EC50, uM) | 92UG029 A Clade T332S/V362I/V370A (EC50, uM) |
|---|---|---|---|---|
| 4 | 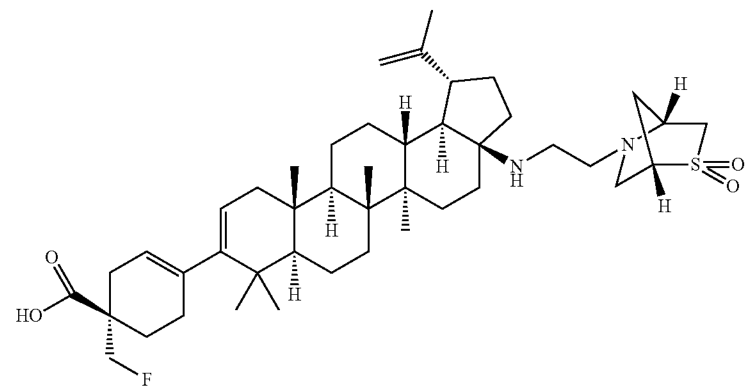 | 0.00141 | 0.0392 | |
| 5 | 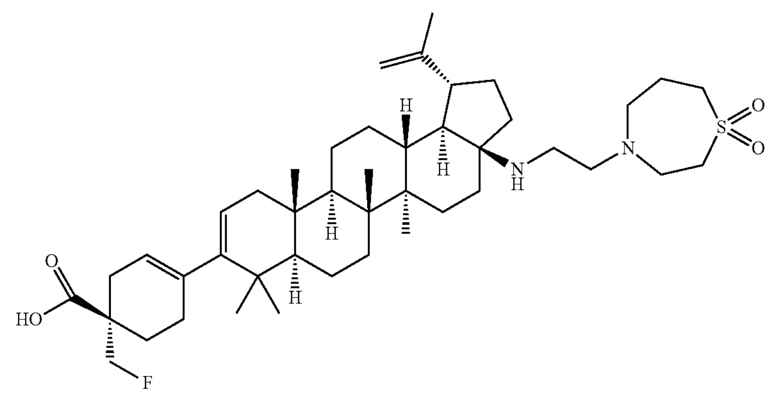 | 0.00160 | 0.0299 | |
| 6 | 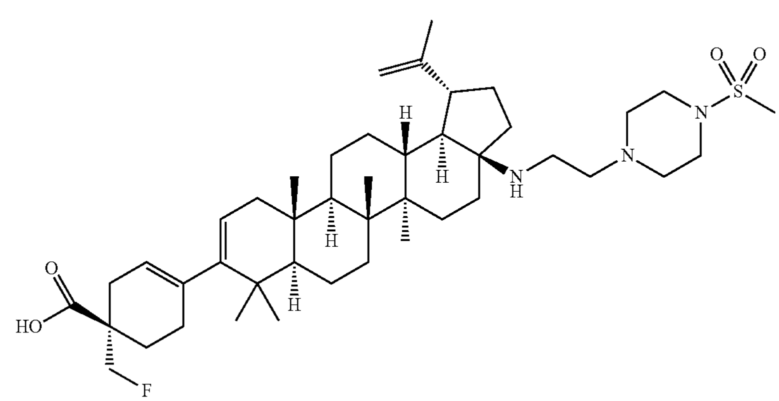 | 0.00195 | 0.0764 | |

TABLE 1-continued

| Example # | Structure | WT(EC50, uM) | A364V (EC50, uM) | 92UG029 A Clade T332S/V362I/V370A (EC50, uM) |
|---|---|---|---|---|
| 7 | 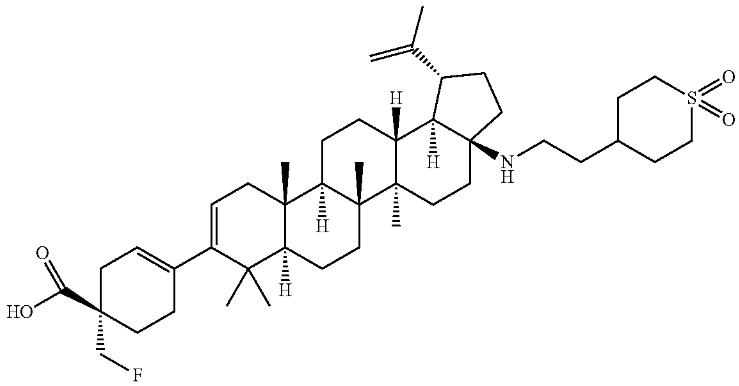 | A | B | |
| 8 | 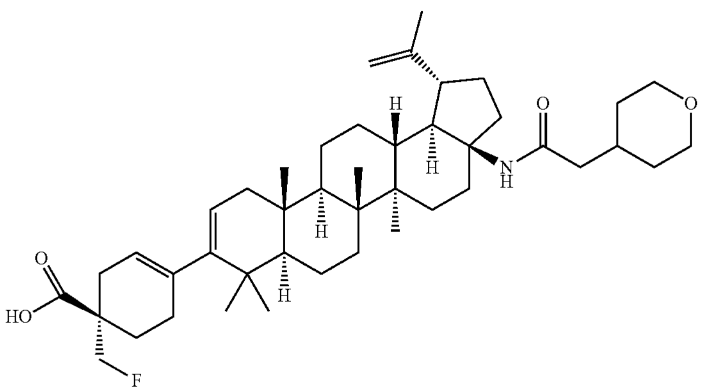 | B | B | |
| 9 | 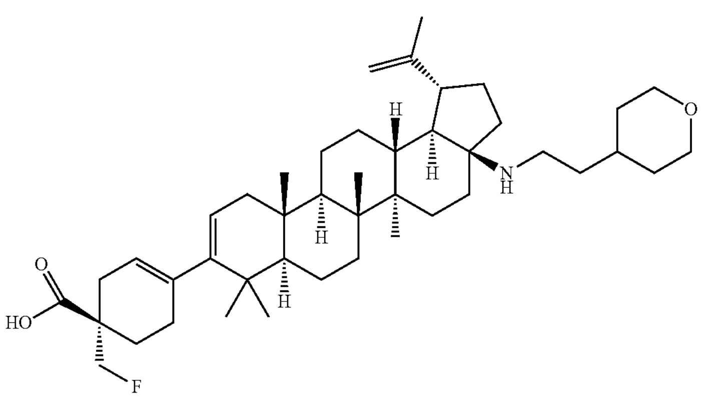 | A | B | |

TABLE 1-continued

| Example # | Structure | WT(EC50, uM) | A364V (EC50, uM) | 92UG029 A Clade T332S/V3 62I/V370 A (EC50, uM) |
|---|---|---|---|---|
| 10 | 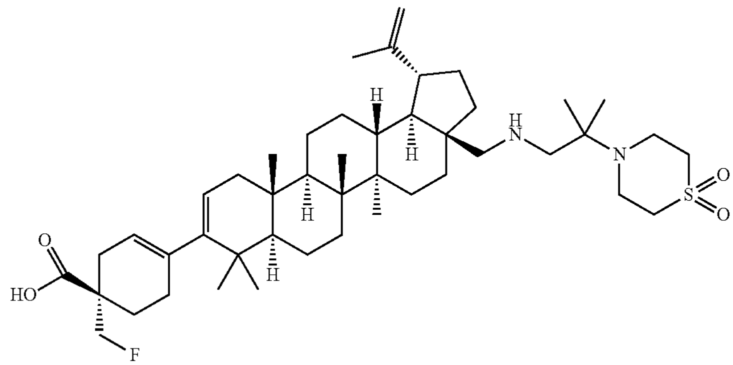 | | A | A |
| 11 | 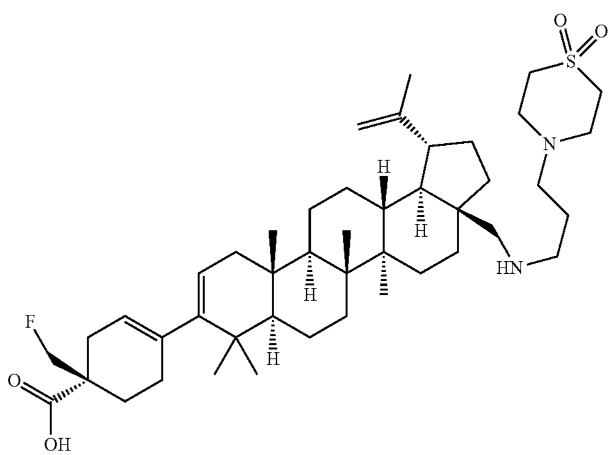 | | A | A |
| 12 | 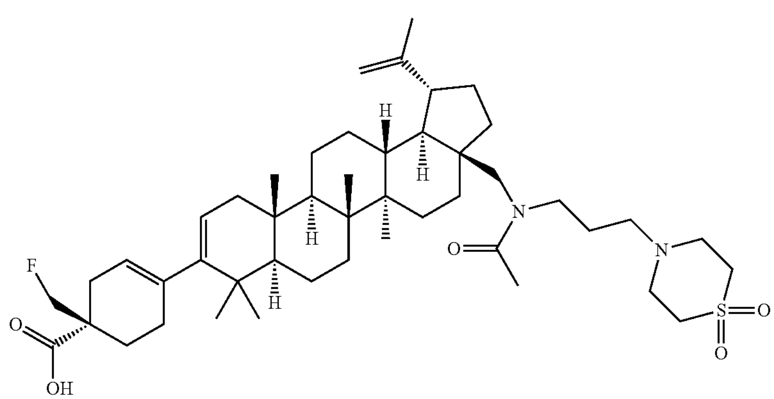 | | A | B |

TABLE 1-continued

| Example # | Structure | WT(EC50, uM) | A364V (EC50, uM) | 92UG029 A Clade T332S/V3 62I/V370 A (EC50, uM) |
|---|---|---|---|---|
| 13 | 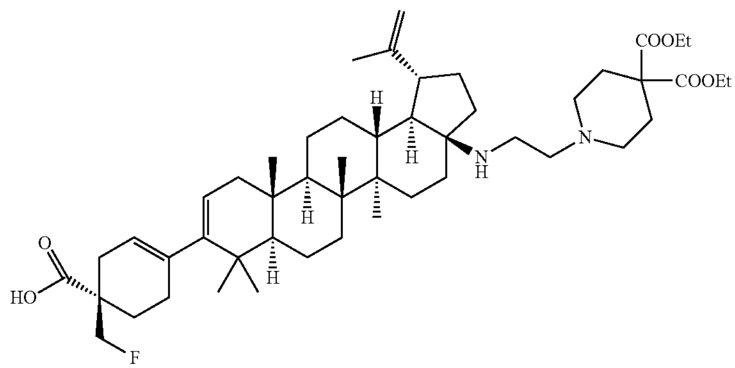 | 0.0188 | 0.196 | |
| 14 | Isomer 1 | A | A | |
| 15 | Isomer 2 | A | A | |

TABLE 1-continued

| Example # | Structure | WT(EC50, uM) | A364V (EC50, uM) | 92UG029 A Clade T332S/V362I/V370A (EC50, uM) |
|---|---|---|---|---|
| 16 | 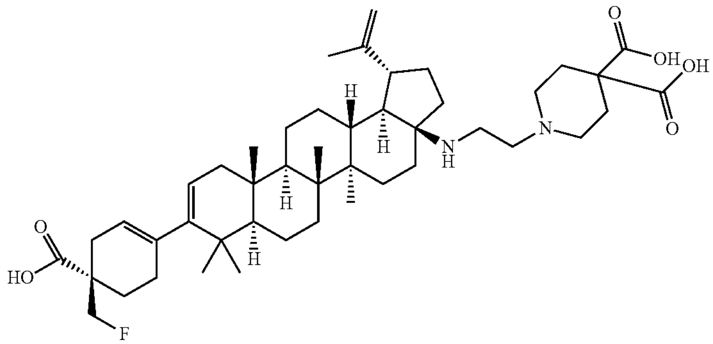 | 0.430 | 3.00 | |
| 17 | 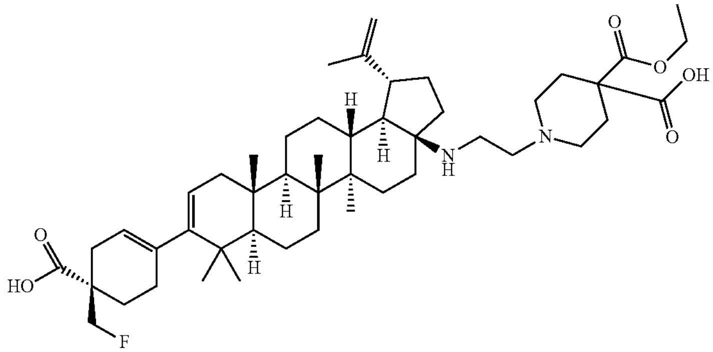 | 0.0194 | 3.00 | |
| 18 | 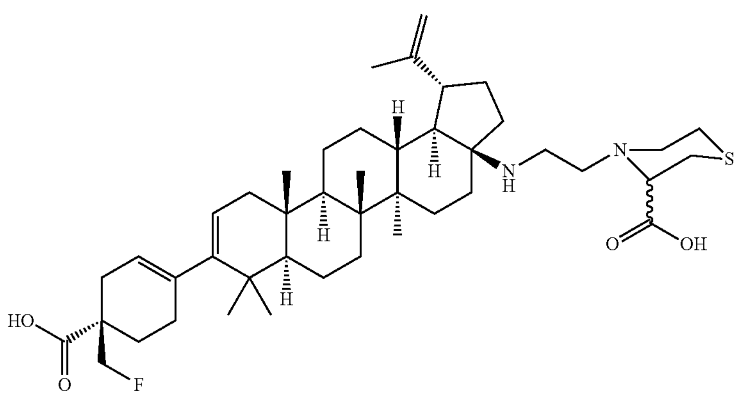 | 0.0243 | 3.00 | |
| 19 | 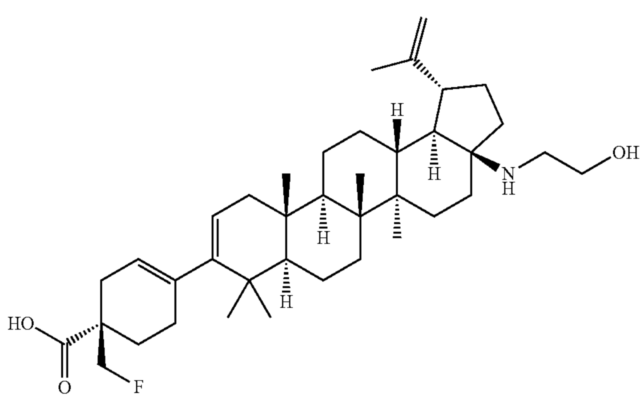 | A | B | |

TABLE 1-continued
| Example # | Structure | WT(EC50, uM) | A364V (EC50, uM) | 92UG029 A Clade T332S/V3 62I/V370 A (EC50, uM) |
|---|---|---|---|---|
| 20 | 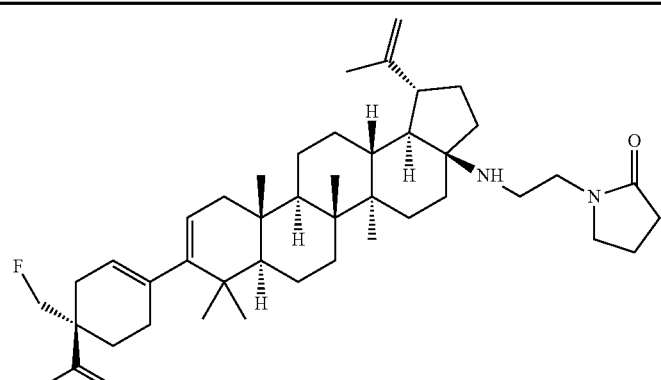 | 0.00253 | 0.129 | |
| 21 | 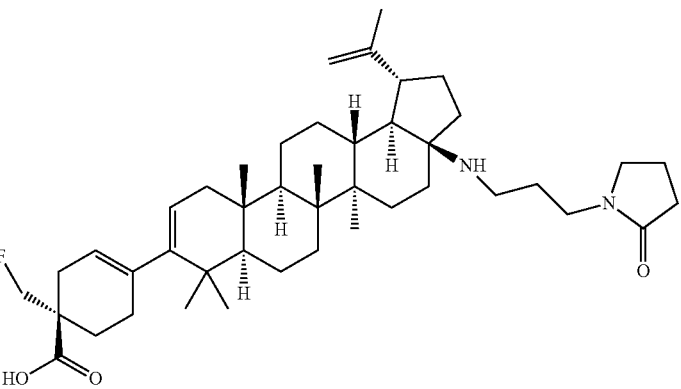 | A | B | |
| 22 | 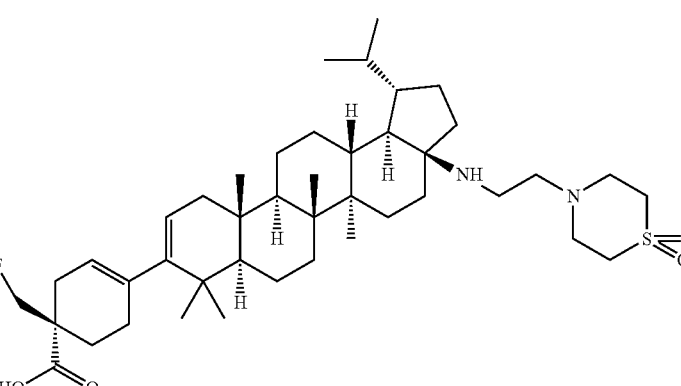 | 0.00134 | 0.0513 | |

TABLE 1-continued

| Example # | Structure | WT(EC50, uM) | A364V (EC50, uM) | 92UG029 A Clade T332S/V3 62I/V370 A (EC50, uM) |
|---|---|---|---|---|
| 23 | 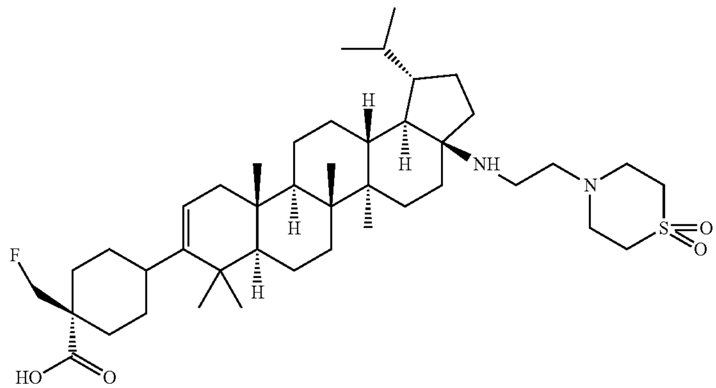 | A | B | |
| 24 | 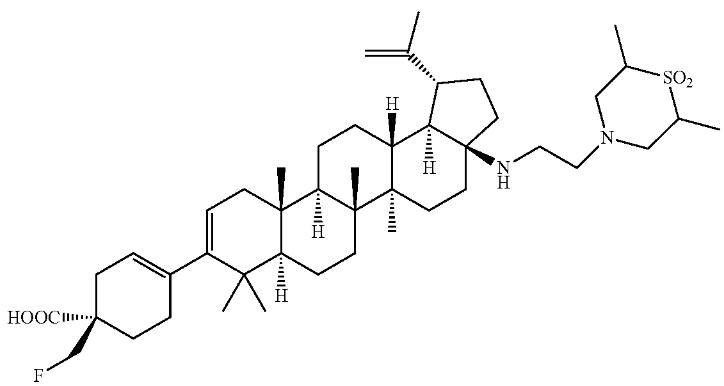 | A | B | |
| 25 | 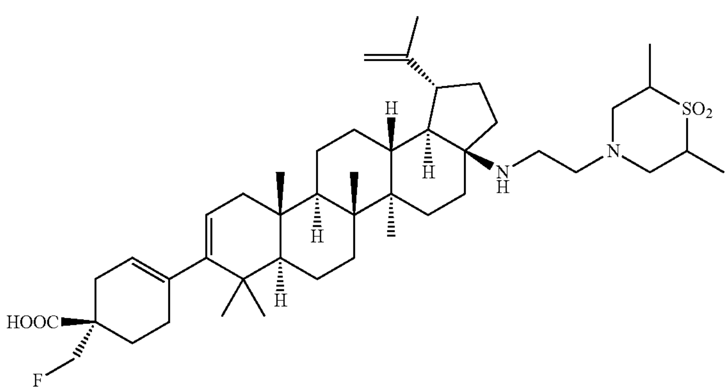 | A | B | |

TABLE 1-continued

| Example # | Structure | WT(EC50, uM) | A364V (EC50, uM) | 92UG029 A Clade T332S/V3 62I/V370 A (EC50, uM) |
|---|---|---|---|---|
| 26 | 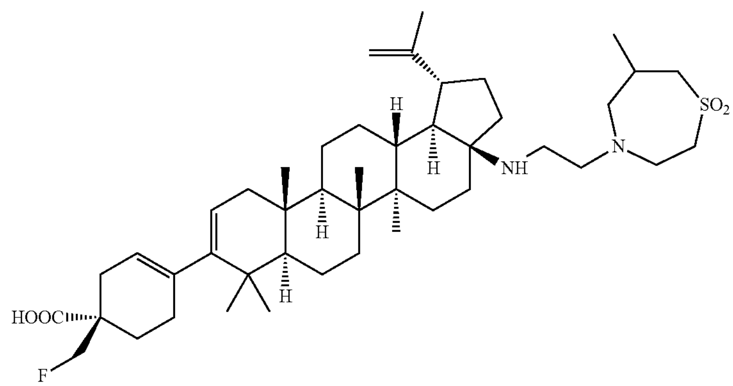 | A | B | |
| 27 | 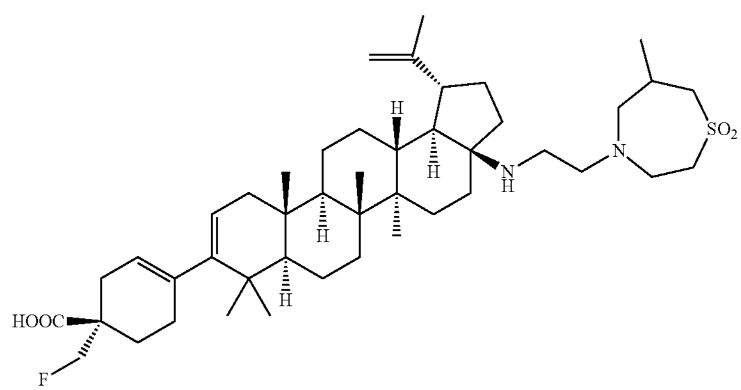 | A | B | |
| 28 | 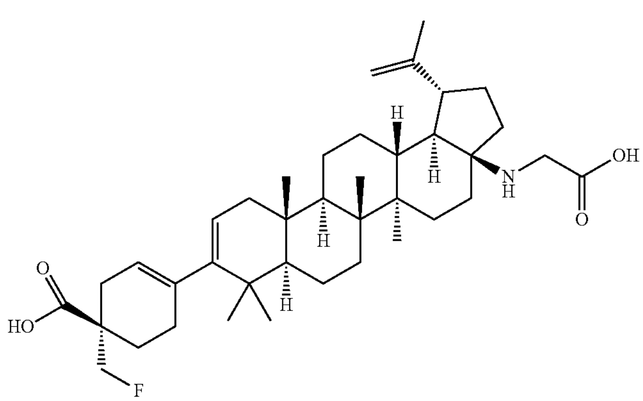 | B | B | |

TABLE 1-continued

| Example # | Structure | WT(EC50, uM) | A364V (EC50, uM) | 92UG029 A Clade T332S/V3 62I/V370 A (EC50, uM) |
|---|---|---|---|---|
| 29 | 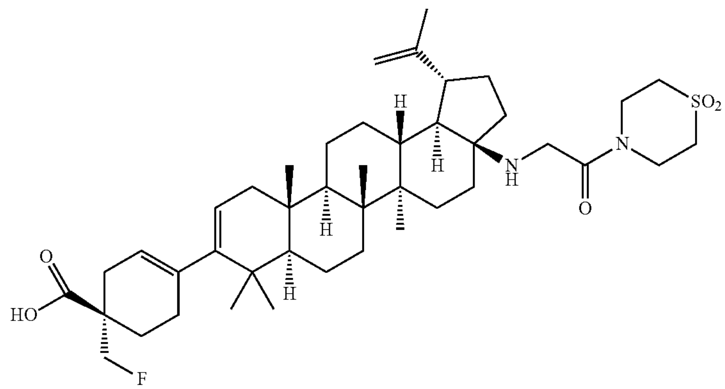 | | A | B |
| 30 | 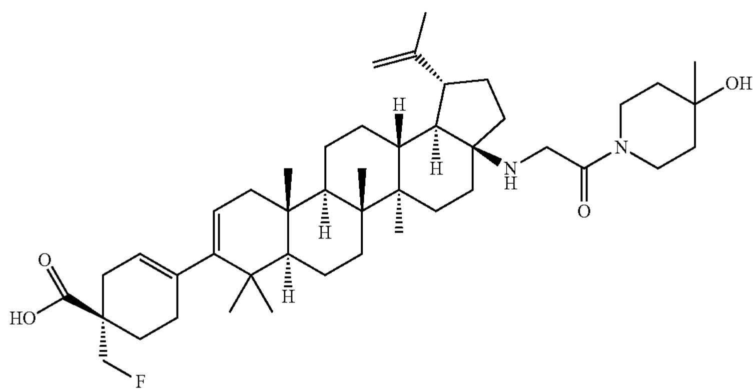 | 0.00298 | 0.551 | |
| 31 | 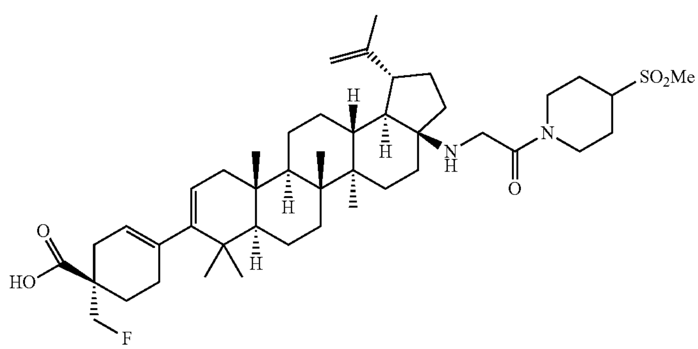 | | A | B |

TABLE 1-continued

| Example # | Structure | WT(EC50, uM) | A364V (EC50, uM) | 92UG029 A Clade T332S/V362I/V370A (EC50, uM) |
|---|---|---|---|---|
| 32 | 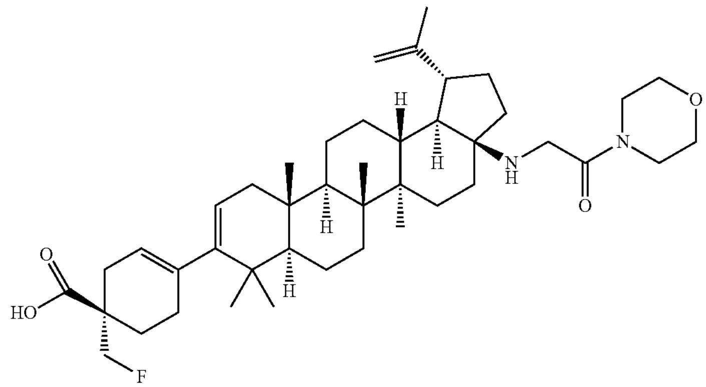 | A | B | |
| 33 | 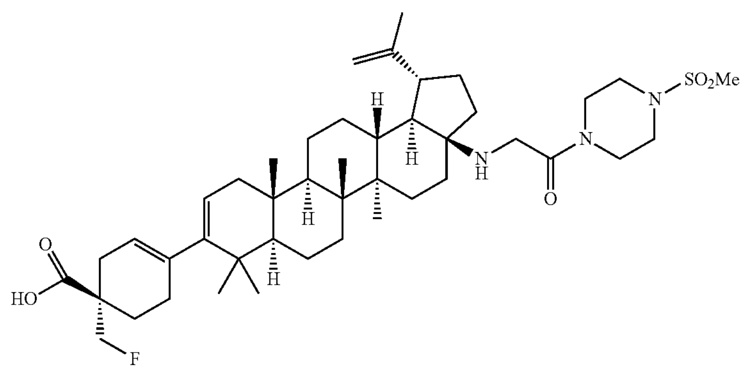 | A | B | |
| 34 | 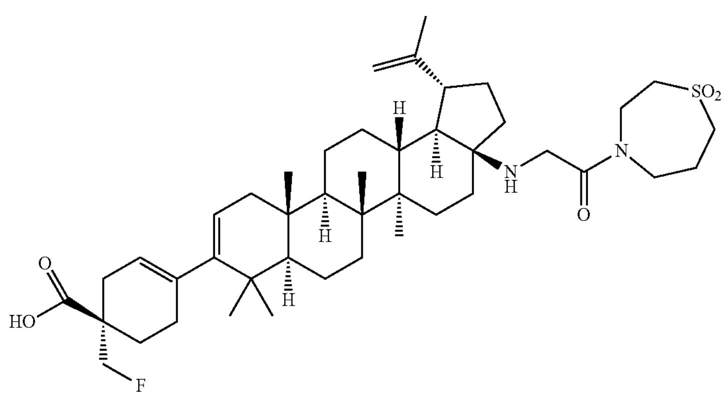 | A | A | |

TABLE 1-continued

| Example # | Structure | WT(EC50, uM) | A364V (EC50, uM) | 92UG029 A Clade T332S/V3 62I/V370 A (EC50, uM) |
|---|---|---|---|---|
| 35 | 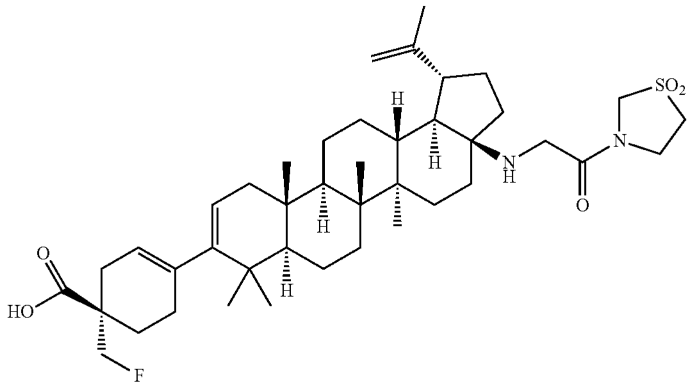 | 0.00157 | 0.157 | |
| 36 | 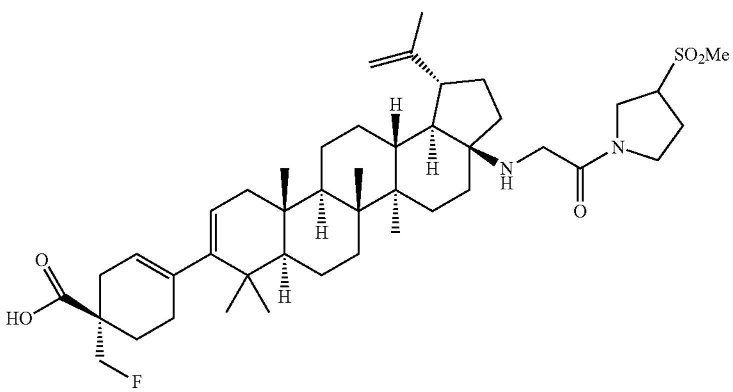 | A | B | |
| 37 | 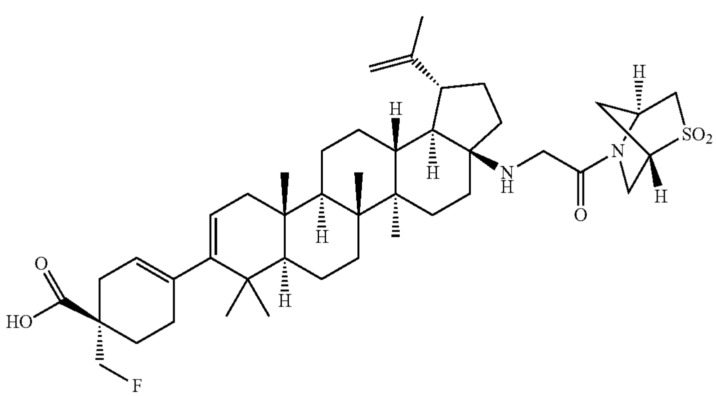 | A | B | |

TABLE 1-continued

| Example # | Structure | WT(EC50, uM) | A364V (EC50, uM) | 92UG029 A Clade T332S/V362I/V370A (EC50, uM) |
|---|---|---|---|---|
| 38 | 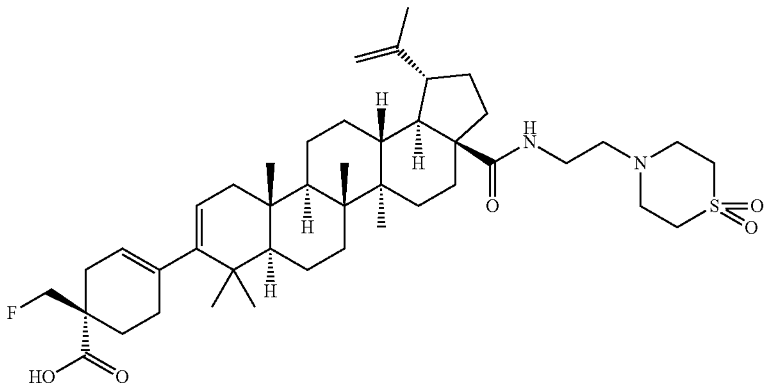 | | A | A |
| 39 | Isomer A | 0.0473 | 2.03 | |
| 40 | Isomer B | 0.0687 | 3.00 | |

TABLE 1-continued
| Example # | Structure | WT(EC50, uM) | A364V (EC50, uM) | 92UG029 A Clade T332S/V3 62I/V370 A (EC50, uM) |
|---|---|---|---|---|
| 41 | 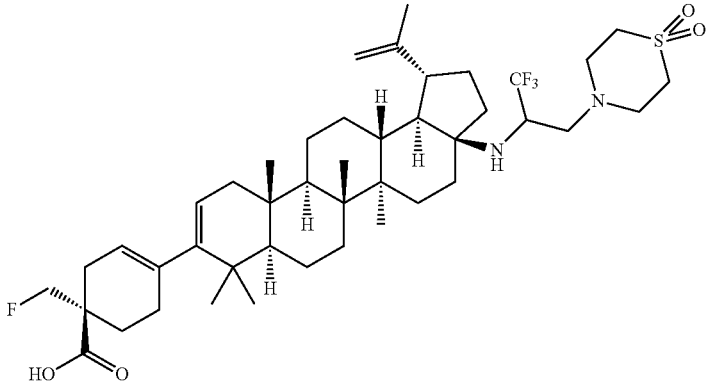 Isomer A | B | B | |
| 42 | 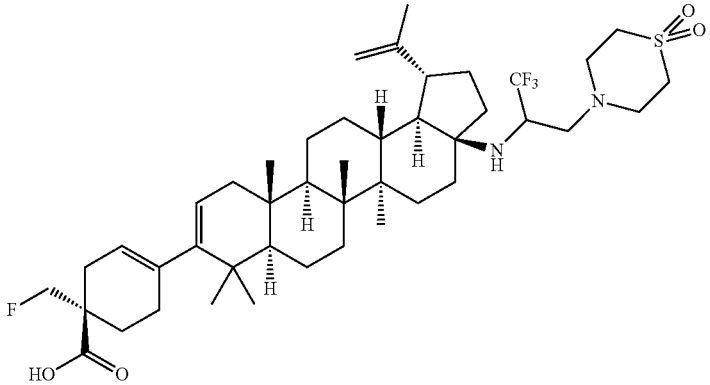 Isomer B | B | B | |
| 43 | 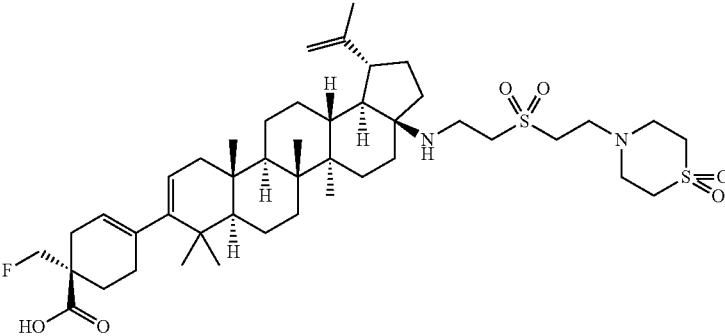 | 0.00335 | 0.585 | |

TABLE 1-continued
| Example # | Structure | WT(EC50, uM) | A364V (EC50, uM) | 92UG029 A Clade T332S/V362I/V370A (EC50, uM) |
|---|---|---|---|---|
| 2-1 | 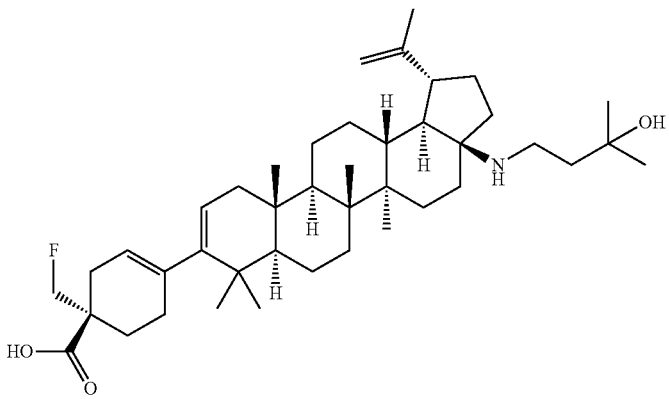 | A | B | |
| 2-2 | 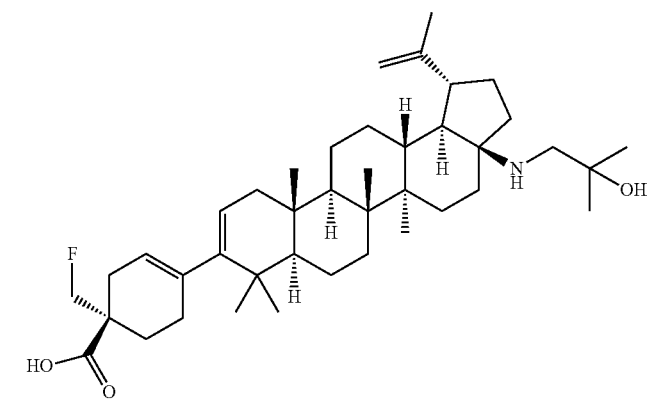 | A | B | |
| 2-3 | 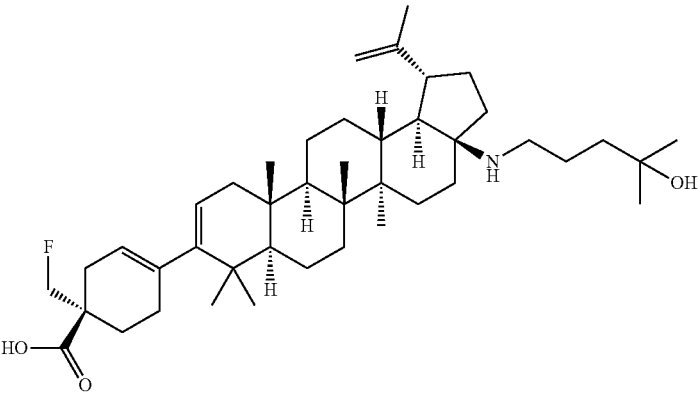 | A | B | |

TABLE 1-continued

| Example # | Structure | WT(EC50, uM) | A364V (EC50, uM) | 92UG029 A Clade T332S/V3 62I/V370 A (EC50, uM) |
|---|---|---|---|---|
| 2-4 | 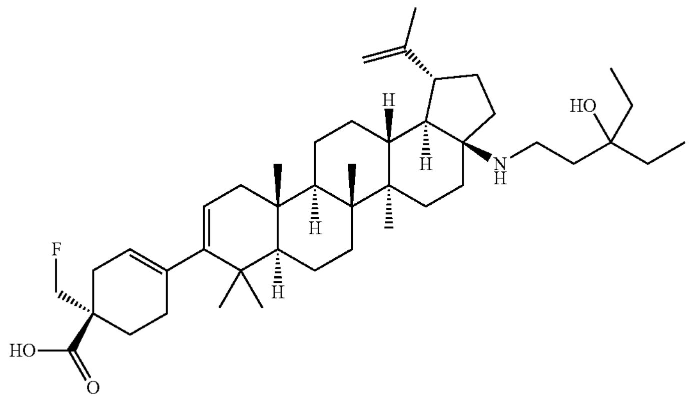 | A | B | |
| 2-5 | 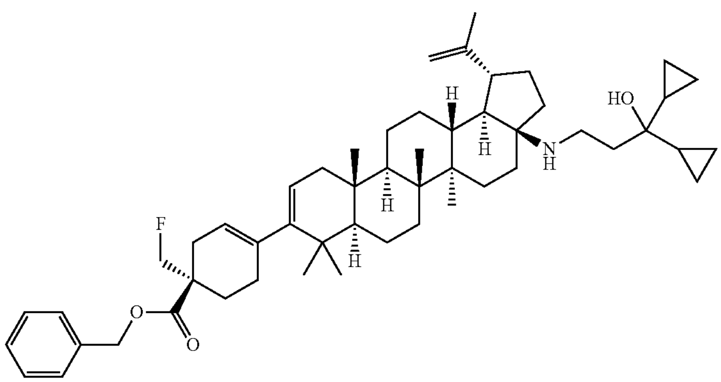 | A | B | |
| 2-6 | 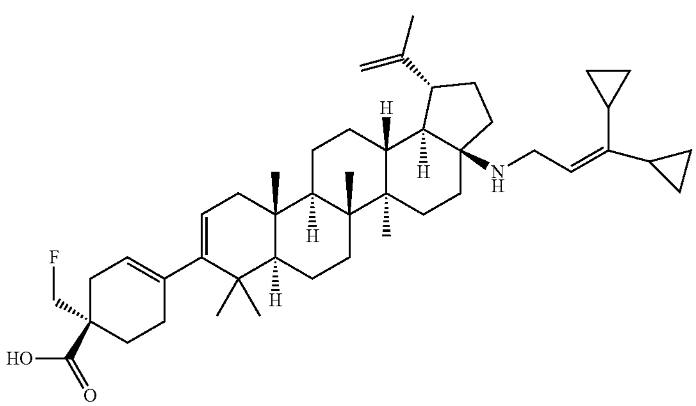 | 0.0110 | 3.00 | |

TABLE 1-continued

| Example # | Structure | WT(EC50, uM) | A364V (EC50, uM) | 92UG029 A Clade T332S/V3 62I/V370 A (EC50, uM) |
|---|---|---|---|---|
| 2-7 | 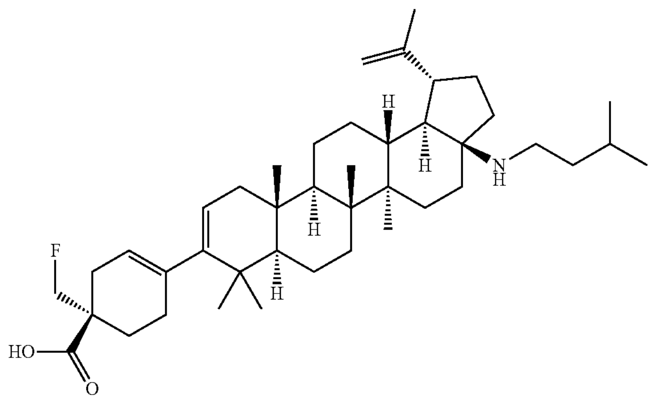 | 0.116 | 3.00 | |
| 2-8 | 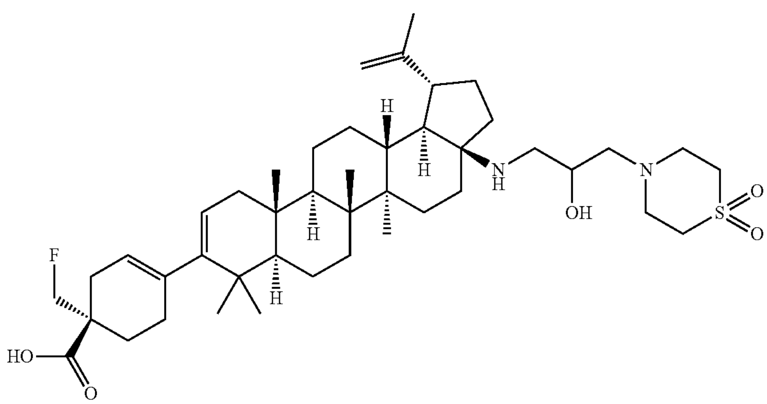 | 0.00233 | 1.91 | |
| 2-9 | 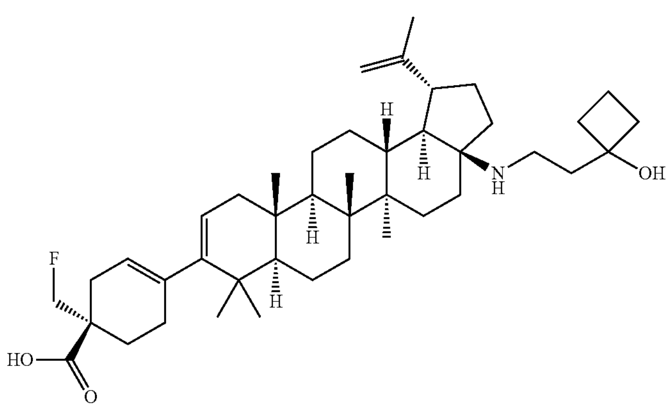 | A | B | |

TABLE 1-continued

| Example # | Structure | WT(EC50, uM) | A364V (EC50, uM) | 92UG029 A Clade T332S/V3 62I/V370 A (EC50, uM) |
|---|---|---|---|---|
| 2-10 | 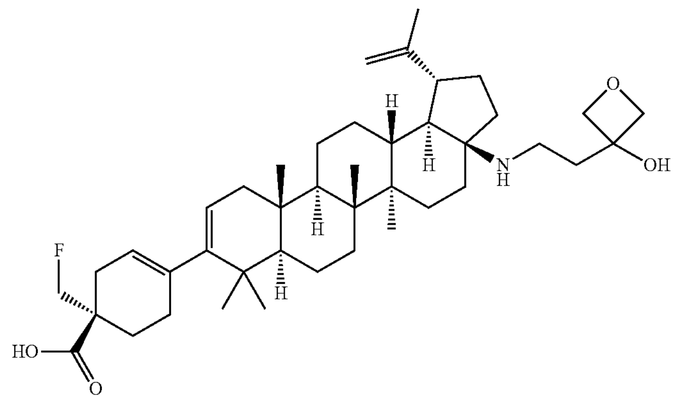 | A | B | |
| 2-11 | 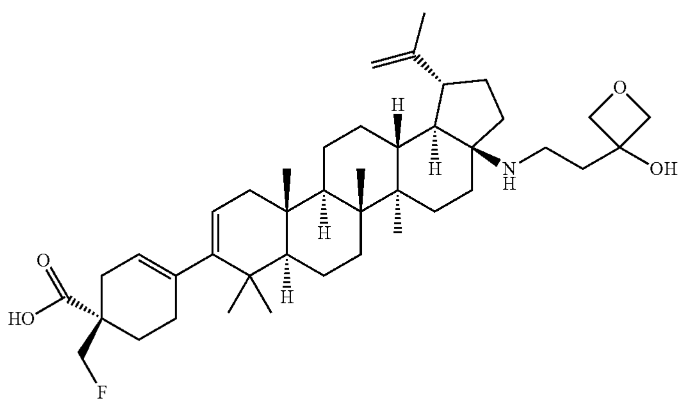 | A | B | 0.0153 |
| 2-12 | 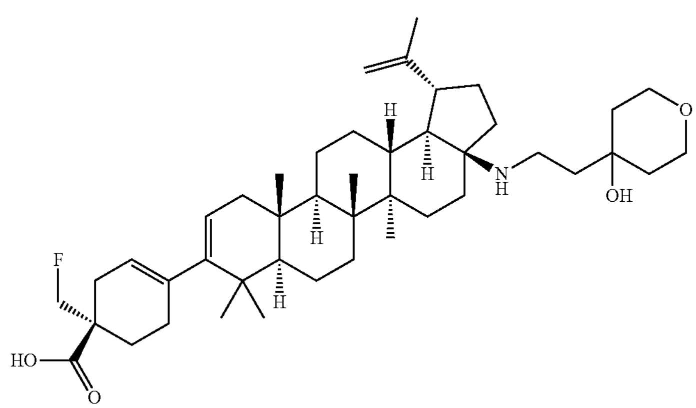 | 0.00201 | 0.348 | |

TABLE 1-continued

| Example # | Structure | WT(EC50, uM) | A364V (EC50, uM) | 92UG029 A Clade T332S/V3 62I/V370 A (EC50, uM) |
|---|---|---|---|---|
| 2-13 | 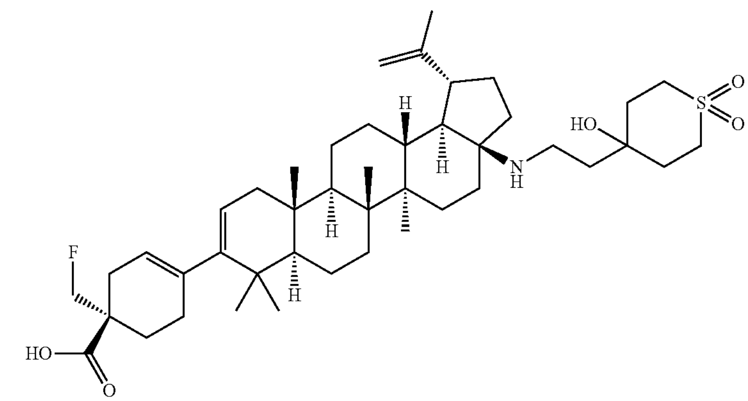 | A | B | |
| 2-14 | 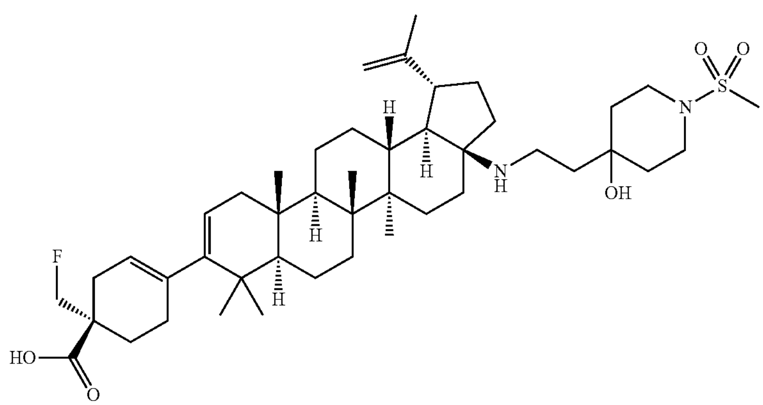 | 0.00256 | 0.0431 | |
| 2-15 | 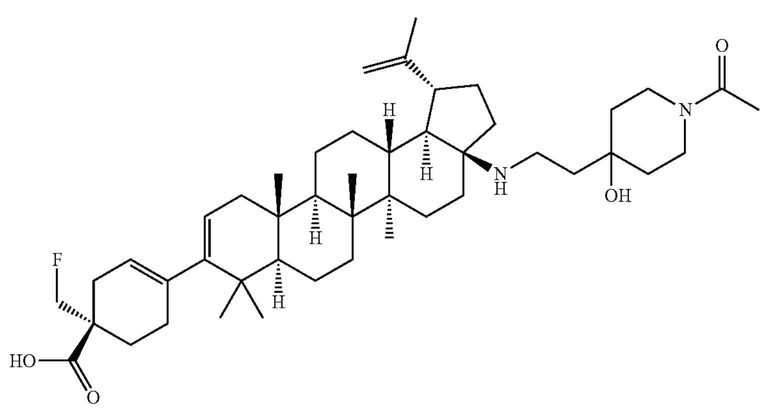 | 0.00173 | 0.151 | |

TABLE 1-continued

| Example # | Structure | WT(EC50, uM) | A364V (EC50, uM) | 92UG029 A Clade T332S/V362I/V370A (EC50, uM) |
|---|---|---|---|---|
| 2-16 | 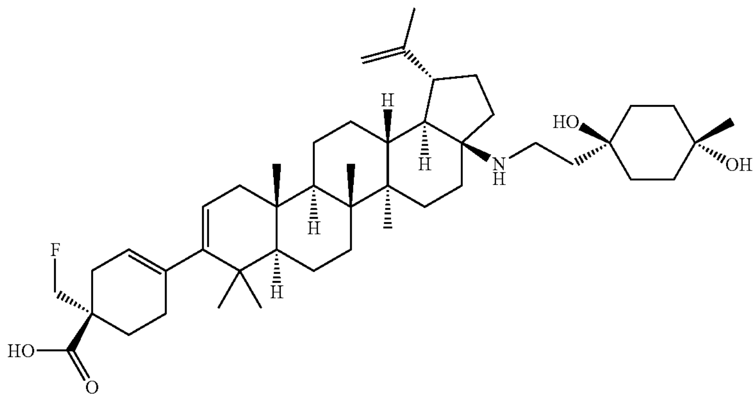 | 0.00210 | 0.0571 | |
| 2-17 | 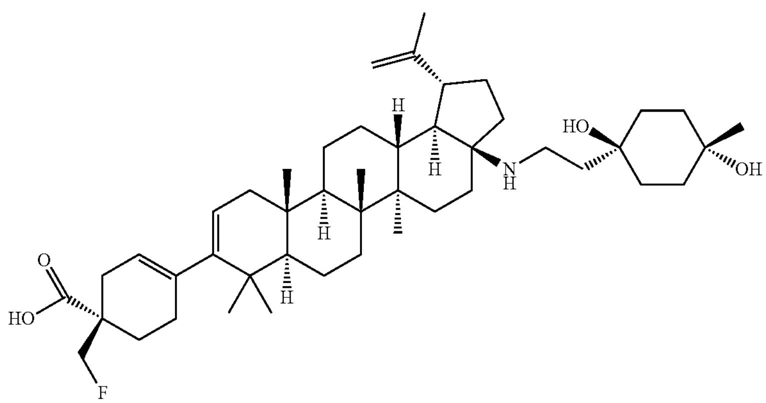 | A | A | 0.00937 |
| 2-18 | 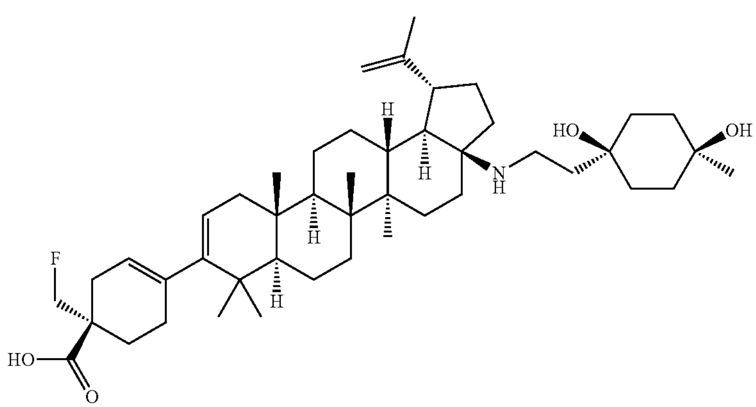 | 0.00165 | 0.854 | |

TABLE 1-continued

| Example # | Structure | WT(EC50, uM) | A364V (EC50, uM) | 92UG029 A Clade T332S/V362I/V370A (EC50, uM) |
|---|---|---|---|---|
| 2-19 | 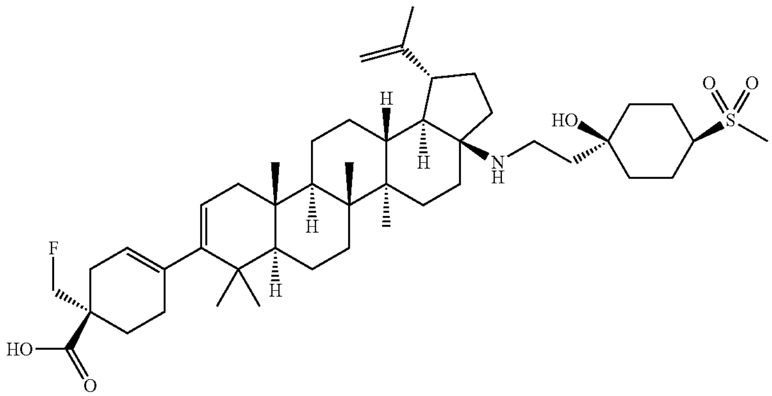 | 0.00135 | 0.0222 | |
| 2-20 | 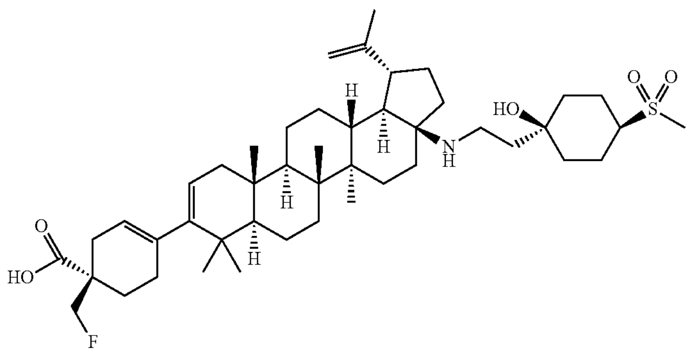 | A | B | A |
| 2-21 | 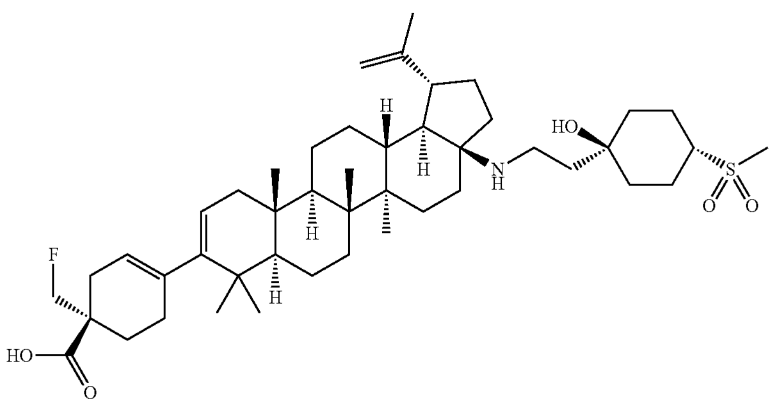 | A | B | |
| 2-22 | 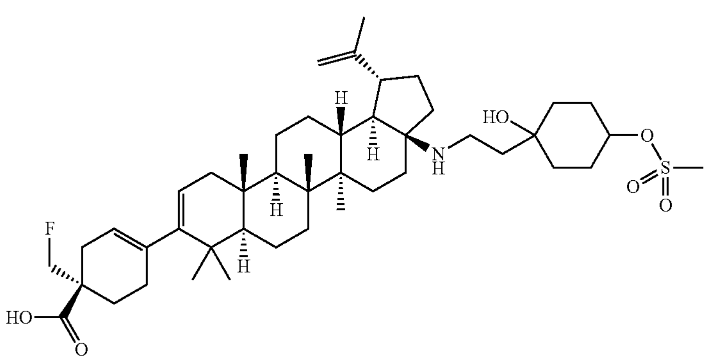 | 0.00315 | 0.107 | |

TABLE 1-continued

| Example # | Structure | WT(EC50, uM) | A364V (EC50, uM) | 92UG029 A Clade T332S/V362I/V370 A (EC50, uM) |
|---|---|---|---|---|
| 2-23 | 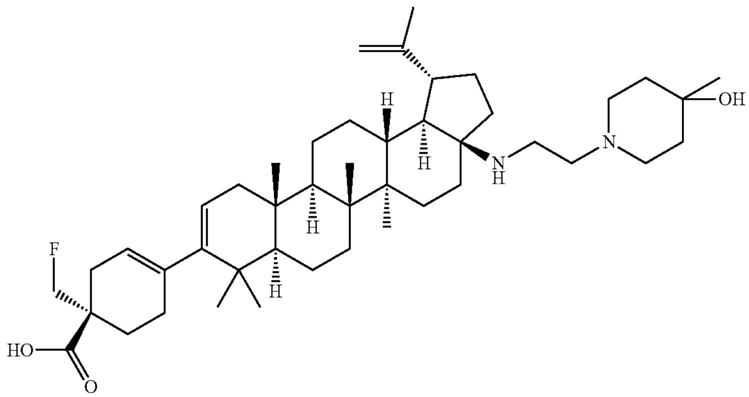 | 0.00121 | 0.0597 | |
| 2-24 | 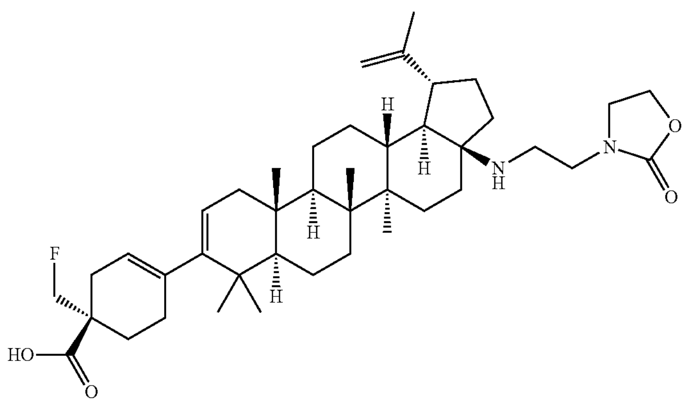 | 0.00530 | 0.932 | |
| 2-25 | 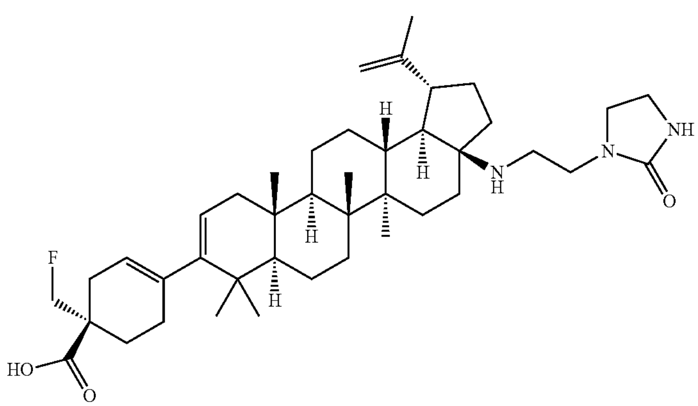 | A | B | |

TABLE 1-continued

| Example # | Structure | WT(EC50, uM) | A364V (EC50, uM) | 92UG029 A Clade T332S/V3 62I/V370 A (EC50, uM) |
|---|---|---|---|---|
| 2-26 | 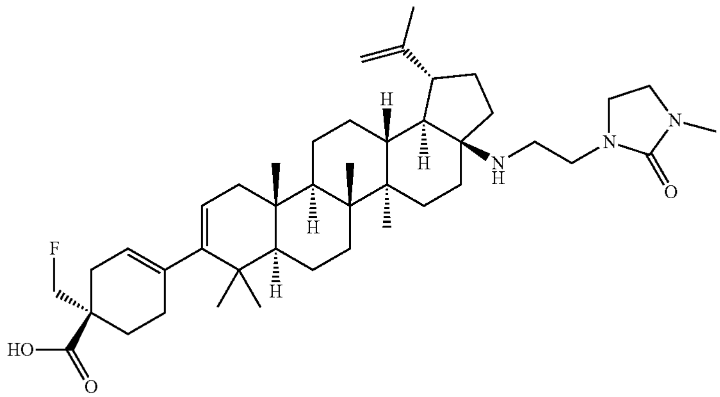 | A | B | |
| 2-27 | 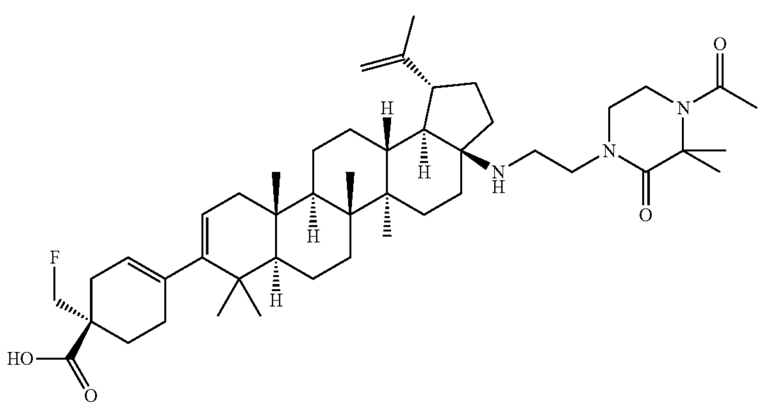 | 0.00577 | 0.0201 | |

Comparative Data—

For this aspect, Comparative Compounds A and B (which have been set forth and described in US 20130210787-WO 2013/123019), as well as Compound 2 as part of the invention herein, were prepared as a mixture of 1-(R) and 1-(S)-diastereomers and evaluated for potency vs. WT, A364V resistant virus, and Glade A virus 92UG029. Compound A displayed good potency vs. WT, but was about 7 fold and >100 fold less potent than Compound 2 vs A364V and 92UC029, respectively. Compound B had comparable potency vs WT when compared with Compound 2. However, compound B was 6 fold less potent than Compound 2 vs the other two viruses (A364V and 92UC029). Selected compounds were also evaluated for their pharmacokinetic properties in the rat (where shown). The results are set forth in Table 2 below. Compound 2 had a better combined profile ($EC_{50}$ WT+$EC_{50}$ A364V+$EC_{50}$92 UC029) as compared to Compounds A and B. Therefore, the single diastereomers Compound 2a and 2b were separated and/or synthesized separately for further evaluation. The single diastereomers (Compounds 2a and 2b) potency/PK were also comparable to what was observed with the mixture of diasteroisomers (compound 2). Therefore 2a and 2b were also viable compounds. Since the development of viral resistance against any antiretroviral drug can be a significant issue in the treatment for HIV-1 infection, those compounds with the best potency profile against both wild-type and mutant forms of the HIV-1 virus are often excellent candidates for drug development.

Compound A

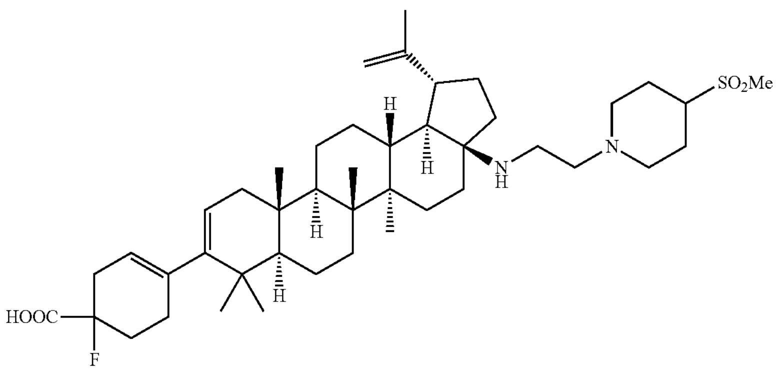

Compound B

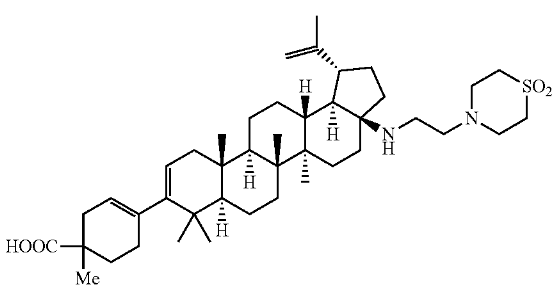

Compound 2

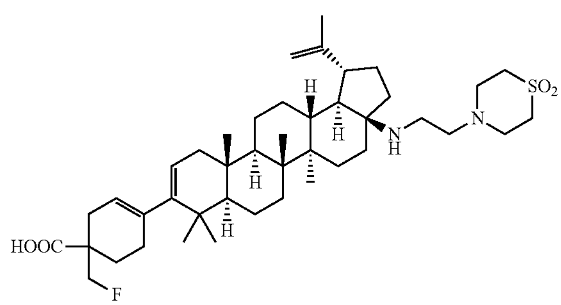

Compound 2a

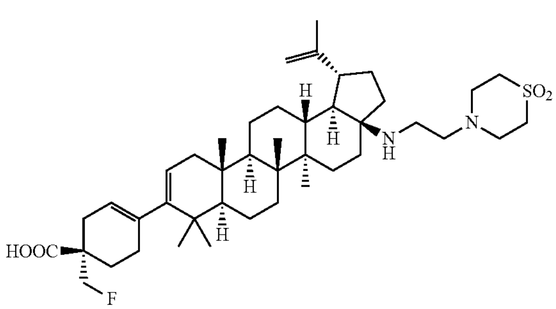

Compound 2b

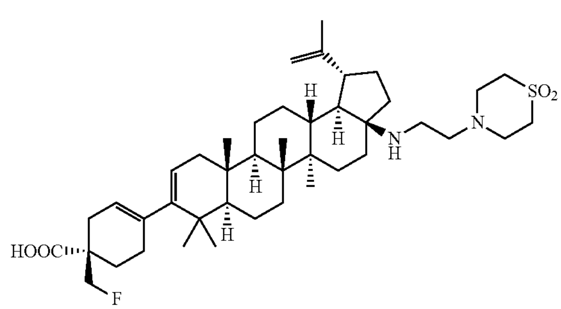

TABLE 2

| Compound | EC$_{50}$ WT (µM) | EC$_{50}$ A364V (µM) | EC$_{50}$ 92UG029 (µM) | Rat AUC (nM*h) |
|---|---|---|---|---|
| A | 0.004 | 1.5 | 0.61 | (not tested) |
| B | 0.002 | 1.3 | 0.03 | 6,457 |
| 2 | 0.002 | 0.21 | 0.005 | 7,933 |
| 2a | 0.002 | 0.78 | 0.02 | 7,032 |
| 2b | 0.003 | 0.17 | 0.001 | 7,394 |

Rat Pharmacokinetic Studies:

For the PO pharmacokinetic studies of the compounds in rats, the compounds were each dissolved in PEG-400/ethanol (90/10) as a solution.

Rat. Male Sprague-Dawley rats (300-350 g, Hilltop Lab Animals, Inc., Scottsdale, Pa.) with cannulas implanted in the jugular vein were used. The rats were fasted overnight in the PO pharmacokinetic studies. Blood samples of 0.3 mL were collected from the jugular vein in EDTA-containing microtainer tubes (Becton Dickinson, Franklin Lakes, N.J.), and centrifuged to separate plasma.

In the PO study of the tested compounds, the rats (n=3) received an oral dose of 5 mg/kg of the indicated compound. Serial blood samples were collected before dosing and 15, 30, 45, 60, 120, 240, 360, 480, and 1440 min after dosing.

Quantitation of Compounds in Plasma. Aliquots of plasma samples from rat, studies were prepared for analysis by precipitating plasma proteins with two volumes of acetonitrile containing an internal standard of a similar compound. The resulting supernates were separated from the precipitated proteins by centrifugation for 10 minutes and transferred to autosampler vials. Samples were either prepared manually, or with the use of the Tomtec automated liquid handler. An aliquot of 5 µL was injected for analysis. The HPLC system consisted of two Shimadzu LC10AD pumps (Columbia, Md.), a Shimadzu SIL-HTC autosampler (Columbia, Md.), and a Hewlett Packard Series 1100 column compartment (Palo Alto, Calif.). The column was a YMC Pro C18 (2.0×50 mm, 3 µm particles, Waters Co., Milford, Mass.), maintained at 60° C. and a flow rate of 0.3 ml/min. The mobile phase consisted of 10 mM ammonium formate and 0.1% formic acid in water (A) and 100% 10 mM ammonium formate and 0.1% formic acid in methanol (B). The initial mobile phase composition was 95% A. After sample injection, the mobile phase was changed to 15% A/85% B over 2 minutes and held at that composition for an additional 1 minute. The mobile phase was then returned to initial conditions and the column re-equilibrated for 1 minute. Total analysis time was 4 minutes.

The HPLC was interfaced to a Micromass Quattro LC. Ultra high purity nitrogen was used as the nebulizing and desolvation gas at flow rates of 100 L/hr for nebulization and 1100 L/hr for desolvation. The desolvation temperature was 300° C. and the source temperature was 150° C. Data acquisition utilized selected reaction monitoring (SRM). Ions representing the (M+H)$^+$ species for the compound and the internal standard were selected in MS1 and collisionally dissociated with argon at a pressure of 2×10$^3$ torr to form specific product ions which were subsequently monitored by MS2.

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:

1. A compound of Formula I, including pharmaceutically acceptable salts thereof:

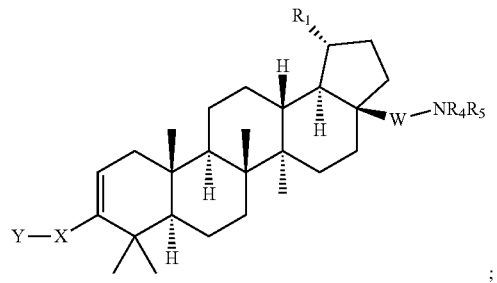

Formula I wherein R$_1$ is isopropenyl or isopropyl;

X is selected from the group of C$_{4-8}$ cycloalkyl, C$_{4-8}$ cycloalkenyl, C$_{4-9}$ spirocycloalkyl, C$_{4-9}$ spirocycloalkenyl, C$_{4-8}$ oxacycloalkyl, C$_{4-8}$ dioxacycloalkyl, C$_{6-8}$ oxacycloalkenyl, C$_{6-8}$ dioxacycloalkenyl, C$_6$ cyclodialkenyl, C$_6$ oxacyclodialkenyl, C$_{6-9}$ oxaspirocycloalkyl and C$_{6-9}$ oxaspirocycloalkenyl ring, wherein X is substituted with A, and wherein A is —C$_{1-6}$ alkyl-halo;

Y is selected from the group of —COOR$_2$, —C(O)NR$_2$SO$_2$R$_3$, —C(O)NHSO$_2$NR$_2$R$_2$, —NR$_2$SO$_2$R$_2$, —SO$_2$NR$_2$R$_2$, —C$_{3-6}$ cycloalkyl-COOR$_2$, —C$_{2-6}$ alkenyl-COOR$_2$, —C$_{2-6}$ alkynyl-COOR$_2$, —C$_{1-6}$ alkyl-COOR$_2$, -alkylsubstituted C$_{1-6}$ alkyl, —CF$_2$—COOR$_2$, —NHC(O)(CH2)$_n$-COOR$_2$, —SO$_2$NR$_2$C(O)R$_2$, -tetrazole, and —CONHOH, wherein n=1-6;

R$_2$ is —H, —C$_{1-6}$ alkyl, -alkylsubstituted C$_{1-6}$ alkyl or -arylsubstituted C$_{1-6}$ alkyl;

W is absent, or is —CH$_2$ or —CO;

R$_3$ is —H, —C$_{1-6}$ alkyl or -alkylsubstituted C$_{1-6}$ alkyl;

R$_4$ is selected from the group of —H, —C$_{1-6}$ alkyl, —C$_{1-6}$alkyl-C$_{3-6}$cycloalkyl, —C$_{1-6}$ substituted —C$_{1-6}$ alkyl, —C$_{1-6}$ alkyl-Q$_1$, —C$_{1-6}$ alkyl-C$_{3-6}$ cycloalkyl-Q$_1$, aryl, heteroaryl, substituted heteroaryl, —COR$_6$, —SO$_2$R$_7$, —SO$_2$NR$_2$R$_2$, and

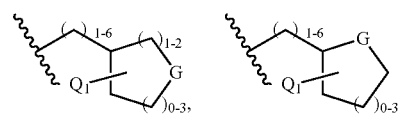

wherein G is selected from the group of —O—, —SO$_2$— and —NR$_{12}$;

wherein Q$_1$ is selected from the group of —C$_{1-6}$ alkyl, —C$_{1-6}$ fluoroalkyl, heteroaryl, substituted heteroaryl, halogen, —CF$_3$, —OR$_2$, —COOR$_2$, —NR$_8$R$_9$, —CONR$_8$R$_9$ and —SO$_2$R$_7$;

R₅ is selected from the group of —H, —C₁₋₆ alkyl, —C₃₋₆ cycloalkyl, —C₁₋₆ alkylsubstituted alkyl, —C₁₋₆ alkyl-NR₈R₉, —COR₃, —SO₂R₇ and —SO₂NR₂R₂;

with the proviso that R₄ or R₅ cannot be —COR₆ when W is —CO;

with the further proviso that only one of R₄ or R₅ can be selected from the group of —COR₆, —SO₂R₇ and —SO₂NR₂R₂;

or when W is absent or is —CH₂, then R₄ and R₅ can be taken together with the adjacent N to form

R₆ is selected from the group of —H, —C₁₋₆ alkyl, —C₁₋₆ alkyl-substitutedalkyl, —C₃₋₆ cycloalkyl, —C₃₋₆ substitutedcycloalkyl-Q₂, —C₁₋₆ alkyl-Q₂, —C₁₋₆ alkyl-substitutedalkyl-Q₂, —C₃₋₆ cycloalkyl-Q₂, aryl-Q₂, —NR₁₃R₁₄, and —OR₁₅;

wherein Q₂ is selected from the group of aryl, heteroaryl, substituted heteroaryl, —OR₂, —COOR₂, —NR₈R₉, SO₂R₇, —CONHSO₂R₃, and —CONHSO₂NR₂R₂;

R₇ is selected from the group of —H, —C₁₋₆ alkyl, —C₁₋₆ substituted alkyl, —C₃₋₆ cycloalkyl, —CF₃, aryl, and heteroaryl;

R₈ and R₉ are independently selected from the group of —H, —C₁₋₆ alkyl, —C₁₋₆ substituted alkyl, aryl, heteroaryl, substituted aryl, substituted heteroaryl, —C₁₋₆ alkyl-Q₂, and —COOR₃, or R₈ and R₉ are taken together with the adjacent N to form a cycle selected from the group of:

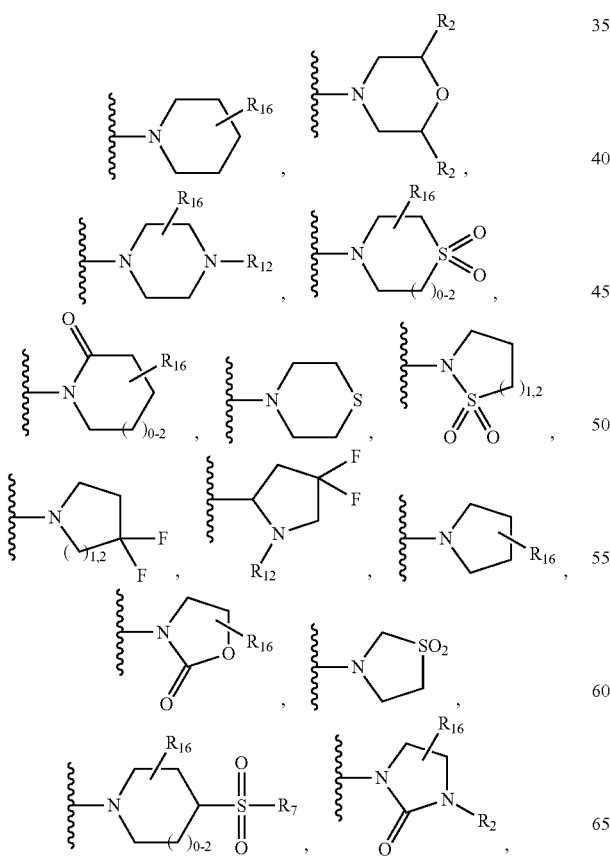

-continued

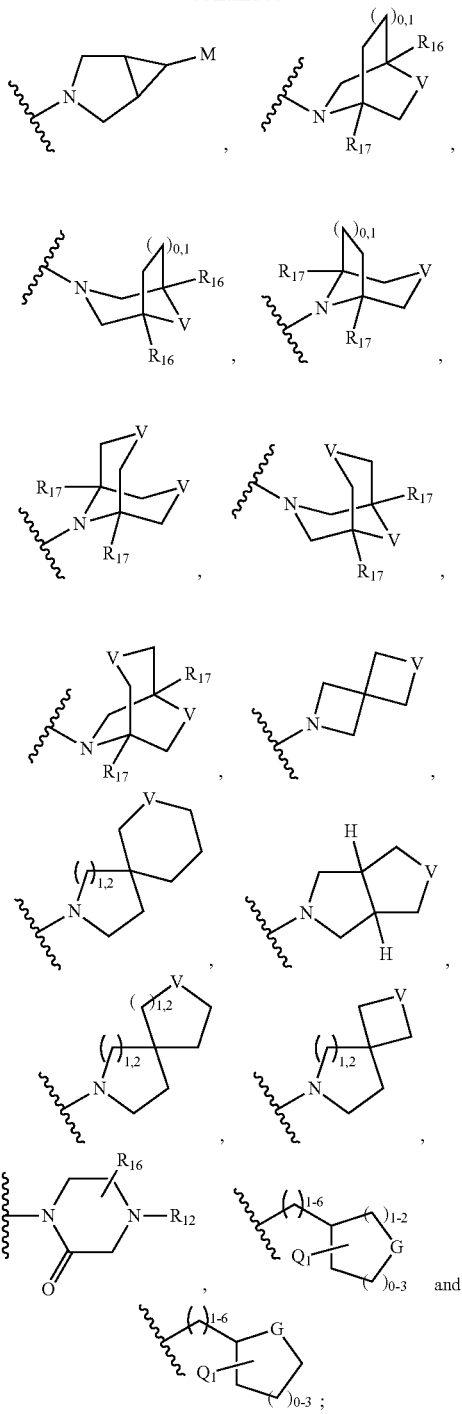

M is selected from the group of —R₁₅, —SO₂R₂, —SO₂NR₂R₂, —OH and —NR₂R₁₂;

V is selected from the group of —CR₁₀R₁₁, —SO₂—, —O— and —NR₁₂—;

with the proviso that only one of R₈ or R₉ can be —COOR₃;

R₁₀ and R₁₁ are independently selected from the group of —H, —C₁₋₆ alkyl, —C₁₋₆ substituted alkyl and —C₃₋₆ cycloalkyl;

R₁₂ is selected from the group of —H, —C₁₋₆ alkyl, -alkylsubstituted C₁₋₆ alkyl, —CONR₂R₂, —SO₂R₃, —SO₂NR₂R₂;

$R_{13}$ and $R_{14}$ are independently selected from the group of —H, —$C_{1-6}$ alkyl, —$C_{3-6}$ cycloalkyl, —$C_{1-6}$ substituted alkyl, —$C_{1-6}$ alkyl-$Q_3$, —$C_{1-6}$ alkyl- $C_{3-6}$ cycloalkyl-$Q_3$ $C_{1-6}$ substituted alkyl-$Q_3$ and

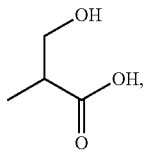

$Q_3$ is selected from the group of heteroaryl, substituted heteroaryl, —$NR_2R_{12}$, —$CONR_2R_2$, —$COOR_2$, —$OR_2$, and —$SO_2R_3$;

$R_{15}$ is selected from the group of —$C_{1-6}$ alkyl, —$C_{3-6}$ cycloalkyl, —$C_{1-6}$ substituted alkyl, —$C_{1-6}$ alkyl- $Q_3$, —C1-6 alkyl-$C_{3-6}$ cycloalkyl-$Q_3$ and —$C_{1-6}$ substituted alkyl-$Q_3$;

$R_{16}$ is selected from the group of —H, —$C_{1-6}$ alkyl, —$NR_2R_2$, and —$COOR_2$;

with the proviso that when V is —$NR_{12}$—; $R_{16}$ cannot be —$NR_2R_2$; and $R_{17}$ is selected from the group of —H, —$C_{1-6}$ alkyl, —$COOR_3$, and aryl.

2. The compound as claimed in claim 1, wherein $R_1$ is isopropenyl.

3. The compound as claimed in claim 2, wherein W is absent.

4. The compound as claimed in claim 1, wherein X is $C_{4-8}$ cycloalkenyl.

5. The compound as claimed in claim 4, wherein X is $C_6$ cycloalkenyl.

6. The compound as claimed in claim 5, wherein A is $C_1$-$C_3$ alkyl-halo.

7. The compound as claimed in claim 6, wherein A is methyl-fluoro.

8. The compound as claimed in claim 1, wherein A is methyl-halo.

9. The compound as claimed in claim 8, wherein A is methyl-fluoro.

10. The compound as claimed in claim 1, wherein Y is —$COOR_2$.

11. The compound as claimed in claim 10, wherein Y is —COOH.

12. A compound, or a pharmaceutically acceptable salt thereof, which is selected from the group of:

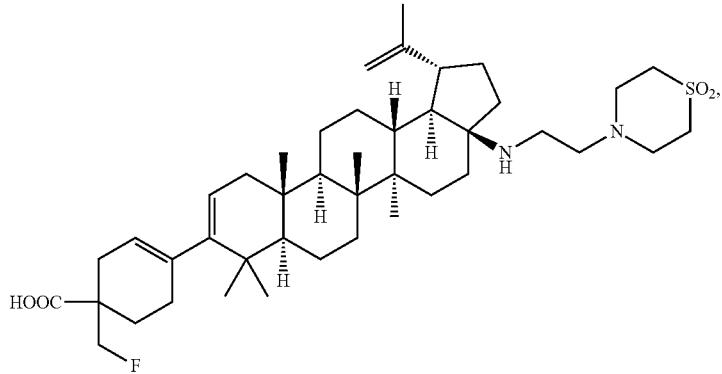

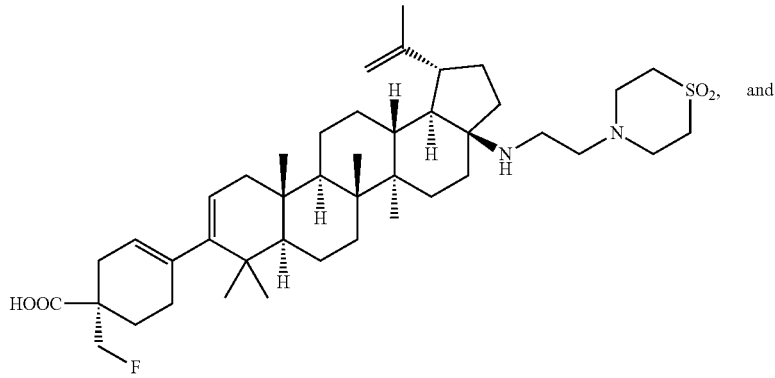

and

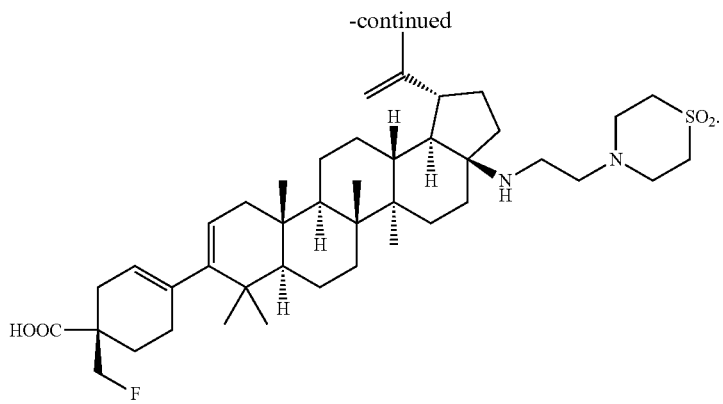

13. A pharmaceutical composition which comprises one or more of the compounds as claimed in claim 1, together with one or more pharmaceutically acceptable carriers, excipients and/or diluents.

14. A pharmaceutical composition which comprises one or more of the compounds as claimed in claim 12, together with one or more pharmaceutically acceptable carriers, excipients and/or diluents.

15. A pharmaceutical composition which comprises the compound

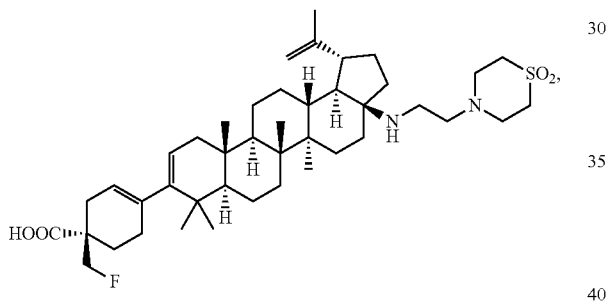

together with one or more pharmaceutically acceptable carriers, excipients and/or diluents.

16. A method for treating a mammal infected with the HIV virus comprising administering to said mammal an antiviral effective amount of a compound as claimed in claim 1, and one or more pharmaceutically acceptable carriers, excipients or diluents.

17. The compound as claimed in claim 9, wherein Y is —COOH.

18. A compound of Formula I, including pharmaceutically acceptable salts-or a pharmaceutically acceptable salt thereof:

Formula I

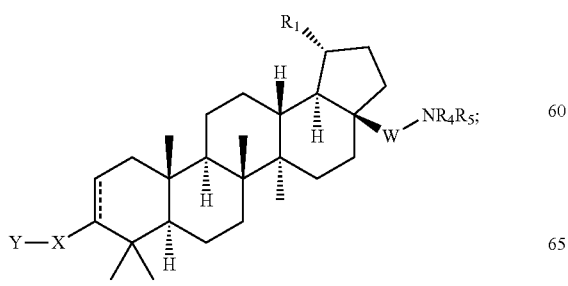

wherein $R_1$ is isopropenyl or isopropyl;

X is selected from the group of $C_{4-8}$ cycloalkyl, $C_{4-8}$ cycloalkenyl, $C_{4-9}$ spirocycloalkyl, $C_{4-9}$ spirocycloalkenyl, $C_{4-8}$ oxacycloalkyl, $C_{4-8}$ dioxacycloalkyl, $C_{6-8}$ oxacycloalkenyl, $C_{6-8}$ dioxacycloalkenyl, $C_6$ cyclodialkenyl, $C_6$ oxacyclodialkenyl, $C_{6-9}$ oxaspirocycloalkyl and $C_{6-9}$ oxaspirocycloalkenyl ring, wherein X is substituted with A, wherein A is —$C_{1-6}$ alkyl-halo;

Y is selected from the group of —$COOR_2$, —$C(O)NR_2SO_2R_3$, —$C(O)NHSO_2NR_2R_2$, —$NR_2SO_2R_2$, —$SO_2NR_2R_2$, —$C_{3-6}$ cycloalkyl-$COOR_2$, —$C_{2-6}$ alkenyl-$COOR_2$, —$C_{2-6}$ alkynyl-$COOR_2$, —$C_{1-6}$ alkyl-$COOR_2$, -alkylsubstituted $C_{1-6}$ alkyl, —$COOR_2$, $CF_2$—$COOR_2$, —$NHC(O)(CH_2)_n$—$COOR_2$, —$SO_2NR_2C(O)R_2$, -tetrazole, and —$CONHOH$, wherein n=1-6;

$R_2$ is —H, —$C_{1-6}$ alkyl, -alkylsubstituted $C_{1-6}$ alkyl or -arylsubstituted $C_{1-6}$ alkyl;

W is absent, $CH_2$ or $CO$;

$R_3$ is —$C_{1-6}$ alkyl or -alkylsubstituted $C_{1-6}$ alkyl;

$R_4$ is selected from the group of —H, —$C_{1-6}$ alkyl, —$C_{1-6}$ alkyl-$C(OR_3)_2$—$C_{3-6}$ cycloalkyl, —$C_{1-6}$ substituted alkyl, —$C_{1-6}$ alkyl-$C_{3-6}$ cycloalkyl, —$C_{1-6}$ alkyl-$Q_1$, —$C_{1-6}$ alkyl-$C_{3-6}$ cycloalkyl-$Q_1$, aryl, heteroaryl, substituted heteroaryl, —$COR_6$, —$COCOR_6$, —$SO_2R_7$, —$SO_2NR_2R_2$,

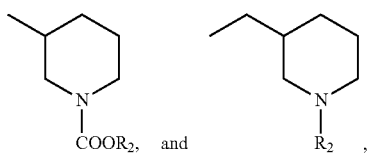

with the proviso that $R_4$ or $R_5$ cannot be $COR_6$ or $COCOR_6$ when W is CO;

wherein $Q_1$ is selected from the group of heteroaryl, substituted heteroaryl, halogen, —$CF3$, —$OR2$, —$COOR_2$, —$NR_8R_9$, —$CONR_{10}R_{11}$ and —$SO_2R_7$;

$R_5$ is selected from the group of —H, —$C_{1-6}$ alkyl, —$C_{3-6}$ cycloalkyl, —$C_{1-6}$ alkylsubstituted alkyl, —$C_{1-6}$ alkyl-$NR_8R_9$, —$COR_{10}$, —$COR_6$, —$COCOR_6$, —$SO_2R_7$ and —$SO_2NR_2R_2$;

with the proviso that only one of $R_4$ or $R_5$ can be selected from the group of —$COR_6$, —$COCOR_6$, —$SO_2R_7$ and —$SO_2NR_2R_2$;

or when W is absent or is CH$_2$, then R$_4$ and R$_5$ can be taken together with the adjacent N to form

;

R$_6$ is selected from the group of —H, —C$_{1-6}$ alkyl, —C$_{1-6}$ alkyl-substitutedalkyl, —C$_{3-6}$ cycloalkyl, —C$_{3-6}$ substitutedcycloalkyl-Q$_2$, —C$_{1-6}$ alkyl-Q$_2$, —C$_{1-6}$ alkyl-substitutedalkyl-Q$_2$, —C$_{3-6}$ cycloalkyl-Q$_2$, aryl-Q$_2$, —NR$_{13}$R$_{14}$, and —OR$_{15}$;

wherein Q$_2$ is selected from the group of aryl, heteroaryl, substituted heteroaryl, —OR$_2$, —COOR$_2$, —NR$_8$R$_9$, SO$_2$R$_7$, —CONHSO$_2$R$_3$, and —CONHSO$_2$NR$_2$R$_2$;

R$_7$ is selected from the group of —C$_{1-6}$ alkyl, —C$_{1-6}$ substituted alkyl, —C$_{3-6}$ cycloalkyl, —CF$_3$, aryl, and heteroaryl;

R$_8$ and R$_9$ are independently selected from the group of —H, —C$_{1-6}$ alkyl, —C$_{1-6}$ substituted alkyl, aryl, heteroaryl, substituted aryl, substituted heteroaryl, —C$_{1-6}$ alkyl-Q$_2$, and —COOR$_3$, and R$_8$ and R$_9$ can also be independently selected from the group of

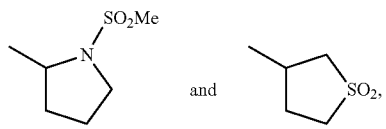

or R$_8$ and R$_9$ are taken together with the adjacent N to form a cycle selected from the group of:

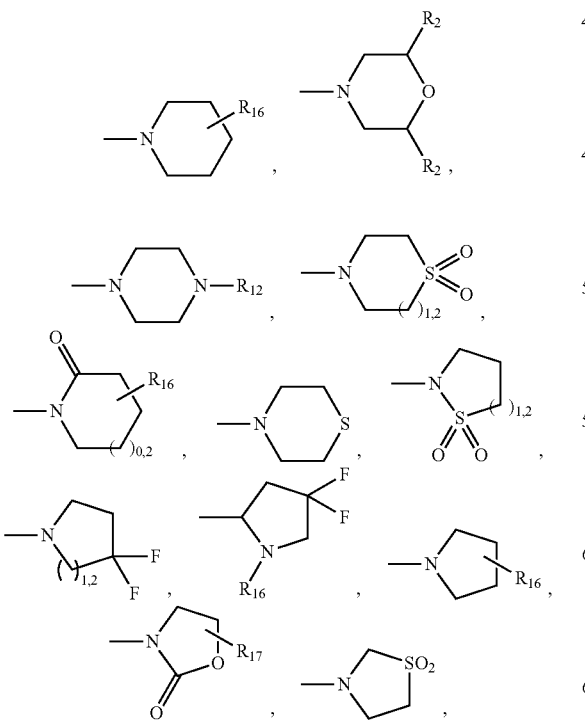

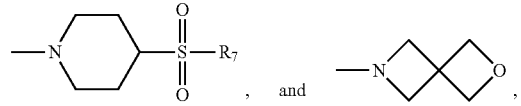

with the proviso that only one of R$_8$ or R$_9$ can be —COOR$_3$;

R$_{10}$ and R$_{11}$ are independently selected from the group of —H, —C$_{1-6}$ alkyl, —C$_{1-6}$ substituted alkyl and —C$_{3-6}$ cycloalkyl, or R$_{10}$ and R$_{11}$ are taken together with the adjacent N to form

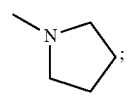;

R$_{12}$ is selected from the group of —C$_{1-6}$ alkyl, —C$_{1-6}$ alkyl-OR; —C$_{1-6}$ alkyl, —C$_{1-6}$ substituted alkyl, —C$_{3-6}$ cycloalkyl, —COR$_3$, —COONR$_{22}$R$_{23}$, —S(O)$_m$ R$_7$, and —SONR$_{24}$R$_{25}$, wherein m=1 or 2;

R$_{13}$ and R$_{14}$ are independently selected from the group of —H, —C$_{1-6}$ alkyl, —C$_{3-6}$ cycloalkyl, —C$_{1-6}$ substituted alkyl, —C$_{1-6}$ alkyl-Q$_3$, —C$_{1-6}$ alkyl-C$_{3-6}$ cycloalkyl-Q$_3$, C$_{1-6}$ substituted alkyl-Q$_3$ and

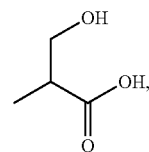

Q$_3$ is selected from the group of heteroaryl, substituted heteroaryl, —NR$_{20}$R$_{21}$, —CONR$_2$R$_2$, —COOR$_2$, —OR$_2$, and —SO$_2$R$_3$;

R$_{15}$ is selected from the group of —C$_{1-6}$ alkyl, —C$_{3-6}$ cycloalkyl, —C$_{1-6}$ substituted alkyl, —C$_{1-6}$ alkyl- Q$_3$, —C$_{1-6}$ alkyl-C$_{3-6}$ cycloalkyl-Q$_3$ and —C$_{1-6}$ substituted alkyl-Q$_3$;

R$_{16}$ is selected from the group of —H, —C$_{1-6}$ alkyl, —NR$_2$R$_2$, and —COOR$_3$;

R$_{17}$ is selected from the group of —H, —C$_{1-6}$ alkyl, —COOR$_3$, and aryl;

R$_{20}$ and R$_{21}$ are independently selected from the group of —H, —C$_{1-6}$ alkyl, —C$_{1-6}$ substituted alkyl, —C$_{1-6}$ substituted alkyl-OR$_2$, and —COR$_3$, or R$_{20}$ and R$_{21}$ are taken together with the adjacent N to form a cycle selected from the group of

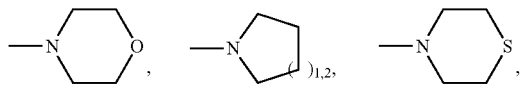

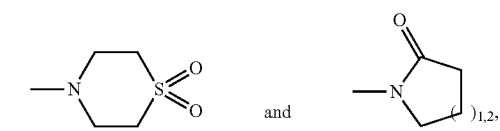

with the proviso that only one of $R_{20}$ or $R_{21}$ can be —$COR_3$;

$R_{22}$ and $R_{23}$ are independently selected from the group of H, —$C_{1-6}$ alkyl, —$C_{1-6}$ substituted alkyl, and —$C_{1-6}$ cycloalkyl, or $R_{22}$ and $R_{23}$ are taken together with the adjacent N to form a cycle selected from the group of

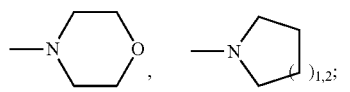

$R_{24}$ and $R_{25}$ are independently from the group of H, —$C_{1-6}$ alkyl, —$C_{1-6}$ substituted alkyl, —$C_{1-6}$ alkyl-$Q_5$, —$C_{1-6}$ cycloalkyl, aryl, substituted aryl, heteroaryl, and substituted heteroaryl; and $Q_5$ is selected from the group of halogen and $SO_2R_3$.

* * * * *

UNITED STATES PATENT AND TRADEMARK OFFICE
CERTIFICATE OF CORRECTION

PATENT NO. : 9,527,882 B2  
APPLICATION NO. : 14/682179  
DATED : December 27, 2016  
INVENTOR(S) : Sing-Yuen Sit et al.

Page 1 of 1

It is certified that error appears in the above-identified patent and that said Letters Patent is hereby corrected as shown below:

In the Claims

In Claim 1, Column 410, Lines 7-8:
The portion of the claim reading:
1. A compound of Formula I, "including" pharmaceutically acceptable salts thereof:

Should read:
1. A compound of Formula I, -- or a -- pharmaceutically acceptable salt thereof:

In Claim 18, Column 418, Line 23:
The portion of the claim reading:
"-$COR_3$,"

Should read:
-- -$COR_7$, --

Signed and Sealed this  
Ninth Day of May, 2017

Michelle K. Lee  
*Director of the United States Patent and Trademark Office*